US012686714B2

(12) United States Patent
Demishtein et al.

(10) Patent No.: US 12,686,714 B2
(45) Date of Patent: Jul. 21, 2026

(54) ENGINEERED DUAL BINDING ANTIBODIES AND USES THEREOF

(71) Applicant: Biolojic Design Ltd., Ness Ziona (IL)

(72) Inventors: Alik Demishtein, Rosh Haayin (IL); Shmuel Bernstein, Lod (IL); Tomer Shlamkovich, Modi'in-Maccabim-Re'ut (IL); Ayelet Chen, Jerusalem (IL); Yehezkel Sasson, Tzur Yigal (IL); Marek Strajbl, Jerusalem (IL); Itay Levin, Herzeliya (IL); Sharon Fischman, Modi'in (IL); Yanay Ofran, Tel Aviv (IL); Guy Nimrod, Tel Aviv (IL); Alexey Shnyder, Petah-Tiqva (IL); Hadar Gattegno, Rehovot (IL); Nikol Malchenko, Ramat Gan (IL); Olga Bluvshtein Yermolaev, Rishon-LeZion (IL); Noam Grossman, Mazkeret Batyia (IL); Liron Danielpur, Hadera (IL); Itzhak Meir, Rehovot (IL); Morya Ifrach, Qiryat Gat (IL); Reut Barak Fuchs, Rehovot (IL); Michael Zhenin, Jerusalem (IL); Yair Fastman, Jerusalem (IL)

(73) Assignee: BIOLOJIC DESIGN LTD., Rehovot (IL)

( * ) Notice: Subject to any disclaimer, the term of this patent is extended or adjusted under 35 U.S.C. 154(b) by 369 days.

(21) Appl. No.: 18/475,358

(22) Filed: Sep. 27, 2023

(65) Prior Publication Data

US 2024/0059769 A1 Feb. 22, 2024
US 2024/0409625 A9 Dec. 12, 2024

Related U.S. Application Data

(63) Continuation-in-part of application No. PCT/IL2022/050572, filed on May 29, 2022, which is a continuation-in-part of application No. PCT/IL2022/050087, filed on Jan. 20, 2022.

(60) Provisional application No. 63/195,021, filed on May 30, 2021, provisional application No. 63/295,905, filed on Jan. 2, 2022.

(51) Int. Cl.
*C07K 16/24* (2006.01)

(52) U.S. Cl.
CPC ........ *C07K 16/244* (2013.01); *C07K 2317/31* (2013.01); *C07K 2317/33* (2013.01); *C07K 2317/52* (2013.01); *C07K 2317/622* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,237,224 A | 12/1980 | Cohen et al. | |
| 4,751,180 A | 6/1988 | Cousens et al. | |
| 4,816,567 A | 3/1989 | Cabilly et al. | |
| 4,935,233 A | 6/1990 | Bell et al. | |
| 5,151,510 A | 9/1992 | Stec et al. | |
| 5,585,089 A | 12/1996 | Queen et al. | |
| 5,693,762 A | 12/1997 | Queen et al. | |
| 5,837,458 A | 11/1998 | Minshull et al. | |
| 7,829,090 B2 | 11/2010 | Monk et al. | |
| 7,935,343 B2 | 5/2011 | Monk et al. | |
| 7,947,273 B2 | 5/2011 | Monk et al. | |
| 7,982,016 B2 | 7/2011 | Comeau et al. | |
| 8,008,449 B2 | 8/2011 | Korman et al. | |
| 8,133,979 B2 | 3/2012 | Brinkmann et al. | |
| 8,163,284 B2 | 4/2012 | Comeau et al. | |
| 8,361,747 B2 | 1/2013 | Brinkmann et al. | |
| 8,394,378 B2 | 3/2013 | Kehoe et al. | |
| 8,399,626 B2 | 3/2013 | Brinkmann et al. | |
| 8,637,019 B2 | 1/2014 | Presta | |
| 9,284,372 B2 | 3/2016 | Comeau et al. | |
| 9,856,317 B2 | 1/2018 | Monk et al. | |
| 9,879,072 B2 | 1/2018 | Richards et al. | |
| 9,889,423 B2 | 2/2018 | Banyai et al. | |
| 10,138,298 B2 | 11/2018 | Rondon et al. | |
| 10,259,881 B2 | 4/2019 | Gray et al. | |
| 10,287,348 B2 | 5/2019 | Comeau et al. | |
| 10,738,113 B2 | 8/2020 | Rondon et al. | |

(Continued)

FOREIGN PATENT DOCUMENTS

| | | | |
|---|---|---|---|
| EP | | 1942939 B2 | 5/2018 |
| WO | WO 1990/004036 A1 | | 4/1990 |

(Continued)

OTHER PUBLICATIONS

Venkataramani S et al. "Design and characterization of Zweimab and Doppelmab, high affinity dual antagonistic anti-TSLP/IL13 bispecific antibodies." Biochem Biophys Res Commc'ns 504: 19-24. (Year: 2018).*

Beard et al. Applying Physics-Based Scoring to Calculate Free Energies of Binding for Single Amino Acid Mutations in Protein-Protein Complexes PLoS One. 2013;8(12).

Beiboer et al. "Guided selection of a pan carcinoma specific antibody reveals similar binding characteristics yet structural divergence between the original murine antibody and its human equivalent" Journal of molecular biology. Feb. 25, 2000;296(3):833-49.

(Continued)

*Primary Examiner* — Lora E Barnhart Driscoll
(74) *Attorney, Agent, or Firm* — Mark S. Cohen; PEARL COHEN ZEDEK LATZER BARATZ LLP

(57) ABSTRACT

Described herein are engineered dual binding antibodies that bind to IL-13 and TSLP and uses thereof. Uses include treating allergic and respiratory conditions. Described herein are also libraries comprising the engineered dual binding antibodies, and methods of producing the engineered dual binding antibodies and functional and biochemical characterization of the antibodies.

22 Claims, 79 Drawing Sheets

Specification includes a Sequence Listing.

(56)        References Cited

U.S. PATENT DOCUMENTS

| | | | |
|---|---|---|---|
| 10,828,365 B2 | 11/2020 | Parnes et al. | |
| 10,870,705 B2 | 12/2020 | Marasco | |
| 11,459,385 B2 | 10/2022 | Rondon et al. | |
| 2009/0238823 A1 | 9/2009 | Comeau et al. | |
| 2009/0304693 A1 | 12/2009 | Ghayur et al. | |
| 2012/0020988 A1 | 1/2012 | Auer et al. | |
| 2013/0045492 A1 | 2/2013 | Babb et al. | |
| 2013/0259867 A1 | 10/2013 | Amler et al. | |
| 2016/0264658 A1 | 9/2016 | Ahmed et al. | |
| 2016/0272706 A1 | 9/2016 | Carmen et al. | |
| 2017/0066823 A1 | 3/2017 | Edwards et al. | |
| 2017/0082608 A1 | 3/2017 | Gorski et al. | |
| 2017/0342144 A1 | 11/2017 | Wei et al. | |
| 2017/0362321 A1 | 12/2017 | Campbell et al. | |
| 2018/0068055 A1 | 3/2018 | Ofran et al. | |
| 2018/0296669 A1 | 10/2018 | Parnes et al. | |
| 2019/0106488 A1 | 4/2019 | Rondon et al. | |
| 2020/0283508 A1 | 9/2020 | Ko et al. | |
| 2021/0040189 A1 | 2/2021 | Richards et al. | |
| 2021/0052726 A1 | 2/2021 | Parnes et al. | |
| 2021/0188965 A1* | 6/2021 | Rommelaere | C07K 16/244 |
| 2023/0340106 A1 | 10/2023 | Rondon et al. | |
| 2024/0101675 A1* | 3/2024 | Demishtein | C07K 16/2878 |

FOREIGN PATENT DOCUMENTS

| | | |
|---|---|---|
| WO | WO 1991/010741 A1 | 7/1991 |
| WO | WO 1992/003918 A1 | 3/1992 |
| WO | WO 1994/002602 A1 | 2/1994 |
| WO | WO 1996/033735 A1 | 10/1996 |
| WO | WO 2005/007699 | 1/2005 |
| WO | WO 2008/027236 | 3/2008 |
| WO | WO 2009/035577 | 3/2009 |
| WO | WO 2010/017468 A1 | 2/2010 |
| WO | WO 2012/163520 A1 | 12/2012 |
| WO | WO 2014/086496 A1 | 6/2014 |
| WO | WO 2015/095539 | 6/2015 |
| WO | WO-2016/086185 A1 | 6/2016 |
| WO | WO 2016/142426 A1 | 9/2016 |
| WO | WO 2017/042701 A1 | 3/2017 |
| WO | WO 2017/220988 A1 | 12/2017 |
| WO | WO 2018/191497 | 10/2018 |
| WO | WO 2020/006486 A1 | 1/2020 |
| WO | WO 2020/094834 A1 | 5/2020 |
| WO | WO 2020/223392 A2 | 11/2020 |
| WO | WO 2020/264318 A1 | 12/2020 |
| WO | WO 2021/001653 A1 | 1/2021 |
| WO | WO 2021/116182 | 6/2021 |
| WO | WO 2022/157773 A2 | 7/2022 |
| WO | WO 2023/164288 A2 | 8/2023 |

OTHER PUBLICATIONS

Benatuil et al. "An improved yeast transformation method for the generation of very large human antibody libraries" Protein engineering, design & selection: PEDS. Apr. 2010;23(4):155-9.

Chao et al. "Isolating and engineering human antibodies using yeast surface display" Nature protocols. 2006;1(2):755-68.

Chaudhary et al. "A rapid method of cloning functional variable-region antibody genes in Escherichia coli as single-chain immunotoxins" Proceedings of the National Academy of Sciences of the United States of America. Feb. 1990;87(3):1066-70.

Chothia et al. "Canonical structures for the hypervariable regions of immunoglobulins" Journal of molecular biology. Aug. 20, 1987;196(4):901-17.

Corren et al. "The effect of tezepelumab on exacerbations in patients with severe, uncontrolled asthma according to baseline serum IL-5 and IL-13 levels: results from the phase 2b Pathway study" In B101. New Biological Treatments for Asthma May 2020 (pp. A4254-A4254). American Thoracic Society. Abstract.

Davis et al. "SEEDbodies: fusion proteins based on strand-exchange engineered domain (SEED) CH3 heterodimers in an Fc analogue platform for asymmetric binders or immunofusions and bispecific antibodies" Protein engineering, design & selection: PEDS. Apr. 2010;23(4):195-202.

Duperret et al. "Synthetic DNA-encoded monoclonal antibody delivery of anti-CTLA-4 antibodies induces tumor shrinkage in vivo" Cancer research. Nov. 11, 2018;78(22):6363.

Fellouse et al. "High-throughput generation of synthetic antibodies from highly functional minimalist phage-displayed libraries" Journal of molecular biology. Nov. 2, 2007;373(4):924-40.

Fischer et al. "Exploiting light chains for the scalable generation and platform purification of native human bispecific IgG" Nature Communications. 2015, 6.6113.

Francis et al. "A novel xenograft model to study the role of TSLP-induced CRLF2 signals in normal and malignant human B lymphopoiesis" Haematologica. Apr. 2016;101(4):417.

Graham et al. "Characteristics of a human cell line transformed by DNA from human adenovirus type 5" The Journal of general virology. Jul. 1977;36(1):59-74.

Guss et al. "Structure of the IgG-binding regions of streptococcal protein G" The EMBO journal. Jul. 1986;5(7):1567-75.

Hanania et al. "Lebrikizumab in moderate-to-severe asthma: pooled data from two randomised placebo-controlled studies" Thorax. Aug. 2015;70(8):748.

Hudson et al. "Engineered antibodies" Nature medicine. Jan. 2003;9(1):129-34.

International Search Report for PCT Application No. PCT/IL2022/050572 dated Nov. 14, 2022.

Kienast et al. "Ang-2-VEGF-A CrossMab, a novel bispecific human IgG1 antibody blocking VEGF-A and Ang-2 functions simultaneously, mediates potent antitumor, antiangiogenic, and antimetastatic efficacy" Clinical cancer research: an official journal of the American Association for Cancer Research. Dec. 15, 2013;19(24):6730-40.

Klimka et al. "Human anti-CD30 recombinant antibodies by guided phage antibody selection using cell panning" British journal of cancer. Jul. 2000;83(2):252-60.

Labrijn et al. "Bispecific antibodies: a mechanistic review of the pipeline" Nature reviews. Drug discovery. Aug. 2019;18(8):585-608.

Laplanche et al. "Phosphorothioate-modified oligodeoxyribonucleotides. III. NMR and UV spectroscopic studies of the Rp-Rp, Sp-Sp, and Rp-Sp duplexes, [d (GGSAATTCC)] 2, derived from diastereomeric O-ethyl phosphorothioates" Nucleic acids research. Nov. 25, 1986;14(22):9081-93.

Lefranc et al. "IMGT®, the international ImMunoGeneTics information system® 25 years on" Nucleic Acids Research. Jan. 1, 2015,43(Database issue):D413.

Lefranc et al. "IMGT unique numbering for immunoglobulin and T cell receptor variable domains and Ig superfamily V-like domains" Developmental and comparative immunology. Jan. 2003;27(1):55-77.

Murphy et al. "Genetic construction, expression, and melanoma-selective cytotoxicity of a diphtheria toxin-related alpha-melanocyte-stimulating hormone fusion protein" Proceedings of the National Academy of Sciences of the United States of America. Nov. 1986;83(21):8258.

Nakajima et al. "Anti-TSLP antibodies: Targeting a master regulator of type 2 immune responses" Allergology international: official journal of the Japanese Society of Allergology. Apr. 2020;69(2):197-203.

Niedziela-Majka et al. "High-throughput screening of formulations to optimize the thermal stability of a therapeutic monoclonal antibody" Journal of biomolecular screening. Apr. 2015;20(4):552-9.

Nilson et al. "Protein L from Peptostreptococcus magnus binds to the kappa light chain variable domain" The Journal of biological chemistry. Feb. 5, 1992;267(4):2234-9.

Nimrod et al. "Computational Design of Epitope-Specific Functional Antibodies" Cell reports. Nov. 20, 2018;25(8):2121-31.

Nygaard et al. "TSLP, IL-31, IL-33 and sST2 are new biomarkers in endophenotypic profiling of adult and childhood atopic dermatitis" Journal of the European Academy of Dermatology and Venereology: JEADV. Nov. 2016;30(11):1930-8.

(56) References Cited

OTHER PUBLICATIONS

Ofran et al. "Automated identification of complementarity determining regions (CDRs) reveals peculiar characteristics of CDRs and B cell epitopes" Journal of immunology (Baltimore, Md.: 1950). Nov. 1, 2008,181(9):6230-5.

Rader et al. "A phage display approach for rapid antibody humanization: Designed combinatorial V gene libraries" Proceedings of the National Academy of Sciences of the United States of America. Jul. 7, 1998;95(15):8910.

Ridgway et al. "'Knobs-into-holes' engineering of antibody CH3 domains for heavy chain heterodimerization" Protein engineering. Jul. 1996;9(7):617-21.

Salam et al. "Structure-based approach to the prediction of disulfide bonds in proteins" Protein engineering, design & selection: PEDS. Oct. 2014;27(10):365-74.

Simpson et al. "Tezepelumab, an anti-thymic stromal lymphopoietin monoclonal antibody, in the treatment of moderate to severe atopic dermatitis: A randomized phase 2a clinical trial" Journal of the American Academy of Dermatology. Apr. 2019;80(4):1013-21.

Soumelis et al. "Human epithelial cells trigger dendritic cell mediated allergic inflammation by producing TSLP" Nature immunology. Jul. 2002;3(7):673-80.

Stein et al. "Physicochemical properties of phosphorothioate oligodeoxynucleotides" Nucleic acids research. Apr. 25, 1988;16(8):3209-21.

Tabasinezhad et al. "Trends in therapeutic antibody affinity maturation: From in-vitro towards next-generation sequencing approaches" Immunology letters. Aug. 2019;212:106-13.

Thom et al. "Probing a protein-protein interaction by in vitro evolution" Proceedings of the National Academy of Sciences of the United States of America. May 5, 2006;103(20):7619.

Urlaub et al. "Isolation of Chinese hamster cell mutants deficient in dihydrofolate reductase activity" Proceedings of the National Academy of Sciences of the United States of America. Jul. 1980;77(7):4216.

Vannella et al. "Combinatorial targeting of TSLP, IL-25, and IL-33 in type 2 cytokine-driven inflammation and fibrosis" Science translational medicine. May 4, 2016;8(337):337ra65.

Venkataramani et al. "Design and characterization of Zweimab and Doppelmab, high affinity dual antagonistic anti-TSLP/IL 13 bispecific antibodies" Biochemical and biophysical research communications. Sep. 26, 2018;504(1):19-24.

Wollenberg et al. "Tralokinumab for moderate-to-severe atopic dermatitis: results from two 52-week, randomized, double-blind, multicentre, placebo-controlled phase III trials (ECZTRA 1 and ECZTRA 2)" The British Journal of Dermatology. Mar. 2021;184(3):437.

Wollenberg et al. "Treatment of atopic dermatitis with tralokinumab, an anti-IL-13 mAb" The Journal of allergy and clinical immunology. Jan. 2019;143(1):135-41.

Wu et al. "An Analysis of the Sequences of the Variable Regions of Bence Jones Proteins and Myeloma Light Chains and Their Implications for Antibody Complementarity" The Journal of Experimental Medicine. Aug. 8, 1970;132(2):211.

Zhu et al. "Antibody structure determination using a combination of homology modeling, energy-based refinement, and loop prediction" Proteins. Aug. 2014;82(8):1646-55.

Eger, et al., "The emergence of new biologics for severe asthma", Current Opinion in Pharmacology, vol. 46, Jun. 1, 2019, pp. 108-115.

Matera, et al., "TSLP Inhibitors for Asthma: Current Status and Future Prospects", Drugs, vol. 8, No. 5, Apr. 1, 2020, pp. 449-458.

Miyata, et al., "Thymic stromal lymphopoietin is a critical mediator of IL-13-driven allergic inflammation", European Journal of Immunology, vol. 39, No. 11, Aug. 5, 2009, pp. 3078-3083.

Bostrom, et al., "High Affinity Antigen Recognition of the Dual Specific Variants of Herceptin is Entropy-Driven in Spite of Structural Plasticity", PLoS One, Apr. 2011, vol. 6, Issue 4, pp. 1-12.

Bostrom, et al., "Variants of the Antibody Herceptin That Interact with HER2 and VEGF at the Antigen Binding Site", Science, Mar. 20, 2009, vol. 323(5921): 1610-1614.

Eigenbrot, et al., "Two-in-One antibodies with dual action Fabs", Current Opinion in Chemical Biology 2013, vol. 17(3): 400-405.

Lee, et al., "A Two-in-One antibody engineered from a humanized interleukin 4 antibody through mutation in heavy chain complementarity determining regions", mAbs, Mar. 11, 2014, vol. 6, Issue 3, pp. 622-627.

Parren, et al., "Two-in-One Designer Antibodies", Science, Mar. 20, 2009, vol. 323 (5921): 1567-1568.

Schaefer, et al., "A Two-in-One Antibody against HER3 and EGFR Has Superior Inhibitory Activity Compared with Monospecific Antibodies", Cancer Cell Oct. 18, 2011, 20(4): 472-486.

Venkataramani, et al., "Design and characterization of Zweimab and Doppelmab, high affinity dual antagonistic anti-TSLP/IL13 bispecific antibodies" Biochemical and Biophysical Research Communications, 2018,504(1): 19-24.

Allakhverdi et al. "Thymic stromal lymphopoietin as a mediator of crosstalk between bronchial smooth muscles and mast cells" Journal of Allergy and Clinical Immunology. Apr. 1, 2009;123(4):958-60.

Allakhverdi et al. "Thymic stromal lymphopoietin is released by human epithelial cells in response to microbes, trauma, or inflammation and potently activates mast cells" The Journal of experimental medicine. Feb. 19, 2007;204(2):253-8.

American Thoracic Society; European Respiratory Society. "ATS / ERS recommendations for standardized procedures for the online and offline measurement of exhaled lower respiratory nitric oxide and nasal nitric oxide, 2005" Am J Respir Crit Care Med. 2005;171(8):912-30.

Antonicelli et al. "Asthma severity and medical resource utilisation" The European Respiratory Journal. May 1, 2004;23(5):723-9.

Barnes et al. "Risk of severe life threatening asthma" Thorax. Nov. 1996;51(11):1073.

Bateman et al. "Can guideline-defined asthma control be achieved? The Gaining Optimal Asthma Control study" American journal of respiratory and critical care medicine. Oct. 15, 2004;170(8):836-44.

Bates et al. "Animal models of asthma" American Journal of Physiology—Lung Cellular and Molecular Physiology. Sep. 2009;297(3):L401-10.

Beckmann et al. "DutaFabs are engineered therapeutic Fab fragments that can bind two targets simultaneously" Nature communications. Jan. 29, 2021;12(1):708.

Bel EH. "Moving upstream—Anti-TSLP in persistent uncontrolled asthma" New England Journal of Medicine. Sep. 7, 2017;377(10):989-91.

Bel et al. "Oral glucocorticoid-sparing effect of mepolizumab in eosinophilic asthma" New England journal of medicine. Sep. 25, 2014;371(13): 1189-97.

Bleck et al. "Diesel exhaust particle-exposed human bronchial epithelial cells induce dendritic cell maturation and polarization via thymic stromal lymphopoietin" Journal of clinical immunology. Mar. 2008;28:147-56.

Bleecker et al. "Efficacy and safety of benralizumab for patients with severe asthma uncontrolled with high-dosage inhaled corticosteroids and long-acting β2-agonists (SIROCCO): a randomised, multicentre, placebo-controlled phase 3 trial" The Lancet. Oct. 29, 2016;388(10056):2115-27.

Brightling et al. "Efficacy and safety of tralokinumab in patients with severe uncontrolled asthma: a randomised, double-blind, placebo-controlled, phase 2b trial" The Lancet Respiratory Medicine. Sep. 1, 2015;3(9):692-701.

Brightling et al. "Targeting TNF-α: a novel therapeutic approach for asthma" Journal of Allergy and Clinical Immunology. Jan. 1, 2008;121(1):5-10.

Calven et al. "Viral stimuli trigger exaggerated thymic stromal lymphopoietin expression by chronic obstructive pulmonary disease epithelium: role of endosomal TLR3 and cytosolic RIG-I-like helicases" Journal of innate immunity. Jun. 20, 2011;4(1):86-99.

Castro et al. "Reslizumab for inadequately controlled asthma with elevated blood eosinophil counts: results from two multicentre, parallel, double-blind, randomised, placebo-controlled, phase 3 trials" The Lancet Respiratory Medicine. May 1, 2015;3(5):355-66.

Chen et al. "Neutralization of TSLP inhibits airway remodeling in a murine model of allergic asthma induced by chronic exposure to house dust mite" Plos One (2013): e51268.

(56)        References Cited

OTHER PUBLICATIONS

Chung et al. "International ERS/ATS guidelines on definition, evaluation and treatment of severe asthma" European respiratory journal. Feb. 1, 2014;43(2):343-73.

Corren et al. "Lebrikizumab treatment in adults with asthma" New England Journal of Medicine. Sep. 22, 2011;365(12):1088-98.

Corren et al. "Tezepelumab demonstrates clinically meaningful improvements in asthma control (ACQ-6) in patients with uncontrolled asthma: results from a phase 2b clinical trial" Journal of Allergy and Clinical Immunology. Feb. 1, 2018;141(2):AB80.

Corren et al. "Tezepelumab in adults with uncontrolled asthma" New England Journal of Medicine. Sep. 7, 2017;377(10):936-46.

Cukic et al. "Asthma and chronic obstructive pulmonary disease (COPD)—differences and similarities" Mater Sociomed. 2012;24(2):100-5.

Diamant et al. "Inhaled allergen bronchoprovocation tests" Journal of allergy and clinical immunology. Nov. 1, 2013;132(5):1045-55.

Dweik et al. "American Thoracic Society Committee on Interpretation of Exhaled Nitric Oxide Levels (FENO) for Clinical Applications. An official ATS clinical practice guideline: interpretation of exhaled nitric oxide levels (FENO) for clinical applications" American journal of respiratory and critical care medicine. Sep. 1, 2011;184(5):602-15.

"Early Data Demonstrate Anti-TSLP Therapy Reduces Early and Late Asthmatic Responses and Several Key Inflammatory Markers" 2014. https://www.amgen.com/newsroom/press-releases/2014/05/the-new-england-journal-of-medicine-publishes-positive-proof-of-concept-data-for-new-asthma-treatment.

Fajt et al. "Asthma phenotypes and the use of biologic medications in asthma and allergic disease: the next steps toward personalized care" Journal of Allergy and Clinical Immunology. Feb. 1, 2015;135(2):299-310.

Fitzgerald et al. "Benralizumab, an anti-interleukin-5 receptor α monoclonal antibody, as add-on treatment for patients with severe, uncontrolled, eosinophilic asthma (CALIMA): a randomised, double-blind, placebo-controlled phase 3 trial" The Lancet. Oct. 29, 2016;388(10056):2128-41.

Froidure et al. "Asthma phenotypes and IgE responses" European Respiratory Journal. Dec. 31, 2015;47(1):304-19.

Gauvreau et al. "Effects of an anti-TSLP antibody on allergen-induced asthmatic responses" New England Journal of Medicine. May 29, 2014;370(22):2102-10.

Gavala et al. "Virus/allergen interactions in asthma" Current allergy and asthma reports. Jun. 2013;13:298-307.

Gilliet et al. "Human dendritic cells activated by TSLP and CD40L induce proallergic cytotoxic T cells" The Journal of experimental medicine. Apr. 21, 2003;197(8):1059-63.

"Global strategy for asthma management and prevention" GINA Report. Aug. 2014. https://ginasthma.org/reports/.

Hanania et al. "Exploring the effects of omalizumab in allergic asthma: an analysis of biomarkers in the EXTRA study" American journal of respiratory and critical care medicine. Apr. 15, 2013;187(8):804-11.

Jakobovits et al. "Analysis of homozygous mutant chimeric mice: deletion of the immunoglobulin heavy-chain joining region blocks B-cell development and antibody production" Proceedings of the National Academy of Sciences. Mar. 15, 1993;90(6):2551-5.

Jakobovits et al. "Germ-line transmission and expression of a human-derived yeast artificial chromosome" Nature. Mar. 18, 1993;362(6417):255-8.

Jia et al. "Periostin is a systemic biomarker of eosinophilic airway inflammation in asthmatic patients" Journal of Allergy and Clinical Immunology. Sep. 1, 2012;130(3):647-54.

Johansson et al. "Revised nomenclature for allergy for global use: Report of the Nomenclature Review Committee of the World Allergy Organization, Oct. 2003" Journal of allergy and clinical immunology. May 1, 2004;113(5):832-6.

Jones et al. "Replacing the complementarity-determining regions in a human antibody with those from a mouse" Nature. May 29, 1986;321(6069):522-5.

Juniper et al. "Determining a minimal important change in a disease-specific quality of life questionnaire" Journal of clinical epidemiology. Jan. 1, 1994;47(1):81-7.

Juniper et al. "Development and validation of a questionnaire to measure asthma control". European respiratory journal. Oct. 1, 1999;14(4):902-7.

Juniper et al. "Identifying 'well-controlled' and 'not well-controlled' asthma using the Asthma Control Questionnaire" Respiratory medicine. Apr. 1, 2006;100(4):616-21.

Juniper et al. "Measurement properties and interpretation of three shortened versions of the asthma control questionnaire" Respiratory medicine. May 1, 2005;99(5):553-8.

Juniper et al. "Validation of a standardized version of the Asthma Quality of Life Questionnaire" Chest. May 1, 1999;115(5):1265-70.

Keene et al. "Analysis of exacerbation rates in asthma and chronic obstructive pulmonary disease: example from the TRISTAN study" Pharmaceutical Statistics: The Journal of Applied Statistics in the Pharmaceutical Industry. Apr. 2007;6(2):89-97.

Kemp et al. World Allergy Organization ad hoc Committee on Epinephrine in Anaphylaxis. "Epinephrine: the drug of choice for anaphylaxis—a statement of the World Allergy Organization" World Allergy Organization Journal. Jan. 1, 2008;1:S18-26.

Kim et al. "TSLP elicits IL-33-independent innate lymphoid cell responses to promote skin inflammation" Science translational medicine. Jan. 1, 2013;5(170):170ra16.

Lane et al. "An international observational prospective study to determine the Cost of Asthma exacerbations (COAX)" Respiratory Medicine. 2006;100:434-50.

Lee et al. "Thymic stromal lymphopoietin is induced by respiratory syncytial virus-infected airway epithelial cells and promotes a type 2 response to infection" The Journal of allergy and clinical immunology. Nov. 2012;130(5):1187.

Legrand et al. "Biologic Therapies Targeting Eosinophils: Current Status and Future Prospects" The journal of allergy and clinical immunology. In practice. Mar. 2015;3(2):167.

Li et al. "Periostin: its role in asthma and its potential as a diagnostic or therapeutic target" Respiratory Research. May 17, 2015;16:57.

May et al. Preclinical development of CAT-354, an IL-13 neutralizing antibody, for the treatment of severe uncontrolled asthma. British Journal of Pharmacology. May 2012;166(1):177.

Medimmune LL. "A phase 2 randomized, double-blind, placebo-controlled study to evaluate the efficacy and safety of MEDI 9929 in adult subjects with inadequately controlled, severe asthma" 2013; Internet access at: o https://www.google.com/url?sa=i&url=https%3A%2F%2Ffilehosting.pharmacm.com.%2FDownloadService.ashx%3Fclient%3DCTR_MED_7111%26studyid%3D1887%26filename%3DCD-RI-MEDI9929-1146_Protocol_Synopsis_Redacted_06.23.17.pdf&psig=AOvVaw0Cgz4e_J0LMYduJylvSJMx&ust=1734100258608000&source=images&cd=vfe&opi=89978449&ved=0CAQQn5wMahcKEwi4v-SAuaKKAxUAAAAAHQAAAAAQBA.

Miller et al. "General considerations for lung function testing" European Respiratory Journal. 2005;26(1):153-61.

Mishra et al. "From bedside to bench to clinic trials: identifying new treatments for severe asthma" Disease Models & Mechanisms. Jul. 2013;6(4):877.

Moore et al. "Identification of Asthma Phenotypes Using Cluster Analysis in the Severe Asthma Research Program" American Journal of Respiratory and Critical Care Medicine. Feb. 2, 2010;181(4):315.

Morrison et al. "Chimeric human antibody molecules: mouse antigen-binding domains with human constant region domains" Proceedings of the National Academy of Sciences. Nov. 1984;81(21):6851-5.

Nagata et al. "Differential role of thymic stromal lymphopoietin in the induction of airway hyperreactivity and Th2 immune response in antigen-induced asthma with respect to natural killer T cell function" International archives of allergy and immunology. Nov. 1, 2007;144(4):305-14.

Nakamura et al. "Cigarette smoke extract induces thymic stromal lymphopoietin expression, leading to TH2-type immune responses and airway inflammation" Journal of Allergy and Clinical Immunology. Dec. 1, 2008;122(6):1208-14.

(56)         References Cited

OTHER PUBLICATIONS

Ortega et al. "Mepolizumab treatment in patients with severe eosinophilic asthma" New England journal of medicine. Sep. 25, 2014;371(13): 1198-207.

Park et al. "Cloning of the Murine Thymic Stromal Lymphopoietin (TSLP) Receptor: Formation of a Functional Heteromeric Complex Requires Interleukin 7 Receptor" The Journal of Experimental Medicine. Sep. 4, 2000;192(5):659-69.

Partridge MR. "Examining the unmet need in adults with severe asthma" European Respiratory Review. Sep. 1, 2007;16(104):67-72.

Paul et al. "How are TH2-type immune responses initiated and amplified?" Nature reviews. Immunology. Apr. 2010;10(4):225-35.

Pavord et al. "Mepolizumab for severe eosinophilic asthma (DREAM): a multicentre, double-blind, placebo-controlled trial" The Lancet. Aug. 18, 2012;380(9842):651-9.

Pavord et al. "The impact of poor asthma control among asthma patients treated with inhaled corticosteroids plus long-acting 2-agonists in the United Kingdom: a cross-sectional analysis" NPJ primary care respiratory medicine. Mar. 9, 2017;27(1):17.

Rabe et al. "Worldwide severity and control of asthma in children and adults : the global asthma insights and reality surveys" Journal of Allergy and Clinical Immunology. Jul. 1, 2004;114(1):40-7.

Reche et al. "Human thymic stromal lymphopoietin preferentially stimulates myeloid cells" J Immunol 167: 336-343.

Riechmann et al. "Reshaping human antibodies for therapy" Nature. Mar. 24, 1988;332(6162):323-7.

Sampson et al. "Second symposium on the definition and management of anaphylaxis: Summary report—Second National Institute of Allergy and Infectious Disease/Food Allergy and Anaphylaxis Network symposium" J Allergy Clin Immunol. 2006;117:391-7.

Sera-Batlles et al. "Costs of asthma according to the degree of severity" Eur Respir J. 1998;12:1322-6.

Shikotra et al. "Increased expression of immunoreactive thymic stromal lymphopoietin in patients with severe asthma" Journal of allergy and clinical immunology. Jan. 1, 2012;129(1):104-11.

Sorkness et al. "Lung function in adults with stable but severe asthma: air trapping and incomplete reversal of obstruction with bronchodilation" J Appl Physiol. 2008;104:394-403.

Swedin et al. "Patient stratification and the unmet need in asthma" Pharmacology & therapeutics. Jan. 1, 2017;169:13-34.

Tabrizi et al. "Biodistribution Mechanisms of Therapeutic Monoclonal Antibodies in Health and Disease" The AAPS Journal. Mar. 2010;12(1):33.

Tanaka et al. "Human TSLP and TLR3 ligands promote differentiation of Th17 cells with a central memory phenotype under Th2-polarizing conditions" Clinical and Experimental Allergy. Jan. 2009;39(1):89.

To et al. "Global asthma prevalence in adults: findings from the cross-sectional world health survey" BMC public health. Dec. 2012;12:1-8.

Tough et al. "Features that distinguish those who die from asthma from community controls with asthma" Journal of Asthma. Jan. 1, 1998;35(8):657-65.

Trotta et al. "A human anti-IL-2 antibody that potentiates regulatory T cells by a structure-based mechanism" Nature medicine. Jul. 2018;24(7):1005-14.

Turner et al. "Risk factors for near-fatal asthma. A case-control study in hospitalized patients with asthma" American journal of respiratory and critical care medicine. Jun. 1998;157(6 Pt 1):1804-9.

Valladares et al. "Designing two-in-one antibodies" Immunotherapy. Sep. 1, 2009;1(5):749-51.

Verhoeyen et al. "Reshaping human antibodies: grafting an antilysozyme activity" Science. Mar. 25, 1988;239(4847):1534-6.

Wenzel et al. "Dupilumab efficacy and safety in adults with uncontrolled persistent asthma despite use of medium-to-high-dose inhaled corticosteroids plus a long-acting $\beta2$ agonist: a randomised double-blind placebo-controlled pivotal phase 2b dose-ranging trial" The Lancet. Jul. 2, 2016;388(10039):31-44.

Wenzel SE. "Emergence of Biomolecular Pathways to Define Novel Asthma Phenotypes. Type-2 Immunity and Beyond" American Journal of Respiratory Cell and Molecular Biology. Jul. 2016;55(1):1.

Woodruff et al. "T-helper Type 2-driven Inflammation Defines Major Subphenotypes of Asthma" American Journal of Respiratory and Critical Care Medicine. Sep. 9, 2009;180(5):388.

Ying et al. "Expression and Cellular Provenance of Thymic Stromal Lymphopoietin and Chemokines in Patients with Severe Asthma and Chronic Obstructive Pulmonary Disease" Immunology. 2008;181:2790-8.

Ying et al. "Thymic stromal lymphopoietin expression is increased in asthmatic airways and correlates with expression of Th2-attracting chemokines and disease severity" The Journal of Immunology. Jun. 15, 2005;174(12):8183-90.

Ziegler et al. "The biology of thymic stromal lymphopoietin (TSLP)" Adv Pharmacol. 2013;66:129-55.

Ragnoli et al., "Dupilumab and tezepelumab in severe refractory asthma: new opportunities": Therapeutic Advances in Chronic Disease, 2022, vol. 13, pp. 1-19 (published online May 25, 2022).

* cited by examiner

BDG33.003-rh-IL-13

BDG33.004-rh-IL-13

| Antibodies | HMW % | IgG % | Clone RT on SEC [min] | Calc. pI |
|---|---|---|---|---|
| 38.074 | | 100 | 5.03 | 7.9 |
| 38.075 | 11.36 | 88.65 | 5.1 | 7.5 |
| 38.077 | | 97.43 | 5.29 | 7.2 |
| 38.078 | 6.37 | 89.12 | 5.57 | 7.2 |
| 38.079 | 1.34 | 96.28 | 5.04 | 7.2 |
| 38.080 | 0.67 | 97.4 | 5.16 | 7.5 |
| 38.081 | | 97.54 | 5.149 | 7.9 |
| 38.082 | | 99.35 | 4.906 | 6.9 |
| 38.083 | 0.39 | 92.88 | 4.985 | 6.6 |

- HMW - High Molecular Weight

| | Tezepelumab | 38.074 | 38.075 | 38.077 |
|---|---|---|---|---|
| EC50 | 4.170 | 3.663 | 3.394 | 8.476 |

| | 37.078 | Tezepelumab | 30.079 | 30.080 |
|---|---|---|---|---|
| EC50 | 4.301 | 4.386 | 3.631 | 3.271 |

| | Tezepelumab | 33.081 | 33.082 | 33.083 |
|---|---|---|---|---|
| EC50 | 3.780 | 2.209 | 2.725 | 3.335 |

Figure 15

| Antibodies | Onset #1 for Ratio | Inflection Point #1 for Ratio |
|---|---|---|
| 38.074 | 60.3°C | 62.2°C |
| 38.075 | 61.0°C | 65.5°C |
| 38.075 | 60.7°C | 65.4°C |
| 38.077 | 66.4°C | 70.4°C |
| 38.077 | 66.0°C | 70.3°C |
| 38.078 | 64.4°C | 67.4°C |
| 38.078 | 64.3°C | 67.4°C |
| 38.079 | 61.4°C | 64.2°C |
| 38.079 | 61.7°C | 64.3°C |
| 38.080 | 63.8°C | 66.8°C |
| 38.080 | 63.7°C | 66.8°C |
| 38.081 | 63.4°C | 65.9°C |
| 38.081 | 63.3°C | 65.9°C |
| 38.082 | 65.6°C | 69.3°C |
| 38.082 | 65.4°C | 69.3°C |
| 38.083 | 66.6°C | 70.1°C |
| 38.083 | 66.8°C | 70.2°C |

Figure 16A

| Antibodies | Human IL-13 | | |
|---|---|---|---|
| | ka (1/Ms) | kd (1/s) | KD (M) |
| 33.023 | 1.52E+06 | 0.004574 | 3.01E-09 |
| 38.075 | 1.72E+07 | 5.47E-04 | 3.18E-11 |
| 38.077 | 1.66E+07 | 5.39E-04 | 3.25E-11 |
| 38.078 | 2.37E+06 | 2.03E-04 | 8.57E-11 |
| 38.080 | 1.59E+07 | 0.00114 | 7.16E-11 |
| 38.081 | 1.71E+07 | 8.72E-04 | 5.09E-11 |
| 38.082 | 8.41E+06 | 9.56E-04 | 1.14E-10 |
| 38.083 | 7.09E+06 | 4.01E-04 | 5.65E-11 |

Figure 16B

| Antibodies | Human TSLP | | |
|---|---|---|---|
| | ka (1/Ms) | kd (1/s) | KD (M) |
| 33.023 | 1.09E+06 | 6.84E-05 | 6.25E-11 |
| 38.075 | 1.98E+06 | 2.38E-05 | 1.20E-11 |
| 38.077 | 8.69E+05 | 1.44E-04 | 1.66E-10 |
| 38.078 | 1.28E+06 | 2.95E-07 | 2.31E-13 |
| 38.080 | 2.50E+06 | 1.81E-05 | 7.22E-12 |
| 38.081 | 1.81E+06 | 1.25E-04 | 6.92E-11 |
| 38.082 | 2.56E+06 | 1.58E-04 | 6.16E-11 |
| 38.083 | 2.45E+06 | 2.41E-04 | 9.83E-11 |

Figure 16C

| | SPR hIL-13 | | | SPR hTSLP | | |
|---|---|---|---|---|---|---|
| | Ka | Kd | KD | Ka | Kd | KD |
| BDG38.076 | 6.53E+06 | 2.31E-04 | 3.54E-11 | 2.00E+07 | 3.22E-05 | 1.61E-12 |
| BDG38.090 | 6.57E+06 | 1.30E-04 | 1.98E-11 | 9.57E+06 | 1.13E-04 | 1.18E-11 |
| BDG38.091 | 3.57E+06 | 2.16E-04 | 6.04E-11 | 1.40E+06 | 8.67E-05 | 6.21E-11 |
| BDG38.092 | 5.65E+06 | 5.37E-05 | 9.50E-12 | 6.28E+06 | 2.46E-05 | 3.92E-12 |
| BDG38.094 | 6.77E+06 | 9.36E-05 | 1.38E-11 | 1.44E+07 | 1.82E-07 | 1.27E-14 |
| BDG38.096 | 6.19E+06 | 1.55E-04 | 2.51E-11 | 6.33E+06 | 1.33E-04 | 2.10E-11 |
| BDG38.098 | 5.80E+06 | 1.38E-04 | 2.39E-11 | 8.60E+06 | 2.37E-04 | 2.75E-11 |
| BDG38.106 | 5.93E+06 | 2.05E-04 | 3.46E-11 | 4.90E+06 | 2.57E-04 | 5.25E-11 |
| BDG38.107 | 7.36E+06 | 2.02E-05 | 2.74E-12 | 5.41E+05 | 8.16E-05 | 1.51E-10 |
| BDG38.110 | 5.75E+06 | 4.27E-04 | 7.42E-11 | 2.31E+06 | 2.98E-04 | 1.29E-10 |
| BDG38.112 | 2.32E+06 | 4.02E-05 | 1.73E-11 | 1.06E+06 | 2.74E-04 | 2.58E-10 |
| BDG38.115 | 3.63E+06 | 4.55E-04 | 1.25E-10 | 6.34E+05 | 5.32E-04 | 8.40E-10 |
| BDG38.116 | 5.51E+06 | 1.16E-04 | 2.10E-11 | 5.44E+06 | 3.95E-05 | 7.27E-12 |
| BDG38.117 | 6.94E+06 | 1.03E-04 | 1.49E-11 | 7.07E+06 | 2.70E-05 | 3.82E-12 |

Figure 16D

| | SPR hIL-13 | | | SPR hTSLP | | |
|---|---|---|---|---|---|---|
| | Ka | Kd | KD | Ka | Kd | KD |
| BDG38.118 | 4.27E+06 | 6.70E-05 | 1.57E-11 | 4.46E+05 | 4.30E-04 | 9.64E-10 |
| BDG38.125 | 6.12E+06 | 4.76E-05 | 7.78E-12 | 4.76E+06 | 1.21E-04 | 2.55E-11 |
| BDG38.126 | 4.92E+06 | 1.43E-04 | 2.91E-11 | 3.87E+06 | 6.72E-05 | 1.74E-11 |
| BDG38.127 | 5.91E+06 | 5.01E-05 | 8.47E-12 | 4.31E+05 | 4.27E-04 | 9.91E-10 |
| BDG38.128 | 5.49E+06 | 1.76E-04 | 3.21E-11 | 4.25E+06 | 3.86E-05 | 9.07E-12 |
| BDG38.129 | 6.96E+06 | 1.16E-04 | 1.67E-11 | 4.03E+06 | 9.12E-05 | 2.26E-11 |
| BDG38.131 | 2.00E+06 | 3.56E-04 | 1.79E-10 | 3.82E+06 | 2.85E-07 | 7.46E-14 |
| BDG38.132 | 1.03E+07 | 1.84E-04 | 1.78E-11 | 1.04E+07 | 3.55E-05 | 3.41E-12 |
| BDG38.134 | 3.07E+06 | 0.001557 | 5.07E-10 | 4.86E+06 | 4.17E-05 | 8.58E-12 |
| BDG38.137 | 4.34E+06 | 2.52E-04 | 5.80E-11 | 4.36E+06 | 7.01E-05 | 1.61E-11 |
| BDG38.138 | 1.19E+07 | 1.60E-04 | 1.34E-11 | 1.50E+07 | 4.28E-05 | 2.85E-12 |
| BDG38.139 | 7.71E+06 | 2.12E-04 | 2.75E-11 | 7.78E+06 | 2.54E-05 | 3.27E-12 |
| BDG38.140_ | 4.88E+06 | 1.68E-04 | 3.44E-11 | 3.38E+06 | 2.79E-05 | 8.27E-12 |

Figure 16E

| Antibodies | CynoIL-13 | | |
|---|---|---|---|
| | ka (1/Ms) | kd (1/s) | KD (M) |
| 38.075 | 3.45E+07 | 0.01564 | 4.54E-10 |
| 38.076 | 8.16E+06 | 0.006706 | 8.22E-10 |
| 38.081 | 8.00E+06 | 0.006749 | 8.44E-10 |
| 38.090 | 2.49E+07 | 0.001872 | 7.52E-11 |
| 38.092 | 3.01E+07 | 0.001288 | 4.28E-11 |
| 38.094 | 2.22E+07 | 0.005999 | 2.70E-10 |
| 38.096 | 5.47E+07 | 0.002419 | 4.42E-11 |
| 38.116 | 3.14E+07 | 8.47E-04 | 2.70E-11 |
| 38.117 | 3.94E+07 | 0.001443 | 3.67E-11 |
| 38.125 | 3.46E+07 | 0.001345 | 3.89E-11 |
| 38.128 | 3.02E+07 | 0.003086 | 1.02E-10 |
| 38.129 | 6.05E+07 | 0.001397 | 2.31E-11 |
| 38.132 | 3.58E+07 | 0.002014 | 5.63E-11 |
| 38.138 | 7.70E+06 | 0.006533 | 8.49E-10 |
| 38.139 | 2.27E+07 | 0.0077 | 3.39E-10 |
| 38.140 | 5.54E+07 | 0.001315 | 2.38E-11 |

Figure 16F

| Antibodies | CynoTSLP | | |
|---|---|---|---|
| | ka (1/Ms) | kd (1/s) | KD (M) |
| 38.075 | 2.72E+06 | 7.59E-06 | 2.79E-12 |
| 38.076 | 7.80E+06 | 3.99E-08 | 5.12E-15 |
| 38.081 | 8.96E+06 | 4.36E-05 | 4.87E-12 |
| 38.090 | 6.14E+06 | 5.53E-05 | 9.01E-12 |
| 38.092 | 3.84E+06 | 1.72E-05 | 4.48E-12 |
| 38.094 | 1.16E+07 | 3.18E-05 | 2.75E-12 |
| 38.096 | 3.39E+06 | 6.14E-05 | 1.81E-11 |
| 38.116 | 1.43E+07 | 3.86E-04 | 2.71E-11 |
| 38.117 | 5.08E+07 | 4.52E-04 | 8.90E-12 |
| 38.125 | 2.64E+06 | 1.19E-04 | 4.52E-11 |
| 38.128 | 1.55E+06 | 7.62E-08 | 4.92E-14 |
| 38.129 | 3.75E+06 | 5.27E-05 | 1.41E-11 |
| 38.132 | 6.83E+06 | 2.19E-06 | 3.21E-13 |
| 38.138 | 1.37E+07 | 1.85E-05 | 1.35E-12 |
| 38.139 | 6.50E+06 | 1.55E-05 | 2.39E-12 |
| 38.140 | 4.53E+06 | 2.78E-06 | 6.14E-13 |

Cycle: 14 CIL13 3.95 nM

Cycle Fitted: 14 CIL13 3.95 nM

Cycle: 12 CIL13 1.76 nM

Cycle Fitted: 12 CIL13 1.76 nM

Cycle: 10 CIL13 1.17 nM

Cycle Fitted: 10 CIL13 1.17 nM

Cycle: 9 CIL13 0.78 nM

Cycle Fitted: 9 CIL13 0.78 nM

Cycle: 8 CIL13 0.52 nM

Cycle Fitted: 8 CIL13 0.52 nM

Cycle: 6 CIL13 0.23 nM

Cycle Fitted: 6 CIL13 0.23 nM

Cycle: 48 CTSLP 3.95 nM

Cycle Fitted: 48 CTSLP 3.95 nM Cycle: 46 CTSLP 1.76 nM

Cycle Fitted: 46 CTSLP 1.76 nM

Cycle: 44 CTSLP 1.76 nM

Cycle Fitted: 44 CTSLP 1.76 nM

Cycle: 42 CTSLP 1.17 nM

Cycle Fitted: 42 CTSLP 1.17 nM

Cycle: 41 CTSLP 0.35 nM

Cycle Fitted: 41 CTSLP 0.35 nM

| hTSLP | ka (1/Ms) | kd (1/s) | KD (M) |
|---|---|---|---|
| BDG38.079 | 1.48E+07 | 3.27E-05 | 2.21E-12 |

Figure 21A

| | hIL-13 | | | hTSLP | | |
|---|---|---|---|---|---|---|
| | ka (1/Ms) | kd (1/s) | KD (M) | ka (1/Ms) | kd (1/s) | KD (M) |
| BDG38.074 | 8.43E+06 | 2.49E-04 | 2.95E-11 | 1.51E+07 | 5.05E-05 | 3.34E-12 |
| BDG38.079 | 1.22E+07 | 3.85E-04 | 3.17E-11 | 1.48E+07 | 3.27E-05 | 2.21E-12 |

| | cynoIL-13 | | | cynoTSLP | | |
|---|---|---|---|---|---|---|
| | ka (1/Ms) | kd (1/s) | KD (M) | ka (1/Ms) | kd (1/s) | KD (M) |
| BDG38.074 | 8.78E+06 | 0.006436 | 7.33E-10 | 1.11E+07 | 4.60E-05 | 4.16E-12 |
| BDG38.079 | 1.56E+07 | 0.01407 | 9.01E-10 | 1.03E+07 | 4.08E-05 | 3.97E-12 |

SEAP inhibition in HEK-Blue™

| | Tralokinumab | 38.074 | 38.079 |
|---|---|---|---|
| IC50 [nM] | 0.1477 | 0.02407 | 0.02530 |

| | Tezepelumab | 38.074 | 38.079 |
|---|---|---|---|
| IC50 [pM] | 27.72 | 35.36 | 13.44 |

| | Anti-IL-13 benchmark | 38.074 | 38.079 |
|---|---|---|---|
| IC50 | 0.07119 | 0.1578 | 0.07179 |

| | Anti-TSLP benchmark | 38.074 | 38.079 |
|---|---|---|---|
| IC50 [nM] | 1.775 | 2.771 | 1.961 |

| ka (1/Ms) | kd (1/s) | KD (M) |
|---|---|---|
| 3.20E+07 | 2.12E-04 | 6.61E-12 |

A- control, no treatment

B- buffer exchange to NaAc pH 3.5

C- buffer exchange to PBS

| BDG38.145 IC50 (hIL-13) | 0.38nM |
| Tralokinumab IC50 (hIL-13) | 0.91nM |
| Lebrikizumab IC50 (hIL-13) | 0.30nM |

| | |
|---|---|
| BDG38.145 IC50 (hIL-13) | 0.26nM |
| Tralokinumab IC50 (hIL-13) | 0.55nM |
| Lebrikizumab IC50 (hIL-13) | 0.14nM |

| | |
|---|---|
| BDG38.145 IC50 (hTSLP) | 1.2nM |
| Tezepelumab IC50 (hTSLP) | 0.5nM |

Figure 34C

*IL-13 & TSLP stimulation*

ENGINEERED DUAL BINDING ANTIBODIES AND USES THEREOF

CROSS-REFERENCE TO RELATED APPLICATIONS

This application is a continuation-in-part application of PCT International Application No. PCT/IL2022/050572, filed May 29, 2022, which claims the benefit of U.S. Provisional Patent Application Nos. 63/195,021, filed May 30, 2021, and 63/295,905, filed Jan. 2, 2022, and which is a continuation-in-part of PCT International Application No. PCT/IL2022/050087, filed Jan. 20, 2022, which are all hereby incorporated by reference.

SEQUENCE LISTING STATEMENT

The instant application contains a Sequence Listing which has been submitted electronically in XML file format and is hereby incorporated by reference in its entirety. Said XML copy, created on Aug. 16, 2023, is named P-605548-US-_SL.xml and is 597,438 bytes in size.

FIELD OF INTEREST

The disclosure relates in general to dual binding antibodies that bind to IL-13 and TSLP. In one embodiment, the antibodies can be used for treating allergic or respiratory conditions.

BACKGROUND

Interleukin 13 (IL-13) is a 12.3 kDa monomeric protein of the class I cytokines. IL-13 has a 4 alpha helical bundle core topology typical of class I short helical cytokines; it is similar in structure to its closely related cytokine IL-4 sharing low sequence identity but high structural identity. Along with IL-4, IL-13 has been shown to control immunoglobulin class switching to IgE in B cells and is involved in mast cell recruitment. IL-13 is secreted by CD4$^+$ Th2 cells, as well as type 2 innate lymphoid cells ILC2. It has been demonstrated that IL-13 can trigger the production of TGF-$\beta$ and in bronchial epithelial cells induces gene expression of MUC5AC and production of mucin. IL-13 can also enhance contraction in smooth bronchial muscle cells. IL-13 binds the IL-4Ra/IL-13Ra1 heterodimeric complex, and upon binding it triggers a JAK-signal transducer and STATE dependent signaling cascade, which in turn triggers Th2 helper T-cell differentiation, polarization of macrophages to the M2 "alternatively activated" phenotype, epithelial mucus production, smooth muscle contractility and chemokine release.

IL-13 has been shown to be involved in protection against parasites, wherein it was demonstrated that in knockout IL-13 mice model, clearance of *N. brasiliensis* is severely delayed. Also, the expulsion of *Trichuris muris* is abolished completely, in spite of an otherwise intact Th2-type response. Further research demonstrated that IL-13 is a double-edged sword, on the one hand it has a major role in protection against parasites, however IL-13 function in situations of dysregulated immune system is also known.

IL-13 has been implicated in the pathogenesis of human asthma as elevated levels of IL-13 mRNA and protein have been detected in lungs of asthmatic patients, which correlate with severity of the disease. In addition, human IL-13 genetic polymorphisms, which lead to elevated IL-13 levels, have been identified and are associated with asthma and atopy, and elevated IL-13 levels have been detected in the lung of asthma patients.

Although IL-13 and IL-4 share similar receptors and signaling pathway, IL-13 has distinguished role in asthma, which is independent of IL-4. It has been shown in mice models that administration of IL-13 alone is sufficient to induce eosinophil derived inflammation, and mucus cell hyperplasia. Moreover, a specific blockade of IL-13 but not IL-4 is sufficient to reverse airway hyperreactivity and mucus production in mice models. Additionally, polymorphism in the human IL-13 locus is known to be associated with high susceptibility for asthma.

Specific inhibition of IL-13 signaling could therefore have positive therapeutic effect on asthma patients, or patients with other known allergic or respiratory conditions.

Thymic stromal lymphopoietin (TSLP) is a cytokine that signals through a heterodimeric receptor consisting of the IL-7Ra subunit and TSLP-R, a unique component with homology to the common γ-receptor-like chain. TSLP is expressed by epithelial cells in the thymus, lung, skin, intestine, and tonsils, as well as airway smooth muscle cells, lung fibroblasts, and stromal cells. These cells produce TSLP in response to proinflammatory stimuli, and TSLP drives allergic inflammatory responses through its activity on a number of innate immune cells, including dendritic cells. TSLP can also promote proliferation of naive T cells and drive their differentiation into Th2 cells expressing high levels of IL-4, IL-5, and IL-13. High level of TSLP expression has been found in asthmatic lung epithelial cells and chronic atopic dermatitis lesions, suggesting a role for TSLP in allergic inflammation. Recent evidence also implicates TSLP in the differentiation of Th17 cells and Th17-driven inflammatory processes. Chronic allergic (atopic) asthma is often characterized by Th2-type inflammation, while non-allergic asthmatic inflammation is predominately neutrophilic with a mixed Th1 and Th17 cytokine milieu. Antagonists to TSLP would be expected to be useful for treating inflammatory conditions.

Thus, there remains an unmet need for compositions and methods of treatment of diseases and conditions triggered by IL-13 and TSLP activation, for example but not limited to allergic and respiratory conditions, including but not limited to asthma.

SUMMARY

In one embodiment, the present disclosure provides an isolated dual binding antibody comprising three complementarity determining regions (CDRs) on a heavy chain (HCDR1, HCDR2, and HCDR3) and three CDRs on a light chain (LCDR1, LCDR2, and LCDR3), wherein the CDRs have the sequences of SEQ ID NOs: 149-154. In another embodiment, the dual binding antibody comprises a heavy chain variable domain (VH) and a light chain variable domain (VL) having the amino acid sequences of SEQ ID Nos:155 and 156, or SEQ ID Nos:157 and 158.

Disclosed herein, in one aspect is an isolated dual binding antibody, wherein the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 359, D D V, and SEQ ID NO: 361 respectively.

In another embodiment, the HCDR1, HCDR2 and HCDR3 comprise the amino acid sequence of SEQ ID NOs:349, 356 and 351 respectively, and the LCDR1, LCDR2 and LCDR3 comprise the amino acid sequence of SEQ ID NO: 364, D D V, and SEQ ID NO: 371 respectively.

In another embodiment, the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 362, D D V, and SEQ ID NO: 384 respectively.

In another embodiment, the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 364, D D V, and SEQ ID NO: 384 respectively.

In another embodiment, the HCDR1, HCDR2 and HCDR3 comprise the amino acid sequences as shown in Table 8 or Table 4, wherein the LCDR1, LCDR2 and LCDR3 comprise the amino acid sequences as shown in Table 9 or Table 5.

Disclosed herein, in one aspect is an isolated dual binding antibody, said dual binding antibody comprising an antibody antigen-binding domain site comprising a heavy chain variable region (VH) domain and a light chain variable region (VL) domain, wherein said VH domain comprises a set of complementarity-determining regions (CDRs), HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid; or wherein said VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCDR3 is set forth as Q V W D LX5 LX6 S D LX7 V V (SEQ ID NO; 146), wherein LX5, LX6, and LX7 are any amino acid; or a combination of (a) and (b).

In a related aspect, wherein the amino acid sequence of HCDR2 is set forth in SEQ ID NO: 137, wherein HX1 is selected from the group consisting of W and S; wherein the amino acid sequence of HCDR3 is set forth in SEQ ID NO: 138, wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M; wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G.

In a further related aspect of the isolated dual binding antibody, HX1 is W, HX2 is selected from the group consisting of A and S, HX6 is selected from the group consisting of E and M, HX7 is selected from the group consisting of L and W, HX8 is selected from the group consisting of V and T, HX9 is selected from the group consisting of H and A, HX12 is selected from the group I and L, LX1 is L, LX2 is I, LX3 is L, LX4 is selected from the group consisting of S and G, LX5 is S, LX6 is S, and LX7 is selected from the group consisting of H and G.

In yet another related aspect of isolated dual binding antibody, an isolated dual bind antibody comprises CDRs wherein HX1 is W, HX2 is A, HX6 is E, HX7 is L, HX8 is T, HX9 is A, HX12 is I, LX4 is S, and LX7 is G; or HX1 is W, HX2 is A, HX6 is M, HX7 is L, HX8 is V, HX9 is A, HX12 is L, LX4 is S, and LX7 is H; or HX1 is W, HX2 is S, HX6 is E, HX7 is W, HX8 is V, HX9 is H, HX12 is L, LX4 is G, and LX7 is G.

In another related aspect of the isolated dual binding antibody, said VH domain comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); said VL domain comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of the VH domain set forth in (a) and the VL domain set forth in (b); wherein the total number of variant positions in said VH domain, said VL domain, or said combination thereof of said dual binding antibody, is at least 2.

In a further related aspect, said at least one variant amino acid in said VH domain comprises a variant at position 106 of SEQ ID NO: 1 (IMTG position 112). In another further related aspect, the amino acid sequence of said VH domain is selected from the sequences set forth in SEQ ID Nos: 4, 6, 8, 10, 12, 14, 16, 18, 20, 22, 24, 26, 28, 30, 32, 34, 36, 38, 40, 42, 44, 46, 48, 50, 52, and 54. In yet another further related aspect, said at least one amino acid variant in said VL domain comprises a variant amino acid in a CDR region. In still another further related aspect, said variant amino acid in said VL domain comprises a variant at any of positions 26, 27, 31, or 96 of SEQ ID NO: 2, or a combination thereof (IMGT positions: 27, 28, 38, or 115, or a combination thereof). In another further related aspect, there are at least two variants in said VL domain and the second variant comprises a variant amino acid in a framework region. In yet another further related aspect, said variant amino acid in a framework region comprises a variant at position 56 or 77 of SEQ ID NO: 2, or a combination thereof (IMGT positions: 70 or 94, or a combination thereof).

In another related aspect, the amino acid sequence of said VL domain is selected from the sequences set forth in SEQ ID Nos: 3, 5, 7, 9, 11, 13, 15, 17, 19 21, 23, 25, 27, 29, 31, 33, 35, 37, 39, 41, 43, 45, 47, 49, 51, and 53. In still another related aspect, the amino acid sequences of a VH domain-VL domain pair are selected from the pair sequences set forth in SEQ ID Nos: 4 and 3, SEQ ID Nos: 6 and 5, SEQ ID Nos: 8 and 7, SEQ ID Nos: 10 and 9, SEQ ID Nos: 12 and 11, SEQ ID Nos: 14 and 13, SEQ ID Nos: 16 and 15, SEQ ID Nos: 18 and 17, SEQ ID Nos: 20 and 19, SEQ ID Nos: 22 and 21, SEQ ID Nos: 24 and 23, SEQ ID Nos: 26 and 25, SEQ ID Nos: 28 and 27, SEQ ID Nos: 30 and 29, SEQ ID Nos: 32 and 31, SEQ ID Nos: 34 and 33, SEQ ID Nos: 36 and 35, SEQ ID Nos: 38 and 37, SEQ ID Nos: 40 and 39, SEQ ID Nos: 42 and 41, SEQ ID Nos: 44 and 43, SEQ ID Nos: 46 and 45, SEQ ID Nos: 48 and 47, SEQ ID Nos: 50 and 49, SEQ ID Nos: 52 and 51, and SEQ ID Nos: 54 and 53.

In another embodiment, the isolated dual binding antibody disclosed herein comprises a heavy chain variable domain (VH) and a light chain variable domain (VL), wherein the VH and VL comprise the amino acid sequences of SEQ ID Nos:209 and 210.

In another embodiment, the isolated dual binding antibody disclosed herein comprises a heavy chain variable domain (VH) and a light chain variable domain (VL), wherein the VH and VL comprise the amino acid sequences of SEQ ID Nos:219 and 220.

In another embodiment, the isolated dual binding antibody disclosed herein comprises a heavy chain variable domain (VH) and a light chain variable domain (VL), wherein the VH and VL comprise the amino acid sequences of SEQ ID Nos:249 and 250.

In another embodiment, the isolated dual binding antibody disclosed herein comprises a heavy chain variable domain (VH) and a light chain variable domain (VL), wherein the VH and VL comprise the amino acid sequences of SEQ ID Nos:337 and 338.

In another embodiment, the isolated dual binding antibody disclosed herein comprises a heavy chain variable domain (VH) and a light chain variable domain (VL), wherein the VH and VL comprise the amino acid sequences as shown in Table 1 or Table 10.

In another related aspect, the dual binding antibody comprises an IgG, an Fv, an scFv, an Fab, an F(ab')$_2$, a minibody, a diabody, or a triabody. In a further related aspect, the IgG comprises IgG1, IgG2, IgG3, or an IgG4. In still another related aspect, said IgG comprises a mutated IgG which is unable to bind to antibody-dependent cellular cytotoxicity components.

Disclosed herein, in one aspect is a composition comprising the isolated dual binding antibody and a pharmaceutically acceptable carrier.

Disclosed herein, in one aspect is a nucleic acid construct, comprising a nucleic acid sequence encoding a dual binding antibody, said antibody comprising an antibody antigen-binding domain site comprising a heavy chain variable region (VH) domain and a light chain variable region (VL) domain, wherein said VH domain comprises a set of CDRs, HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid; or wherein said VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCDR3 is set forth as Q V W D LX5 LX6 S D LX7 V V (SEQ ID NO; 146), wherein LX5, LX6, and LX7 are any amino acid; or a combination of (a) and (b).

In a related aspect of the nucleic acid, the encoded amino acid sequence of HCDR2 is set forth in SEQ ID NO: 137, wherein HX1 is selected from the group consisting of W and S; wherein the amino acid sequence of HCDR2 is set forth in SEQ ID NO: 138, wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M; wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G.

In a related aspect of the nucleic acid, the encoded amino acid for HX1 is W, HX2 is selected from the group consisting of A and S, HX6 is selected from the group consisting of E and M, HX7 is selected from the group consisting of L and W, HX8 is selected from the group consisting of V and T, HX9 is selected from the group consisting of H and A, HX12 is selected from the group I and L, LX1 is L, LX2 is I, LX3 is L, LX4 is selected from the group consisting of S and G, LX5 is S, LX6 is S, and LX7 is selected from the group consisting of H and G. A further related aspect, wherein the encoded amino acid for HX1 is W, HX2 is A, HX6 is E, HX7 is L, HX8 is T, HX9 is A, HX12 is I, LX4 is S, and LX7 is G; or HX1 is W, HX2 is A, HX6 is M, HX7 is L, HX8 is V, HX9 is A, HX12 is L, LX4 is S, and LX7 is H; or HX1 is W, HX2 is S, HX6 is E, HX7 is W, HX8 is V, HX9 is H, HX12 is L, LX4 is G, and LX7 is G.

In a related aspect of the nucleic acid construct, said VH domain comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); said VL domain comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of VH domain set forth in (a) and the VL domain set forth in (b); wherein the total number of variant positions in the encoded VH domain, the encoded VL domain, or a combination thereof, is at least 2. In a further related aspect, said sequence comprises two nucleic acid sequences, one encoding the variant dual binding antibody VH domain, and one encoding the variant dual binding antibody VL domain. In a further related aspect, the nucleic acid sequence encoding said VH domain is selected from the sequences set forth in SEQ ID Nos: 57, 59, 61, 63, 65, 67, 69, 71, 73, 75, 77, 79, 81, 83, 85, 87, 89, 91, 93, 95, 97, 99, 101, 105, and 107. In another further related aspect, the nucleic acid sequence encoding said VL domain is selected from the sequences set forth in SEQ ID Nos: 58, 60, 62, 64, 66, 68, 70, 72, 74, 76, 78, 80, 82, 84, 86, 88, 90, 92, 94, 96, 98, 100, 102, 104, 106, and 108. In yet another further related aspect, the nucleic acid sequences encoding the dual antibody VH domain-VL domain pair are selected from the paired sequences set forth in SEQ ID Nos: 57 and 58, SEQ ID Nos: 59 an 60, SEQ ID Nos: 61 and 62, SEQ ID Nos: 63 and 64, SEQ ID Nos: 65 and 66, SEQ ID Nos: 67 and 68, SEQ ID Nos: 69 and 70, SEQ ID Nos: 71 and 72, SEQ ID Nos: 73 and 74, SEQ ID Nos: 75 and 76, SEQ ID Nos: 77 and 78, SEQ ID Nos: 79 and 80, SEQ ID Nos: 81 and 82, SEQ ID Nos: 83 and 84, SEQ ID Nos: 85 and 86, SEQ ID Nos: 87 and 88, SEQ ID Nos: 89 and 90, SEQ ID Nos: 91 and 92, SEQ ID Nos: 93 and 94, SEQ ID Nos: 95 and 96, SEQ ID Nos: 97 and 98, SEQ ID Nos: 99 and 100, SEQ ID Nos: 101 and 102, SEQ ID Nos: 103 and 104, SEQ ID Nos: 105 and 106, and SEQ ID Nos: 107 and 108.

In a related aspect of the nucleic acid construct, said antibody comprises an IgG, a Fv, a scFv, a Fab, a F(ab')$_2$, a minibody, a diabody, or a triabody. In a further related aspect, said IgG comprises a mutated IgG which is unable to bind to antibody-dependent cellular cytotoxicity components.

In another related aspect, the nucleic acid construct further comprises a regulatory sequence operably linked to said nucleic acid sequence.

Disclosed herein, in one aspect is an expression vector comprising the nucleic acid construct encoding a dual binding antibody, said antibody comprising an antibody antigen-binding domain site comprising a heavy chain variable region (VH) domain and a light chain variable region (VL) domain.

Disclosed herein, in one aspect is a host cell comprising the expression vector comprising a nucleic acid construct encoding a dual binding antibody, said antibody comprising an antibody antigen-binding domain site comprising a heavy chain variable region (VH) domain and a light chain variable region (VL) domain Disclosed herein, in one aspect is a composition comprising a nucleic acid construct encoding a dual binding antibody, said antibody comprising an antibody antigen-binding domain site comprising a heavy chain variable region (VH) domain and a light chain variable region (VL) domain and a pharmaceutically acceptable carrier.

Disclosed herein, in one aspect is a method of producing a dual binding antibody comprising an antibody antigen-binding domain site comprising a heavy chain variable region (VH) domain and a light chain variable region (VL) domain, said method comprising culturing the host cell comprising the expression vector comprising a nucleic acid construct encoding a dual binding antibody, said antibody comprising an antibody antigen-binding domain site comprising a heavy chain variable region (VH) domain and a light chain variable region (VL) domain; expressing said nucleic acid construct from said vector; isolating said dual binding antibody.

Disclosed herein, in one aspect is a library of immunoglobulins or fragments thereof comprising an antibody antigen-binding domain site comprising a heavy chain variable region (VH) domain and a light chain variable region (VL) domain, wherein said VH domain comprises a set of CDRs, HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid; or wherein said VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCDR3 is set forth as Q V W D LX5 LX6 S D LX7 V V (SEQ ID NO; 146), wherein LX5, LX6, and LX7 are any amino acid.

In a related aspect of the library, the amino acid sequence of HCDR2 is set forth in SEQ ID NO: 137, wherein HX1 is selected from the group consisting of W and S; wherein the amino acid sequence of HCDR2 is set forth in SEQ ID NO: 138, wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M; wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G.

In a further related aspect of the library, HX1 is W, HX2 is selected from the group consisting of A and S, HX6 is selected from the group consisting of E and M, HX7 is selected from the group consisting of L and W, HX8 is selected from the group consisting of V and T, HX9 is selected from the group consisting of H and A, HX12 is selected from the group I and L, LX1 is L, LX2 is I, LX3 is L, LX4 is selected from the group consisting of S and G, LX5 is S, LX6 is S, and LX7 is selected from the group consisting of H and G.

In yet another further related aspect of the library, HX1 is W, HX2 is A, HX6 is E, HX7 is L, HX8 is T, HX9 is A, HX12 is I, LX4 is S, and LX7 is G; HX1 is W, HX2 is A, HX6 is M, HX7 is L, HX8 is V, HX9 is A, HX12 is L, LX4 is S, and LX7 is H; or HX1 is W, HX2 is S, HX6 is E, HX7 is W, HX8 is V, HX9 is H, HX12 is L, LX4 is G, and LX7 is G. In still another further related aspect of the library, said VH domain comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); said VL domain comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of the VH domain set forth in (a) and the VL domain set forth in (b); wherein the total number of variant positions in the VH domain, the VL domain, or a combination thereof is at least 2.

In another related aspect of the library, the immunoglobulin comprises an IgG, an Fv, an scFv, an Fab, an F(ab')$_2$, a minibody, a diabody, or a triabody.

In another related aspect of the library, the IgG comprises a mutated IgG which is unable to bind to antibody-dependent cellular cytotoxicity components.

Disclosed herein in one aspect, is a method of treating a subject suffering from a disease or condition comprising an allergic or respiratory condition, an inflammatory and/or autoimmune condition of the skin or gastrointestinal organs; scleroderma; or tumors or cancers including Hodgkin's lymphoma, said method comprising administering to said subject an isolated dual binding antibody disclosed herein.

In one related aspect of the method of treating a subject, said allergic or respiratory condition is asthma; allergic asthma; nonallergic asthma; severe asthma; mild asthma; chronic obstructive pulmonary disease (COPD); a condition involving airway inflammation including eosinophilia, fibrosis and excess mucus production, cystic fibrosis, allergic lung disease, airway hyperresponsiveness, goblet cell metaplasia, mucus hypersecretion, airway remodeling, pulmonary fibrosis; atopic disorders including atopic dermatitis, urticaria, eczema, allergic enterogastritis, and allergic rhinitis; or a combination thereof; or said inflammatory and/or autoimmune conditions including inflammatory bowel diseases (IBD) and liver conditions including cirrhosis or fibrosis; or a combination thereof.

BRIEF DESCRIPTION OF THE DRAWINGS

The subject matter of engineered dual binding antibodies is particularly pointed out and distinctly claimed in the concluding portion of the specification. These dual binding antibodies, however, both as to their generation and method of use, together with objects, features, and advantages thereof, may best be understood by reference to the following detailed description when read with the accompanying drawings in which:

FIG. 2A shows binding of isolated yeast-surface display anti-IL13 clones to 10 nM rh-IL-13. FIG. 2B shows binding of isolated yeast-surface display anti-TSLP clones to 10 nM rhTSLP. Data was normalized to the yeast surface expression levels of each clone, and to an anti-hIL-13 and anti-hTSLP mean fluorescence intensity (MFI) binding signal of positive control yeast clones.

FIG. 4A: DSF of BDG33.023 T-onset of 64.2° C. and first transition point at 67.7° C. FIG. 4B: DSF of BDG33.025 T-onset of 56.4° C., first transition point at 60.9° C. and second transition point at 67.4° C.

FIG. 7A: Indicated antibodies (anti-TSLP-control; anti-IL-13 control; BDG33.023; BDG33.025) were pre-incubated with increasing levels of hIL-13 and added to a plate that was pre-coated with hIL-13. BDG33.023 and BDG33.025 binding to plate-bound hIL-13 was inhibited as soluble hIL-13 concentration increased. FIG. 7B: Indicated antibodies (anti-TSLP-control; anti-IL-13 control; BDG33.023; BDG33.025) were pre-incubated with increasing levels of hTSLP and added to a plate that was pre-coated with hTSLP. BDG33.023 and BDG33.025 binding to plate-bound hTSLP was inhibited as soluble hTSLP concentration increased. FIG. 7C: Antibodies (anti-TSLP-control; anti-IL-13 control; BDG33.023; BDG33.025) were pre-incubated with increasing levels of hTSLP and added to a plate pre-coated with hIL-13, BDG33.023 binding to IL-13 was inhibited as soluble hTSLP concentration increased. FIG. 7D: Indicated antibodies (anti-TSLP-control; anti-IL-13 control; BDG33.023; BDG33.025) were pre-incubated with increasing levels of hIL-13 and added to a plate pre-coated with hTSLP. BDG33.023 binding to plate-bound hTSLP was inhibited as soluble hIL-13 concentration increased. Anti-TSLP and anti-IL-13 control antibodies only showed binding with their respective ligands, and only competed with their respective ligands.

FIGS. 12A-12C present TSLP signaling pathway inhibition data TSLP dependent pSTAT5 signaling activation pathway, and inhibition of the activation by BDG 33.023 in human leukemia MUTZ5 cells. FIG. 12A shows flow-cytometry analysis of MUTZ 5 CD127 (IL-7a) receptor and TSLP-R receptor expression, as follows. Unstained cells (panel a), cells stained for CD127+ wherein approximately 36% of the total cell population was labeled (panel b), cells stained for TSLP-R+, wherein approximately 96% of the total cell population was labeled (panel c), and cells stained for both TSLP-R+ and CD127+ wherein approximately 41% of total cell population was labeled (panel d) (FIG. 12A). FIG. 12B shows MUTZ5 pSTAT5 activation. EC50 of hTSLP phosphor-STATS (pSTAT5) activation in MUTZ5 cells. Percent (%) positive cells represents pSTAT5 positive cells as a percentage of the parent population. FIG. 12C shows inhibition of MUTZ5 pSTAT5 activation. IC50 of BDG33.023 inhibition of TSLP dependent pSTAT5 activation in MUTZ5 cells. TSLP was pre-incubated for 30 min with 0.48 pM to 500 pM of BDG33.023 and added to MUTZ5 cells. Positive cells are representing pSTAT5 positive population as a percentage of the parent population (FIG. 12C).

FIG. 13 shows retention time and calculated pI for some of the dual binding antibodies disclosed herein. IgG marker retention time was 4.77 min.

FIG. 15 shows results of nanoscale differential scanning fluorimetry (nanoDSF) analysis of some of the dual binding antibodies disclosed herein. Tm threshold for lambda chain was >65° C. and T-onset >60° C.

FIGS. 16A-16F show the results of SPR (Surface Plasmon Resonance) analysis for some of the dual binding antibodies disclosed herein for human IL-13 and TSLP.

FIG. 18A shows binding affinities of antibody BDG38.074 to IL-13. The results show antibody BDG38.074 binds human IL-13 with double digit picomolar affinities. FIG. 18B shows binding affinities of antibody BDG38.074 to human TSLP. The results show antibody BDG38.074 binds human TSLP with double digit picomolar affinities. FIG. 18C shows binding affinities of antibody BDG38.074 to cyno IL-13. FIG. 18D shows binding affinities of antibody BDG38.074 to cyno TSLP.

FIG. 19B is a graph of the 1st derivative of the measurement. DSF values are summarized in FIG. 15.

FIG. 20A shows binding affinities of antibody BDG38.079 to human IL-13. The results show antibody BDG38.079 binds human IL-13 with double digit picomolar affinities. FIG. 20B shows binding affinities of antibody BDG38.079 to human TSLP. The results show antibody BDG38.079 binds human TSLP with single digit picomolar affinities. FIG. 20C shows binding affinities of antibody BDG38.079 to cyno IL-13. FIG. 20D shows binding affinities of antibody BDG38.079 to cyno TSLP.

FIGS. 21A and 21B show SPR (Surface Plasmon Resonance) analysis of antibodies BDG38.074 and BDG38.079 for human or cyno IL-13 or TSLP.

FIG. 22 shows antibodies BDG38.074 and BDG38.079 inhibit IL-13 function in HEK reporter cell line with double digit picomolar affinity. hIL-13 pSTAT6 signaling inhibition data. The results are based on stimulation of HEK-Blue cell's IL-13 activation pathway by recombinant rh-IL-13 and inhibition of this stimulation by indicated IgGs. rh-IL-13 (0.4 nM) was incubated with indicated antibodies at an antibody concentration range of 0 nM-100 nM After the incubation the hIL-13/IgG mixture was added to the cells, secreted embryonic alkaline phosphatase (SEAP) activity was quantified with QUANTI-Blue 24 h post incubation. Data shown is the mean of triplicate experiments, and error bars represent standard deviation. Antibodies assayed were Tralokinumab, BDG38.074 and BDG38.079 respectively.

FIG. 24A shows antibodies BDG38.074 and BDG38.079 exhibit similar inhibition of CD23 expression to the anti-IL-13 benchmark (Tralokinumab). $IC_{50}$ of antibody inhibition of IL-13 was determined by measuring CD23 expression level in monocytes. At the end of 48 hours incubation of the cells with different concentrations of antibodies, monocytes were detached from the bottom of the wells and stained with CD3 (Bio Legend, CAT: 300450), CD14 (Bio Legend, CAT: 301814), CD19 (Bio Legend, CAT: 302212) and CD23 (Bio Legend, CAT: 338506) antibodies. CD23 percentage of CD14+ population was measured using CytoFLEX flow cytometer (Beckman Coulter). FIG. 24B shows antibodies BDG38.074 and BDG38.079 inhibit Thymus and activation-regulated chemokine (TARC) expression similarity to anti-TSLP benchmark (Tezepelumab). $IC_{50}$ of antibody inhibition of hTSLP was determined by TARC inhibition. TARC levels were determined using TARC DUOSET ELISA kit DY364 (R&D systems) according to kit instructions. ELISA plates were read at 450 nm. Values were analyzed using standard sample curve.

FIG. 26A shows binding affinities of antibody BDG38.094 to human IL-13. FIG. 26B shows binding affinities of antibody BDG38.094 to human TSLP. FIG. 26C shows binding affinities of antibody BDG38.094 to cyno IL-13. FIG. 26B shows binding affinities of antibody BDG38.094 to cyno TSLP.

FIG. 27B is the 1st derivative of the measurement. DSF values are summarized in Table 11.

FIG. 28A shows binding affinities of antibody BDG38.138 to human IL-13. FIG. 28B shows binding affinities of antibody BDG38.138 to human TSLP. FIG. 28C shows binding affinities of antibody BDG38.138 to cyno IL-13. FIG. 28D shows binding affinities of antibody BDG38.138 to cyno TSLP.

(FIG. 29A) Binding of 38.138 (IgG1 LALAPG) to hIL-13. (FIG. 29B) Binding of 38.145 (IgG1 LALA) to hIL-13. (FIG. 29C) Binding of 38.138 (IgG1 LALAPG) to hTSLP. (FIG. 29D) Binding of 38.145 (IgG1 LALA) to hTSLP.

(FIG. 30A) SEC analysis of 38.138 and 38.145 after incubation under viral inactivation conditions (sodium acetate (NaAc)) compared to non-treated antibodies (ctrl) and Abs that went through the same viral inactivation process but in PBS (PBS). (FIG. 30B) SDS-PAGE analysis in reduced and a non-reduced conditions of 38.138 and 38.145 after incubation in viral inactivation conditions (NaAc) compared to non-treated antibodies (ctrl) and Ab went the same viral inactivation process but in PBS (PBS pH7.4). (FIG. 30C) HIC analysis of 38.138 and 38.145 after incubation in viral inactivation conditions (NaAc) compared to non-treated antibodies (ctrl) and Abs went the same viral inactivation process but in PBS (PBS). Veltuzumab, Tralokinumab (hIgG1), Tezepelumab (hIgG1) and Dupilumab were analyzed as controls.

(FIG. 31A) ELISA EC50 binding to human TSLP of 38.138 (hIgG1 LALAPG) after incubation in viral inactivation conditions (NaAc) compared to non-treated antibodies (PBS control (ctrl)). Both treated and control antibodies went through the same viral inactivation process but control incubations were in PBS (PBS). Anti-TSLP antibody 33.001 was used as positive control. (FIG. 31B) ELISA EC50 binding to human TSLP of 38.145 (hIgG1 LALA) after incubation in viral inactivation conditions (NaAc) compared to non-treated antibodies (PBS; ctrl). Control antibodies went through the same viral inactivation process but incubations were in PBS (PBS). Anti-TSLP antibody 33.001 was used as a positive control. (FIG. 31C) ELISA EC50 binding to human IL-13 of 38.138 (hIgG1 LALAPG) after incubation in viral inactivation conditions (NaAc) compared to non-treated antibodies (PBS; ctrl). Control antibodies went through the same viral inactivation process but incubation was in PBS (PBS). Anti IL-13 antibody 33.002 was used as a positive control. (FIG. 31D) ELISA EC50 binding to human IL-13 of 38.145 (hIgG1 LALA) after incubation in viral inactivation conditions (NaAc) compared to non-treated antibodies (PBS; ctrl). Control antibodies went through the same viral inactivation process, but incubations were in PBS (PBS). Anti IL-13 antibody 33.002 was used as a positive control.

FIG. 32A: CD23 expression levels in monocytes, presented as percentage of the parental population (CD14+ cells). The cells were labeled with fluorescent antibodies to CD14 and CD23. The values shown in the graph are the % of CD23+ cells, out of the CD14+ cells (and not out of the total population). FIG. 32B: TARC levels secreted to the supernatant measured by ELISA.

FIG. 33A: Gating strategy for CD23+ monocyte population. FIG. 33B: CD23 expression-gating strategy. CD23 expression levels in monocytes, present as percentage of the parental population (CD14+ cells). Tezepelumab, an anti-TSLP antibody, has no effect on CD23 expression. 38.145, lebrikizumab, and tralokinumab lower CD23 expression in a dose-dependent manner 38.145 demonstrates better inhibition properties than tralokinumab and similar inhibition to lebrikizumab.

Figure 34C:
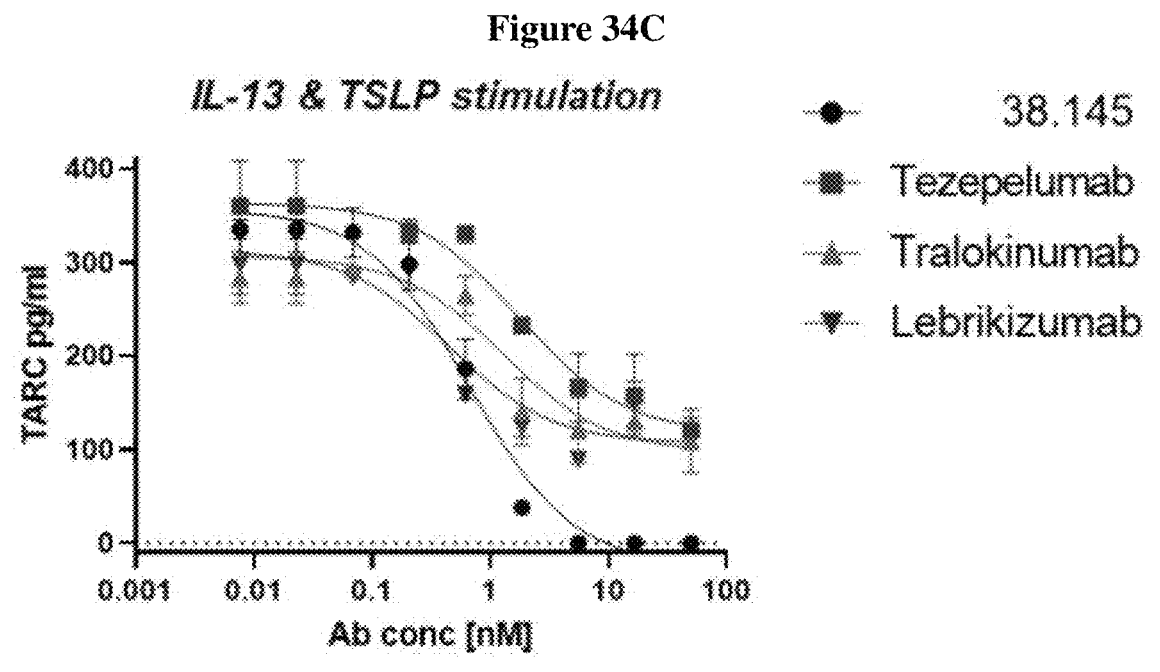

FIGS. 34A-34C show TARC levels in hPBMCs supernatant is inhibited by BDG38.145. hPBMCs were stimulated for 48 h with either IL-13, TSLP, or with the combination of both cytokines. Immediately following stimulation, cells were treated with tested antibodies: 38.145 compared to Tezepelumab (anti-TSLP), Tralokinumab (anti-IL-13), and Lebrikizumab (anti-IL-13). TARC levels in the supernatant were measured by ELISA. (FIG. 34A) Cells stimulated with 0.7 nM IL-13. TARC levels are inhibited fully by 38.145 and anti-IL-13 Abs. (FIG. 34B) Cells stimulated with 70 pM TSLP. TARC levels are inhibited fully by 38.145 and anti-TSLP Ab. (FIG. 34C) Cells were stimulated with 0.7 nM IL-13 and 70 pM TSLP. In the presence of both cytokines, 38.145 demonstrates full inhibition of TARC while benchmark antibodies show partial inhibitions.

DETAILED DESCRIPTION

Figure 1A:
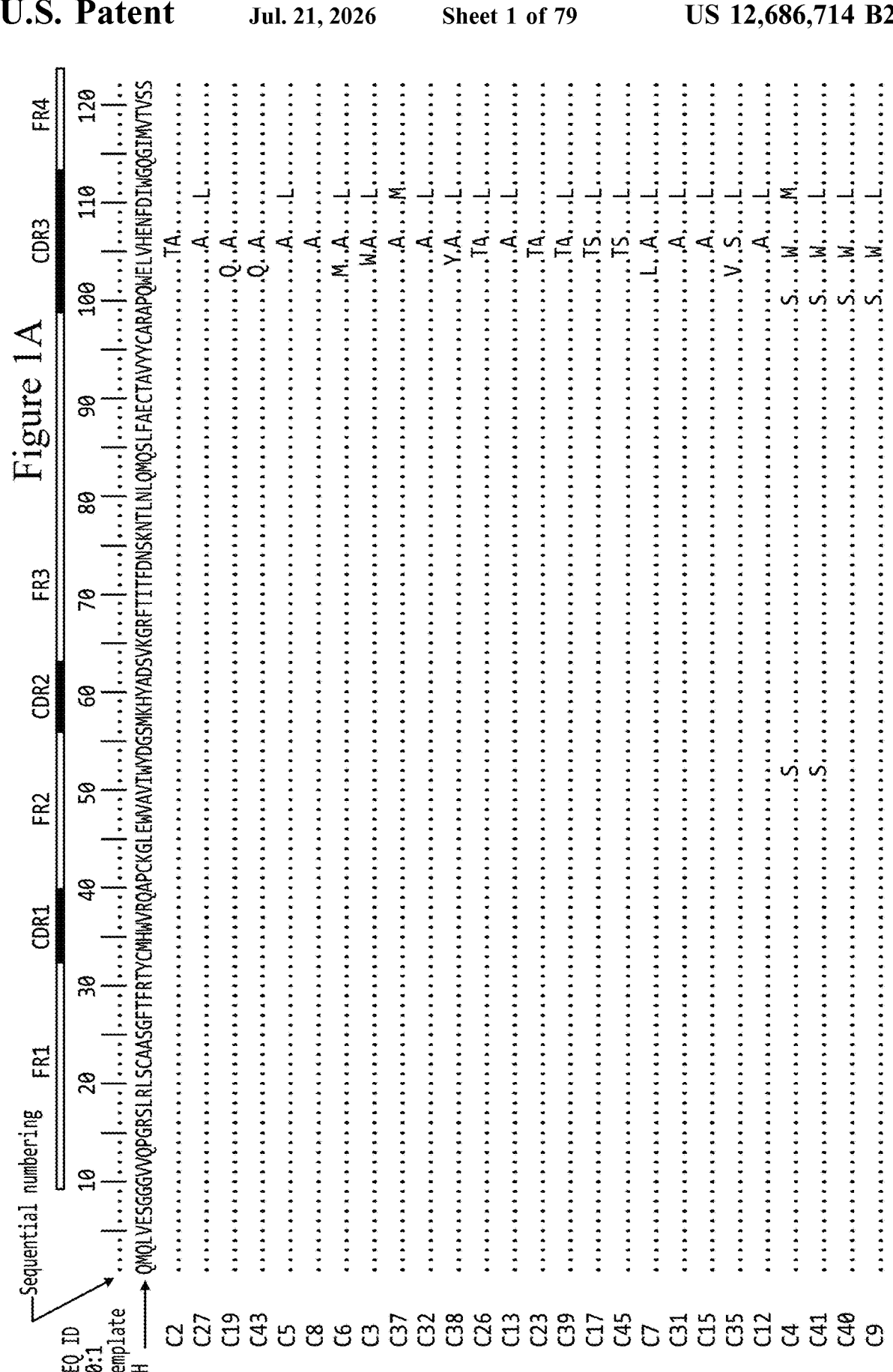
FIGS. 1A and 1B present the template antibody heavy chain (SEQ ID NO: 1) (FIG. 1A) and light chain (SEQ ID NO: 2) amino acid sequences (FIG. 1B), respectively, indicating the framework (FR) and complementarity-determining regions (CDR) regions. For the Heavy (H) chain, the different regions are labeled FR1, CDR1, FR2, CDR2, FR3, CDR3, and FR4, and in some embodiments are referred to as HFR1, HCDR1, HFR2, HCDR2, HFR3, HCDR3, and HFR4. For the Light (L) chain, the different regions are labeled FR1, CDR1, FR2, CDR2, FR3, CDR3, and FR4, and in some embodiments are referred to as LFR1, LCDR1, LFR2, LCDR2, LFR3, LCDR3, and LFR4. Below the template amino acid sequences, the variant amino acids of the engineered dual binding clones are displayed and aligned within the CDR and FR regions.

In the following detailed description, numerous specific details are set forth in order to provide a thorough understanding of the engineered dual binding antibodies disclosed herein, including a description of their heavy chain and light chain variable regions. However, it will be understood by those skilled in the art that preparation and use dual binding antibodies may in certain cases, be practiced without these specific details. In other instances, well-known methods, procedures, and components have not been described in detail so as not to obscure the disclosure presented herein.

Antigen binding sequences are conventionally located within the heavy chain and light chain variable region sequences of an antibody. These heavy and light chain variable regions may, in certain instances, be manipulated to create new binding sites, for example to create antibodies or fragments thereof, that bind to a different antigen or an epitope of a different antigen thereof. In some embodiments, as described herein, manipulating the sequence of a heavy chain variable region or the sequence of a light chain variable region, or both, creates a new binding site for an epitope while maintaining antibody functionality. In one embodiment, twenty-one specific sites within the heavy and light chain variable regions are identified, wherein the presence of variant amino acids at these sites, in certain embodiments, creates an engineered dual binding antibody or fragment thereof. In some embodiments, the 21 potential variant sites provide a unique platform from which to engineer dual binding antibodies or fragments thereof.

Disclosed herein are engineered dual binding antibodies or fragments thereof, wherein either a heavy chain variable region, or a light chain variable region, or both, have been mutated to include variant amino acids. In some embodiments, these engineered dual binding antibodies may be identified and selected from a library created to include variant amino acid residues at particular sites within a variable heavy chain or variable light region, or both. In some embodiments, these engineered dual binding antibodies may be produced by specifically mutating target amino acid sites within a variable heavy chain or variable light region, or both. In some embodiments, these engineered dual binding antibodies may be used in a therapeutic method for treating a subject suffering from an allergic or respiratory condition.

Engineered Dual Binding Antibodies

As used herein, the term "dual binding antibodies" refers to antibodies that have two binding specificities. In certain embodiments, the dual binding antibodies disclosed herein bind to IL-13 and TSLP.

In some embodiments, the present disclosure provides an isolated dual binding antibody comprising three complementarity determining regions (CDRs) on a heavy chain (HCDR1, HCDR2, and HCDR3) and three CDRs on a light chain (LCDR1, LCDR2, and LCDR3) (see e.g. Tables 8 and 9). In some embodiments, the CDRs have the sequences of SEQ ID NOs:149-154. In some embodiments, the dual binding antibody comprises a heavy chain variable domain (VH) and a light chain variable domain (VL) having the amino acid sequences of SEQ ID Nos:155 and 156, or SEQ ID Nos:157 and 158.

In one embodiment, the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 359, D D V, and SEQ ID NO: 361, respectively.

In another embodiment, the HCDR1, HCDR2 and HCDR3 comprise the amino acid sequence of SEQ ID NOs:349, 356 and 351 respectively, and the LCDR1, LCDR2 and LCDR3 comprise the amino acid sequence of SEQ ID NO: 364, D D V, and SEQ ID NO: 371, respectively.

In another embodiment, the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 362, D D V, and SEQ ID NO: 384, respectively.

In another embodiment, the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 364, D D V, and SEQ ID NO: 384, respectively.

In another embodiment, the HCDR1, HCDR2 and HCDR3 comprise the amino acid sequences as shown in Table 8 or Table 4, wherein the LCDR1, LCDR2 and LCDR3 comprise the amino acid sequences as shown in Table 9 or Table 5, respectively.

In some embodiments, disclosed herein is an isolated dual binding antibody comprising three complementarity determining regions (CDRs) on a heavy chain (HCDR1, HCDR2, and HCDR3) and three CDRs on a light chain (LCDR1, LCDR2, and LCDR3), wherein (i) the HCDR1 comprises the amino acid sequence of SEQ ID NO: 349 or 355, or the amino acid sequence of SEQ ID NO: 149 or SEQ ID NO: 136;

(ii) the HCDR2 comprises the amino acid sequence of one of SEQ ID NOs:350, 352, 354 and 356, or the amino acid sequence of SEQ ID NO: 150 or the sequence set forth as: I HX1 Y D G S N K (SEQ ID NO: 142), wherein HX1 is any amino acid;

(iii) the HCDR3 comprises the amino acid sequence of one of SEQ ID NOs:351, 353, 357, and 358, or the amino acid sequence of SEQ ID NO: 151 or the sequence set forth as: A R HX2 HX3 HX4 HX5 HX6 HX7 HX8 HX9 HX10 HX11 F D HX12 (SEQ ID NO: 143), wherein HX2, HX3, HX4, HX5, HX6, HX7, HX8, HX9, HX10, HX11, and HX12 are any amino acid;

(iv) the LCDR1 comprises the amino acid sequence of one of SEQ ID NOs:359, 362, 364, 366, 369, and 375, or the amino acid sequence of SEQ ID NO: 152 or the sequence set forth as LX1, LX2, G S K LX3 V (SEQ ID NO: 144), wherein LX1, LX2, and LX3 are any amino acid;

(v) the LCDR2 comprises the amino acid sequence of D D V or D D S, or the sequence set forth as D D LX4, wherein LX4 is any amino acid; and (vi) the LCDR3 comprises the amino acid sequence of one of SEQ ID NOs:361, 363, 365, 368, 370-374, 376-407, or the amino acid sequence of SEQ ID NO: 154 or the sequence set forth as Q V W D LX5 LX6 S D LX7 V V (SEQ ID NO; 146), wherein LX5, LX6, and LX7 are any amino acid.

In some embodiments, disclosed herein is an isolated anti-IL-13, anti-TSLP dual binding antibody comprising a heavy chain variable region (VH) and a light chain variable region (VL), wherein said VH comprises heavy chain complementarity determining regions (HCDRs) HCDR1, HCDR2, and HCDR3, said VL comprises light chain complementarity determining regions (LCDRs) LCDR1, LCDR2, and LCDR3, wherein (a) the HCDR1 comprises the amino acid sequence set forth in any one of SEQ ID NOs: 349, 355, 149 and 136;

(b) the HCDR2 comprises the amino acid sequence set forth in any one of SEQ ID NOs: 350, 352, 354, 356, and 150 or the sequence set forth as: I HX1 Y D G S N K (SEQ ID NO: 142), wherein HX1 is any amino acid;

(c) the HCDR3 comprises the amino acid sequence set forth in any one of SEQ ID NOs: 351, 353, 357, 358, and 151 or the sequence set forth as: A R HX2 HX3 HX4 HX5 HX6 HX7 HX8 HX9 HX10 HX11 F D HX12 (SEQ ID NO: 143), wherein HX2, HX3, HX4, HX5, HX6, HX7, HX8, HX9, HX10, HX11, and HX12 are any amino acid;

(d) the LCDR1 comprises the amino acid sequence of one of SEQ ID NOs: 364, 359, 362, 366, 369, 375, and 152 or the sequence set forth as LX1, LX2, G S K LX3 V (SEQ ID NO: 144), wherein LX1, LX2, and LX3 are any amino acid;

(e) the LCDR2 comprises the amino acid sequence of DDV or DDS, or the sequence set forth as D D LX4, wherein LX4 is any amino acid; and (f) the LCDR3 comprises the amino acid sequence set forth in any one of SEQ ID NOs: 384, 361, 363, 365, 368, 370-374, 376-383, 385-407, and 154 or the sequence set forth as Q V W D LX5 LX6 S D LX7 V V (SEQ ID NO; 146), wherein LX5, LX6, and LX7 are any amino acid.

In some embodiments, disclosed herein is an isolated dual binding antibody wherein the HCDR1, HCDR2 and HCDR3 comprise the amino acid sequences of SEQ ID NOs:349, 350 and 351 respectively, and the LCDR1, LCDR2 and LCDR3 comprise the amino acid sequences of SEQ ID NO: 359, D D V, and SEQ ID NO: 361, respectively; or the HCDR1, HCDR2 and HCDR3 comprise the amino acid sequences of SEQ ID NOs:349, 356 and 351 respectively, and the LCDR1, LCDR2 and LCDR3 comprise the amino acid sequences of SEQ ID NO: 364, D D V, and SEQ ID NO: 371, respectively; or the HCDR1, HCDR2 and HCDR3 comprise the amino acid sequences of SEQ ID NOs:349, 350 and 351 respectively, and the LCDR1, LCDR2 and LCDR3 comprise the amino acid sequences of SEQ ID NO: 362, D D V, and SEQ ID NO: 384 respectively; or the HCDR1, HCDR2 and HCDR3 comprise the amino acid sequences of SEQ ID NOs:349, 350 and 351 respectively, and the LCDR1, LCDR2 and LCDR3 comprise the amino acid sequences of SEQ ID NO: 364, D D V, and SEQ ID NO: 384, respectively.

In some embodiments, disclosed herein is an isolated dual binding antibody, wherein the HCDR1, HCDR2 and HCDR3 comprise the amino acid sequences as shown in Table 8 or Table 4, wherein the LCDR1, LCDR2 and LCDR3 comprise the amino acid sequences as shown in Table 9 or Table 5, respectively.

In some embodiments, disclosed herein is an isolated dual binding antibody, wherein HX1 is W or S; HX2 is A or S; HX3 is P; HX4 is Q; HX5 is W; HX6 is E, Q, M, L, or V; HX7 is L, W, or Y; HX8 is V or T; HX9 is H, A, or S; HX10 is E; HX11 is A; HX12 is I, L, or M; wherein LX1 is N, L, or I; LX2 is L or I; LX3 is S or L; LX4 is S or G; LX5 is S or T; LX6 is S or G; LX7 is H or G.

In some embodiments, disclosed herein is an isolated dual binding antibody, wherein HX1 is W, HX2 is A or S, HX6 is E or M, HX7 is L or W, HX8 is V or T, HX9 is H or A, HX12 is I or L, LX1 is L, LX2 is I, LX3 is L, LX4 is S or G, LX5 is S, LX6 is S, LX7 is H or G.

In some embodiments, disclosed herein is an isolated dual binding antibody, wherein (a) HX1 is W, HX2 is A, HX6 is E, HX7 is L, HX8 is T, HX9 is A, HX12 is I, LX4 is S, and LX7 is G; or (b) HX1 is W, HX2 is A, HX6 is M, HX7 is L, HX8 is V, HX9 is A, HX12 is L, LX4 is S, and LX7 is H; or (c) HX1 is W, HX2 is S, HX6 is E, HX7 is W, HX8 is V, HX9 is H, HX12 is L, LX4 is G, and LX7 is G.

In some embodiments, disclosed herein is an isolated dual binding antibody comprising a heavy chain variable region comprising the amino acid sequence set forth in SEQ ID NO: 1 with at least one amino acid variant at any position or a light chain variable region comprising the amino acid sequence set forth in SEQ ID NO: 2 with at least one amino acid variant at any of position, or a combination thereof, wherein the total number of variant positions in said heavy chain variable region, said light chain variable region, or said combination thereof, is at least 2. In some embodiments, disclosed herein is an isolated dual binding antibody comprising a heavy chain variable region comprising the amino acid sequence set forth in SEQ ID NO: 1 and a light chain variable region comprising the amino acid sequence set forth in SEQ ID NO: 2, wherein there are at least two amino acid variants within the heavy chain variable region or the light chain variable region or the combination thereof. In some embodiments, disclosed herein is an isolated dual binding antibody comprising a heavy chain variable region comprising the amino acid sequence set forth in SEQ ID NO: 1 with at least two amino acid variants at any position and any light chain variable region. In some embodiments, disclosed herein is an isolated dual binding antibody comprising a light chain variable region comprising the amino acid sequence set forth in SEQ ID NO: 2 with at least two amino acid variants at any position and any heavy chain variable region.

As used herein, the term "heavy chain variable region" may be used interchangeable with the term "VH domain" or the term "VH", having all the same meanings and qualities. As used herein, the term "light chain variable region" may be used interchangeably with the term "VL domain" or the term "VL", having all the same meanings and qualities.

In certain embodiments, a specific variant VH and/or VL domain, described herein, may be used to screen a library of the complementary variable region to identify VH/VL, respectively, with desirable properties, such as increased affinity for an antigen. Such methods are described, for example, in Portolano et al., J. Immunol. (1993) 150:880-887; Clarkson et al., Nature (1991) 352:624-628. Fischer et al., (2015) Exploiting light chains for the scalable generation and platform purification of native human bispecific IgG. *Nature Communications* volume 6, Article number: 6113.

Other methods may also be used to mix and match VH and VL domains to identify a Fab or F(ab) 2 having desired dual binding activity. For example: Klimka et al., British Journal of Cancer (2000) 83: 252-260, describe a screening process using a mouse VL and a human VH library with CDR3 and PR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antigen-binding fragments of antibodies according to several embodiments of the disclosure described herein, using routine methodology in the art.

A skilled artisan would appreciate that dual binding antibody encompasses in its broadest sense an antibody that specifically binds an antigenic determinant of IL-13 and TSLP. The skilled artisan would appreciate that specificity for binding to IL-13 or TSLP reflects that the binding is selective for the antigen and can be discriminated from unwanted or nonspecific interactions. In certain embodiments, the dual binding antibody comprises an antibody fragment or fragments.

In some embodiments, an antigenic determinant comprises an IL-13 or TSLP epitope. The term "epitope" includes any determinant, in certain embodiments, a polypeptide determinant, capable of specific binding to an anti-IL-13 or anti-TSLP binding domain. An epitope is a region of an antigen that is bound by an antibody or an antigen-binding fragment thereof. In some embodiments, the antigen-binding fragment of an antibody comprises a heavy chain variable region, a light chain variable region, or a combination thereof as described herein.

In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, the dual binding antibody is said to specifically bind an IL-13 or TSLP epitope when it preferentially recognizes IL-13 or TSLP in a complex mixture of proteins and/or macromolecules. The dual binding antibody is said to specifically bind an epitope when the equilibrium dissociation constant is $\leq 10^{-6}$, or $10^{-7}$ M. In some embodiments, the equilibrium dissociation constant may be $\leq 10^{-8}$ M or $10^{-9}$ M. In some further embodiments, the equilibrium dissociation constant may be $\leq 10^{-10}$ M, $10^{-11}$ M, or $10^{-12}$ M. In some embodiments, the equilibrium dissociation constant may be in the range of $\leq 10^{-5}$ M to $10^{-12}$ M.

An antibody binding domain can be a fragment of an antibody or a genetically engineered product of one or more fragments of the antibody, which fragment is involved in specifically binding with the antigen. By "specifically binding" is meant that the binding is selective for the antigen of interest, for example for IL-13 or TSLP in embodiments described herein and can be discriminated from unwanted or nonspecific interactions. As used herein, the term "dual binding antibody" may in certain embodiments, encompass complete immunoglobulin structures, fragments thereof, or domains thereof.

Examples of antibody binding domains include, without limitation, a complementarity determining region (CDR), a variable region (Fv), a VH domain, a light chain variable region (VL), a heavy chain, a light chain, a single chain variable region (scFv), and a Fab fragment. A skilled artisan would appreciate that an scFv is not actually a fragment of an antibody, but instead is a fusion polypeptide comprising the variable heavy chain (VH) and variable light chain (VL) regions of an immunoglobulin, connected by a short linker peptide of for example but not limited to ten to about 25 amino acids. The skilled artisan would also appreciate that the term "Fab" with regard to an antibody, generally encompasses that portion of the antibody consisting of a single light chain (both variable and constant regions) bound to the variable region and first constant region of a single heavy chain by a disulfide bond.

In some embodiments, an antibody encompasses whole antibody molecules, including monoclonal, polyclonal and multispecific (e.g., bispecific) antibodies. In some embodiments, an antibody encompasses an antibody fragment or fragments that retain binding specificity including, but not limited to, variable heavy chain (VH) fragments, variable light chain (VL) fragments, Fab fragments, F(ab')$_2$ fragments, scFv fragments, Fv fragments, minibodies, diabodies, triabodies, and tetrabodies (see, e.g., Hudson and Souriau, Nature Med. 9: 129-134 (2003) (hereby incorporated by reference in their entirety)). Also encompassed are humanized, primatized, and chimeric antibodies.

As used herein, in some embodiments, the term "Antibody" may be used interchangeably with the term "Immunoglobulin" having all the same qualities and meanings. Similarly, as used herein, in some embodiments, the term "Antibody or fragments thereof" may be used interchangeably with the term "Immunoglobulin or fragments thereof" having all the same qualities and meanings. Thus, a skilled artisan would appreciate that in some embodiments, "an antibody or fragments thereof", or "immunoglobulins or fragments thereof" may encompass IgG immunoglobulins or fragments thereof or structures comprising a fragment or fragments thereof, including but not limited to an IgG, an scFv fragment, an Fab fragment, an F(ab')$_2$ fragment, Fv fragments, minibodies, diabodies, triabodies, and tetrabodies.

A skilled artisan would recognize that a "Heavy chain variable region" or "VH" with regard to an antibody encompasses the fragment of the heavy chain that contains three CDRs interposed between flanking stretches known as framework (FR) regions, which are more highly conserved than the CDRs, and form a scaffold to support the CDRs. In certain embodiments, the terms a "Heavy chain variable region" or a "VH" may be used interchangeably with "VH domain".

A skilled artisan would recognize that a "Light chain variable region" or "VL" with regard to an antibody encompasses the fragment of the light chain that contains three CDRs interposed between framework (FR) regions. In certain embodiments, the terms a "Light chain variable region" or a "VL" may be used interchangeably with "VL domain".

Figure 1B:
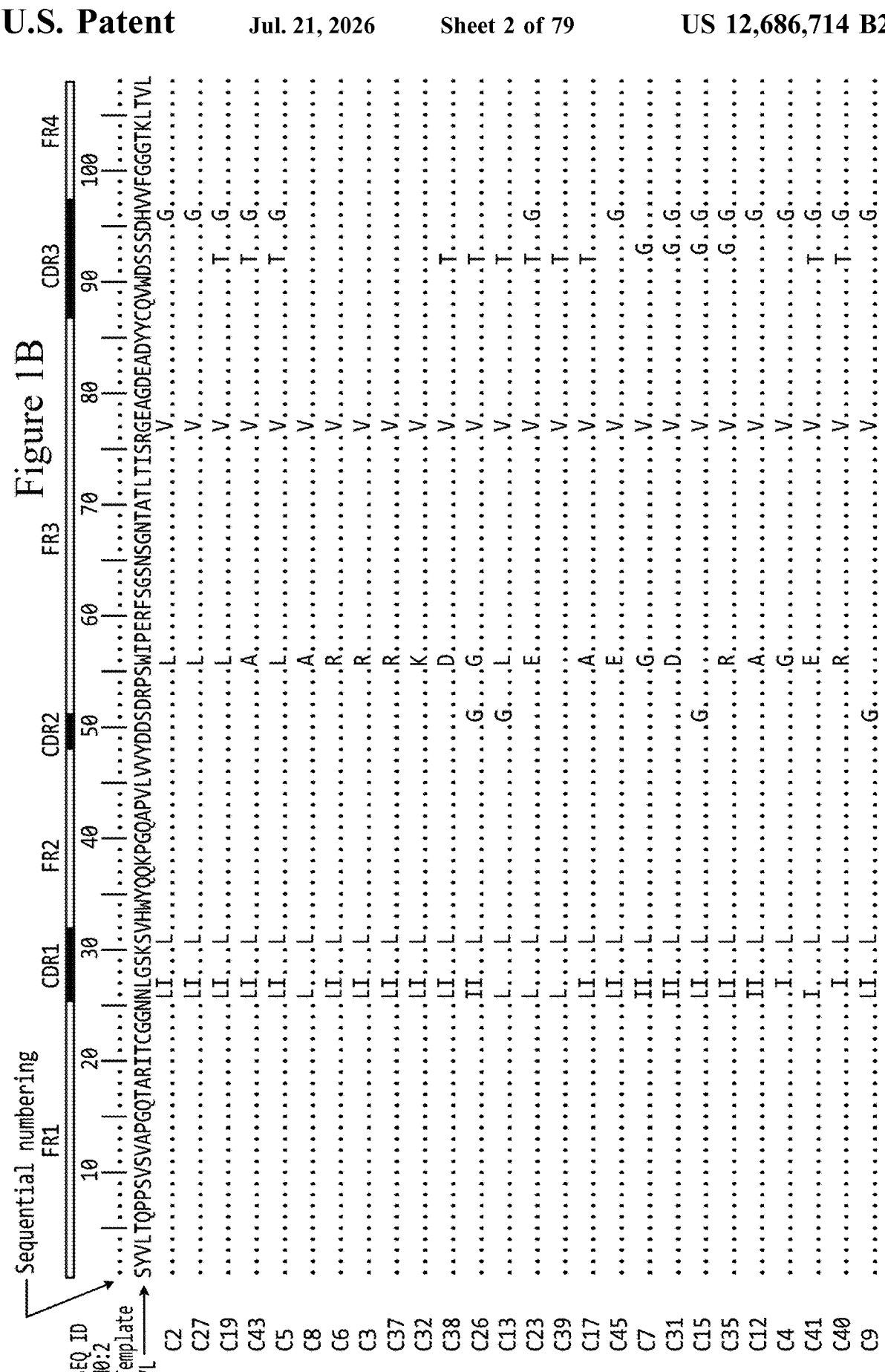

Disclosed herein are a number of amino acid sequences for HCDR1, HCDR2, HCDR3, LCDR1, LCDR2, LCDR3, as well as VH and VL regions for dual binding antibodies that bind to IL-13 and TSLP. Discussion on some embodiments of representative sequences disclosed herein is presented below. FIG. 1A presents the template VH domain amino acid sequence, set forth in SEQ ID NO: 1, and the location of the three heavy-chain (H) CDR regions (HCDR1, HCDR2, HCDR3) and four FR regions (HFR1, HFR2, HFR3, HFR4), while FIG. 1B presents the template VL domain amino acid sequence, set forth in SEQ ID NO: 2, and the location of the three light-chain (L) CDR regions (LCDR1, LCDR2, LCDR3) and four FR regions (LFR1, HCDR2, LFR3, LFR4). The amino acid residues including variant residues, present in each of the CDR regions and each of the FR regions of the re-epitoped clones, are clearly identified by comparing the linear schematic representation of the template VH or template VL sequence with the numbering and amino acids provided below (FIGS. 1A and 1B).

In some embodiments, an isolated dual binding antibody comprises an antibody antigen-binding domain site comprising a VH domain and a VL domain, wherein said VH domain comprises a set of CDRs, HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid. A skilled artisan would recognize the 12 unique sites within the VH domain presented in FIG. 1A, wherein a variant amino acid may be found, which are herein identified as HX and may in certain embodiments, encompass the presence of a variant amino acid within the template sequence of the heavy chain.

In some embodiments, a VH domain of a dual binding antibody comprises HCDR1 (SEQ ID NO: 136), HCDR2 (SEQ ID NO: 142), and HCDR3 (SEQ ID NO: 143), wherein the VH domain comprises a variant amino acid at, at least one of HX1, HX2, HX3, HX4, HX5, HX6, HX7, HX8, HX9, HX10, HX11, and HX12.

In some embodiments, a VH domain of a dual binding antibody comprises HCDR1 (SEQ ID NO: 136), HCDR2 (SEQ ID NO: 137) wherein HX1 is selected from the group consisting of W and S; and HCDR3 (SEQ ID NO: 138) wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M. In certain embodiments, the isolated dual binding antibody comprises variant amino acids comprising CDR1 (SEQ ID NO: 136), CDR2 (SEQ ID NO: 137) wherein HX1 is W, CDR3 (SEQ ID NO: 138) wherein HX2 is selected from the group consisting of A and S, wherein HX3 is P, wherein HX4 is Q, wherein HX5 is W, HX6 is selected from the group consisting of E and M, HX7 is selected from the group consisting of L and W, HX8 is selected from the group consisting of V and T, HX9 is selected from the group consisting of H and A, HX10 is E, HX11 is A, and HX12 is selected from the group I and L.

In some embodiments, the dual binding antibody may have a VH domain comprising an HCDR1 (SEQ ID NO: 136), an HCDR2 (SEQ ID NO: 137) wherein HX1 is W, and an HCDR3 (SEQ ID NO: 138) wherein HX2 is A, HX3 is P, HX4 is Q, HX5 is W, HX6 is E, HX7 is L, HX8 is T, HX9 is A, HX10 is E, HX11 is A, and HX12 is I; or an HCDR1 (SEQ ID NO: 136), an HCDR2 (SEQ ID NO: 137) wherein HX1 is W, and an HCDR3 (SEQ ID NO: 138) wherein HX2 is A, HX3 is P, HX4 is Q, HX5 is W, HX6 is M, HX7 is L, HX8 is V, HX9 is A, HX10 is E, HX11 is A, and HX12 is L; or an HCDR1 (SEQ ID NO: 136), an HCDR2 (SEQ ID NO: 137) wherein HX1 is W, and an HCDR3 (SEQ ID NO: 138) wherein HX2 is S, HX3 is P, HX4 is Q, HX5 is W, HX6 is E, HX7 is W, HX8 is V, HX9 is H, HX10 is E, HX11 is A, and HX12 is L.

Engineered antibody clones having variants in the VH domain as described above, are presented in FIG. 1A.

In some embodiments, an isolated dual binding antibody comprises an antibody antigen-binding domain site comprising a VH domain and a VL domain, wherein said in some embodiments the VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCDR3 is set forth as Q V W D LX5 LX6 S D LX7 V V (SEQ ID NO; 146), wherein LX5, LX6, and LX7 are any amino acid. A skilled artisan would recognize the 7 unique sites within the VL domain presented in FIG. 1B, wherein a variant amino acid may be found within a CDR, which are herein identified as LX and may in certain embodiments, encompass the presence of a variant amino acid within the template sequence of the light chain.

In some embodiments, a variant amino acid within the light chain may reside in one of the framework regions. In some embodiments, a variant amino acid within the VL domain is in the LFR3 region.

In some embodiments, a VL domain of the dual binding antibody comprises LCDRs wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; and wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G. In certain embodiments, the isolated dual binding antibody comprises variant amino acids wherein LCDR1 (SEQ ID NO: 139) wherein LX1 is L, LX2 is I, LX3 is L, LCDR2 (D D LX4, wherein LX4 is selected from the group consisting of S and G), and LCDR3 (SEQ ID NO: 141) wherein LX5 is S, LX6 is S, and LX7 is selected from the group consisting of H and G.

In some embodiments, the dual binding antibody may have a VL domain comprising an LCDR1 (SEQ ID NO: 139) wherein LX1 is L, LX2 is I, and LX3 is L, an LCDR2 (D D LX4, wherein LX4 is S), and LCDR3 (SEQ ID NO: 141) wherein LX5 is S, LX6 is S, and LX7 is G; or an LCDR1 (SEQ ID NO: 139) wherein LX1 is L, LX2 is I, and LX3 is L, an LCDR2 (D D LX4, G wherein LX4 is S), and LCDR3 (SEQ ID NO: 141) wherein LX5 is S, LX6 is S, and LX7 is H, or an LCDR1 (SEQ ID NO: 139) wherein LX1 is L, LX2 is I, and LX3 is L, an LCDR2 (D D LX4, wherein LX4 is G), and LCDR3 (SEQ ID NO: 141) wherein LX5 is S, LX6 is S, and LX7 is G.

Engineered antibody clones having variants in the VL domain as described above, are presented in FIG. 1B.

In some embodiments, disclosed herein is an isolated antibody comprising a heavy chain variable domain (VH) and a light chain variable domain (VL), said VH and VL comprise the amino acid sequences of SEQ ID Nos:209 and 210, SEQ ID Nos:219 and 220, SEQ ID Nos:249 and 250, SEQ ID Nos:337 and 338, SEQ ID Nos:155 and 156, SEQ ID Nos:157 and 158, SEQ ID Nos:4 and 3, SEQ ID Nos:6 and 5, SEQ ID Nos:8 and 7, SEQ ID Nos:10 and 9, SEQ ID Nos:12 and 11, SEQ ID Nos:14 and 13, SEQ ID Nos:16 and 15, SEQ ID Nos:18 and 17, SEQ ID Nos:20 and 19, SEQ ID Nos:22 and 21, SEQ ID Nos:24 and 23, SEQ ID Nos:26 and 25, SEQ ID Nos:28 and 27, SEQ ID Nos:30 and 29, SEQ ID Nos:32 and 31, SEQ ID Nos:34 and 33, SEQ ID Nos:36 and 35, SEQ ID Nos:38 and 37, SEQ ID Nos:40 and 39, SEQ ID Nos:42 and 41, SEQ ID Nos:44 and 43, SEQ ID Nos:46 and 45, SEQ ID Nos:48 and 47, SEQ ID Nos:50 and 49, SEQ ID Nos:52 and 51, or SEQ ID Nos:54 and 53.

In some embodiments, disclosed herein is an isolated antibody comprising a heavy chain variable domain (VH) and a light chain variable domain (VL), said antibody comprising the sequence that is at least 80% identical (e.g., 80%, 85%, 90%, 95%, 98%, or 99% identical) to the sequences set forth in any of SEQ ID Nos:209 and 210, SEQ ID Nos:219 and 220, SEQ ID Nos:249 and 250, SEQ ID Nos:337 and 338, SEQ ID Nos:155 and 156, SEQ ID Nos:157 and 158, SEQ ID Nos:4 and 3, SEQ ID Nos:6 and 5, SEQ ID Nos:8 and 7, SEQ ID Nos:10 and 9, SEQ ID Nos:12 and 11, SEQ ID Nos:14 and 13, SEQ ID Nos:16 and 15, SEQ ID Nos:18 and 17, SEQ ID Nos:20 and 19, SEQ ID Nos:22 and 21, SEQ ID Nos:24 and 23, SEQ ID Nos:26 and 25, SEQ ID Nos:28 and 27, SEQ ID Nos:30 and 29, SEQ ID Nos:32 and 31, SEQ ID Nos:34 and 33, SEQ ID Nos:36 and 35, SEQ ID Nos:38 and 37, SEQ ID Nos:40 and 39, SEQ ID Nos:42 and 41, SEQ ID Nos:44 and 43, SEQ ID Nos:46 and 45, SEQ ID Nos:48 and 47, SEQ ID Nos:50 and 49, SEQ ID Nos:52 and 51, or SEQ ID Nos:54 and 53.

In some embodiments, disclosed herein is an isolated, wherein the antibody comprises a heavy chain variable domain (VH) and a light chain variable domain (VL), said VH and VL comprise the amino acid sequences as shown in Table 10 or Table 1. In some embodiments, disclosed herein is an isolated antibody comprising a heavy chain variable domain (VH) and a light chain variable domain (VL), said antibody comprising the sequence that is at least 80% identical (e.g., 80%, 85%, 90%, 95%, 98%, or 99% identical) to the sequences set forth in Table 10 or Table 1.

In some embodiments, disclosed herein is an isolated antibody comprising a heavy chain variable domain (VH) and a light chain variable domain (VL), wherein (a) said VH domain comprises the amino acid sequence set forth in SEQ ID NO: 1 with amino acid variants at two or more of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); and (b) said VL domain comprises the amino acid sequence set forth in SEQ ID NO: 2 with amino acid variants at two or more of positions 26, 27, 31, 51, 56, 77, 92, 93, or 96, or any combination thereof (IMGT positions: 27, 28, 38, 65, 70, 94, 109, 110, or 115, or a combination thereof).

In one embodiment, the isolated dual binding antibody disclosed herein comprises a heavy chain variable domain (VH) and a light chain variable domain (VL), wherein the VH and VL comprise the amino acid sequences of SEQ ID Nos:209 and 210.

In another embodiment, the isolated dual binding antibody disclosed herein comprises a heavy chain variable domain (VH) and a light chain variable domain (VL), wherein the VH and VL comprise the amino acid sequences of SEQ ID Nos:219 and 220.

In another embodiment, the isolated dual binding antibody disclosed herein comprises a heavy chain variable domain (VH) and a light chain variable domain (VL), wherein the VH and VL comprise the amino acid sequences of SEQ ID Nos:249 and 250.

In another embodiment, the isolated dual binding antibody disclosed herein comprises a heavy chain variable domain (VH) and a light chain variable domain (VL), wherein the VH and VL comprise the amino acid sequences of SEQ ID Nos:337 and 338.

In another embodiment, the isolated dual binding antibody disclosed herein comprises a heavy chain variable domain (VH) and a light chain variable domain (VL), wherein the VH and VL comprise the amino acid sequences as shown in Table 1 or Table 10.

In another embodiment, the isolated dual binding antibody disclosed herein comprises VH and VL sequences that are at least 80%, 85%, 90%, 95%, 98%, or 99% identical to the VH and VL sequences disclosed herein.

In some embodiments, an isolated dual binding antibody comprising an antibody antigen-binding domain site comprising a VH domain and a VL domain comprising a combination of VH domain HCDRs and VL domain LCDRs described above. For example, but not limited to, in certain embodiments, a VH domain comprises a set of CDRs, HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid; and wherein said VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCD3 is set forth as Q V W D LX5 LX6 S D LX7 V V (SEQ ID NO; 146), wherein LX5, LX6, and LX7 are any amino acid.

In some embodiments, a VH domain comprises a set of CDRs, HCDR1, HCDR2, and HCDR3, wherein the amino acid sequence of HCDR1 is set forth in SEQ ID NO: 136, wherein the amino acid sequence of HCDR2 is set forth in SEQ ID NO: 137, wherein HX1 is selected from the group consisting of W and S; wherein the amino acid sequence of HCDR3 is set forth in SEQ ID NO: 138, wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M; and a VL domain comprises a set of CDRs, HCDR1, HCDR2, and HCDR3, wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G.

In certain embodiments, the isolated dual binding antibody comprises a VH domain comprising a set of CDRs, HCDR1, HCDR2, and HCDR3, wherein the amino acid sequence of HCDR1 is set forth in SEQ ID NO: 136, wherein the amino acid sequence of HCDR2 is set forth in SEQ ID NO: 137, wherein HX1 is W, wherein the amino acid sequence of HCDR3 is set forth in SEQ ID NO: 138, wherein HX2 is selected from the group consisting of A and S, HX3 is P, HX4 is Q, HX5 is W, HX6 is selected from the group consisting of E and M, HX7 is selected from the group consisting of L and W, HX8 is selected from the group consisting of V and T, HX9 is selected from the group consisting of H and A, HX10 is E, HX11 is A, HX12 is selected from the group I and L, and comprising a VL domain comprising a set of CDRs, LCDR1, LCDR2, and LCDR3, wherein the amino acid sequence of LCDR1 is set forth in SEQ ID NO: 139 wherein LX1 is L, LX2 is I, LX3 is L, wherein the amino acid sequence of LCDR2 is set forth as D D LX4, wherein LX4 is selected from the group consisting of S and G, wherein the amino acid sequence of LCDR3 is set forth in SEQ ID NO: 141 wherein LX5 is S, LX6 is S, and LX7 is selected from the group consisting of H and G.

In some embodiments, the dual binding antibody comprises a VH domain comprising a set of CDRs, HCDR1, HCDR2, and HCDR3, and a VL domain comprising a set of CDRs, LCDR1, LCDR2, and LCDR3, wherein the amino acid sequences of each CDR are as set forth in FIGS. 1A and 1B for the clones set forth there, for example but not limited to: Clone C2: HCDR1 (SEQ ID NO: 136), HCDR2 (SEQ ID NO: 137) wherein HX1 is W, HCDR3 (SEQ ID NO: 138) wherein HX2 is A, HX3 is P, HX4 is Q, HX5 is W, HX6 is E, HX7 is L, HX8 is T, HX9 is A, HX10 is E, HX11 is A, HX12 is I, LCDR1 (SEQ ID NO: 139) wherein LX1 is L, LX2 is I, LX3 is L, LCDR2 (D D LX4, wherein LX4 is S), and LCDR3 (SEQ ID NO: 141) wherein LX5 is S, LX6 is S, and LX7 is G; Clone C6: HCDR1 (SEQ ID NO: 136), HCDR2 (SEQ ID NO: 137) wherein HX1 is W, HCDR3 (SEQ ID NO: 138) wherein HX2 is A, HX3 is P, HX4 is Q, HX5 is W, HX6 is M, HX7 is L, HX8 is V, HX9 is A, HX10 is E, HX11 is A, HX12 is L, LCDR1 (SEQ ID NO: 139) wherein LX1 is L, LX2 is I, LX3 is L, LCDR2 (D D LX4, wherein LX4 is S), and LCDR3 (SEQ ID NO: 141) wherein LX5 is S, LX6 is S, and LX7 is H; or Clone C9: HCDR1 (SEQ ID NO: 136), HCDR2 (SEQ ID NO: 137) wherein HX1 is W, HCDR3 (SEQ ID NO: 138) wherein HX2 is S, HX3 is P, HX4 is Q, HX5 is W, HX6 is E, HX7 is W, HX8 is V, HX9 is H, HX10 is E, HX11 is A, HX12 is L, LCDR1 (SEQ ID NO: 139) wherein LX1 is L, LX2 is I, LX3 is L, LCDR2 (D D LX4, wherein LX4 is G), and LCDR3 (SEQ ID NO: 141) wherein LX5 is S, LX6 is S, and LX7 is G.

In some embodiments, the dual binding antibody comprises a set of HCDRs as disclosed herein, and any VL domain. In some embodiments, the dual binding antibody comprises a set of LCDRs as disclosed herein, and any VH domain. In some embodiments, the dual binding antibody comprises a paired set of HCDRs-LCDRs, as disclosed herein.

In certain embodiments, the dual binding antibody comprising a VH domain comprising HCDRs as described herein may be encoded by a nucleic acid construct. In certain embodiments, the dual binding antibody comprising a VL domain comprising LCDRS as described herein may be encoded by a nucleic acid construct. In certain embodiments, the dual binding antibody comprising a VH domain comprising HCDRs and a VL domain comprising HCDRs as described herein, may be encoded by a nucleic acid construct.

In certain embodiments, the dual binding antibody comprising a VH domain comprising HCDRs as described herein, may be encoded by a nucleic acid construct. In certain embodiments, the dual binding antibody comprising a VL domain comprising LCDRs as described herein may be encoded by a nucleic acid construct. In certain embodiments, the dual binding antibody comprising a VH domain comprising HCDRs and a VL domain comprising HCDRs as described herein, may be encoded by a nucleic acid construct.

In certain embodiments, the dual binding antibody comprising a VH domain comprising HCDRs as described herein, may be comprised within a library of immunoglobulins. In certain embodiments, the dual binding antibody comprising a VL domain comprising LCDRs as described herein may be comprised within a library of immunoglobulins. In certain embodiments, the dual binding antibody comprising a VH domain comprising HCDRs and a VL domain comprising HCDRs as described herein, may be comprised within a library of immunoglobulins.

In certain embodiments, the dual binding antibody comprising a VH domain comprising HCDRs as described herein, may be produced by expressing a nucleic acid construct comprising a nucleic acid sequence encoding the HCDRs from a host cell and isolating the antibody. In certain embodiments, the dual binding antibody comprising a VL domain comprising LCDRs as described herein may be produced by expressing a nucleic acid construct comprising a nucleic acid sequence encoding the LCDRs from a host cell and isolating the antibody. In certain embodiments, the dual binding antibody comprising a VH domain comprising HCDRs and a VL domain comprising HCDRs as described herein, may be produced by expressing a nucleic acid construct comprising a nucleic acid sequence encoding the HCDRs and LCDRs from a host cell and isolating the antibody.

In certain embodiments, the dual binding antibody comprising a VH domain comprising HCDRs as described herein may be administered in a method of treating a subject in need, wherein said subject suffers from a disease or condition comprising an allergic or respiratory condition, an inflammatory and/or autoimmune condition of the skin or gastrointestinal organs; scleroderma; or tumors or cancers including Hodgkin's lymphoma. In certain embodiments, the dual binding antibody comprising a VL domain comprising LCDRs as described herein may be administered in a method of treating a subject in need, wherein said subject suffers from a disease or condition comprising an allergic or respiratory condition, an inflammatory and/or autoimmune condition of the skin or gastrointestinal organs; scleroderma; or tumors or cancers including Hodgkin's lymphoma. In certain embodiments, the dual binding antibody comprising a VH domain comprising HCDRs and a VL domain comprising LCDRs as described herein, may be administered in a method of treating a subject in need, wherein said subject suffers from a disease or condition comprising an allergic or respiratory condition, an inflammatory and/or autoimmune condition of the skin or gastrointestinal organs; scleroderma; or tumors or cancers including Hodgkin's lymphoma.

In some embodiments, an antibody comprising a heavy chain variable region amino acid sequence set forth in SEQ ID NO: 1 or a light chain variable region amino acid sequence set forth in SEQ ID NO: 2, or the combination thereof, does not bind an IL-13 epitope. Accordingly, the dual binding antibodies described herein are engineered to comprise a binding region not previously present in the antibody. In other words, the dual binding antibodies comprise "re-epitoped" antibodies. As used throughout, the term "engineered" and "re-epitoped" may in certain embodiments, be used interchangeably having all the same qualities and meanings. In some embodiments, a "re-epitoped" antibody comprises improved binding compared to available antibodies. In some embodiments, a "re-epitoped" antibody comprises improved association and dissociation constants ($K_{on}$ and $K_{off}$), compared to the parent antibodies. In some embodiments, a "re-epitoped" antibody comprises improved stability compared with the parent antibodies. In certain embodiments, incorporating variant amino acid residues in at least two of the unique set of 21 variant sites within the CDRs and FR of the VH domain and VL domain, as described herein, results in a "re-epitoped" dual binding antibody comprising improved characteristics compared with the parent antibodies. These re-epitoped antibodies may provide advantageous characteristics.

A skilled artisan would recognize that a "Fv" with regard to an antibody encompasses the smallest fragment of the antibody to bear the complete antigen binding site. An Fv fragment consists of the variable region of a single light chain (VL) bound to the variable region of a single heavy chain (VH).

A skilled artisan would recognize that a "single-chain Fv antibody" or "scFv" with regard to an antibody encompasses an engineered antibody consisting of a VL domain and a VH domain connected to one another directly or via a peptide linker sequence. The skilled artisan would appreciate that a linker, in some embodiments, may comprise a linear amino acid sequence. In some embodiments, the linear amino acid sequence ("linker") comprises an enzyme cleavage site and may, in certain embodiments, be termed a "cleavable linker" or a "linker" or a "cleavable peptide". In some embodiments, a linker may be a cleavable linker. In some embodiments, a linker may be a non-cleavable. In some embodiments, a linker sequence is set forth in SEQ ID NO: 147 (GGGGSGGGGSGGGGS; SEQ ID NO: 147).

In some embodiments, peptide linker sequences contain, for example, Gly, Asn, and or Ser residues, in various combinations. Other near neutral amino acids, such as Thr and Ala, may also be included in the linker sequence.

Other amino acid sequences which may be usefully employed as linkers include those disclosed in Maratea et al., Gene 40:39 46 (1985); Murphy et al., Proc. Natl. Acad. Sci. USA 83:8258 8262 (1986); U.S. Pat. Nos. 4,935,233 and 4,751,180; Chaudhary et al., 1990, Proc. Natl. Acad. Sci. U.S.A. 87:1066-1070; Bird et al., 1988, Science 242:423-426, incorporated herein in their entirety.

In some embodiments, coding sequences of VH and VL domains of the dual binding antibody or fragment thereof can be fused directly without any junctional amino acids or by using a flexible polylinker composed.

A peptide linker, in certain embodiments, is designed to enable the correct interaction between two beta-sheets forming the variable region of the single chain antibody. Any suitable linkers can be used to make an indirect link, such as without limitation, peptide linker, polymer linker, and chemical linker. In certain embodiments, the covalent link is an indirect link through a peptide linker.

In some embodiments, an antibody comprises a mutated immunoglobulin. Examples of mutated immunoglobulins include but are not limited to an IgG that does not bind antibody-dependent cellular cytotoxicity (ADCC) components. IgG comprising $L_{234}A/L_{235}A$ (LALA) mutations cannot bind the Fc receptor (See, Xu D, Alegre M L, Varga S S, Rothermel A L, Collins A M, Pulito V L, et al. In vitro characterization of five humanized OKT3 effector function variant antibodies. Cell Immunol. (2000) 200:16-26.). In some embodiments, the dual binding antibody comprises an IgG comprising the $L_{234}A/L_{235}A$ (LALA) mutations. In some embodiments, the dual binding antibody comprises an IgG comprising the L234A/L235A/P329G (LALAPG) mutations. (See, Wilkenson et al (2021) Fc-engineered antibodies with immune effector functions completely abolished. PLOS ONE I https://doi.org/10.1371/journal-.pone.0260954) The mutations as numbered here are based on an EU numbering convention used for the constant region, (See, Xu D, Alegre M L, Varga S S, Rothermel A L, Collins A M, Pulito V L, et al. In vitro characterization of five humanized OKT3 effector function variant antibodies. Cell Immunol. (2000) 200:16-26. 10.1006/cimm.2000.1617).

In some embodiments, a heavy chain (HC) of an IgG comprising a LALA mutation has the amino acid sequence set forth in SEQ ID NO: 410. In some embodiments, a heavy chain of an IgG comprising a LALAPG mutation has the amino acid sequence set forth in SEQ ID NO: 408.

In some embodiments, an IgG comprising an Fc mutation in the HC resulting in reduced binding to an Fc receptor and an IgG that does not bind antibody-dependent cellular cytotoxicity (ADCC) components, the IgG comprises a HC having the amino acids set forth in SEQ ID NO: 410 and a light chain (LC) having the amino acid sequence set forth in SEQ ID NO: 409. In some embodiments, an IgG comprising an Fc mutation in the HC resulting in reduced binding to an Fc receptor and in an IgG that does not bind antibody-dependent cellular cytotoxicity (ADCC) components, the IgG comprises a HC having the amino acids set forth in SEQ ID NO: 408 and a light chain (LC) having the amino acid sequence set forth in SEQ ID NO: 409.

In some embodiments, a mutated IgG comprises an IgG1, wherein the Fc region is engineered. In some embodiments, a mutated IgG comprises an IgG2, wherein the Fc region is engineered. In some embodiments, a mutated IgG comprises an IgG3, wherein the Fc region is engineered. In some embodiments, a mutated IgG comprises an IgG4, wherein the Fc region is engineered. In certain embodiments, mutations within an Fc region of an antibody abolishes immune effector functions of the antibody.

In some embodiments, an isolated dual binding antibody comprises an IgG, an Fv, an scFv, an Fab, an F(ab')2, a minibody, a diabody, or a triabody. In some embodiments, an isolated dual binding antibody comprises an IgG, wherein said IgG is IgG1, IgG2, IgG3, or IgG4.

In some embodiments, an isolated dual binding antibody comprises a mutated IgG, wherein said mutant IgG is unable to bind to antibody-dependent cellular cytotoxicity components.

In some embodiments, the dual binding antibody described herein comprises an IgG immunoglobulin. In some embodiments, the dual binding antibody described herein comprises an IgG1 immunoglobulin, an IgG2 immunoglobulin, an IgG3 immunoglobulin, or an IgG4 immunoglobulin. In some embodiments, the dual binding antibody comprises an IgG1 immunoglobulin. In some embodiments, the dual binding antibody comprises an IgG2 immunoglobulin. In some embodiments, the dual binding antibody comprises an IgG3 immunoglobulin. In some embodiments, the dual binding antibody comprises an IgG4 immunoglobulin. In some embodiments, the dual binding antibody comprises an IgG1 immunoglobulin or an IgG4 immunoglobulin.

In some embodiments, the dual binding antibody described herein comprises an Fab immunoglobulin fragment. In some embodiments, the dual binding antibody described herein comprises an F(ab')$_2$ immunoglobulin fragment. In some embodiments, the dual binding antibody described herein comprises an Fv immunoglobulin construct. In some embodiments, the dual binding antibody described herein comprises an scFv immunoglobulin construct. In some embodiments, the dual binding antibody described herein comprises a minibody immunoglobulin construct comprising a pair of single-chain Fv fragments which are linked via CH3 domains.

In some embodiments, the dual binding antibody described herein comprises a diabody immunoglobulin construct. In some embodiments, a diabody immunoglobulin construct comprises a heavy chain variable (VH) and light chain variable (VL) regions connected by a small peptide linker. In some embodiments, a diabody immunoglobulin construct comprises single-chain (Fv) 2 in which two scFv fragments are covalently linked to each other. In some embodiments, the dual binding antibody described herein comprises a diabody immunoglobulin construct comprising three scFv fragments covalently linked to each other. Diabodies have been shown in the art to have dissociation constants up to 40-fold lower than corresponding scFvs, meaning that they have a much higher affinity to their target. Consequently, use of a diabody in a method of use as described below, could result in much lower dosing of a diabody or triabody, than an IgG comprising the same VH and VL domains.

In some embodiments, the dual binding antibody comprising a linker or linkers between binding components, for example but not limited to between a VH and a VL in an scFv, a minibody, a diabody, a triabody, or a tetrabody. In some embodiments, the dual binding antibody does not comprise a linker or linkers between binding components, for example but not limited to between a VH and a VL in an scFv, a minibody, a diabody, a triabody, or a tetrabody. In some embodiments, a linker may comprise a single amino acid. In some embodiments, a linker comprises any known linker in the art. In some embodiments, a linker comprises the amino acid sequence set forth in SEQ ID NO: 147.

A skilled artisan would appreciate that the term "variant" encompasses a polypeptide differing from a specifically recited polypeptide sequences, for example the amino acid sequences set forth in SEQ ID NO: 1 and SEQ ID NO: 2, by single or multiple amino acid insertions, deletions, and/or substitutions, created using, e.g., recombinant DNA techniques. Variants of the antigen binding molecules disclosed herein include antigen binding molecules wherein one or several of the amino acid residues are modified by at last one substitution, addition and/or deletion in such manner that the antigen binding affinity is newly created in the antigen binding molecules.

The dual binding portion of the antibodies described herein comprises an immunoglobulin heavy chain variable region and an immunoglobulin light chain variable region (VH and VL, respectively), wherein the amino acid sequence set forth in SEQ ID NO: 1 comprises a VH template and the amino acid sequence set forth in SEQ ID NO: 2 comprises a VL template, and the dual binding region comprises at least two variants within the VH template sequence, or within the VL template sequence, or a combination thereof.

A skilled artisan would appreciate that an "isolated dual binding antibody", in certain embodiments, encompasses an antibody that (1) is free of at least some other proteins with which it would typically be found in nature or with which it would typically be found during synthesis thereof, (2) is essentially free of other non-identical binding antibodies from the same source, (3) may be expressed recombinantly by a cell, (4) has been separated from at least about 50 percent of polynucleotides, lipids, carbohydrates, or other materials with which it is associated in during synthesis, or (5) does not occur in nature, or a combination thereof. Such an isolated antibody may be encoded by genomic DNA, cDNA, mRNA or other RNA, or may be of synthetic origin, or any combination thereof. In certain embodiments, the isolated antibody is substantially free from proteins or polypeptides or other contaminants that would interfere with its use (therapeutic, diagnostic, prophylactic, research or otherwise). As used throughout, the terms "dual antibody" and "dual binding antibody" may be used interchangeably having all the same meanings and qualities.

In some embodiments, disclosed herein is an isolated dual binding antibody comprising a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT numbering of heavy chain variable region variant positions: 57, 107, 108, 109, 110, 111, 111A, 112A, 112, 113, 114, or 117, or a combination thereof); a light chain variable region comprising the amino acid sequence set forth in SEQ ID NO: 2 with at least one amino acid variant at any of positions 26, 27, 31, 51, 56, 77, 92, 93, or 96, or any combination thereof (IMGT numbering of light chain variable region variant positions: 27, 28, 38, 65, 70, 94, 109, 110, or 115, or a combination thereof); or a combination of the variant heavy chain variable region and the variant light chain variable region; wherein the total number of variant positions in said heavy chain variable region, said light chain variable region, or said combination thereof, is at least 2.

IMGT® is the international ImMunoGeneTics informa-tion System®, (See, Nucleic Acids Res. 2015 January; 43(Database issue): D413-22. Doi: 10.1093/nar/gku1056. Epub 2014 Nov. 5 Free article. PMID: 25378316 LIGM:441 and Dev Comp Immunol. 2003 January; 27(1):55-77). IMGT is a unique numbering system for immunoglobulin and T cell receptor variable domains and Ig superfamily V-like domains, (Lefranc MP1, Pommié C, Ruiz M, Giudi-celli V, Foulquier E, Truong L, Thouvenin-Contet V, Lefranc G. Dev Comp Immunol 27: 55-77. (2003)). IMGT® pres-ents a uniform numbering system for these IG and TcR variable domain sequences, based on aligning 5 or more000 IG and TcR variable region sequences, taking into account and combining the Kabat definition of FRs and CDRs, structural data, and Chothia's characterization of the hyper-variable loops. IMGT is considered a universal numbering scheme for antibodies well known in the art.

In describing variant amino acid positions present in the VH and VL domains, in some embodiments the IMGT numbering is used. In some embodiments, variant amino acid positions are presented as the specific positions within a given sequence, for example but not limited to SEQ ID NO: 1 and SEQ ID NO: 2. In some embodiments, variant amino acid positions are identified by both the specific positions within a given SEQ ID NO: sequence and the IMGT numbering system. A skilled artisan would recognize that the actual amino acid position number of an amino acid identified by position number relative to a SEQ ID NO: may differ from the IMGT numbering system, yet the residue identified is identical. For example, but not limited to the amino acid residue at position 106 of SEQ ID NO: 1 is the identical residue identified at position 112 by the IMGT numbering system. The skilled artisan would recognize that while the same amino acid residue may be identified as having different positions depending what system is used, the amino acid residue's location and identity within a contiguous amino acid sequence is clear.

In some embodiments, disclosed herein is an isolated dual binding antibody comprising a heavy chain variable region comprising the amino acid sequence set forth in SEQ ID NO: 1 with at least one amino acid variants at any of positions 52, 99, 100, 101, 102, 103, 104, 105, 106, 107, 108, or 111, or any combination thereof (IMGT numbering of heavy chain variable region variant positions: 57, 107, 108, 109, 110, 111, 111A, 112A, 112, 113, 114, or 117, or a combination thereof), and a light chain variable region comprising the amino acid sequence set forth in SEQ ID NO: 2, wherein optionally said amino acid sequence SEQ ID NO: 2 comprises at least one variant amino acid, wherein the total number of variant positions in said heavy chain vari-able region, light chain variable region, or a combination thereof is at least 2. In some embodiments, disclosed herein is an isolated dual binding antibody comprising a heavy chain variable region comprising the amino acid sequence set forth in SEQ ID NO: 1 with at least two amino acid variants at any of positions 52, 99, 100, 101, 102, 103, 104, 105, 106, 107, 108, or 111, or any combination thereof (IMGT numbering of heavy chain variable region variant positions: 57, 107, 108, 109, 110, 111, 111A, 112A, 112, 113, 114, or 117, ora combination thereof), and any light chain variable region.

The amino acid sequences of many light chain variable regions, in and of themselves, are known as such in the art. The skilled person would be able to use such known sequences, and in conjunction with the heavy chain variable regions described herein, analyze for dual binding using routine methodologies and techniques well known in the art (See for example but not limited to, Example 1 below).

In some embodiments, disclosed herein is an isolated dual binding antibody comprising a light chain variable region comprising the amino acid sequence set forth in SEQ ID NO: 2 with at least one amino acid variants at any of positions 26, 27, 31, 51, 56, 77, 92, 93, or 96, or any combination thereof (IMGT numbering of light chain vari-able region variant positions: 27, 28, 38, 65, 70, 94, 109, 110, or 115, or a combination thereof), and a heavy chain variable region comprising the amino acid sequence set forth in SEQ ID NO: 1, wherein optionally said amino acid sequence SEQ ID NO: 1 comprises at least one variant amino acid, wherein the total number of variant positions in said heavy chain variable region, said light chain variable region, or a combination thereof is at least 2. In some embodiments, disclosed herein is an isolated dual binding antibody comprising a light chain variable region compris-ing the amino acid sequence set forth in SEQ ID NO: 2 with at least two amino acid variants at any of positions 26, 27, 31, 51, 56, 77, 92, 93, or 96, or any combination thereof (IMGT numbering of light chain variable region variant positions: 27, 28, 38, 65, 70, 94, 109, 110, or 115, or a combination thereof), and any heavy chain variable region.

The amino acid sequences of many heavy chain variable regions, in and of themselves, are known as such in the art. The skilled person would be able to use such known sequences, and in conjunction with the light chain variable regions described herein, analyze for dual binding using routine methodologies and techniques well known in the art (See for example but not limited to, Example 1 below).

In some embodiments, a VH domain described herein comprises the amino acid sequence set forth in SEQ ID NO: 1 with at least one amino acid variants at any position. In some embodiments, a VH comprising the amino acid sequence set forth in SEQ ID NO: 1 comprises at least two amino acid variants at any position. In some embodiments, a VH comprising the amino acid sequence set forth in SEQ ID NO: 1 comprises at least between 1-10 amino acid variants at any position. In some embodiments, a VH comprising the amino acid sequence set forth in SEQ ID NO: 1 comprises 1-5 amino acid variants at any position. In some embodiments, a VH comprising the amino acid sequence set forth in SEQ ID NO: 1 comprises 1, 2, 3, 4, 5, 6, 7, 8, 9, 10, or more amino acid variants at any position.

In some embodiments, a VL domain described herein comprises the amino acid sequence set forth in SEQ ID NO: 2 with at least one amino acid variants at any position. In some embodiments, a VL comprising the amino acid sequence set forth in SEQ ID NO: 2 comprises at least two amino acid variants at any position. In some embodiments, a VL comprising the amino acid sequence set forth in SEQ ID NO: 2 comprises at least between 1-10 amino acid variants at any position. In some embodiments, a VL com-prising the amino acid sequence set forth in SEQ ID NO: 2 comprises 1-5 amino acid variants at any position. In some embodiments, a VL comprising the amino acid sequence set forth in SEQ ID NO: 2 comprises 1, 2, 3, 4, 5, 6, 7, 8, 9, 10, or more amino acid variants at any position.

In some embodiments, a VH domain and a VL domain described herein comprising the amino acid sequences set forth in SEQ ID NO: 1 and SEQ ID NO: 2, respectfully have a combined number of variant positions of at least 2. In some embodiments, a VH domain and a VL domain described herein comprising the amino acid sequences set forth in SEQ ID NO: 1 and SEQ ID NO: 2, respectfully have a combined number of variant positions of between 2-20. In some embodiments, a VH domain and a VL domain described herein comprising the amino acid sequences set forth in SEQ ID NO: 1 and SEQ ID NO: 2, respectfully have a combined number of variant positions of at least 2, 3, 4, 5, 6, 7, 8, 9, 10, 11, 12, 13, 14, 15, 16 17, 18, 19, or 20. In some embodiments, a VH domain and a VL domain described herein comprising the amino acid sequences set forth in SEQ ID NO: 1 and SEQ ID NO: 2, respectfully have a combined number of variant positions of more than 20.

In certain embodiments, dual antibody binding regions, as described herein include a heavy chain and a light chain CDR set, respectively, interposed between a heavy chain and a light chain framework region (FR) set which provide support to the CDRs and define the spatial relationship of the CDRs relative to each other. As used herein, the term "CDR set" refers to the three hypervariable regions of a heavy or light chain variable region. Proceeding from the N-terminus of a heavy or light chain polypeptide, these regions are denoted as "CDR1," "CDR2," and "CDR3" respectively. An antigen binding site, therefore, includes six CDRs, comprising the CDR set from each of a heavy and a light chain variable region. Crystallographic analysis of a number of antigen-antibody complexes has demonstrated that the amino acid residues of CDRs form extensive contact with a bound antigen, wherein the most extensive antigen contact is with the heavy chain CDR3. Thus, the CDR regions are primarily responsible for the specificity of an antigen binding site.

As used herein, the term "FR set" refers to the four flanking amino acid sequences which frame the CDRs of a CDR set of a heavy or light chain variable region. Some FR residues may contact bound antigen; however, FRs are primarily responsible for folding the variable region into the antigen-binding site, particularly the FR residues directly adjacent to the CDRs. Within FRs, certain amino residues and certain structural features are very highly conserved. In this regard, all variable region sequences contain an internal disulfide loop of around 90 amino acid residues. When the variable regions fold into a binding-site, the CDRs are displayed as projecting loop motifs which form an antigen-binding surface. It is generally recognized that there are conserved structural regions of FRs, which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

In some embodiments, an at least one variant in said VH comprises a variant amino acid in a CDR region. In some embodiments, an at least one variant in said VL comprises a variant amino acid in a CDR region. In some embodiments, an at least one variant in said VH comprises a variant amino acid in a FR region. In some embodiments, an at least one variant in said VL comprises a variant amino acid in a FR region. In some embodiments, an at least two variants in said VH comprises variant amino acids in a CDR region, an FR region, or both. In some embodiments, an at least two variants in said VL comprises variant amino acids in a CDR region, an FR region, or both. In some embodiments, variant positions in the VH include variants in at least one CDR and at least one FR region. In some embodiments, variant positions in the VL include variants in at least one CDR and at least one FR region.

In some embodiments, a VH comprising the amino acid sequence set forth in SEQ ID NO: 1 comprises an amino acid variant at any of positions 52, 99, 100, 101, 102, 103, 104, 105, 106, 107, 108, or 111, or any combination thereof (IMGT numbering of heavy chain variable region variant positions: 57, 107, 108, 109, 110, 111, 111A, 112A, 112, 113, 114, or 117, or a combination thereof). In some embodiments, a VH comprising the amino acid sequence set forth in SEQ ID NO: 1 comprises an amino acid variant at position 52 (IMGT position 57). In some embodiments, a VH comprising the amino acid sequence set forth in SEQ ID NO: 1 comprises an amino acid variant at position 99 (IMGT position 107). In some embodiments, a VH comprising the amino acid sequence set forth in SEQ ID NO: 1 comprises an amino acid variant at position 100 (IMGT position 108). In some embodiments, a VH comprising the amino acid sequence set forth in SEQ ID NO: 1 comprises an amino acid variant at position 101 (IMGT position 109). In some embodiments, a VH comprising the amino acid sequence set forth in SEQ ID NO: 1 comprises an amino acid variant at position 102 (IMGT position 110). In some embodiments, a VH comprising the amino acid sequence set forth in SEQ ID NO: 1 comprises an amino acid variant at position 103 (IMGT position 111). In some embodiments, a VH comprising the amino acid sequence set forth in SEQ ID NO: 1 comprises an amino acid variant at position 104 (IMGT position 111A). In some embodiments, a VH comprising the amino acid sequence set forth in SEQ ID NO: 1 comprises an amino acid variant at position 105 (IMGT position 112A). In some embodiments, a VH comprising the amino acid sequence set forth in SEQ ID NO: 1 comprises an amino acid variant at position 106 (IMGT position 112). In some embodiments, a VH comprising the amino acid sequence set forth in SEQ ID NO: 1 comprises an amino acid variant at position 107 (IMGT position 113). In some embodiments, a VH comprising the amino acid sequence set forth in SEQ ID NO: 1 comprises an amino acid variant at position 108 (IMGT position 114). In some embodiments, a VH comprising the amino acid sequence set forth in SEQ ID NO: 1 comprises an amino acid variant at position 111 (IMGT position 117).

In some embodiments, a VH comprising the amino acid sequence set forth in SEQ ID NO: 1 comprises an amino acid variant at position 52 (IMGT position 57) and between 1-3 additional variant amino acids. In some embodiments, a VH comprising the amino acid sequence set forth in SEQ ID NO: 1 comprises an amino acid variant at position 99 (IMGT position 107) and between 1-3 additional variant amino acids. In some embodiments, a VH comprising the amino acid sequence set forth in SEQ ID NO: 1 comprises an amino acid variant at position 100 (IMGT position 108) and between 1-3 additional variant amino acids. In some embodiments, a VH comprising the amino acid sequence set forth in SEQ ID NO: 1 comprises an amino acid variant at position 101 (IMGT position 109) and between 1-3 additional variant amino acids. In some embodiments, a VH comprising the amino acid sequence set forth in SEQ ID NO: 1 comprises an amino acid variant at position 102 (IMGT position 110) and between 1-3 additional variant amino acids. In some embodiments, a VH comprising the amino acid sequence set forth in SEQ ID NO: 1 comprises an amino acid variant at position 103 (IMGT position 111) and between 1-3 additional variant amino acids. In some embodiments, a VH comprising the amino acid sequence set forth in SEQ ID NO: 1 comprises an amino acid variant at position 104 (IMGT position 111A) and between 1-3 additional variant amino acids. In some embodiments, a VH comprising the amino acid sequence set forth in SEQ ID NO: 1 comprises an amino acid variant at position 105 (IMGT position 112A) and between 1-3 additional variant amino acids. In some embodiments, a VH comprising the amino acid sequence set forth in SEQ ID NO: 1 comprises an amino acid variant at position 106 (IMGT position 112) and between 1-3 additional variant amino acids. In some embodiments, a VH comprising the amino acid sequence set forth in SEQ ID NO: 1 comprises an amino acid variant at position 107 (IMGT position 113) and between 1-3 additional variant amino acids. In some embodiments, a VH comprising the amino acid sequence set forth in SEQ ID NO: 1 comprises an amino acid variant at position 108 (IMGT position 114) and between 1-3 additional variant amino acids. In some embodiments, a VH comprising the amino acid sequence set forth in SEQ ID NO: 1 comprises an amino acid variant at position 111 (IMGT position 117) and between 1-3 additional variant amino acids.

In some embodiments, a VH comprising the amino acid sequence set forth in SEQ ID NO: 1 comprises an amino acid variant at positions 105 and 106 (IMGT positions 112A and 112). In some embodiments, a VH comprising the amino acid sequence set forth in SEQ ID NO: 1 comprises an amino acid variant at positions 106 and 111 (IMGT positions 112 and 117). In some embodiments, a VH comprising the amino acid sequence set forth in SEQ ID NO: 1 comprises an amino acid variant at positions 103 and 106 (IMGT positions 111 and 112). In some embodiments, a VH comprising the amino acid sequence set forth in SEQ ID NO: 1 comprises an amino acid variant at positions 104 and 106 (IMGT positions 111A and 112). In some embodiments, a VH comprising the amino acid sequence set forth in SEQ ID NO: 1 comprises an amino acid variant at positions 104, 106, and 111 (IMGT positions 111A, 112, and 117). In some embodiments, a VH comprising the amino acid sequence set forth in SEQ ID NO: 1 comprises an amino acid variant at positions 105, 106, and 111 (IMGT positions 112A, 112, and 117). In some embodiments, a VH comprising the amino acid sequence set forth in SEQ ID NO: 1 comprises an amino acid variant at positions 103, 106, and 111 (IMGT positions 111, 112, and 117). In some embodiments, a VH comprising the amino acid sequence set forth in SEQ ID NO: 1 comprises an amino acid variant at positions 99, 104, and 111 (IMGT positions 107, 111A, and 117). In some embodiments, a VH comprising the amino acid sequence set forth in SEQ ID NO: 1 comprises an amino acid variant at positions 52, 99, 104, and 111 (IMGT positions 57, 107, 111A, and 117).

In some embodiments, a VL comprising the amino acid sequence set forth in SEQ ID NO: 2 comprises an amino acid variant at any of positions 26, 27, 31, 51, 56, 77, 92, 93, or 96, or any combination thereof (IMGT numbering of light chain variable region variant positions: 27, 28, 38, 65, 70, 94, 109, 110, or 115, or a combination thereof). In some embodiments, a VL comprising the amino acid sequence set forth in SEQ ID NO: 2 comprises an amino acid variant at position 26 (IMGT position 27). In some embodiments, a VL comprising the amino acid sequence set forth in SEQ ID NO: 2 comprises an amino acid variant at position 27 (IMGT position 28). In some embodiments, a VL comprising the amino acid sequence set forth in SEQ ID NO: 2 comprises an amino acid variant at position 31 (IMGT position 38). In some embodiments, a VL comprising the amino acid sequence set forth in SEQ ID NO: 2 comprises an amino acid variant at position 51 (IMGT position 65). In some embodiments, a VL comprising the amino acid sequence set forth in SEQ ID NO: 2 comprises an amino acid variant at position 56 (IMGT position 70). In some embodiments, a VL comprising the amino acid sequence set forth in SEQ ID NO: 2 comprises an amino acid variant at position 77 (IMGT position 94). In some embodiments, a VL comprising the amino acid sequence set forth in SEQ ID NO: 2 comprises an amino acid variant at position 92 (IMGT position 109). In some embodiments, a VL comprising the amino acid sequence set forth in SEQ ID NO: 2 comprises an amino acid variant at position 93 (IMGT position 110). In some embodiments, a VL comprising the amino acid sequence set forth in SEQ ID NO: 2 comprises an amino acid variant at position 96 (IMGT position 115).

In some embodiments, a VL comprising the amino acid sequence set forth in SEQ ID NO: 2 comprises an amino acid variant at position 26 (IMGT position 27) and between 1-7 additional variant amino acids. In some embodiments, a VL comprising the amino acid sequence set forth in SEQ ID NO: 2 comprises an amino acid variant at position 27 (IMGT position 28) and between 1-7 additional variant amino acids. In some embodiments, a VL comprising the amino acid sequence set forth in SEQ ID NO: 2 comprises an amino acid variant at position 31 (IMGT position 38) and between 1-7 additional variant amino acids. In some embodiments, a VL comprising the amino acid sequence set forth in SEQ ID NO: 2 comprises an amino acid variant at position 51 (IMGT position 65) and between 1-7 additional variant amino acids. In some embodiments, a VL comprising the amino acid sequence set forth in SEQ ID NO: 2 comprises an amino acid variant at position 56 (IMGT position 70) and between 1-7 additional variant amino acids. In some embodiments, a VL comprising the amino acid sequence set forth in SEQ ID NO: 2 comprises an amino acid variant at position 77 (IMGT position 94) and between 1-7 additional variant amino acids. In some embodiments, a VL comprising the amino acid sequence set forth in SEQ ID NO: 2 comprises an amino acid variant at position 92 (IMGT position 109) and between 1-7 additional variant amino acids. In some embodiments, a VL comprising the amino acid sequence set forth in SEQ ID NO: 2 comprises an amino acid variant at position 93 (IMGT position 110) and between 1-7 additional variant amino acids. In some embodiments, a VL comprising the amino acid sequence set forth in SEQ ID NO: 2 comprises an amino acid variant at position 96 (IMGT position 115) and between 1-7 additional variant amino acids.

In some embodiments, a VL comprising the amino acid sequence set forth in SEQ ID NO: 2 comprises an amino acid variant at positions 26, 27, 31, 56, 77, and 96 (IMGT positions 27, 28, 38, 70, 94, and 115). In some embodiments, a VL comprising the amino acid sequence set forth in SEQ ID NO: 2 comprises an amino acid variant at positions 26, 27, 31, 56, 77, 92, and 96 (IMGT positions 27, 28, 38, 70, 94, 109, and 115). In some embodiments, a VL comprising the amino acid sequence set forth in SEQ ID NO: 2 comprises an amino acid variant at positions 26, 31, 56, and 77 (IMGT positions 27, 38, 70, and 94). In some embodiments, a VL comprising the amino acid sequence set forth in SEQ ID NO: 2 comprises an amino acid variant at positions 26, 27, 31, 56, and 77 (IMGT positions 27, 28, 38, 70, and 94). In some embodiments, a VL comprising the amino acid sequence set forth in SEQ ID NO: 2 comprises an amino acid variant at positions 26, 27, 31, 56, 77, and 92 (IMGT positions 27, 28, 38, 70, 94, and 109). In some embodiments, a VL comprising the amino acid sequence set forth in SEQ ID NO: 2 comprises an amino acid variant at positions 26, 27, 31, 51, 56, 77, and 92 (IMGT positions 27, 28, 38, 65, 70, 94, and 109). In some embodiments, a VL comprising the amino acid sequence set forth in SEQ ID NO: 2 comprises an amino acid variant at positions 26, 31, 56, 77, 92, and 96 (IMGT positions 27, 38, 70, 94, 109, and 115). In some embodiments, a VL comprising the amino acid sequence set forth in SEQ ID NO: 2 comprises an amino acid variant at positions 26, 31, 77, and 92 (IMGT positions 27, 38, 94, and 109). In some embodiments, a VL comprising the amino acid sequence set forth in SEQ ID NO: 2 comprises an amino acid variant at positions 26, 27, 31, 56, 77, and 93 (IMGT positions 27, 28, 38, 70, 94, and 110). In some embodiments, a VL comprising the amino acid sequence set forth in SEQ ID NO: 2 comprises an amino acid variant at positions 26, 27, 31, 56, 77, 93, and 96 (IMGT positions 27, 28, 38, 70, 94, 110, and 115). In some embodiments, a VL comprising the amino acid sequence set forth in SEQ ID NO: 2 comprises an amino acid variant at positions 26, 27, 31, 51, 77, 93, and 96 (IMGT positions 27, 28, 38, 65, 94, 110, and 115). In some embodiments, a VL comprising the amino acid sequence set forth in SEQ ID NO: 2 comprises an amino acid variant at positions 26, 27, 31, 56, 77, 93, and 96 (IMGT positions 27, 28, 38, 70, 94, 110, and 115). In some embodiments, a VL comprising the amino acid sequence set forth in SEQ ID NO: 2 comprises an amino acid variant at positions 27, 31, 56, 77, and 96 (IMGT positions 28, 38, 70, 94, and 115). In some embodiments, a VL comprising the amino acid sequence set forth in SEQ ID NO: 2 comprises an amino acid variant at positions 27, 31, 56, 77, 92, and 96 (IMGT positions 28, 38, 70, 94, 109, and 115). In some embodiments, a VL comprising the amino acid sequence set forth in SEQ ID NO: 2 comprises an amino acid variant at positions 26, 27, 31, 51, 77, and 96 (IMGT positions 27, 28, 38, 65, 94, and 115). In some embodiments, a VL comprising the amino acid sequence set forth in SEQ ID NO: 2 comprises an amino acid variant at positions 26, 27, 31, or 96 (IMGT positions 27, 28, 38, and 115), or any combination thereof.

In some embodiments, a VL comprising the amino acid sequence set forth in SEQ ID NO: 2 comprises amino acid variants at positions in a framework region at any of positions 56 or 77 of SEQ ID NO: 2, or a combination thereof (IMGT positions: 70 or 94, or a combination thereof). In some embodiments, a VL comprising the amino acid sequence set forth in SEQ ID NO: 2 comprises at least one amino acid variant at a position within a framework region at any of positions 56 or 77 of SEQ ID NO: 2, or a combination thereof (IMGT positions: 70 or 94, or a combination thereof), wherein the variant amino acid at position 56 comprises a leucine, an alanine, an arginine, a lysine, an aspartic acid, a glycine, or a glutamic acid, and or the variant amino acid at position 77 comprises a valine.

In some embodiments, disclosed herein is an isolated dual binding antibody comprising: a heavy chain variable region comprising the amino acid sequence set forth in SEQ ID NO: 1 with at least one amino acid variant at any of positions (IMGT) 57, 107, 108, 109, 110, 111, 111A, 112A, 112, 113, 114, or 117, or a combination thereof; and a light chain variable region comprising the amino acid sequence set forth in SEQ ID NO: 2 with at least one amino acid variant at any of positions (IMGT) 27, 28, 38, 65, 70, 94, 109, 110, or 115, or a combination thereof; wherein the total number of variant positions in said dual binding antibody is at least 2.

In some embodiments, an isolated dual binding antibody comprises a variant VH or a variant VL, or a combination thereof, with variant amino acids at positions other than (IMGT) 57, 107, 108, 109, 110, 111, 111A, 112A, 112, 113, 114, or 117 in the heavy chain variable region and or (IMGT) 27, 28, 38, 65, 70, 94, 109, 110, or 115 in the light chain variable region.

In some embodiments, an at least one amino acid variant in a VH comprises a variant amino acid in a CDR region. In some embodiments, an at least one amino acid variant in a VH comprises a variant amino acid in a CDR1 region. In some embodiments, an at least one amino acid variant in a VH comprises a variant amino acid in a CDR2 region. In some embodiments, an at least one amino acid variant in a VH comprises a variant amino acid in a CDR3. In some embodiments, an at least two amino acid variants in a VH comprises variant amino acids in two different CDR regions. In some embodiments, an at least two amino acid variants in a VH comprises variant amino acids in a same CDR region. In some embodiments, an at least two amino acid variants in a VH comprises variant amino acids in a same CDR1 region. In some embodiments, an at least two amino acid variants in a VH comprises variant amino acids in a same CDR2 region. In some embodiments, an at least two amino acid variants in a VH comprises variant amino acids in a same CDR3 region. In some embodiments, an at least two amino acid variants in a VH comprises variant amino acids in a CDR1 and a CDR2 region. In some embodiments, an at least two amino acid variants in a VH comprises variant amino acids in a CDR1 and a CDR3 region. In some embodiments, an at least two amino acid variants in a VH comprises variant amino acids in a CDR2 and a CDR3 region. In some embodiments, an at least three amino acid variants in a VH comprises variant amino acids in a single CDR region. In some embodiments, an at least three amino acid variants in a VH comprises variant amino acids in a CDR1 region. In some embodiments, an at least three amino acid variants in a VH comprises variant amino acids in a CDR2 region. In some embodiments, an at least three amino acid variants in a VH comprises variant amino acids in a CDR3 region. In some embodiments, an at least three amino acid variants in a VH comprises variant amino acids in a CDR1 region and a CDR2 region. In some embodiments, an at least three amino acid variants in a VH comprises variant amino acids in a CDR1 region and a CDR3 region. In some embodiments, an at least three amino acid variants in a VH comprises variant amino acids in a CDR2 region and a CDR3 region. In some embodiments, an at least three amino acid variants in a VH comprises variant amino acids in a CDR1 region, a CDR2 region, and a CDR3 region. In some embodiments, an at least 4 amino acid variants in a VH comprises variant amino acids in a single CDR region. In some embodiments, an at least 4 amino acid variants in a VH comprises variant amino acids in a CDR1 region. In some embodiments, an at least 4 amino acid variants in a VH comprises variant amino acids in a CDR2 region. In some embodiments, an at least 4 amino acid variants in a VH comprises variant amino acids in a CDR3 region. In some embodiments, an at least 4 amino acid variants in a VH comprises variant amino acids in a CDR1 region and a CDR2 region. In some embodiments, an at least 4 amino acid variants in a VH comprises variant amino acids in a CDR1 region and a CDR3 region. In some embodiments, an at least 4 amino acid variants in a VH comprises variant amino acids in a CDR2 region and a CDR3 region. In some embodiments, an at least 4 amino acid variants in a VH comprises variant amino acids in a CDR1 region, a CDR2 region, and a CDR3 region. In some embodiments, when there are 5 or more amino acid variants in a VH, variant positions comprise variant amino acids in a single CDR region. In some embodiments, when there are 5 or more amino acid variants in a VH, variant positions comprise amino acids in a CDR1 region. In some embodiments, when there are 5 or more amino acid variants in a VH, variant positions comprise variant amino acids in a CDR2 region. In some embodiments, when there are 5 or more amino acid variants in a VH, variant positions comprise variant amino acids in a CDR3 region. In some embodiments, when there are 5 or more amino acid variants in a VH, variant positions comprise variant amino acids in a CDR1 region and a CDR2 region. In some embodiments, when there are 5 or more amino acid variants in a VH, variant positions comprise variant amino acids in a CDR1 region and a CDR3 region. In some embodiments, when there are 5 or more amino acid variants in a VH, variant positions comprise variant amino acids in a CDR2 region and a CDR3 region. In some embodiments, when there are 5 or more amino acid variants in a VH, variant positions comprise variant amino acids in a CDR1 region, a CDR2 region, and a CDR3 region.

In some embodiments, an at least one amino acid variant in a VL comprises a variant amino acid in a CDR region. In some embodiments, an at least one amino acid variant in a VL comprises a variant amino acid in a CDR1 region. In some embodiments, an at least one amino acid variant in a VL comprises a variant amino acid in a CDR2 region. In some embodiments, an at least one amino acid variant in a VL comprises a variant amino acid in a CDR3. In some embodiments, an at least two amino acid variants in a VL comprises variant amino acids in two different CDR regions. In some embodiments, an at least two amino acid variants in a VL comprises variant amino acids in a same CDR region. In some embodiments, an at least two amino acid variants in a VL comprises variant amino acids in a same CDR1 region. In some embodiments, an at least two amino acid variants in a VL comprises variant amino acids in a same CDR2 region. In some embodiments, an at least two amino acid variants in a VL comprises variant amino acids in a same CDR3 region. In some embodiments, an at least two amino acid variants in a VL comprises variant amino acids in a CDR1 and a CDR2 region. In some embodiments, an at least two amino acid variants in a VL comprises variant amino acids in a CDR1 and a CDR3 region. In some embodiments, an at least two amino acid variants in a VL comprises variant amino acids in a CDR2 and a CDR3 region. In some embodiments, an at least three amino acid variants in a VL comprises variant amino acids in a single CDR region. In some embodiments, an at least three amino acid variants in a VL comprises variant amino acids in a CDR1 region. In some embodiments, an at least three amino acid variants in a VL comprises variant amino acids in a CDR2 region. In some embodiments, an at least three amino acid variants in a VL comprises variant amino acids in a CDR3 region. In some embodiments, an at least three amino acid variants in a VL comprises variant amino acids in a CDR1 region and a CDR2 region. In some embodiments, an at least three amino acid variants in a VL comprises variant amino acids in a CDR1 region and a CDR3 region. In some embodiments, an at least three amino acid variants in a VL comprises variant amino acids in a CDR2 region and a CDR3 region. In some embodiments, an at least three amino acid variants in a VL comprises variant amino acids in a CDR1 region, a CDR2 region, and a CDR3 region. In some embodiments, an at least 4 amino acid variants in a VL comprises variant amino acids in a single CDR region. In some embodiments, an at least 4 amino acid variants in a VL comprises variant amino acids in a CDR1 region. In some embodiments, an at least 4 amino acid variants in a VL comprises variant amino acids in a CDR2 region. In some embodiments, an at least 4 amino acid variants in a VL comprises variant amino acids in a CDR3 region. In some embodiments, an at least 4 amino acid variants in a VL comprises variant amino acids in a CDR1 region and a CDR2 region. In some embodiments, an at least 4 amino acid variants in a VL comprises variant amino acids in a CDR1 region and a CDR3 region. In some embodiments, an at least 4 amino acid variants in a VL comprises variant amino acids in a CDR2 region and a CDR3 region. In some embodiments, an at least 4 amino acid variants in a VL comprises variant amino acids in a CDR1 region, a CDR2 region, and a CDR3 region. In some embodiments, when there are 5 amino acid variants in a VL, variant positions comprise variant amino acids in a single CDR region. In some embodiments, when there are 5 amino acid variants in a VL, variant positions comprise amino acids in a CDR1 region. In some embodiments, when there are 5 amino acid variants in a VL, variant positions comprise variant amino acids in a CDR2 region. In some embodiments, when there are 5 amino acid variants in a VL, variant positions comprise variant amino acids in a CDR3 region. In some embodiments, when there are 5 amino acid variants in a VL, variant positions comprise variant amino acids in a CDR1 region and a CDR2 region. In some embodiments, when there are 5 amino acid variants in a VL, variant positions comprise variant amino acids in a CDR1 region and a CDR3 region. In some embodiments, when there are 5 amino acid variants in a VL, variant positions comprise variant amino acids in a CDR2 region and a CDR3 region. In some embodiments, when there are 5 amino acid variants in a VL, variant positions comprise variant amino acids in a CDR1 region, a CDR2 region, and a CDR3 region. In some embodiments, when there are 6 amino acid variants in a VL, variant positions comprise variant amino acids in a single CDR region. In some embodiments, when there are 6 amino acid variants in a VL, variant positions comprise amino acids in a CDR1 region. In some embodiments, when there are 6 amino acid variants in a VL, variant positions comprise variant amino acids in a CDR2 region. In some embodiments, when there are 6 amino acid variants in a VL, variant positions comprise variant amino acids in a CDR3 region. In some embodiments, when there are 6 amino acid variants in a VL, variant positions comprise variant amino acids in a CDR1 region and a CDR2 region. In some embodiments, when there are 6 amino acid variants in a VL, variant positions comprise variant amino acids in a CDR1 region and a CDR3 region. In some embodiments, when there are 6 amino acid variants in a VL, variant positions comprise variant amino acids in a CDR2 region and a CDR3 region. In some embodiments, when there are 6 amino acid variants in a VL, variant positions comprise variant amino acids in a CDR1 region, a CDR2 region, and a CDR3 region. In some embodiments, when there are 7 or more amino acid variants in a VL, variant positions comprise variant amino acids in a single CDR region. In some embodiments, when there are 7 or more amino acid variants in a VL, variant positions comprise amino acids in a CDR1 region. In some embodiments, when there are 7 or more amino acid variants in a VL, variant positions comprise variant amino acids in a CDR2 region. In some embodiments, when there are 7 or more amino acid variants in a VL, variant positions comprise variant amino acids in a CDR3 region. In some embodiments, when there are 7 or more amino acid variants in a VL, variant positions comprise variant amino acids in a CDR1 region and a CDR2 region. In some embodiments, when there are 7 or more amino acid variants in a VL, variant positions comprise variant amino acids in a CDR1 region and a CDR3 region. In some embodiments, when there are 7 or more amino acid variants in a VL, variant positions comprise variant amino acids in a CDR2 region and a CDR3 region. In some embodiments, when there are 7 or more amino acid variants in a VL, variant positions comprise variant amino acids in a CDR1 region, a CDR2 region, and a CDR3 region.

In some embodiments, an amino acid variant comprises a substitution of one amino acid residue for another. In some embodiments, an amino acid variant comprises a substitution of a hydrophobic residue for a non-hydrophobic residue. In some embodiments, an amino acid variant comprises a substitution of a charged residue for a non-charged residue. In some embodiments, an amino acid variant comprises a neutral substitution, wherein the amino acid being substituted has similar qualities. In some embodiments, an amino acid variant comprises a substitution of an aromatic residue for a non-aromatic residue. In some embodiments, natural aromatic amino acids such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, a variant substitution comprises substituting a modified amino acid or a non-amino acid monomer (e.g. fatty acid, complex carbohydrates etc.). A skilled artisan would appreciate that while the choice of amino acid residues at each variant position may in certain embodiments, affect the 3D structure of the VH, VL, and/or combination thereof, the choice of amino acid residues at each variant position is considered independently.

In some embodiments, "amino acid" or "amino acid residue" or "residue" is understood to include the 20 naturally occurring, encoded amino acid residues, and those amino acids often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In some embodiments, "amino acid" includes both D- and L-amino acid. In some embodiments, an amino acid variant substitution is a D-amino acid. In some embodiments, an amino acid variant substitution is an L-amino acid. In some embodiments, a variant residue comprises a naturally occurring amino acid. In some embodiments, a variant residue comprises a naturally occurring, encoded amino acid residue. In some embodiments, a variant residue comprises a naturally occurring, non-encoded amino acid residue. In some embodiments, a variant residue comprises a non-naturally occurring amino acid.

In some embodiments, a variant residue comprises a non-naturally occurring, non-proteinogenic amino acid.

In some embodiments, the amino acid sequence of a VH domain of the dual binding antibody is selected from, but not limited to, the sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54. In some embodiments, an isolated dual binding antibody comprises a heavy chain variable region comprising the amino acid sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54; and any variable light chain region. In some embodiments, an isolated dual binding antibody comprises a heavy chain variable region comprising the amino acid sequences set forth in SEQ ID NOs: 4 and any variable light chain region. In some embodiments, an isolated dual binding antibody comprises a heavy chain variable region comprising the amino acid sequences set forth in SEQ ID NOs: 6 and any variable light chain region. In some embodiments, an isolated dual binding antibody comprises a heavy chain variable region comprising the amino acid sequences set forth in SEQ ID NOs: 8 and any variable light chain region. In some embodiments, an isolated dual binding antibody comprises a heavy chain variable region comprising the amino acid sequences set forth in SEQ ID NOs: 10 and any variable light chain region. In some embodiments, an isolated dual binding antibody comprises a heavy chain variable region comprising the amino acid sequences set forth in SEQ ID NOs: 12 and any variable light chain region. In some embodiments, an isolated dual binding antibody comprises a heavy chain variable region comprising the amino acid sequences set forth in SEQ ID NOs: 14 and any variable light chain region. In some embodiments, an isolated dual binding antibody comprises a heavy chain variable region comprising the amino acid sequences set forth in SEQ ID NOs: 16 and any variable light chain region. In some embodiments, an isolated dual binding antibody comprises a heavy chain variable region comprising the amino acid sequences set forth in SEQ ID NOs:18 and any variable light chain region. In some embodiments, an isolated dual binding antibody comprises a heavy chain variable region comprising the amino acid sequences set forth in SEQ ID NOs: 20 and any variable light chain region. In some embodiments, an isolated dual binding antibody comprises a heavy chain variable region comprising the amino acid sequences set forth in SEQ ID NOs: 22 and any variable light chain region. In some embodiments, an isolated dual binding antibody comprises a heavy chain variable region comprising the amino acid sequences set forth in SEQ ID NOs: 24 and any variable light chain region. In some embodiments, an isolated dual binding antibody comprises a heavy chain variable region comprising the amino acid sequences set forth in SEQ ID NOs: 26 and any variable light chain region. In some embodiments, an isolated dual binding antibody comprises a heavy chain variable region comprising the amino acid sequences set forth in SEQ ID NOs: 28 and any variable light chain region. In some embodiments, an isolated dual binding antibody comprises a heavy chain variable region comprising the amino acid sequences set forth in SEQ ID NOs: 30 and any variable light chain region. In some embodiments, an isolated dual binding antibody comprises a heavy chain variable region comprising the amino acid sequences set forth in SEQ ID NOs: 32 and any variable light chain region. In some embodiments, an isolated dual binding antibody comprises a heavy chain variable region comprising the amino acid sequences set forth in SEQ ID NOs: 34 and any variable light chain region. In some embodiments, an isolated dual binding antibody comprises a heavy chain variable region comprising the amino acid sequences set forth in SEQ ID NOs: 36 and any variable light chain region. In some embodiments, an isolated dual binding antibody comprises a heavy chain variable region comprising the amino acid sequences set forth in SEQ ID NOs: 38 and any variable light chain region. In some embodiments, an isolated dual binding antibody comprises a heavy chain variable region comprising the amino acid sequences set forth in SEQ ID NOs: 40 and any variable light chain region. In some embodiments, an isolated dual binding antibody comprises a heavy chain variable region comprising the amino acid sequences set forth in SEQ ID NOs: 42 and any variable light chain region. In some embodiments, an isolated dual binding antibody comprises a heavy chain variable region comprising the amino acid sequences set forth in SEQ ID NOs: 44 and any variable light chain region. In some embodiments, an isolated dual binding antibody comprises a heavy chain variable region comprising the amino acid sequences set forth in SEQ ID NOs: 46 and any variable light chain region. In some embodiments, an isolated dual binding antibody comprises a heavy chain variable region comprising the amino acid sequences set forth in SEQ ID NOs: 48 and any variable light chain region. In some embodiments, an isolated dual binding antibody comprises a heavy chain variable region comprising the amino acid sequences set forth in SEQ ID NOs: 50 and any variable light chain region. In some embodiments, an isolated dual binding antibody comprises a heavy chain variable region comprising the amino acid sequences set forth in SEQ ID NOs: 52 and any variable light chain region. In some embodiments, an isolated dual binding antibody comprises a heavy chain variable region comprising the amino acid sequences set forth in SEQ ID NOs: 54 and any variable light chain region.

In some embodiments, the amino acid sequence of a VH domain of the dual binding antibody is one of those set forth in Table 1 or Table 10. In some embodiments, an isolated dual binding antibody comprises a heavy chain variable region comprising one of the amino acid sequences set forth in Table 1 or Table 10; and any variable light chain region.

In some embodiments, the amino acid sequence of a VL domain of the dual binding antibody is selected from, but not limited to, the sequences set forth in any of SEQ ID NOs: 3, 5, 7, 9, 11, 13, 15, 17, 19 21, 23, 25, 27, 29, 31, 33, 35, 37, 39, 41, 43, 45, 47, 49, 51, and 53. In some embodiments, an isolated dual binding antibody comprises a light chain variable region comprising the amino acid sequences set forth in any of SEQ ID NOs: 3, 5, 7, 9, 11, 13, 15, 17, 19 21, 23, 25, 27, 29, 31, 33, 35, 37, 39, 41, 43, 45, 47, 49, 51, and 53; and any variable heavy chain region. In some embodiments, an isolated dual binding antibody comprises a light chain variable region comprising the amino acid sequences set forth in SEQ ID NOs: 3 and any variable heavy chain region. In some embodiments, an isolated dual binding antibody comprises a light chain variable region comprising the amino acid sequences set forth in SEQ ID NOs: 5 and any variable heavy chain region. In some embodiments, an isolated dual binding antibody comprises a light chain variable region comprising the amino acid sequences set forth in SEQ ID NOs: 7 and any variable heavy chain region. In some embodiments, an isolated dual binding antibody comprises a light chain variable region comprising the amino acid sequences set forth in SEQ ID NOs: 9 and any variable heavy chain region. In some embodiments, an isolated dual binding antibody comprises a light chain variable region comprising the amino acid sequences set forth in SEQ ID NOs: 11 and any variable heavy chain region. In some embodiments, an isolated dual binding antibody comprises a light chain variable region comprising the amino acid sequences set forth in SEQ ID NOs: 13 and any variable heavy chain region. In some embodiments, an isolated dual binding antibody comprises a light chain variable region comprising the amino acid sequences set forth in SEQ ID NOs: 15 and any variable heavy chain region. In some embodiments, an isolated dual binding antibody comprises a light chain variable region comprising the amino acid sequences set forth in SEQ ID NOs: 17 and any variable heavy chain region. In some embodiments, an isolated dual binding antibody comprises a light chain variable region comprising the amino acid sequences set forth in SEQ ID NOs: 19 and any variable heavy chain region. In some embodiments, an isolated dual binding antibody comprises a light chain variable region comprising the amino acid sequences set forth in SEQ ID NOs: 21 and any variable heavy chain region. In some embodiments, an isolated dual binding antibody comprises a light chain variable region comprising the amino acid sequences set forth in SEQ ID NOs: 23 and any variable heavy chain region. In some embodiments, an isolated dual binding antibody comprises a light chain variable region comprising the amino acid sequences set forth in SEQ ID NOs: 25 and any variable heavy chain region. In some embodiments, an isolated dual binding antibody comprises a light chain variable region comprising the amino acid sequences set forth in SEQ ID NOs: 27 and any variable heavy chain region. In some embodiments, an isolated dual binding antibody comprises a light chain variable region comprising the amino acid sequences set forth in SEQ ID NOs: 29 and any variable heavy chain region. In some embodiments, an isolated dual binding antibody comprises a light chain variable region comprising the amino acid sequences set forth in SEQ ID NOs: 31 and any variable heavy chain region. In some embodiments, an isolated dual binding antibody comprises a light chain variable region comprising the amino acid sequences set forth in SEQ ID NOs: 33 and any variable heavy chain region. In some embodiments, an isolated dual binding antibody comprises a light chain variable region comprising the amino acid sequences set forth in SEQ ID NOs: 35 and any variable heavy chain region. In some embodiments, an isolated dual binding antibody comprises a light chain variable region comprising the amino acid sequences set forth in SEQ ID NOs: 37 and any variable heavy chain region. In some embodiments, an isolated dual binding antibody comprises a light chain variable region comprising the amino acid sequences set forth in SEQ ID NOs: 39 and any variable heavy chain region. In some embodiments, an isolated dual binding antibody comprises a light chain variable region comprising the amino acid sequences set forth in SEQ ID NOs: 42 and any variable heavy chain region. In some embodiments, an isolated dual binding antibody comprises a light chain variable region comprising the amino acid sequences set forth in SEQ ID NOs: 43 and any variable heavy chain region. In some embodiments, an isolated dual binding antibody comprises a light chain variable region comprising the amino acid sequences set forth in SEQ ID NOs: 45 and any variable heavy chain region. In some embodiments, an isolated dual binding antibody comprises a light chain variable region comprising the amino acid sequences set forth in SEQ ID NOs: 47 and any variable heavy chain region. In some embodiments, an isolated dual binding antibody comprises a light chain variable region comprising the amino acid sequences set forth in SEQ ID NOs: 49 and any variable heavy chain region. In some embodiments, an isolated dual binding antibody comprises a light chain variable region comprising the amino acid sequences set forth in SEQ ID NOs: 51 and any variable heavy chain region. In some embodiments, an isolated dual binding antibody comprises a light chain variable region comprising the amino acid sequences set forth in SEQ ID NOs: 53 and any variable heavy chain region.

In some embodiments, the amino acid sequence of a VL domain of the dual binding antibody is one of those set forth Table 1 or Table 10. In some embodiments, an isolated dual binding antibody comprises a light chain variable region comprising one of the amino acid sequences set forth in Table 1 or Table 10; and any variable heavy chain region.

A skilled artisan would recognize that when pairing a VH or VL domain comprising a known amino acid sequence, with a VL or VH domain, respectively, to comprise an antigen binding region, such a pairing may be analyzed for binding properties using methods well known in the art (See for example, the disclosure herein and Examples below).

In some embodiments, the amino acid sequence of a heavy chain variable region—light chain variable region pair are selected from, but not limited to, the pair sequences set forth in SEQ ID NOs: 4 and 3, SEQ ID Nos: 6 and 5, SEQ ID Nos: 8 and 7, SEQ ID Nos: 10 and 9, SEQ ID Nos: 12 and 11, SEQ ID Nos: 14 and 13, SEQ ID Nos: 16 and 15, SEQ ID Nos: 18 and 17, SEQ ID Nos: 20 and 19, SEQ ID Nos: 22 and 21, SEQ ID Nos: 24 and 23, SEQ ID Nos: 26 and 25, SEQ ID Nos: 28 and 27, SEQ ID Nos: 30 and 29, SEQ ID Nos: 32 and 31, SEQ ID Nos: 34 and 33, SEQ ID Nos: 36 and 35, SEQ ID Nos: 38 and 37, SEQ ID Nos: 40 and 39, SEQ ID Nos: 42 and 41, SEQ ID Nos: 44 and 43, SEQ ID Nos: 46 and 45, SEQ ID Nos: 48 and 47, SEQ ID Nos: 50 and 49, SEQ ID Nos: 52 and 51, and SEQ ID Nos: 54 and 53. In some embodiments, an isolated dual binding antibody comprises a heavy chain variable region-light chain variable region pair are selected from the pair sequences set forth in SEQ ID NOs: 4 and 3. In some embodiments, an isolated dual binding antibody comprises a heavy chain variable region-light chain variable region pair are selected from the pair sequences set forth in SEQ ID NOs: SEQ ID Nos: 6 and 5. In some embodiments, an isolated dual binding antibody comprises a heavy chain variable region-light chain variable region pair are selected from the pair sequences set forth in SEQ ID NOs: SEQ ID Nos: 8 and 7. In some embodiments, an isolated dual binding antibody comprises a heavy chain variable region-light chain variable region pair are selected from the pair sequences set forth in SEQ ID NOs: SEQ ID Nos: 10 and 9. In some embodiments, an isolated dual binding antibody comprises a heavy chain variable region-light chain variable region pair are selected from the pair sequences set forth in SEQ ID NOs: SEQ ID Nos: 12 and 11. In some embodiments, an isolated dual binding antibody comprises a heavy chain variable region-light chain variable region pair are selected from the pair sequences set forth in SEQ ID NOs: SEQ ID Nos: 14 and 13. In some embodiments, an isolated dual binding antibody comprises a heavy chain variable region-light chain variable region pair are selected from the pair sequences set forth in SEQ ID NOs: SEQ ID Nos: 16 and 15. In some embodiments, an isolated dual binding antibody comprises a heavy chain variable region-light chain variable region pair are selected from the pair sequences set forth in SEQ ID NOs: SEQ ID Nos: 18 and 17. In some embodiments, an isolated dual binding antibody comprises a heavy chain variable region-light chain variable region pair are selected from the pair sequences set forth in SEQ ID NOs: SEQ ID Nos: 20 and 19. In some embodiments, an isolated dual binding antibody comprises a heavy chain variable region-light chain variable region pair are selected from the pair sequences set forth in SEQ ID NOs: SEQ ID Nos: 22 and 21. In some embodiments, an isolated dual binding antibody comprises a heavy chain variable region-light chain variable region pair are selected from the pair sequences set forth in SEQ ID NOs: SEQ ID Nos: 24 and 23. In some embodiments, an isolated dual binding antibody comprises a heavy chain variable region-light chain variable region pair are selected from the pair sequences set forth in SEQ ID NOs: SEQ ID Nos: 26 and 25. In some embodiments, an isolated dual binding antibody comprises a heavy chain variable region-light chain variable region pair are selected from the pair sequences set forth in SEQ ID NOs: SEQ ID Nos: 28 and 27. In some embodiments, an isolated dual binding antibody comprises a heavy chain variable region-light chain variable region pair are selected from the pair sequences set forth in SEQ ID NOs: SEQ ID Nos: 30 and 29. In some embodiments, an isolated dual binding antibody comprises a heavy chain variable region-light chain variable region pair are selected from the pair sequences set forth in SEQ ID NOs: SEQ ID Nos: 32 and 31. In some embodiments, an isolated dual binding antibody comprises a heavy chain variable region-light chain variable region pair are selected from the pair sequences set forth in SEQ ID NOs: SEQ ID Nos: 34 and 33. In some embodiments, an isolated dual binding antibody comprises a heavy chain variable region-light chain variable region pair are selected from the pair sequences set forth in SEQ ID NOs: SEQ ID Nos: 36 and 35. In some embodiments, an isolated dual binding antibody comprises a heavy chain variable region-light chain variable region pair are selected from the pair sequences set forth in SEQ ID NOs: SEQ ID Nos: 38 and 37. In some embodiments, an isolated dual binding antibody comprises a heavy chain variable region-light chain variable region pair are selected from the pair sequences set forth in SEQ ID NOs: SEQ ID Nos: 40 and 39. In some embodiments, an isolated dual binding antibody comprises a heavy chain variable region-light chain variable region pair are selected from the pair sequences set forth in SEQ ID NOs: SEQ ID Nos: 42 and 41. In some embodiments, an isolated dual binding antibody comprises a heavy chain variable region-light chain variable region pair are selected from the pair sequences set forth in SEQ ID NOs: SEQ ID Nos: 44 and 43. In some embodiments, an isolated dual binding antibody comprises a heavy chain variable region-light chain variable region pair are selected from the pair sequences set forth in SEQ ID NOs: SEQ ID Nos: 46 and 45. In some embodiments, an isolated dual binding antibody comprises a heavy chain variable region-light chain variable region pair are selected from the pair sequences set forth in SEQ ID NOs: 48 and 47. In some embodiments, an isolated dual binding antibody comprises a heavy chain variable region-light chain variable region pair are selected from the pair sequences set forth in SEQ ID NOs: 50 and 49. In some embodiments, an isolated dual binding antibody comprises a heavy chain variable region-light chain variable region pair are selected from the pair sequences set forth in SEQ ID NOs: 52 and 51. In some embodiments, an isolated dual binding antibody comprises a heavy chain variable region-light chain variable region pair are selected from the pair sequences set forth in SEQ ID Nos: 54 and 53.

In some embodiments, the amino acid sequences of a heavy chain variable region-light chain variable region pair are selected from the pair sequences set forth in any one of the following: SEQ ID NOs:209 and 210, SEQ ID NOs:211 and 212, SEQ ID NOs:213 and 214, SEQ ID NOs:215 and 216, SEQ ID NOs:217 and 218, SEQ ID NOs:219 and 220, SEQ ID NOs:221 and 222, SEQ ID NOs:223 and 224, SEQ ID NOs:225 and 226, SEQ ID NOs:227 and 228, SEQ ID NOs:229 and 230, SEQ ID NOs:231 and 232, SEQ ID NOs:233 and 234, SEQ ID NOs:235 and 236, SEQ ID NOs:237 and 238, SEQ ID NOs:239 and 240, SEQ ID NOs:241 and 242, SEQ ID NOs:243 and 244, SEQ ID NOs:245 and 246, SEQ ID NOs:247 and 248, SEQ ID NOs:249 and 250, SEQ ID NOs:251 and 252, SEQ ID NOs:253 and 254, SEQ ID NOs:255 and 256, SEQ ID NOs:257 and 258, SEQ ID NOs:259 and 260, SEQ ID NOs:261 and 262, SEQ ID NOs:263 and 264, SEQ ID NOs:265 and 266, SEQ ID NOs:267 and 268, SEQ ID NOs:269 and 270, SEQ ID NOs:271 and 272, SEQ ID NOs:273 and 274, SEQ ID NOs:275 and 276, SEQ ID NOs:277 and 278, SEQ ID NOs:279 and 280, SEQ ID NOs:281 and 282, SEQ ID NOs:283 and 284, SEQ ID NOs:285 and 286, SEQ ID NOs:287 and 288, SEQ ID NOs:289 and 290, SEQ ID NOs:291 and 292, SEQ ID NOs:293 and 294, SEQ ID NOs:295 and 296, SEQ ID NOs:297 and 298, SEQ ID NOs:299 and 300, SEQ ID NOs:301 and 302, SEQ ID NOs:303 and 304, SEQ ID NOs:305 and 306, SEQ ID NOs:307 and 308, SEQ ID NOs:309 and 310, SEQ ID NOs:311 and 312, SEQ ID NOs:313 and 314, SEQ ID NOs:315 and 316, SEQ ID NOs:317 and 318, SEQ ID NOs:319 and 320, SEQ ID NOs:321 and 322, SEQ ID NOs:323 and 324, SEQ ID NOs:325 and 326, SEQ ID NOs:327 and 328, SEQ ID NOs:329 and 330, SEQ ID NOs:331 and 332, SEQ ID NOs:333 and 334, SEQ ID NOs:335 and 336, SEQ ID NOs:337 and 338, SEQ ID NOs:339 and 340, SEQ ID NOs:341 and 342, SEQ ID NOs:343 and 344, SEQ ID NOs:345 and 346, SEQ ID NOs:347 and 348.

In some embodiments, the amino acid sequence of an scFv fragment comprises the pair of sequences set forth in, but not limited to, any of the following pairs: SEQ ID NOs: 4 and 3, SEQ ID Nos: 6 and 5, SEQ ID Nos: 8 and 7, SEQ ID Nos: 10 and 9, SEQ ID Nos: 12 and 11, SEQ ID Nos: 14 and 13, SEQ ID Nos: 16 and 15, SEQ ID Nos: 18 and 17, SEQ ID Nos: 20 and 19, SEQ ID Nos: 22 and 21, SEQ ID Nos: 24 and 23, SEQ ID Nos: 26 and 25, SEQ ID Nos: 28 and 27, SEQ ID Nos: 30 and 29, SEQ ID Nos: 32 and 31, SEQ ID Nos: 34 and 33, SEQ ID Nos: 36 and 35, SEQ ID Nos: 38 and 37, SEQ ID Nos: 40 and 39, SEQ ID Nos: 42 and 41, SEQ ID Nos: 44 and 43, SEQ ID Nos: 46 and 45, SEQ ID Nos: 48 and 47, SEQ ID Nos: 50 and 49, SEQ ID Nos: 52 and 51, and SEQ ID Nos: 54 and 53.

Nucleotide Sequences Encoding Engineered "Re-Epitoped" VH Domains, VL Domains, or Both VH and VL Domains, and Vectors and Host Cells Comprising these Nucleotide Sequences The present disclosure provides dual binding antibodies comprising a VH domain, a VL domain, or both a VH and VL domain, comprising variant amino acid sequences compared with template VH and VL sequences SEQ ID NO: 1 and SEQ ID NO: 2, respectively. As described in detail above, in some embodiments the dual binding antibody comprises a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of heavy chain variable region set forth in (a) and the light chain variable region set forth in (b); wherein the total number of variant positions in the encoded heavy chain variable region, the encoded light chain variable region, or a combination thereof, is at least 2.

In some embodiments, a nucleic acid construct comprising a nucleic acid sequence encodes an isolated dual binding antibody comprises an antibody antigen-binding domain site comprising a VH domain and a VL domain, wherein said VH domain comprises a set of CDRs, HCDR1, HCDR2, and HCDR3 as disclosed herein. In some embodiments, a nucleic acid construct comprising a nucleic acid sequence encodes an isolated dual binding antibody comprises an antibody antigen-binding domain site comprising a VH domain and a VL domain, wherein said VH domain comprises a set of CDRs, HCDR1, HCDR2, and HCDR3 as disclosed in Table 8 or Table 4. In some embodiments, the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7

HX8 HX9 HX10 HX11 F D HX12 (SEQ ID NO: 143), wherein XH2, HX3, HX4, HX5, HX6, HX7, HX8, HX9, HX10, HX11, and HX12 are any amino acid.

In some embodiments, a nucleic acid construct comprising a nucleic acid sequence encodes a VH domain of a dual binding antibody comprises HCDR1 (SEQ ID NO: 136), HCDR2 (SEQ ID NO: 142), and HCDR3 (SEQ ID NO: 143), wherein the VH domain comprises a variant amino acid at, at least one of HX1, HX2, HX3, HX4, HX5, HX6, HX7, HX8, HX9, HX10, HX11, and HX12.

In some embodiments, a nucleic acid construct comprising a nucleic acid sequence encodes a VH domain of a dual binding antibody comprises HCDR1 (SEQ ID NO: 136), HCDR2 (SEQ ID NO: 137) wherein HX1 is selected from the group consisting of W and S; and HCDR3 (SEQ ID NO: 138) wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 Is E, wherein HX11 is A, wherein HX12 is selected from the group consisting of I, L, and M. In certain embodiments, a nucleic acid construct comprising a nucleic acid sequence encoding a dual binding antibody comprising variant amino acids comprising HCDR1 (SEQ ID NO: 136), HCDR2 (SEQ ID NO: 137) wherein HX1 is W, HX2 is selected from the group consisting of A and S, HX3 is P, HX4 is Q, HX5 is W, HX6 is selected from the group consisting of E and M, HX7 is selected from the group consisting of L and W, HX8 is selected from the group consisting of V and T, HX9 is selected from the group consisting of H and A, HX10 is E, HX11 is A, and HX12 is selected from the group I and L.

In some embodiments, a nucleic acid construct comprising a nucleic acid sequence encodes a dual binding antibody comprising a VH domain comprising an HCDR1 (SEQ ID NO: 136), an HCDR2 (SEQ ID NO: 137) wherein HX1 is W, and an HCDR3 (SEQ ID NO: 138) wherein HX2 is A, HX3 is P, HX4 is Q, HX5 is W, HX6 is E, HX7 is L, HX8 is T, HX9 is A, HX10 is E, HX11 is A, and HX12 is I; or an HCDR1 (SEQ ID NO: 136), an HCDR2 (SEQ ID NO: 137) wherein HX1 is W, and an HCDR3 (SEQ ID NO: 138) wherein HX2 is A, HX3 is P, HX4 is Q, HX5 is W, HX6 is M, HX7 is L, HX8 is V, HX9 is A, HX10 is E, HX11 is A, and HX12 is L; or an HCDR1 (SEQ ID NO: 136), an HCDR2 (SEQ ID NO: 137) wherein HX1 is W, and an HCDR3 (SEQ ID NO: 138) wherein HX2 is S, HX3 is P, HX4 is Q, HX5 is W, HX6 is E, HX7 is W, HX8 is V, HX9 is H, HX10 is E, HX11 is A, and HX12 is L.

In some embodiments, a nucleic acid construct comprising a nucleic acid sequence encodes an isolated dual binding antibody comprising an antibody antigen-binding domain site comprising a VH domain and a VL domain, wherein said in some embodiments the VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCDR3 is set forth as Q V W D LX5 LX6 S D LX7 V V (SEQ ID NO; 146), wherein LX5, LX6, and LX7 are any amino acid.

In some embodiments, a nucleic acid construct comprising a nucleic acid sequence encodes a VL domain of a dual binding antibody comprising LCDRs. In some embodiments, a nucleic acid construct comprising a nucleic acid sequence encodes an isolated dual binding antibody comprises an antibody antigen-binding domain site comprising a VH domain and a VL domain, wherein said VL domain comprises a set of CDRs, LCDR1, LCDR2, and LCDR3 as disclosed in Table 9 or Table 5. In some embodiments, the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as D D LX4, wherein LX4 is selected from the group consisting of S and G; and wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G. In certain embodiments, a nucleic acid construct comprising a nucleic acid sequence encodes the isolated dual binding antibody comprising variant amino acids wherein LCDR1 (SEQ ID NO: 139) LX1 is L, LX2 is I, LX3 is L, LCDR2 (D D LX4, wherein LX4 is selected from the group consisting of S and G), LCDR3 (SEQ ID NO: 141) wherein LX5 is S, LX6 is S, and LX7 is selected from the group consisting of H and G.

In some embodiments, a nucleic acid construct comprising a nucleic acid sequence encodes a dual binding antibody comprising a VL domain comprising an LCDR1 (SEQ ID NO: 139) wherein LX1 is L, LX2 is I, and LX3 is L, an LCDR2 (D D LX4, wherein LX4 is S), and LCDR3 (SEQ ID NO: 141) wherein LX5 is S, LX6 is S, and LX7 is G; or an LCDR1 (SEQ ID NO: 139) wherein LX1 is L, LX2 is I, and LX3 is L, an LCDR2 (D D LX4, wherein LX4 is S), and LCDR3 (SEQ ID NO: 141) wherein LX5 is S, LX6 is S, and LX7 is H, or an LCDR1 (SEQ ID NO: 139) wherein LX1 is L, LX2 is I, and LX3 is L, an LCDR2 (D D LX4, wherein LX4 is G), and LCDR3 (SEQ ID NO: 141) wherein LX5 is S, LX6 is S, and LX7 is G.

In some embodiments, a nucleic acid construct comprising a nucleic acid sequence encodes an isolated dual binding antibody comprising an antibody antigen-binding domain site comprising a VH domain and a VL domain comprises a combination of VH domain HCDRs and VL domain LCDRs described above. For example, but not limited to, in certain embodiments, a nucleic acid construct comprising a nucleic acid sequence encodes a VH domain comprising a set of CDRs, HCDR1, HCDR2, and HCDR3, wherein the amino acid sequence of HCDR1 is set forth in SEQ ID NO: 136; wherein the amino acid sequence of HCDR2 is set forth as: I HX1 Y D G S N K (SEQ ID NO: 142), wherein HX1 is any amino acid; and wherein the amino acid sequence of HCDR3 is set forth as: A R HX2 HX3 HX4 HX5 HX6 HX7 HX8 HX9 HX10 HX11 F D HX12 (SEQ ID NO: 143), wherein XH2, HX3, HX4, HX5, HX6, HX7, HX8, HX9, HX10, HX11, and HX12 are any amino acid; and wherein said VL domain comprises a set of CDRs, LCDR1, LCDR2, and LCDR3, wherein the amino acid sequence of LCDR1 is set forth as LX1, LX2, G S K LX3 V (SEQ ID NO: 144), wherein LX1, LX2, and LX3 are any amino acid; wherein the amino acid sequence of LCDR2 is set forth as D D LX4, wherein LX4 is any amino acid; and wherein the amino acid sequence of LCD3 is set forth as Q V W D LX5 LX6 S D LX7 V V (SEQ ID NO; 146), wherein LX5, LX6, and LX7 are any amino acid.

In some embodiments, a nucleic acid construct comprising a nucleic acid sequence encodes a VH domain comprising a set of CDRs, HCDR1, HCDR2, and HCDR3, wherein the amino acid sequence of HCDR1 is set forth in SEQ ID NO: 136, wherein the amino acid sequence of HCDR2 is set forth in SEQ ID NO: 137, wherein HX1 is selected from the group consisting of W and S; wherein the amino acid sequence of HCDR3 is set forth in SEQ ID NO: 138, wherein HX2 is selected from the group consisting of A and S, wherein HX3 is P, wherein HX4 is Q, wherein HX5 is W, wherein HX6 is selected from the group consisting of E, Q, M, L, and V, wherein HX7 is selected from the group consisting of L, W, and Y, wherein HX8 is selected from the group consisting of V and T, wherein HX9 is selected from the group consisting of H, A, S, wherein HX10 is E, wherein HX11 is A, wherein HX12 is selected from the group consisting of I, L, and M; and a VL domain comprises a set of CDRs, HCDR1, HCDR2, and HCDR3, wherein the amino acid sequence of LCDR1 is set forth in SEQ ID NO: 139, wherein LX1 is selected from the group consisting of N, L, and I, wherein LX2 is selected from the group consisting of L and I, wherein LX3 is selected from the group consisting of S and L; wherein the amino acid sequence of LCDR2 is set forth as A D D LX4, wherein LX4 is selected from the group consisting of S and G; wherein the amino acid sequence of LCDR3 is set forth in SEQ ID NO: 141, wherein LX5 is selected from the group consisting of S and T, wherein LX6 is selected from the group consisting of S and G, and wherein LX7 is selected from the group consisting of H and G.

In certain embodiments, a nucleic acid construct comprising a nucleic acid sequence encodes the isolated dual binding antibody comprising a VH domain comprising a set of CDRs, HCDR1, HCDR2, and HCDR3, wherein the amino acid sequence of HCDR1 is set forth in SEQ ID NO: 136, wherein the amino acid sequence of HCDR2 is set forth in SEQ ID NO: 137, wherein HX1 is W, wherein the amino acid sequence of HCDR3 is set forth in SEQ ID NO: 138, wherein HX2 is selected from the group consisting of A and S, HX3 is P, HX4 is Q, HX5 is W, HX6 is selected from the group consisting of E and M, HX7 is selected from the group consisting of L and W, HX8 is selected from the group consisting of V and T, HX9 is selected from the group consisting of H and A, HX10 is E, HX11 is A, HX12 is selected from the group I and L, and comprising a VL domain comprising a set of CDRs, LCDR1, LCDR2, and LCDR3, wherein the amino acid sequence of LCDR1 is set forth in SEQ ID NO: 139 wherein LX1 is L, LX2 is I, LX3 is L, wherein the amino acid sequence of LCDR2 is set forth as D D LX4, wherein LX4 is selected from the group consisting of S and G, wherein the amino acid sequence of LCDR3 is set forth in SEQ ID NO: 141 wherein LX5 is S, LX6 is S, and LX7 is selected from the group consisting of H and G.

In some embodiments, a nucleic acid construct comprising a nucleic acid sequence encodes a re-epitoped dual binding antibody comprising a VH domain comprising a set of CDRs, HCDR1, HCDR2, and HCDR3, and a VL domain comprising a set of CDRs, LCDR1, LCDR2, and LCDR3, wherein the amino acid sequences of each CDR are as set forth in FIGS. 1A and 1B for the clones set forth there, for example but not limited to: Clone C2: HCDR1 (SEQ ID NO: 136), HCDR2 (SEQ ID NO: 137) wherein HX1 is W, HCDR3 (SEQ ID NO: 138) wherein HX2 is A, HX3 is P, HX4 is Q, HX5 is W, HX6 is E, HX7 is L, HX8 is T, HX9 is A, HX10 is E, HX11 is A, HX12 is I, LCDR1 (SEQ ID NO: 139) wherein LX1 is L, LX2 is I, LX3 is L, LCDR2 (D D LX4) wherein LX4 is S), and LCDR3 (SEQ ID NO: 141) wherein LX5 is S, LX6 is S, and LX7 is G;

Clone C6: HCDR1 (SEQ ID NO: 136), HCDR2 (SEQ ID NO: 137) wherein HX1 is W, HCDR3 (SEQ ID NO: 138)

wherein HX2 is A, HX3 is P, HX4 is Q, HX5 is W, HX6 is M, HX7 is L, HX8 is V, HX9 is A, HX10 is E, HX11 is A, HX12 is L, LCDR1 (SEQ ID NO: 139) wherein LX1 is L, LX2 is I, LX3 is L, LCDR2 (D D LX4, wherein LX4 is S, and LCDR3 (SEQ ID NO: 141) wherein LX5 is S, LX6 is S, and LX7 is H; or Clone C9: HCDR1 (SEQ ID NO: 136), HCDR2 (SEQ ID NO: 137) wherein HX1 is W, HCDR3 (SEQ ID NO: 138) wherein HX2 is S, HX3 is P, HX4 is Q, HX5 is W, HX6 is E, HX7 is W, HX8 is V, HX9 is H, HX10 is E, HX11 is A, HX12 is L, LCDR1 (SEQ ID NO: 139) wherein LX1 is L, LX2 is I, LX3 is L, LCDR2 (D D LX4, wherein LX4 is G, and LCDR3 (SEQ ID NO: 141) wherein LX5 is S, LX6 is S, and LX7 is G.

In certain embodiments, a nucleic acid construct comprises a single nucleic acid sequence. In certain embodiments, a nucleic acid construct comprises two nucleic acid sequence. In certain embodiments, a nucleic acid construct comprises a single nucleic acid sequence, wherein a VH domain and a VL domain are encoded by the nucleic acid sequence. In certain embodiments, a nucleic acid construct comprises two nucleic acid sequences, wherein a VH domain is encoded by one nucleic acid sequence, and a VL domain is encoded by the other nucleic acid sequence.

A described herein, the present disclosure provides the polynucleotide sequences encoding the variant VH, VL, or both VH and VL domains described herein. In certain embodiments, the template VH domain is encoded by the nucleotide sequence set forth in SEQ ID NO: 55 and the template VL domain is encoded by the nucleotide sequence set forth in SEQ ID NO: 56.

In some embodiments, disclosed herein is nucleic acid construct, comprising a nucleic acid sequence encoding a dual binding antibody, said antibody comprising: a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of heavy chain variable region set forth in (a) and the light chain variable region set forth in (b); wherein the total number of variant positions in the encoded heavy chain variable region, the encoded light chain variable region, or a combination thereof, is at least 2.

In some embodiments, the nucleotide construct sequence comprises two nucleic acid sequences, one encoding a variant heavy chain variable region, and one a variant light chain variable region. In some embodiments, the nucleotide sequence or sequences encoding the dual binding antibody heavy chain variable region, light chain variable region, or both, is optimized for mammalian transcription and translation.

The present disclosure further provides, in certain embodiments, an isolated nucleic acid construct encoding the nucleic acid sequence as described herein. Illustrative polynucleotide sequence encoding variant VH and VL domains are provided in Table 2 below. Illustrative nucleic acid constructs, comprising a nucleic acid sequence encoding variant VH domains linked to VL domains are provided in Table 3 below.

Nucleic acids include DNA and RNA. These and related embodiments may include polynucleotides encoding the dual binding antibody as described herein. The term "isolated polynucleotide" as used herein shall mean a polynucleotide of genomic, cDNA, or synthetic origin, or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

A skilled artisan would appreciate that the terms "polynucleotide" and "nucleic acid sequence" may in some embodiments be used interchangeably having all the same meanings and qualities.

In some embodiments, isolated nucleic acid sequences disclosed herein, encode a VH domain comprising set of HCDRs as disclosed throughout and in FIG. 1A, a VL domain comprising set of a set of LCDRs as disclosed throughout and in FIG. 1B, a VH domain comprising a set of HCDRs and a VL domain comprising set of set of LCDRs as disclosed throughout and in FIGS. 1A and 1B, a VL domain or a VL domain, or a VH and a VL domain, of a dual binding antibody as described herein throughout in detail.

The term "polynucleotide" as used herein encompasses single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotide" includes deoxyribonucleotides and ribonucleotides. The term "modified nucleotide" includes nucleotides with modified or substituted sugar groups and the like. The term "oligonucleotide linkage" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

In other related embodiments, polynucleotide variants may have substantial identity to a polynucleotide template sequence, though the template sequence does not encode a dual binding antibody, or fragment thereof, or domain thereof.

In some embodiments, polynucleotide variants will contain one or more substitutions, additions, deletions and/or insertions, such that the binding affinity of a binding domain encoded by the variant polynucleotide newly binds to an epitope, relative to the unmodified template as specifically set forth herein.

In some embodiments, a nucleic acid sequence encodes the heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof). In some embodiments, a nucleic acid sequence encodes the heavy chain variable region comprising the amino acid sequence set forth in SEQ ID NO: 1 with at least two amino acid variants at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof). In some embodiments, a nucleic acid sequence encodes the heavy chain variable region comprising the amino acid sequence set forth in SEQ ID NO: 1 with at least 1, 2, 3, 4, 5, 6, 7, 8, 9, or 10 amino acid variants at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, ora combination thereof).

In some embodiments, the nucleic acid construct comprises a nucleic acid sequence encoding a heavy chain variable region comprising a sequence selected from the sequences set forth in SEQ ID Nos: 57, 59, 61, 63, 65, 67, 69, 71, 73, 75, 77, 79, 81, 83, 85, 87, 89, 91, 93, 95, 97, 99, 101, 105, and 107. In some embodiments, the nucleic acid sequence encoding a heavy chain variable region comprises the sequences set forth in SEQ ID Nos: 57. In some embodiments, the nucleic acid sequence encoding a heavy chain variable region comprises the sequences set forth in SEQ ID Nos: 59. In some embodiments, the nucleic acid sequence encoding a heavy chain variable region comprises the sequences set forth in SEQ ID Nos: 61. In some embodiments, the nucleic acid sequence encoding a heavy chain variable region comprises the sequences set forth in SEQ ID Nos: 63. In some embodiments, the nucleic acid sequence encoding a heavy chain variable region comprises the sequences set forth in SEQ ID Nos: 65. In some embodiments, the nucleic acid sequence encoding a heavy chain variable region comprises the sequences set forth in SEQ ID Nos: 67. In some embodiments, the nucleic acid sequence encoding a heavy chain variable region comprises the sequences set forth in SEQ ID Nos: 69. In some embodiments, the nucleic acid sequence encoding a heavy chain variable region comprises the sequences set forth in SEQ ID Nos: 71. In some embodiments, the nucleic acid sequence encoding a heavy chain variable region comprises the sequences set forth in SEQ ID Nos: 73. In some embodiments, the nucleic acid sequence encoding a heavy chain variable region comprises the sequences set forth in SEQ ID Nos: 75. In some embodiments, the nucleic acid sequence encoding a heavy chain variable region comprises the sequences set forth in SEQ ID Nos: 77. In some embodiments, the nucleic acid sequence encoding a heavy chain variable region comprises the sequences set forth in SEQ ID Nos: 79. In some embodiments, the nucleic acid sequence encoding a heavy chain variable region comprises the sequences set forth in SEQ ID Nos: 81. In some embodiments, the nucleic acid sequence encoding a heavy chain variable region comprises the sequences set forth in SEQ ID Nos: 83. In some embodiments, the nucleic acid sequence encoding a heavy chain variable region comprises the sequences set forth in SEQ ID Nos: 85. In some embodiments, the nucleic acid sequence encoding a heavy chain variable region comprises the sequences set forth in SEQ ID Nos: 87. In some embodiments, the nucleic acid sequence encoding a heavy chain variable region comprises the sequences set forth in SEQ ID Nos: 89. In some embodiments, the nucleic acid sequence encoding a heavy chain variable region comprises the sequences set forth in SEQ ID Nos: 91. In some embodiments, the nucleic acid sequence encoding a heavy chain variable region comprises the sequences set forth in SEQ ID Nos: 93. In some embodiments, the nucleic acid sequence encoding a heavy chain variable region comprises the sequences set forth in SEQ ID Nos: 95. In some embodiments, the nucleic acid sequence encoding a heavy chain variable region comprises the sequences set forth in SEQ ID Nos: 97. In some embodiments, the nucleic acid sequence encoding a heavy chain variable region comprises the sequences set forth in SEQ ID Nos: 99. In some embodiments, the nucleic acid sequence encoding a heavy chain variable region comprises the sequences set forth in SEQ ID Nos: 101. In some embodiments, the nucleic acid sequence encoding a heavy chain variable region comprises the sequences set forth in SEQ ID Nos: 105. In some embodiments, the nucleic acid sequence encoding a heavy chain variable region comprises the sequences set forth in SEQ ID Nos: 107.

In some embodiments, the nucleic acid construct comprises a nucleic acid sequence encoding a dual binding antibody heavy chain variable region sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54. In some embodiments, the nucleic acid sequence encodes a dual binding antibody heavy chain variable region sequence set forth in SEQ ID NO: 4. In some embodiments, the nucleic acid sequence encodes a dual binding antibody heavy chain variable region sequence set forth in SEQ ID NO: 6. In some embodiments, the nucleic acid sequence encodes a dual binding antibody heavy chain variable region sequence set forth in SEQ ID NO: 8. In some embodiments, the nucleic acid sequence encodes a dual binding antibody heavy chain variable region sequence set forth in SEQ ID NO: 10. In some embodiments, the nucleic acid sequence encodes a dual binding antibody heavy chain variable region sequence set forth in SEQ ID NO: 12. In some embodiments, the nucleic acid sequence encodes a dual binding antibody heavy chain variable region sequence set forth in SEQ ID NO: 14. In some embodiments, the nucleic acid sequence encodes a dual binding antibody heavy chain variable region sequence set forth in SEQ ID NO: 16. In some embodiments, the nucleic acid sequence encodes a dual binding antibody heavy chain variable region sequence set forth in SEQ ID NO: 18. In some embodiments, the nucleic acid sequence encodes a dual binding antibody heavy chain variable region sequence set forth in SEQ ID NO: 20. In some embodiments, the nucleic acid sequence encodes a dual binding antibody heavy chain variable region sequence set forth in SEQ ID NO: 22. In some embodiments, the nucleic acid sequence encodes a dual binding antibody heavy chain variable region sequence set forth in SEQ ID NO: 24. In some embodiments, the nucleic acid sequence encodes a dual binding antibody heavy chain variable region sequence set forth in SEQ ID NO: 26. In some embodiments, the nucleic acid sequence encodes a dual binding antibody heavy chain variable region sequence set forth in SEQ ID NO: 28. In some embodiments, the nucleic acid sequence encodes a dual binding antibody heavy chain variable region sequence set forth in SEQ ID NO: 30. In some embodiments, the nucleic acid sequence encodes a dual binding antibody heavy chain variable region sequence set forth in SEQ ID NO: 32. In some embodiments, the nucleic acid sequence encodes a dual binding antibody heavy chain variable region sequence set forth in SEQ ID NO: 34. In some embodiments, the nucleic acid sequence encodes a dual binding antibody heavy chain variable region sequence set forth in SEQ ID NO: 36. In some embodiments, the nucleic acid sequence encodes a dual binding antibody heavy chain variable region sequence set forth in SEQ ID NO: 38. In some embodiments, the nucleic acid sequence encodes a dual binding antibody heavy chain variable region sequence set forth in SEQ ID NO: 40. In some embodiments, the nucleic acid sequence encodes a dual binding antibody heavy chain variable region sequence set forth in SEQ ID NO: 42. In some embodiments, the nucleic acid sequence encodes a dual binding antibody heavy chain variable region sequence set forth in SEQ ID NO: 44. In some embodiments, the nucleic acid sequence encodes a dual binding antibody heavy chain variable region sequence set forth in SEQ ID NO: 46. In some embodiments, the nucleic acid sequence encodes a dual binding antibody heavy chain variable region sequence set forth in SEQ ID NO: 48. In some embodiments, the nucleic acid sequence encodes a dual binding antibody heavy chain variable region sequence set forth in SEQ ID NO: 50. In some embodiments, the nucleic acid sequence encodes a dual binding antibody heavy chain variable region sequence set forth in SEQ ID NO: 52. In some embodiments, the nucleic acid sequence encodes a dual binding antibody heavy chain variable region sequence set forth in SEQ ID NO: 54.

In some embodiments, the nucleic acid construct comprises a nucleic acid sequence encoding a dual binding antibody heavy chain variable region sequence set forth in Table 10 or Table 1; for example, the VH may comprise any one of SEQ ID NOs: 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345 and 347. In another embodiment, the nucleic acid construct comprises a nucleic acid sequence encoding a VH that is at least 80%, 85%, 90%, 95%, 98%, or 99% identical to the VH sequences disclosed herein.

In some embodiments, a nucleic acid sequence encodes the light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof). In some embodiments, a nucleic acid sequence encodes the light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof). In some embodiments, a nucleic acid sequence encodes the light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof).

In some embodiments, the nucleic acid construct comprises a nucleic acid sequence encoding a light chain variable region comprising a sequence selected from the sequences set forth in SEQ ID NOs: 58, 60, 62, 64, 66, 68, 70, 72, 74, 76, 78, 80, 82, 84, 86, 88, 90, 92, 94, 96, 98, 100, 102, 104, 106, and 108. In some embodiments, the nucleic acid sequence encoding a light chain variable region comprises the sequences set forth in SEQ ID NO: 58. In some embodiments, the nucleic acid sequence encoding a light chain variable region comprises the sequences set forth in SEQ ID NO: 60. In some embodiments, the nucleic acid sequence encoding a light chain variable region comprises the sequences set forth in SEQ ID NO: 62. In some embodiments, the nucleic acid sequence encoding a light chain variable region comprises the sequences set forth in SEQ ID NO: 64. In some embodiments, the nucleic acid sequence encoding a light chain variable region comprises the sequences set forth in SEQ ID NO: 66. In some embodiments, the nucleic acid sequence encoding a light chain variable region comprises the sequences set forth in SEQ ID NO: 68. In some embodiments, the nucleic acid sequence encoding a light chain variable region comprises the sequences set forth in SEQ ID NO: 70. In some embodiments, the nucleic acid sequence encoding a light chain variable region comprises the sequences set forth in SEQ ID NO: 72. In some embodiments, the nucleic acid sequence encoding a light chain variable region comprises the sequences set forth in SEQ ID NO: 74. In some embodiments, the nucleic acid sequence encoding a light chain variable region comprises the sequences set forth in SEQ ID NO: 76. In some embodiments, the nucleic acid sequence encoding a light chain variable region comprises the sequences set forth in SEQ ID NO: 78. In some embodiments, the nucleic acid sequence encoding a light chain variable region comprises the sequences set forth in SEQ ID NO: 80. In some embodiments, the nucleic acid sequence encoding a light chain variable region comprises the sequences set forth in SEQ ID NO: 82. In some embodiments, the nucleic acid sequence encoding a light chain variable region comprises the sequences set forth in SEQ ID NO: 84. In some embodiments, the nucleic acid sequence encoding a light chain variable region comprises the sequences set forth in SEQ ID NO: 86. In some embodiments, the nucleic acid sequence encoding a light chain variable region comprises the sequences set forth in SEQ ID NO: 88. In some embodiments, the nucleic acid sequence encoding a light chain variable region comprises the sequences set forth in SEQ ID NO: 90. In some embodiments, the nucleic acid sequence encoding a light chain variable region comprises the sequences set forth in SEQ ID NO: 92. In some embodiments, the nucleic acid sequence encoding a light chain variable region comprises the sequences set forth in SEQ ID NO: 94. In some embodiments, the nucleic acid sequence encoding a light chain variable region comprises the sequences set forth in SEQ ID NO: 96. In some embodiments, the nucleic acid sequence encoding a light chain variable region comprises the sequences set forth in SEQ ID NO: 98. In some embodiments, the nucleic acid sequence encoding a light chain variable region comprises the sequences set forth in SEQ ID NO: 100. In some embodiments, the nucleic acid sequence encoding a light chain variable region comprises the sequences set forth in SEQ ID NO: 102. In some embodiments, the nucleic acid sequence encoding a light chain variable region comprises the sequences set forth in SEQ ID NO: 104. In some embodiments, the nucleic acid sequence encoding a light chain variable region comprises the sequences set forth in SEQ ID NO: 106. In some embodiments, the nucleic acid sequence encoding a light chain variable region comprises the sequences set forth in SEQ ID NO: 108.

In some embodiments, the nucleic acid construct comprises a nucleic acid sequence encoding a dual binding antibody light chain variable region sequences set forth in any of SEQ ID NOs: 3, 5, 7, 9, 11, 13, 15, 17, 19, 21, 23, 25, 27, 29, 31, 33, 35, 37, 39, 41, 43, 45, 47, 49, 51, and 53. In some embodiments, the nucleic acid sequence encodes a dual binding antibody light chain variable region sequence set forth in SEQ ID NO: 3. In some embodiments, the nucleic acid sequence encodes a dual binding antibody light chain variable region sequence set forth in SEQ ID NO: 5. In some embodiments, the nucleic acid sequence encodes a dual binding antibody light chain variable region sequence set forth in SEQ ID NO: 7. In some embodiments, the nucleic acid sequence encodes a dual binding antibody light chain variable region sequence set forth in SEQ ID NO: 9. In some embodiments, the nucleic acid sequence encodes a dual binding antibody light chain variable region sequence set forth in SEQ ID NO: 11. In some embodiments, the nucleic acid sequence encodes a dual binding antibody light chain variable region sequence set forth in SEQ ID NO: 13. In some embodiments, the nucleic acid sequence encodes a dual binding antibody light chain variable region sequence set forth in SEQ ID NO: 15. In some embodiments, the nucleic acid sequence encodes a dual binding antibody light chain variable region sequence set forth in SEQ ID NO: 17. In some embodiments, the nucleic acid sequence encodes a dual binding antibody light chain variable region sequence set forth in SEQ ID NO: 19. In some embodiments, the nucleic acid sequence encodes a dual binding antibody light chain variable region sequence set forth in SEQ ID NO: 21. In some embodiments, the nucleic acid sequence encodes a dual binding antibody light chain variable region sequence set forth in SEQ ID NO: 23. In some embodiments, the nucleic acid sequence encodes a dual binding antibody light chain variable region sequence set forth in SEQ ID NO: 25. In some embodiments, the nucleic acid sequence encodes a dual binding antibody light chain variable region sequence set forth in SEQ ID NO: 27. In some embodiments, the nucleic acid sequence encodes a dual binding antibody light chain variable region sequence set forth in SEQ ID NO: 29. In some embodiments, the nucleic acid sequence encodes a dual binding antibody light chain variable region sequence set forth in SEQ ID NO: 31. In some embodiments, the nucleic acid sequence encodes a dual binding antibody light chain variable region sequence set forth in SEQ ID NO: 33. In some embodiments, the nucleic acid sequence encodes a dual binding antibody light chain variable region sequence set forth in SEQ ID NO: 35. In some embodiments, the nucleic acid sequence encodes a dual binding antibody light chain variable region sequence set forth in SEQ ID NO: 37. In some embodiments, the nucleic acid sequence encodes a dual binding antibody light chain variable region sequence set forth in SEQ ID NO: 39. In some embodiments, the nucleic acid sequence encodes a dual binding antibody light chain variable region sequence set forth in SEQ ID NO: 41. In some embodiments, the nucleic acid sequence encodes a dual binding antibody light chain variable region sequence set forth in SEQ ID NO: 43. In some embodiments, the nucleic acid sequence encodes a dual binding antibody light chain variable region sequence set forth in SEQ ID NO: 45. In some embodiments, the nucleic acid sequence encodes a dual binding antibody light chain variable region sequence set forth in SEQ ID NO: 47. In some embodiments, the nucleic acid sequence encodes a dual binding antibody light chain variable region sequence set forth in SEQ ID NO: 49. In some embodiments, the nucleic acid sequence encodes a dual binding antibody light chain variable region sequence set forth in SEQ ID NO: 51. In some embodiments, the nucleic acid sequence encodes a dual binding antibody light chain variable region sequence set forth in SEQ ID NO: 53.

In some embodiments, the nucleic acid construct comprises a nucleic acid sequence encoding a dual binding antibody light chain variable region sequence set forth in Table 10 or Table 1; for example, the VL may comprise one of SEQ ID NOs: 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346 and 348. In another embodiment, the nucleic acid construct comprises a nucleic acid sequence encoding a VL that is at least 80%, 85%, 90%, 95%, 98%, or 99% identical to the VL sequences disclosed herein.

In some embodiments, a nucleic acid construct comprises a nucleic acid sequence encoding a dual binding antibody heavy chain variable region-light chain variable region pair, said nucleic acid sequence selected from the paired sequences set forth in SEQ ID NOs: 57 and 58, SEQ ID Nos: 59 an 60, SEQ ID Nos: 61 and 62, SEQ ID Nos: 63 and 64, SEQ ID Nos: 65 and 66, SEQ ID Nos: 67 and 68, SEQ ID Nos: 69 and 70, SEQ ID Nos: 71 and 72, SEQ ID Nos: 73 and 74, SEQ ID Nos: 75 and 76, SEQ ID Nos: 77 and 78, SEQ ID Nos: 79 and 80, SEQ ID Nos: 81 and 82, SEQ ID Nos: 83 and 84, SEQ ID Nos: 85 and 86, SEQ ID Nos: 87 and 88, SEQ ID Nos: 89 and 90, SEQ ID Nos: 91 and 92, SEQ ID Nos: 93 and 94, SEQ ID Nos: 95 and 96, SEQ ID Nos: 97 and 98, SEQ ID Nos: 99 and 100, SEQ ID Nos: 101 and 102, SEQ ID Nos: 103 and 104, SEQ ID Nos: 105 and 106, and SEQ ID Nos: 107 and 108.

In some embodiments, a nucleic acid construct comprises a nucleic acid sequence encoding a dual binding antibody heavy chain variable region-light chain variable region pair as shown in Table 10 or Table 1; for example, the VH and VL pair can be one of the following: SEQ ID NOs:209 and 210, SEQ ID NOs:211 and 212, SEQ ID NOs:213 and 214, SEQ ID NOs:215 and 216, SEQ ID NOs:217 and 218, SEQ ID NOs:219 and 220, SEQ ID NOs:221 and 222, SEQ ID NOs:223 and 224, SEQ ID NOs:225 and 226, SEQ ID NOs:227 and 228, SEQ ID NOs:229 and 230, SEQ ID NOs:231 and 232, SEQ ID NOs:233 and 234, SEQ ID NOs:235 and 236, SEQ ID NOs:237 and 238, SEQ ID NOs:239 and 240, SEQ ID NOs:241 and 242, SEQ ID NOs:243 and 244, SEQ ID NOs:245 and 246, SEQ ID NOs:247 and 248, SEQ ID NOs:249 and 250, SEQ ID NOs:251 and 252, SEQ ID NOs:253 and 254, SEQ ID NOs:255 and 256, SEQ ID NOs:257 and 258, SEQ ID NOs:259 and 260, SEQ ID NOs:261 and 262, SEQ ID NOs:263 and 264, SEQ ID NOs:265 and 266, SEQ ID NOs:267 and 268, SEQ ID NOs:269 and 270, SEQ ID NOs:271 and 272, SEQ ID NOs:273 and 274, SEQ ID NOs:275 and 276, SEQ ID NOs:277 and 278, SEQ ID NOs:279 and 280, SEQ ID NOs:281 and 282, SEQ ID NOs:283 and 284, SEQ ID NOs:285 and 286, SEQ ID NOs:287 and 288, SEQ ID NOs:289 and 290, SEQ ID NOs:291 and 292, SEQ ID NOs:293 and 294, SEQ ID NOs:295 and 296, SEQ ID NOs:297 and 298, SEQ ID NOs:299 and 300, SEQ ID NOs:301 and 302, SEQ ID NOs:303 and 304, SEQ ID NOs:305 and 306, SEQ ID NOs:307 and 308, SEQ ID NOs:309 and 310, SEQ ID NOs:311 and 312, SEQ ID NOs:313 and 314, SEQ ID NOs:315 and 316, SEQ ID NOs:317 and 318, SEQ ID NOs:319 and 320, SEQ ID NOs:321 and 322, SEQ ID NOs:323 and 324, SEQ ID NOs:325 and 326, SEQ ID NOs:327 and 328, SEQ ID NOs:329 and 330, SEQ ID NOs:331 and 332, SEQ ID NOs:333 and 334, SEQ ID NOs:335 and 336, SEQ ID NOs:337 and 338, SEQ ID NOs:339 and 340, SEQ ID NOs:341 and 342, SEQ ID NOs:343 and 344, SEQ ID NOs:345 and 346, SEQ ID NOs:347 and 348. In another embodiment, the VH and VL pair is at least 80%, 85%, 90%, 95%, 98%, or 99% identical to the VH and VL sequences disclosed herein.

A skilled artisan would appreciate that in some embodiments, the sequence encoding a VH domain and the sequence encoding the VL domain are linked by a sequence encoding a linker sequence. In some embodiments, a nucleic acid sequence encodes a polypeptide linker. ggcggtggtggtagcggaggcggaggatcaggtggaggcggcagt (SEQ ID NO: 148).

In some embodiments, a nucleic acid construct comprises a nucleic acid sequence encoding a dual binding antibody heavy chain variable region-light chain variable region scFv, said nucleic acid sequence selected from the sequences set forth in SEQ ID NOs: 109-135.

In some embodiments, a nucleic acid construct comprising a nucleic acid sequence encoding a dual antibody described herein, encodes an IgG immunoglobulin. In some embodiments, a nucleic acid sequence encoding a dual antibody encodes an IgG1 immunoglobulin, an IgG2 immunoglobulin, an IgG3 immunoglobulin, or an IgG4 immunoglobulin. In some embodiments, a nucleic acid sequence encoding a dual antibody encodes an IgG1 immunoglobulin. In some embodiments, a nucleic acid sequence encoding a dual antibody encodes an IgG2 immunoglobulin. In some embodiments, a nucleic acid sequence encoding a dual antibody encodes an IgG3 immunoglobulin. In some embodiments, a nucleic acid sequence encoding a dual antibody encodes an IgG4 immunoglobulin. In some embodiments, a nucleic acid sequence encoding a dual antibody encodes an IgG1 immunoglobulin or an IgG4 immunoglobulin.

In some embodiments, a nucleic acid sequence encoding a dual antibody encodes an Fab immunoglobulin fragment. In some embodiments, a nucleic acid sequence encoding a dual antibody encodes an F(ab')2 immunoglobulin fragment. In some embodiments, a nucleic acid sequence encoding a dual antibody encodes an Fv immunoglobulin construct. In some embodiments, a nucleic acid sequence encoding a dual antibody encodes an scFv immunoglobulin construct. In some embodiments, a nucleic acid sequence encoding a dual antibody encodes a minibody immunoglobulin construct comprising a pair of single-chain Fv fragments, which are linked via CH3 domains.

In some embodiments, a nucleic acid sequence encoding a dual antibody encodes a diabody immunoglobulin construct. In some embodiments, a diabody immunoglobulin construct comprises a heavy chain variable (VH) and light chain variable (VL) regions connected by a small peptide linker. In some embodiments, a diabody immunoglobulin construct comprises single-chain (Fv) 2 in which two scFv fragments are covalently linked to each other. In some embodiments, a nucleic acid sequence encoding a dual antibody encodes a diabody immunoglobulin construct comprising three scFv fragments covalently linked to each other.

In some embodiments, an isolated polynucleotide construct encodes an isolated dual binding antibody, as disclosed herein.

In some embodiments, a nucleic acid sequence encoding a dual antibody encodes a mutated immunoglobulin. In some embodiments, a nucleic acid sequence encoding a dual antibody encodes a mutant IgG unable to bind antibody-dependent cellular cytotoxicity components. In some embodiments, a nucleic acid sequence encoding a dual antibody encodes a mutant IgG1 unable to bind antibody-dependent cellular cytotoxicity components. In some embodiments, a nucleic acid sequence encoding a dual binding antibody encodes an IgG comprising the $L_{234}A/L_{235}A$ (LALA) mutations. In some embodiments, a nucleic acid sequence encoding a dual binding antibody encodes an IgG1 comprising the $L_{234}A/L_{235}A/P329G$ (LALAPG) mutations.

In some embodiments, as disclosed herein, a mutagenesis approach, such as site-specific mutagenesis, may be employed for the preparation of variants VH, VL, or VH and VL nucleic acid sequences encoding the variant VH, VL, or VH and VL amino acid sequences. Template VH and VL nucleic acid sequences SEQ ID NO: 55 and 56, respectively, encode the template amino acid sequences SEQ ID NO: 1 and SEQ ID NO: 2, respectively. In some embodiments, a dual binding antibody comprises a variant VH domain, a variant VL domain, or both, encoded by a variant VH, VL, or VH and VL nucleotide sequences, wherein said nucleotide sequence comprises site-specific mutagenesis of the nucleotide template sequences SEQ ID NO: 55 and SEQ ID NO: 56, respectively. By this approach, specific modifications in a polypeptide sequence can be made through mutagenesis of the underlying polynucleotides that encode them. These techniques provide a straightforward approach to prepare and test sequence variants, for example but not limited to, introducing one or more nucleotide sequence changes into the polynucleotide in view of the amino acid variant sites desired, as described above in detail.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, mutagenesis of the polynucleotide sequences that encode component parts of the dual binding antibody (VH domains, VL domain, or a combination thereof, as disclosed herein, is contemplated in order to alter the binding properties of the encoded template VH or VL or both, such that the resulting antibody comprises a dual binding affinity. The techniques of site-specific mutagenesis are well-known in the art and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phages are readily commercially available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. In some embodiments, methods of preparing libraries includes those known in the art, for example but not limited to methods described in U.S. Pat. No. 9,889,423, which are included herein in their entirety. In some embodiments, a method for designing the sequence variants within a library comprises designing the variant sequences on a computer and then having the sequence synthesized, a method that involves both chemical and biochemical processes.

As used herein, the term "oligonucleotide directed mutagenesis procedure" encompasses template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" encompasses a process that involves the template-dependent extension of a primer molecule. The term "template dependent process" encompasses nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide VH and VL variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In certain embodiments, the polynucleotides described above, e.g., VH, VL, or VH and VL variant polynucleotides, fragments and hybridizing sequences, encoding the amino acid VH, VL, or VH and VL variants, are comprised in a dual biding antibody.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

In certain embodiments, the isolated polynucleotide is inserted into a vector. In some embodiments, a vector comprises an expression vector comprising a polynucleotide construct disclosed herein.

The term "vector" as used herein encompasses a vehicle into which a polynucleotide encoding a protein may be covalently inserted so as to bring about the expression of that protein and/or the cloning of the polynucleotide. The isolated polynucleotide may be inserted into a vector using any suitable methods known in the art, for example, without limitation, the vector may be digested using appropriate restriction enzymes and then may be ligated with the isolated polynucleotide having matching restriction ends.

Examples of suitable vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Examples of categories of animal viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

For expression of the dual antibody or components thereof, the vector may be introduced into a host cell to allow expression of the polypeptide within the host cell. The expression vectors may contain a variety of elements for controlling expression, including without limitation, promoter sequences, transcription initiation sequences, enhancer sequences, selectable markers, and signal sequences. These elements may be selected as appropriate by a person of ordinary skill in the art. In some embodiments, these elements may be considered "control" elements.

A skilled artisan would appreciate that the term "control sequence" may encompass polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

In some embodiments, for example but not limited to, the promoter sequences may be selected to promote the transcription of the polynucleotide in the vector. Suitable promoter sequences include, without limitation, T7 promoter, T3 promoter, SP6 promoter, beta-actin promoter, EF 1a promoter, CMV promoter, and SV40 promoter Enhancer sequences may be selected to enhance the transcription of the polynucleotide. Selectable markers may be selected to allow selection of the host cells inserted with the vector from those not, for example, the selectable markers may be genes that confer antibiotic resistance. Signal sequences may be selected to allow the expressed polypeptide to be transported outside of the host cell.

A vector may also include materials to aid in its entry into the cell, including but not limited to a viral particle, a liposome, or a protein coating. In some embodiments, a host cell comprises an expression vector disclosed herein.

In some embodiments, an expression vector comprises an isolated nucleic acid sequence encoding a dual antibody or a component thereof, for example but not limited to a VH domain, a VL domain, a combined VH-VL domain as may be present in Fab elements, F(ab')2 elements, an scFv, an Fv, a minibody, a diabody, or a triabody, as described above. Dual binding domains and the components thereof have been described in detail above.

In some embodiments, an expression vector comprises an isolated nucleic acid sequence encoding a VH domain. In some embodiments, an expression vector comprises an isolated nucleic acid sequence encoding a VL domain. In some embodiments, an expression vector comprises an isolated nucleic acid sequence encoding a VH and a VL domain. In some embodiments, an expression vector comprises an isolated nucleic acid sequence encoding two VH and VL domains. In some embodiments, an expression vector comprises an isolated nucleic acid sequence encoding three VH and VL domains.

In some embodiments, an expression vector comprises an isolated nucleic acid sequence encoding a VH domain component of a dual antibody. In some embodiments, an expression vector comprises an isolated nucleic acid sequence encoding a VL domain component of a dual antibody. In some embodiments, an expression vector comprises an isolated nucleic acid sequence encoding VH and VL domain components of a dual antibody.

In some embodiments, an expression vector comprises an isolated nucleic acid sequence encoding a VH domain component of a dual IgG antibody or a fragment thereof. In some embodiments, an expression vector comprises an isolated nucleic acid sequence encoding a VL domain component of a dual IgG antibody or a fragment thereof. In some embodiments, an expression vector comprises an isolated nucleic acid sequence encoding VH and VL domain components of a dual IgG antibody or a fragment thereof.

In some embodiments, an expression vector comprises an isolated nucleic acid sequence encoding a VH domain component of a scFv. In some embodiments, an expression vector comprises an isolated nucleic acid sequence encoding a VL domain component of a scFv. In some embodiments, an expression vector comprises an isolated nucleic acid sequence encoding VH and VL domain components of a scFv.

Dual binding antibodies have been described in detail above. The skilled artisan, using the knowledge in the art and specific details newly described herein would surely appreciate the range of components that may be encoded by an isolated nucleic acid described herein.

For cloning of the polynucleotide, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide(s) contained in the vector.

In some embodiments, a recombinant host cell comprises one or more constructs as described above. A nucleic acid encoding any CDR or set of CDR's or VH domain or VL domain or antibody antigen-binding site or antibody molecule, for example but not limited to an IgG, an Fv, an scFv, an Fab, an F(ab')$_2$, a minibody, a diabody, or a triabody. In some embodiments, disclosed herein is a method of production of the encoded product, which method comprises expression from encoding nucleic acid constructs. Expression may in some embodiments, be achieved by culturing under appropriate conditions recombinant host cells containing the nucleic acid construct. Following production by expression a VH or VL domain, or a VH-VL pair, or an antibody, may be isolated and/or purified using any suitable technique, then used as appropriate, for example in methods of treatment as described herein.

In some embodiments, dual binding antibodies, VH and/or VL domains, and encoding nucleic acid molecules and vectors according to the present invention may be prepared and isolated and/or purified, in substantially pure or homogeneous form.

In some embodiments, systems for cloning and expression of a polypeptide in a variety of different host cells are well known. Suitable host cells can include, without limitation, prokaryotic cells, fungal cells, yeast cells, or higher eukaryotic cells such as insect cells or mammalian cells.

Suitable prokaryotic cells for this purpose include, without limitation, eubacteria, such as Gram-negative or Gram-positive organisms, for example, Enterobactehaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*.

The expression of antibodies and antigen-binding fragments in prokaryotic cells such as *E. coli* is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable fungal cells for this purpose include, without limitation, filamentous fungi and yeast. Illustrative examples of fungal cells include, *Saccharomyces cerevisiae*, common baker's yeast, *Schizosaccharomyces pombe, Kluyveromyces* hosts such as, eg., *K. lactis, K fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402, 226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Higher eukaryotic cells, in particular, those derived from multicellular organisms can be used for expression of glycosylated VH and VL domains, as provided herein. Suitable higher eukaryotic cells include, without limitation, invertebrate cells and insect cells, and vertebrate cells. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruiffly), and *Bombyx mori* have been identified. A variety of viral strains for transfection are publicly available, e.g., the K-1 variant of *Autographa californica* NPV and the Bm-5 strain of *Bombyx mori* NPV, and such viruses may be used as the virus herein as described herein, particularly for transfection of *Spodoptera frugiperda* cells. Plant cell cultures of cotton, corn, potato, soybean, petunia, tomato, and tobacco can also be utilized as hosts Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. Non-limiting examples of vertebrate cells include mammalian host cell lines such as monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); ExpiCHO-S(TM) cells (ThermoFisher Scientific cat. #A29133); mouse Sertoli cells (TM4, Mather, Biol. Reprod. 23:243-251 (1980)); monkey kidney cells (CV1 ATCC CCL 70); African green monkey kidney cells (VERO-76, ATCC CRK-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

In some embodiments, an expression vector comprises a nucleic acid construct described herein. Suitable vectors can be chosen or constructed, containing appropriate regulatory sequences, including promoter sequences, terminator sequences, polyadenylation sequences, enhancer sequences, marker genes and other sequences as appropriate. Regulatory sequences may be operably linked to the nucleic acid sequence(s) comprised within a nucleic acid construct. Vectors may be plasmids, viral e.g. 'phage, or phagemid, as appropriate. For further details see, for example, Molecular Cloning: a Laboratory Manu*al*: 3rd edition, Sambrook and Russell, 2001, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1988, Short Protocols in Molecular Biology: A Compendium of Methods from Current Protocols in Molecular Biology, Ausubel et al. eds., John Wiley & Sons, 4.sup.th edition 1999. The disclosures of Sambrook et al. and Ausubel et al. (both) are incorporated herein by reference.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art.

In some embodiments, provided herein is a host cell containing nucleic acid as disclosed herein. Such a host cell may be in vitro and may be in culture. Such a host cell may be in vivo. In vivo presence of the host cell may allow intracellular expression of the dual binding antibodies described herein, as "intrabodies" or intracellular antibodies. Intrabodies may be used for gene therapy.

In certain embodiments, the host cells comprise a first vector encoding a first polypeptide, e.g., a VH domain, and a second vector encoding a second polypeptide, e.g., a VL domain. In certain embodiments, the host cells comprise a vector encoding a first polypeptide, e.g., a VH domain, and a second polypeptide, e.g., a VL domain.

In certain embodiments, the host cells comprise a first vector encoding a variant VH domain and a second vector encoding a variant VL domain. In certain embodiments, the host cells comprise a single vector encoding a variant VH domain and a variant VL domain.

In some embodiments, an isolated cell comprises an isolated nucleic acid sequence, as disclosed herein. In some embodiments, an isolated cell comprises two isolated nucleic acid sequences as disclosed herein, wherein one nucleic acid encodes a variant VH domain and the other nucleic acid encodes a variant VL domain. In some embodiments, an isolated cell comprises a single isolated nucleic acid sequence as disclosed herein, that encodes a variant VH domain and a variant VL domain.

In certain embodiments, a first vector and a second vector may or may not be introduced simultaneously. In certain embodiments, the first vector and the second vector may be introduced together into the host cell. In certain embodiments, the first vector may be introduced first into the host cell, and then the second vector may be introduced. In certain embodiments, the first vector may be introduced into the host cell, which is then established into a stable cell line expressing the first polypeptide, and then the second vector may be introduced into the stable cell line.

In certain embodiments, the host cells comprise a vector encoding for at least one variant VH domain and at least one a variant VL comprised within a dual binding antibody.

The introduction may be followed by causing or allowing expression from the nucleic acid, e.g. by culturing host cells under conditions for expression of the gene. In certain embodiments, the present disclosure provides methods of expressing the polypeptide provided herein, comprising culturing the host cell containing the vector under conditions in which the inserted polynucleotide in the vector is expressed.

In some embodiments, the nucleic acid is integrated into the genome (e.g. chromosome) of the host cell. Integration may be promoted by inclusion of sequences which promote recombination with the genome, in accordance with standard techniques. In some embodiments, the nucleic acid construct is not integrated into the genome and the vector is episomal.

In some embodiments, disclosed herein is a method which comprises using a construct as stated above in an expression system in order to express a dual binding antibody or fragment thereof, as described herein above.

Suitable conditions for expression of the polynucleotide may include, without limitation, suitable medium, suitable density of host cells in the culture medium, presence of necessary nutrients, presence of supplemental factors, suitable temperatures and humidity, and absence of microorganism contaminants A person with ordinary skill in the art can select the suitable conditions as appropriate for the purpose of the expression.

Methods of Synthesizing an Engineered, "Re-Epitoped" Dual Antibody

In some embodiments, described herein is a method of producing a dual binding antibody comprising a VH domain comprising HCDRs as described herein. In some embodiments, described herein is a method of producing a dual binding antibody comprising a VL domain comprising LCDRs as described herein. In some embodiments, described herein is a method of producing a dual binding antibody comprising a VH domain comprising HCDRs as described herein and a VL domain comprising LCDRs as described herein.

In some embodiments, a method of producing a dual binding antibody a heavy chain variable region comprising: (a) the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or (c) a combination of the heavy chain variable region set forth in (a) and the light chain variable region set forth in (b); wherein the total number of variant positions in said heavy chain variable region, said light chain variable region, or said combination thereof of said dual binding antibody, is at least 2; comprises steps of culturing a cell or cells comprising a nucleic acid sequence encoding at least a VH and a VL of the dual binding antibody, wherein polypeptides comprising the variant VH and variant VL domains are expressed and isolated, and wherein said isolated variant VH and variant VL domains form a heterodimer. As disclosed herein in detail, the isolated nucleic acid sequences encoding variant VH and variant VL domains may be comprised within vectors, wherein the same vector or different vectors are used. In some embodiments, each variant VH domain and variant VL domain may be expressed from a different host cell, wherein dimerization occurs following isolation or purification of the component variant VH and variant VL domains. In some embodiments variant VH and variant VL domains may be expressed from a same host cell, wherein dimerization occurs in culture or following isolation or purification of the component variant VH and variant VL domains.

A skilled artisan would appreciate that producing a dual binding antibody comprises synthesizing amino acid polypeptide components comprising VH domains, VL domains, or both. In some embodiments, said synthesis starts from a nucleic acid construct as described herein in detail. The terms "producing" and "synthesizing" may in some embodiments, be used herein interchangeably having all the same qualities and meanings.

In some embodiments, synthesizing a dual binding antibody comprises synthesizing an IgG heavy chain comprising a variant VH domain, synthesizing an IgG light chain comprising a variant VL domain, or both. In some embodiments, synthesizing a dual binding antibody comprises synthesizing an IgG heavy chain comprising a variant VH domain. In some embodiments, synthesizing a dual binding antibody comprises synthesizing an IgG light chain comprising a variant VL domain. In some embodiments, synthesizing a dual binding antibody comprises synthesizing both an IgG heavy chain comprising a variant VH domain and an IgG light chain comprising a variant VL domain. In some embodiments, synthesizing a dual binding antibody comprises synthesizing an Fab comprising a fragment of an IgG heavy chain comprising a variant VH domain and a fragment of an IgG light chain comprising a variant VL domain. In some embodiments, synthesizing a dual binding antibody comprises synthesizing an F(ab')2 comprising a fragment of an IgG heavy chain comprising a variant VH domain and a fragment of an IgG light chain comprising a variant VL domain. In some embodiments, synthesizing a dual binding antibody comprises synthesizing an Fv comprising a variant VH domain and a variant VL domain. In some embodiments, synthesizing a dual binding antibody comprises synthesizing a scFv comprising a variant VH domain and a variant VL domain. In some embodiments, synthesizing a dual binding antibody comprises synthesizing a minibody comprising a variant VH domain and a variant VL domain. In some embodiments, synthesizing a dual binding antibody comprises synthesizing a diabody comprising a variant VH domain and a variant VL domain. In some embodiments, synthesizing a dual binding antibody comprises synthesizing a triabody comprising a variant VH domain and a variant VL domain. In some embodiments, synthesizing a dual binding antibody comprises synthesizing a variant VH domain. In some embodiments, synthesizing an dual binding antibody comprises synthesizing a variant VL domain.

In certain embodiments, the polypeptide expressed in the host cell can form a dimer and thus produce a dual binding antibody or the binding component thereof.

In some embodiments, methods of synthesizing a dual binding antibody comprise a step of mutating a nucleic acid sequence encoding a template heavy chain variable region that does not comprise a dual binding VH domain in order to create a variant VH domain that may comprise a dual binding VH domain. In some embodiments, methods of synthesizing a dual binding antibody comprise a step of mutating a nucleic acid sequence encoding a template light chain variable region that does not comprise a dual binding VL domain in order to create a variant VL domain that may comprise a dual binding VL domain. In some embodiments, methods of synthesizing a dual binding antibody comprise a step of mutating a nucleic acid sequence encoding a template heavy chain variable region that does not comprise a dual binding VH domain in order to create a variant VH domain that may comprise a dual binding VH domain, and mutating a nucleic acid sequence encoding a template light chain variable region that does not comprise a dual binding VL domain in order to create a variant VL domain that may comprise a dual binding VL domain, wherein the variant VH and VL domains comprise a dual variable region of an antibody. Methods of mutating nucleic acid sequences have been described in detail above and are exemplified below in the Examples.

In some embodiments, a template nucleic acid sequence encoding the template heavy chain variable region is set forth in SEQ ID NO: 55. In some embodiments, a template nucleic acid sequence encoding the template light chain variable region is set forth in SEQ ID NO: 56. As stated throughout, template VH and VL sequences do not comprise dual binding regions.

In some embodiments, methods of synthesizing a dual binding antibody comprise introducing at least 2 variant sites within VH and VL domains. In some embodiments, methods of synthesizing a dual binding antibody comprise introducing at least 3, 4, 5, 6, 7, 8, 9, 10, 11, 12, 13, 14, or 15 variant sites within VH and VL domains Variant sites may be distributed between the VH domain and the VL domain. In some embodiments, variant sites are within CDR regions of a VH domain. In some embodiments, variant sites are within CDR regions of a VL domain. In some embodiments, variant sites are within FR regions of a VH domain. In some embodiments, variant sites are within FR regions of a VL domain. In some embodiments, variant sites are within CDR and or FR regions of a VH domain. In some embodiments, variant sites are within CDR and or FR regions of a VL domain. In some embodiments, variant sites are within CDR and or FR regions of a VH domain, and within CDR and or FR regions of a VL domain.

In certain embodiments, the variant VH and variant VL domains complex may be formed inside the host cell. For example, the variant VH and variant VL domains heterodimer may be formed inside the host cell with the aid of relevant enzymes and/or cofactors. In certain embodiments, the variant VH and variant VL domains polypeptide complex may be secreted out of the cell. In certain embodiments, the variant VH and variant VL domains may be secreted out of the host cell and form a heterodimer outside of the host cell.

In certain embodiments, the variant VH and variant VL domains may be separately expressed and allowed to dimerize under suitable conditions. For example, the variant VH and variant VL domains may be combined in a suitable buffer and allow the variant VH and variant VL domains to dimerize through appropriate interactions such as hydrophobic interactions. For another example, variant VH and variant VL domains may be combined in a suitable buffer containing an enzyme and/or a cofactor which can promote the dimerization of the variant VH and variant VL domains. For another example, the variant VH and variant VL domains may be combined in a suitable vehicle and allow them to react with each other in the presence of a suitable reagent and/or catalyst.

In certain embodiments, the variant VH and variant VL domains may be comprised within longer polypeptide sequences, which may include for example but not limited to constant regions, hinge regions, linker regions, Fc regions, or disulfide binding regions, or any combination thereof. A constant domain is an immunoglobulin fold unit of the constant part of an immunoglobulin molecule, also referred to as a domain of the constant region (e.g. CH1, CH2, CH3, CH4, Ck, Cl). In some embodiments, the longer polypeptide may comprise multiple copies of a variant VH domain, a variant VL domain, or both, for example but not limited to when the dual binding antibody comprises a diabody or a triabody.

In certain embodiments, the variant VH and variant VL domains are generated by DNA synthesis and PCR, and translation of nucleotide sequences generated thereof. In certain embodiments, the generated sequences may be subcloned into an expression vector. In certain embodiments, the generated sequences may be subcloned into two expression vectors. In certain embodiments, said expression vector is a plasmid. In certain embodiments, said the variant VH and variant VL domains are constructed on an IgG template, wherein said IgG template does not have dual binding capabilities.

In certain embodiments, transient expression is performed by co-transfecting the expression vector encoding the variant VH and variant VL domains or by transfecting an expression vector encoding both into a suitable cell. A skilled artisan would appreciate that there are a number of transfection methods and protocols that can be used for this purpose. In certain embodiments, transfection or co-transfection is executed using the PEI method.

The expressed polypeptides comprising the variant VH and variant VL domains and/or the polypeptide complex can be collected using any suitable methods. The variant VH and variant VL domains and/or the polypeptide complex can be expressed intracellularly, in the periplasmic space or be secreted outside of the cell into the medium. If the polypeptides comprising variant VH and variant VL domains and/or the polypeptide complex is expressed intracellularly, the host cells containing the polypeptides comprising variant VH and variant VL domains and/or the polypeptide complex may be lysed and polypeptide and/or the polypeptide complex may be isolated from the lysate by removing the unwanted debris by centrifugation or ultrafiltration. If the polypeptides comprising variant VH and variant VL domains and/or the polypeptide complex is secreted into periplasmic space of *E. coli*, the cell paste may be thawed in the presence of agents such as sodium acetate (pH 3.5), EDTA, and phenylmethylsulfonylfluoride (PMSF) over about 30 min, and cell debris can be removed by centrifugation (Carter et al., BioTechnology 10:163-167 (1992)). If the polypeptides comprising variant VH and variant VL domains and/or the polypeptide complex is secreted into the medium, the supernatant of the cell culture may be collected and concentrated using a commercially available protein concentration filter, for example, an Amincon or Millipore Pellicon ultrafiltration unit. A protease inhibitor and/or an antibiotic may be included in the collection and concentration steps to inhibit protein degradation and/or growth of contaminated microorganisms.

The expressed polypeptides comprising variant VH and variant VL domains and/or the polypeptide complex can be further purified by a suitable method, such as without limitation, affinity chromatography, hydroxylapatite chromatography, size exclusion chromatography, gel electrophoresis, dialysis, ion exchange fractionation on an ion-exchange column, ethanol precipitation, reverse phase HPLC, chromatography on silica, chromatography on heparin Sepharose, chromatography on an anion or cation exchange resin (such as a polyaspartic acid column), chromatofocusing, SDS-PAGE, and ammonium sulfate precipitation (see, for review, Bonner, P. L., Protein purification, published by Taylor & Francis, 2007; Janson, J. C., et al, Protein purification: principles, high resolution methods and applications, published by Wiley-VCH, 1998).

In certain embodiments, the polypeptides comprising variant VH and variant VL domains and/or polypeptide dimer complexes can be purified by affinity chromatography. In certain embodiments, protein A chromatography or protein A/G (fusion protein of protein A and protein G) chromatography can be useful for purification of polypeptides and/or polypeptide complexes comprising a component derived from antibody CH2 domain and/or CH3 domain (Lindmark et al., J. Immunol Meth. 62:1-13 (1983)); Zettlit, K. A., Antibody Engineering, Part V, 531-535, 2010). In certain embodiments, a dual binding antibody disclosed herein does not bind to protein A. In certain embodiments, protein G chromatography can be useful for purification of polypeptides and/or polypeptide complexes comprising IgGγ3 heavy chain (Guss et al., EMBO J. 5:1567 1575 (1986)). In certain embodiments, protein L chromatography can be useful for purification of polypeptides and/or polypeptide complexes comprising K light chain (Sudhir, P., Antigen engineering protocols, Chapter 26, published by Humana Press, 1995; Nilson, B. H. K. et al, J. Biol. Chem., 267, 2234-2239 (1992)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX resin (J. T. Baker, Phillipsburg, N.J.) is useful for purification.

Following any preliminary purification step(s), the mixture comprising the dual binding antibody and contaminants may be subjected to low pH hydrophobic interaction chromatography using an elution buffer at a pH between about 2.5-4.5, preferably performed at low salt concentrations (e.g., from about 0-0.25M salt).

In certain embodiments, the polypeptides comprising variant VH and variant VL domains and/or polypeptide dimer complexes can be purified by affinity chromatography and size exclusion chromatography (SEC). A skilled artisan would appreciate that there are a number of methods and protocols suitable for this purpose. In certain embodiments, protein purification by affinity chromatography and SEC is performed using an AKTA pure instrument (GE Lifesciences). In certain embodiments, affinity capture of the dual binding antibody is achieved by passing the harvested supernatants over a column of CaptureSelect™ CH1-XL Affinity Matrix (Thermo Scientific). After washing column with PBS, the protein is eluted with 0.1M Glycine, pH 2.5, and immediately neutralized with ⅙ volume of 1M Tris-HCl, pH 8.0. The affinity purified protein is then concentrated to 5-10 mg/ml using Amicon 30 kD concentrator (Merck Millipore) and subjected to SEC purification on a Superdex®200 column (GE Lifesciences) equilibrated with PBS. Protein fractions are then collected and analyzed using SDS-PAGE and HPLC-SEC.

Binding to an epitope of the synthesized dual binding immunoglobulins may be analyzed using well known methods in the art, as described herein, including ELISA analysis, SPR analysis, DSF analysis, and cell-based binding assays.

In some embodiments, a method of synthesizing a dual binding antibody comprising: a heavy chain variable region comprising a template amino acid sequence set forth in SEQ ID NO: 1, wherein said template comprises at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); and a light chain variable region comprising a template amino acid sequence set forth in SEQ ID NO: 2, wherein said template comprises at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); wherein the total number of variant positions in said heavy chain variable region, said light chain variable region, or the combination thereof, is at least 2; comprises the following steps:

(a) mutating the template heavy chain variable region, the template light chain variable region, or both, (i) wherein said mutating said template heavy variable chain region comprises mutating the template heavy chain variable region set forth in SEQ ID NO: 1, wherein said selected template variable chain does not comprise a dual binding region, (ii) wherein said mutating said template light chain variable region comprises mutating the template light chain variable region set forth in SEQ ID NO: 2, wherein said selected template variable chain does not comprise a dual binding region;

(iii) wherein said mutating both said template heavy variable chain region and said template light chain variable region comprises mutating the template heavy chain variable region set forth in SEQ ID NO: 1 and mutating the template light chain variable region set forth in SEQ ID NO: 2, wherein said selected template variable chains together do not comprise a dual binding region, and wherein said mutating comprises mutating at least two residue position in said template heavy chain variable region, said template light chain variable region or a combination thereof;

(b) synthesizing the mutated template variant heavy chain variable chain and the mutated template variant light chain variable chain;

(c) formatting said mutated template variant heavy chain variable chain and said mutated template variant light chain variable chain into a human antibody format; and (d) screening the human antibody of (c) for binding to dual antigens;

thereby producing a dual binding antibody.

As described herein and exemplified below, in some embodiments, that antibody synthesized comprises an IgG immunoglobulin. In some embodiments, the antibody synthesized comprises an IgG1 immunoglobulin, an IgG2 immunoglobulin, an IgG3 immunoglobulin, or an IgG4 immunoglobulin. In some embodiments, the antibody synthesized comprises an IgG1 immunoglobulin. In some embodiments, the antibody synthesized comprises an IgG2 immunoglobulin. In some embodiments, the antibody synthesized comprises an IgG3 immunoglobulin. In some embodiments, the antibody synthesized comprises an IgG4 immunoglobulin. In some embodiments, the antibody synthesized comprises an IgG1 immunoglobulin or an IgG4 immunoglobulin.

In some embodiments, the antibody synthesized comprises an Fab immunoglobulin fragment. In some embodiments, the antibody synthesized comprises an $F(ab')_2$ immunoglobulin fragment. In some embodiments, the antibody synthesized comprises an Fv immunoglobulin construct In some embodiments, the antibody synthesized comprises an scFv immunoglobulin construct In some embodiments, the antibody synthesized comprises a minibody immunoglobulin construct comprising a pair of single-chain Fv fragments which are linked via CH3 domains.

In some embodiments, the antibody synthesized comprises a diabody immunoglobulin construct. In some embodiments, the antibody synthesized comprises a diabody immunoglobulin construct comprising three scFv fragments covalently linked to each other. In some embodiments, the antibody synthesized comprises a triabody.

In some embodiments, the antibody synthesized comprises a mutated IgG that is unable to bind antibody-dependent cellular cytotoxicity components. In some embodiments, the antibody synthesized comprises a mutated IgG1 that is unable to bind antibody-dependent cellular cytotoxicity components. In some embodiments, the antibody synthesized comprises a mutated IgG4 that is unable to bind antibody-dependent cellular cytotoxicity components.

Immunoglobulin Libraries

In certain embodiments, disclosed herein is a library of immunoglobulins or fragments thereof, comprising variant VH domains, variant VL domains, or variant VH and VL domains, as described herein in detail (See, Examples below). A library of immunoglobulins or fragments thereof comprising a variant VH domains, a variant VL domains, or variant VH and VL domains, may in some embodiments, be screened for dual binding antibodies, fragments thereof, or components thereof.

In some embodiments, a library of immunoglobulins or fragments thereof, comprises a library of variable heavy chain domains. In some embodiments, a library of immunoglobulins or fragments thereof, comprises a library of variable light chain domains. In some embodiments, a library of immunoglobulins or fragments thereof, comprises a library of variable heavy chain domains and variable light chain domains.

In some embodiments, a method for generating a library of dual antigen binding immunoglobulin variable heavy chain regions, for screening for binding to an epitope comprises: (a) selecting the VH template antigen-binding molecule set forth in SEQ ID NO: 1, wherein said selected template does not specifically bind an epitope; (b) selecting at least one residue position from positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof) in said template SEQ ID NO: 1, for mutation; and (c) selecting at least one variant residue to substitute at the at least one residue position selected in (b); such that a library containing a plurality of variants of said template VH is generated. In some embodiments, a method for generating a library of dual antigen binding immunoglobulin variable light chain regions, for screening for binding to an epitope comprises: (a) selecting the VL template antigen-binding molecule set forth in SEQ ID NO: 2, wherein said selected template does not specifically bind an epitope; (b) selecting at least one residue position from positions 26, 27, 31, 51, 56, 77, 92, 93, or 96, or any combination thereof (IMGT positions: 27, 28, 38, 65, 70, 94, 109, 110, or 115, or a combination thereof) in said template SEQ ID NO: 2, for mutation; and (c) selecting at least one variant residue to substitute at the at least one residue position selected in (b); such that a library containing a plurality of variants of said template VL is generated.

In some embodiments, a method for generating a library of dual antigen binding immunoglobulin comprising variable heavy chain regions and variable light chain regions, for screening for binding to an epitope comprises: (a) selecting the VH template antigen-binding molecule set forth in SEQ ID NO: 1, wherein said selected template does not specifically bind an epitope; (b) selecting the VL template antigen-binding molecule set forth in SEQ ID NO: 2, wherein said selected template does not specifically bind an epitope; (c) selecting at least one residue position from positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof) in said template SEQ ID NO: 1, for mutation; (d) selecting at least one residue position from positions 26, 27, 31, 51, 56, 77, 92, 93, or 96, or any combination thereof (IMGT positions: 27, 28, 38, 65, 70, 94, 109, 110, or 115, or a combination thereof) in said template SEQ ID NO: 2, for mutation; and (e) selecting at least one variant residue to substitute at the at least one residue position selected in (c) or selecting at least one variant residue to substitute at the at least one residue position selected in (d), such that the total number of variant residues in each potentially dual binding immunoglobulins is a least 2, and such that a library containing a plurality of variants of said template VH and variants of said template VL is generated.

In some embodiments, methods for constructing a library can be found in the examples. In some embodiments, a library generated as described herein, may be used to identify immunoglobulins binding to dual targets. In some embodiments, a library generated as described herein, may be used to identify immunoglobulins binding to specific epitopes.

In some embodiments, use of a protein library comprising an immunoglobulin comprising a variant VH, a variant VL, or a variant VH and variant VL as described herein in detail, provides a method to identify immunoglobulins binding to dual targets. In some embodiments, use of a protein library comprising an immunoglobulin comprising a variant VH, a variant VL, or a variant VH and variant VL as described herein in detail, provides a method to identify immunoglobulins binding to specific epitopes.

In some embodiments, a protein library comprising an immunoglobulin comprising a variant VH and variant VL comprises a library of antibody molecules. In some embodiments, a protein library comprising an immunoglobulin comprising a variant VH and variant VL comprises a library of IgG molecules. In some embodiments, a protein library comprising an immunoglobulin comprising a variant VH and variant VL comprises a library of IgG1, IgG2, IgG3, or IgG4 molecules. In some embodiments, the IgG molecule is a mutant IgG molecule, unable to bind antibody-dependent cellular cytotoxicity components.

In some embodiments, a protein library comprising an immunoglobulin comprising a variant VH and variant VL comprises a library of Fab or F(ab')$_2$ molecules. In some embodiments, a protein library comprising an immunoglobulin comprising a variant VH and variant VL comprises a library of Fv molecules, scFv molecules, minibody molecules, diabody molecules, or triabody molecules.

In some embodiments, existing immunoglobulin VH and VL templates can be changed to introduce variant amino acids at specific positions with the goal of generating dual antigen binding sites in said variant VH and VL domains, wherein a protein library of the variant VH and VL domains comprises at least 10; 100; 1,000; 10,000; 100,000; or 1,000,000 variant VH, variant VL, or variant VH and variant VL domains with at least two variant positions. In some embodiments, a protein library of the variant VH and VL domains comprises between 1,000 to 1,000,000 variant VH, variant VL, or variant VH and variant VL domains with at least two variant positions. In some embodiments, a protein library of the variant VH and VL domains comprises between 10,000 to 1,000,000 variant VH, variant VL, or variant VH and variant VL domains with at least two variant positions.

In some embodiments, a protein library of the variant VH and VL domains comprises between 1,000 to 1,000,000 variant VH, variant VL, or variant VH and variant VL domains with at least 2, 3, 4, 5, 6, 7, 8, 9, 10, 11, 12, 13, 14, 15, or more variant positions. In some embodiments, a protein library of the variant VH and VL domains comprises between 10,000 to 1,000,000 variant VH, variant VL, or variant VH and variant VL domains with at least 2, 3, 4, 5, 6, 7, 8, 9, 10, 11, 12, 13, 14, 15, or more variant positions.

In some embodiments, a protein library of the variant VH and VL domains comprises between $10^6$ to $10^{14}$ variant VH, variant VL, or variant VH and variant VL domains with at least 2, 3, 4, 5, 6, 7, 8, 9, 10, 11, 12, 13, 14, 15, or more variant positions. In some embodiments, a protein library of the variant VH and VL domains comprises between $10^6$ to $10^{14}$ variant VH, variant VL, or variant VH and variant VL domains with at least 2, 3, 4, 5, 6, 7, 8, 9, 10, 11, 12, 13, 13, 14, 15, or more variant positions.

The library is then screened for binding to one or more antigens. After molecular characterization for the desired properties a selected antibody domain or region, for example but not limited to a VH or VL domain or both, is cloned into an immunoglobulin molecule by genetic engineering techniques, so that it replaces the corresponding region. Alternatively, only the DNA coding for the VH, or VL, or both regions, or coding for the mutated amino acids may be exchanged to obtain an immunoglobulin with the additional binding site for a molecule. In some embodiments, selection of the immunoglobulin molecule into which the variant regions are cloned, may be selected from an IgG, an Fv, an scFv, an Fab, an F(ab')₂, a minibody, a diabody, or a triabody. In some embodiments, an IgG is an IgG1, an IgG2, an IgG3, or an IgG4. In some embodiments, an IgG comprises a mutant IgG unable to bind antibody-dependent cellular cytotoxicity components.

In some embodiments, the CDRs expressed are as described above for HCDR1, HCDR2, HCD3, LCDR1, LCDR2, and LCDR3, wherein certain positions comprise variant amino acids, as described in detail above and is shown in FIGS. 1A and 1B.

The sites for mutation are describe above, and in certain embodiments include from positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof) in said template SEQ ID NO: 1, and positions 26, 27, 31, 51, 56, 77, 92, 93, or 96, or any combination thereof (IMGT positions: 27, 28, 38, 65, 70, 94, 109, 110, or 115, or a combination thereof) in said template SEQ ID NO: 2. In some embodiments, additional sites within said VH template or said VL template may be mutated.

In certain embodiments, the method of generating a library further comprises synthesizing the template variants (VH, VL, or both VH and VL) from said nucleic acid constructs, described above in detail, to form the library.

The result of generating a library as described above comprises a library of immunoglobulins comprising: (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or (c) a combination of the heavy chain variable region set forth in (a) and the light chain variable region set forth in (b); wherein the total number of variant positions in the heavy chain variable region, the light chain variable region, or a combination thereof is at least 2.

Mammalian cell expression systems have been described above. These expression systems offer a number of potential advantages for therapeutic antibody generation to create a library of potential dual binding immunoglobulins, including the ability to co-select for key manufacturing-related properties such as high-level expression and stability, while displaying functional glycosylated IgGs on the cell surface.

In some embodiments, a library of immunoglobulins comprises IgG molecules, Fab molecules, F(ab')₂ molecules, FV molecules, VH molecules, VL molecules, scFv molecules, diabodies, minibodies, or triabodies. In some embodiments, an IgG molecule comprises an IgG1, an IgG2, an IgG3, or an IgG4. In some embodiments, an IgG comprises a mutated IgG that is unable to bind antibody-dependent cellular cytotoxicity components. In some embodiments, an IgG1 comprises a mutated IgG1 that is unable to bind antibody-dependent cellular cytotoxicity components.

In some embodiments, disclosed herein are methods directed to screening the library with antigen molecules or a portion thereof, in order to select for dual-binding molecules that have desired properties (e.g., binding affinity, stability, etc.). In some embodiments, a portion of an antigen comprises an at least one IL-13 antigenic epitope. In some embodiments, disclosed herein is a dual-binding molecule isolated from the library after said screening.

In some embodiments, disclosed herein is a method for screening a library of immunoglobulins as described, for dual-binding molecules, comprising: (a) screening the library with an antigen molecules or fragment thereof to identify dual-binding molecules that bind said epitopes of interest; (b) sequencing the binders identified in step (a) to determine which residues are variants and which variant residues are enriched in the binding immunoglobulins; (c) using the information from step (b) to synthesize an optimized library of variants of the dual binders; and (d) repeating steps (a)-(c) using the optimized library. In some embodiments, disclosed herein is a method for screening a library of immunoglobulins as described, for dual-binding molecules, comprising: (a) screening the library with epitopes of interest to identify dual-binding molecules that bind said epitope of interest; (b) sequencing the binders identified in step (a) to determine which residues are variants and which variant residues are enriched in the binding immunoglobulins; (c) using the information from step (b) to synthesize an optimized library of variants of the dual binders; and (d) repeating steps (a)-(c) using the optimized library.

According to some embodiments, the specific binding of the variant immunoglobulins to the antigen molecule is determined by a binding assay selected from the group consisting of immunological assays, including but not limited to enzyme linked immunosorbent assays (ELISA), surface plasmon resonance assays, saturation transfer difference nuclear magnetic resonance spectroscopy, transfer NOE (trNOE) nuclear magnetic resonance spectroscopy, competitive assays, tissue binding assays, live cell binding assays and cellular extract assays.

Binding assays can be carried out using a variety of methods known in the art, including but not limited to FRET (Fluorescence Resonance Energy Transfer) and BRET (Bioluminescence Resonance Energy Transfer)-based assays, AlphaScreen.™. (Amplified Luminescent Proximity Homogeneous Assay), Scintillation Proximity Assay, ELISA (Enzyme-Linked Immunosorbent Assay), SPR (Surface Plasmon Resonance, also known as BIACORE®), isothermal titration calorimetry, differential scanning calorimetry, gel electrophoresis, and chromatography including gel filtration. These and other methods may take advantage of some fusion partner or label.

The variant immunoglobulin is, in some embodiments, conjugated to a label selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Conjugation to a label may in certain embodiments, allow the simple detection of said conjugate in, for instance, binding assays (e.g. ELISA) and binding studies.

Compositions of Use

In some embodiments, described herein are pharmaceutical compositions comprising the dual binding antibody, as described herein in detail, which provides a therapeutic agent. In some embodiments, described herein are pharmaceutical compositions comprising the dual binding antibody comprising a therapeutic agent comprising a mutant IgG unable to bind antibody-dependent cellular cytotoxicity components. In some embodiments, described herein are pharmaceutical compositions comprising a dual binding antibody having therapeutic properties against allergic or respiratory conditions.

In some embodiments, a pharmaceutical composition comprises a dual binding antibody comprising a variant VH, a variant VL, or a variant VH and a variant VL, and a pharmaceutically acceptable carrier. The amino acid sequences of variant VH and variant VL domains, and pair thereof, have been described in detail above (See for example, but not limited to Table 1).

In certain embodiments, a composition comprises any of the isolated dual binding antibodies disclosed herein, and a pharmaceutically acceptable carrier.

In one embodiment, the pharmaceutical composition comprises a dual binding antibody having HCDR1, HCDR2 and HCDR3 comprising the amino acid sequence of SEQ ID NOs:349, 350 and 351 respectively, and LCDR1, LCDR2 and LCDR3 comprising the amino acid sequence of SEQ ID NO: 359, D D V, and SEQ ID NO: 361, respectively.

In another embodiment, the pharmaceutical composition comprises a dual binding antibody having HCDR1, HCDR2 and HCDR3 comprising the amino acid sequence of SEQ ID NOs:349, 356 and 351 respectively, and LCDR1, LCDR2 and LCDR3 comprising the amino acid sequence of SEQ ID NO: 364, D D V, and SEQ ID NO: 371, respectively.

In another embodiment, the pharmaceutical composition comprises a dual binding antibody having HCDR1, HCDR2 and HCDR3 comprising the amino acid sequence of SEQ ID NOs:349, 350 and 351 respectively, and LCDR1, LCDR2 and LCDR3 comprising the amino acid sequence of SEQ ID NO: 362, D D V, and SEQ ID NO: 384 respectively.

In another embodiment, the pharmaceutical composition comprises a dual binding antibody having HCDR1, HCDR2 and HCDR3 comprising the amino acid sequence of SEQ ID NOs:349, 350 and 351 respectively, and LCDR1, LCDR2 and LCDR3 comprising the amino acid sequence SEQ ID NO: 364, D D V, and SEQ ID NO: 384, respectively.

In another embodiment, the pharmaceutical composition comprises a dual binding antibody having HCDR1, HCDR2 and HCDR3 comprising the amino acid sequence as shown in Table 8 or Table 4, and LCDR1, LCDR2 and LCDR3 comprising the amino acid sequence as shown in Table 9 or Table 5.

In another embodiment, the pharmaceutical composition comprises a dual binding antibody comprising a heavy chain variable domain (VH) and a light chain variable domain (VL), wherein the VH and VL comprise the amino acid sequences of SEQ ID Nos:209 and 210.

In another embodiment, the pharmaceutical composition comprises a dual binding antibody comprising a heavy chain variable domain (VH) and a light chain variable domain (VL), wherein the VH and VL comprise the amino acid sequences of SEQ ID Nos:219 and 220.

In another embodiment, the pharmaceutical composition comprises a dual binding antibody comprising a heavy chain variable domain (VH) and a light chain variable domain (VL), wherein the VH and VL comprise the amino acid sequences of SEQ ID Nos:249 and 250.

In another embodiment, the pharmaceutical composition comprises a dual binding antibody comprising a heavy chain variable domain (VH) and a light chain variable domain (VL), wherein the VH and VL comprise the amino acid sequences of SEQ ID Nos:337 and 338.

In another embodiment, the pharmaceutical composition comprises a dual binding antibody comprising a heavy chain variable domain (VH) and a light chain variable domain (VL), wherein the VH and VL comprise the amino acid sequences as shown in Table 10 or Table 1.

In another embodiment, the pharmaceutical composition comprises a dual binding antibody comprising a heavy chain variable domain (VH) and a light chain variable domain (VL), wherein the VH and VL are at least 80%, 85%, 90%, 95%, 98%, or 99% identical to the VH and VL sequences disclosed herein.

In some embodiments, a pharmaceutical composition comprising a dual binding antibody comprises any dual antibody described herein comprising a variant VH, a variant VL, or a variant VH and a variant VL. In some embodiments, a pharmaceutical composition comprising a dual binding antibody comprises a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of the heavy chain variable region set forth in (a) and the light chain variable region set forth in (b); wherein the total number of variant positions in the heavy chain variable region, the light chain variable region, or a combination thereof is at least 2.

A skilled artisan would recognize that in some embodiments, the term "dual binding antibody" may be used interchangeably with the term "drug" or "agent" having all the same meanings and qualities. In some embodiments, a drug comprising a dual binding antibody comprises a pharmaceutical composition.

In some embodiments, described herein are compositions comprising the dual binding antibody as described herein and administration of such composition in a variety of therapeutic settings.

Administration of the dual binding antibodies described herein, in pure form or in an appropriate pharmaceutical composition, can be carried out via any of the accepted modes of administration of agents for serving similar utilities. The pharmaceutical compositions can be prepared by combining a dual binding antibody or a dual binding antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients and/or suitable excipients such as salts, buffers and stabilizers may, but need not, be present within the composition. Administration may be achieved by a variety of different routes, including oral, parenteral, nasal, intravenous, intradermal, subcutaneous or topical. In some embodiments, modes of administration depend upon the nature of the condition to be treated or prevented. An amount that, following administration, reduces, inhibits, prevents or delays the progression and/or metastasis of a cancer is considered effective. A skilled artisan would appreciate that the term "physiologically acceptable carrier, diluent or excipient", may in some embodiments be used interchangeably with the term "pharmaceutically acceptable carrier" having all the same means and qualities.

In some embodiments, a pharmaceutical composition described herein comprises a nucleotide sequence encoding a dual binding antibody. In some embodiments, a nucleotide sequence encoding a dual binding antibody disclosed herein, comprises a single linear nucleotide sequence. In some embodiments, a nucleotide sequence encoding a dual binding antibody disclosed herein, comprises two nucleotide sequences. In some embodiments, a nucleotide sequence encoding a dual binding antibody disclosed herein, comprises two nucleotide sequences present on the same vector. In some embodiments, a nucleotide sequence encoding a dual binding antibody disclosed herein, comprises two nucleotide sequences present on different vectors.

In some embodiments, the nucleotide sequence encodes a variant VH or a variant VL domain or a combination thereof. In some embodiments, the same nucleotide sequence encodes a variant VH or a variant VL domain or a combination thereof. In some embodiments, different nucleotide sequences encode a variant VH or a variant VL domain or a combination thereof. In some embodiments, one nucleotide sequence encodes a variant VH domain and another nucleotide sequence encodes a variant VL domain. In some embodiments, one nucleotide sequence encodes variant VH domain and another nucleotide sequence encodes a variant VL domain having a linker sequence between them, thus allowing a variant VH and a variant VL domain to heterodimerize, as described in Duperret E K et al., Cancer Res, October 4 (doi: 10.1158/0008-5472.CAN-18-1429).

In some embodiments, a method of treating an allergic or respiratory condition in a subject, or a combination thereof, comprises a step of administering a pharmaceutical composition comprising a dual binding antibody comprising (a) a variant VH domain comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); and (b) a variant VL domain comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); to a subject in need, wherein the method treats the allergic or respiratory condition, or a combination thereof, compared with a subject not administered said pharmaceutical composition.

In some embodiments, a method of treating an allergic or respiratory condition in a subject, or a combination thereof, comprises a step of administering a pharmaceutical composition comprising a dual binding antibody comprising (a variant VH domain comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); to a subject in need, wherein the method treats the allergic or respiratory condition, or a combination thereof, compared with a subject not administered said pharmaceutical composition.

In some embodiments, a method of treating an allergic or respiratory condition in a subject, or a combination thereof, comprises a step of administering a pharmaceutical composition comprising a dual binding antibody comprising a variant VL domain comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); to a subject in need, wherein the method treats the allergic or respiratory condition, or a combination thereof, compared with a subject not administered said pharmaceutical composition.

Methods of Use

In some embodiments, disclosed herein is a method of treating a subject suffering from a disease or condition, said method comprises administering to said subject a composition comprising an isolated dual binding antibody as disclosed herein. In some embodiments, the disease or condition is an allergic or respiratory condition, an inflammatory or autoimmune condition, or tumors or cancers. In some embodiments, said disease or condition is asthma, allergic asthma, nonallergic asthma, severe asthma, mild asthma, chronic obstructive pulmonary disease (COPD), a condition involving airway inflammation, cystic fibrosis, allergic lung disease, airway hyperresponsiveness, goblet cell metaplasia, mucus hypersecretion, airway remodeling, pulmonary fibrosis, atopic dermatitis, urticaria, eczema, allergic enterogastritis, allergic rhinitis, inflammatory bowel diseases, liver cirrhosis or fibrosis, or a combination thereof.

In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising a heavy chain variable region comprising HCDRs (HCDR1, HCDR2, HCDR3 as described herein in detail; for example, see Table 8 or Table 4). In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising a light chain variable region comprising LCDRs (LCDR1, LCDR2, LCDR3 as described herein in detail; for example, see Table 9 or Table 5). In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising a heavy chain variable region comprising HCDRs (HCDR1, HCDR2, HCDR3) and LCDRs (LCDR1, LCDR2, LCDR3 as described herein in detail).

In certain embodiments, a method of treating a subject suffering from a disease or condition comprises administering a dual binding antibody comprising three complementarity determining regions (CDRs) on a heavy chain (HCDR1, HCDR2, and HCDR3) and three CDRs on a light chain (LCDR1, LCDR2, and LCDR3), wherein the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 359, D D V, and SEQ ID NO: 361, respectively; or the HCDR1, HCDR2 and HCDR3 comprise the amino acid sequence of SEQ ID NOs:349, 356 and 351 respectively, and the LCDR1, LCDR2 and LCDR3 comprise the amino acid sequence of SEQ ID NO: 364, D D V, and SEQ ID NO: 371, respectively; or the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 362, D D V, and SEQ ID NO: 384, respectively; or the HCDR1, HCDR2 and HCDR3 comprise the amino acid sequence of SEQ ID NOs:349, 350 and 351 respectively, and the LCDR1, LCDR2 and LCDR3 comprise the amino acid sequence of SEQ ID NO: 364, D D V, and SEQ ID NO: 384, respectively; or the CDRs having the sequences of SEQ ID NOs:149-152, D D S, and SEQ ID NO: 154.

In some embodiments a method of treating a subject suffering from a disease or condition comprises administering a dual binding antibody comprising three complementarity determining regions (CDRs) on a heavy chain (HCDR1, HCDR2, and HCDR3) and three CDRs on a light chain (LCDR1, LCDR2, and LCDR3), wherein the HCDR1, HCDR2 and HCDR3 comprise the amino acid sequences as shown in Table 8 or Table 4, wherein the LCDR1, LCDR2 and LCDR3 comprise the amino acid sequences as shown in Table 9 or Table 5.

In some embodiments a method of treating a subject suffering from a disease or condition comprises administering a dual binding antibody comprising VH and VL having the sequences of SEQ ID Nos:209 and 210, SEQ ID Nos:219 and 220, SEQ ID Nos:249 and 250, SEQ ID Nos:337 and 338, SEQ ID NOs:155 and 156, SEQ ID NOs:157 and 158. In some embodiments a method of treating a subject suffering from a disease or condition comprises administering a dual binding antibody comprising VH and VL domains having the sequences as shown in Table 10 or Table 1.

In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or a combination of the heavy chain variable region set forth in (a) and the light chain variable region set forth in (b); wherein the total number of variant positions in said heavy chain variable region, said light chain variable region, or said combination thereof, is at least 2, to a subject in need, wherein the method treats the allergic or respiratory condition, an inflammatory and/or autoimmune condition of the skin or gastrointestinal organs; scleroderma; or tumors or cancers including Hodgkin's lymphoma in said subject, compared with a subject not administered said dual binding antibody, or pharmaceutical composition thereof.

In some embodiments, a method of treating an allergic or respiratory condition, an inflammatory and/or autoimmune condition of the skin or gastrointestinal organs; scleroderma; or tumors or cancers including Hodgkin's lymphoma n in a subject, or any combination thereof, comprises a step of administering a pharmaceutical composition comprising a dual binding antibody or a pharmaceutical composition thereof, said dual binding antibody comprising a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof), wherein the total number of variant positions in said heavy chain variable region is at least 2, to a subject in need, wherein the method treats the allergic or respiratory condition, an inflammatory and/or autoimmune condition of the skin or gastrointestinal organs; scleroderma; or tumors or cancers including Hodgkin's lymphoma in said subject, compared with a subject not administered said dual binding antibody, or pharmaceutical composition thereof.

In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof), wherein the total number of variant positions in said light chain variable region is at least 2, to a subject in need, wherein the method treats the allergic or respiratory condition, an inflammatory and/or autoimmune condition of the skin or gastrointestinal organs; scleroderma; or tumors or cancers including Hodgkin's lymphoma in said subject, compared with a subject not administered said dual binding antibody, or pharmaceutical composition thereof.

In some embodiments, a method of treating an allergic or respiratory condition, an inflammatory and/or autoimmune condition of the skin or gastrointestinal organs; scleroderma; or tumors or cancers including Hodgkin's lymphoma in a subject, or any combination thereof, comprises a step of administering a pharmaceutical composition comprising a dual binding antibody or a pharmaceutical composition thereof, said dual binding antibody comprising (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); and (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof);

wherein the total number of variant positions in said heavy chain variable region, said light chain variable region, or said combination thereof of is at least 2, to a subject in need, wherein the method treats the allergic or respiratory condition, an inflammatory and/or autoimmune condition of the skin or gastrointestinal organs; scleroderma; or tumors or cancers including Hodgkin's lymphoma in said subject, compared with a subject not administered said dual binding antibody, or pharmaceutical composition thereof.

In some embodiments of a method of treating an allergic or respiratory condition, an inflammatory and/or autoimmune condition of the skin or gastrointestinal organs; scleroderma; or tumors or cancers including Hodgkin's lymphoma, the amino acid sequence of the variant VH domain is selected from, but not limited to, the sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54. In some embodiments of a method of treating an allergic or respiratory condition, an inflammatory and/or autoimmune condition of the skin or gastrointestinal organs; scleroderma; or tumors or cancers including Hodgkin's lymphoma, a dual binding antibody comprises a heavy chain variable region comprising the amino acid sequences set forth in, but not limited to, any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54; and any variable light chain region. In some embodiments of a method disclosed herein, the amino acid sequence of the variant VH domain comprises the sequence that is at least 80% identical (e.g., 80%, 85%, 90%, 95%, 98%, or 99% identical) to the sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54.

In some embodiments of method disclosed herein, the VH domain of the dual binding antibody is selected from the sequences set forth in any one of SEQ ID NOs:209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345 and 347. In another embodiment, the VH domain is at least 80%, 85%, 90%, 95%, 98%, or 99% identical to the VH sequences disclosed herein.

One skilled in the art would appreciate that percent sequence identity may be determined using any of a number of publicly available software application, for example but not limited to BlastP software of the National Center of Biotechnology Information (NCBI) using default parameters.

In some embodiments of a method of treating an allergic or respiratory condition, an inflammatory and/or autoimmune condition of the skin or gastrointestinal organs; scleroderma; or tumors or cancers including Hodgkin's lymphoma, the amino acid sequence of the variant light chain variable region (VL) is selected from, but not limited to, the sequences set forth in any of SEQ ID NOs: 3, 5, 7, 9, 11, 13, 15, 17, 19 21, 23, 25, 27, 29, 31, 33, 35, 37, 39, 41, 43, 45, 47, 49, 51, and 53. In some embodiments of a method of treating an allergic or respiratory condition, an inflammatory and/or autoimmune condition of the skin or gastrointestinal organs; scleroderma; or tumors or cancers including Hodgkin's lymphoma, a dual binding antibody comprises a light chain variable region comprising the amino acid sequences set forth in, but not limited to, any of SEQ ID NOs: 3, 5, 7, 9, 11, 13, 15, 17, 19 21, 23, 25, 27, 29, 31, 33, 35, 37, 39, 41, 43, 45, 47, 49, 51, and 53, and any variable heavy chain region. In some embodiments of a method disclosed herein, the amino acid sequence of the variant VH domain comprises the sequence that is at least 80% identical (e.g., 80%, 85%, 90%, 95%, 98%, or 99% identical) to the sequences set forth in any of SEQ ID NOs: 3, 5, 7, 9, 11, 13, 15, 17, 19 21, 23, 25, 27, 29, 31, 33, 35, 37, 39, 41, 43, 45, 47, 49, 51, and 53, and any variable heavy chain region.

In some embodiments of methods disclosed herein, the VL domain of the dual binding antibody is selected from the sequences set forth in any one of SEQ ID NOs: 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346 and 348. In another embodiment, the VL domain is at least 80%, 85%, 90%, 95%, 98%, or 99% identical to the VL sequences disclosed herein.

In some embodiments of a method of treating an allergic or respiratory condition, an inflammatory and/or autoimmune condition of the skin or gastrointestinal organs; scleroderma; or tumors or cancers including Hodgkin's lymphoma, the amino acid sequence of the variant VH domain is selected from, but not limited to, the sequences set forth in any of SEQ ID NOs: 4, 6, 8, 10, 12, 14, 16, 18, 20, 22, 24, 26, 28, 30, 32, 34, 36, 38, 40, 42, 44, 46, 48, 50, 52, and 54; and the amino acid sequence of the variant light chain variable region (VH) is selected from, but not limited to, the sequences set forth in any of SEQ ID NOs: 3, 5, 7, 9, 11, 13, 15, 17, 19 21, 23, 25, 27, 29, 31, 33, 35, 37, 39, 41, 43, 45, 47, 49, 51, and 53. In some embodiments of a method of treating an allergic or respiratory condition, an inflammatory and/or autoimmune condition of the skin or gastrointestinal organs; scleroderma; or tumors or cancers including Hodgkin's lymphoma, the amino acid sequences of a heavy chain variable region-light chain variable region pair are selected from, but not limited to, the pair sequences set forth in SEQ ID Nos: 4 and 3, SEQ ID Nos: 6 and 5, SEQ ID Nos: 8 and 7, SEQ ID Nos: 10 and 9, SEQ ID Nos: 12 and 11, SEQ ID Nos: 14 and 13, SEQ ID Nos: 16 and 15, SEQ ID Nos: 18 and 17, SEQ ID Nos: 20 and 19, SEQ ID Nos: 22 and 21, SEQ ID Nos: 24 and 23, SEQ ID Nos: 26 and 25, SEQ ID Nos: 28 and 27, SEQ ID Nos: 30 and 29, SEQ ID Nos: 32 and 31, SEQ ID Nos: 34 and 33, SEQ ID Nos: 36 and 35, SEQ ID Nos: 38 and 37, SEQ ID Nos: 40 and 39, SEQ ID Nos: 42 and 41, SEQ ID Nos: 44 and 43, SEQ ID Nos: 46 and 45, SEQ ID Nos: 48 and 47, SEQ ID Nos: 50 and 49, SEQ ID Nos: 52 and 51, and SEQ ID Nos: 54 and 53. In some embodiments, the amino acid sequences of the VH-VL pair are selected from the pair sequences set forth in any one of the following: SEQ ID NOs:209 and 210, SEQ ID NOs:211 and 212, SEQ ID NOs:213 and 214, SEQ ID NOs:215 and 216, SEQ ID NOs:217 and 218, SEQ ID NOs:219 and 220, SEQ ID NOs:221 and 222, SEQ ID NOs:223 and 224, SEQ ID NOs:225 and 226, SEQ ID NOs:227 and 228, SEQ ID NOs:229 and 230, SEQ ID NOs:231 and 232, SEQ ID NOs:233 and 234, SEQ ID NOs:235 and 236, SEQ ID NOs:237 and 238, SEQ ID NOs:239 and 240, SEQ ID NOs:241 and 242, SEQ ID NOs:243 and 244, SEQ ID NOs:245 and 246, SEQ ID NOs:247 and 248, SEQ ID NOs:249 and 250, SEQ ID NOs:251 and 252, SEQ ID NOs:253 and 254, SEQ ID NOs:255 and 256, SEQ ID NOs:257 and 258, SEQ ID NOs:259 and 260, SEQ ID NOs:261 and 262, SEQ ID NOs:263 and 264, SEQ ID NOs:265 and 266, SEQ ID NOs:267 and 268, SEQ ID NOs:269 and 270, SEQ ID
NOs:271 and 272, SEQ ID NOs:273 and 274, SEQ ID
NOs:275 and 276, SEQ ID NOs:277 and 278, SEQ ID
NOs:279 and 280, SEQ ID NOs:281 and 282, SEQ ID
NOs:283 and 284, SEQ ID NOs:285 and 286, SEQ ID
NOs:287 and 288, SEQ ID NOs:289 and 290, SEQ ID
NOs:291 and 292, SEQ ID NOs:293 and 294, SEQ ID
NOs:295 and 296, SEQ ID NOs:297 and 298, SEQ ID
NOs:299 and 300, SEQ ID NOs:301 and 302, SEQ ID
NOs:303 and 304, SEQ ID NOs:305 and 306, SEQ ID
NOs:307 and 308, SEQ ID NOs:309 and 310, SEQ ID
NOs:311 and 312, SEQ ID NOs:313 and 314, SEQ ID
NOs:315 and 316, SEQ ID NOs:317 and 318, SEQ ID
NOs:319 and 320, SEQ ID NOs:321 and 322, SEQ ID
NOs:323 and 324, SEQ ID NOs:325 and 326, SEQ ID
NOs:327 and 328, SEQ ID NOs:329 and 330, SEQ ID
NOs:331 and 332, SEQ ID NOs:333 and 334, SEQ ID
NOs:335 and 336, SEQ ID NOs:337 and 338, SEQ ID
NOs:339 and 340, SEQ ID NOs:341 and 342, SEQ ID
NOs:343 and 344, SEQ ID NOs:345 and 346, SEQ ID
NOs:347 and 348.

In some embodiments, a method of treating one or more
conditions in a subject as described herein comprises a step
of administering a pharmaceutical composition comprising
an isolated dual binding antibody comprising three comple-
mentarity determining regions (CDRs) on a heavy chain
(HCDR1, HCDR2, and HCDR3) and three CDRs on a light
chain (LCDR1, LCDR2, and LCDR3), wherein the CDRs
have the sequences of SEQ ID NOs:149-154. In another
embodiment, the dual binding antibody comprises a heavy
chain variable domain (VH) and a light chain variable
domain (VL) having the amino acid sequences of SEQ ID
Nos:155 and 156, or SEQ ID Nos:157 and 158.

In some embodiments, a method of treating one or more
conditions in a subject as described herein comprises a step
of administering a pharmaceutical composition comprising
an isolated dual binding antibody comprising three comple-
mentarity determining regions (CDRs) on a heavy chain
(HCDR1, HCDR2, and HCDR3) and three CDRs on a light
chain (LCDR1, LCDR2, and LCDR3), wherein the CDRs
have the sequences set forth in SEQ ID NOs:349, 350 and
351, respectively, and SEQ ID NO: 359, D D V, and SEQ ID
NO: 361, respectively.

In some embodiments, a method of treating one or more
conditions in a subject as described herein comprises a step
of administering a pharmaceutical composition comprising
an isolated dual binding antibody comprising three comple-
mentarity determining regions (CDRs) on a heavy chain
(HCDR1, HCDR2, and HCDR3) and three CDRs on a light
chain (LCDR1, LCDR2, and LCDR3), wherein the CDRs
have the sequences set forth in SEQ ID NOs:349, 356, and
351, respectively, and SEQ ID NO: 364, D D V, and SEQ ID
NO: 371, respectively.

In some embodiments, a method of treating one or more
conditions in a subject as described herein comprises a step
of administering a pharmaceutical composition comprising
an isolated dual binding antibody comprising three comple-
mentarity determining regions (CDRs) on a heavy chain
(HCDR1, HCDR2, and HCDR3) and three CDRs on a light
chain (LCDR1, LCDR2, and LCDR3), wherein the CDRs
have the sequences set forth in SEQ ID NOs:349, 350, and
351, respectively, and SEQ ID NO: 362, D D V, and SEQ ID
NO: 384, respectively.

In some embodiments, a method of treating one or more
conditions in a subject as described herein comprises a step
of administering a pharmaceutical composition comprising
an isolated dual binding antibody comprising three complementarity determining regions (CDRs) on a heavy chain
(HCDR1, HCDR2, and HCDR3) and three CDRs on a light
chain (LCDR1, LCDR2, and LCDR3), wherein the CDRs
have the sequences set forth in SEQ ID NOs:349, 350, and
351, respectively, and SEQ ID NO: 364, D D V, and SEQ ID
NO: 384, respectively.

In some embodiments, a method of treating one or more
conditions in a subject as described herein comprises a step
of administering a pharmaceutical composition comprising
an isolated dual binding antibody comprising three comple-
mentarity determining regions (CDRs) on a heavy chain
(HCDR1, HCDR2, and HCDR3) and three CDRs on a light
chain (LCDR1, LCDR2, and LCDR3), wherein the CDRs
have the sequences set forth in Table 8 or Table 4, and Table
9 or Table 5.

In some embodiments, a method of treating one or more
conditions in a subject as described herein comprises a step
of administering a pharmaceutical composition comprising
an isolated dual binding antibody comprising a heavy chain
variable domain (VH) and a light chain variable domain
(VL), wherein the VH and VL comprise the amino acid
sequences of SEQ ID Nos:209 and 210.

In some embodiments, a method of treating one or more
conditions in a subject as described herein comprises a step
of administering a pharmaceutical composition comprising
an isolated dual binding antibody comprising the amino acid
sequences of SEQ ID Nos:219 and 220.

In some embodiments, a method of treating one or more
conditions in a subject as described herein comprises a step
of administering a pharmaceutical composition comprising
an isolated dual binding antibody comprising amino acid
sequences of SEQ ID Nos:249 and 250.

In some embodiments, a method of treating one or more
conditions in a subject as described herein comprises a step
of administering a pharmaceutical composition comprising
an isolated dual binding antibody comprising the amino acid
sequences of SEQ ID Nos:337 and 338.

In some embodiments, a method of treating one or more
conditions in a subject as described herein comprises a step
of administering a pharmaceutical composition comprising
an isolated dual binding antibody comprising the amino acid
sequences as shown in Table 10 or Table 1.

In some embodiments, a method of treating one or more
conditions in a subject as described herein comprises a step
of administering a pharmaceutical composition comprising
an isolated dual binding antibody, wherein the VH and VL
are at least 80%, 85%, 90%, 95%, 98%, or 99% identical to
the VH and VL sequences disclosed herein.

The variant VH and VL domains have been described in
detail above, including methods of creating these variant VH
and VL domains by re-epitoping template sequence. That
disclosure is incorporated herein in full, wherein methods of
treating an allergic or respiratory condition, an inflammatory
and/or autoimmune condition of the skin or gastrointestinal
organs; scleroderma; or tumors or cancers including Hodg-
kin's lymphoma comprise use of any variant VH or VL
domain described herein.

A skilled artisan would appreciate that the term "treating"
and grammatical forms thereof, may in some embodiments
encompass both therapeutic treatment and prophylactic or
preventative measures with respect to an allergic or respi-
ratory condition, as described herein, wherein the object is
to treat, prevent, reduce, or alleviate, the allergic or respi-
ratory condition, or symptoms thereof, or a combination
thereof. Thus, in some embodiments of methods disclosed
herein, treating may include directly affecting or curing,
suppressing, inhibiting, preventing, reducing the severity of, delaying the onset of, reducing symptoms associated with the disease, disorder or condition, or a combination thereof; for example, when said disease or disorder comprises an allergic or respiratory condition. In some embodiments, "treating" encompasses enhancing the ability of host immune cells to destroy intracellular pathogens. In some embodiments, "treating" encompasses interference with the IL-13receptor/IL-4receptor signaling cascade. In some embodiments, "treating" encompasses inhibition of IL-13 activities. In some embodiments, "treating" encompasses reduction of IL-13 activities.

In some embodiments, "preventing" encompasses delaying the onset of symptoms or an allergic or respiratory condition. In some embodiments, "suppressing" or "inhibiting", encompass reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, the subject is a mammal, e.g., a human suffering from one or more IL-13-associated disorders, including but not limited to respiratory disorders or conditions (e.g., asthma (e.g., allergic and nonallergic asthma for example but not limited to asthma due to infection with, e.g., respiratory syncytial virus (RSV), e.g., in younger children), severe asthma, mild asthma), chronic obstructive pulmonary disease (COPD), and other conditions involving airway inflammation, eosinophilia, fibrosis and excess mucus production (e.g., cystic fibrosis and pulmonary fibrosis); atopic disorders (e.g., atopic dermatitis, urticaria, eczema, allergic enterogastritis, and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; or tumors or cancers, e.g., Hodgkin's lymphoma.

In some embodiments, methods of treating comprising treating, reducing, preventing, or ameliorating, symptoms of an allergic or respiratory condition, an inflammatory and/or autoimmune condition of the skin or gastrointestinal organs; scleroderma; or tumors or cancers including Hodgkin's lymphoma, or any combination thereof. For example, symptoms of asthma may include, but are not limited to, wheezing, shortness of breath, bronchoconstriction, airway hyperreactivity, decreased lung capacity, fibrosis, airway inflammation, and mucus production. The method comprises administering to the subject a dual binding antibody or a pharmaceutical composition thereof, as described herein, in an amount sufficient to treat (e.g., reduce, ameliorate) or prevent one or more symptoms. The dual binding antibody can be administered therapeutically or prophylactically, or both. The dual binding antibody can be administered to the subject, alone or in combination with other therapeutic modalities.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time or may be divided into a number of smaller doses to be administered at intervals of time. For any particular subject, specific dosage regimens may be adjusted over time according to the individual need.

In some embodiments, compositions comprising a nucleic acid construct, comprising a nucleic acid sequence encoding a dual binding antibody comprising: (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); or (c) a combination of heavy chain variable region set forth in (a) and the light chain variable region set forth in (b); wherein the total number of variant positions in the encoded heavy chain variable region, the encoded light chain variable region, or a combination thereof, is at least 2, may be administered alone or in combination with other known allergic or respiratory condition, an inflammatory and/or autoimmune condition of the skin or gastrointestinal organs; scleroderma; or tumors or cancers including Hodgkin's lymphoma treatments.

In some embodiments, methods of treatment comprise administration of a composition comprising a nucleic acid construct comprising a dual binding antibody comprising an VH domain comprising HCDRs (HCDR1, HCDR2, HCDR3 as described herein; for example, see Table 8 or Table 4). In some embodiments, methods of treatment comprise administration of a composition comprising a nucleic acid construct comprising a dual binding antibody comprising an VL domain comprising LCDRs (LCDR1, LCDR2, LCDR3 as described herein; for example, see Table 9 or Table 5). In some embodiments, methods of treatment comprise administration of a composition comprising a nucleic acid construct comprising a dual binding antibody comprising an VH domain comprising HCDRs (HCDR1, HCDR2, HCDR3 as described herein) and a VL domain comprising LCDRs (LCDR1, LCDR2, LCDR3 as described herein).

In some embodiments, compositions comprising a nucleic acid construct, comprising a nucleic acid sequence encoding a dual binding antibody comprising: (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); wherein the total number of variant positions in the encoded heavy chain variable region is at least 2, may be administered alone or in combination with other known allergic or respiratory condition treatments. In some embodiments, compositions comprising a nucleic acid construct, comprising a nucleic acid sequence encoding a dual binding antibody comprising: a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); wherein the total number of variant positions in the encoded light chain variable region is at least 2, may be administered alone or in combination with other known allergic or respiratory condition treatments. In some embodiments, compositions comprising a nucleic acid construct, comprising a nucleic acid sequence encoding a dual binding antibody comprising: (a) a heavy chain variable region comprising the amino acid sequence set forth in SEQ ID NO: 1 with at least one amino acid variant at any of positions 52, 99, 100, 101, 102, 103, 104, 105, 106, 107, 108, or 111, or any combination thereof (IMGT positions: 57, 107, 108, 109, 110, 111, 111A, 112A, 112, 113, 114, or 117, or a combination thereof); and (b) a light chain variable region comprising the amino acid sequence set forth in SEQ ID NO: 2 with at least one amino acid variant at any of positions 26, 27, 31, 51, 56, 77, 92, 93, or 96, or any combination thereof (IMGT positions: 27, 28, 38, 65, 70, 94, 109, 110, or 115, or a combination thereof); wherein the total number of variant positions in the encoded heavy chain variable region, the encoded light chain variable region, or a combination thereof, is at least 2, may be administered alone or in combination with other known allergic or respiratory condition treatments.

In some embodiments of a method of treating an allergic or respiratory condition, the nucleotide construct encoding the variant VH domain is selected from the sequences set forth in any of SEQ ID NOs: 57, 59, 61, 63, 65, 67, 69, 71, 73, 75, 77, 79, 81, 83, 85, 87, 89, 91, 93, 95, 97, 99, 101, 105, and 107. In some embodiments of a method of treating an allergic or respiratory condition, the nucleotide construct encoding the variant light chain variable region (VH) is selected from the sequences set forth in any of SEQ ID NOs: 58, 60, 62, 64, 66, 68, 70, 72, 74, 76, 78, 80, 82, 84, 86, 88, 90, 92, 94, 96, 98, 100, 102, 104, 106, and 108. In some embodiments of a method of treating an allergic or respiratory condition, the nucleotide construct encoding the variant VH domain is selected from the sequences set forth in any of SEQ ID NOs: 57, 59, 61, 63, 65, 67, 69, 71, 73, 75, 77, 79, 81, 83, 85, 87, 89, 91, 93, 95, 97, 99, 101, 105, and 107; and, the nucleotide construct encoding the variant light chain variable region (VH) is selected from the sequences set forth in any of SEQ ID NOs: 58, 60, 62, 64, 66, 68, 70, 72, 74, 76, 78, 80, 82, 84, 86, 88, 90, 92, 94, 96, 98, 100, 102, 104, 106, and 108. In some embodiments of a method of treating an allergic or respiratory condition, the nucleotide construct encoding a dual binding antibody heavy chain variable region-light chain variable region scFv, is selected from the sequences set forth in SEQ ID NOs: 109-135.

The nucleotide sequences encoding variant VH and VL domains have been described in detail above, including methods of creating these nucleotide sequences encoding the variant VH and VL domains by mutating template sequence. That disclosure is incorporated herein in full, wherein methods of treating an allergic or respiratory condition comprise use of any nucleic acid construct encoding variant VH or VL domain described herein.

In some embodiments of a method of treating an allergic or respiratory condition, a dual binding antibody described herein comprises an IgG immunoglobulin. In some embodiments of a method of treating an allergic or respiratory condition, a dual binding antibody comprises an IgG1 immunoglobulin, an IgG2 immunoglobulin, an IgG3 immunoglobulin, or an IgG4 immunoglobulin. In some embodiments of a method of treating an allergic or respiratory condition, a dual binding antibody comprises an IgG1 immunoglobulin. In some embodiments of a method of treating an allergic or respiratory condition, a dual binding antibody comprises an IgG2 immunoglobulin. In some embodiments, a dual binding antibody comprises an IgG3 immunoglobulin. In some embodiments of a method of treating an allergic or respiratory condition, a dual binding antibody comprises an IgG4 immunoglobulin. In some embodiments of a method of treating an allergic or respiratory condition, a dual binding antibody comprises an IgG1 immunoglobulin or an IgG4 immunoglobulin.

In some embodiments of a method of treating an allergic or respiratory condition, a dual binding antibody comprises a mutated IgG, said mutant IgG unable to bind antibody-dependent cellular cytotoxicity components. In some embodiments of a method of treating an allergic or respiratory condition, a dual binding antibody comprises a mutated IgG1, said mutant IgG1 unable to bind antibody-dependent cellular cytotoxicity components. In some embodiments of a method of treating an allergic or respiratory condition, a dual binding antibody comprises a mutated IgG4, said mutant IgG4 unable to bind antibody-dependent cellular cytotoxicity components.

In some embodiments of a method of treating an allergic or respiratory condition, a dual binding antibody comprises an Fab immunoglobulin fragment. In some embodiments of a method of treating an allergic or respiratory condition, a dual binding antibody comprises an F(ab')$_2$ immunoglobulin fragment. In some embodiments of a method of treating an allergic or respiratory condition, a dual binding antibody comprises an Fv immunoglobulin construct. In some embodiments of a method of treating an allergic or respiratory condition, a dual binding antibody comprises an scFv immunoglobulin construct. In some embodiments of a method of treating an allergic or respiratory condition, a dual binding antibody comprises a minibody immunoglobulin construct comprising a pair of single-chain Fv fragments which are linked via CH3 domains.

In some embodiments of a method of treating an allergic or respiratory condition, a dual binding antibody comprises a diabody immunoglobulin construct. In some embodiments of a method of treating an allergic or respiratory condition, a dual binding antibody comprises a triabody immunoglobulin construct.

Typical routes of administering these and related dual binding antibodies or pharmaceutical compositions thereof, include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Dual binding antibodies or pharmaceutical compositions thereof according to certain embodiments as described herein, are formulated so as to allow the active ingredients contained therein to be bioavailable upon administration of the composition to a patient. Dual binding antibodies or pharmaceutical compositions thereof that will be administered to a subject or patient may take the form of one or more dosage units, where for example, a tablet may be a single dosage unit, and a container of a herein described dual binding antibody in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The dual binding antibodies or pharmaceutical compositions thereof to be administered will, in any event, contain a therapeutically effective amount of a dual binding antibody of the present disclosure, for treatment of an allergic or respiratory condition.

A pharmaceutical composition may be in the form of a solid or liquid. In some embodiments, the pharmaceutically acceptable carrier(s) are particulate, so that the compositions are, for example, in tablet or powder form. The pharmaceutically acceptable carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible pharmaceutically acceptable carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid pharmaceutically acceptable carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a dual binding antibody as herein disclosed such that a suitable dosage will be obtained.

The pharmaceutical composition may be intended for topical administration, in which case the pharmaceutically acceptable carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredient (a dual binding antibody) may be encased in a gelatin capsule. The pharmaceutical composition in solid or liquid form may include an agent that binds to the antibody as disclosed herein, and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a dual binding antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the dual binding antibody composition so as to facilitate dissolution or homogeneous suspension of the dual binding antibody in the aqueous delivery system.

The compositions may be administered in a therapeutically effective amount, which will vary depending upon a variety of factors including the activity of the dual binding antibody employed; the metabolic stability and length of action of the dual binding antibody; the age, body weight, general health, sex, and diet of the patient; the mode and time of administration; the rate of excretion; the drug combination; the severity of the particular allergic or respiratory disorder or condition; and the subject undergoing therapy.

Compositions comprising the dual binding antibody of the present disclosure or comprising a nucleotide sequence encoding the dual binding antibody may also be administered simultaneously with, prior to, or after administration of one or more other therapeutic agents. Such combination therapy may include administration of a single pharmaceutical dosage formulation which contains a dual binding antibody as disclosed herein, and one or more additional active agents, as well as administration of compositions comprising dual binding antibody as disclosed herein, and each active agent in its own separate pharmaceutical dosage formulation. For example, a dual binding antibody or comprising a nucleotide sequence encoding the dual binding antibody, as described herein, and the other active agent can be administered to the patient together in a single oral dosage composition such as a tablet or capsule, or each agent administered in separate oral dosage formulations. Similarly, a dual binding antibody or comprising a nucleotide sequence encoding the dual binding antibody, as described herein, and the other active agent can be administered to the patient together in a single parenteral dosage composition such as in a saline solution or other physiologically acceptable solution, or each agent administered in separate parenteral dosage formulations. Where separate dosage formulations are used, the compositions comprising dual binding antibody or comprising a nucleotide sequence encoding the dual binding antibody, and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of dual binding antibody compositions of this disclosure or comprising a nucleotide sequence encoding the dual binding antibody, in combination with one or more other therapeutic agents. Such therapeutic agents may be accepted in the art as a standard treatment for a particular disease state as described herein, such as an allergic or respiratory condition.

In some embodiments, a pharmaceutically acceptable carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens, phenols or cresols, mercurials, chlorobutanol, methyl and propyl p-hydroxybenzoic acid esters, thimerosal, benzalkonium chloride and benzethonium chloride); antioxidants (such as ascorbic acid and sodium bisulfite; methionine, sodium thiosulfate, platinum, catalase, citric acid, cysteine, thioglycerol, thioglycolic acid, thiosorbitol, butylated hydroxyanisol, butylated hydroxytoluene, and/or propyl gallate) and chelating agents (such as ethylenediaminetetraacetic acid (EDTA)); buffers (such as acetates, citrates and phosphates). If administered intravenously, suitable pharmaceutically acceptable carriers include physiological saline or phosphate buffered saline (PBS), and solutions containing thickening and solubilizing agents, such as glucose, polyethylene glycol, polypropylene glycol and mixtures thereof.

The compositions comprising a dual binding antibody as described herein, may be prepared with pharmaceutically acceptable carriers that protect the dual binding antibody against rapid elimination from the body, such as time release formulations or coatings. Such pharmaceutically acceptable carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

As used herein, the singular form "a", "an" and "the" include plural references unless the context clearly dictates otherwise. For example, the term "an immunoglobulin" or "at least one immunoglobulin" may include a plurality of immunoglobulins, including mixtures thereof.

Throughout this application, various embodiments may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

EXAMPLES

Example 1: Experimental Procedures

Objective: To generate unique, dual binding antibodies. Library Design Methods:

To generate a dual binding antibody that binds IL-13 and TSLP, a "re-epitoping" approach was applied to an existing antibody. The re-epitoping process allows for the introduction of new specificity to an existing antibody, e.g. a known antibody with 3-dimensional structure and well established biochemical and biophysical properties. The re-epitoped antibody is likely therefore to have both a new specificity and desirable developability properties. Briefly, re-epitoping is an engineering approach that allows the redirection of an existing antibody toward a new epitope, possibly on a new antigen unrelated to the cognate antigen of the original antibody. The computational process of re-epitoping requires two steps: (i) using any computational analysis that identifies putative contacts between an existing antibody and a new epitope, and (ii) application of any computational analysis or tool that can suggest the introduction of specific mutations into the antibody that are predicted to enhance its binding to the new, desired epitope. In (Ref: Ofran Y et al, US20180068055A1; Nimrod G, et al, Cell Rep. 2018 Nov. 20; 25(8):2121-2131) some examples of possible such computational processes are presented. In particular, two libraries were designed using the sequence of the variable domains of a template antibody (SEQ ID NO: 1-template variable heavy chain sequence; SEQ ID NO: 2—template variable light chain sequence)) as a starting point.

Template Variable Heavy Chain:

(SEQ ID NO: 1)

QMQLVESGGGVVQPGRSLRLSCAASGFTFRTYGMHWVRQAPGKGLEWV

AVIWYDGSNKHYADSVKGRFTITRDNSKNTLNLQMNSLRAEDTAVYYC

ARAPQWELVHEAFDIWGQGTMVTVSS.

-continued

Template Variable Light Chain:

(SEQ ID NO: 2)

SYVLTQPPSVSVAPGQTARITCGGNNLGSKSVHWYQQKPGQAPVLVVY

DDSDRPSWIPERFSGSNSGNTATLTISRGEAGDEADYYCQVWDSSSDH

VVFGGGTKLTVL.

Each library contained 21 positions that were chosen for variation with respect to the template original sequences. These positions are located in both CDRs (H2, H3, L1, L2, and L3) and framework (FIGS. 1A-1B). The following positions were chosen for variation in the libraries (IMGT® numbering scheme [the international ImMunoGeneTics information System® http://www.imgt.org): Variable H chain (SEQ ID NO: 1): 57(H2), 107(H3), 108(H3), 109(H3), 110(H3), 111(H3), 111A(H3), 112A(H3), 112(H3), 113(H3), 114(H3), 117(H3).

Variable L chain (SEQ ID NO: 2): 27(L1), 28(L1), 38 (P1(2), 65(L2), 70(1-R3), 94(FR3), 109(L3), 110(L3), 115 (L3).

The resulting IL13/TSLP binding antibodies comprising variant heavy chain/variant light chain pairs, included a clone (C2) that contained 8 mutations relative to the template starting sequences (See, FIGS. 1A and 1B).

Library Construction Methods:

Libraries were constructed on the 5J13 template (PDB5J13) by overlapping extension PCR with degenerate oligonucleotides encoding the diversity 2*10^14. PCR to introduce diversity was done using Phusion high fidelity DNA polymerase (New England Biolabs USA, Cat: M0530) according to manufacturer instructions in a 3-step reaction (98° C. for 30 sec, 65° C. for 20 sec, 72° C. for 30 sec, 30 cycles). The PCR products were gel purified by gel purification kit and assembled (100 ng from each) in equimolar ratios in a 3-step PCR reaction, as above, in the absence of primers. The assembled PCR product was reused as the template for PCR amplifying the full scFv library, as above, using forward and reverse primers adding vector sequences 5' and 3' to the scFv library to efficiently perform homologous recombination in yeast cells.

Library transformation was carried out as published (Benatuil et al., (2010) An improved yeast transformation method for the generation of very large human antibody libraries. Protein Eng. Des. Sel. 23, 155-159. 400 µl of a yeast suspension (EBY100, ATCC, USA) per 0.2 cm cuvette (cell projects) was electroporated (BioRad, USA, GenePulser) with 4 µg linearized vector (pCTcon3) and 12 µg DNA insert (scFv Library) in a 1:3 vector to insert ratio (Chao, G. et al. Isolating and engineering human antibodies using yeast surface display. Nat. Protoc. 1, 755-768 (2006)). The number of transformants of each library was determined to ~1×10^8 by serial dilutions of transformed cells (Benatuil et al. (2010) ibid)

Methods of Screening and Selection Using Yeast Surface Display:

Yeast-displayed scFv libraries were grown in a SDCAA selective medium and induced for expression with 2% w/v galactose at 30° C. overnight according to established protocols (Chao et al., (2006) ibid) The library was screened on BioRad S3e Fluorescence Activated Cell Sorter for high affinity binders of rh-IL-13-Fc (Reprokine, Israel) using mouse anti Myc-FITC (Santa Cruze, USA) and goat anti human Fc-APC (Jackson Immuno research, USA). Isolated clones from the final sort were sequenced by extraction of plasmid DNA from the yeast clones using a Zymoprep kit (Zymo Research, USA) and the DNA was sequenced. The chosen clones were incubated with either 10 nM recombinant human IL-13 (rh-IL-13)-Fc or 10 nM recombinant human TSLP (hTSLP)-Fc for 1 hour at room temperature. Cells were washed and resuspended in ice-cold PBS 0.1% BSA buffer containing a fluorescent labeled secondary antibody as described above for 20 min and analyzed using a flow cytometer. The values obtained were normalized to expression levels and to a positive control (an anti-IL-13 or anti TSLP binding antibody).

Methods of IgG-Roduction—Production of the IgGs Including the Light Chain (LC) and Heavy Chain (HC) Variable Regions:

Sequences of the selected clones were synthesized as GeneBlock (GB) with 5' 25 bp region homologous to the cloning regions of pSF-CMV-HuIgG1_HC and pSF-CMV-HuLambda_LC (Oxford genetics, Oxford UK), the GB codon usage was optimized for mammalian expression (integrated DNA Technologies. Coralville, Iowa USA). The pSF-CMV-HuIgG1_HC and pSF-CMV-HuLambda_LC were digested using BseRI and NcoI, and the LC and HC variable region DNA fragments were cloned into the expression corresponding vectors using NEBuilder (NEB Ipswich, Massachusetts, USA). The expression vectors were transfected and expressed in ExpiCHO Expression System (ThermoFisher Scientific, USA) according to the manufacturer's instructions. Briefly: 25 ml CHO cells were grown at 37° C. to a density of 6*10^6 cell/ml, 25 µg expression vector 1:2 HC/LC ratio were transfected into CHO cells, 20 hours post transfection the cells growth conditions were changed to 32° C. with 120 rpm shaking for 10 days. Subsequently the cells were centrifuged and IgGs were purified from the supernatant using proteinA beads, followed by size exclusion chromatography on a Superdex® 200 10/300 increase column (GE) with PBS serving as mobile phase.

Methods of Determination of IgG EC50 Binding to Human and Cynomolgus Monkey TSLP Plates (Greiner Bio-One Cat: 655081) were coated with 45.5 ng/well human or cynomolgus monkey (cyno) TSLP antigen, then washed and blocked with 3% skim milk in PBS with 0.05% tween. Post blocking the tested IgG was added to the wells in a concentration range of 1 nM-1000 nM and incubated for 1 hour at room temperature (RT). The plates were washed and goat anti-human Fc-HRP conjugated secondary antibody (Jackson cat: 109-035-008) diluted 1:20000 in PBS, was added. The reaction was developed and stopped using TMB (Southern-Biotech cat: 0410-01) and stop solution (Southern-Biotech cat: 0412-01) respectively and read at 450 nm.

Methods of Determination of IC50 Competition Between IL-13 and TSLP

Plates were coated with ing/ul hTSLP washed with TBS 0.05% tween (TBS-T) and blocked with TBS-T 2% BSA. 20 nM of tested IgG was incubated with rhIL-13 at a concertation range of 0.78 nM to 200 nM for 1 hour, then the mixture was loaded on the plates for 10 minutes and the wells were washed and a bound IgG was detected using anti human Fc-HRP conjugate as described for the ELISA EC50 experiment above. A reciprocal competition experiment was conducted using the same conditions except this time IL-13 was coated on the wells, and TSLP served as free competing ligand at the same concentration range.

Methods of Determination of IgG IC50 Inhibition Constant of Blocking TSLP from Binding to TSLP-R:

150 ng/well of TSLP-R-Fc tag (ACRO biosystems TSR-H525a) was diluted in 0.015M NaHCO₃, pH=9.5, and was then used to coat the wells of a 96 well plate (Greiner Bio-One Cat: 655081). Wells were then washed three times with TBS 0.05% tween (TBS-T) and blocked with TBS-T containing 2% BSA (w/v). Competitor IgG at a concentration range of 0.11 nM to 300 nM was mixed with 3 nM hTSLP-His (ACRO biosystems cat: TSP-H52Hb) for one hour, then the mixture was loaded into the wells of the 96 well plate, incubated for 10 minutes, followed by washing the plate three times with TBS-T. Subsequently 1:200 anti-His-HRP conjugated secondary antibody was added (Santa Cruz Biotechnology cat SC-8036). The reaction was developed and stopped using TMB (Southern-Biotech cat: 0410-01) and stop solution (Southern-Biotech cat: 0412-01) respectively, and read at 450 nm.

Methods of Specificity Determination by ELISA 96 well plates (Greiner Bio-One Cat: 655081) were coated with a total of 250 ng ligand, blocked with PBS-T containing 0.5% (w/v) BSA, and incubated with 100 nM IgG. Plates were developed using the same reagents and conditions as in the TSLP EC50 experiment described herein.

Methods of Calibration of MUTZ5 TSLP Reporter Cell Line:

The in-vitro activity of anti-TSLP blockade of TSLP binding to its cognate receptor is based on detection of pSTAT5 activation by human TSLP in MUTZ5 human leukemia cell line (Francis et al., (2016) Hematopoiesis, 101(4):417-426). In order to determine the EC50 value of hTSLP STATS activation of MUTZ5 cell line, cells were inoculated in a total volume of 150 μl, $250 \times 10^5$ cells/well and incubated for 1 hr at 37° C. 5% $CO_2$ in a 96 well plate. Then TSLP at concentration range of 0.1 pg/mml to 1000 pg/ml was added for 30 minutes. Subsequently cells were washed, blocked with Fc blocker (BD bioscience FC Blocker-MIX cat #BD564220), and fixated with cytofix fixation buffer (BD bioscience Cat #554655). The cells were permeabilized with 90% methanol, washed and labeled with anti-pSTAT5-PE (BD bioscience cat #562077). Treated MUTZ5 cells were analyzed for pSTST5 activation on a CytoFLEX S flow cytometer (Beckman). Cells gated for singlets and pSTAT5 were marked as pSTAT5 positive.

Methods of Determination of IgG IC50 Inhibition of MUTZ5 pSTAT5 Activation by hTSLP To test functional blocking of pSTAT5 activation, IgG at a concentration range of 0.48 pM to 500 pM, was mixed with 14 pM hTSLP (ACROBiosystems, cat #TSP-H52Hb) and incubated for 30 minutes, then added to the cells for another 60 minutes. Subsequently the cells were washed, fixated, labeled, and analyzed as described for the calibration of MUTZ5 cells.

Methods of Surface Plasmon Resonance (SPR) Analysis

Measurements of IgG binding to human IL-13: The SPR analysis was done on Biacore 200 (GE) on CMS chips cat: br10005-30 (GE), the chip was crosslinked with primary capture Ab (Cat: br-1008-39 GE) to a target of 8000RU, after cross linking of the primary Ab, the tested antibodies were immobilized on the primary Ab to a target of 500RU. The hIL-13 (Peprotech) analyte was streamed in HEB-EP buffer at concentrations ranging from 800 nM to 1.6 nM in a series of two-fold dilutions, one concentration for each cycle. Subsequent to a cycle, the analyte and tested antibody were stripped from the chip and new tested Ab was loaded on the chip as described above. KD was determined at a steady state condition.

Measurements of Binding to Cynomolgus Monkey IL-13 (cIL-13, Sino Biological, USA) and Human TSLP The SPR analysis was done on ProteOn™ XPR36 (Bio-Rad) on a GLC chips cat: 176-5011 (BioRad). The chip was crosslinked with primary capture Ab (Cat: br-1008-39 GE)

to a target of 5500RU. After cross-linking of the primary Ab tested, antibodies 33.003 and 33.004 were immobilized on the primary Ab to a target of 2000RU. The cyno IL-13 analyte was streamed in HEB-EP buffer at concentrations ranging from 200 nM to 12.5 nM in a series of two-fold dilutions. KD was determined at a steady state condition. For measurements of binding kinetics to hTSLP, the same conditions were used but with TSLP serving as analyte at concentrations ranging from 3.2 nM to 0.2 nM in a series of two-fold dilutions.

Method of Dynamic Scanning Fluorescence (DSF)

Dynamic Scanning Fluorescence was measured as reported by (Niedziela-Majka et al., 2015) with minor modifications. Briefly: 0.3 mg/ml tested antibody in sodium acetate pH 5.5 buffer was mixed 1:1 with 20xsypro orange (Thermo Fisher, USA cat #56650) in the same buffer Changes in fluorescence were monitored on a Bio-Rad cfx96 light cycler with setting of 0.5° C./min from 25° C.-100° C. Tm was determined as the temperature corresponding to the maximum value of the first derivative of the DSF melting curve. Where mentioned, antibodies were diluted to 0.5 mg/ml in PBS and analyzed using NanoDSF Prometheus NT.48 (Nanotemper, Germany) in a temperature elevation rate of 1° C./min Methods of Cell Based Assays HEK-Blue IL-4/IL-13 Cells (Invivogen, France Catalog #hkb-il1413) were used to determine IL-13 inhibition. HEK-Blue cells were cultured in growth medium comprising of DMEM, 4.5 g/l glucose, 10% (v/v) fetal bovine serum (PBS), 50 U/ml penicillin, 50 mg/ml streptomycin, 100 mg/ml Normocin, 2 mM L-glutamine, 10 μg/ml of blasticidin and 100 pg/ml of Zeocin. HEK-Blue IL-4/IL-13 cells are specifically designed to monitor the activation of the STAT6 pathway induced by IL-4 and IL-13. These cells were generated by stably introducing the human STAT6 gene into HEK293 cells to obtain a fully active STAT6 signaling pathway. The other genes of the pathway are naturally expressed in sufficient amounts. HEK-BlueIL-4/dual cells stably express the reporter gene, secreted embryonic alkaline phosphatase (SEAP), under the control of the IFNβ minimal promoter fused to four STAT6 binding sites. Activation of the STAT6 pathway in HEK-Blue IL-4/IL-13 cells induces the expression of the reporter gene. SEAP, which is secreted in the supernatant is easily detectable when using QUANTI-Blue, a medium that turns purple/blue in the presence of SEAP.

Methods of Calibration of HEK-Blue IL-4/IL-13 System

In order to determine the $EC_{50}$ value for rh-IL-13 on HEK-Blue IL-4/IL-13 cells, 50000 cells (5*10^4/ELISA well) were incubated with rh-IL-13 antibody (Peprotech, Israel) at concentration of 0 nM to 8.13 nM for 24 hrs at 37° C., 5% CO 2 in a 96 well plate. At the end of the incubation, 20 ul of the cell's supernatant was incubated with 180111 of QUANTI-Blue reagent (Invivogen, France) for an additional 2 hrs, and the reaction was analyzed by measuring the absorbance at 620-655 nm using a plate reader spectrophotometer (Synergy Neo2, BioTek Instruments, Inc. USA). Data shown is the mean of triplicate experiments, and error bars represent standard deviation.

$IC_{50}$ of Antibody Inhibition of IL-13 Downstream Signaling:

0.4 nM of rh-IL-13 was incubated with antibodies at a range of concentrations for 1 hr at room temperature. After the incubation, the mixture of rh-IL-13-antibody was added to a total volume of 200 μl, 50,000 cells/well and incubated for 24 hrs at 37 C 5% CO 2 in a 96 well plate. At the end of the incubation, 20 μl of the cell's supernatant was incubated with 180 ul of QUANTI-Blue reagent for additional 2 hrs, and the reaction was analyzed by measuring the absorbance at 620-655 nm using a plate reader spectrophotometer. Data shown is the mean of triplicate experiments, and error bars represent standard deviation.

Example 2: Screening And Selection of Dual Binding Antibodies

Objective: Screen engineered dual binding antibodies to identify those with highest binding for IL-13 and TSLP.

Results: Following screening and selection of the libraries to bind both IL-13 and TSLP, 45 clones were selected, isolated, and sequenced resulting in 26 unique Heavy chain (VH)—Light chain (VL) pair variable regions, wherein the amino acid sequences of the Heavy chain and Light chain pairs are presented in Table 1 (antibodies 1-26), the nucleotide sequences of the Heavy chain and Light chain scFv for antibodies 1-26, including the encoded linker sequences, are presented in Table 2, and the nucleic acid sequences of the Heavy chain and Light chain pairs for antibodies 1-26, are presented in Table 3. The Clone ID number for antibodies 1-26, is provided as "C #"—of each "Name" provided, for example at row 2, Clone C2 variable region pair comprises C2 VL sequence SEQ ID NO: 3 and C2 VH sequence SEQ ID NO: 4.

Subsequently, an affinity maturation library was screened and additional dual binding antibody clones identified that showed YSD tight binding to both hIL-13 and hTSLP (Ab clone #s: 33.023, 33.025, 38.014, 38.015. 38.018, 38.019, 38.021, 38.026, 38.040). The amino acid sequences of the VH/VL regions of clones 33.023, 33.025, 38.014, 38.015. 38.018, 38.019, 38.021, 38.026, 38.040, are presented in Table 1 and the nucleotide sequences encoding the VH/VL regions are presented in Table 3. The CDR regions of VH/VL pairs from Ab clone #s: 33.023, 33.025, 38.014, 38.015. 38.018, 38.019, 38.021, 38.026, 38.040, are provided in Table 4 and Table 5 below. These clones were selected for IgG production.

TABLE 1

Engineered dual binding antibodies:
Variable Light chain (VL) and Variable Heavy chain (VH)
amino acid sequences (See also FIGS. 1A and 1B)

| Ab # | SEQ ID NO: | Name | VL Sequence | SEQ ID NO: | Name | VH Sequence |
|------|------------|------|-------------|------------|------|-------------|
| 1 | 3 | C2-VL | SYVLTQPPSVSVAP GQTARITCGGNLIG SKLVHWYQQKPGQ APVLVVYDDSDRP SLIPERFSGSNSGNT ATLTISRVEAGDEA DYYCQVWDSSSDG VVFGGGTKLTVL | 4 | C2-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTAEAFDIWGQG TMVTVSS |
| 2 | 5 | C27-VL | SYVLTQPPSVSVAP GQTARITCGGNLIG SKLVHWYQQKPGQ APVLVVYDDSDRP SLIPERFSGSNSGNT ATLTISRVEAGDEA DYYCQVWDSSSDG VVFGGGTKLTVL | 6 | C27-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |
| 3 | 7 | C19-VL | SYVLTQPPSVSVAP GQTARITCGGNLIG SKLVHWYQQKPGQ APVLVVYDDSDRP SLIPERFSGSNSGNT ATLTISRVEAGDEA DYYCQVWDTSSDG VVFGGGTKLTVL | 8 | C19-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWQLVAEAFDIWGQG TMVTVSS |
| 4 | 9 | C43-VL | SYVLTQPPSVSVAP GQTARITCGGNLIG SKLVHWYQQKPGQ APVLVVYDDSDRP SAIPERFSGSNSGNT ATLTISRVEAGDEA DYYCQVWDTSSDG VVFGGGTKLTVL | 10 | C43-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWQLVAEAFDIWGQG TMVTVSS |
| 5 | 11 | C5-VL | SYVLTQPPSVSVAP GQTARITCGGNLIG SKLVHWYQQKPGQ APVLVVYDDSDRP SLIPERFSGSNSGNT ATLTISRVEAGDEA DYYCQVWDTSSDG VVFGGGTKLTVL | 12 | C5-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |

TABLE 1-continued

Engineered dual binding antibodies:
Variable Light chain (VL) and Variable Heavy chain (VH)
amino acid sequences (See also FIGS. 1A and 1B)

| Ab # | SEQ ID NO: | Name | VL Sequence | SEQ ID NO: | Name | VH Sequence |
|---|---|---|---|---|---|---|
| 6 | 13 | C8-VL | SYVLTQPPSVSVAP GQTARITCGGNLLG SKLVHWYQQKPGQ APVLVVYDDSDRP SAIPERFSGSNSGNT ATLTISRVEAGDEA DYYCQVWDSSSDH VVFGGGTKLTVL | 14 | C8-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDIWGQG TMVTVSS |
| 7 | 15 | C6-VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDSSSDH VVFGGGTKLTVL | 16 | C6-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWMLVAEAFDLWGQ GTMVTVSS |
| 8 | 17 | C3-VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDSSSDH VVFGGGTKLTVL | 18 | C3-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWEWVAEAFDLWGQ GTMVTVSS |
| 9 | 19 | C37-VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDSSSDH VVFGGGTKLTVL | 20 | C37-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDMWGQ GTMVTVSS |
| 10 | 21 | C32-VL | SYVLTQPPSVSVAP GQTARITCGGNLIG SKLVHWYQQKPGQ APVLVVYDDSDRP SKIPERFSGSNSGNT ATLTISRVEAGDEA DYYCQVWDSSSDH VVFGGGTKLTVL | 22 | C32-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |
| 11 | 23 | C38-VL | SYVLTQPPSVSVAP GQTARITCGGNLIG SKLVHWYQQKPGQ APVLVVYDDSDRP SDIPERFSGSNSGNT ATLTISRVEAGDEA DYYCQVWDTSSDH VVFGGGTKLTVL | 24 | C38-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWEYVAEAFDLWGQ GTMVTVSS |
| 12 | 25 | C26-VL | SYVLTQPPSVSVAP GQTARITCGGNIIGS KLVHWYQQKPGQ APVLVVYDDGDRP SGIPERFSGSNSGNT ATLTISRVEAGDEA DYYCQVWDTSSDH VVFGGGTKLTVL | 26 | C26-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTAEAFDLWGQG TMVTVSS |
| 13 | 27 | C13-VL | SYVLTQPPSVSVAP GQTARITCGGNLLG SKLVHWYQQKPGQ APVLVVYDDGDRP SLIPERFSGSNSGNT ATLTISRVEAGDEA DYYCQVWDTSSDH VVFGGGTKLTVL | 28 | C13-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |

TABLE 1-continued

Engineered dual binding antibodies:
Variable Light chain (VL) and Variable Heavy chain (VH)
amino acid sequences (See also FIGS. 1A and 1B)

| Ab # | SEQ ID NO: | Name | VL Sequence | SEQ ID NO: | Name | VH Sequence |
|---|---|---|---|---|---|---|
| 14 | 29 | C23-VL | SYVLTQPPSVSVAP GQTARITCGGNLLG SKLVHWYQQKPGQ APVLVVYDDSDRP SEIPERFSGSNSGNT ATLTISRVEAGDEA DYYCQVWDTSSDG VVFGGGTKLTVL | 30 | C23-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTAEAFDIWGQG TMVTVSS |
| 15 | 31 | C39-VL | SYVLTQPPSVSVAP GQTARITCGGNLLG SKLVHWYQQKPGQ APVLVVYDDSDRP SWIPERFSGSNSGN TATLTISRVEAGDE ADYYCQVWDTSSD HVVFGGGTKLTVL | 32 | C39-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTAEAFDLWGQG TMVTVSS |
| 16 | 33 | C17-VL | SYVLTQPPSVSVAP GQTARITCGGNLIG SKLVHWYQQKPGQ APVLVVYDDSDRP SAIPERFSGSNSGNT ATLTISRVEAGDEA DYYCQVWDTSSDH VVFGGGTKLTVL | 34 | C17-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTSEAFDLWGQG TMVTVSS |
| 17 | 35 | C45-VL | SYVLTQPPSVSVAP GQTARITCGGNLIG SKLVHWYQQKPGQ APVLVVYDDSDRP SEIPERFSGSNSGNT ATLTISRVEAGDEA DYYCQVWDSSSDG VVFGGGTKLTVL | 36 | C45-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELTSEAFDLWGQG TMVTVSS |
| 18 | 37 | C7-VL | SYVLTQPPSVSVAP GQTARITCGGNIIGS KLVHWYQQKPGQ APVLVVYDDSDRP SGIPERFSGSNSGNT ATLTISRVEAGDEA DYYCQVWDSGSD HVVFGGGTKLTVL | 38 | C7-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWLLVAEAFDLWGQG TMVTVSS |
| 19 | 39 | C31-VL | SYVLTQPPSVSVAP GQTARITCGGNIIGS KLVHWYQQKPGQ APVLVVYDDSDRP SDIPERFSGSNSGNT ATLTISRVEAGDEA DYYCQVWDSGSD GVVFGGGTKLTVL | 40 | C31-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |
| 20 | 41 | C15-VL | SYVLTQPPSVSVAP GQTARITCGGNLIG SKLVHWYQQKPGQ APVLVVYDDGDRP SWIPERFSGSNSGN TATLTISRVEAGDE ADYYCQVWDSGS DGVVFGGGTKLTVL | 42 | C15-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |
| 21 | 43 | C35-VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDSGSD GVVFGGGTKLTVL | 44 | C35-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWVLVSEAFDLWGQG TMVTVSS |

TABLE 1-continued

Engineered dual binding antibodies:
Variable Light chain (VL) and Variable Heavy chain (VH)
amino acid sequences (See also FIGS. 1A and 1B)

| Ab # | SEQ ID NO: | Name | VL Sequence | SEQ ID NO: | Name | VH Sequence |
|---|---|---|---|---|---|---|
| 22 | 45 | C12-VL | SYVLTQPPSVSVAP GQTARITCGGNIIGS KLVHWYQQKPGQ APVLVVYDDSDRP SAIPERFSGSNSGNT ATLTISRVEAGDEA DYYCQVWDSSSDG VVFGGGTKLTVL | 46 | C12-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARAPQWELVAEAFDLWGQG TMVTVSS |
| 23 | 47 | C4-VL | SYVLTQPPSVSVAP GQTARITCGGNNIG SKLVHWYQQKPGQ APVLVVYDDSDRP SGIPERFSGSNSGNT ATLTISRVEAGDEA DYYCQVWDSSSDG VVFGGGTKLTVL | 48 | C4-VH | QMQLVESGGGVVQPGRSLR LSCAASGFTFRTYGMHWVR QAPGKGLEWVAVISYDGSN KHYADSVKGRFTITRDNSKN TLNLQMNSLRAEDTAVYYC ARSPQWEWVHEAFDMWGQ GTMVTVSS |
| 24 | 49 | C41-VL | SYVLTQPPSVSVAP GQTARITCGGNILG SKLVHWYQQKPGQ APVLVVYDDSDRP SEIPERFSGSNSGNT ATLTISRVEAGDEA DYYCQVWDTSSDG VVFGGGTKLTVL | 50 | C41-VH | QMQLVESGGGVVQPGRSLR LSCAASGFTFRTYGMHWVR QAPGKGLEWVAVISYDGSN KHYADSVKGRFTITRDNSKN TLNLQMNSLRAEDTAVYYC ARSPQWEWVHEAFDLWGQ GTMVTVSS |
| 25 | 51 | C40-VL | SYVLTQPPSVSVAP GQTARITCGGNNIG SKLVHWYQQKPGQ APVLVVYDDSDRP SRIPERFSGSNSGNT ATLTISRVEAGDEA DYYCQVWDTSSDG VVFGGGTKLTVL | 52 | C40-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARSPQWEWVHEAFDLWGQ GTMVTVSS |
| 26 | 53 | C9-VL | SYVLTQPPSVSVAP GQTARITCGGNLIG SKLVHWYQQKPGQ APVLVVYDDGDRP SWIPERFSGSNSGN TATLTISRVEAGDE ADYYCQVWDSSSD GVVFGGGTKLTVL | 54 | C9-VH | QMQLVESGGGVVQPGRSLR LSCAASGFTFRTYGMHWVR QAPGKGLEWVAVIWYDGSN KHYADSVKGRFTITRDNSKN TLNLQMNSLRAEDTAVYYC ARSPQWEWVHEAFDLWGQ GTMVTVSS |
|  | 156 | 33.023 VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDHSSD HVVFGGGTKLTVL | 155 | 33.023 VH | QMQLVESGGGVVQPGRSLR LSCAASGFAFRTYGMHWVR QAPGKGLEWVAVIWYDGSN THYADSVKGRFTITRDNSKN TLNLQMNSLRAEDTAVYYC ARAPQWYLSAEAFDLWGQG TMVTVSS |
|  | 160 | 33.025 VL | SYVLTQPPSVSVAP GQTARITCGGNLIG SKLVHWYQQKPGQ APVLVVYDDSDRP SLIPERFSGSNSGNT ATLTISRVEAGDEA DYYCQVWDSSSDG VVFGGGTKLTVL | 159 | 33.025 VH | QMQLVESGGGVVQPGRSLR LSCAASGFTFRTYGMHWVR QAPGKGLEWVADIWYDGSN KHYADSVKGRFTITRDNSKN TLNLQMNSLRAEDTAVYYC ARAPQWYLVAEPFDLWGQG TMVTVSS |
|  | 170 | 38.014 VL | SYVLTQPPSVSVAP GQTARITCGGNLIG AKLVHWYQQKPG QAPVLVVYDDSDR PSRIPERFSGSNSGN TATLTISRVEAGDE ADYYCQVWDHSS DHVVFGGGTKLTVL | 169 | 38.014 VH | QMQLVESGGGVVQPGRSLR LSCAASGFAFRTYGMHWVR QAPGKGLEWVAVIWYDGSN THYADSVKGRFTITRDNSKN TLNLQMNSLRAEDTAVYYC VRAPQWYLSAEAFDLWGQG TMVTVSS |

TABLE 1-continued

Engineered dual binding antibodies:
Variable Light chain (VL) and Variable Heavy chain (VH)
amino acid sequences (See also FIGS. 1A and 1B)

| Ab # | SEQ ID NO: | Name | VL Sequence | SEQ ID NO: | Name | VH Sequence |
|---|---|---|---|---|---|---|
| | 172 | 38.018 VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDHSSD HVVFGGGTKLTVL | 171 | 38.018 VH | QMQLVESGGGVVQPGRSLR LSCAASGFAFRTYGMHWVR QAPGKGLEWVAVIWDDGSN THYADSVKGRFTITRDNSKN TLNLQMNSLRAEDTAVYYC ARAPQWYLSAEAFDLWGQG TMVTVSS |
| | 174 | 38.019 VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDYSSN HVVFGGGTKLTVL | 173 | 38.019 VH | QMQLVESGGGVVQPGRSLR LSCAASGFAFRTYGMHWVR QAPGKGLEWVAVIWYDGSN THYADSVKGRFTITRDNSKN TLNLQMNSLRAEDTAVYYC VRAPQWYLSAEAFDLWGQG TMVTVSS |
| | 176 | 38.021 VL | SYVLTQPPSVSVAP GQTARITCGGNLIG SKLVHWYQQKPGQ APVLVVYDDSDRP SRIPERFSGSNSGNT ATLTISRVEAGDEA DYYCQVWDHSSD HYVFGGGTKLTVL | 175 | 38.021 VH | QMQLVESGGGVVQPGRSLR LSCAASGFAFDTYGMHWVR QAPGKGLEWVAVIWYDGSN TVYADSVKGRFTITRDNSKN TLNLQMNSLRAEDTAVYYC ARAPQWYLSAEAFDLWGQG TMVTVSS |
| | 178 | 38.025 VL | SYVLTQPPSVSVAP GETATITCGGNLIG SKLVHWYQQKPGQ APVLVVYDDSDRP SRIPERFSGSNSGNT ATLTISRVEAGDEA DYYCQVWDHSSD HVVFGGGTKLTVL | 177 | 38.025 VH | QMQLVESGGGVVQPGRSLR LSCAASGFAFRTYGMHWVR QAPGKGLEWVAVIWYDGSN THYADSVKGRFTITRDNSKN TLNLQMNSLRAEDTAVYYC VRAPQWYLSAEAFDLWGQG TMVTVSS |
| | 180 | 38.026 VL | SYVLTQPPSVSVAP GQTATITCGGNLIG SKLVHWYQQKPGQ APVLVVYDDSDRP SRIPERFSGSNIGNT ATLTISRVEAGDEA DYYCQVWDHSSD HVVFGGGTKLTVL | 179 | 38.026 VH | QMQLVESGGGVVQPGRSLR LSCAASGFAFRTYGMHWVR QAPGKGLEWVAVIWYDGSA THYADSVKGRFTITRDNSKN TLNLQMNSLRAEDTAVYYC VRAPQWYLSAEAFDLWGQG TMVTVSS |
| | 182 | 38.040 VL | SYVLTQPPSVSVAP GQTARITCGGNLIG TKLVHWYQQKPG QAPVLVVYDDSDR PSRIPERFSGSNSGN TATLTISRVEAGDE ADYYCQVWDHNE DEVVFGGGTKLTV L | 181 | 38.040 VH | QMQLVESGGGVVQPGRSLR LSCAASGFDFRTYGMHWVR QAPGKGLEWVAVIWYDGSI THYADSVKGRFTITRDNSKN TLNLQMNSLRAEDTAVYYC VRAPQWYLTAEAFDLWGQG TMVTVSS |

TABLE 2

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | 109 | Template VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCAGTTTATTAC |
| | | | TGTGCCCGTGCACCACAGTGGGAATTAGTACACGAAGCAT |
| | | | TCGATATCTGGGGTCAGGGTACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | AATCTGGGCTCTAAGTCTGTTCACTGGTATCAGCAAAAACC |
| | | | AGGCCAGGCACCAGTACTGGTTGTGTACGATGATTCCGATC |
| | | | GTCCAAGCTGGATTCCAGAGCGTTTCAGCGGCTCTAATTCC |
| | | | GGCAACACCGCTACTCTGACTATTTCCCGTGGGGAAGCCGG |
| | | | CGATGAAGCCGACTACTATTGCCAGGTCTGGGACTCTTCTT |
| | | | CCGACCATGTAGTCTTTGGCGGGGGCACCAAACTGACCGTT |
| | | | TTG |
| 1 | 110 | C2-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGGAATTAACGGCGGAAGCAT |
| | | | TCGATATTTGGGGCCAGGGCACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | CTGATCGGCTCTAAGCTGGTTCACTGGTATCAGCAAAAACC |
| | | | AGGCCAGGCACCAGTACTGGTTGTGTACGATGATAGCGAT |
| | | | CGTCCAAGCCTGATTCCAGAGCGTTTCAGCGGCTCTAATTC |
| | | | CGGCAACACCGCTACTCTGACTATTTCCCGTGTTGAAGCCG |
| | | | GCGATGAAGCCGACTACTATTGCCAGGTCTGGGACTCTAGC |
| | | | TCCGACGGTGTAGTCTTTGGCGGGGGCACCAAACTGACCGT |
| | | | TTTG |
| 2 | 111 | C27-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGGAATTAGTAGCGGAAGCAT |
| | | | TCGATCTGTGGGGCCAGGGCACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | CTGATCGGCTCTAAGCTGGTTCACTGGTATCAGCAAAAACC |
| | | | AGGCCAGGCACCAGTACTGGTTGTGTACGATGATAGCGAT |
| | | | CGTCCAAGCCTGATTCCAGAGCGTTTCAGCGGCTCTAATTC |
| | | | CGGCAACACCGCTACTCTGACTATTTCCCGTGTTGAAGCCG |
| | | | GCGATGAAGCCGACTACTATTGCCAGGTCTGGGACTCTAGC |
| | | | TCCGACGGTGTAGTCTTTGGCGGGGGCACCAAACTGACCGT |
| | | | TTTG |
| 3 | 112 | C19-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGCAGTTAGTAGCGGAAGCAT |
| | | | TCGATATTTGGGGCCAGGGCACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | CTGATCGGCTCTAAGCTGGTTCACTGGTATCAGCAAAAACC |
| | | | AGGCCAGGCACCAGTACTGGTTGTGTACGATGATAGCGAT |
| | | | CGTCCAAGCCTTATTCCAGAGCGTTTCAGCGGCTCTAATTC |
| | | | CGGCAACACCGCTACTCTGACTATTTCCCGTGTTGAAGCCG |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | | | GCGATGAAGCCGACTACTATTGCCAGGTCTGGGACACCAG CTCCGACGGTGTAGTCTTTGGCGGGGGCACCAAACTGACC GTTTTG |
| 4 | 113 | C43-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGCAGTTAGTAGCCGAAGCATT CGATATATGGGGCCAGGGCACTATGGTGACCGTTAGCTCTG GCGGTGGTGGTAGCGGAGGCGGAGGATCAGGTGGAGGCG GCAGTTCTTACGTGCTGACTCAACCACCATCAGTGTCTGTA GCACCAGGCCAGACCGCACGTATTACCTGTGGCGGTAACC TGATCGGCTCTAAGCTGGTTCACTGGTATCAGCAAAAACCA GGCCAGGCACCAGTACTGGTTGTGTACGATGATAGCGATC GTCCAAGCGCTATTCCAGAGCGTTTCAGCGGCTCTAATTCC GGCAACACCGCTACTCTGACTATTTCCCGTGTTGAAGCCGG CGATGAAGCCGACTACTATTGCCAGGTCTGGGACACTAGCT CCGACGGTGTAGTCTTTGGCGGGGGCACCAAACTGACCGTT TTG |
| 5 | 114 | C5-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTAGTGGCGGAAGCAT TCGATCTTTGGGGCCAGGGCACTATGGTGACCGTTAGCTCT GGTGGTGGTGGTAGCGGAGGCGGAGGATCAGGTGGAGGCG GCAGTTCTTACGTGCTGACTCAACCACCATCAGTGTCTGTA GCACCAGGCCAGACCGCACGTATTACCTGTGGCGGTAACC TGATCGGCTCTAAGCTGGTTCACTGGTATCAGCAAAAACCA GGCCAGGCACCAGTACTGGTTGTGTACGATGATAGCGATC GTCCAAGCCTTATTCCAGAGCGTTTCAGCGGCTCTAATTCC GGCAACACCGCTACTCTGACTATTTCCCGTGTTGAAGCCGG CGATGAAGCCGACTACTATTGCCAGGTCTGGGACACCAGC TCCGACGGTGTAGTCTTTGGCGGGGGCACCAAACTGACCGT TTTG |
| 6 | 115 | C8-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTGGTAGCCGAAGCAT TCGATATCTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC CTGCTGGGCTCTAAGCTGGTTCACTGGTATCAGCAAAAACC AGGCCAGGCACCAGTACTGGTTGTGTACGATGATAGCGAT CGTCCAAGCGCAATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACTCTAGC TCCGACCACGTAGTCTTTGGCGGGGGCACCAAACTGACCGT TTTG |
| 7 | 116 | C6-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGATGTTAGTAGCCGGAAGCATT |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
|  |  |  | CGATCTATGGGGCCAGGGCACTATGGTGACCGTTAGCTCTG |
|  |  |  | GCGGTGGTGGTAGCGGAGGCGGAGGATCAGGTGGAGGCG |
|  |  |  | GCAGTTCTTACGTGCTGACTCAACCACCATCAGTGTCTGTA |
|  |  |  | GCACCAGGCCAGACCGCACGTATTACCTGTGGCGGTAACC |
|  |  |  | TGATCGGCTCTAAGCTGGTTCACTGGTATCAGCAAAAACCA |
|  |  |  | GGGCAGGCACCAGTACTGGTTGTGTACGATGATAGCGATC |
|  |  |  | GTCCAAGCCGGATTCCAGAGCGTTTCAGCGGCTCTAATTCC |
|  |  |  | GGCAACACCGCTACTCTGACTATTTCCCGTGTTGAAGCCGG |
|  |  |  | CGATGAAGCCGACTACTATTGCCAGGTCTGGGACTCCAGCT |
|  |  |  | CCGACCATGTAGTCTTTGGCGGGGGCACCAAACTGACCGTT |
|  |  |  | TTG |
| 8 | 117 | C3-VH-L-VL | CAAATGCAGCTGGTCGAGTCTGGCGGTGGGGTAGTGCAAC |
|  |  |  | CAGGCCGTTCTCTGCGTCTTAGCTGCGCCGCATCTGGTTTT |
|  |  |  | ACCTTTCGTACCTACGGTATGCACTGGGTGCGTCAGGCACC |
|  |  |  | AGGCAAAGGTCTGGAATGGGTCGCAGTAATCTGGTATGAT |
|  |  |  | GGTAGCAATAAACACTATGCTGACTCAGTCAAAGGCCGTTT |
|  |  |  | CACCATCACCCGTGATAACAGCAAGAACACTCTTAACTTAC |
|  |  |  | AGATGAACTCTCTGCGTGCCGAAGACACCGCCGTTTACTAC |
|  |  |  | TGTGCCCGTGCACCACAGTGGGAATGGGTAGCCGAAGCAT |
|  |  |  | TCGATCTGTGGGGCCAGGGCACTATGGTGACCGTTAGCTCT |
|  |  |  | GGCGGTGGTGGTAGCGGAGGCGGAGGATCAGGTGGAGGC |
|  |  |  | GGCAGTTCTTACGTGCTGACTCAACCACCATCAGTGTCTGT |
|  |  |  | AGCACCAGGCCAGACCGCACGTATTACCTGTGGCGGTAAC |
|  |  |  | CTGATCGGCTCTAAGCTGGTTCACTGGTATCAGCAAAAACC |
|  |  |  | AGGCCAGGCACCAGTACTGGTTGTGTACGATGATAGCGAT |
|  |  |  | CGTCCAAGCCGGATTCCAGAGCGTTTCAGCGGCTCTAATTC |
|  |  |  | CGGCAACACCGCTACTCTGACTATTTCCCGTGTTGAAGCCG |
|  |  |  | GCGATGAAGCCGACTACTATTGCCAGGTCTGGGACTCCAG |
|  |  |  | CTCCGACCACGTAGTCTTTGGCGGGGGCACCAAACTGACC |
|  |  |  | GTTTTG |
| 9 | 118 | C37-VH-L-VL | CAAATGCAGCTGGTCGAGTCTGGCGGTGGGGTAGTGCAAC |
|  |  |  | CAGGCCGTTCTCTGCGTCTTAGCTGCGCCGCATCTGGTTTT |
|  |  |  | ACCTTTCGTACCTACGGTATGCACTGGGTGCGTCAGGCACC |
|  |  |  | AGGCAAAGGTCTGGAATGGGTCGCAGTAATCTGGTATGAT |
|  |  |  | GGTAGCAATAAACACTATGCTGACTCAGTCAAAGGCCGTTT |
|  |  |  | CACCATCACCCGTGATAACAGCAAGAACACTCTTAACTTAC |
|  |  |  | AGATGAACTCTCTGCGTGCCGAAGACACCGCCGTTTACTAC |
|  |  |  | TGTGCCCGTGCACCACAGTGGGAATTAGTAGCCGAGGCAT |
|  |  |  | TCGATATGTGGGGCCAGGGCACTATGGTGACCGTTAGCTCT |
|  |  |  | GGCGGTGGTGGTAGCGGAGGCGGAGGATCAGGTGGAGGC |
|  |  |  | GGCAGTTCTTACGTGCTGACTCAACCACCATCAGTGTCTGT |
|  |  |  | AGCACCAGGCCAGACCGCACGTATTACCTGTGGCGGTAAC |
|  |  |  | CTGATCGGCTCTAAGCTGGTTCACTGGTATCAGCAAAAACC |
|  |  |  | AGGCCAGGCACCAGTACTGGTTGTGTACGATGATAGCGAT |
|  |  |  | CGTCCAAGCCGGATTCCAGAGCGTTTCAGCGGCTCTAATTC |
|  |  |  | CGGCAACACCGCTACTCTGACTATTTCCCGTGTTGAAGCCG |
|  |  |  | GCGATGAAGCCGACTACTATTGCCAGGTCTGGGACTCTAGC |
|  |  |  | TCCGACCATGTAGTCTTTGGCGGGGGCACCAAACTGACCGT |
|  |  |  | TTTG |
| 10 | 119 | C32-VH-L-VL | CAAATGCAGCTGGTCGAGTCTGGCGGTGGGGTAGTGCAAC |
|  |  |  | CAGGCCGTTCTCTGCGTCTTAGCTGCGCCGCATCTGGTTTT |
|  |  |  | ACCTTTCGTACCTACGGTATGCACTGGGTGCGTCAGGCACC |
|  |  |  | AGGCAAAGGTCTGGAATGGGTCGCAGTAATCTGGTATGAT |
|  |  |  | GGTAGCAATAAACACTATGCTGACTCAGTCAAAGGCCGTTT |
|  |  |  | CACCATCACCCGTGATAACAGCAAGAACACTCTTAACTTAC |
|  |  |  | AGATGAACTCTCTGCGTGCCGAAGACACCGCCGTTTACTAC |
|  |  |  | TGTGCCCGTGCACCACAGTGGGAATTAGTAGCCGAAGCAT |
|  |  |  | TCGATCTGTGGGGCCAGGGCACTATGGTGACCGTTAGCTCT |
|  |  |  | GGCGGTGGTGGTAGCGGAGGCGGAGGATCAGGTGGAGGC |
|  |  |  | GGCAGTTCTTACGTGCTGACTCAACCACCATCAGTGTCTGT |
|  |  |  | AGCACCAGGCCAGACCGCACGTATTACCTGTGGCGGTAAC |
|  |  |  | CTGATCGGCTCTAAGCTGGTTCACTGGTATCAGCAAAAACC |
|  |  |  | AGGCCAGGCACCAGTACTGGTTGTGTACGATGATAGCGAT |
|  |  |  | CGTCCAAGCAAAATTCCAGAGCGTTTCAGCGGCTCTAATTC |
|  |  |  | CGGCAACACCGCTACTCTGACTATTTCCCGTGTTGAAGCCG |
|  |  |  | GCGATGAAGCCGACTACTATTGCCAGGTCTGGGACTCCAG |
|  |  |  | CTCCGACCATGTAGTCTTTGGCGGGGGCACCAAACTGACCG |
|  |  |  | TTTTG |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|------|------------|------|------------------------|
| 11 | 120 | C38-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATACGTAGCGGAAGCAT TCGATCTGTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC CTGATCGGCTCTAAGCTGGTTCACTGGTATCAGCAAAAACC AGGCCAGGCACCAGTACTGGTTGTGTACGATGATAGCGAT CGTCCAAGCGATATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACACCAG CTCCGACCATGTAGTCTTTGGCGGGGGCACCAAACTGACCG TTTTG |
| 12 | 121 | C26-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTAACGGCCGAAGCAT TCGATCTTTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC ATCATCGGCTCTAAGCTGGTTCACTGGTATCAGCAAAAACC AGGCCAGGCACCAGTACTGGTTGTGTACGATGATGGCGAT CGTCCAAGCGGTATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACACTAG CTCCGACCACGTAGTCTTTGGCGGGGGCACCAAACTGACC GTTTTG |
| 13 | 122 | C13-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTAGTGGCGGAAGCAT TCGATCTTTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC CTGCTGGGCTCTAAGCTGGTTCACTGGTATCAGCAAAAACC AGGCCAGGCACCAGTACTGGTTGTGTACGATGATGGCGAT CGTCCAAGCCTGATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACACTAG CTCCGACCACGTAGTCTTTGGCGGGGGCACCAAACTGACC GTTTTG |
| 14 | 123 | C23-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTAACGGCGGAAGCAT TCGATATTTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|------|------------|------|------------------------|
| | | | CTGCTGGGCTCTAAGCTGGTTCACTGGTATCAGCAAAAACC<br>AGGCCAGGCACCAGTACTGGTTGTGTACGATGATAGCGAT<br>CGTCCAAGCGAAATTCCAGAGCGTTTCAGCGGCTCTAATTC<br>CGGCAACACCGCTACTCTGACTATTTCCCGTGTTGAAGCCG<br>GCGATGAAGCCGACTACTATTGCCAGGTCTGGGACACCAG<br>CTCCGACGGTGTAGTCTTTGGCGGGGGCACCAAACTGACC<br>GTTTTG |
| 15 | 124 | C39-<br>VH-L-VL | CAAATGCAGCTGGTCGAGTCTGGCGGTGGGGTAGTGCAAC<br>CAGGCCGTTCTCTGCGTCTTAGCTGCGCCGCATCTGGTTTT<br>ACCTTTCGTACCTACGGTATGCACTGGGTGCGTCAGGCACC<br>AGGCAAAGGTCTGGAATGGGTCGCAGTAATCTGGTATGAT<br>GGTAGCAATAAACACTATGCTGACTCAGTCAAAGGCCGTTT<br>CACCATCACCCGTGATAACAGCAAGAACACTCTTAACTTAC<br>AGATGAACTCTCTGCGTGCCGAAGACACCGCCGTTTACTAC<br>TGTGCCCGTGCACCACAGTGGGAATTAACGGCCGAAGCAT<br>TCGATCTTTGGGGCCAGGGCACTATGGTGACCGTTAGCTCT<br>GGCGGTGGTGGTAGCGGAGGCGGAGGATCAGGTGGAGGC<br>GGCAGTTCTTACGTGCTGACTCAACCACCATCAGTGTCTGT<br>AGCACCAGGCCAGACCGCACGTATTACCTGTGGCGGTAAC<br>CTGCTGGGCTCTAAGCTGGTTCACTGGTATCAGCAAAAACC<br>AGGCCAGGCACCAGTACTGGTTGTGTACGATGATAGCGAT<br>CGTCCAAGCTGGATTCCAGAGCGTTTCAGCGGCTCTAATTC<br>CGGCAACACCGCTACTCTGACTATTTCCCGTGTTGAAGCCG<br>GCGATGAAGCCGACTACTATTGCCAGGTCTGGGACACTAG<br>CTCCGACCATGTAGTCTTTGGCGGGGGCACCAAACTGACCG<br>TTTTG |
| 16 | 125 | C17-<br>VH-L-VL | CAAATGCAGCTGGTCGAGTCTGGCGGTGGGGTAGTGCAAC<br>CAGGCCGTTCTCTGCGTCTTAGCTGCGCCGCATCTGGTTTT<br>ACCTTTCGTACCTACGGTATGCACTGGGTGCGTCAGGCACC<br>AGGCAAAGGTCTGGAATGGGTCGCAGTAATCTGGTATGAT<br>GGTAGCAATAAACACTATGCTGACTCAGTCAAAGGCCGTTT<br>CACCATCACCCGTGATAACAGCAAGAACACTCTTAACTTAC<br>AGATGAACTCTCTGCGTGCCGAAGACACCGCCGTTTACTAC<br>TGTGCCCGTGCACCACAGTGGGAATTAACGTCGGAAGCAT<br>TCGATCTTTGGGGCCAGGGCACTATGGTGACCGTTAGCTCT<br>GGCGGTGGTGGTAGCGGAGGCGGAGGATCAGGTGGAGGC<br>GGCAGTTCTTACGTGCTGACTCAACCACCATCAGTGTCTGT<br>AGCACCAGGCCAGACCGCACGTATTACCTGTGGCGGTAAC<br>CTGATCGGCTCTAAGCTGGTTCACTGGTATCAGCAAAAACC<br>AGGCCAGGCACCAGTACTGGTTGTGTACGATGATAGCGAT<br>CGTCCAAGCGCAATTCCAGAGCGTTTCAGCGGCTCTAATTC<br>CGGCAACACCGCTACTCTGACTATTTCCCGTGTTGAAGCCG<br>GCGATGAAGCCGACTACTATTGCCAGGTCTGGGACACCAG<br>CTCCGACCACGTAGTCTTTGGCGGGGGCACCAAACTGACC<br>GTTTTG |
| 17 | 126 | C45-<br>VH-L-VL | CAAATGCAGCTGGTCGAGTCTGGCGGTGGGGTAGTGCAAC<br>CAGGCCGTTCTCTGCGTCTTAGCTGCGCCGCATCTGGTTTT<br>ACCTTTCGTACCTACGGTATGCACTGGGTGCGTCAGGCACC<br>AGGCAAAGGTCTGGAATGGGTCGCAGTAATCTGGTATGAT<br>GGTAGCAATAAACACTATGCTGACTCAGTCAAAGGCCGTTT<br>CACCATCACCCGTGATAACAGCAAGAACACTCTTAACTTAC<br>AGATGAACTCTCTGCGTGCCGAAGACACCGCCGTTTACTAC<br>TGTGCCCGTGCACCACAGTGGGAATTAACCTCCGAAGCATT<br>CGATCTTTGGGGCCAGGGCACTATGGTGACCGTTAGCTCTG<br>GCGGTGGTGGTAGCGGAGGCGGAGGATCAGGTGGAGGCG<br>GCAGTTCTTACGTGCTGACTCAACCACCATCAGTGTCTGTA<br>GCACCAGGCCAGACCGCACGTATTACCTGTGGCGGTAACC<br>TGATCGGCTCTAAGCTGGTTCACTGGTATCAGCAAAAACCA<br>GGCCAGGCACCAGTACTGGTTGTGTACGATGATAGCGATC<br>GTCCAAGCGAAATTCCAGAGCGTTTCAGCGGCTCTAATTCC<br>GGCAACACCGCTACTCTGACTATTTCCCGTGTTGAAGCCGG<br>CGATGAAGCCGACTACTATTGCCAGGTCTGGGACTCCAGCT<br>CCGACGGTGTAGTCTTTGGCGGGGGCACCAAACTGACCGTT<br>TTG |
| 18 | 127 | C7-<br>VH-L-VL | CAAATGCAGCTGGTCGAGTCTGGCGGTGGGGTAGTGCAAC<br>CAGGCCGTTCTCTGCGTCTTAGCTGCGCCGCATCTGGTTTT<br>ACCTTTCGTACCTACGGTATGCACTGGGTGCGTCAGGCACC<br>AGGCAAAGGTCTGGAATGGGTCGCAGTAATCTGGTATGAT |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGCTGTTAGTAGCGGAAGCATT |
| | | | CGATCTCTGGGGCCAGGGCACTATGGTGACCGTTAGCTCTG |
| | | | GCGGTGGTGGTAGCGGAGGCGGAGGATCAGGTGGAGGCG |
| | | | GCAGTTCTTACGTGCTGACTCAACCACCATCAGTGTCTGTA |
| | | | GCACCAGGCCAGACCGCACGTATTACCTGTGGCGGTAACA |
| | | | TCATCGGCTCTAAGCTGGTTCACTGGTATCAGCAAAAACCA |
| | | | GGCCAGGCACCAGTACTGGTTGTGTACGATGATAGCGATC |
| | | | GTCCAAGCGGTATTCCAGAGCGTTTCAGCGGCTCTAATTCC |
| | | | GGCAACACCGCTACTCTGACTATTTCCCGTGTTGAAGCCGG |
| | | | CGATGAAGCCGACTACTATTGCCAGGTCTGGGACTCTGGCT |
| | | | CCGACCACGTAGTCTTTGGCGGGGGCACCAAACTGACCGTT |
| | | | TTG |
| 19 | 128 | C31-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGGAATTAGTAGCGGAAGCAT |
| | | | TCGATCTCTTTGGGGCCAGGGCACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | ATCATCGGCTCTAAGCTGGTTCACTGGTATCAGCAAAAACC |
| | | | AGGCCAGGCACCAGTACTGGTTGTGTACGATGATAGCGAT |
| | | | CGTCCAAGCGATATTCCAGAGCGTTTCAGCGGCTCTAATTC |
| | | | CGGCAACACCGCTACTCTGACTATTTCCCGTGTTGAAGCCG |
| | | | GCGATGAAGCCGACTACTATTGCCAGGTCTGGGACTCCGG |
| | | | CTCCGACGGTGTAGTCTTTGGCGGGGGCACCAAACTGACC |
| | | | GTTTTG |
| 20 | 129 | C15-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGGAATTAGTAGCGGAAGCAT |
| | | | TCGATCTGTGGGGCCAGGGCACTATGGTGACCGTTAGCTCT |
| | | | GGCGGTGGTGGTAGCGGAGGCGGAGGATCAGGTGGAGGC |
| | | | GGCAGTTCTTACGTGCTGACTCAACCACCATCAGTGTCTGT |
| | | | AGCACCAGGCCAGACCGCACGTATTACCTGTGGCGGTAAC |
| | | | CTGATCGGCTCTAAGCTGGTTCACTGGTATCAGCAAAAACC |
| | | | AGGCCAGGCACCAGTACTGGTTGTGTACGATGATGGCGAT |
| | | | CGTCCAAGCTGGATTCCAGAGCGTTTCAGCGGCTCTAATTC |
| | | | CGGCAACACCGCTACTCTGACTATTTCCCGTGTTGAAGCCG |
| | | | GCGATGAAGCCGACTACTATTGCCAGGTCTGGGACTCTGGC |
| | | | TCCGACGGTGTAGTCTTTGGCGGGGGCACCAAACTGACCGT |
| | | | TTTG |
| 21 | 130 | C35-VH-L-VL | CAAATGCAGCTGGTCGAGTCTGGCGGTGGGGTAGTGCAAC |
| | | | CAGGCCGTTCTCTGCGTCTTAGCTGCGCCGCATCTGGTTTT |
| | | | ACCTTTCGTACCTACGGTATGCACTGGGTGCGTCAGGCACC |
| | | | AGGCAAAGGTCTGGAATGGGTCGCAGTAATCTGGTATGAT |
| | | | GGTAGCAATAAACACTATGCTGACTCAGTCAAAGGCCGTTT |
| | | | CACCATCACCCGTGATAACAGCAAGAACACTCTTAACTTAC |
| | | | AGATGAACTCTCTGCGTGCCGAAGACACCGCCGTTTACTAC |
| | | | TGTGCCCGTGCACCACAGTGGGTCTTAGTATCCGAAGCATT |
| | | | CGATCTTTGGGGCCAGGGCACTATGGTGACCGTTAGCTCTG |
| | | | GCGGTGGTGGTAGCGGAGGCGGAGGATCAGGTGGAGGCG |
| | | | GCAGTTCTTACGTGCTGACTCAACCACCATCAGTGTCTGTA |
| | | | GCACCAGGCCAGACCGCACGTATTACCTGTGGCGGTAACC |
| | | | TGATCGGCTCTAAGCTGGTTCACTGGTATCAGCAAAAACCA |
| | | | GGCCAGGCACCAGTACTGGTTGTGTACGATGATAGCGATC |
| | | | GTCCAAGCGCGTATTCCAGAGCGTTTCAGCGGCTCTAATTCC |
| | | | GGCAACACCGCTACTCTGACTATTTCCCGTGTTGAAGCCGG |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | | | CGATGAAGCCGACTACTATTGCCAGGTCTGGGACTCCGGCT CCGACGGTGTAGTCTTTGGCGGGGGCACCAAACTGACCGTT TTG |
| 22 | 131 | C12-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTGCACCACAGTGGGAATTAGTAGCGGAGGCAT TCGATCTGTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC ATCATCGGCTCTAAGCTGGTTCACTGGTATCAGCAAAAACC AGGCCAGGCACCAGTACTGGTTGTGTACGATGATAGCGAT CGTCCAAGCGCAATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACTCCAG CTCCGACGGTGTAGTCTTTGGCGGGGGCACCAAACTGACC GTTTTG |
| 23 | 132 | C4-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTCTTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTAGCCCACAGTGGGAATGGGTACACGAAGCAT TCGATATGTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC AACATCGGCTCTAAGCTGGTTCACTGGTATCAGCAAAAACC AGGCCAGGCACCAGTACTGGTTGTGTACGATGATAGCGAT CGTCCAAGCGGTATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACTCTAGC TCCGACGGTGTAGTCTTTGGCGGGGGCACCAAACTGACCGT TTTG |
| 24 | 133 | C41-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTCTTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTTCGCCACAGTGGGAATGGGTACACGAAGCAT TCGATCTCTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC ATCCTGGGCTCTAAGCTGGTTCACTGGTATCAGCAAAAACC AGGCCAGGCACCAGTACTGGTTGTGTACGATGATAGCGAT CGTCCAAGCGAAATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACACCAG CTCCGACGGTGTAGTCTTTGGCGGGGGCACCAAACTGACC GTTTTG |
| 25 | 134 | C40-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTAGCCCACAGTGGGAATGGGTACACGAAGCAT |

TABLE 2-continued

Nucleotide Sequences Encoding Engineered
dual Binding scFv: Variable Heavy
chain (VH)-Linker-Variable Light chain (VL)

| Ab # | SEQ ID NO: | Name | VH-Linker-VL Sequence |
|---|---|---|---|
| | | | TCGATCTATGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC AACATCGGCTCTAAGCTGGTTCACTGGTATCAGCAAAAACC AGGCCAGGCACCAGTACTGGTTGTGTACGATGATAGCGAT CGTCCAAGCCGGATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACACTAG CTCCGACGGTGTAGTCTTTGGCGGGGGCACCAAACTGACC GTTTTG |
| 26 | 135 | C9-VH-L-VL | CAAATGCAGCTGGTCGAGTCTGGCGGTGGGGTAGTGCAAC CAGGCCGTTCTCTGCGTCTTAGCTGCGCCGCATCTGGTTTT ACCTTTCGTACCTACGGTATGCACTGGGTGCGTCAGGCACC AGGCAAAGGTCTGGAATGGGTCGCAGTAATCTGGTATGAT GGTAGCAATAAACACTATGCTGACTCAGTCAAAGGCCGTTT CACCATCACCCGTGATAACAGCAAGAACACTCTTAACTTAC AGATGAACTCTCTGCGTGCCGAAGACACCGCCGTTTACTAC TGTGCCCGTTCGCCACAGTGGGAATGGGTACACGAAGCAT TCGATCTCTGGGGCCAGGGCACTATGGTGACCGTTAGCTCT GGCGGTGGTGGTAGCGGAGGCGGAGGATCAGGTGGAGGC GGCAGTTCTTACGTGCTGACTCAACCACCATCAGTGTCTGT AGCACCAGGCCAGACCGCACGTATTACCTGTGGCGGTAAC CTGATCGGCTCTAAGCTGGTTCACTGGTATCAGCAAAAACC AGGCCAGGCACCAGTACTGGTTGTGTACGATGATGGCGAT CGTCCAAGCTGGATTCCAGAGCGTTTCAGCGGCTCTAATTC CGGCAACACCGCTACTCTGACTATTTCCCGTGTTGAAGCCG GCGATGAAGCCGACTACTATTGCCAGGTCTGGGACTCCAG CTCCGACGGTGTAGTCTTTGGCGGGGGCACCAAACTGACC GTTTTG |

TABLE 3

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | 56 | Template-VL | TCTTACGTGCTGACTCA ACCACCATCAGTGTCTG TAGCACCAGGCCAGAC CGCACGTATTACCTGTG GCGGTAACAATCTGGG CTCTAAGTCTGTTCACT GGTATCAGCAAAAACC AGGCCAGGCACCAGTA CTGGTTGTGTACGATGA TTCCGATCGTCCAAGCT GGATTCCAGAGCGTTTC AGCGGCTCTAATTCCGG CAACACCGCTACTCTGA CTATTTCCCGTGGGGAA GCCGGCGATGAAGCCG ACTACTATTGCCAGGTC TGGGACTCTTCTTCCGA CCATGTAGTCTTTGGCG GGGGCACCAAACTGAC CGTTTTG | 55 | Template-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCAGTTTATTACTGTGCC CGTGCCACCAGTGGGA ATTAGTACACGAAGCAT TCGATATCTGGGGTCAG GGTACTATGGTGACCGT TAGCTCT |
| 1 | 58 | C2-VL | TCTTACGTGCTGACTCA ACCACCATCAGTGTCTG TAGCACCAGGCCAGAC CGCACGTATTACCTGTG | 57 | C2-VH | CAAATGCAGCTGGTCGA GTCTGGCGGTGGGGTAG TGCAACCAGGCCGTTCT CTGCGTCTTAGCTGCGC |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC TGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCTAGCTCCGA CGGTGTAGTCTTTGGCG GGGGCACCAAACTGAC CGTTTTG | | | CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACGGCGGAAGCAT TCGATATTGGGGCCAG GGCACTATGGTGACCGT TAGCTCT |
| 2 | 60 | C27-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC TGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCTAGCTCCGA CGGTGTAGTCTTTGGCG GGGGCACCAAACTGAC CGTTTTG | 59 | C27-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTAT GCTGACTCAGTCAAAGG CCGTTTCACCATCACCC GTGATAACAGCAAGAAC ACTCTTAACTTACAGAT GAACTCTCTGCGTGCCG AAGACACCGCCGTTTAC TACTGTGCCCGTGCACC ACAGTGGGAATTAGTAG CGGAAGCATTCGATCTG TGGGGCCAGGGCACTAT GGTGACCGTTAGCTCT |
| 3 | 62 | C19-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC TTATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACACCAGCTCCG ACGGTGTAGTCTTTGGC GGGGGCACCAAACTGA CCGTTTTG | 61 | C19-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGCA GTTAGTAGCGGAAGCAT TCGATATTGGGGCCAG GGCACTATGGTGACCGT TAGCTCT |
| 4 | 64 | C43-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC | 63 | C43-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | AGGCCAGGCACCAGTA CTGGTTGTGTACGATGA TAGCGATCGTCCAAGC GCTATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACTAGCTCCG ACGGTGTAGTCTTTGGC GGGGGCACCAAACTGA CCGTTTTG | | | CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGCA GTTAGTAGCCGAAGCAT TCGATATATGGGGCCAG GGCACTATGGTGACCGT TAGCTCT |
| 5 | 66 | C5-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC TTATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACACCAGCTCCG ACGGTGTAGTCTTTGGC GGGGGCACCAAACTGA CCGTTTTG | 65 | C5-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAGTGGCGGAAGCAT TCGATCTTTGGGGCCAG GGCACTATGGTGACCGT TAGCTCT |
| 6 | 68 | C8-VL | TCTTACGTGCTGACTCA ACCACCATCAGTGTCTG TAGCACCAGGCCAGAC CGCACGTATTACCTGTG GCGGTAACCTGCTGGG CTCTAAGCTGGTTCACT GGTATCAGCAAAAACC AGGCCAGGCACCAGTA CTGGTTGTGTACGATGA TAGCGATCGTCCAAGC GCAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCTAGCTCCG ACCACGTAGTCTTTGGC GGGGGCACCAAACTGA CCGTTTTG | 67 | C8-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTGGTAGCCGAAGCAT TCGATATCTGGGGCCAG GGCACTATGGTGACCGT TAGCTCT |
| 7 | 70 | C6-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGGCAGGCACCAGTA CTGGTTGTGTACGATGA TAGCGATCGTCCAAGCC | 69 | C6-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCCAGCTCCGA CCATGTAGTCTTTGGCG GGGGCACCAAACTGAC CGTTTTG | | | AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGAT GTTAGTAGCGGAAGCAT TCGATCTATGGGGCCAG GGCACTATGGTGACCGT TAGCTCT |
| 8 | 72 | C3-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCCAGCTCCGA CCACGTAGTCTTTGGCG GGGGCACCAAACTGAC CGTTTTG | 71 | C3-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATGGGTAGCCGAAGCAT TCGATCTGTGGGGCCAG GGCACTATGGTGACCGT TAGCTCT |
| 9 | 74 | C37-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCTAGCTCCGA CCATGTAGTCTTTGGCG GGGGCACCAAACTGAC CGTTTTG | 73 | C37-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAGTAGCCGAGGCAT TCGATATGTGGGGCCAG GGCACTATGGTGACCGT TAGCTCT |
| 10 | 76 | C32-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGC AAAATTCCAGAGCGTTT CAGCGGCTCTAATTCCG GCAACACCGCTACTCTG | 75 | C32-VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | ACTATTTCCCGTGTTGA AGCCGGCGATGAAGCC GACTACTATTGCCAGGT CTGGGACTCCAGCTCCG ACCATGTAGTCTTTGGC GGGGGCACCAAACTGA CCGTTTTG | | | AGCAAGAACACTCTTAA CTTACAGATGAACTCTC TGCGTGCCGAAGACACC GCCGTTTACTACTGTGCC CGTGCACCACAGTGGGA ATTAGTAGCCGAAGCAT TCGATCTGTGGGGCCAG GGCACTATGGTGACCGT TAGCTCT |
| 11 | 78 | C38-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGC GATATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACCAGCTCC GACCATGTAGTCTTTGG CGGGGGCACCAAACTG ACCGTTTTG | 77 | C38-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATACGTAGCGGAAGCAT TCGATCTGTGGGGCCAG GGCACTATGGTGACCGT TAGCTCT |
| 12 | 80 | C26-VL | TCTTACGTGCTGACTCA ACCACCATCAGTGTCTG TAGCACCAGGCCAGAC CGCACGTATTACCTGTG GCGGTAACATCATCGG CTCTAAGCTGGTTCACT GGTATCAGCAAAAACC AGGCCAGGCACCAGTA CTGGTTGTGTACGATGA TGGCGATCGTCCAAGC GGTATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACTAGCTCCG ACCACGTAGTCTTTGGC GGGGGCACCAAACTGA CCGTTTTG | 79 | C26-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACGGCCGAAGCAT TCGATCTTTGGGGCCAG GGCACTATGGTGACCGT TAGCTCT |
| 13 | 82 | C13-VL | TCTTACGTGCTGACTCA ACCACCATCAGTGTCTG TAGCACCAGGCCAGAC CGCACGTATTACCTGTG GCGGTAACCTGCTGGG CTCTAAGCTGGTTCACT GGTATCAGCAAAAACC AGGCCAGGCACCAGTA CTGGTTGTGTACGATGA TGGCGATCGTCCAAGCC TGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC | 81 | C13-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | TGGGACACTAGCTCCG ACCACGTAGTCTTTGGC GGGGGCACCAAACTGA CCGTTTTG | | | GCCGTTTACTACTGTGCC CGTGCACCACAGTGGGA ATTAGTGGCGGAAGCAT TCGATCTTTGGGGCCAG GGCACTATGGTGACCGT TAGCTCT |
| 14 | 84 | C23-VL | TCTTACGTGCTGACTCA ACCACCATCAGTGTCTG TAGCACCAGGCCAGAC CGCACGTATTACCTGTG GCGGTAACCTGCTGGG CTCTAAGCTGGTTCACT GGTATCAGCAAAAACC AGGCCAGGCACCAGTA CTGGTTGTGTACGATGA TAGCGATCGTCCAAGC GAAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACCAGCTCC GACGGTGTAGTCTTTGG CGGGGGCACCAAACTG ACCGTTTTG | 83 | C23-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACGGCGGAAGCAT TCGATATTTGGGGCCAG GGCACTATGGTGACCGT TAGCTCT |
| 15 | 86 | C39-VL | TCTTACGTGCTGACTCA ACCACCATCAGTGTCTG TAGCACCAGGCCAGAC CGCACGTATTACCTGTG GCGGTAACCTGCTGGG CTCTAAGCTGGTTCACT GGTATCAGCAAAAACC AGGCCAGGCACCAGTA CTGGTTGTGTACGATGA TAGCGATCGTCCAAGCT GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACACTAGCTCCG ACCATGTAGTCTTTGGC GGGGGCACCAAACTGA CCGTTTTG | 85 | C39-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACGGCCGAAGCAT TCGATCTTTGGGGCCAG GGCACTATGGTGACCGT TAGCTCT |
| 16 | 88 | C17-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGC GCAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACCAGCTCC GACCACGTAGTCTTTGG CGGGGGCACCAAACTG | 87 | C17-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACGTCGGAAGCAT |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | ACCGTTTTG | | | TCGATCTTTGGGGCCAG GGCACTATGGTGACCGT TAGCTCT |
| 17 | 90 | C45- VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGC GAAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCCAGCTCCG ACGGTGTAGTCTTTGGC GGGGGCACCAAACTGA CCGTTTTG | 89 | C45- VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAACCTCCGAAGCAT TCGATCTTTGGGGCCAG GGCACTATGGTGACCGT TAGCTCT |
| 18 | 92 | C7- VL | TCTTACGTGCTGACTCA ACCACCATCAGTGTCTG TAGCACCAGGCCAGAC CGCACGTATTACCTGTG GCGGTAACATCATCGG CTCTAAGCTGGTTCACT GGTATCAGCAAAAACC AGGCCAGGCACCAGTA CTGGTTGTGTACGATGA TAGCGATCGTCCAAGC GGTATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCTGGCTCCG ACCACGTAGTCTTTGGC GGGGGCACCAAACTGA CCGTTTTG | 91 | C7- VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGCT GTTAGTAGCGGAAGCAT TCGATCTCTGGGGCCAG GGCACTATGGTGACCGT TAGCTCT |
| 19 | 94 | C31- VL | TCTTACGTGCTGACTCA ACCACCATCAGTGTCTG TAGCACCAGGCCAGAC CGCACGTATTACCTGTG GCGGTAACATCATCGG CTCTAAGCTGGTTCACT GGTATCAGCAAAAACC AGGCCAGGCACCAGTA CTGGTTGTGTACGATGA TAGCGATCGTCCAAGC GATATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCCGGCTCCG ACGGTGTAGTCTTTGGC GGGGGCACCAAACTGA CCGTTTTG | 93 | C31- VH | CAAATGCAGCTGGTCGA GTCTGGCGGTGGGGTAG TGCAACCAGGCCGTTCT CTGCGTCTTAGCTGCGC CGCATCTGGTTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAGTAGCGGAAGCAT TCGATCTTTGGGGCCAG GGCACTATGGTGACCGT TAGCTCT |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| 20 | 96 | C15-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TGGCGATCGTCCAAGCT GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCTGGCTCCGA CGGTGTAGTCTTTGGCG GGGGCACCAAACTGAC CGTTTTG | 95 | C15-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAGTAGCGGAAGCAT TCGATCTGTGGGGCCAG GGCACTATGGTGACCGT TAGCTCT |
| 21 | 98 | C35-VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC GTATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCCGGCTCCGA CGGTGTAGTCTTTGGCG GGGGCACCAAACTGAC CGTTTTG | 97 | C35-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGT CTTAGTATCCGAAGCAT TCGATCTTTGGGGCCAG GGCACTATGGTGACCGT TAGCTCT |
| 22 | 100 | C12-VL | TCTTACGTGCTGACTCA ACCACCATCAGTGTCTG TAGCACCAGGCCAGAC CGCACGTATTACCTGTG GCGGTAACATCATCGG CTCTAAGCTGGTTCACT GGTATCAGCAAAAACC AGGCCAGGCACCAGTA CTGGTTGTGTACGATGA TAGCGATCGTCCAAGC GCAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCCAGCTCCG ACGGTGTAGTCTTTGGC GGGGGCACCAAACTGA CCGTTTTG | 99 | C12-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGGA ATTAGTAGCGGAGGCAT TCGATCTGTGGGGCCAG GGCACTATGGTGACCGT TAGCTCT |
| 23 | 102 | C4-VL | TCTTACGTGCTGACTCA ACCACCATCAGTGTCTG | 101 | C4-VH | CAAATGCAGCTGGTCGA GTCTGGCGGTGGGGTAG |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | TAGCACCAGGCCAGAC CGCACGTATTACCTGTG GCGGTAACAACATCGG CTCTAAGCTGGTTCACT GGTATCAGCAAAAACC AGGCCAGGCACCAGTA CTGGTTGTGTACGATGA TAGCGATCGTCCAAGC GGTATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACTCTAGCTCCG ACGGTGTAGTCTTTGGC GGGGGCACCAAACTGA CCGTTTTG | | | TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT CTTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTAGCCCACAGTGGGA ATGGGTACACGAAGCAT TCGATATGTGGGGCCAG GGCACTATGGTGACCGT TAGCTCT |
| 24 | 104 | C41-VL | TCTTACGTGCTGACTCA ACCACCATCAGTGTCTG TAGCACCAGGCCAGAC CGCACGTATTACCTGTG GCGGTAACATCCTGGG CTCTAAGCTGGTTCACT GGTATCAGCAAAAACC AGGCCAGGCACCAGTA CTGGTTGTGTACGATGA TAGCGATCGTCCAAGC GAAATTCCAGAGCGTTT CAGCGGCTCTAATTCCG GCAACACCGCTACTCTG ACTATTTCCCGTGTTGA AGCCGGCGATGAAGCC GACTACTATTGCCAGGT CTGGGACACCAGCTCC GACGGTGTAGTCTTTGG CGGGGGCACCAAACTG ACCGTTTTG | 103 | C41-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT CTTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTTCGCCACAGTGGGA ATGGGTACACGAAGCAT TCGATCTCTGGGGCCAG GGCACTATGGTGACCGT TAGCTCT |
| 25 | 106 | C40-VL | TCTTACGTGCTGACTCA ACCACCATCAGTGTCTG TAGCACCAGGCCAGAC CGCACGTATTACCTGTG GCGGTAACAACATCGG CTCTAAGCTGGTTCACT GGTATCAGCAAAAACC AGGCCAGGCACCAGTA CTGGTTGTGTACGATGA TAGCGATCGTCCAAGCC GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACACTAGCTCCG ACGGTGTAGTCTTTGGC GGGGGCACCAAACTGA CCGTTTTG | 105 | C40-VH | CAAATGCAGCTGGTCGA GTCTGGCGGTGGGGTAG TGCAACCAGGCCGTTCT CTGCGTCTTAGCTGCGC CGCATCTGGTTTTACCTT TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTAGCCCACAGTGGGA ATGGGTACACGAAGCAT TCGATCTATGGGGCCAG GGCACTATGGTGACCGT TAGCTCT |
| 26 | 108 | C9-VL | TCTTACGTGCTGACTCA ACCACCATCAGTGTCTG TAGCACCAGGCCAGAC CGCACGTATTACCTGTG GCGGTAACCTGATCGG | 107 | C9-VH | CAAATGCAGCTGGTCGA GTCTGGCGGTGGGGTAG TGCAACCAGGCCGTTCT CTGCGTCTTAGCTGCGC CGCATCTGGTTTTACCTT |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | CTCTAAGCTGGTTCACT GGTATCAGCAAAAACC AGGCCAGGCACCAGTA CTGGTTGTGTACGATGA TGGCGATCGTCCAAGCT GGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCCAGCTCCGA CGGTGTGAGTCTTTGGC GGGGGCACCAAACTGAC CGTTTTG | | | TCGTACCTACGGTATGC ACTGGGTGCGTCAGGCA CCAGGCAAAGGTCTGGA ATGGGTCGCAGTAATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTTCGCCACAGTGGGA ATGGGTACACGAAGCAT TCGATCTCTGGGGCCAG GGCACTATGGTGACCGT TAGCTCT |
| 162 | 162 | 33.023 VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC GTATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACCACAGCTCCG ACCATGTAGTCTTTGGC GGGGGCACCAAACTGA CCGTTTTG | 161 | 33.023 VH | CAAATGCAGCTGGTCGA GTCTGGCGGTGGGGTAG TGCAACCAGGCCGTTCT CTGCGTCTTAGCTGCGC CGCATCTGGTTTTGCGTT TCGTACCTACGGTATGC ACTGGGTGCGTCAGGCA CCAGGCAAAGGTCTGGA ATGGGTCGCAGTAATCT GGTATGATGGTAGCAAT ACCCACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGTA CTTAAGCGCGGAAGCAT TCGATCTATGGGGCCAG GGCACTATGGTGACCGT TAGCTCT |
| 164 | 164 | 33.025 VL | TCTTACGTGCTGACTCA ACCACCATCAGTGTCTG TAGCACCAGGCCAGAC CGCACGTATTACCTGTG GCGGTAACCTGATCGG CTCTAAGCTGGTTCACT GGTATCAGCAAAAACC AGGCCAGGCACCAGTA CTGGTTGTGTACGATGA TAGCGATCGTCCAAGCC TGATTCCAGAGCGTTTC AGCGGCTCTAATTCCGG CAACACCGCTACTCTGA CTATTTCCCGTGTTGAA GCCGGCGATGAAGCCG ACTACTATTGCCAGGTC TGGGACTCTAGCTCCGA CGGTGTGAGTCTTTGGC GGGGCACCAAACTGAC CGTTTTG | 163 | 33.025 VH | CAAATGCAGCTGGTCGA GTCTGGCGGTGGGGTAG TGCAACCAGGCCGTTCT CTGCGTCTTAGCTGCGC CGCATCTGGTTTTTACTT TCGTACCTACGGTATGC ACTGGGTGCGTCAGGCA CCAGGCAAAGGTCTGGA ATGGGTCGCAGACATCT GGTATGATGGTAGCAAT AAACACTATGCTGACTC AGTCAAAGGCCGTTTCA CCATCACCCGTGATAAC AGCAAGAACACTCTTAA CTTACAGATGAACTCTC TGCGTGCCGAAGACACC GCCGTTTACTACTGTGCC CGTGCACCACAGTGGTA CTTAGTAGCGGAACCGT TCGATCTATGGGGCCAG GGCACTATGGTGACCGT TAGCTCT |
| 184 | 184 | 38.014 VL | AGTTACGTGCTGACACA ACCTCCAAGTGTTAGTG TCGCACCAGGACAAAC AGCACGTATTACATGTG GAGGAAATCTTATCGGT GCCAAGCTGGTGCACT GGTACCAGCAGAAACC TGGTCAGGCCCCAGTAC | 183 | 38.014 VH | CAGATGCAGTTGGTGGA GTCCGGAGGTGGAGTGG TGCAACCAGGGCGTTCC TTGCGTTTGTCTTGTGCT GCTTCCGGATTCGCCTTT CGTACATATGGCATGCA TTGGGTGCGTCAAGCAC CTGGTAAGGGCCTGGAG |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|------|-----------|------|-------------|-----------|------|-------------|
| | | | TGGTTGTGTATGATGAC AGCGACCGTCCAAGCC GTATCCCAGAACGTTTT TCTGGGAGCAACTCAG GTAATACAGCCACTCTG ACCATTTCACGTGTTGA GGCAGGAGATGAGGCC GATTATTATTGCCAAGT ATGGGACCACAGCTCT GACCATGTTGTTTTTGG CGGAGGGACTAAGCTG ACCGTGCTT | | | TGGGTTGCCGTTATTTGG TACGACGGCTCCAACAC CCACTACGCAGATAGCG TGAAAGGACGTTTCACT ATTACCCGTGATAACTC CAAGAATACCCTTAACC TGCAGATGAATAGCTTG CGTGCTGAGGACACAGC AGTATATTACTGCGTCC GTGCACCACAATGGTAC CTGAGCGCCGAGGCCTT TGATCTGTGGGGGCAGG GCACAATGGTGACCGTT TCCTCA |
| 186 | 186 | 38.018 VL | TCCTATGTGCTGACACA GCCACCTAGCGTGAGC GTCGCCCAGGTCAGA CCGCTCGTATCACTTGT GGCGGGAACCTTATCG GCAGCAAGCTGGTGCA CTGGTACCAGCAGAAG CCTGGCCAAGCACCTGT GCTGGTCGTTTATGACG ACTCTGACCGTCCATCC CGTATCCCAGAACGTTT CTCTGGCTCTAACTCTG GGAATACCGCTACCCTG ACAATCTCACGTGTTGA AGCTGGCGACGAGGCA GATTATTATTGCCAAGT CTGGGATCACTCCAGCG ATCACGTCGTGTTCGGA GGCGGAACAAAATTGA CTGTCCTG | 185 | 38.018 VH | CAGATGCAACTGGTGGA GTCAGGAGGCGGCGTGG TGCAGCCAGGACGTTCT CTGCGTCTGTCTTGCGCA GCTTCCGGGTTCGCCTTT CGTACCTATGGGATGCA TTGGGTGCGTCAGGCTC CAGGTAAGGGACTGGAG TGGGTCGCTGTTATTTGG GACGACGGAAGTAACAC TCATTACGCCGACAGCG TGAAGGGCCGTTTCACA ATTACCCGTGACAATTC CAAGAATACCTTGAACC TGCAGATGAACTCTCTT CGTGCTGAAGATACCGC CGTGTACTATTGCGCCC GTGCTCCACAGTGGTAT CTGTCAGCAGAGGCCTT CGACCTGTGGGGACAGG GAACAATGGTGACCGTA TCTTCA |
| 188 | 188 | 38.019 VL | TCTTACGTGTTGACACA ACCACCAAGTGTTAGTG TCGCACCTGGCCAAACC GCTCGTATCACCTGTGG TGGGAATCTTATTGGCT CTAAGCTGGTGCACTGG TATCAGCAGAAACCAG GCCAGGCTCCAGTACTG GTGGTGTACGACGACTC TGACCGTCCAAGCCGTA TCCCAGAGCGTTTCAGT GGCTCTAACTCCGGGA ACACAGCAACTCTTACA ATTTCACGTGTGGAGGC CGGTGATGAAGCCGAC TACTATTGCCAGGTTTG GGACTACAGTAGTAAT CACGTGGTTTTCGGTGG TGGTACCAAGCTGACTG TGTTG | 187 | 38.019 VH | CAAATGCAGCTGGTGGA ATCCGGGGGTGGGGTCG TCCAGCCTGGCCGTAGT CTGCGTCTTTCCTGTGCC GCATCAGGCTTTGCTTTC CGTACCTACGGGATGCA CTGGGTGCGTCAGGCCC CAGGAAAGGGACTTGAA TGGGTGGCTGTCATCTG GTACGATGGTTCCAACA CACACTATGCCGATTCA GTGAAAGGGCGTTTCAC CATTACTCGTGACAATA GTAAGAATACTCTGAAT CTGCAAATGAATTCACT GCGTGCTGAGGACACCG CTGTTTATTACTGTGTGC GTGCTCCTCAGTGGTAC CTGAGTGCCGAAGCTTT CGATTTGTGGGGACAGG GCACAATGGTGACAGTC AGTTCT |
| 190 | 190 | 38.021 VL | AGCTATGTTCTGACTCA ACCACCTAGTGTGAGTG TGGCCCCTGGTCAGACT GCACGTATTACCTGTGG CGGAAACCTTATCGGC AGTAAGCTGGTTCATTG GTATCAGCAGAAGCCA GGACAGGCACCAGTGC TGGTCGTTTACGACGAT AGTGACCGTCCATCACG TATCCCAGAGCGTTTTA | 189 | 38.021 VH | CAGATGCAGCTGGTTGA ATCTGGCGGCGGTGTGG TCCAGCCTGGTCGTAGC CTGCGTCTGTCCTGTGCT GCAAGCGGATTTGCCTT TGACACCTATGGGATGC ACTGGGTACGTCAGGCC CCAGGAAAGGGCCTGGA ATGGGTGGCAGTTATCT GGTATGATGGTTCTAAT ACCGTGTATGCCGACTC |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|---|---|---|---|---|---|---|
| | | | GCGGGTCCAATTCCGG AAATACAGCAACCTTG ACCATTAGCCGTGTGGA AGCCGGCGATGAAGCT GATTATTACTGCCAGGT ATGGGACCATTCCTCCG ACCACTACGTTTTTGGT GGCGGAACTAAGCTGA CAGTCTTG | | | CGTTAAAGGCCGTTTCA CTATCACCCGTGATAAT AGTAAAAACACACTGAA CCTGCAGATGAATAGCT TGCGTGCTGAGGACACC GCAGTGTACTACTGTGC CCGTGCTCCTCAGTGGT ATCTGTCAGCAGAGGCC TTCGATCTGTGGGGCCA AGGGACAATGGTGACCG TGTCTTCC |
| 192 | 192 | 38.025 VL | TCTTACGTGCTTACTCA GCCTCCTAGCGTCTCAG TGGCCCCAGGCGAGAC AGCAACCATTACATGC GGGGGTAATTTGATCG GTAGCAAGCTGGTGCA TTGGTATCAGCAGAAG CCTGGCCAGGCCCCAGT GCTGGTTGTATATGACG ATAGTGATCGTCCAAGT CGTATCCCTGAGCGTTT TAGCGGATCTAACTCCG GCAACACAGCCACATT GACAATCAGCCGTGTG GAGGCAGGCGATGAGG CCGACTACTACTGCCAA GTTTGGGACCACTCCTC TGACCACGTGGTATTTG GCGGAGGAACAAAGCT TACAGTTTTG | 191 | 38.025 VH | CAGATGCAGCTTGTTGA GAGCGGCGGAGGCGTGG TGCAACCAGGCCGTTCA TTGCGTCTGTCCTGCGCC GCCAGCGGCTTTGCTTTT CGTACATACGGCATGCA CTGGGTGCGTCAGGCCC CTGGCAAGGGGCTGGAA TGGGTCGCCGTGATTTG GTATGACGGTAGTAACA CCCATTATGCTGATTCCG TCAAGGGACGTTTCACT ATCACCCGTGACAATAG CAAAAATACACTGAATC TGCAAATGAATTCATTG CGTGCCGAAGACACCGC CGTATATTACTGTGTCCG TGCCCCACAGTGGTACC TGAGCGCTGAGGCCTTC GATCTGTGGGGTCAGGG GACTATGGTGACCGTAT CATCC |
| 194 | 194 | 38.026 VL | TCTTATGTTTTGACCCA ACCTCCATCCGTTAGCG TGGCTCCAGGTCAAAC AGCTACCATCACATGTG GCGGTAACCTTATTGGC TCAAAGCTGGTTCATTG GTATCAACAGAAACCA GGCCAAGCCCCAGTGC TGGTGGTGTATGACGAC AGTGACCGTCCTTCTCG TATTCCTGAGCGTTTTT CCGGCTCTAATATTGGC AACACTGCCACCCTGAC CATTTCTCGTGTGGAAG CAGGAGATGAGGCAGA CTATTATTGTCAGGTTT GGGATCACTCCAGCGA TCATGTGGTATTCGGAG GTGGGACAAAACTTAC TGTTCTT | 193 | 38.026 VH | CAGATGCAGCTGGTGGA GAGTGGAGGTGGTGTGG TGCAACCTGGGCGTAGC CTGCGTTTGAGCTGCGC TGCCTCTGGATTTGCCTT CCGTACCTATGGCATGC ACTGGGTGCGTCAGGCT CCAGGAAAGGGGGTTGGA ATGGGTGGCTGTGATTT GGTACGACGGGAGCGCC ACACATTACGCAGACAG CGTTAAGGGCCGTTTCA CAATTACCCGTGACAAT AGCAAAAATACATTGAA CCTGCAGATGAATTCCC TGCGTGCAGAGGATACT GCAGTGTACTATTGCGT CCGTGCCCCACAGTGGT ATCTGTCAGCCGAAGCC TTCGATCTGTGGGGGCA GGGTACTATGGTCACCG TAAGTTCC |
| 196 | 196 | 38.040 VL | AGCTACGTGCTTACCCA GCCACCATCAGTCAGTG TGGCTCCAGGCCAAACT GCCCGTATCACCTGCGG CGGCAATTTGATTGGCA CCAAGCTTGTGCACTGG TACCAACAGAAGCCAG GGCAGGCCCCTGTGCTG GTTGTCTACGACGATAG TGATCGTCCTTCCCGTA TTCCTGAACGTTTCTCT GGAAGCAATTCCGGAA ACACAGCCACACTTACC ATTTCTCGTGTTGAGGC | 195 | 38.040 VH | CAGATGCAGCTGGTGGA AAGTGGTGGGGGAGTCG TGCAACCAGGACGTTCC TTGCGTCTGTCATGCGCT GCTTCAGGTTTCGACTTT CGTACCTACGGCATGCA TTGGGTGCGTCAGGCTC CAGGTAAAGGACTTGAG TGGGTCGCAGTGATCTG GTACGACGGATCAATTA CTCACTACGCCGATAGC GTGAAAGGCCGTTTCAC CATCACCCGTGACAACT CCAAGAACACCCTGAAC |

TABLE 3-continued

Nucleotide Sequences Encoding Engineered dual
binding antibodies: Variable Light chain (VL)
and Variable Heavy chain (VH) nucleic acid sequences

| Ab # | SEQ ID NO: | Name | VL Sequence | SEQ ID NO: | Name | VH Sequence |
|------|-----------|------|-------------|-----------|------|-------------|
| | | | TGGGGATGAAGCCGAC TACTATTGCCAGGTTTG GGACCACAATGAAGAC GAAGTTGTTTTTGGAGG AGGAACTAAGCTGACA GTTCTG | | | TTGCAGATGAACAGTCT GCGTGCAGAAGACACTG CAGTATATTATTGTGTCC GTGCCCCACAGTGGTAC TTGACCGCCGAGGCTTT TGATCTGTGGGGACAGG GCACAATGGTGACCGTA TCTAGC |

TABLE 4

Amino Acid Sequences of Heavy-chain
CDR Regions for Antibody Clone #s.
33.023, 33.025, 38.014, 38.015. 38.018,
38.019, 38.021, 38.026, 38.040

| CLONE | HCDR1 | SEQ ID | HCDR2 | SEQ ID | HCDR3 | SEQ ID |
|-------|-------|--------|-------|--------|-------|--------|
| BDG33_023_VH | GFAFRTYG | 149 | IWYDGSNT | 150 | ARAPQWYLSAEAFDL | 151 |
| BDG33_025_VH | GFTFRTYG | 165 | IWYDGSNK | 166 | ARAPQWYLVAEPFDL | 167 |
| BDG38_014_VH | GFAFRTYG | 149 | IWYDGSNT | 150 | VRAPQWYLSAEAFDL | 201 |
| BDG38_018_VH | GFAFRTYG | 149 | IWDDGSNT | 208 | ARAPQWYLSAEAFDL | 151 |
| BDG38_019_VH | GFAFRTYG | 149 | IWYDGSNT | 150 | VRAPQWYLSAEAFDL | 201 |
| BDG38_021_VH | GFAFDTYG | 197 | IWYDGSNT | 150 | VRAPQWYLSAEAFDL | 151 |
| BDG38_025_VH | GFAFRTYG | 149 | IWYDGSNT | 150 | VRAPQWYLSAEAFDL | 201 |
| BDG38_026_VH | GFAFRTYG | 149 | IWYDGSAT | 199 | VRAPQWYLSAEAFDL | 201 |
| BDG38_040_VH | GFDFRTYG | 198 | IWYDGSIT | 200 | VRAPQWYLTAEAFDL | 202 |

TABLE 5

Amino Acid Sequences of Light-chain
CDR Regions for Antibody Clone #s.
33.023, 33.025, 38.014, 38.015. 38.018,
38.019, 38.021, 38.026, 38.040

| CLONE | LCDR1 | SEQ ID | LCDR2 | LCDR3 | SEQ ID |
|-------|-------|--------|-------|-------|--------|
| BDG33_023_VL | LIGSKL | 152 | DDS | QVWDHSSDHVV | 154 |
| BDG33_025_VL | LIGSKL | 152 | DDS | QVWDSSSDGVV | 168 |
| BDG38_014_VL | LIGAKL | 203 | DDS | QVWDHSSDHVV | 154 |
| BDG38_018_VL | LIGSKL | 152 | DDS | QVWDHSSDHVV | 154 |
| BDG38_019_VL | LIGSKL | 152 | DDS | QVWDYSSNHVV | 205 |
| BDG38_021_VL | LIGSKL | 152 | DDS | QVWDHSSDHYV | 206 |
| BDG38_025_VL | LIGSKL | 152 | DDS | QVWDHSSDHVV | 154 |
| BDG38_026_VL | LIGSKL | 152 | DDS | QVWDHSSDHVV | 154 |
| BDG38_040_VL | LIGTKL | 204 | DDS | QVWDHNEDEVV | 207 |

Figure 2A:
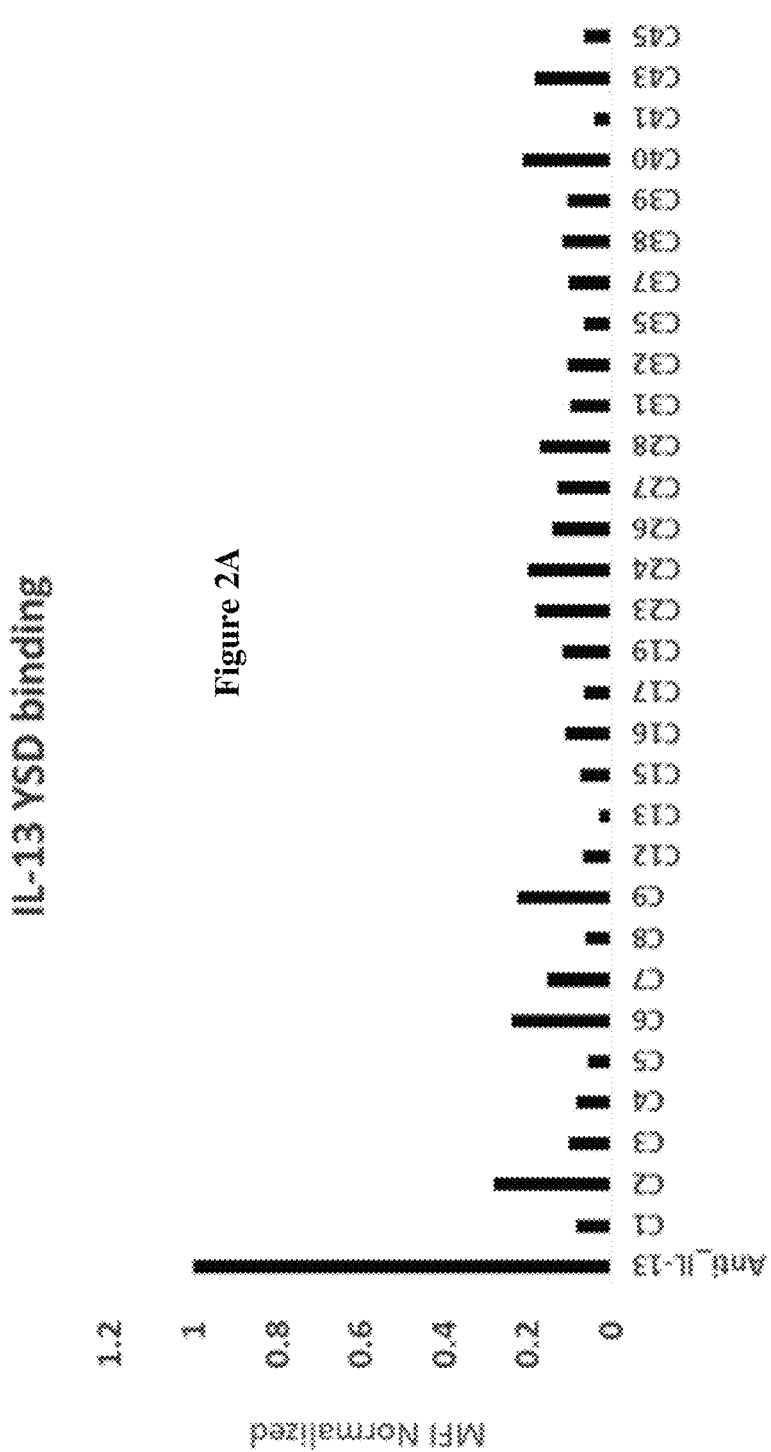
FIGS. 2A and 2B present bar graphs showing binding of re-epitoped antibodies displayed on yeast to recombinant human IL-13 (rh-IL-13) (FIG. 2A) or recombinant human TSLP (rhTSLP) (FIG. 2B).
Figure 2B:
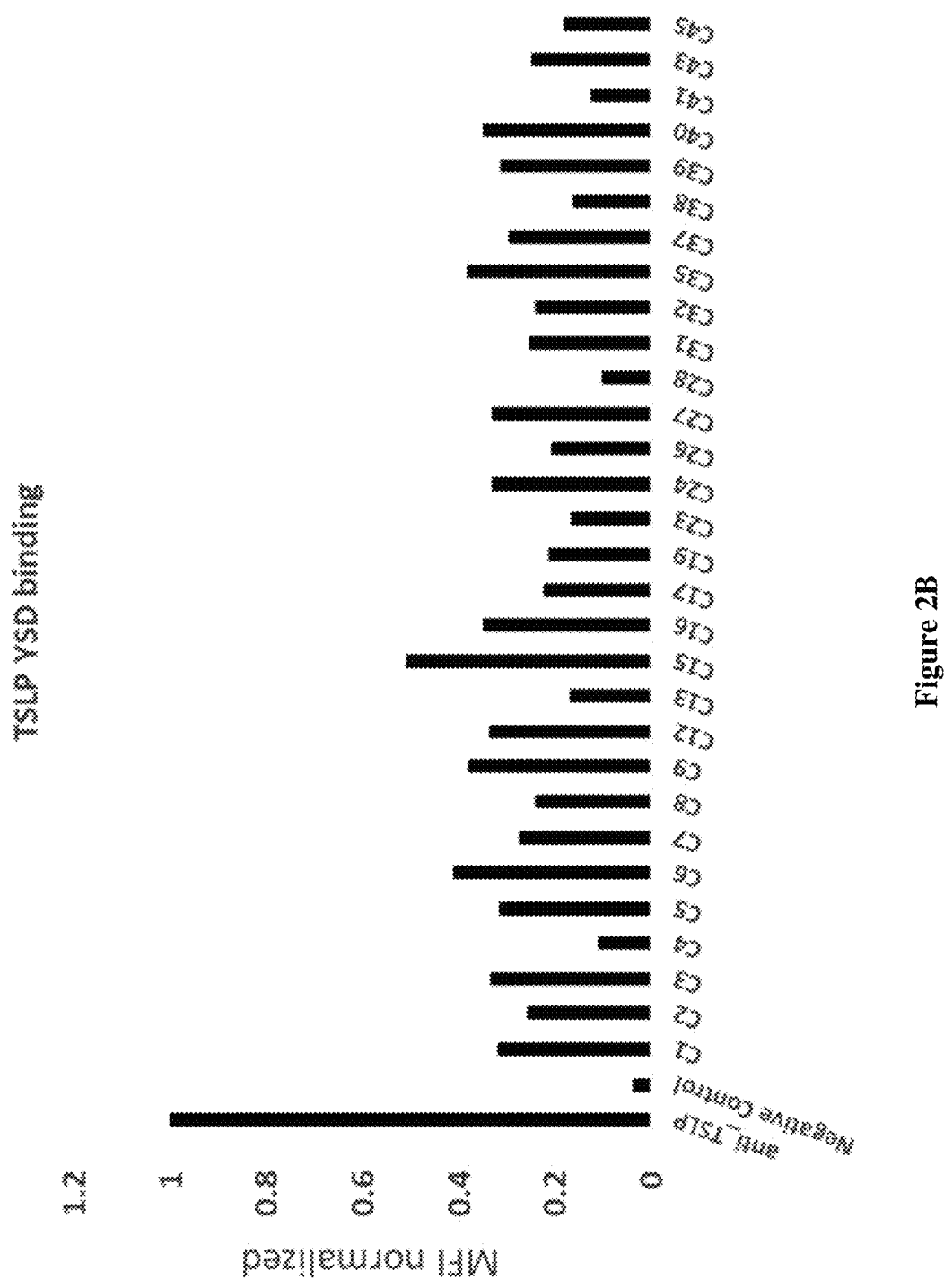

The clones were tested for their binding to 10 nM rh-IL-13 in yeast scFv format and were compared to a positive rh-IL-13 binder displayed on yeast as well. The affinity was normalized based on the mean fluorescence values of the positive control (normalized MFI). Relative affinity of the isolated clones for rh-IL-13 was between 3% and 30% of the affinity displayed by the positive control (FIG. 2A). C2, C6, C9, and C40 clones that exhibited above 20% of the relative affinity for rh-IL-13 and were shown to bind 10 nM TSLP in YSD (FIG. 2B) were chosen to be expressed as human IgG1.

Example 3: Ab Production And Biochemical Characterization

Objective: To reformat the selected clones to a human IgG1 format and analyze the IgG1 antibodies for dual IL-13 and TSLP binding.

Results: Subsequent to characterization in the yeast surface display format described in Example 2, the selected clones C2, C6, and C9, were reformatted to human IgG1 by subcloning the variable domain into two separate expression vectors, pSF-CMV-HuIgG1_HC and pSF-CMV-Hu-Lambda_LC, as described in Example 1 (Methods).

Clones BDG 33.003, BDG 33.004, and BDG 33.005 (Clones C2, C6, and C9, respectively) were expressed and purified as described in Example 1 (Methods), following protein A purification, the IgGs were >95% pure as evident from an SDS PAGE analysis (data not shown). Size exclusion chromatography of BDG 33.003 (clone C2), BDG 33.004 (clone C6), and BDG 33.005 (clone C9) on Superdex®200 10/300, showed two main peaks the first with a retention time of 9.2 ml (0.36 CV), typical of large aggregate and a second peak with retention of approximately 13.2 ml (0.528 CV), typical of an ordinary human IgG1 (hIgG1). The integrated area under the curve of these two peaks showed a ratio of 22% and 78% respectively (FIGS. 3A-3D).

Figure 3A:
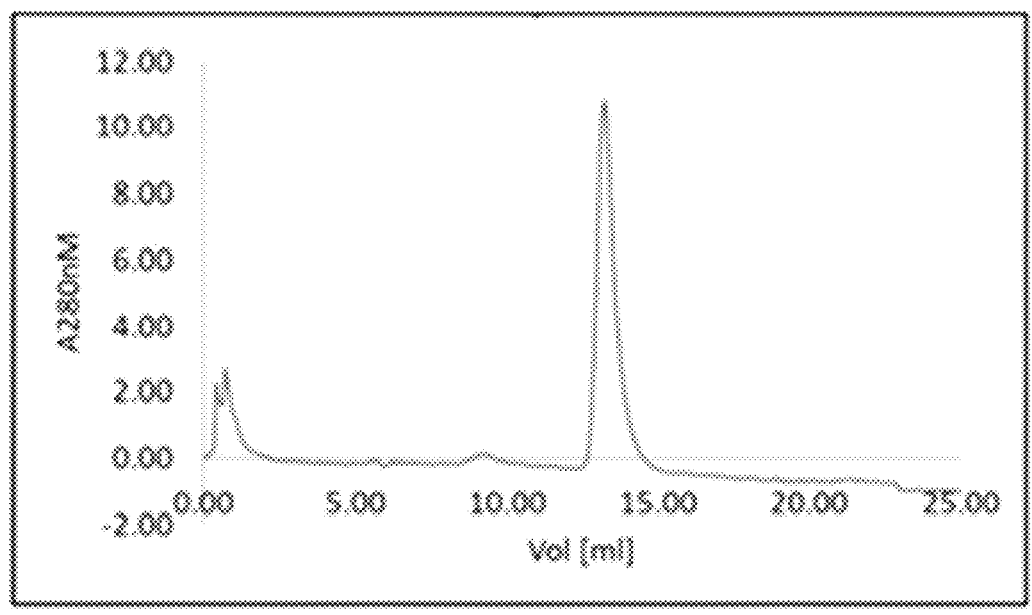
FIGS. 3A-3F presents size exclusion chromatography (SEC) scans of a human standard IgG1 (FIG. 3A), BDG33.003 (FIG. 3B), BDG33.004 (FIG. 3C), BDG 33.005 (FIG. 3D), BDG33.023 (FIG. 3E), and BDG33.025 (FIG. 3F). The purified IgGs were run on a GE Superdex®200 10/300 increase (column volume (CV)=25 ml) in PBS buffer at 0.5 ml/min. In the antibody scans shown in FIGS. 3B-3D, the leading peak corresponds to (0.36 CV) that typical of a large aggregate, and a second peak with retention of approximately 13.2 ml (0.528 CV) that is typical of an ordinary human IgG. Area Under the Curve (AUC) peak ratio is approximately 23% misfolded/77% folded IgG fraction, respectively. For the antibody scans shown in FIGS. 3E-3F, the leading peak corresponds to (0.36 CV) that typical of a large diameter aggregate, and a second peak with retention of approximately 13.8 ml (0.55 CV) that is typical of an ordinary human IgG. Area Under the Curve (AUC) peak ratio is 97.3% folded/2.8% misfolded and 98.5% folded/1.5% misfolded for BDG33.023 (FIG. 3E) and BDG33.025 (FIG. 3F) respectively.
Figure 3B:
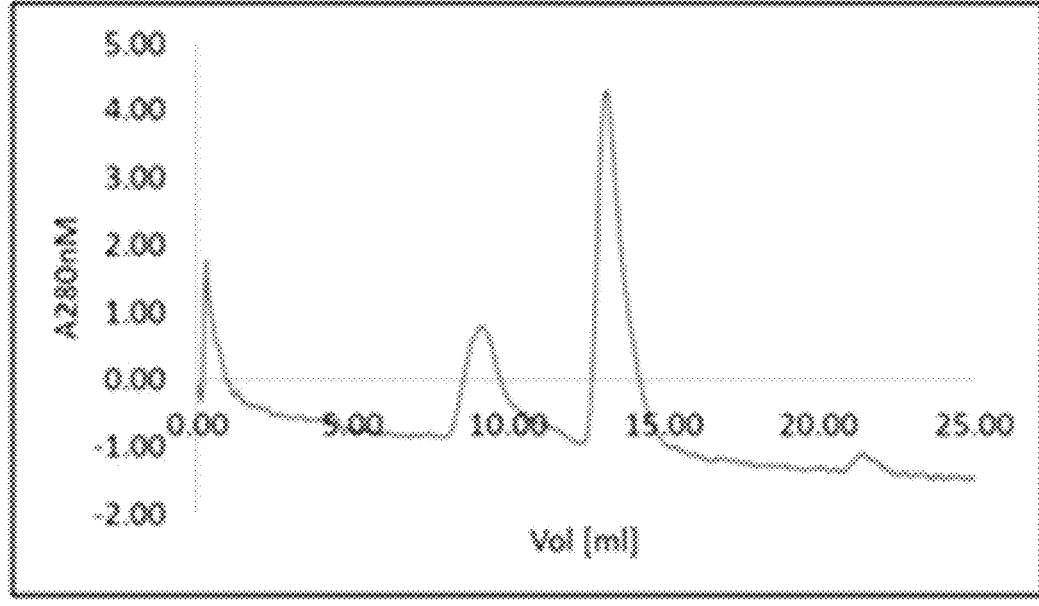
Figure 3C:
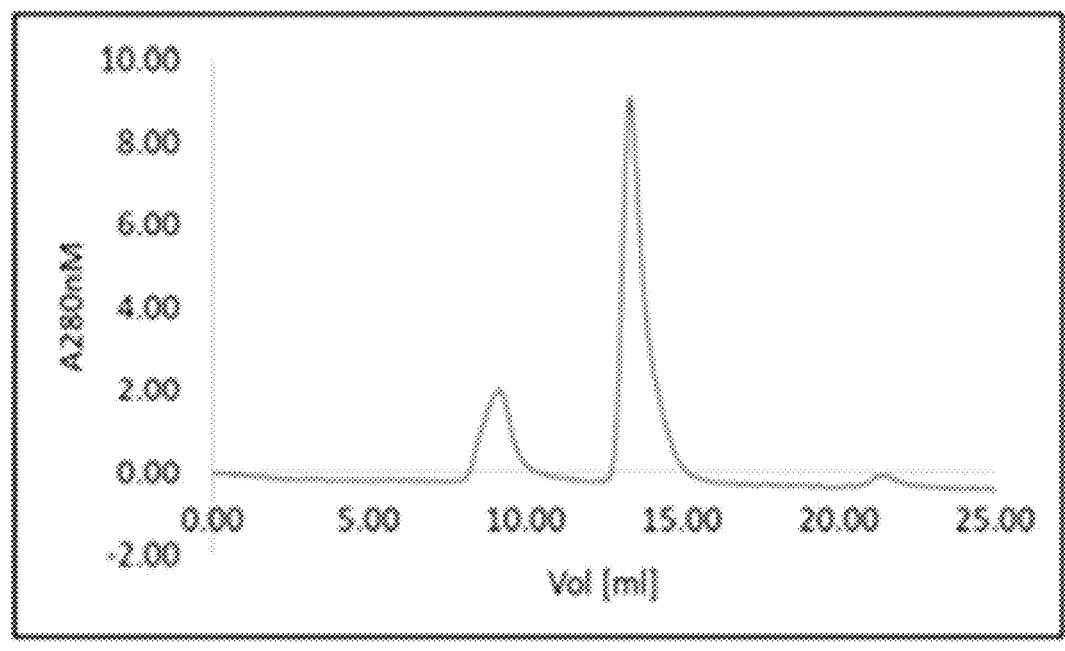
Figure 3D:
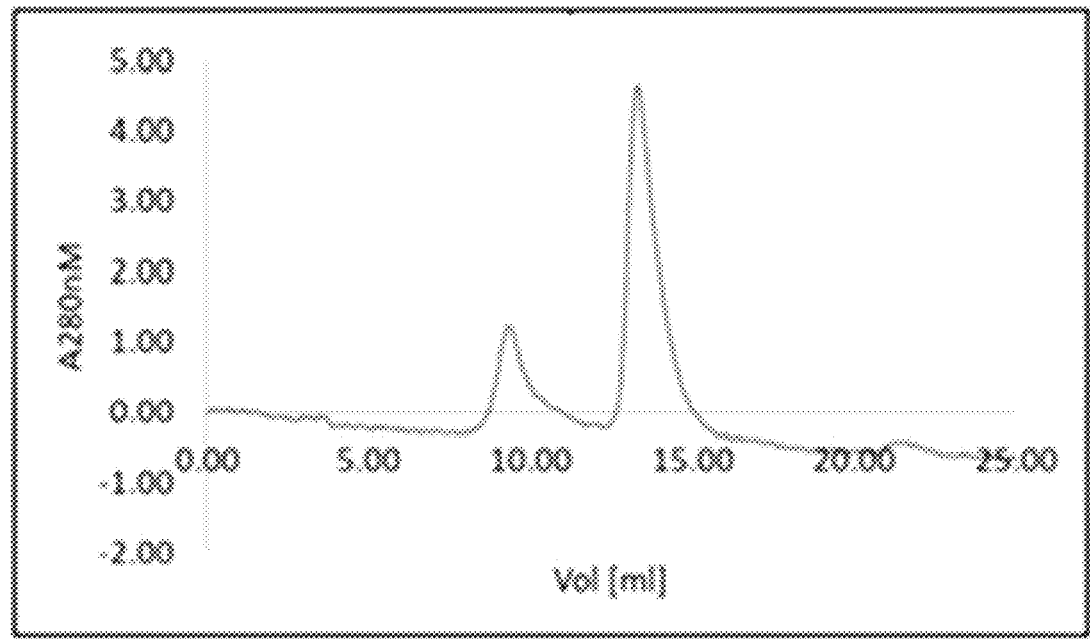
Figure 3E:
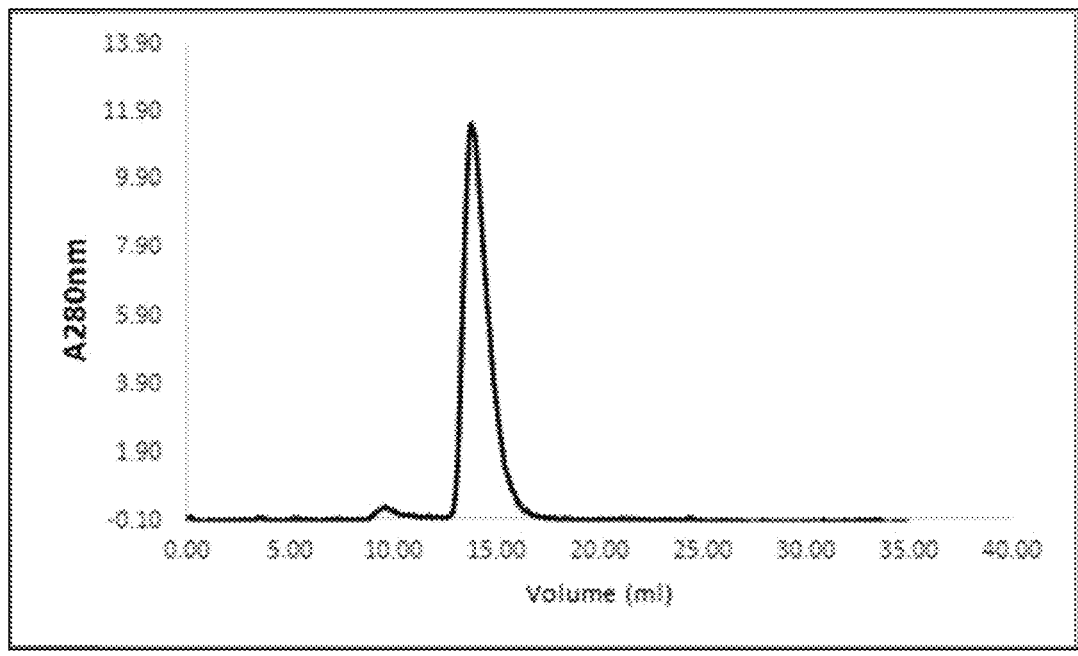
Figure 3F:
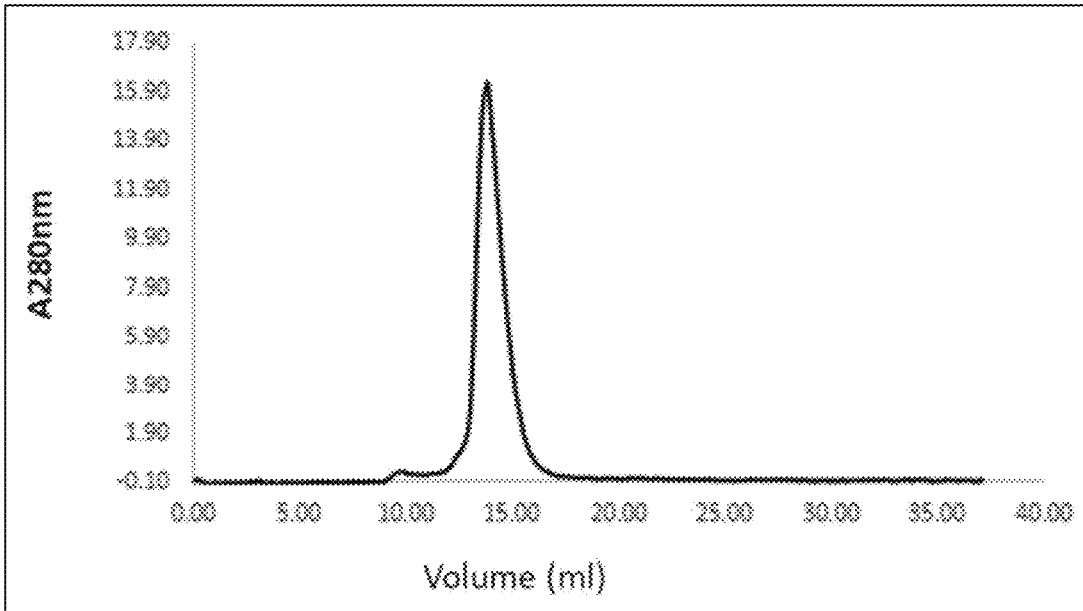

Both BDG33.0023 and BDG33.025 migrated on Superdex®200 10/300 with small leading peak corresponds to (0.36 CV) that is typical of a large diameter aggregate, and a second peak with retention of approximately 13.8 ml (0.55 CV) that is typical of an ordinary human IgG. Area Under the Curve (AUC) peak ratio is 97.3% folded/2.8% misfolded and 98.5% folded/1.5% misfolded for BDG33.023 and BDG33.025 respectively (FIGS. 3E-3F).

To test the thermostability of clones BDG 33.003, BDG 30.004, and BDG 30.005, the clones' thermal melting was monitored by differential scanning fluorescence (DSF) as described in Example 1. As was evident from the first derivative of the fluorescence thermal shift graph, BDG 33.004 had one distinct transition at point at 62° C. which could possibly correspond to both Tm1 and Tm2. (Data not shown). BDG 33.003 and BDG33.005 each had two transition points, a major one at 62° C. (BDG 33.003) and 64.5° C. (BDG 33.005), respectively, and a minor one at 73° C. (BDG 33.003) and 74.5° C. (BDG 33.005), respectively.

Figure 4A:
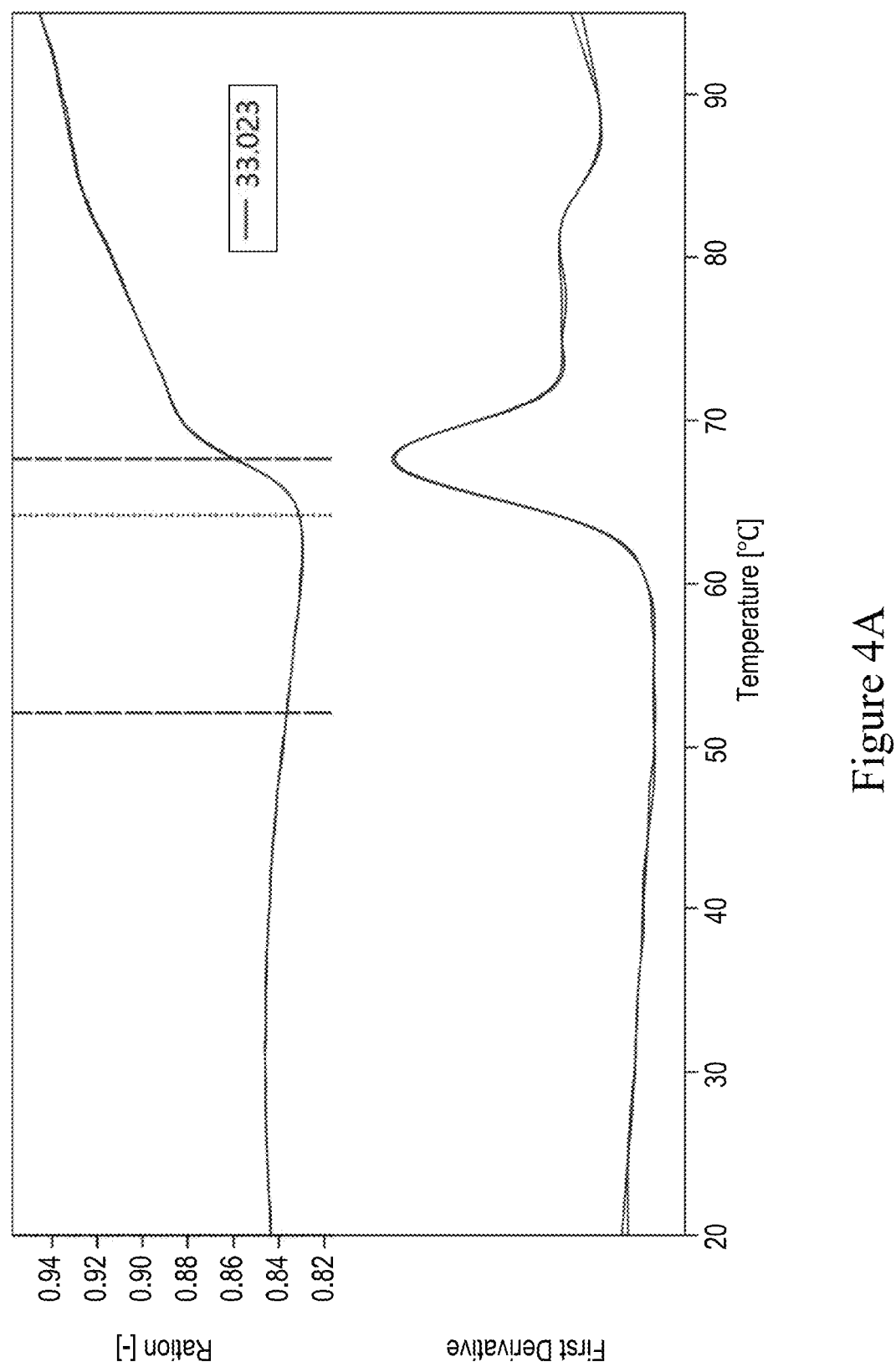
FIGS. 4A and 4B present Differential Scanning Fluorimetry (DSF) analysis of the melting point of indicated IgGs BDG33.023 (FIG. 4A) and BDG33.025 (FIG. 4B). Light gray dashed line in the upper graph represents the T-onset and bold gray dashed lines represents the Tm1 and Tm2. The lower graph is the 1st derivative of the measurement.
Figure 4B:
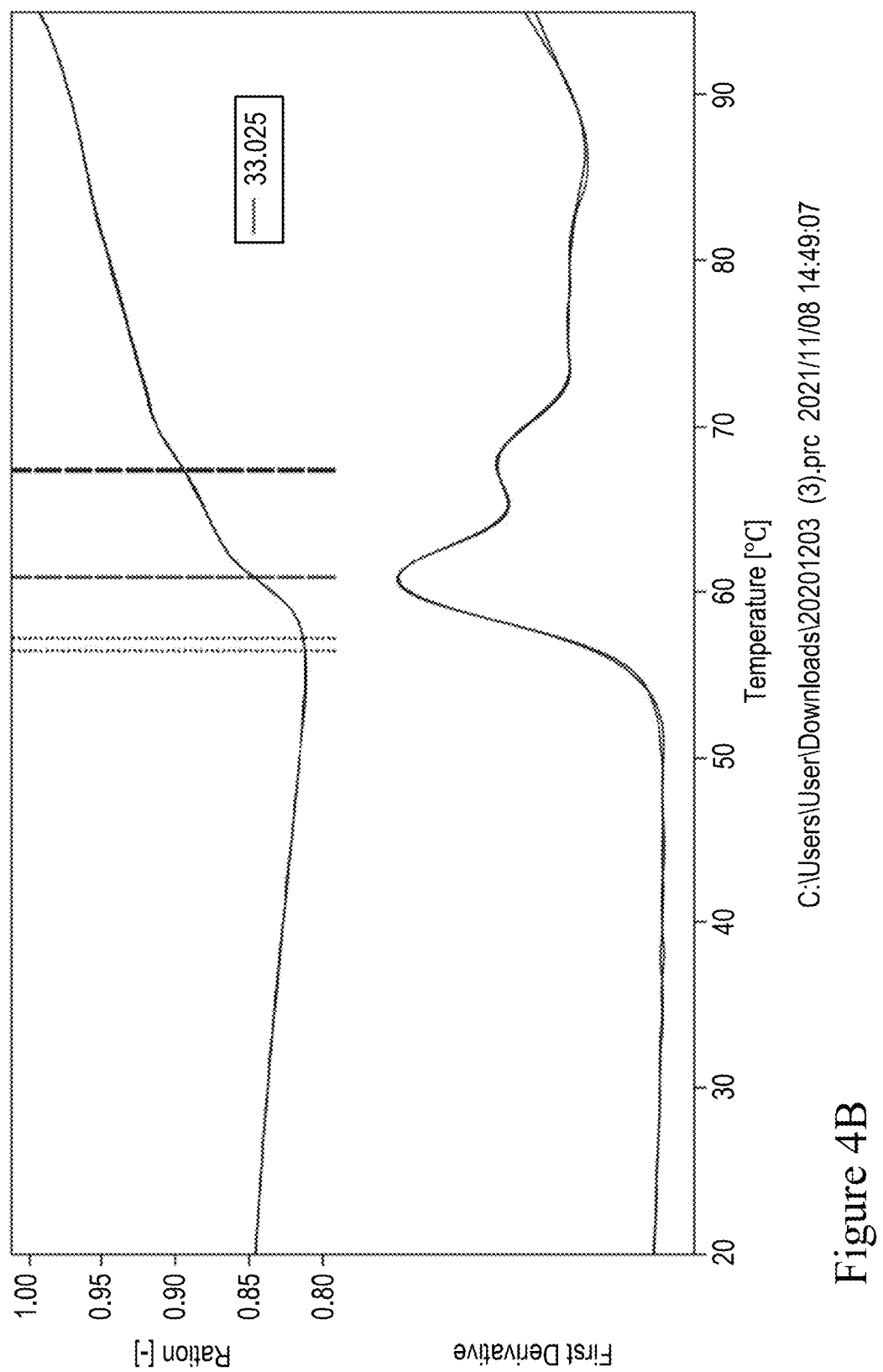

BDG 33.023 and BDG33.025 were tested using NanoDSF Prometheus NT.48 (NanoTemper Technologies, Germany). BDG33.0023 had a T-onset of 64.2° C. and first transition point at 67.7° C., BDG33.0025 had a T-onset of 56.4° C. and first transition point at 60.9° C. and second transition point at 67.4° C. (FIGS. 4A-4B)

Figure 5A:
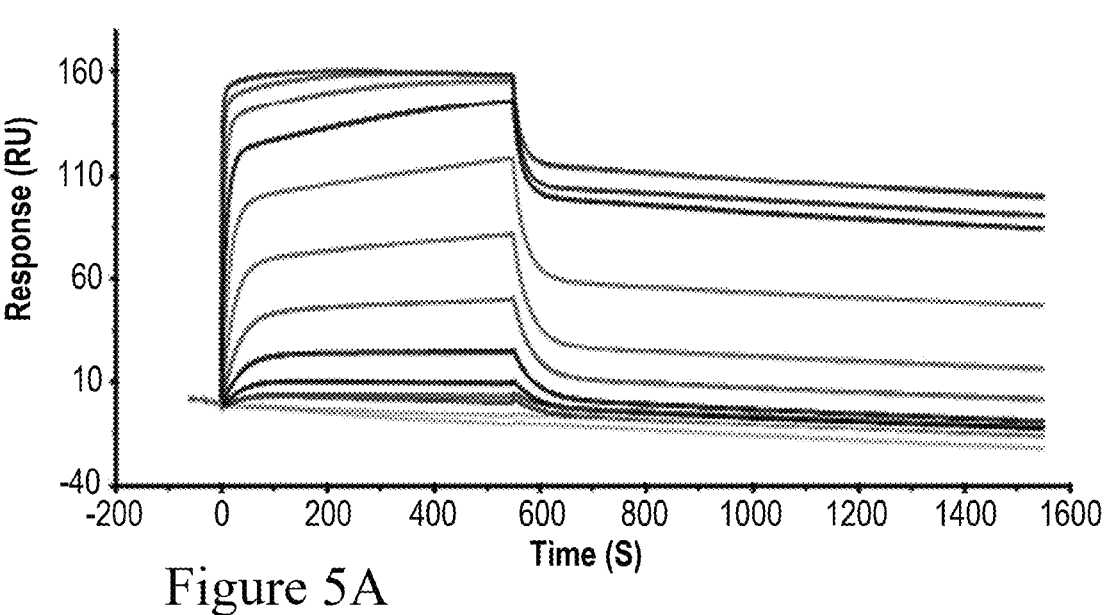
FIGS. 5A-5F presents Surface Plasmon Resonance (SPR) analysis of antibodies binding to human IL-13, Cyno IL-13, and human TSLP. Representative SPR sonograms of BDG33.003 and BDG33.004 binding to IL-13 are presented in FIGS. 5A-5D. Recombinant human IL-13 (rh-IL-13) was tested at 800 nM with a 2-fold dilution (FIGS. 5A-5B). Recombinant cyno IL-13 (rc-IL-13) was tested at 200 nM with a 2-fold dilution (FIGS. 5C-5D). Representative SPR sensorgrams of BDG33.003 and BDG33.004 binding to human TSLP (h-TSLP) are presented in FIGS. 5E and 5F. hTSLP served as analyte at concentrations of 3.2 nM to 0.2 nM with two-fold dilutions (FIGS. 5E-F). Representative SPR sensorgrams of BDG33.023 and BDG33.025 binding to human IL-13 (h-IL-13) are presented in FIGS. 5G and 5H. hIL-13 served as analyte at concentrations of 20 nM to 0.6 nM with tow fold dilutions (FIGS. 5G-5H).
Figure 5B:
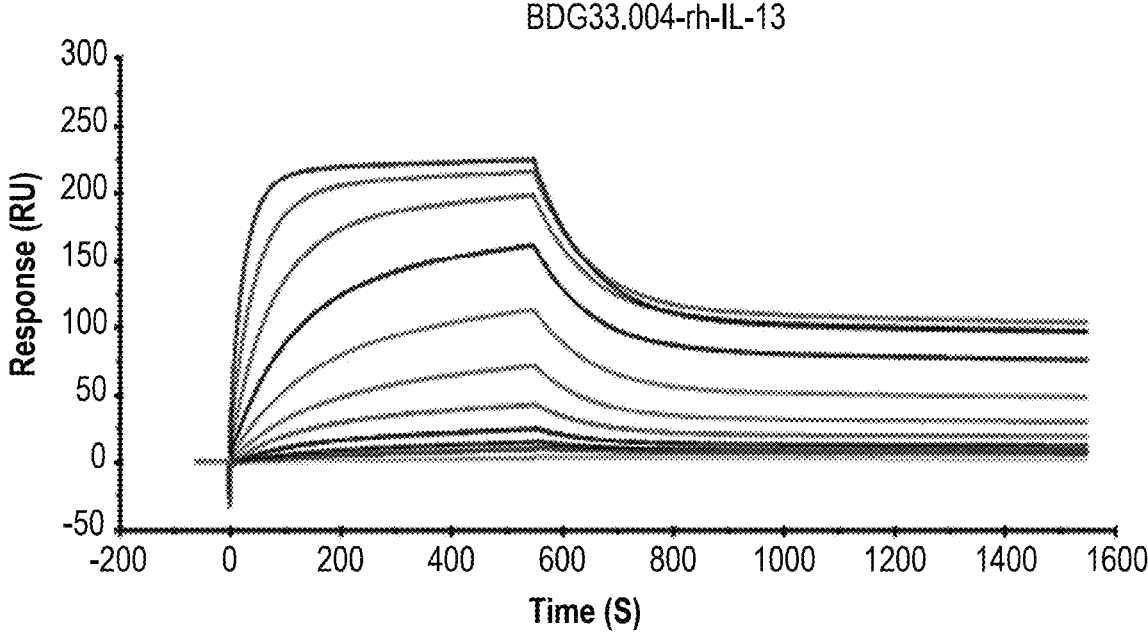

The affinities of the IgGs to human TSLP, human IL-13, and cynomolgus monkey IL-13 were tested. Binding kinetics of hIL-13 to BDG33.023 and BDG33.025 was tested on BJAcoreT200 as described herein, (FIG. 5G-H). BDG33.003 and BDG33.004 clones were tested by SPR analysis on BiacoreT200 and ProteOn™ XPR36, respectively, using the GE capture antibody kit. While it was not possible to obtain kinetics parameters for binding the human IL-13, steady-state binding measurement resulted in an apparent KD of 21.6 nM and 57.4 nM for BDG33.003 and BDG33.004, respectively (FIGS. 5A-5B). For all other measurements of BDG33.003, BDG 33.004, BDG33.023, and BDG33.025, kinetics of binding to hTSLP and hIL-13 are presented in Tables 6A and 6B, and FIGS. 5E and 5H.

Figure 5C:
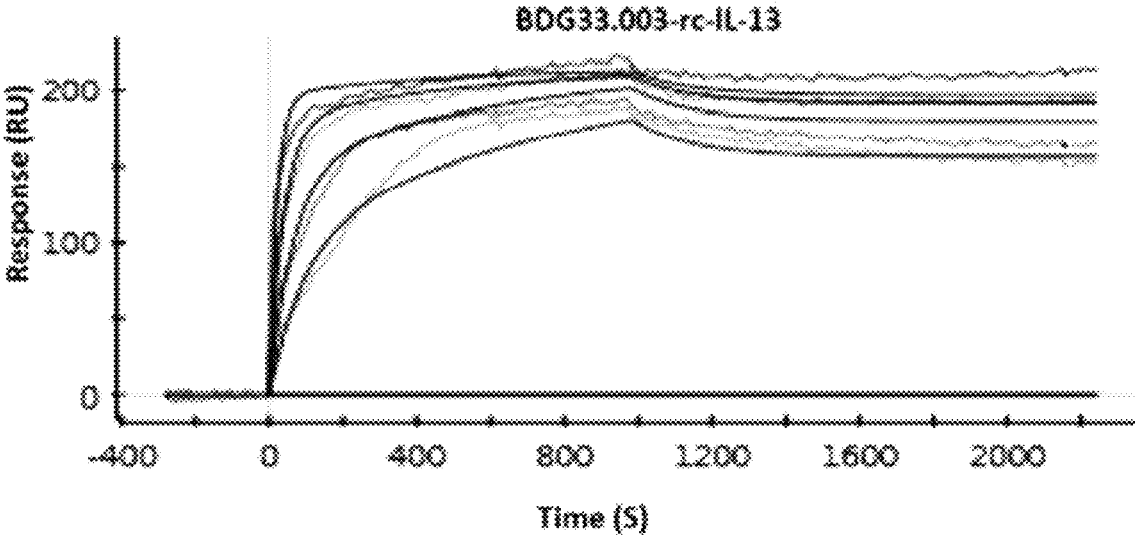
Figure 5D:
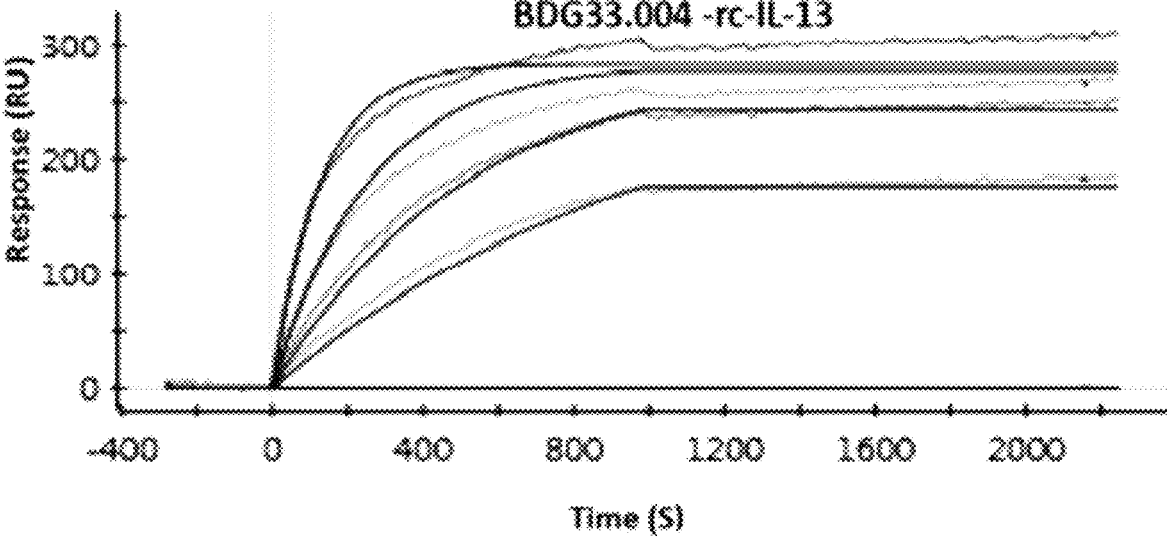
Figure 5E:
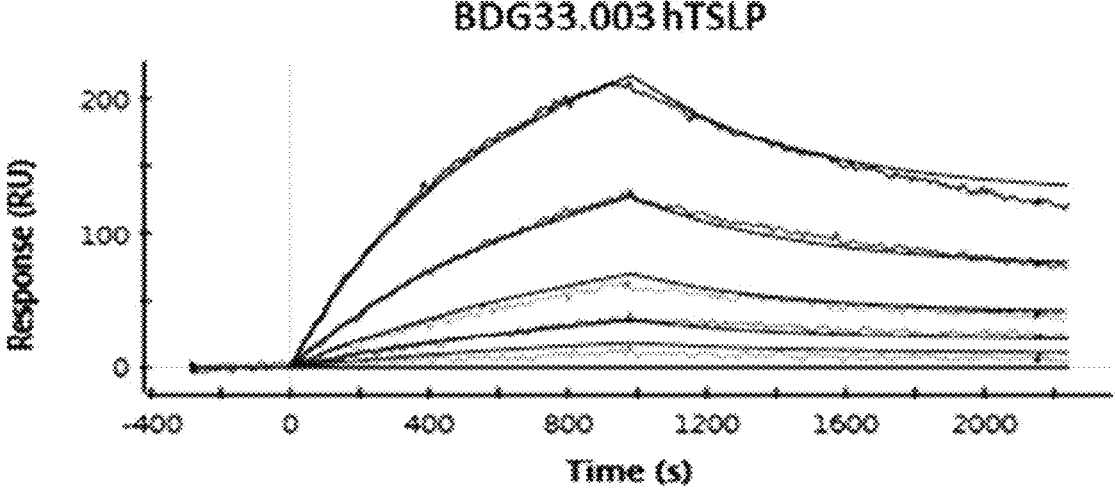
Figure 5F:
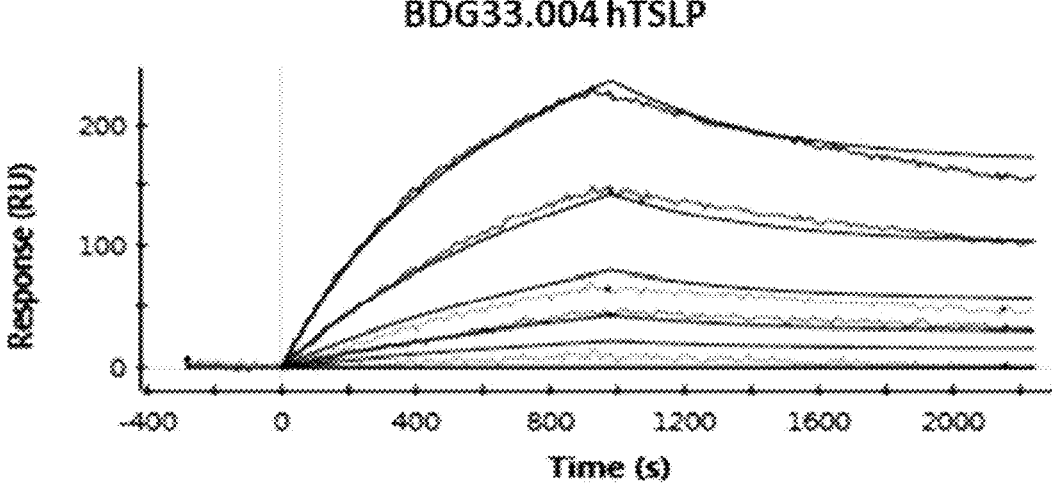
Figure 5G:
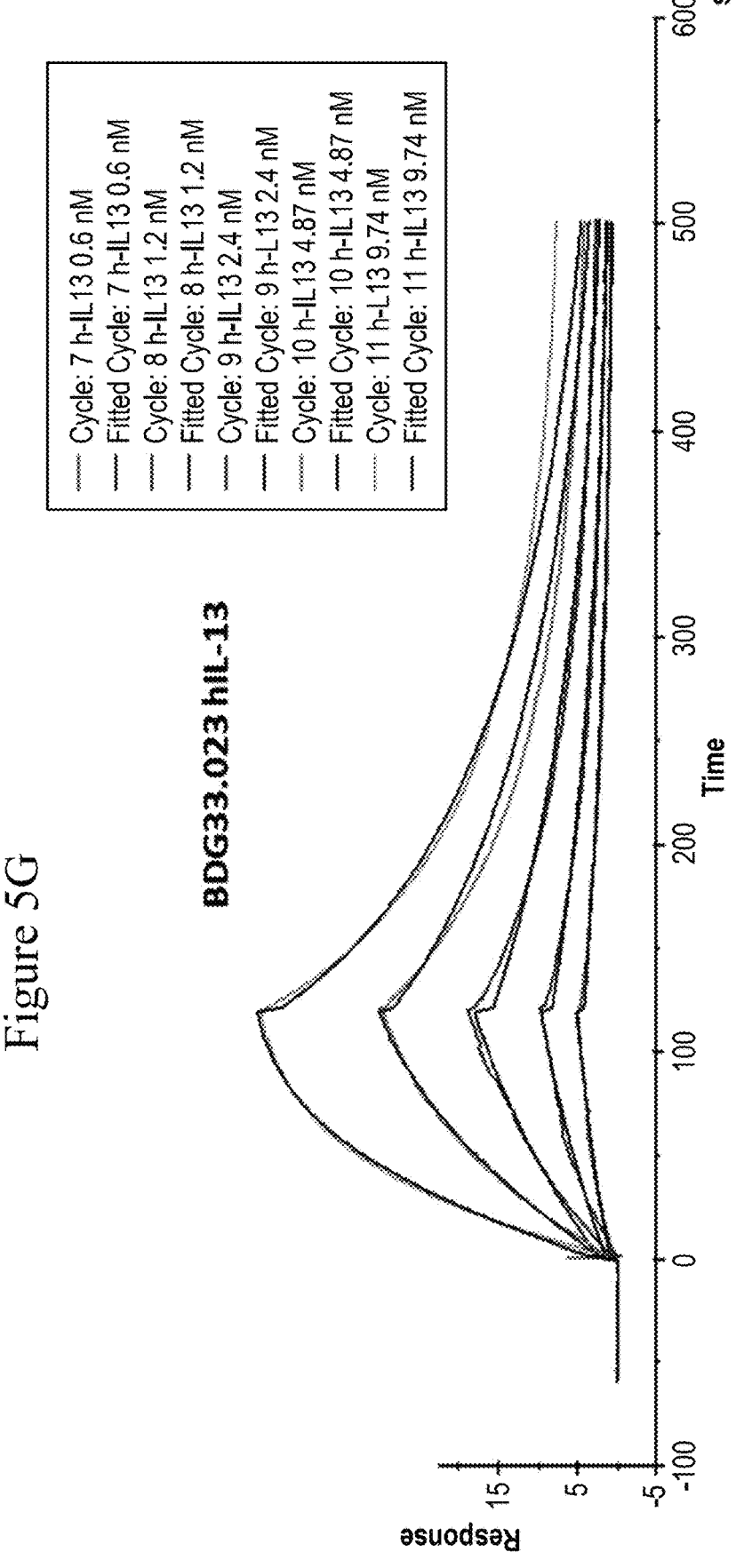
Figure 5H:
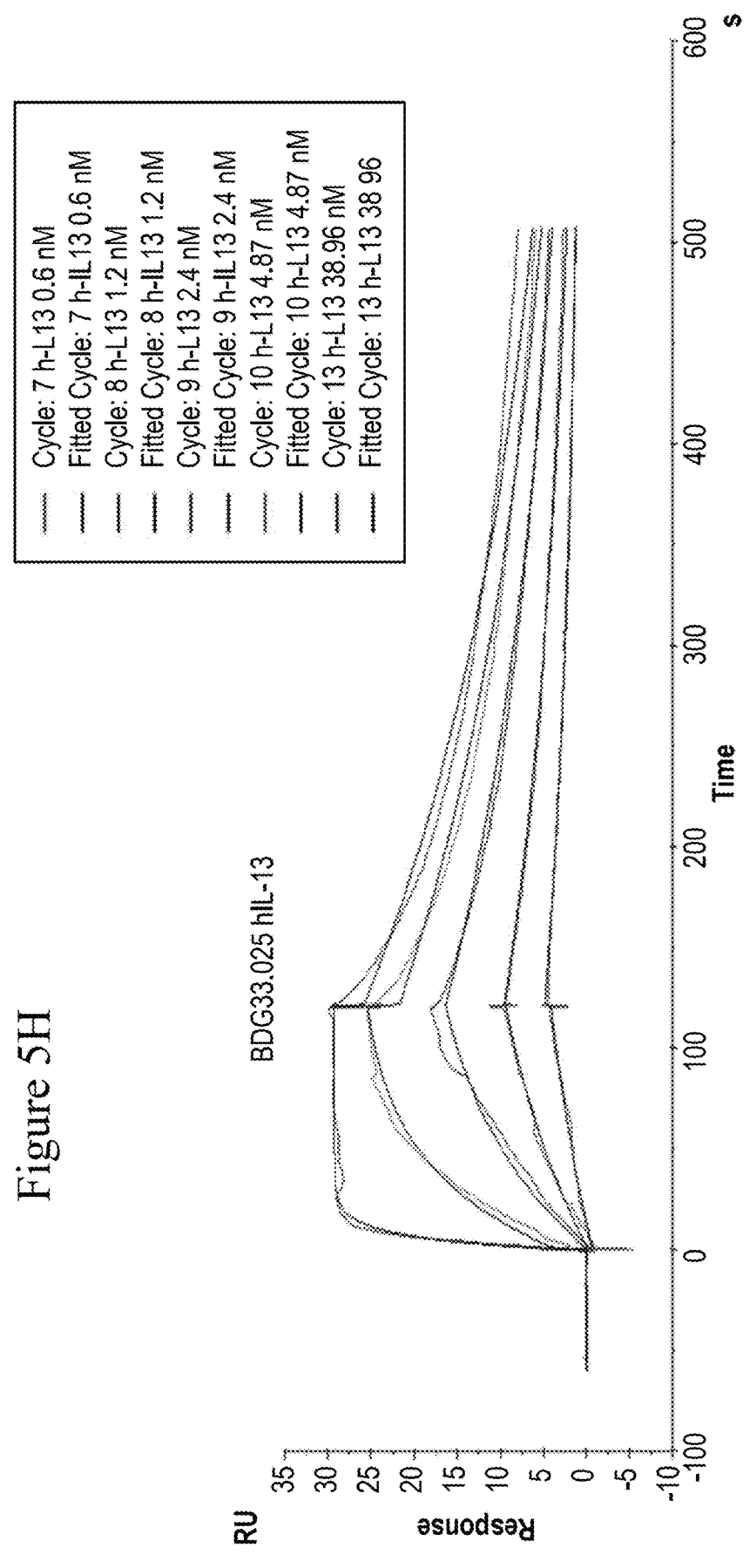
Figure 6A:
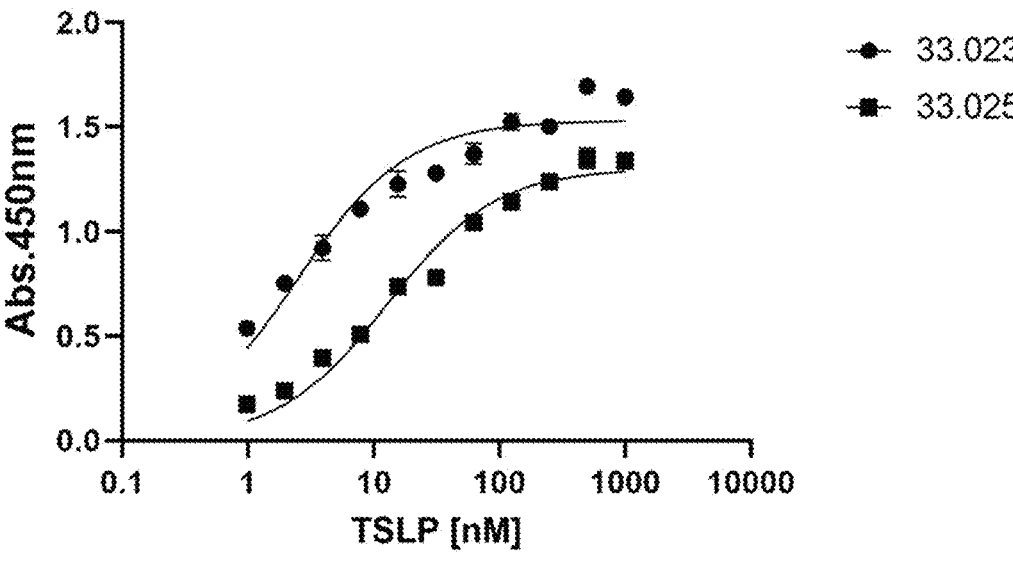
FIGS. 6A-6E present ELISA EC50 binding of BDG33.023 and BDG33.025 to human TSLP, cytomegaly monkey (cyno) TSLP or cytomegaly monkey (cyno) IL-13. Binding of BDG33.023 (filled circles) and BDG33.025 (filled squares) to human TSLP (FIG. 6A-human TSLP). Binding of BDG33.023 to cyno-TSLP (FIG. 6B-33.023 cyno TSLP). Binding of BDG33.025 to cyno-TSLP (FIG. 6C-33.025 cyno TSLP). Binding of BDG33.023 to cyno-IL-13 (FIG. 6D-33.023 cyno IL-13). Binding of BDG33.025 to cyno-IL-13 (FIG. 6E-33.025 cyno IL-13).
Figure 6B:
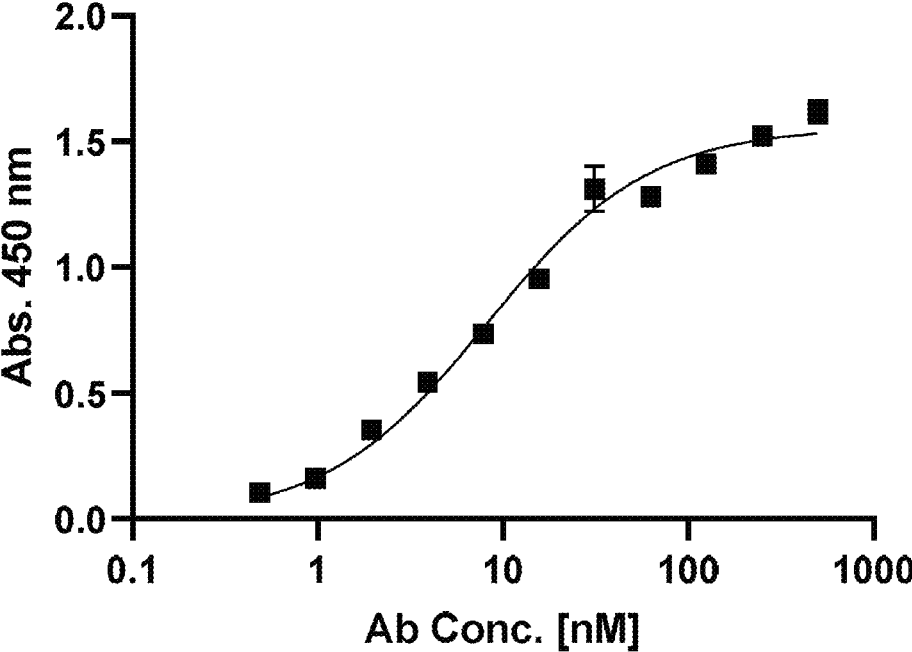
Figure 6C:
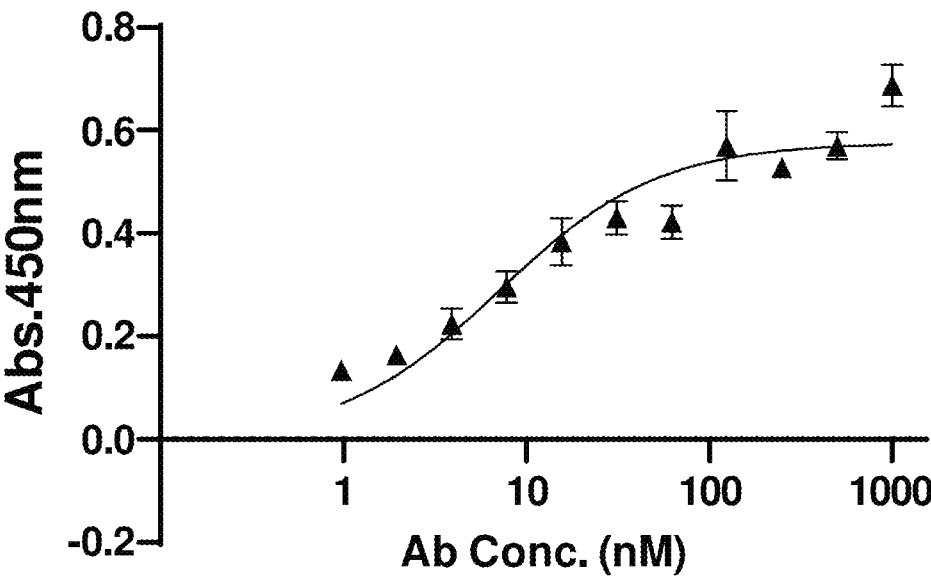
Figure 6D:
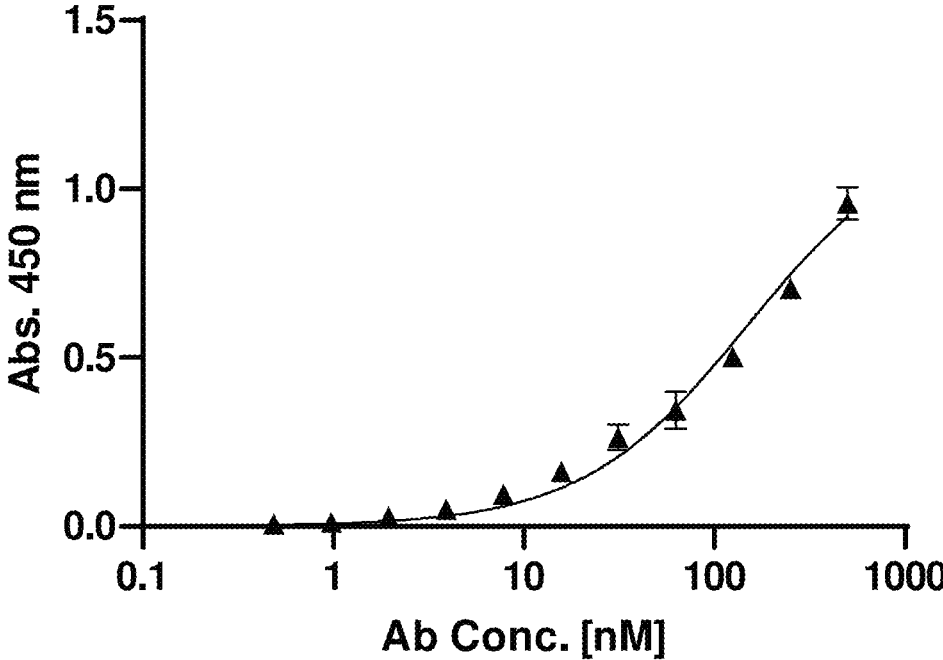
Figure 6E:
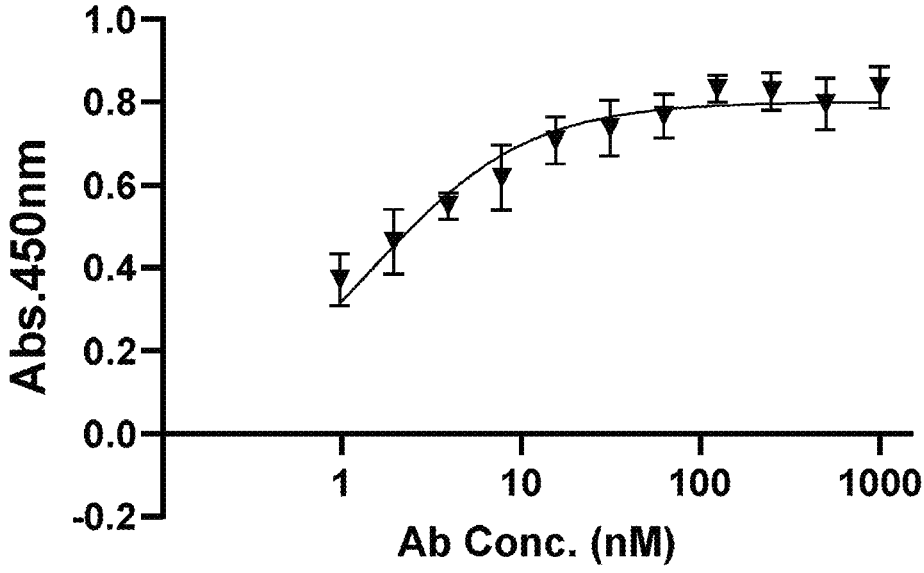

The antibodies were also tested for binding of recombinant cynomolgus monkey IL-13 (rc-IL-13), which shares 85% identity and 88% homology with the human IL-13, as can be seen in FIGS. 5C-5D, injection of cIL-13 as analyte, resulted in strong, dose dependent response indicating that BDG33.003 and BDG33.004 bind to rc-IL-13. Although kinetics for rc-IL-13 could not be obtained, the binding and dissociation slopes had similar profile for rh-IL-13 and rc-IL-13, suggesting that the binding mode for recombinant h-IL-13 and rc-IL-13 is likely similar (FIGS. 5A-5B for human IL-13 and FIGS. 5C-5D for cyno IL-13).

To further test the IgGs affinity to human TSLP, cynomolgus monkey TSLP and cynomolgus monkey IL-13, an ELISA EC50 experiment was done as described herein.

Briefly, wells were coated with the respective ligand, then incubated with clones BDG33.003, BDG33.004, BDG33.023, or BDG33.025 at a concentration range of 1 nM to 1000 nM, washed and developed using HRP conjugated secondary antibody. EC50 values are presented in Table 7. Since the IgGs mentioned in the above sections are symmetrical IgGs, and since these same IgGs bind both hIL-13 and hTSLP this data demonstrates that BGD33.003, BGD33.004, BGD33.023, and BGD33.025 antibodies bind the two unrelated targets—TSLP and/or IL-13 from the same standard IgG CDRs, as appose to bi-specific antibody where the Light chain variable domain binds one target and heavy chain binds the other target (FIGS. 6A-6E).

Figure 7A:
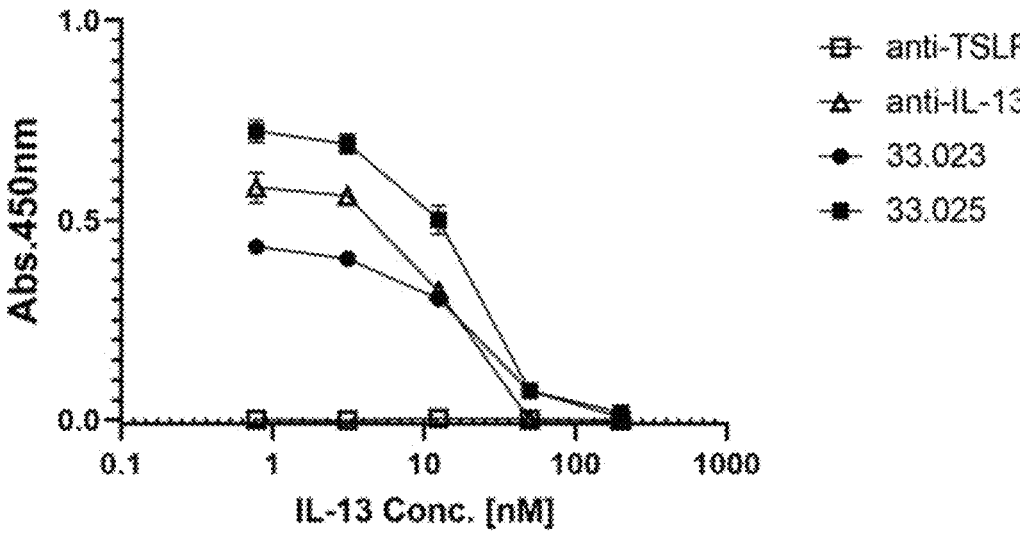
FIGS. 7A-7D present competitive binding assay of antibodies to hTSLP or hIL-13.
Figures 7B, 7C:
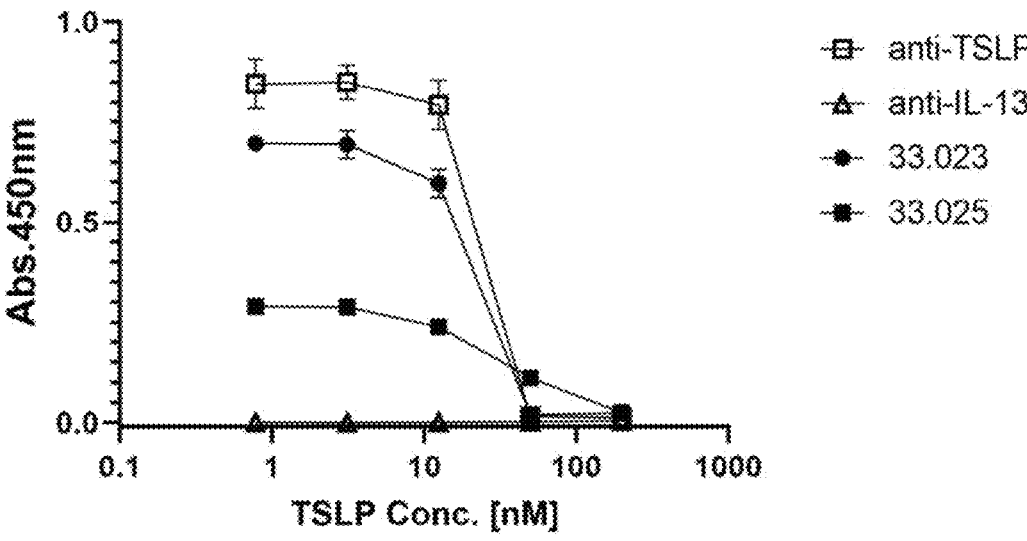
Figure 7D:
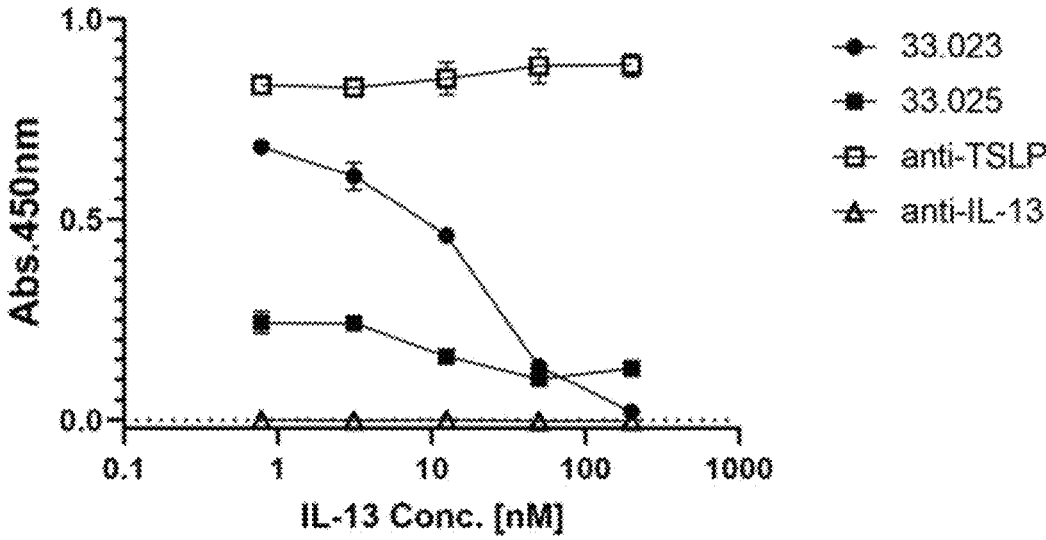

To test whether the IgGs are binding IL-13 and TSLP with overlapping paratopes, a competition assay was done as described herein. Briefly, BDG 33.023 or BDG33.025 were incubated with hIL-13 or hTSLP in concentration range of 0.78 nM to 200 nM and then tested for binding to either IL-13 or TSLP that were pre-coated on an ELISA plate. As can be seen in FIGS. 7A-7D, IL-13 blocks BDG33.023 from binding to IL-13 coated wells, and TSLP blocks BDG33.023 and BDG33.025 from binding to TSLP coated wells (FIGS. 7A-7B). In addition, IL-13 blocked binding of BDG33.023 from binding to TSLP coated wells and reciprocally TSLP blocked binding of BDG33.023 from binding to IL-13 coated wells (FIGS. 7C-7D). This experiment indicates that each of IL-13 and TSLP share at least partially BDG33.023 binding paratope.

Figure 8:
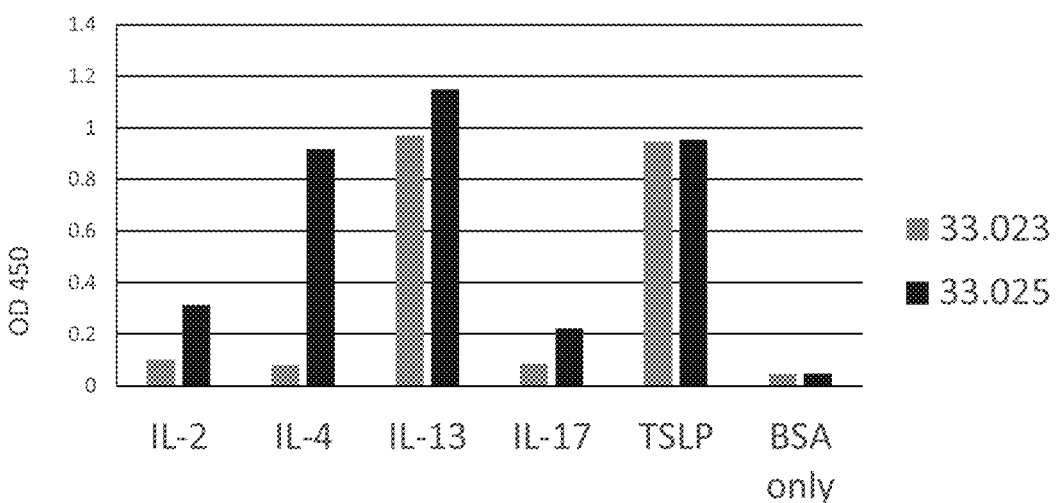
FIG. 8 presents the results of an ELISA specificity test that compared non-specific binding to specific binding of BDG330.23 and BDG33.025. The ELISA plate was coated with hIL-13, hTSLP, and the non-related cytokines IL-2, IL-17, and IL-4. BSA binding signal corresponds to assay background level.

IL-13 and TSLP are sequence and structurally unrelated. To test whether binding to these ligands by BDG33.023 and BDG33.025 is specific and not a result of non-specific binding or "stickiness", BGD33.0023 and BGD33.025 binding to IL-4, IL-2, IL-17, BSA IL-13, and TSLP was tested by ELISA as described herein. As can be seen in FIG. 8, while BDG33.025 shows strong binding to TSLP and IL-4, but not to IL-2 and IL-17. BDG33.023 bind strongly to TSLP and IL-13 but shows no binding to the other ligands, indicating that its binding to IL-13 and TSLP is specific.

Figure 9:
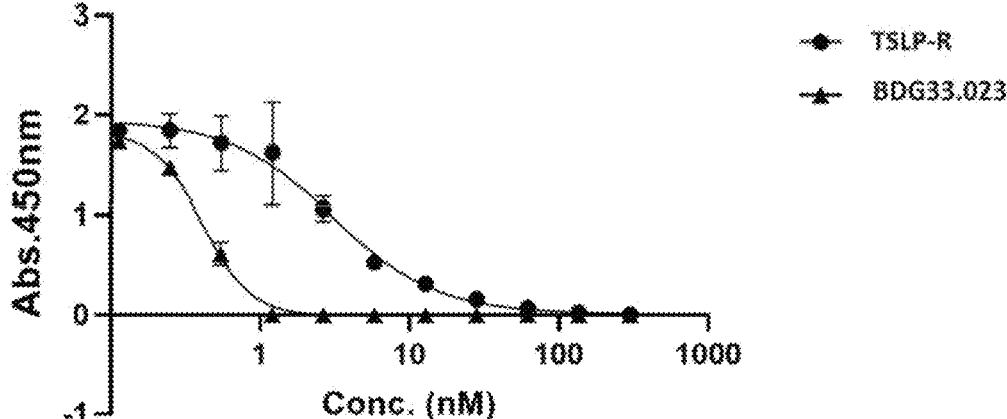
FIG. 9 presents the results of an IC50 inhibition assay that measured IgG specific blocking of hTSLP from binding to an ELISA plate coated with TSLP receptor (TSLP-R). The X-axis represents concentration of competitor. Competitors: TSLP-R (black circles) with a resultant IC50=3 nM; and BGD33.023 (black triangles) with a resultant IC50=0.41 nM.

To test if BDG33.023 binds TSLP at a functional epitope, the ability of BDG33.023 to cross-block TSLP from binding to a TSLP receptor was tested. Briefly TSLP-R was coated on ELISA plate wells, and its ability to bind hTSLP in the presence of 0 nM to 500 nM BDG33.023 was tested. As can be seen in FIG. 9, BDG 33.023 can cross block TSLP binding to TSLP-R with an IC 50 of 0.41 nM indicating that BDG33.023 binds tightly TSLP at a biologically functional site.

TABLE 6A

| KD values of antibody clones for human IL-13 and TSLP | | |
| --- | --- | --- |
| | Human IL-13 | |
| Antibody | $K_{D\ (Steady\ state)}$ (M) | $SE(K_D)$ (M) |
| BDG33.003 | 2.16E−08 | 2.5E−09 |
| BDG33.004 | 5.74E−08 | 4.1E−09 |
| | Human TSLP | | |
| | ka (1/Ms) | kd (1/s) | KD (M) |
| BDG33.003 | 2.87E+05 | 1.29E−3 | 4.5E−9 |
| BDG33.004 | 3.44E+05 | 1.14E−3 | 3.33E−9 |

TABLE 6B

KD values of antibody clones for human IL-13 and TSLP

| Antibody | Human IL-13 | | |
| | ka (1/Ms) | kd (1/s) | KD (M) |
|---|---|---|---|
| BDG33.023 | 4.31E+06 | 0.01573 | 3.65E−09 |
| BDG33.025 | 4.07E+6 | 0.0036 | 9.03E−10 |

TABLE 7

EC50 values for human and cyno TSLP, and cyno IL-13

| IgG | EC50 value for ligand | | |
| | hTSLP | cTSLP | cIL-13 |
|---|---|---|---|
| BDG33.023 | 2.5 nM | 8.2 nM | 7.1 nM |
| BDG33.025 | 12.8 nM | 148 nM | 1.5 nM |

Example 4: Cell Based Assays for the Inhibitor Antibody BDG33.003 (Clone C2)

Objective: Analyze the IgG1 antibodies for the ability to inhibit IL-13 activity.

Figure 10:
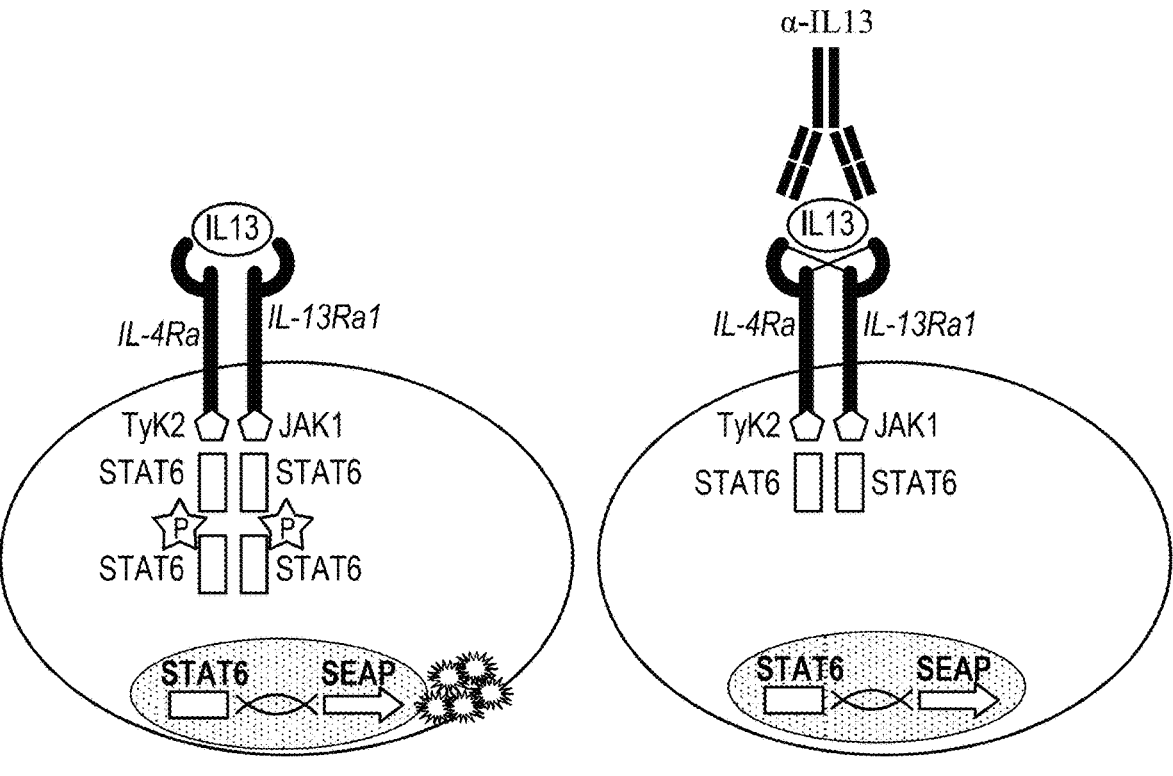
FIG. 10 presents a schematic representation of the HEK-Blue IL-13 system downstream signaling.
Figure 11A:
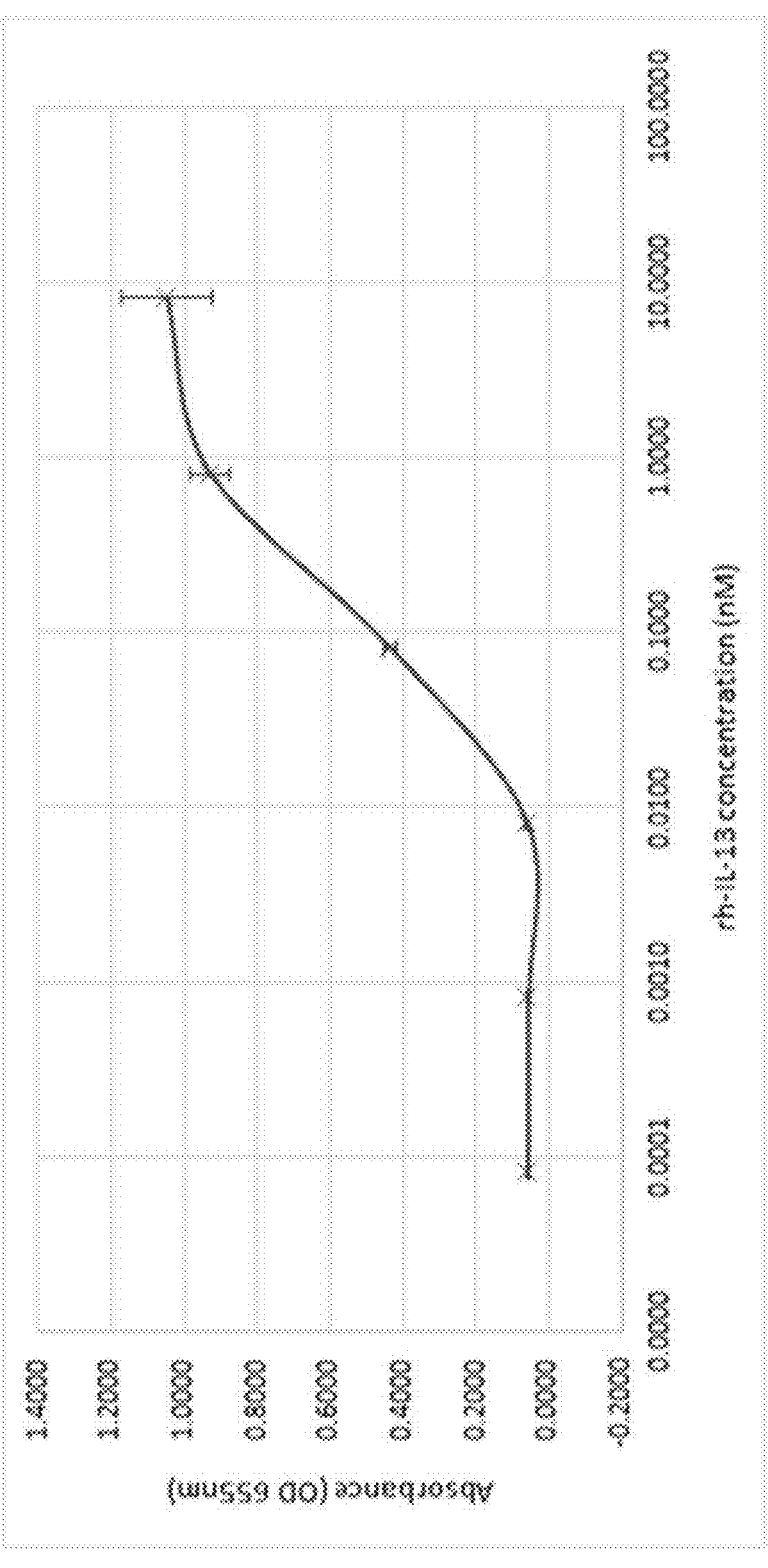
FIGS. 11A-11D present hIL-13 pSTAT6 signaling inhibition data. The results are based on stimulation of HEK-Blue cell's IL-13 activation pathway by recombinant rh-IL-13 and inhibition of this stimulation by indicated IgGs. HEK-Blue IL-13 cells (50,000 cells/well) were incubated with rh-IL-13 at a range of concentrations (0 nM-8 nM). IL-13 downstream signaling was quantified with QUANTI-Blue 24 h post incubation (FIG. 11A). hIL-13 downstream inhibition on HEK-BLUE IL-13 cells by engineered dual binding antibodies was analyzed as follows. rh-IL-13 (0.4 nM) was incubated with indicated antibodies at an antibody concentration range of 0 nM-750 nM. Antibodies assayed were BDG33.002 (positive control), BDG33.003 (Clone C2), and BDG33.006 (negative control), respectively (FIG. 11B). Clones BDG33.023 and BDG33.025 were assayed at an antibody concentration range of 0 nM-100 nM (FIGS. 11C and 11D show 33.023 IL-13 pSTAT6 inhibition, and 33.025 IL-13 pSTAT6 inhibition, respectively. After the incubation the hIL-13/IgG mixture was added to the cells, secreted embryonic alkaline phosphatase (SEAP) activity was quantified with QUANTI-Blue 24 h post incubation. Data shown is the mean of triplicate experiments, and error bars represent standard deviation.
Figure 11B:
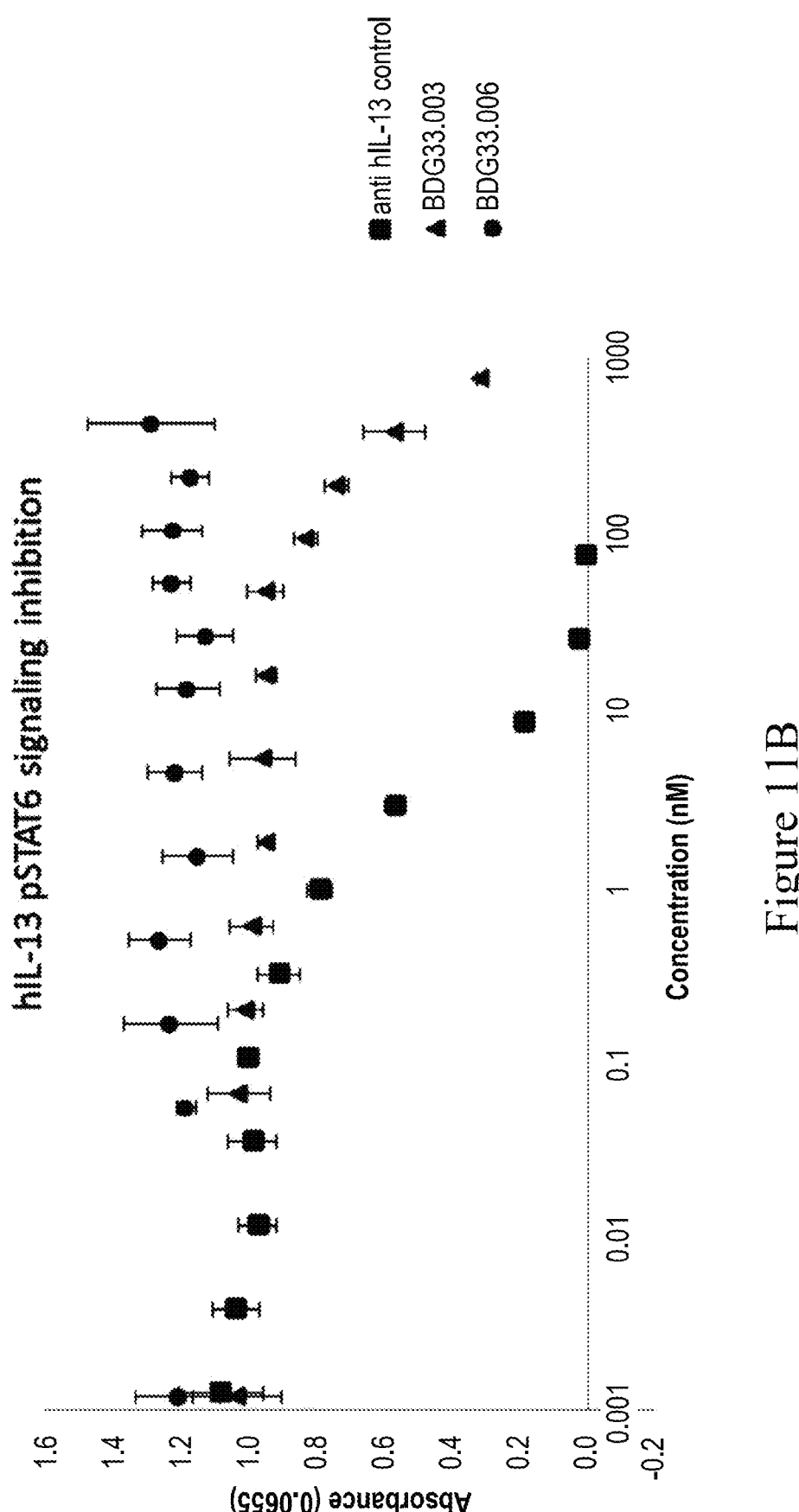
Figure 11C:
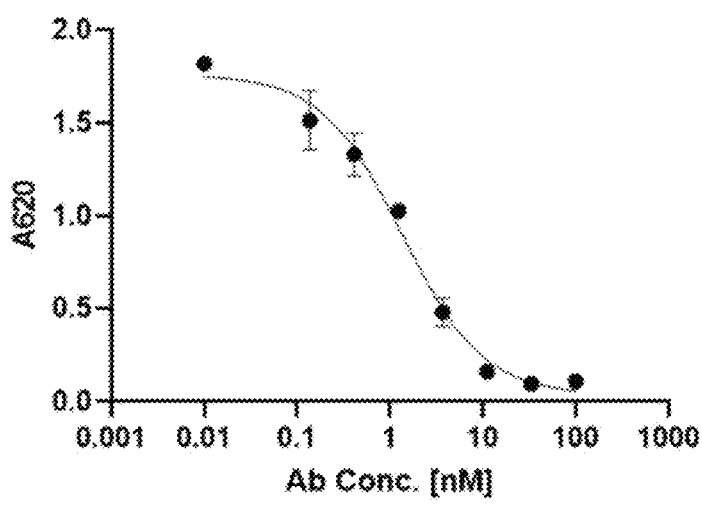
Figure 11D:
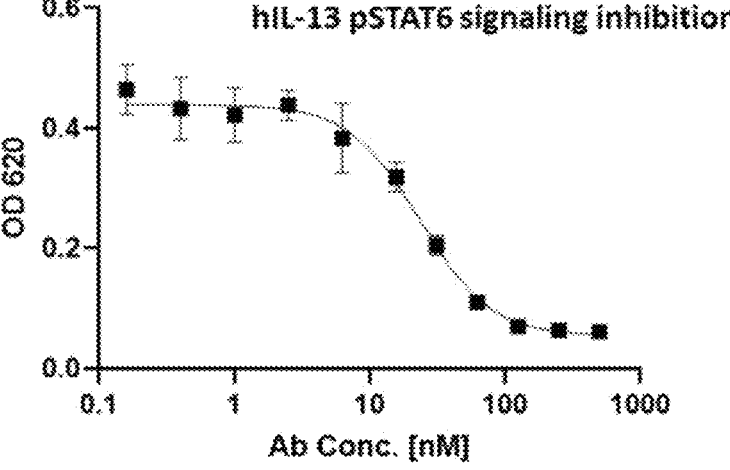

Results: To evaluate the capability of the antibody to inhibit rh-IL-13, the HEK-Blue IL-4/IL-13 system was used. The system uses HEK293 cells, which were stably transfected with human STAT6 gene and the reporter gene secreted embryonic alkaline phosphatase (SEAP) under the control of the IFNβ minimal promoter fused to four STAT6 binding sites (Example 1 (Methods), and FIG. 10). The system was initially tested by introducing rh-IL-13 to the cells and following the cell signaling cascade resulting in IL-13R (IL-13 receptor) activation by rh-IL-13. The results showed that IL-13 had an EC50 of about 0.12 nM to the cells (FIG. 11). Next, the engineered BDG33.003 (clone C2), BDG33.023 and BDG33.025 antibodies were tested to determine if they could inhibit IL-13 mediated activation of the cell's signaling cascade. The antibody was incubated with 0.4 nM rh-IL-13, which was shown to activate IL-13R to approximately 70% of the saturation level, and the IgG/IL-13 mixture was introduced to the cells for 24 hrs. The results obtained showed that the antibodies were able to inhibit IL-13 from binding to the IL-13R/IL-4R receptor complex, thus interfering with the signaling cascade. While for BDG33.003 the exact IC50 value was hard to determine, it is clear that BDG33.003 is inhibiting IL-13 signaling cascade. In addition, BDG33.023 and BDG33.025 inhibited IL-13 signaling cascade with an IC50 of 1.3 nM and 25 nM respectively, indicating that the IgGs are functionally blocking IL-13 in a biologically relevant setting. (FIGS. 11B-11D).

Figure 12A:
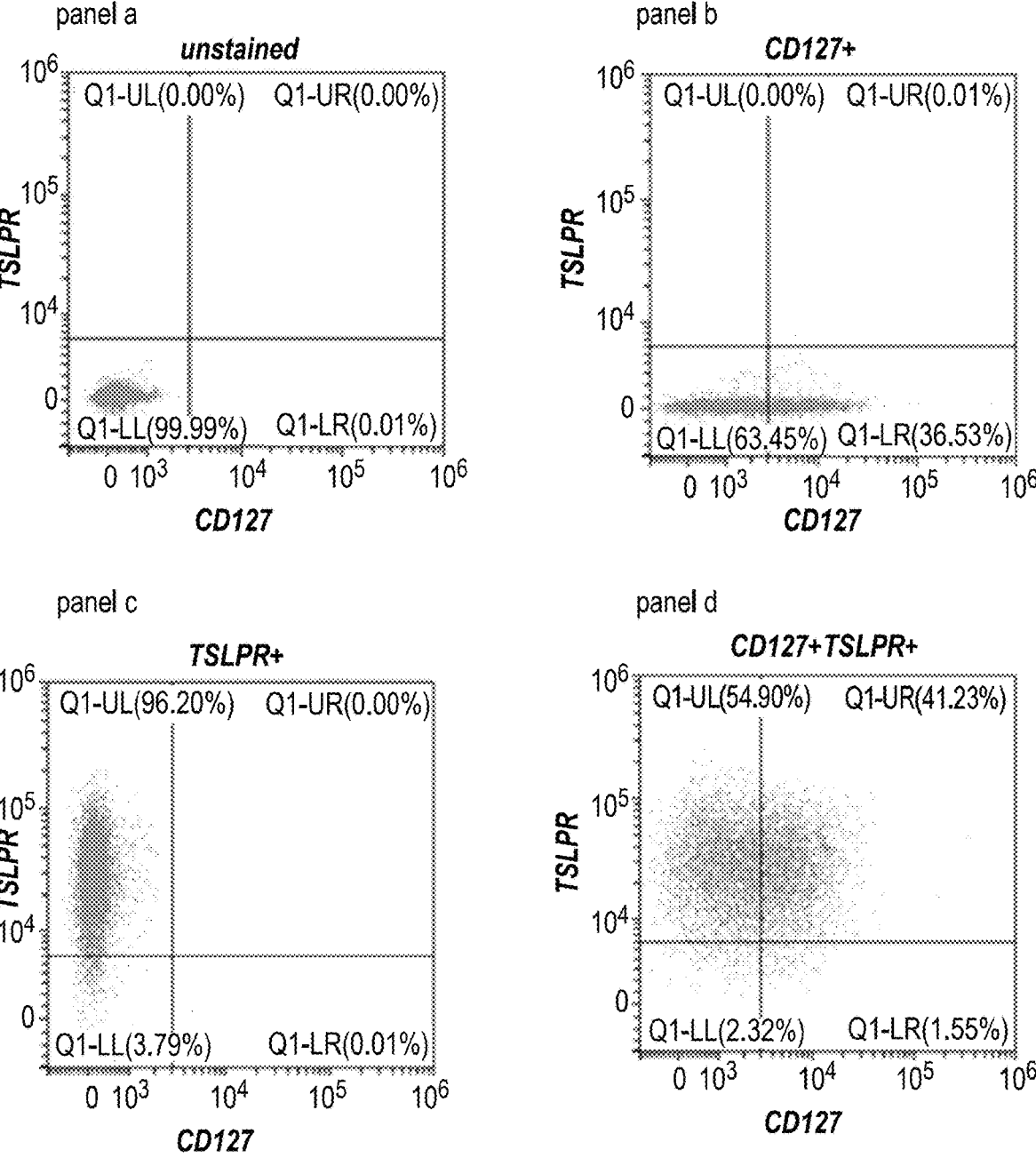
Figure 12B:
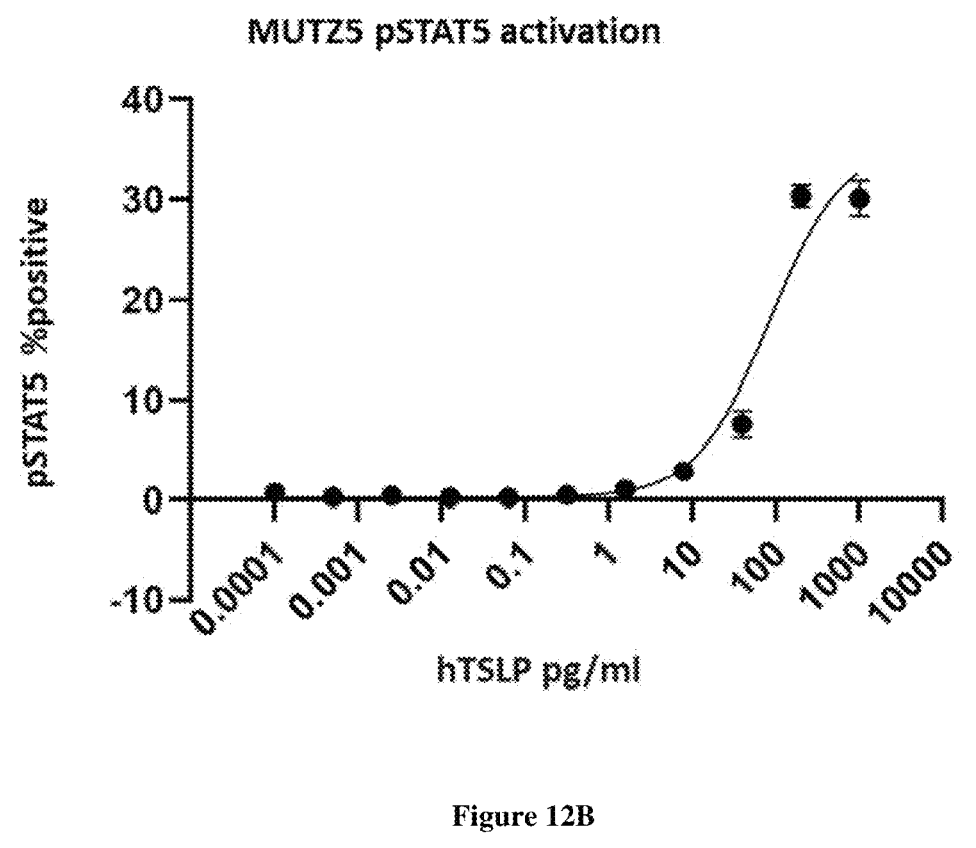
Figure 12C:
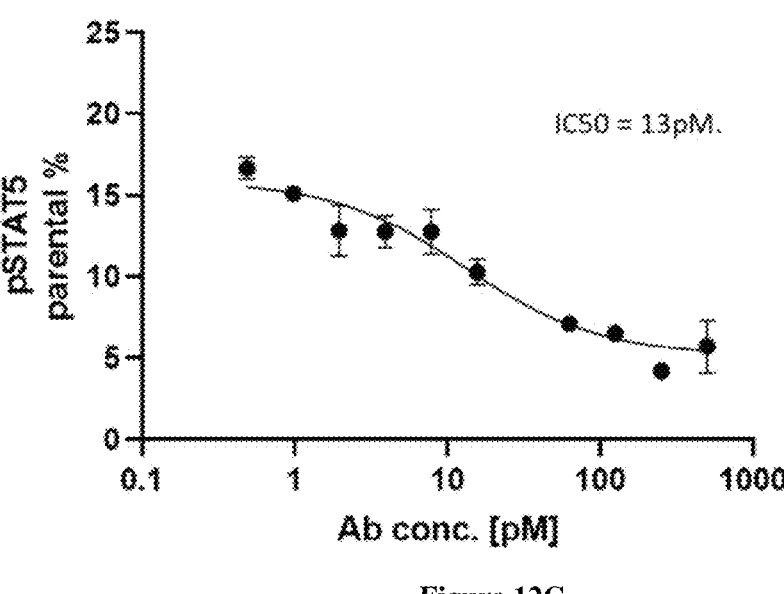

To evaluate the capability of the antibodies to inhibit human TSLP in cells, MUTZ5 cells were used to test pSTAT5 TSLP dependent activation in a similar manner reported by Francis O L et al (Hematopoiesis 2016). TSLP induced phospho-STAT5 (pSTAT5) cellular activation cascade requires IL-7 receptor and TSLP-R receptor to function, as can be seen in FIG. 12A both are expressed on the MUTZ5 cell line surface indicating that these cells have the necessary receptors for this assay. To establish the cellular response to TSLP cells were incubated with TSLP at a concentration range of 0.0001 to 1000 pg/ml and their pSTAT5 activation levels were determined by flow cytometry. As can be seen in FIG. 12B treatment of MUTZ 5 cells with TSLP activates pSTAT5 in a dose dependent manner, indicating that these cells respond to TSLP via the pSTAT5 pathway. To test BDG33.023 inhibition of TSLP dependent STAT5 activation, TSLP at a concentration of 14 pM was mixed with 0.48 pM to 500 pM BDG33.023 and incubated with MUTZ cells, as can be seen in FIG. 12C. BDG33.023 inhibits TSLP pSTAT5 activation with an IC50 value of 13 pM. These experiments demonstrate that BDG33.023 is functionally blocking TSLP in a biologically relevant cell-based setting.

Summary: The "re-epitoped" engineered BDG33.003 (clone 2), BDG33.023, and BDG33.025 antibodies were shown to bind both TSLP and IL-13 In contrast to the bispecific antibody format where each Fv has a specificity to a single antigen, these three antibodies are a standard IgG format, and each Fv has specificity to both IL-13 and TSLP In addition BDG33.023's paratopes for IL-13 and TSLP was shown to be at least partly overlapping. All three IgGs interfere with the IL-13R/IL4R and TSLPR/IL-7R signaling cascade. Such antibodies could be used as a component of a therapeutic treatment, for example but not limited to severe asthma, atopic dermatitis, and other allergic and respiratory conditions.

Example 5: Biochemical Characterization of Dual Binding Antibodies

Objective: To examine the biochemical and functional properties of dual binding antibodies BDG38.074 to BDG38.143.

Methods:

Peripheral blood mononuclear cells (PBMCs) (Cell Generation, CAT: 101061021) were used to determine IL-13 and hTLSP inhibition. PBMCs were thawed and cultured in growth medium comprising of RPMI—1640, 10% PBS, 1% Glutamax, 1% Sodium-Pyruvate, 0.1% 2-ME, 1% Pen-Strep and 1% nonessential AA. The cells were seeded in 96 well plate at $5 \times 10^5$ cells/well. Fifteen ng/mL hTSLP and 1.25 ng/mL IL-13 were incubated with antibodies for half an hour in 37° C., then added to the cells, to a total of 200 uL. Cells were incubated for 48 hours at 37° C., 5% $CO_2$.

CD23 upregulates in human monocytes in the presence of IL-13 (RD May et. al, 2011). $IC_{50}$ of antibody inhibition of IL-13 was determined by measuring CD23 expression level in monocytes. At the end of 48 hours incubation of the cells with different concentrations of antibodies, monocytes were detached from the bottom of the wells using cold PBS and scraping. Cells were marked using CD3 (Bio Legend, CAT: 300450), CD14 (Bio Legend, CAT: 301814), CD19 (Bio Legend, CAT: 302212) and CD23 (Bio Legend, CAT: 338506) antibodies. CD23 percentage of CD14+ population was measured using CytoFLEX flow cytometer (Beckman Coulter).

$IC_{50}$ of antibody inhibition of hTSLP was determined by TARC inhibition. TARC levels were determined using TARC DUOSET ELISA kit DY364 (R&D systems) according to kit instructions. Briefly, ELISA high bonding protein plates were plated with capture (non-biotinylated) antibody, diluted in PBSX1. Plates were sealed and incubated overnight. The following day plates were washed and blocked using PBST 2% BSA in room temperature, shaking, for two hours. Supernatant from the PBMCs plates was transferred to the wells. Detection was preformed using the kit's detection antibodies (Biotinylated) in PBS 1% BSA and Streptavidin-HRP in PBST 2% BSA. After adding TMB stop solution, ELISA plates were read at 450 nm. Values were analyzed using standard sample curve.

Other methods used to provide the results described and presented in this Example have been described in Example 1 above.

Results: The tables below present the amino acid sequences for antibodies BDG38.074 to BDG38.143. The VH and VL sequences are shown in Table 10, whereas the heavy and light chain CDRs are shown in Table 8 and 9 respectively.

TABLE 8

Amino Acid Sequences of Heavy-Chain
CDR Regions for Antibodies BDG38.074
to BDG38.143

| Antibodies | HCDR1 | SEQ ID NO | HCDR2 | SEQ ID NO | HCDR3 | SEQ ID NO |
|---|---|---|---|---|---|---|
| BDG38_074_VH | GFAFRTYG | 349 | IWDDGSNT | 350 | VRAPQWYLTAEAFDL | 351 |
| BDG38_079_VH | GFAFRTYG | 349 | IWYDGSNT | 356 | VRAPQWYLTAEAFDL | 351 |
| BDG38_094_VH | GFAFRTYG | 349 | IWDDGSNT | 350 | VRAPQWYLTAEAFDL | 351 |
| BDG38_138_VH | GFAFRTYG | 349 | IWDDGSNT | 350 | VRAPQWYLTAEAFDL | 351 |
| BDG38_075_VH | GFAFRTYG | 349 | IWYDGSAT | 352 | VRAPQWYLSAEAFDL | 353 |
| BDG38_076_VH | GFAFRTYG | 349 | IWDDGSAT | 354 | VRAPQWYLTAEAFDL | 351 |
| BDG38_077_VH | GFAFRTYG | 349 | IWYDGSAT | 352 | VRAPQWYLTAEAFDL | 351 |
| BDG38_078_VH | GFEFRTYG | 355 | IWYDGSNT | 356 | VRAPQWYLTAEAFDL | 351 |
| BDG38_080_VH | GFAFRTYG | 349 | IWYDGSAT | 352 | VRAPQWYLSAEAFDL | 353 |
| BDG38_081_VH | GFAFRTYG | 349 | IWDDGSNT | 350 | VRAPQWYLTAEAFDL | 351 |
| BDG38_082_VH | GFAFRTYG | 349 | IWDDGSNT | 350 | VRAPQWYLTAEAFDL | 351 |
| BDG38_083_VH | GFEFRTYG | 355 | IWDDGSNT | 350 | ARAPQWYLTAEAFDL | 357 |
| BDG38_084_VH | GFAFRTYG | 349 | IWDDGSNT | 350 | VRAPQWYLTAEAFDL | 351 |
| BDG38_085_VH | GFEFRTYG | 355 | IWYDGSNT | 356 | VRAPQWYLTAEAFDL | 351 |
| BDG38_086_VH | GFEFRTYG | 355 | IWYDGSNT | 356 | VRAPQWYLTAEAFDL | 351 |
| BDG38_087_VH | GFAFRTYG | 349 | IWDDGSNT | 350 | VRAPQWYLTAEAFDL | 351 |
| BDG38_088_VH | GFEFRTYG | 355 | IWYDGSNT | 356 | VRAPQWYLTAEAFDL | 351 |
| BDG38_089_VH | GFEFRTYG | 355 | IWYDGSAT | 352 | VRAPQWYLTAEAFDL | 351 |
| BDG38_090_VH | GFEFRTYG | 355 | IWDDGSNT | 350 | ARAPQWYLTAEAFDL | 357 |
| BDG38_091_VH | GFEFRTYG | 355 | IWYDGSNT | 356 | VRAPQWYLTAEAFDL | 351 |
| BDG38_092_VH | GFEFRTYG | 355 | IWDDGSNT | 350 | VRAPQWYLTAEAFDL | 351 |
| BDG38_093_VH | GFEFRTYG | 355 | IWYDGSNT | 356 | VRAPQWYLTAEAFDL | 351 |
| BDG38_095_VH | GFEFRTYG | 355 | IWYDGSAT | 352 | VRAPQWYLTAEAFDL | 351 |
| BDG38_096_VH | GFEFRTYG | 355 | IWDDGSNT | 350 | VRAPQWYLTAEAFDL | 351 |
| BDG38_097_VH | GFEFRTYG | 355 | IWYDGSAT | 352 | VRAPQWYLTAEAFDL | 351 |
| BDG38_098_VH | GFEFRTYG | 355 | IWDDGSNT | 350 | VRAPQWYLTAEAFDL | 351 |
| BDG38_099_VH | GFEFRTYG | 355 | IWYDGSNT | 356 | VRAPQWYLTAEAFDL | 351 |
| BDG38_100_VH | GFEFRTYG | 355 | IWYDGSNT | 356 | VRAPQWYLTAEAFDL | 351 |
| BDG38_101_VH | GFEFRTYG | 355 | IWYDGSAT | 352 | VRAPQWYLTAEAFDL | 351 |
| BDG38_102_VH | GFEFRTYG | 355 | IWYDGSNT | 356 | VRAPQWYLTAEAFDL | 351 |
| BDG38_103_VH | GFEFRTYG | 355 | IWYDGSNT | 356 | VRAPQWYLTAEAFDL | 351 |
| BDG38_104_VH | GFEFRTYG | 355 | IWYDGSAT | 352 | VRAPQWYLTAEAFDL | 351 |
| BDG38_105_VH | GFEFRTYG | 355 | IWYDGSNT | 356 | VRAPQWYLTAEAFDL | 351 |

TABLE 8-continued

Amino Acid Sequences of Heavy-Chain
CDR Regions for Antibodies BDG38.074
to BDG38.143

| Antibodies | HCDR1 | SEQ ID NO | HCDR2 | SEQ ID NO | HCDR3 | SEQ ID NO |
|---|---|---|---|---|---|---|
| BDG38_106_VH | GFEFRTYG | 355 | IWDDGSNT | 350 | VRAPQWYLTAEAFDL | 351 |
| BDG38_107_VH | GFEFRTYG | 355 | IWYDGSNT | 356 | VRAPQWYLTAEAFDL | 351 |
| BDG38_108_VH | GFEFRTYG | 355 | IWYDGSNT | 356 | VRAPQWYLTAEAFDL | 351 |
| BDG38_109_VH | GFEFRTYG | 355 | IWYDGSNT | 356 | VRAPQWYLTAEAFDL | 351 |
| BDG38_110_VH | GFEFRTYG | 355 | IWDDGSNT | 350 | VRAPQWYLTAEAFDL | 351 |
| BDG38_111_VH | GFEFRTYG | 355 | IWDDGSAT | 354 | VRAPQWYLTAEAFDL | 351 |
| BDG38_112_VH | GFEFRTYG | 355 | IWYDGSNT | 356 | VRAPQWYLTAEAFDL | 351 |
| BDG38_113_VH | GFEFRTYG | 355 | IWYDGSNT | 356 | VRAPQWYLTAEAFDL | 351 |
| BDG38_114_VH | GFEFRTYG | 355 | IWYDGSNT | 356 | VRAPQWYLTAEAFDL | 351 |
| BDG38_115_VH | GFEFRTYG | 355 | IWYDGSNT | 356 | VRAPQWYLTAEAFDL | 351 |
| BDG38_116_VH | GFEFRTYG | 355 | IWDDGSNT | 350 | VRAPQWYLTAEAFDL | 351 |
| BDG38_117_VH | GFEFRTYG | 355 | IWDDGSNT | 350 | ARAPQWYLTAEAFDL | 357 |
| BDG38_118_VH | GFEFRTYG | 355 | IWYDGSAT | 352 | VRAPQWYLTAEAFDL | 351 |
| BDG38_119_VH | GFEFRTYG | 355 | IWYDGSNT | 356 | VRAPQWYLTAEAFDL | 351 |
| BDG38_120_VH | GFEFRTYG | 355 | IWDDGSNT | 350 | VRAPQWYLTAEAFDL | 351 |
| BDG38_121_VH | GFEFRTYG | 355 | IWYDGSNT | 356 | VRAPQWYLTAEAFDL | 351 |
| BDG38_122_VH | GFEFRTYG | 355 | IWDDGSNT | 350 | VRAPQWYLTAEAFDL | 351 |
| BDG38_123_VH | GFEFRTYG | 355 | IWDDGSNT | 350 | VRAPQWYLTAEAFDL | 351 |
| BDG38_124_VH | GFEFRTYG | 355 | IWDDGSNT | 350 | VRAPQWYLTAEAFDL | 351 |
| BDG38_125_VH | GFEFRTYG | 355 | IWDDGSNT | 350 | VRAPQWYLTAEAFDL | 351 |
| BDG38_126_VH | GFEFRTYG | 355 | IWDDGSNT | 350 | VRAPQWYLTAEAFDL | 351 |
| BDG38_127_VH | GFEFRTYG | 355 | IWYDGSAT | 352 | ARAPQWYLTAEAFDL | 357 |
| BDG38_128_VH | GFEFRTYG | 355 | IWDDGSNT | 350 | VRAPQWYLTAEAFDL | 351 |
| BDG38_129_VH | GFEFRTYG | 355 | IWDDGSNT | 350 | ARAPQWYLTAEAFDL | 357 |
| BDG38_130_VH | GFAFRTYG | 349 | IWDDGSNT | 350 | VRAPQWYLTAEAFDL | 351 |
| BDG38_131_VH | GFEFRTYG | 355 | IWDDGSNT | 350 | VRAPQWYLTAEAFDL | 351 |
| BDG38_132_VH | GFEFRTYG | 355 | IWDDGSNT | 350 | VRAPQWYLTAEAFDL | 351 |
| BDG38_133_VH | GFEFRTYG | 355 | IWDDGSNT | 350 | VRAPQWYLTAEAFDL | 351 |
| BDG38_134_VH | GFEFRTYG | 355 | IWYDGSNT | 356 | VRAPQWYNSAEAFDL | 358 |
| BDG38_135_VH | GFAFRTYG | 349 | IWYDGSNT | 356 | VRAPQWYNSAEAFDL | 358 |
| BDG38_136_VH | GFEFRTYG | 355 | IWYDGSNT | 356 | VRAPQWYNSAEAFDL | 358 |
| BDG38_137_VH | GFEFRTYG | 355 | IWDDGSNT | 350 | VRAPQWYLTAEAFDL | 351 |
| BDG38_139_VH | GFAFRTYG | 349 | IWDDGSNT | 350 | VRAPQWYLSAEAFDL | 353 |
| BDG38_140_VH | GFEFRTYG | 355 | IWDDGSNT | 350 | ARAPQWYLTAEAFDL | 357 |
| BDG38_141_VH | GFEFRTYG | 355 | IWDDGSNT | 350 | VRAPQWYLTAEAFDL | 351 |

TABLE 8-continued

Amino Acid Sequences of Heavy-Chain
CDR Regions for Antibodies BDG38.074
to BDG38.143

| Antibodies | HCDR1 | SEQ ID NO | HCDR2 | SEQ ID NO | HCDR3 | SEQ ID NO |
|---|---|---|---|---|---|---|
| BDG38_142_VH | GFEFRTYG | 355 | IWDDGSNT | 350 | VRAPQWYLTAEAFDL | 351 |
| BDG38_143_VH | GFEFRTYG | 355 | IWDDGSAT | 354 | VRAPQWYLTAEAFDL | 351 |

TABLE 9

Amino Acid Sequences of Light-Chain
CDR Regions for Antibodies BDG38.074 to
BDG38.143

| Antibodies | LCDR1 | SEQ ID NO | LCDR2 | LCDR3 | SEQ ID NO |
|---|---|---|---|---|---|
| BDG38_074_VL | MIGAYL | 359 | DDV | QVWDHNTDKMV | 361 |
| BDG38_079_VL | MIGGYL | 364 | DDV | QVWDHDSNTMV | 371 |
| BDG38_094_VL | LIGAYL | 362 | DDV | QVWDHNSNHMV | 384 |
| BDG38_138_VL | MIGGYL | 364 | DDV | QVWDHNSNHMV | 384 |
| BDG38_075_VL | LIGAYL | 362 | DDV | QVWDHDTNTMV | 363 |
| BDG38_076_VL | MIGGYL | 364 | DDV | QVWDHDTNHMV | 365 |
| BDG38_077_VL | LIGSRL | 366 | DDS | QVWDHSSNTYV | 368 |
| BDG38_078_VL | LIGARL | 369 | DDS | QVWDYYSDHMV | 370 |
| BDG38_080_VL | LIGAYL | 362 | DDS | QVWDHNTNHMV | 372 |
| BDG38_081_VL | MIGAYL | 359 | DDV | QVWDHNTQQMV | 373 |
| BDG38_082_VL | MIGGYL | 364 | DDV | QVWDHDTNQVV | 374 |
| BDG38_083_VL | LIGAKL | 375 | DDS | QVWDYSSDTMV | 376 |
| BDG38_084_VL | LIGAYL | 362 | DDV | QVWDHSTNTMV | 377 |
| BDG38_085_VL | LIGARL | 369 | DDS | QVWDYSSNSYV | 378 |
| BDG38_086_VL | LIGARL | 369 | DDS | QVWDYSSNTYV | 379 |
| BDG38_087_VL | MIGAYL | 359 | DDV | QVWDHNSNQMV | 380 |
| BDG38_088_VL | LIGARL | 369 | DDS | QVWDYSSNTYV | 379 |
| BDG38_089_VL | LIGARL | 369 | DDS | QVWDHSSNHYV | 381 |
| BDG38_090_VL | LIGARL | 369 | DDS | QVWDYYSDHMV | 370 |
| BDG38_091_VL | LIGSRL | 366 | DDS | QVWDHYSNHYV | 382 |
| BDG38_092_VL | LIGARL | 369 | DDS | QVWDYYSDHMV | 370 |
| BDG38_093_VL | LIGARL | 369 | DDS | QVWDYSADSYV | 383 |
| BDG38_095_VL | LIGSRL | 366 | DDS | QVWDYYSDSYV | 385 |
| BDG38_096_VL | LIGARL | 369 | DDS | QVWDYSSDSMV | 386 |
| BDG38_097_VL | LIGARL | 369 | DDS | QVWDYYSDHYV | 387 |
| BDG38_098_VL | LIGARL | 369 | DDS | QVWDYSSDSMV | 386 |
| BDG38_099_VL | LIGARL | 369 | DDS | QVWDYSSDSYV | 388 |
| BDG38_100_VL | LIGARL | 369 | DDS | QVWDYYSNSYV | 389 |

TABLE 9-continued

Amino Acid Sequences of Light-Chain
CDR Regions for Antibodies BDG38.074 to
BDG38.143

| Antibodies | LCDR1 | SEQ ID NO | LCDR2 | LCDR3 | SEQ ID NO |
|---|---|---|---|---|---|
| BDG38_101_VL | LIGARL | 369 | DDS | QVWDYSSNTYV | 379 |
| BDG38_102_VL | LIGARL | 369 | DDS | QVWDYSSNTYV | 379 |
| BDG38_103_VL | LIGARL | 369 | DDS | QVWDYYSNSYV | 389 |
| BDG38_104_VL | LIGARL | 369 | DDS | QVWDYYSDSYV | 390 |
| BDG38_105_VL | LIGARL | 369 | DDS | QVWDYYSNSYV | 389 |
| BDG38_106_VL | LIGSRL | 366 | DDS | QVWDHYSDHMV | 391 |
| BDG38_107_VL | LIGARL | 369 | DDS | QVWDYSSDSYV | 388 |
| BDG38_108_VL | LIGARL | 369 | DDS | QVWDYYSNSYV | 389 |
| BDG38_109_VL | LIGARL | 369 | DDS | QVWDYSSNSYV | 378 |
| BDG38_110_VL | LIGAKL | 375 | DDS | QVWDYSSNHMV | 392 |
| BDG38_111_VL | LIGARL | 369 | DDS | QVWDYYANSYV | 393 |
| BDG38_112_VL | LIGARL | 369 | DDS | QVWDYSSDTYV | 394 |
| BDG38_113_VL | LIGARL | 369 | DDS | QVWDYSSDSYV | 388 |
| BDG38_114_VL | LIGARL | 369 | DDS | QVWDYSANSYV | 395 |
| BDG38_115_VL | LIGARL | 369 | DDS | QVWDYSSNTYV | 379 |
| BDG38_116_VL | LIGARL | 369 | DDS | QVWDYYSDTMV | 396 |
| BDG38_117_VL | LIGAKL | 375 | DDS | QVWDYSSDTMV | 376 |
| BDG38_118_VL | LIGARL | 369 | DDS | QVWDYSSDHYV | 397 |
| BDG38_119_VL | LIGARL | 369 | DDS | QVWDYSSNTYV | 379 |
| BDG38_120_VL | LIGARL | 369 | DDS | QVWDYSSDHMV | 398 |
| BDG38_121_VL | LIGARL | 369 | DDS | QVWDYSSNTYV | 379 |
| BDG38_122_VL | LIGARL | 369 | DDS | QVWDYSSDSYV | 388 |
| BDG38_123_VL | LIGARL | 369 | DDS | QVWDYSSDTYV | 394 |
| BDG38_124_VL | LIGARL | 369 | DDS | QVWDYSSDTYV | 394 |
| BDG38_125_VL | LIGARL | 369 | DDS | QVWDYSSDHMV | 398 |
| BDG38_126_VL | LIGAKL | 375 | DDS | QVWDYSSDHMV | 398 |
| BDG38_127_VL | LIGAKL | 375 | DDS | QVWDYYSDTYV | 399 |

TABLE 9-continued

| Amino Acid Sequences of Light-Chain CDR Regions for Antibodies BDG38.074 to BDG38.143 | | | | | |
|---|---|---|---|---|---|
| Antibodies | LCDR1 | SEQ ID NO | LCDR2 | LCDR3 | SEQ ID NO |
| BDG38_128_VL | LIGAKL | 375 | DDS | QVWDYYADTMV | 400 |
| BDG38_129_VL | LIGAKL | 375 | DDS | QVWDYSSDHMV | 398 |
| BDG38_130_VL | LIGARL | 369 | DDS | QVWDYSSNSYV | 378 |
| BDG38_131_VL | LIGAKL | 375 | DDS | QVWDYYSNTMV | 401 |
| BDG38_132_VL | LIGARL | 369 | DDS | QVWDYSSDHMV | 398 |
| BDG38_133_VL | LIGARL | 369 | DDS | QVWDYSSDTYV | 394 |
| BDG38_134_VL | LIGARL | 369 | DDS | QVWDYSADTMV | 402 |
| BDG38_135_VL | LIGARL | 369 | DDS | QVWDHSADTMV | 403 |

TABLE 9-continued

| Amino Acid Sequences of Light-Chain CDR Regions for Antibodies BDG38.074 to BDG38.143 | | | | | |
|---|---|---|---|---|---|
| Antibodies | LCDR1 | SEQ ID NO | LCDR2 | LCDR3 | SEQ ID NO |
| BDG38_136_VL | LIGAKL | 375 | DDS | QVWDYSSDTMV | 376 |
| BDG38_137_VL | LIGARL | 369 | DDS | QVWDYSADTMV | 402 |
| BDG38_139_VL | MIGAYL | 359 | DDV | QVWDHNSDHMV | 404 |
| BDG38_140_VL | LIGAKL | 375 | DDS | QVWDYSANHMV | 405 |
| BDG38_141_VL | LIGSRL | 366 | DDS | QVWDYYSNHMV | 406 |
| BDG38_142_VL | LIGAKL | 375 | DDS | QVWDYYSHTMV | 407 |
| BDG38_143_VL | LIGARL | 369 | DDS | QVWDYSSNTYV | 379 |

TABLE 10

| Amino Acid Sequences of VH and VL Regions for Antibodies BDG38.074 to BDG38.143 | | |
|---|---|---|
| Antibodies | Amino Acid Sequence | SEQ ID NO: |
| BDG38_074_VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 209 |
| BDG38_074_VL | SYVLTQPPSVSVAPGQTATITCGGNMIGAYLVHWYQQKPGQAPLL VVYDDVDRPNRIPERFSGSNSGNTATLTISRVEAGDEADYYCQVWD HNTDKMVFGGGTKLTVL | 210 |
| BDG38_079_VH | QMQLVESGGGVVQPGRSLRLSCAASGFAFRTYGMHWVRQAPGKG LEWVAVIWYDGSNTHYADSVKGRFTITRDNSKNTLNLQMNSLRAE DTAVYYCVRAPQWYLTAEAFDLWGQGTMVTVSS | 219 |
| BDG38_079_VL | SYVLTQPPSVSVAPGETATITCGGNMIGGYLVHWYQQKPGQAPLLV IYDDVDRPDRIPERFSGSNSGNTATLTISRVEAGDEADYYCQVWDH DSNTMVFGGGTKLTVL | 220 |
| BDG38_094_VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 249 |
| BDG38_094_VL | SYVLTQPPSVSVAPGETASITCGGNLIGAYLVHWYQQKPGQAPLLVI YDDVDRPARIPERFSGSNSGNTATLTISRVEAGDEADYYCQVWDHN SNHMVFGGGTKLTVL | 250 |
| BDG38_138_VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 337 |
| BDG38_138_VL | SYVLTQPPSVSVAPGETASITCGGNMIGGYLVHWYQQKPGQAPVLV IYDDVDRPSRIPERFSGSNSGNTATLTISRVEAGDEADYYCQVWDH NSNHMVFGGGTKLTVL | 338 |
| BDG38_075_VH | QMQLVESGGGVVQPGRSLRLSCAASGFAFRTYGMHWVRQAPGKG LEWVAVIWYDGSATHYADSVKGRFTITRDNSKNTLNLQMNSLRAE DTAVYYCVRAPQWYLSAEAFDLWGQGTMVTVSS | 211 |
| BDG38_075_VL | SYVLTQPPSVSVAPGETATITCGGNLIGAYLVHWYQQKPGQAPVLV IYDDVDRPARIPERFSGSNSGNTATLTISRVEAGDEADYYCQVWDH DTNTMVFGGGTKLTVL | 212 |
| BDG38_076_VH | QMQLVESGGGVVQPGRSLRLSCAASGFAFRTYGMHWVRQAPGKG LEWVAVIWDDGSATHYADSVKGRFTITRDNSKNTLNLQMNSLRAE DTAVYYCVRAPQWYLTAEAFDLWGQGTMVTVSS | 213 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_076_ VL | SYVLTQPPSVSVAPGETASITCGGNMIGGYLVHWYQQKPGQAPLLV IYDDVDRPARIPERFSGSNSGNTATLTISRVEAGDEADYYCQVWDH DTNHMVFGGGTKLTVL | 214 |
| BDG38_077_ VH | QMQLVESGGGVVQPGRSLTLSCAASGFAFRTYGMHWVRQAPGKG LEWVGVIWYDGSATHYADSVKGRFTITRDNSKNTLNLQMNSLRAE DTAVYYCVRAPQWYLTAEAFDLWGQGTMVTVSS | 215 |
| BDG38_077_ VL | SYVLTQPPSVSVAPGETATITCGGALIGSRLVHWYQQKPGQAPVLVI YDDSDRPSRIPERFSGSNIGNTATLTISDVEAGDEADYYCQVWDHSS NTYVFGGGTKLTVL | 216 |
| BDG38_078_ VH | QMQLVESGGGVVQPGRSLRLSCAASGFEFRTYGMHWVRQAPGKG LEWLGVIWYDGSNTHYADSVKGRFTITRDNSKNTLNLQMNSLRVE DTAVYYCVRAPQWYLTAEAFDLWGQGTMVTVSS | 217 |
| BDG38_078_ VL | SYILTQPPSVSVAPGETATITCGGNLIGARLVHWYQQKPGQAPVLVI YDDSDRPSRIPERFSGSNIGNTATLTIERVEAGDEADYYCQVWDYYS DHMVFGGGTKLTVL | 218 |
| BDG38_080_ VH | QMQLVESGGGVVQPGRSLRLSCAASGFAFRTYGMHWVRQAPGKG LEWVAVIWYDGSATHYADSVKGRFTITRDNSKNTLNLQMNSLRAE DTAVYYCVRAPQWYLSAEAFDLWGQGTMVTVSS | 221 |
| BDG38_080_ VL | SYVLTQPPSVSVAPGETATITCGGNLIGAYLVHWYQQKPGQAPVLV IYDDSDRPDRIPERFSGSNSGNTATLTISRVEAGDEADYYCQVWDH NTNHMVFGGGTKLTVL | 222 |
| BDG38_081_ VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 223 |
| BDG38_081_ VL | SYVLTQPPSVSVAPGQTARITCGGNMIGAYLVHWYQQKPGQAPLL VIYDDVDRPDRIPERFSGSNSGNTATLTISRVEAGDEADYYCQVWD HNTQQMVFGGGTKLTVL | 224 |
| BDG38_082_ VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 225 |
| BDG38_082_ VL | SYVLTQPPSVSVAPGETATITCGGNMIGGYLVHWYQQKPGQAPVL VIYDDVDRPDRIPERFSGSNSGNTATLTISRVEAGDEADYYCQVWD HDTNQVVFGGGTKLTVL | 226 |
| BDG38_083_ VH | QMQLVESGGGVVQPGRSLTLSCAASGFEFRTYGMHWVRQAPGKG LEWVGVIWDDGSNTHYADSVKGRFTITRDNSKNTLNLQMNSLRAE DTAVYYCARAPQWYLTAEAFDLWGQGTMVTVSS | 227 |
| BDG38_083_ VL | SYILTQPPSVSVAPGQTATITCGGNLIGAKLVHWYQQKPGQAPVLVI YDDSDRPSRIPERFSGSNIGNTATLTISDVEEGDEADYYCQVWDYSS DTMVFGGGTKLTVL | 228 |
| BDG38_084_ VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 229 |
| BDG38_084_ VL | SYVLTQPPSVSVAPGETATITCGGNLIGAYLVHWYQQKPGQAPVLV VYDDVDRPDRIPERFSGSNSGNTATLTISRVEAGDEADYYCQVWDH STNTMVFGGGTKLTVL | 230 |
| BDG38_085_ VH | QMQLVESGGGVVQPGRSLTLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 231 |
| BDG38_085_ VL | SYVLTQPPSVSVAPGETATITCGGNLIGARLVHWYQQKPGQAPVLV IYDDSDRPSRIPERFSGSNIGNTATLTIERVEAGDEADYYCQVWDYS SNSYVFGGGTKLTVL | 232 |
| BDG38_086_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 233 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_086_ VL | SYVLTQPPSVSVAPGQTARITCGGNLIGARLVHWYQQKPGQAPVLV VYDDSDRPSRIPERFSGSNIGNTATLTISDVEEGDEADYYCQVWDYS SNTYVFGGGTKLTVL | 234 |
| BDG38_087_ VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 235 |
| BDG38_087_ VL | SYVLTQPPSVSVAPGQTATITCGGNMIGAYLVHWYQQKPGQAPVL VIYDDVDRPDRIPERFSGSNSGNTATLTISRVEAGDEADYYCQVWD HNSNQMVFGGGTKLTVL | 236 |
| BDG38_088_ VH | QMQLVESGGGVVQPGRSLTLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 237 |
| BDG38_088_ VL | SYVLTQPPSVSVAPGETATITCGGNLIGARLVHWYQQKPGQAPVLV IYDDSDRPSRIPERFSGSNIGNTATLTISDVEAGDEADYYCQVWDYS SNTYVFGGGTKLTVL | 238 |
| BDG38_089_ VH | QMQLVESGGGVVQPGRSLRLSCAASGFEFRTYGMHWVRQAPGKG LEWVGVIWYDGSATHYADSVKGRFTITRDNSKNTLNLQMNSLRVE DTAVYYCVRAPQWYLTAEAFDLWGQGTMVTVSS | 239 |
| BDG38_089_ VL | SYILTQPPSVSVAPGETATITCGGNLIGARLVHWYQQKPGQAPVLVI YDDSDRPSRIPERFSGSNIGNTATLTISRVEEGDEADYYCQVWDHSS NHYVFGGGTKLTVL | 240 |
| BDG38_090_ VH | QMQLVESGGGVVQPGRSLTLSCAASGFEFRTYGMHWVRQAPGKG LEWLGVIWDDGSNTHYADSVKGRFTITRDNSKNTLNLQMNSLRVE DTAVYYCARAPQWYLTAEAFDLWGQGTMVTVSS | 241 |
| BDG38_090_ VL | SYILTQPPSVSVAPGETARITCGGNLIGARLVHWYQQKPGQAPVLV VYDDSDRPSRIPERFSGSNIGNTATLTIEDVEEGDEADYYCQVWDY YSDHMVFGGGTKLTVL | 242 |
| BDG38_091_ VH | QMQLVESGGGVVQPGRSLTLSCAASGFEFRTYGMHWVRQAPGKG LEWLGVIWYDGSNTHYADSVKGRFTITRDNSKNTLNLQMNSLRVE DTAVYYCVRAPQWYLTAEAFDLWGQGTMVTVSS | 243 |
| BDG38_091_ VL | SYILTQPPSVSVAPGETATITCGGNLIGSRLVHWYQQKPGQAPVLVI YDDSDRPSRIPERFSGSNIGNTATLTISDVEAGDEADYYCQVWDHYS NHYVFGGGTKLTVL | 244 |
| BDG38_092_ VH | QMQLVESGGGVVQPGRSLTLSCAASGFEFRTYGMHWVRQAPGKG LEWLAVIWDDGSNTHYADSVKGRFTITRDNSKNTLNLQMNSLRVE DTAVYYCVRAPQWYLTAEAFDLWGQGTMVTVSS | 245 |
| BDG38_092_ VL | SYVLTQPPSVSVAPGETATITCGGNLIGARLVHWYQQKPGQAPVLV IYDDSDRPSRIPERFSGSNIGNTATLTISDVEEGDEADYYCQVWDYY SDHMVFGGGTKLTVL | 246 |
| BDG38_093_ VH | QMQLVESGGGVVQPGRSLTLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 247 |
| BDG38_093_ VL | SYVLTQPPSVSVAPGQTARITCGGNLIGARLVHWYQQKPGQAPVLV IYDDSDRPSRIPERFSGSNIGNTATLTIERVEEGDEADYYCQVWDYS ADSYVFGGGTKLTVL | 248 |
| BDG38_095_ VH | QMQLVESGGGVVQPGRSLTLSCAASGFEFRTYGMHWVRQAPGKG LEWVGVIWYDGSATHYADSVKGRFTITRDNSKNTLNLQMNSLRAE DTAVYYCVRAPQWYLTAEAFDLWGQGTMVTVSS | 251 |
| BDG38_095_ VL | SYVLTQPPSVSVAPGQTATITCGGALIGSRLVHWYQQKPGQAPVLV VYDDSDRPSRIPERFSGSNIGNTATLTISRVEEGDEADYYCQVWDYY SDSYVFGGGTKLTVL | 252 |
| BDG38_096_ VH | QMQLVESGGGVVQPGRSLRLSCAASGFEFRTYGMHWVRQAPGKG LEWVAVIWDDGSNTHYADSVKGRFTITRDNSKNTLNLQMNSLRVE DTAVYYCVRAPQWYLTAEAFDLWGQGTMVTVSS | 253 |

TABLE 10-continued

Amino Acid Sequences of VH and VL
Regions for Antibodies BDG38.074 to
BDG38.143

| Antibodies | Amino Acid Sequence | SEQ ID NO: |
| --- | --- | --- |
| BDG38_096_ VL | SYILTQPPSVSVAPGETARITCGGNLIGARLVHWYQQKPGQAPVLVI YDDSDRPSRIPERFSGSNIGNTATLTISRVEEGDEADYYCQVWDYSS DSMVFGGGTKLTVL | 254 |
| BDG38_097_ VH | QMQLVESGGGVVQPGRSLRLSCAASGFEFRTYGMHWVRQAPGKG LEWLGVIWYDGSATHYADSVKGRFTITRDNSKNTLNLQMNSLRAE DTAVYYCVRAPQWYLTAEAFDLWGQGTMVTVSS | 255 |
| BDG38_097_ VL | SYILTQPPSVSVAPGETATITCGGNLIGARLVHWYQQKPGQAPVLVI YDDSDRPSRIPERFSGSNIGNTATLTIERVEEGDEADYYCQVWDYSS DHYVFGGGTKLTVL | 256 |
| BDG38_098_ VH | QMQLVESGGGVVQPGRSLTLSCAASGFEFRTYGMHWVRQAPGKG LEWVAVIWDDGSNTVYADSVKGRFTITRDNSKNTLNLQMNSLRVE DTAVYYCVRAPQWYLTAEAFDLWGQGTMVTVSS | 257 |
| BDG38_098_ VL | SYVLTQPPSVSVAPGQTATITCGGNLIGARLVHWYQQKPGQAPVLV IYDDSDRPSRIPERFSGSNIGNTATLTISRVEAGDEADYYCQVWDYS SDSMVFGGGTKLTVL | 258 |
| BDG38_099_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 259 |
| BDG38_099_ VL | SYILTQPPSVSVAPGETARITCGGNLIGARLVHWYQQKPGQAPVLVI YDDSDRPSRIPERFSGSNIGNTATLTIEDVEEGDEADYYCQVWDYSS DSYVFGGGTKLTVL | 260 |
| BDG38_100_ VH | QMQLVESGGGVVQPGRSLRLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 261 |
| BDG38_100_ VL | SYVLTQPPSVSVAPGETARITCGGNLIGARLVHWYQQKPGQAPVLV IYDDSDRPSRIPERFSGSNIGNTATLTIERVEEGDEADYYCQVWDYY SNSYVFGGGTKLTVL | 262 |
| BDG38_101_ VH | QMQLVESGGGVVQPGRSLRLSCAASGFEFRTYGMHWVRQAPGKG LEWVGVIWYDGSATHYADSVKGRFTITRDNSKNTLNLQMNSLRVE DTAVYYCVRAPQWYLTAEAFDLWGQGTMVTVSS | 263 |
| BDG38_101 VL | SYILTQPPSVSVAPGETATITCGGNLIGARLVHWYQQKPGQAPVLVI YDDSDRPSRIPERFSGSNIGNTATLTISRVEEGDEADYYCQVWDYSS NTYVFGGGTKLTVL | 264 |
| BDG38_102_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 265 |
| BDG38_102_ VL | SYVLTQPPSVSVAPGETATITCGGNLIGARLVHWYQQKPGQAPVLV VYDDSDRPSRIPERFSGSNIGNTATLTIEDVEAGDEADYYCQVWDY SSNTYVFGGGTKLTVL | 266 |
| BDG38_103_ VH | QMQLVESGGGVVQPGRSLRLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 267 |
| BDG38_103_ VL | SYVLTQPPSVSVAPGQTATITCGGNLIGARLVHWYQQKPGQAPVLV VYDDSDRPSRIPERFSGSNIGNTATLTISDVEEGDEADYYCQVWDY YSNSYVFGGGTKLTVL | 268 |
| BDG38_104_ VH | QMQLVESGGGVVQPGRSLTLSCAASGFEFRTYGMHWVRQAPGKG LEWVGVIWYDGSATHYADSVKGRFTITRDNSKNTLNLQMNSLRAE DTAVYYCVRAPQWYLTAEAFDLWGQGTMVTVSS | 269 |
| BDG38_104_ VL | SYILTQPPSVSVAPGETATITCGGNLIGARLVHWYQQKPGQAPVLVI YDDSDRPSRIPERFSGSNIGNTATLTIEDVEEGDEADYYCQVWDYSS DSYVFGGGTKLTVL | 270 |
| BDG38_105_ VH | QMQLVESGGGVVQPGRSLTLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 271 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_105_ VL | SYVLTQPPSVSVAPGETATITCGGNLIGARLVHWYQQKPGQAPVLV IYDDSDRPSRIPERFSGSNIGNTATLTIERVEAGDEADYYCQVWDYY SNSYVFGGGTKLTVL | 272 |
| BDG38_106_ VH | QMQLVESGGGVVQPGRSLTLSCAASGFEFRTYGMHWVRQAPGKG LEWVAVIWDDGSNTVYADSVKGRFTITRDNSKNTLNLQMNSLRVE DTAVYYCVRAPQWYLTAEAFDLWGQGTMVTVSS | 273 |
| BDG38_106_ VL | SYILTQPPSVSVAPGQTATITCGGNLIGSRLVHWYQQKPGQAPVLVI YDDSDRPSRIPERFSGSNIGNTATLTIEDVEEGDEADYYCQVWDHYS DHMVFGGGTKLTVL | 274 |
| BDG38_107_ VH | QMQLVESGGGVVQPGRSLTLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 275 |
| BDG38_107_ VL | SYILTQPPSVSVAPGQTATITCGGNLIGARLVHWYQQKPGQAPVLVI YDDSDRPSRIPERFSGSNIGNTATLTIERVEEGDEADYYCQVWDYSS DSYVFGGGTKLTVL | 276 |
| BDG38_108_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 277 |
| BDG38_108_ VL | SYILTQPPSVSVAPGETATITCGGNLIGARLVHWYQQKPGQAPVLVI YDDSDRPSRIPERFSGSNIGNTATLTISDVEEGDEADYYCQVWDYYS NSYVFGGGTKLTVL | 278 |
| BDG38_109_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 279 |
| BDG38_109_ VL | SYILTQPPSVSVAPGQTATITCGGNLIGARLVHWYQQKPGQAPVLVI YDDSDRPSRIPERFSGSNIGNTATLTIERVEEGDEADYYCQVWDYSS NSYVFGGGTKLTVL | 280 |
| BDG38_110_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 281 |
| BDG38_110_ VL | SYILTQPPSVSVAPGETTRITCGGNLIGAKLVHWYQQKPGQAPVLVI YDDSDRPSRIPERFSGSNIGNTATLTIEDVEAGDEADYYCQVWDYSS NHMVFGGGTKLTVL | 282 |
| BDG38_111_ VH | QMQLVESGGGVVQPGRSLTLSCAASGFEFRTYGMHWVRQAPGKG LEWVGVIWDDGSATHYADSVKGRFTITRDNSKNTLNLQMNSLRVE DTAVYYCVRAPQWYLTAEAFDLWGQGTMVTVSS | 283 |
| BDG38_111_ VL | SYVLTQPPSVSVAPGETATITCGGALIGARLVHWYQQKPGQAPVLV VYDDSDRPSRIPERFSGSNIGNTATLTISRVEAGDEADYYCQVWDY YANSYVFGGGTKLTVL | 284 |
| BDG38_112_ VH | QMQLVESGGGVVQPGRSLRLSCAASGFEFRTYGMHWVRQAPGKG LEWLGVIWYDGSNTHYADSVKGRFTITRDNSKNTLNLQMNSLRAE DTAVYYCVRAPQWYLTAEAFDLWGQGTMVTVSS | 285 |
| BDG38_112_ VL | SYILTQPPSVSVAPGQTATITCGGNLIGARLVHWYQQKPGQAPVLVI YDDSDRPSRIPERFSGSNIGNTATLTIERVEEGDEADYYCQVWDYSS DTYVFGGGTKLTVL | 286 |
| BDG38_113_ VH | QMQLVESGGGVVQPGRSLTLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 287 |
| BDG38_113_ VL | SYVLTQPPSVSVAPGETATITCGGNLIGARLVHWYQQKPGQAPVLV IYDDSDRPSRIPERFSGSNIGNTATLTIEDVEEGDEADYYCQVWDYS SDSYVFGGGTKLTVL | 288 |
| BDG38_114_ VH | QMQLVESGGGVVQPGRSLTLSCAASGFEFRTYGMHWVRQAPGKG LEWVGVIWYDGSNTHYADSVKGRFTITRDNSKNTLNLQMNSLRVE DTAVYYCVRAPQWYLTAEAFDLWGQGTMVTVSS | 289 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_114_ VL | SYILTQPPSVSVAPGQTATITCGGNLIGARLVHWYQQKPGQAPVLVI YDDSDRPSRIPERFSGSNIGNTATLTIEDVEEGDEADYYCQVWDYSA NSYVFGGGTKLTVL | 290 |
| BDG38_115_ VH | QMQLVESGGGVVQPGRSLTLSCAASGFEFRTYGMHWVRQAPGKG LEWLGVIWYDGSNTHYADSVKGRFTITRDNSKNTLNLQMNSLRAE DTAVYYCVRAPQWYLTAEAFDLWGQGTMVTVSS | 291 |
| BDG38_115_ VL | SYILTQPPSVSVAPGQTATITCGGNLIGARLVHWYQQKPGQAPVLVI YDDSDRPSRIPERFSGSNSGNTATLTISDVEEGDEADYYCQVWDYSS NTYVFGGGTKLTVL | 292 |
| BDG38_116_ VH | QMQLVESGGGVVQPGRSLTLSCAASGFEFRTYGMHWVRQAPGKG LEWVAVIWDDGSNTHYADSVKGRFTITRDNSKNTLNLQMNSLRVE DTAVYYCVRAPQWYLTAEAFDLWGQGTMVTVSS | 293 |
| BDG38_116_ VL | SYVLTQPPSVSVAPGQTATITCGGNLIGARLVHWYQQKPGQAPVLV IYDDSDRPSRIPERFSGSNIGNTATLTIERVEAGDEADYYCQVWDYY SDTMVFGGGTKLTVL | 294 |
| BDG38_117_ VH | QMQLVESGGGVVQPGRSLTLSCAASGFEFRTYGMHWVRQAPGKG LEWVGVIWDDGSNTHYADSVKGRFTITRDNSKNTLNLQMNSLRAE DTAVYYCARAPQWYLTAEAFDLWGQGTMVTVSS | 295 |
| BDG38_117_ VL | SYVLTQPPSVSVAPGETATITCGGNLIGAKLVHWYQQKPGQAPVLV IYDDSDRPSRIPERFSGSNIGNTATLTIEDVEAGDEADYYCQVWDYS SDTMVFGGGTKLTVL | 296 |
| BDG38_118_ VH | QMQLVESGGGVVQPGRSLRLSCAASGFEFRTYGMHWVRQAPGKG LEWVGVIWYDGSATHYADSVKGRFTITRDNSKNTLNLQMNSLRVE DTAVYYCVRAPQWYLTAEAFDLWGQGTMVTVSS | 297 |
| BDG38_118_ VL | SYILTQPPSVSVAPGETATITCGGNLIGARLVHWYQQKPGQAPVLVI YDDSDRPSRIPERFSGSNIGNTATLTISDVEEGDEADYYCQVWDYSS DHYVFGGGTKLTVL | 298 |
| BDG38_119_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 299 |
| BDG38_119_ VL | SYILTQPPSVSVAPGETATITCGGNLIGARLVHWYQQKPGQAPVLVI YDDSDRPSRIPERFSGSNIGNTATLTISRVEEGDEADYYCQVWDYSS NTYVFGGGTKLTVL | 300 |
| BDG38_120_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 301 |
| BDG38_120_ VL | SYILTQPPSVSVAPGETATITCGGNLIGARLVHWYQQKPGQAPVLVI YDDSDRPSRIPERFSGSNSGNTATLTISDVEAGDEADYYCQVWDYS SDHMVFGGGTKLTVL | 302 |
| BDG38_121_ VH | QMQLVESGGGVVQPGRSLRLSCAASGFEFRTYGMHWVRQAPGKG LEWVGVIWYDGSNTHYADSVKGRFTITRDNSKNTLNLQMNSLRAE DTAVYYCVRAPQWYLTAEAFDLWGQGTMVTVSS | 303 |
| BDG38_121_ VL | SYILTQPPSVSVAPGETATITCGGNLIGARLVHWYQQKPGQAPVLVI YDDSDRPSRIPERFSGSNIGNTATLTISRVEAGDEADYYCQVWDYSS NTYVFGGGTKLTVL | 304 |
| BDG38_122_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 305 |
| BDG38_122_ VL | SYILTQPPSVSVAPGETATITCGGNLIGARLVHWYQQKPGQAPVLVI YDDSDRPSRIPERFSGSNIGNTATLTISRVEEGDEADYYCQVWDYSS DSYVFGGGTKLTVL | 306 |
| BDG38_123_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 307 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_123_ VL | SYILTQPPSVSVAPGETATITCGGNLIGARLVHWYQQKPGQAPVLVI YDDSDRPSRIPERFSGSNIGNTATLTISDVEAGDEADYYCQVWDYSS DTYVFGGGTKLTVL | 308 |
| BDG38_124_ VH | QMQLVESGGGVVQPGRSLRLSCAASGFEFRTYGMHWVRQAPGKG LEWVGVIWDDGSNTHYADSVKGRFTITRDNSKNTLNLQMNSLRAE DTAVYYCVRAPQWYLTAEAFDLWGQGTMVTVSS | 309 |
| BDG38_124_ VL | SYILTQPPSVSVAPGETATITCGGNLIGARLVHWYQQKPGQAPVLVI YDDSDRPSRIPERFSGSNIGNTATLTISDVEAGDEADYYCQVWDYSS DTYVFGGGTKLTVL | 310 |
| BDG38_125_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 311 |
| BDG38_125_ VL | SYVLTQPPSVSVAPGETATITCGGNLIGARLVHWYQQKPGQAPVLV IYDDSDRPSRIPERFSGSNIGNTATLTIERVEEGDEADYYCQVWDYS SDHMVFGGGTKLTVL | 312 |
| BDG38_126_ VH | QMQLVESGGGVVQPGRSLRLSCAASGFEFRTYGMHWVRQAPGKG LEWVGVIWDDGSNTHYADSVKGRFTITRDNSKNTLNLQMNSLRAE DTAVYYCVRAPQWYLTAEAFDLWGQGTMVTVSS | 313 |
| BDG38_126_ VL | SYILTQPPSVSVAPGQTARITCGGNLIGAKLVHWYQQKPGQAPVLVI YDDSDRPSRIPERFSGSNIGNTATLTIERVEEGDEADYYCQVWDYSS DHMVFGGGTKLTVL | 314 |
| BDG38_127_ VH | QMQLVESGGGVVQPGRSLTLSCAASGFEFRTYGMHWVRQAPGKG LEWVGVIWYDGSATHYADSVKGRFTITRDNSKNTLNLQMNSLRAE DTAVYYCARAPQWYLTAEAFDLWGQGTMVTVSS | 315 |
| BDG38_127_ VL | SYILTQPPSVSVAPGETATITCGGNLIGAKLVHWYQQKPGQAPVLVI YDDSDRPSRIPERFSGSNIGNTATLTISDVEAGDEADYYCQVWDYYS DTYVFGGGTKLTVL | 316 |
| BDG38_128_ VH | QMQLVESGGGVVQPGRSLTLSCAASGFEFRTYGMHWVRQAPGKG LEWVAVIWDDGSNTHYADSVKGRFTITRDNSKNTLNLQMNSLRVE DTAVYYCVRAPQWYLTAEAFDLWGQGTMVTVSS | 317 |
| BDG38_128_ VL | SYILTQPPSVSVAPGETATITCGGNLIGAKLVHWYQQKPGQAPVLVI YDDSDRPSRIPERFSGSNSGNTATLTISDVEEGDEADYYCQVWDYY ADTMVFGGGTKLTVL | 318 |
| BDG38_129_ VH | QMQLVESGGGVVQPGRSLTLSCAASGFEFRTYGMHWVRQAPGKG LEWVGVIWDDGSNTHYADSVKGRFTITRDNSKNTLNLQMNSLRVE DTAVYYCARAPQWYLTAEAFDLWGQGTMVTVSS | 319 |
| BDG38_129_ VL | SYILTQPPSVSVAPGQTATITCGGNLIGAKLVHWYQQKPGQAPVLVI YDDSDRPSRIPERFSGSNIGNTATLTISDVEEGDEADYYCQVWDYSS DHMVFGGGTKLTVL | 320 |
| BDG38_130_ VH | QMQLVESGGGVVQPGRSLTLSCAASGFAFRTYGMHWVRQAPGKG LEWVAVIWDDGSNTHYADSVKGRFTITRDNSKNTLNLQMNSLRVE DTAVYYCVRAPQWYLTAEAFDLWGQGTMVTVSS | 321 |
| BDG38_130_ VL | SYILTQPPSVSVAPGETATITCGGNLIGARLVHWYQQKPGQAPVLVI YDDSDRPSRIPERFSGSNIGNTATLTIERVEAGDEADYYCQVWDYSS NSYVFGGGTKLTVL | 322 |
| BDG38_131_ VH | QMQLVESGGGVVQPGRSLTLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 323 |
| BDG38_131_ VL | SYILTQPPSVSVAPGETATITCGGNLIGAKLVHWYQQKPGQAPVLVI YDDSDRPSRIPERFSGSNIGNTATLTISDVEEGDEADYYCQVWDYYS NTMVFGGGTKLTVL | 324 |
| BDG38_132_ VH | QMQLVESGGGVVQPGRSLRLSCAASGFEFRTYGMHWVRQAPGKG LEWVGVIWDDGSNTHYADSVKGRFTITRDNSKNTLNLQMNSLRAE DTAVYYCVRAPQWYLTAEAFDLWGQGTMVTVSS | 325 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_132_ VL | SYILTQPPSVSVAPGETATITCGGNLIGARLVHWYQQKPGQAPVLVI YDDSDRPSRIPERFSGSNIGNTATLTISRVEAGDEADYYCQVWDYSS DHMVFGGGTKLTVL | 326 |
| BDG38_133_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 327 |
| BDG38_133_ VL | SYILTQPPSVSVAPGETATITCGGNLIGARLVHWYQQKPGQAPVLVI YDDSDRPSRIPERFSGSNIGNTATLTISRVEAGDEADYYCQVWDYSS DTYVFGGGTKLTVL | 328 |
| BDG38_134_ VH | QMQLVESGGGVVQPGQSLRLSCAASGFEFRTYGMHWVRQAPGKG LEWLAVIWYDGSNTHYADSVKGRFTITRDNSKNTLNLQMNSLRAE DTAVYYCVRAPQWYNSAEAFDLWGQGTMVTVSS | 329 |
| BDG38_134_ VL | SYVLTQPPSVSVAPGQTARITCGGNLIGARLVHWYQQKPGQAPVLV IYDDSDRPSHIPERFSGSNSGNTATLTISRVEAGDEADYYCQVWDYS ADTMVFGGGTKLTVL | 330 |
| BDG38_135_ VH | QMQLVESGGGVVQPGQSLRLSCAASGFAFRTYGMHWVRQAPGKG LEWLAVIWYDGSNTHYADSVKGRFTITRDNSKNTLNLQMNSLRAE DTAVYYCVRAPQWYNSAEAFDLWGQGTMVTVSS | 331 |
| BDG38_135_ VL | SYVLTQPPSVSVAPGQTARITCGGNLIGARLVHWYQQKPGQAPVLV VYDDSDRPSHIPERFSGSNSGNTATLTISRVEAGDEADYYCQVWDH SADTMVFGGGTKLTVL | 332 |
| BDG38_136_ VH | QMQLVESGGGVVQPGRSLRLSCAASGFEFRTYGMHWVRQAPGKG LEWLAVIWYDGSNTHYADSVKGRFTITRDNSKNTLNLQMNSLRAE DTAVYYCVRAPQWYNSAEAFDLWGQGTMVTVSS | 333 |
| BDG38_136_ VL | SYVLTQPPSVSVAPGQTARITCGGNLIGAKLVHWYQQKPGQAPVLV IYDDSDRPSHIPERFSGSNSGNTATLTISRVEAGDEADYYCQVWDYS SDTMVFGGGTKLTVL | 334 |
| BDG38_137_ VH | QMQLVESGGGVVQPGQSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 335 |
| BDG38_137_ VL | SYVLTQPPSVSVAPGETATITCGGNLIGARLVHWYQQKPGQAPVLV IYDDSDRPSHIPERFSGSNSGNTATLTISRVEAGDEADYYCQVWDYS ADTMVFGGGTKLTVL | 336 |
| BDG38_139_ VH | QMQLVESGGGVVQPGRSLRLSCAASGFAFRTYGMHWVRQAPGKG LEWVAVIWDDGSNTHYADSVKGRFTITRDNSKNTLNLQMNSLRAE DTAVYYCVRAPQWYLSAEAFDLWGQGTMVTVSS | 339 |
| BDG38_139_ VL | SYVLTQPPSVSVAPGETATITCGGNMIGAYLVHWYQQKPGQAPLLV IYDDVDRPARIPERFSGSNSGNTATLTISRVEAGDEADYYCQVWDH NSDHMVFGGGTKLTVL | 340 |
| BDG38_140_ VH | QMQLVESGGGVVQPGRSLTLSCAASGFEFRTYGMHWVRQAPGKG LEWVGVIWDDGSNTHYADSVKGRFTITRDNSKNTLNLQMNSLRVE DTAVYYCARAPQWYLTAEAFDLWGQGTMVTVSS | 341 |
| BDG38_140_ VL | SYILTQPPSVSVAPGETATITCGGNLIGAKLVHWYQQKPGQAPVLVI YDDSDRPSRIPERFSGSNIGNTATLTIEDVEAGDEADYYCQVWDYS ANHMVFGGGTKLTVL | 342 |
| BDG38_141_ VH | QMQLVESGGGVVQPGRSLRLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 343 |
| BDG38_141_ VL | SYILTQPPSVSVAPGETATITCGGALIGSRLVHWYQQKPGQAPVLVI YDDSDRPSRIPERFSGSNIGNTATLTISDVEEGDEADYYCQVWDYS NHMVFGGGTKLTVL | 344 |
| BDG38_142_ VH | QMQLVESGGGVVQPGRSLTLSCAASGFEFRTYGMHWVRQAPGKG LEWVAVIWDDGSNTHYADSVKGRFTITRDNSKNTLNLQMNSLRAE DTAVYYCVRAPQWYLTAEAFDLWGQGTMVTVSS | 345 |

TABLE 10-continued

Amino Acid Sequences of VH and VL
Regions for Antibodies BDG38.074 to
BDG38.143

| Antibodies | Amino Acid Sequence | SEQ ID NO: |
|---|---|---|
| BDG38_142_ VL | SYILTQPPSVSVAPGQTATITCGGNLIGAKLVHWYQQKPGQAPVLV VYDDSDRPSRIPERFSGSNIGNTATLTIERVEEGDEADYYCQVWDY YSHTMVFGGGTKLTVL | 346 |
| BDG38_143_ VH | QMQLVESGGGVVQPGRSLRLSCAASGFEFRTYGMHWVRQAPGKG LEWVGVIWDDGSATHYADSVKGRFTITRDNSKNTLNLQMNSLRVE DTAVYYCVRAPQWYLTAEAFDLWGQGTMVTVSS | 347 |
| BDG38_143_ VL | SYILTQPPSVSVAPGQTATITCGGALIGARLVHWYQQKPGQAPVLVI YDDSDRPSRIPERFSGSNIGNTATLTISRVEEGDEADYYCQVWDYSS NTYVFGGGTKLTVL | 348 |

Data presented below demonstrates biochemical and functional properties for some of the dual binding antibodies disclosed herein. FIG. 13 shows retention time and calculated pI for some of the dual binding antibodies disclosed herein, demonstrating that BDG antibodies are monodispersed and highly homogenic.

Figure 14A:
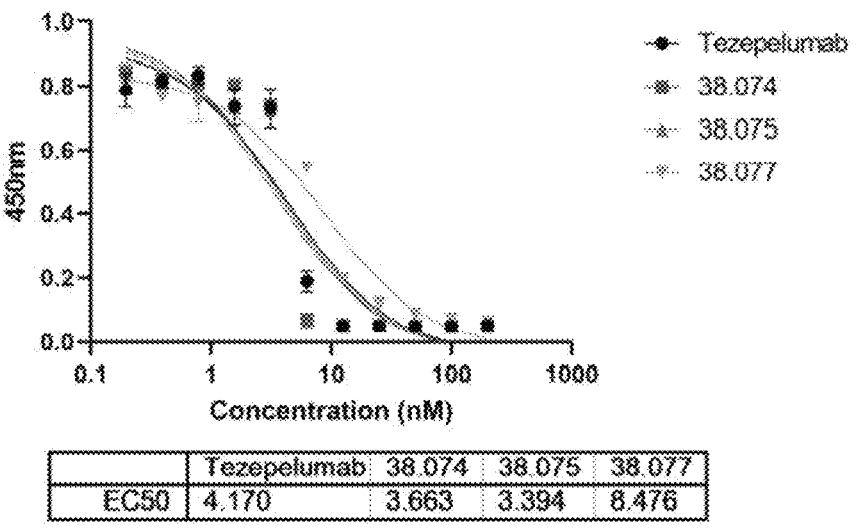
FIGS. 14A-14C shows competitive ELISA of some of the dual binding antibodies and 33.001 (Tezepelumab) over TSLP. ELISA plates were coated over night at 4° C. with 50 ng/well of 33.001. Dual binding antibodies were double diluted and pre-incubated with 7 nM constant concentration of TSLP-HIS for 1 hour at room temperature. After blocking and washing steps, the dual binding antibodies-TSLP mix were subjected over the plates, incubated for 10 minutes and washed again before 30 minutes incubation with anti-HIS. The results show all tested dual binding antibodies presented a similar IC50.
Figure 14B:
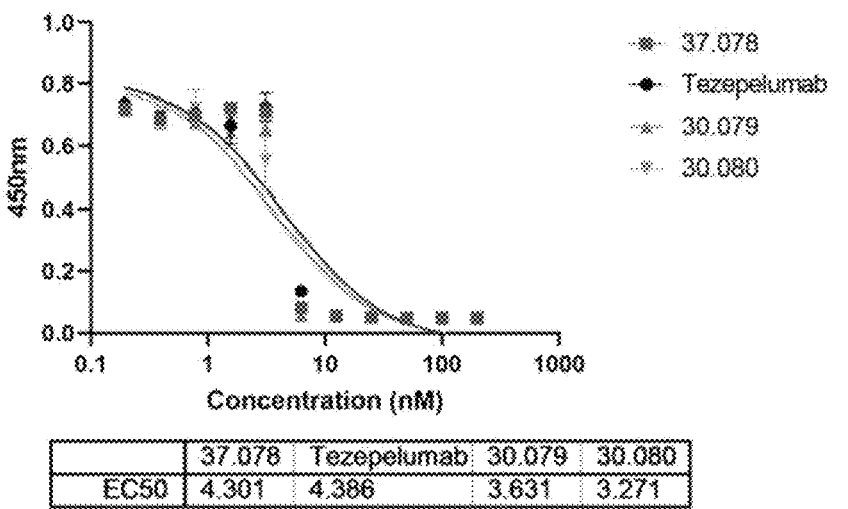
Figure 14C:
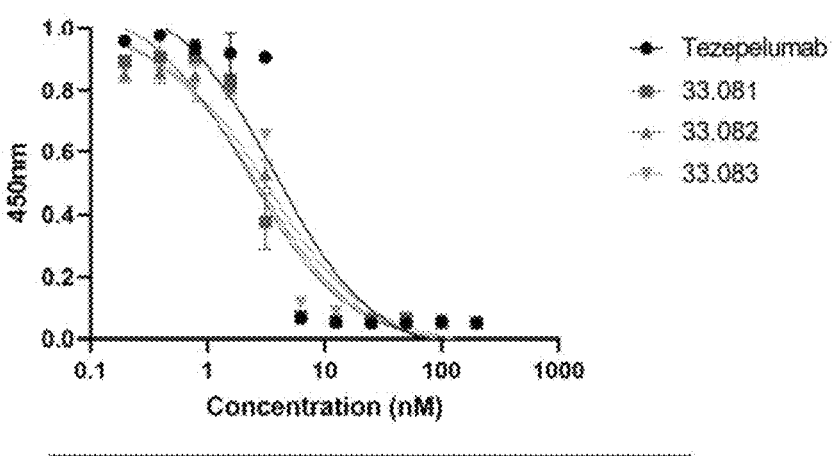

FIGS. 14A-14C show competitive ELISA of some of the dual binding antibodies and Tezepelumab with TSLP. ELISA plates were coated overnight at 4° C. with 50 ng/well Tezepelumab. BDG antibodies were double diluted and pre-incubated with a constant concentration of 7 nM TSLP-His for 1 hour at room temperature. After blocking and washing steps, BDG antibodies-TSLP mix were added to the plates, incubated for 10 minutes and washed again, followed by a 30 minute incubation with anti-HIS. BDG antibodies exhibited similar IC50 values and complete competition with Tezepelumab at the TSLP epitope.

FIG. 15 shows nanoscale differential scanning fluorimetry (nanoDSF) analysis of some of the dual binding antibodies disclosed herein. All BDG antibodies were analyzed to test stability over a range of thermal changes using nanoDSF (See, Table 11 below). Antibodies with a Tm>60° C. were selected to further characterizations.

TABLE 11

SEC and DSF summary table. SEC column presents Area
Under the Curve (AUC) peak ratio of monodispersed
BDG antibodies fraction. DSF columns present T-onset
and Tm values of the different BDG antibodies.

| Antibody# | SEC (%) | DSF 1st repetion | | DSF 2nd repetition | |
| | | T-onset | Tm-1 | T-onset | Tm-1 |
|---|---|---|---|---|---|
| BDG38.074 | 100 | 60.3 | 62.2 | | |
| BDG38.075 | 88.65 | 61 | 65.5 | 60.7 | 65.4 |
| BDG38.076 | 91.98 | | | | |
| BDG38.077 | 97.43 | 66.4 | 70.4 | 66 | 70.3 |
| BDG38.078 | 89.12 | 64.3 | 67.4 | 64.4 | 67.4 |
| BDG38.079 | 96.28 | 61.4 | 64.2 | 61.7 | 64.3 |
| BDG38.080 | 97.4 | 63.7 | 66.8 | 63.8 | 66.8 |
| BDG38.081 | 97.54 | 63.3 | 65.9 | 63.4 | 65.9 |
| BDG38.082 | 99.35 | 65.6 | 69.3 | 65.4 | 69.3 |
| BDG38.083 | 92.88 | 66.6 | 70.1 | 66.8 | 70.2 |
| BDG38.084 | 96.7 | 20.0° C. | 49.6° C. | 23.7° C. | 48.4° C. |
| BDG38.085 | 90 | | 51.1° C. | | 51.5° C. |
| BDG38.086 | 68 | | 51.3° C. | | 51.1° C. |
| BDG38.087 | | | | | |
| BDG38.088 | 84.3 | 65.2° C. | 71.5° C. | | 51.6° C. |
| BDG38.089 | 92.34 | 61.0° C. | 71.2° C. | 60.8° C. | 71.3° C. |
| BDG38.090 | 96.6 | 63.5° C. | 69.7° C. | 63.5° C. | 69.7° C. |
| BDG38.091 | 86.78 | 57.6° C. | 72.0° C. | 58.0° C. | 72.1° C. |

TABLE 11-continued

SEC and DSF summary table. SEC column presents Area
Under the Curve (AUC) peak ratio of monodispersed
BDG antibodies fraction. DSF columns present T-onset
and Tm values of the different BDG antibodies.

| Antibody# | SEC (%) | DSF 1st repetion | | DSF 2nd repetition | |
| | | T-onset | Tm-1 | T-onset | Tm-1 |
|---|---|---|---|---|---|
| BDG38.092 | 95.8 | 64.5° C. | 68.4° C. | 63.9° C. | 68.2° C. |
| BDG38.093 | 82.33 | | 49.6° C. | | 49.6° C. |
| BDG38.094 | 96.15 | 21.4° C. | 49.7° C. | 62.4° C. | 65.3° C. |
| BDG38.095 | 98.01 | 64.6° C. | 68.2° C. | 53.0° C. | 53.5° C. |
| BDG38.096 | 97 | 63.5° C. | 66.9° C. | 64.2° C. | 67.0° C. |
| BDG38.097 | 68 | 65.0° C. | 68.5° C. | 64.7° C. | 68.5° C. |
| BDG38.098 | 95.8 | 63.4° C. | 66.1° C. | 62.8° C. | 66.2° C. |
| BDG38.099 | 75.2 | | 49.4° C. | | 58.3° C. |
| BDG38.100 | 84 | | 50.8° C. | | 51.2° C. |
| BDG38.101 | 97 | 63.6° C. | 70.6° C. | 64.5° C. | 70.5° C. |
| BDG38.102 | 70.6 | | 58.9° C. | 65.4° C. | 68.8° C. |
| BDG38.103 | 78.26 | 51.0° C. | 51.2° C. | 65.5° C. | 69.2° C. |
| BDG38.104 | 76.36 | 65.0° C. | 69.3° C. | 65.4° C. | 69.3° C. |
| BDG38.105 | 74.87 | | 51.8° C. | 64.7° C. | 71.2° C. |
| BDG38.106 | 96.8 | 63.9° C. | 67.5° C. | 64.3° C. | 67.6° C. |
| BDG38.107 | 69.19 | | 49.3° C. | 49.1° C. | 49.2° C. |
| BDG38.108 | 75.47 | 42.2° C. | 42.9° C. | | 51.5° C. |
| BDG38.109 | 56 | | 51.2° C. | | 51.4° C. |
| BDG38.110 | 77.15 | 27.7° C. | 56.8° C. | 26.0° C. | 57.2° C. |
| BDG38.111 | 92 | 23.4° C. | 55.4° C. | 43.9° C. | 54.9° C. |
| BDG38.112 | 71.97 | | 49.5° C. | | 49.3° C. |
| BDG38.113 | 71 | | 49.6° C. | | 50.0° C. |
| BDG38.114 | 67.9 | | 59.1° C. | | 52.0° C. |
| BDG38.115 | 72.41 | | 56.8° C. | 57.4° C. | 71.5° C. |
| BDG38.116 | 88 | 63.8° C. | 67.6° C. | 64.3° C. | 67.9° C. |
| BDG38.117 | 96 | 64.6° C. | 69.7° C. | 63.9° C. | 69.7° C. |
| BDG38.118 | 90.5 | 64.5° C. | 69.6° C. | 64.8° C. | 69.7° C. |
| BDG38.119 | 63.19 | | 51.7° C. | | 59.9° C. |
| BDG38.120 | 82 | 28.3° C. | 55.8° C. | 62.9° C. | 66.8° C. |
| BDG38.121 | 51 | | 49.9° C. | | 50.1° C. |
| BDG38.122 | 67 | 58.5° C. | 58.9° C. | | 59.0° C. |
| BDG38.123 | 59 | | 50.6° C. | | 50.5° C. |
| BDG38.124 | 69 | 57.5° C. | 58.5° C. | 56.2° C. | 58.3° C. |
| BDG38.125 | 85.47 | 63.9° C. | 67.2° C. | 63.6° C. | 67.1° C. |
| BDG38.126 | 93 | 63.9° C. | 67.3° C. | 64.0° C. | 67.3° C. |
| BDG38.127 | 89 | 62.9° C. | 69.3° C. | 62.8° C. | 69.3° C. |
| BDG38.128 | 81 | 63.4° C. | 67.4° C. | 63.2° C. | 67.4° C. |
| BDG38.129 | 95.98 | 63.8° C. | 70.1° C. | 63.4° C. | 70.1° C. |
| BDG38.130 | 38.5 | | 60.2° C. | | 60.5° C. |
| BDG38.131 | 71.5 | 64.2° C. | 68.8° C. | 64.4° C. | 68.8° C. |
| BDG38.132 | 94.35 | 63.3° C. | 67.1° C. | 63.6° C. | 67.1° C. |
| BDG38.133 | 61.3 | | 50.8° C. | | 50.4° C. |
| BDG38.134 | 93.57 | 63.5° C. | 67.4° C. | 63.6° C. | 67.4° C. |
| BDG38.135 | 92.78 | 62.6° C. | 65.6° C. | 62.6° C. | 65.6° C. |
| BDG38.136 | 93.38 | 63.8° C. | 67.3° C. | 63.6° C. | 67.3° C. |
| BDG38.137 | 77.8 | 63.4° C. | 67.9° C. | 62.7° C. | 67.8° C. |
| BDG38.138 | 94.8 | 20.0° C. | 50.4° C. | 62.8° C. | 66.0° C. |

TABLE 11-continued

SEC and DSF summary table. SEC column presents Area
Under the Curve (AUC) peak ratio of monodispersed
BDG antibodies fraction. DSF columns present T-onset
and Tm values of the different BDG antibodies.

| Antibody# | SEC (%) | DSF 1st repetion | | DSF 2nd repetition | |
|---|---|---|---|---|---|
| | | T-onset | Tm-1 | T-onset | Tm-1 |
| BDG38.139 | 90 | 61.6° C. | 64.8° C. | 62.0° C. | 64.8° C. |
| BDG38.140 | 82.2 | 63.6° C. | 70.6° C. | 20.0° C. | 50.9° C. |
| BDG38.141 | 73.25 | 20.0° C. | 55.2° C. | 20.0° C. | 56.1° C. |
| BDG38.142 | 80 | 63.8° C. | 67.8° C. | 63.8° C. | 67.7° C. |
| BDG38.143 | 74 | 21.3° C. | 57.5° C. | | 56.9° C. |

FIGS. 16A-16F show the results of SPR (Surface Plasmon Resonance) analysis for some of the dual binding antibodies disclosed herein for human/cyno IL-13 and TSLP. SPR analysis was performed to assess the kinetics of BDG antibodies binding to TSLP and IL-13. SPR data indicates dissociation constants of double digit pM for BDG antibodies binding to IL-13 and TSLP.

Table 12 presents IC50 inhibition values of CD23 expression on monocytes and IC50 inhibition values of Thymus and activation-regulated chemokine (TARC) secretion by PBMCs. This data demonstrates that each BDG dual antibody can inhibit both IL-13 and TSLP functions in human PBMCs.

TABLE 12

PBMC Functional Assay Summary Table.

| Antibody# | PBMC Functional Assay | |
|---|---|---|
| | IC50 CD23 [nM] | IC50 TARC [nM] |
| BDG38.074 | 0.1578 | 2.771 |
| BDG38.075 | 0.09752 | 4.168 |
| BDG38.076 | 0.3078 | 3.206 |
| BDG38.077 | 0.01245 | 2.466 |
| BDG38.078 | 0.1252 | 6.516 |
| BDG38.079 | 0.07179 | 1.961 |
| BDG38.080 | 0.2011 | 0.7904 |
| BDG38.081 | 0.03386 | 5.929 |
| BDG38.082 | 0.03908 | 1.577 |
| BDG38.083 | 0.02146 | 11.37 |
| BDG38.090 | 0.006556 | 0.007555 |
| BDG38.092 | 0.06747 | 5.876 |
| BDG38.094 | 0.1724 | 0.3556 |
| BDG38.096 | 0.2504 | 23.41 |
| BDG38.106 | 0.1616 | NaN |
| BDG38.112 | 0.05937 | 0.1039 |
| BDG38.116 | 0.08366 | 59.36 |
| BDG38.117 | 0.1207 | 5.40E+15 |
| BDG38.125 | 0.0527 | NaN |
| BDG38.126 | 0.0868 | 2.575 |
| BDG38.128 | 0.01492 | NaN |
| BDG38.129 | 0.029 | NaN |
| BDG38.131 | 0.07 | NaN |
| BDG38.132 | 0.43 | 22.39 |
| BDG38.135 | 0.4075 | 0.8042 |
| BDG38.137 | 0.3728 | 0.8233 |
| BDG38.138 | 0.1638 | 2.358 |
| BDG38.139 | 0.012 | — |
| BDG38.140 | 0.146 | — |

*NaN—stands for values that could not be determined.

Table 13 presents the IC50 values obtained from competitive ELISA with Tezepelumab. The data demonstrates that BDG dual antibodies compete with Tezepelumab for TSLP binding.

TABLE 13

IC50 Competition ELISA Values Summary Table.

| Antibody# | IC50(nM) vs anti-TSLP benchmark |
|---|---|
| BDG38.074 | 3.66 |
| BDG38.075 | 3.94 |
| BDG38.076 | 5.382 |
| BDG38.077 | 8.47 |
| BDG38.078 | 4.3 |
| BDG38.079 | 3.63 |
| BDG38.080 | 3.27 |
| BDG38.081 | 2.2 |
| BDG38.082 | 2.7 |
| BDG38.083 | 3.33 |
| BDG38.090 | 7.31 |
| BDG38.092 | 7.382 |
| BDG38.096 | 5.871 |
| BDG38.106 | 10.09 |
| BDG38.112 | 29.14 |
| BDG38.116 | 5.123 |
| BDG38.117 | 6.137 |
| BDG38.125 | 8.442 |
| BDG38.126 | 5.953 |
| BDG38.128 | 5.378 |
| BDG38.129 | 5.494 |
| BDG38.132 | 9.203 |
| BDG38.137 | 10.89 |
| BDG38.139 | 9.571 |
| BDG38.140 | 5.628 |

Table 14 presents data from a TSLP functional inhibition assay using MUTZ5 cells (human B cell precursor leukemia cells). IC50 values of STATS phosphorylation inhibition are presented in pM, and the R2 column presents goodness of fit values. These results demonstrate that BDG dual antibodies can inhibit TSLP function in the MUTZ5 cell line expressing the native TSLP-receptor heterocomplex (TLSP-R and IL-7R).

TABLE 14

TSLP Functional Inhibition Assay in MUTZ5 cell line.

| Antibody# | IC50 [pM] | $R^2$ |
|---|---|---|
| BDG38.074 | 46.74 | 0.925 |
| BDG38.075 | 43.86 | 0.9919 |
| BDG38.076 | 30.14 | 0.9322 |
| BDG38.077 | 304.1 | 0.7798 |
| BDG38.078 | 337.5 | 0.9148 |
| BDG38.079 | 21.84 | 0.8359 |
| BDG38.080 | 34.33 | 0.9534 |
| BDG38.081 | 38.74 | 0.9556 |
| BDG38.086 | 830.1 | 0.01605 |
| BDG38.090 | 43.35 | 0.2951 |
| BDG38.091 | 0.5069 | 0.43 |
| BDG38.092 | 33.05 | 0.5048 |
| BDG38.094 | 27.16 | 0.9719 |
| BDG38.096 | 5.44E−05 | 0.6063 |
| BDG38.098 | 68.84 | 0.07219 |
| BDG38.107 | 0.5081 | 0.3199 |
| BDG38.110 | 0.2951 | 0.8273 |
| BDG38.112 | 11383 | 0.05737 |
| BDG38.115 | 300.3 | 0.1132 |
| BDG38.117 | 0.3628 | 0.5132 |
| BDG38.118 | 0.6884 | 0.4463 |
| BDG38.120 | 0.2315 | 0.7447 |
| BDG38.125 | 8.74E−05 | 0.7192 |
| BDG38.126 | 0.04215 | 0.7997 |
| BDG38.127 | 0.1433 | 0.5647 |
| BDG38.128 | 0.004796 | 0.639 |
| BDG38.129 | 0.6765 | 0.5382 |
| BDG38.132 | 0.3858 | 0.737 |
| BDG38.134 | 32.04 | 0.7965 |
| BDG38.137 | 1.855 | 0.08069 |

TABLE 14-continued

| TSLP Functional Inhibition Assay in MUTZ5 cell line. | | |
| --- | --- | --- |
| Antibody# | IC50 [pM] | $R^2$ |
| BDG38.138 | 45.24 | 0.9313 |
| BDG38.139 | 88.95 | 0.8952 |
| BDG38.140 | 2.211 | 0.5831 |

Table 15 shows the results of a functional inhibition assay in IL-4/IL-13 reporter HEK 293 cells. IC50 values of STATE phosphorylation inhibition is presented in nM. This data demonstrated that BDG dual antibodies can inhibit IL-13 function in reporter HEK cell line cells expressing the IL-13-receptor heterocomplex (IL-13Rα1 and IL-4Rα).

TABLE 15

| IL-13 Functional Inhibition Assay in IL-4/IL-13 Reporter HEK 293 cell line. | |
| --- | --- |
| Antibody# | HEK-IL-13 [nM] |
| BDG38.074 | 0.02407 |
| BDG38.075 | 0.06912 |
| BDG38.076 | 0.04938 |
| BDG38.077 | 0.05055 |
| BDG38.078 | 0.05079 |
| BDG38.079 | 0.0253 |
| BDG38.080 | 0.05923 |
| BDG38.081 | 0.04828 |
| BDG38.082 | 0.04295 |
| BDG38.083 | 0.04194 |
| BDG38.084 | 0.0419 |
| BDG38.085 | 0.02355 |
| BDG38.086 | 0.0174 |
| BDG38.087 | — |
| BDG38.088 | 0.04861 |
| BDG38.089 | 0.07497 |
| BDG38.090 | 0.1035 |
| BDG38.091 | 0.08321 |
| BDG38.092 | 0.1197 |
| BDG38.093 | 0.04018 |
| BDG38.094 | 0.04873 |
| BDG38.095 | 0.08224 |
| BDG38.096 | 0.1505 |
| BDG38.097 | 0.04645 |
| BDG38.098 | 0.08838 |
| BDG38.099 | 0.06009 |
| BDG38.100 | 0.08009 |
| BDG38.101 | 0.04035 |
| BDG38.102 | 0.04211 |
| BDG38.103 | 0.084 |
| BDG38.104 | 0.03805 |
| BDG38.105 | 0.1341 |
| BDG38.106 | 0.01134 |
| BDG38.107 | 0.09427 |
| BDG38.108 | 0.06595 |
| BDG38.109 | 0.06295 |
| BDG38.110 | 0.02988 |
| BDG38.111 | 0.05454 |
| BDG38.112 | 0.03665 |
| BDG38.113 | 0.02843 |
| BDG38.114 | 0.09887 |
| BDG38.115 | 0.06638 |
| BDG38.116 | 0.1799 |
| BDG38.117 | 0.08006 |
| BDG38.118 | 0.08044 |
| BDG38.119 | 0.06617 |
| BDG38.120 | 0.2649 |
| BDG38.121 | 0.05618 |
| BDG38.122 | 0.07895 |
| BDG38.123 | 0.04405 |
| BDG38.124 | 0.05233 |
| BDG38.125 | 0.05618 |
| BDG38.126 | 0.07895 |
| BDG38.127 | 0.04405 |
| BDG38.128 | 0.05233 |

TABLE 15-continued

| IL-13 Functional Inhibition Assay in IL-4/IL-13 Reporter HEK 293 cell line. | |
| --- | --- |
| Antibody# | HEK-IL-13 [nM] |
| BDG38.129 | 0.07253 |
| BDG38.130 | 0.06463 |
| BDG38.131 | 0.0443 |
| BDG38.132 | 0.08986 |
| BDG38.133 | 0.02895 |
| BDG38.134 | 0.2711 |
| BDG38.135 | 0.4058 |
| BDG38.136 | 0.1509 |
| BDG38.137 | 0.1951 |
| BDG38.138 | 0.02862 |
| BDG38.139 | 0.04644 |
| BDG38.140 | 0.04303 |
| BDG38.141 | 0.08244 |
| BDG38.142 | 0.05843 |
| BDG38.143 | 0.04382 |

Antibody BDG38.074

Figure 17A:
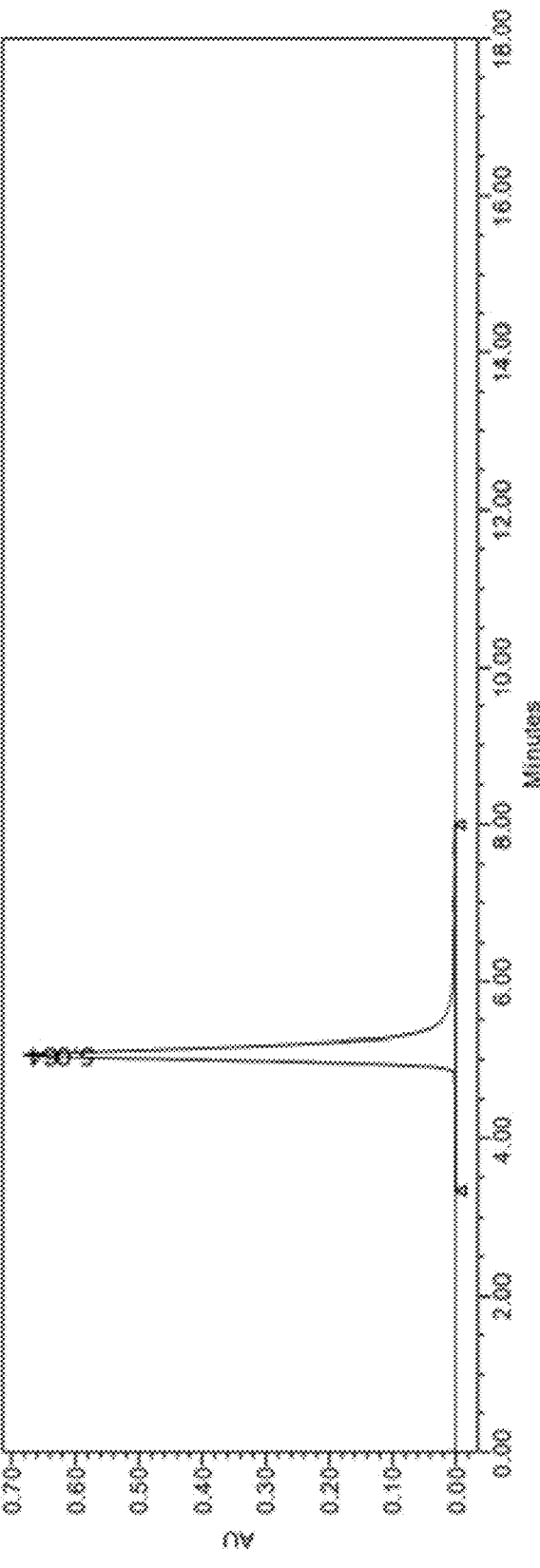
FIGS. 17A and B show size exclusion chromatography (SEC) scans (FIG. 17A), and nano-differential scanning fluorimetry (DSF) analysis of the melting point (FIG. 17B) for antibody BDG38.074. Representative analysis of the melting point of indicated IgGs were analyzed in duplicate. Light gray dashed line represents the T-onset and bold gray dashed lines represents the Tm1 and Tm2.
Figure 17B:
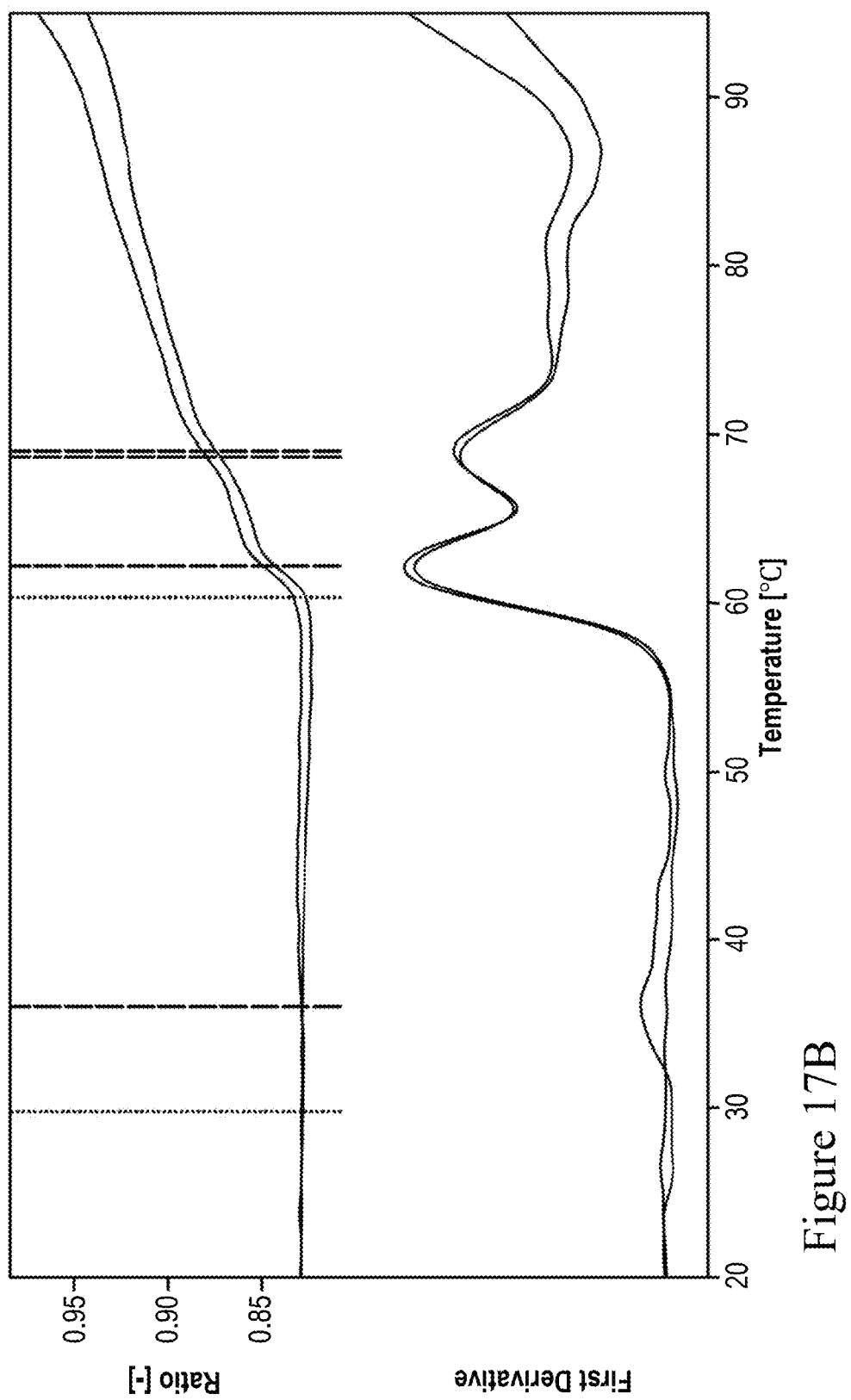
FIG. 17B shows the 1st derivative of the measurement. DSF values are summarized in FIG. 15.
Figure 18A:
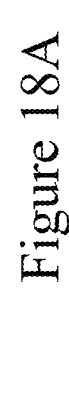
FIGS. 18A-18D show binding affinities of representative clone BDG38.74.
Figure 18B:
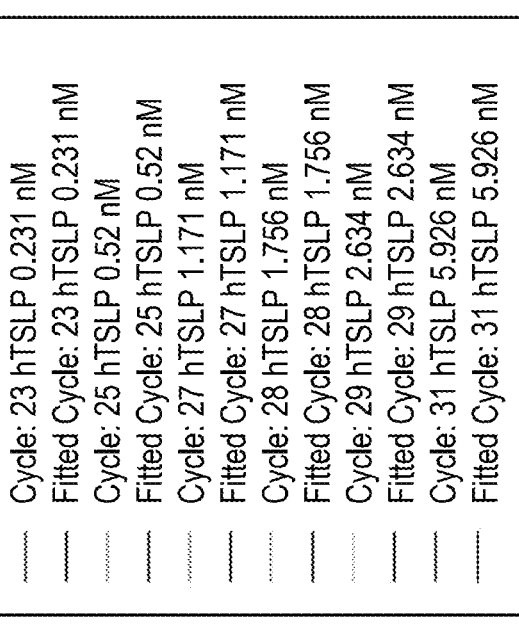
Figure 18B:
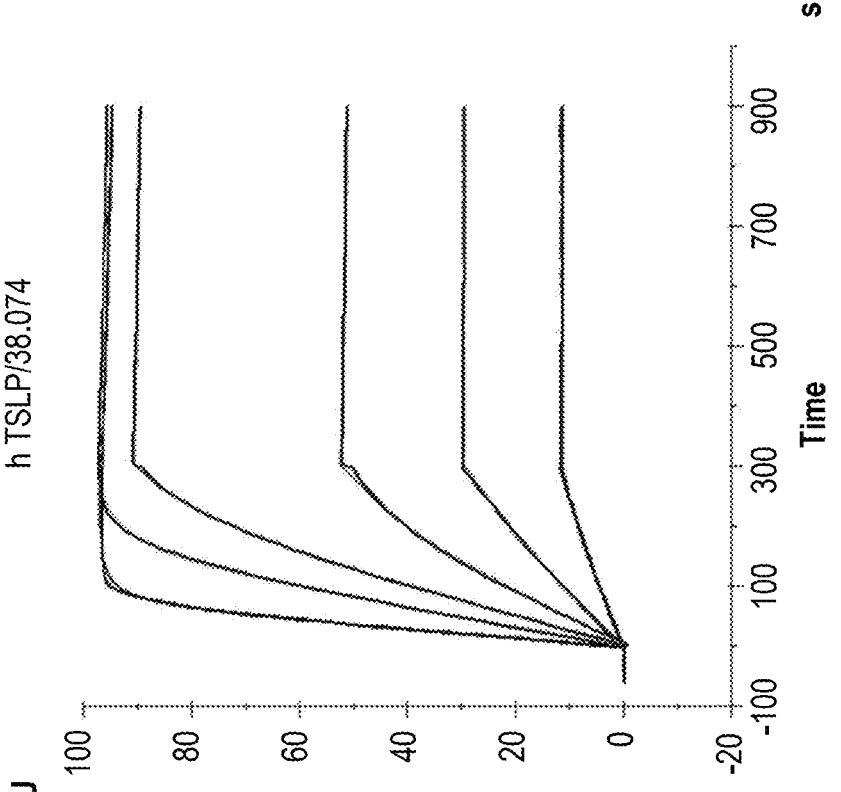
Figure 18B:
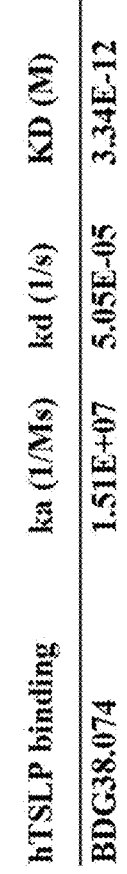
Figure 18C:
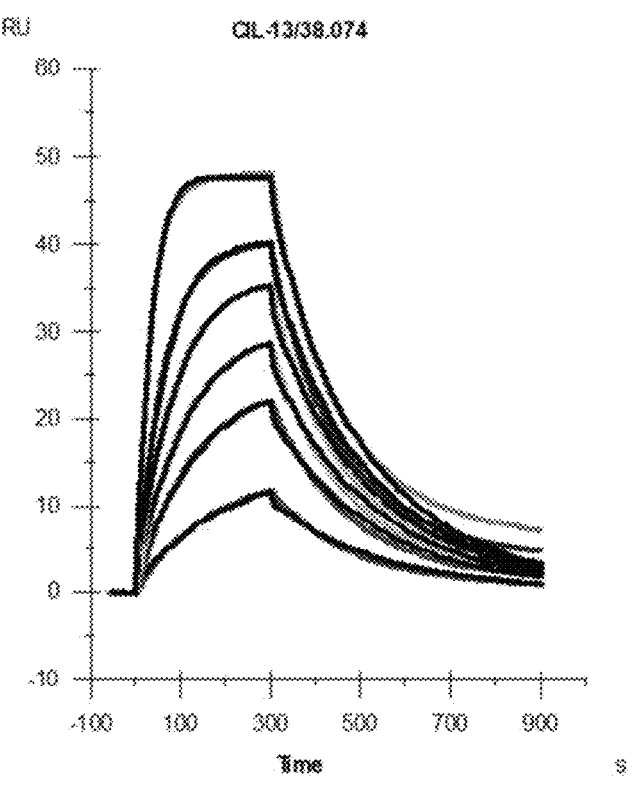
Figure 18D:
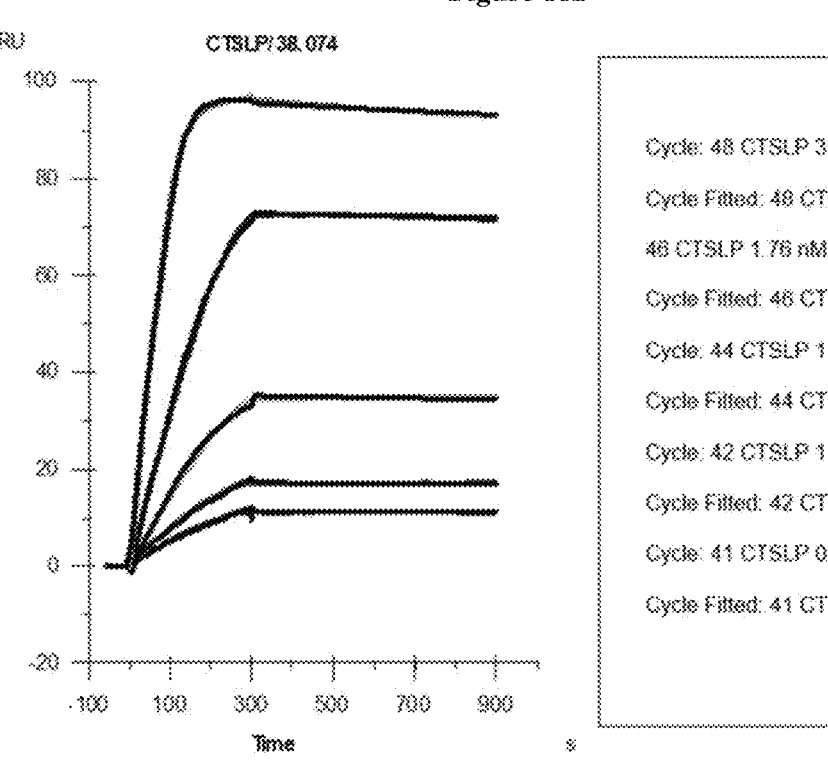

The size exclusion chromatography (SEC) scans and nano-differential scanning fluorimetry (DSF) analysis of the melting point for antibody BDG38.074 are shown in FIGS. 17A and 17B. SEC analysis (FIG. 17A) was performed using BioResolve SEC mAb Column, 200 Å, 2.5 μm, 4.6×300 mm at 0.5 ml/min in PBS as a mobile phase and analyzed at 280 nm. BDG38.074 shows a predominant monodisperse peak with undetectable aggregates. DSF analysis (FIG. 17B) was performed using nanoDSF at a 1° C./min from 20-95° C.

NanoDSF is monitoring the thermal unfolding of BDG38.074 according to the intrinsic fluorescence change at 350 and 330 nm. The top half of the graph in FIG. 17B shows the fluorescence ratio of 350 nm/330 nm as a function of temperature and the bottom half shows the first derivative as a function of temperature. BDG38.074 was analyzed at 0.5 mg/ml in PBS showed to have a T-onset of 60.3° C. and Tm of 62.2° C. suggesting a relatively stable fold.

The binding affinities of antibody BDG38.074 to human/cyno IL-13 and human/cyno TSLP are shown in FIGS. 18A-18D. Surface Plasmon Resonance (SPR) analysis of BDG38.074 binding to human IL-13 (FIG. 18A), human TSLP (FIG. 18B), cyno IL-13 (FIG. 18C) and cyno TSLP (FIG. 18D) using BiacoreT200. CMS chip was coated with human antibody capture kit to obtain 3000-5000 RU and the antibody, served as the capture, was injected at a flow rate of 10 ul/ml to obtain 250-350 RU. Human/cynoTSLP and human/cynoIL-13 served as analytes in a concentration range of 30-0.153 nM. Contact time 300 sec and dissociation time 600 sec at a flow rate of 30 ul/min BDG38.074 shows a high affinity to all cytokines with KD values for hIL-13: 2.95E-11M, for hTSLP: 3.34E-12 M, for cyno IL-13: 7.33E-10 M and for cyno TSLP: 4.16E-12 M.

Figures 21B, 22:
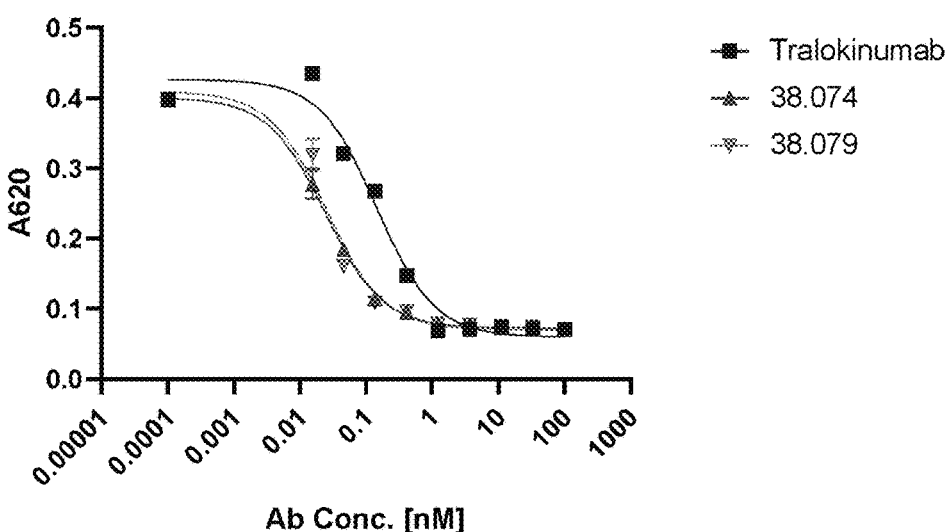

The results of SPR (Surface Plasmon Resonance) analysis of antibody BDG38.074 for human or cyno IL-13 or TSLP are shown in FIGS. 21A and 21B. Based on the SPR analysis, the affinities of BDG 38.074 to human and cyno-molgus IL-13 are at double and triple digit picomolar, respectively, and the affinities to human and cynomolgus TSLP at a single digit picomolar.

FIG. 22A shows antibody BDG38.074 exhibits inhibition of CD23 expression similar to the anti-IL-13 benchmark (Tralokinumab). FIG. 22B shows antibody BDG38.074 inhibits TARC expression similar to anti-TSLP benchmark (Tezepelumab). These data demonstrate that while the anti-TSLP benchmark has only limited effect at inhibiting CD23 expression in monocytes, and the anti-IL-13 benchmark has only limited effect at inhibiting TARC levels, BDG38.074 inhibits both CD23 and TARC expression, demonstrating the unique ability of BDG dual antibodies to exert two distinct functions as a single standard IgG1 (LALA PG) antibody.

Figure 23:
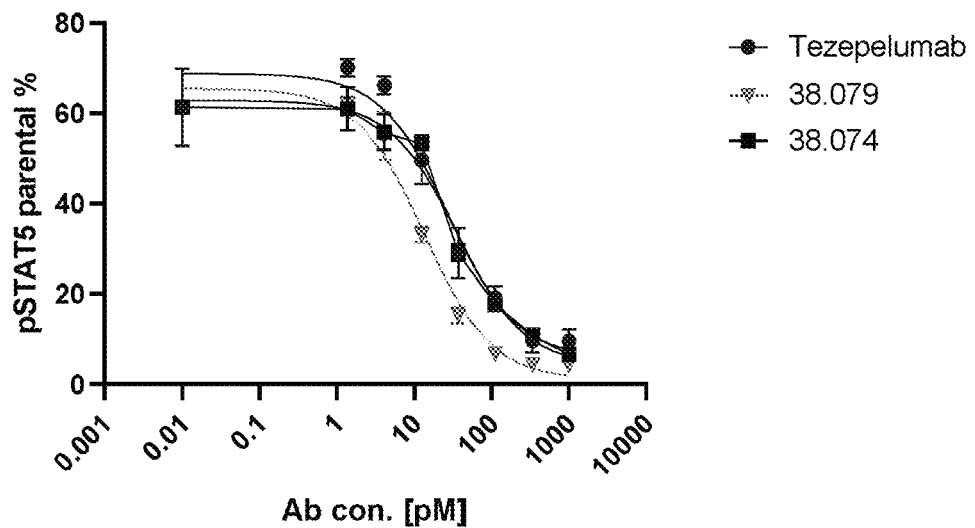
FIG. 23 shows antibodies BDG38.074 and BDG38.079 exhibit similar functional inhibition to anti-TSLP benchmarks in MUTZ-5 cell line. MUTZ5 cells were stimulated with human TSLP (hTSLP) and phosphorylated STATS (pSTAT5) staining was evaluated by phospho-flow cytometry.

FIG. 23 shows antibody BDG38.074 exhibits functional inhibition similar to anti-TSLP benchmarks in MUTZ-5 cell line, demonstrating that BDG38.074 inhibits TSLP function with an IC50 of about 35 pM in cells expressing the native TSLP receptor subunits.

FIG. 24 shows antibody BDG38.074 inhibits IL-13 function in HEK reporter cell line with double digit picomolar affinity, demonstrating that BDG 38.074 inhibits IL-13 function in cells expressing the IL-13 receptor heterocomplex IL-4Ra and IL-13Rα1.
Antibody BDG38.079

Figure 19A:
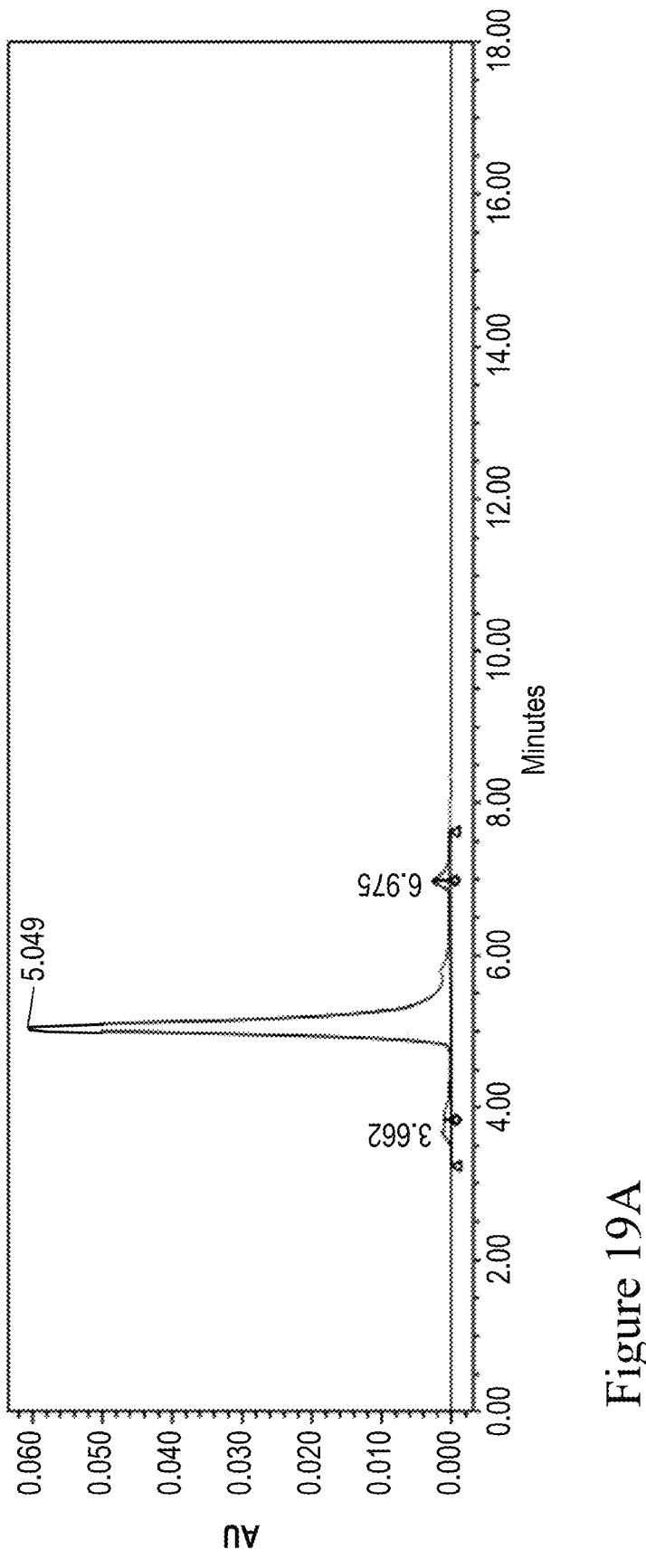
FIGS. 19A and 19B shows size exclusion chromatography (SEC) scans (FIG. 19A), and nano-differential scanning fluorimetry (DSF) analysis of the melting point (FIG. 19B) for antibody BDG38.079. Shown representative DSF analysis of the melting point of indicated IgGs (analyzed in duplicates). Light gray dashed line represents the T-onset and bold gray dashed lines represents the Tm1 and Tm2.
Figure 19B:
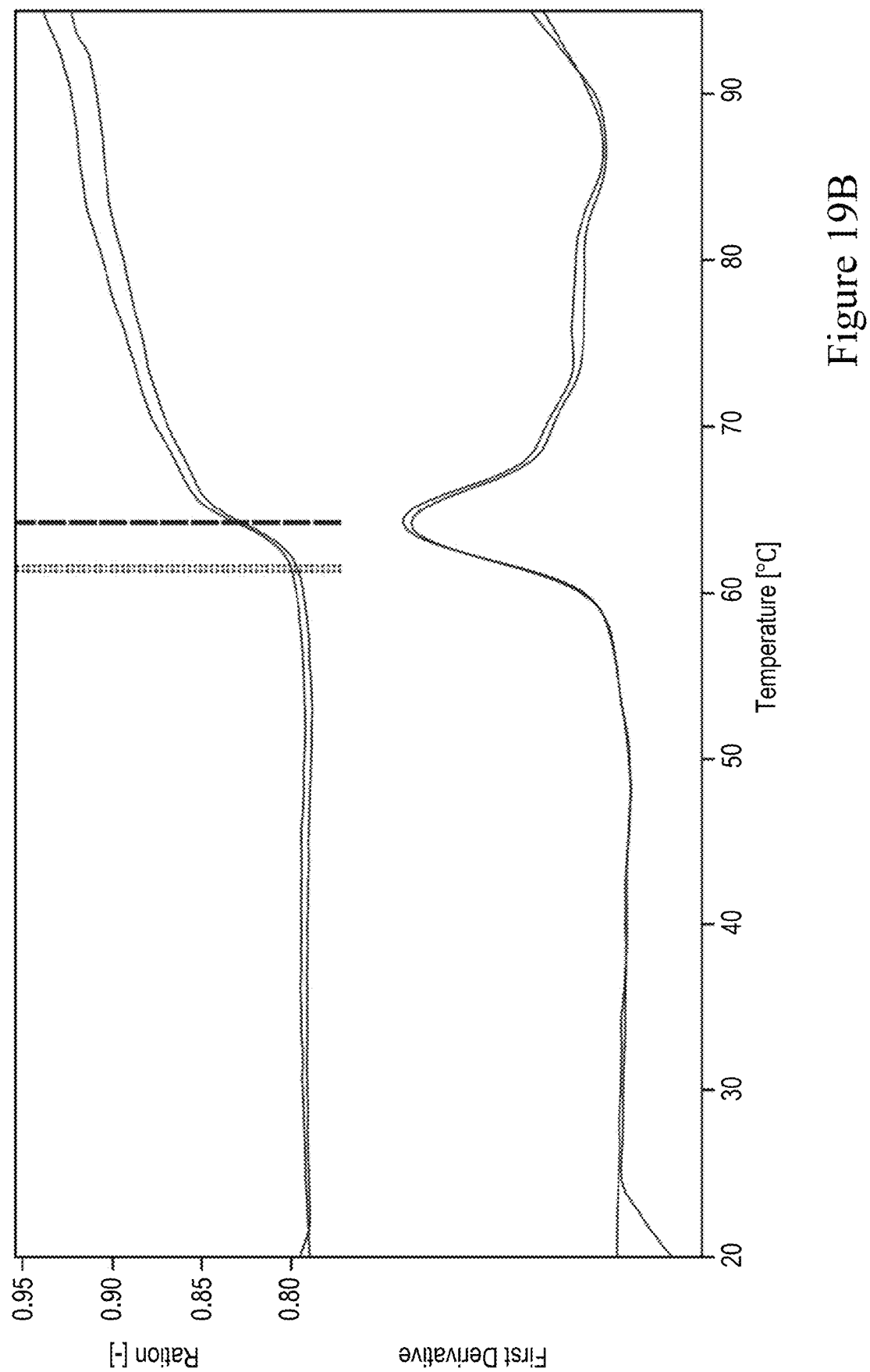
Figure 20A:
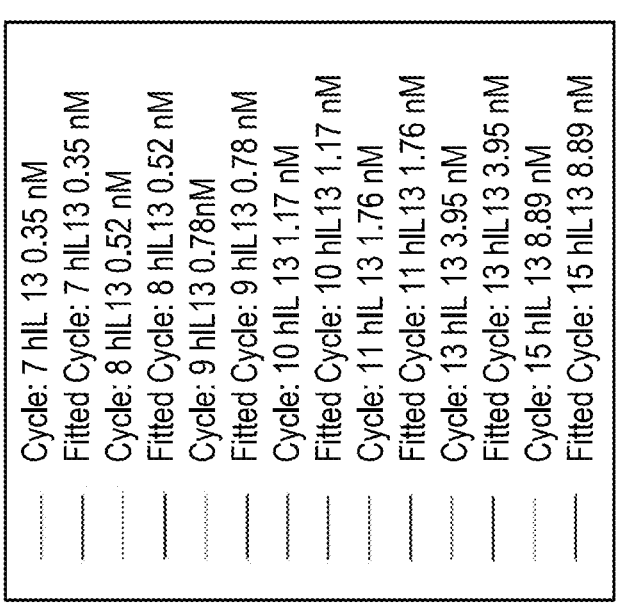
FIGS. 20A-20D show IL-13 and TSLP binding of representative clone BDG38.079.
Figure 20A:
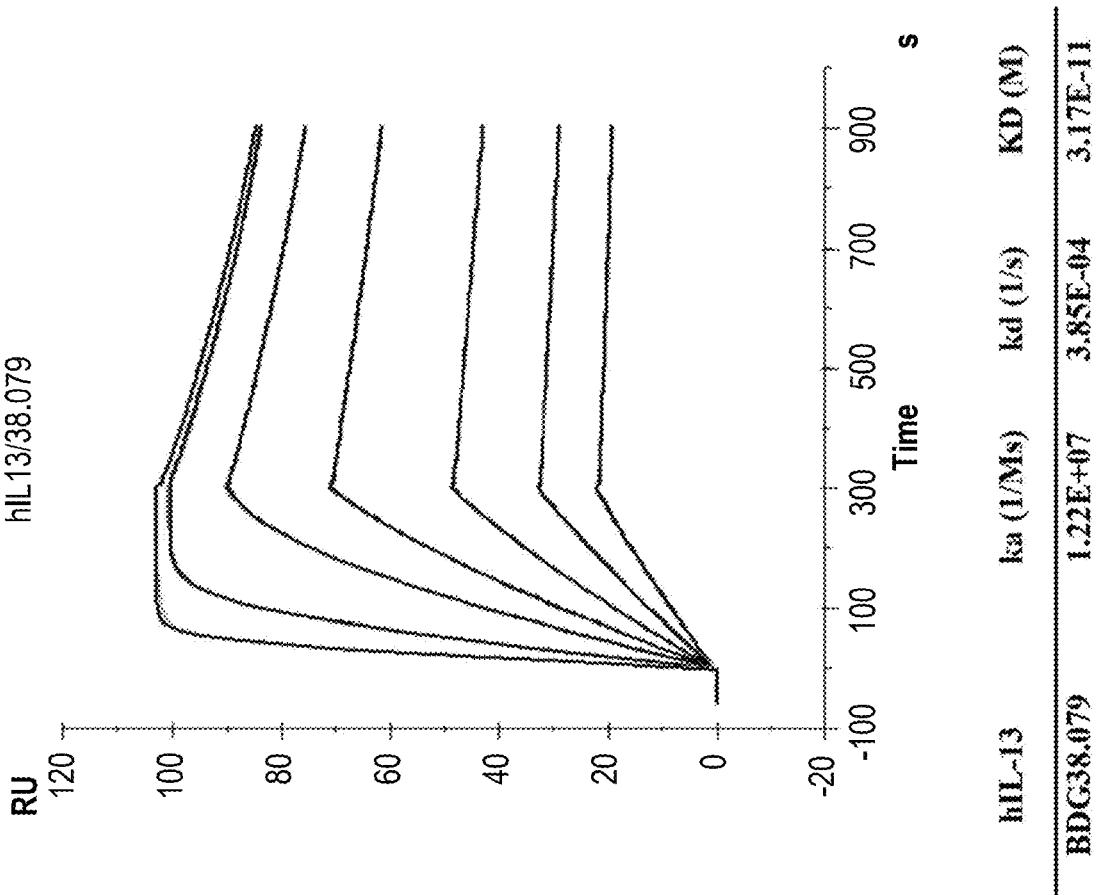
Figure 20B:
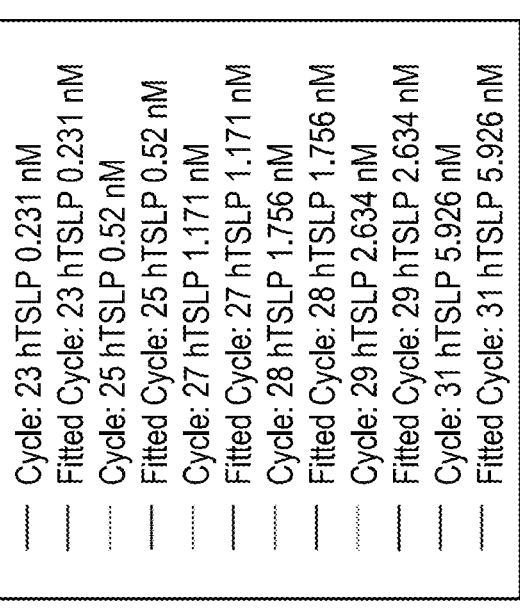
Figure 20B:
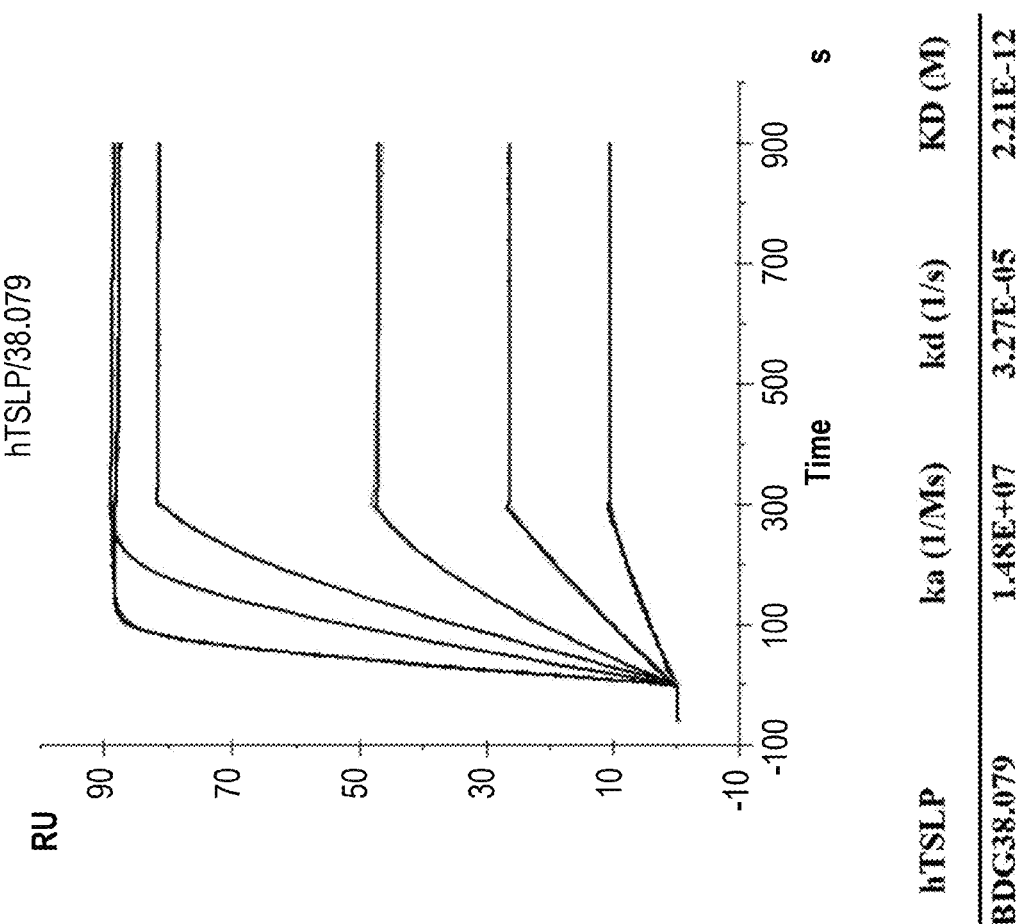
Figure 20C:
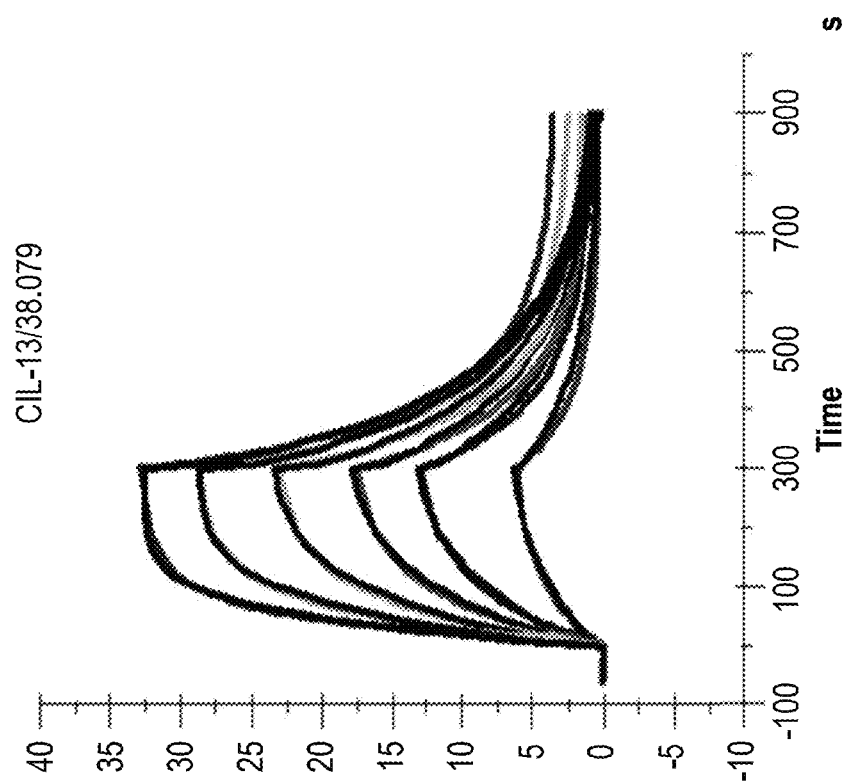
Figure 20D:
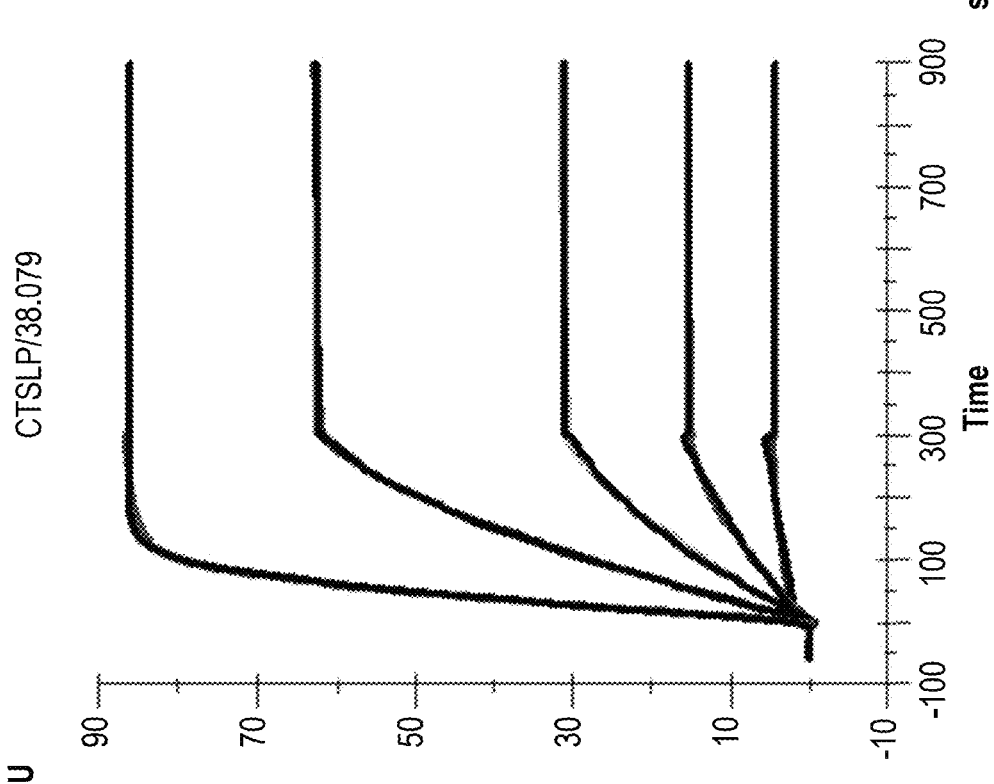

The size exclusion chromatography (SEC) scans and nano-differential scanning fluorimetry (DSF) analysis of the melting point for antibody BDG38.074 are shown in FIGS. 19A and 19B.

SEC analysis (FIG. 19A) was performed using BioResolve SEC mAb Column, 200 Å, 2.5 μm, 4.6×300 mm at 0.5 ml/min in PBS as a mobile phase and analyzed at 280 nm. BDG38.079 shows a predominant monodisperse peak with a minor percentage of aggregates (1.34%). DSF analysis (FIG. 19B) was performed using nanoDSF at a 1° C./min from 20-95° C. NanoDSF is monitoring the thermal unfolding of BDG38.079 according to the intrinsic fluorescence change at 350 and 330 nm. The top half of the graph shows the fluorescence ratio of 350 nm/330 nm as a function of temperature and the bottom half shows the first derivative as a function of temperature. BDG38.079 was analyzed at 0.5 mg/ml in PBS showed to have a T-onset of 61.4° C. and Tm of 64.2° C. suggesting a relatively stable fold.

The binding affinities of antibody BDG38.079 to human/cyno IL-13 and human/cyno TSLP are shown in FIGS. 20A-20D. Surface Plasmon Resonance (SPR) analysis of BDG38.079 binding to human IL-13 (FIG. 20A), human TSLP (FIG. 20B), cyno IL-13 (FIG. 20C) and cyno TSLP (FIG. 20D) using BiacoreT200. CMS chip was coated with human antibody capture kit to obtain 3000-5000 RU and the antibody, served as the capture, was injected at a flow rate of 10 ul/ml to obtain 250-350 RU. Human/cynoTSLP and human/cynoIL-13 served as analytes in a concentration range of 30-0.153 nM. Contact time is 300 sec and dissociation time is 600 sec at a flow rate of 30 ul/min BDG38.079 exhibits high affinity binding to all cytokines tested, with KD values for hIL-13: 3.17E-11 M, for hTSLP: 2.21E-12 M, for cyno IL-: 13 9.01E-10 M and for cyno TSLP: 3.97E-12M.

Results of SPR (Surface Plasmon Resonance) analysis of antibody BDG38.079 for human or cyno IL-13 or TSLP are shown in FIG. 21. From the SPR analysis, the affinities of BDG 38.079 to human and cynomolgus IL-13 are double and triple digit picomolar respectively and the affinities to human and cynomolgus TSLP are single digit picomolar.

FIG. 22 shows antibody BDG38.079 inhibits IL-13 function in HEK reporter cell line with double digit picomolar affinity, demonstrating that BDG 38.079 inhibits IL-13 function in cells expressing the IL-13 receptor heterocomplex IL-4Ra and IL-13Rα1.

FIG. 23 shows antibody BDG38.079 exhibits similar functional inhibition to anti-TSLP benchmarks in MUTZ-5 cell line, demonstrating that BDG38.079 inhibits TSLP function with an IC50 of about 13 pM in cells expressing the native TSLP receptor subunits.

Figure 24A:
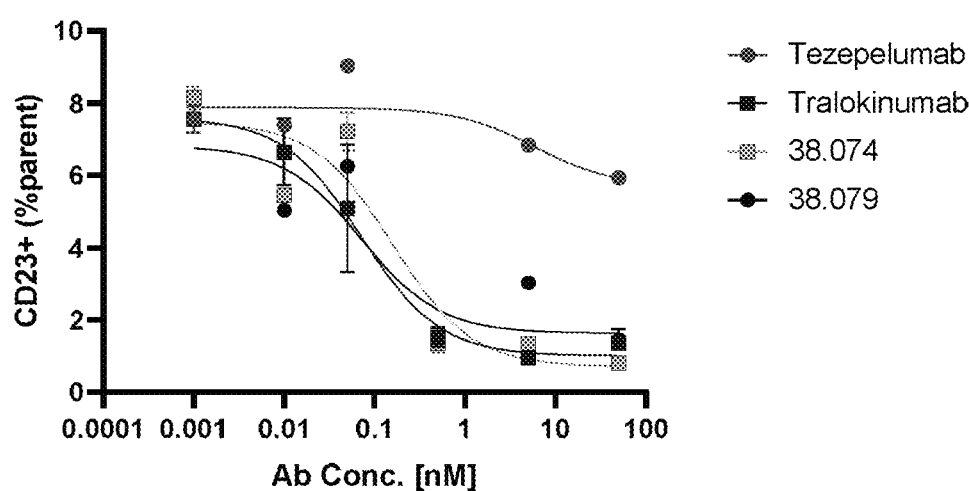
FIGS. 24A and 24B show inhibition results for representative clones
Figure 24B:
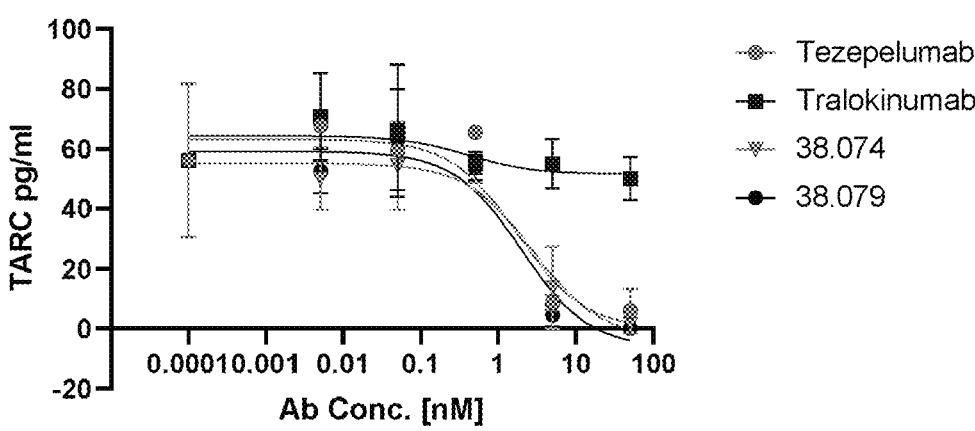

FIG. 24A shows antibody BDG38.079 exhibits similar inhibition of CD23 expression as the anti-IL-13 benchmark (Tralokinumab). FIG. 24B shows antibody BDG38.079 inhibits TARC expression similarly to anti-TSLP benchmark (Tezepelumab).

These data demonstrate that while the anti-TSLP benchmark has only limited effect at inhibiting CD23 expression in monocytes, and the anti-IL-13 benchmark has only limited effect at inhibiting TARC levels, BDG38.079 inhibits both CD23 and TARC expression, demonstrating the unique ability of BDG dual antibodies to exert two distinct functions as a single standard IgG1 (LALA PG) antibody.
Antibody BDG38.094

Figure 25A:
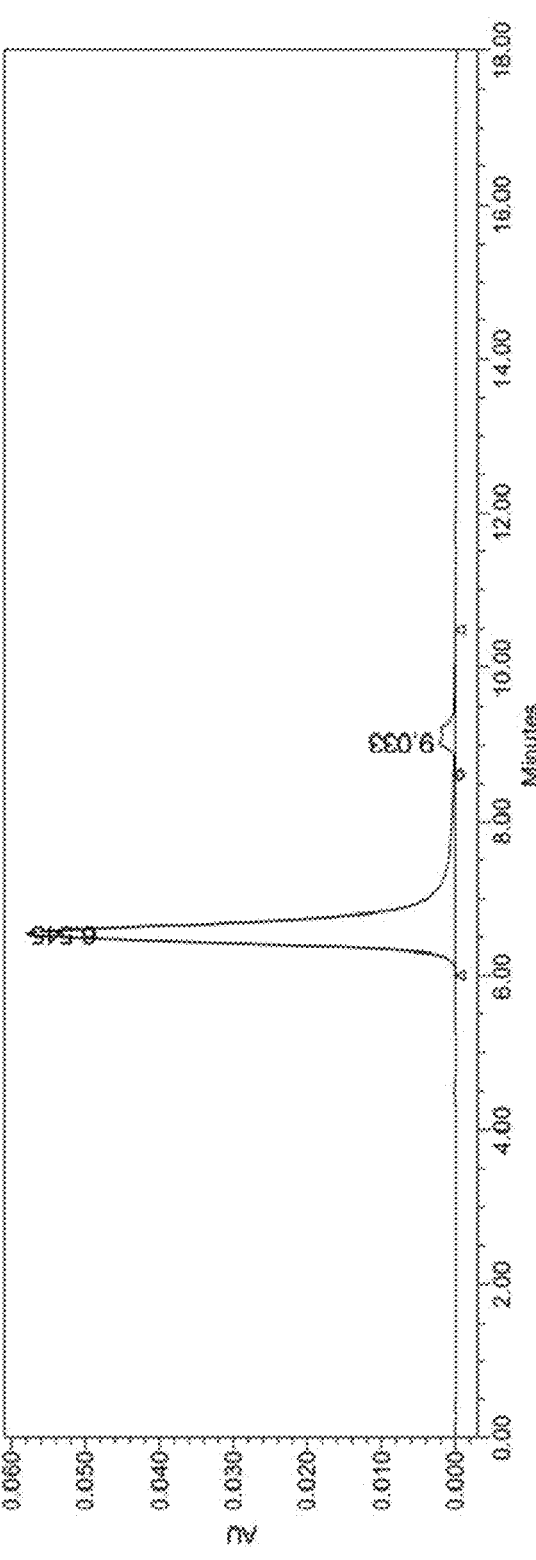
FIGS. 25A and 25B show size exclusion chromatography (SEC) scans (FIG. 25A), and nano-differential scanning fluorimetry (DSF) analysis of the melting point (FIG. 25B) for antibody BDG38.094. Shown representative DSF analysis of the melting point of indicated IgGs (analyzed in duplicates). Light gray dashed line in the upper graph represents the T-onset and bold gray dashed lines represents the Tm1 and Tm2. The FIG. 25B is the 1st derivative of the measurement. DSF values are summarized in Table 11
Figure 25B:
Figure 26A:
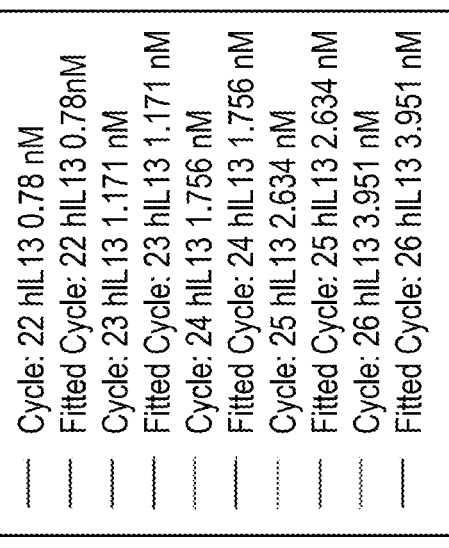
FIGS. 26A-26D show binding affinities of a representative clone.
Figure 26A:
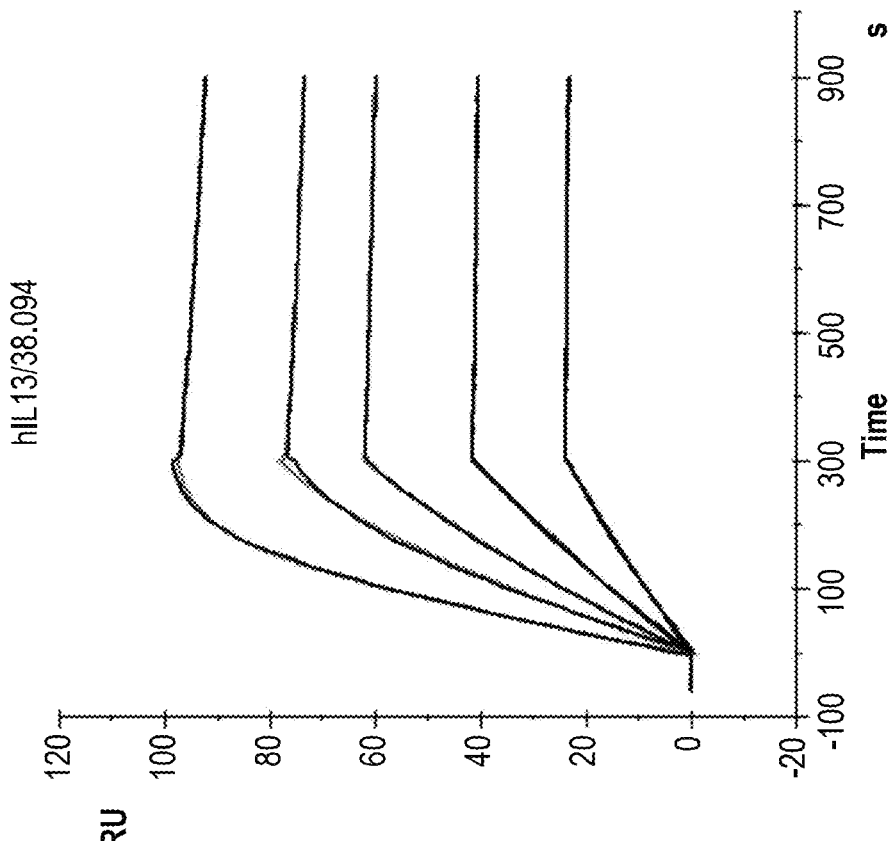
Figure 26B:
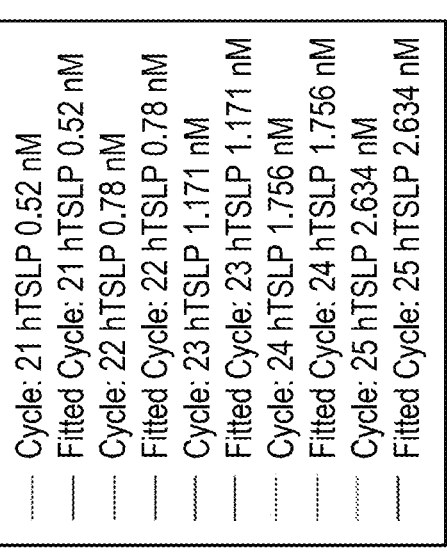
Figure 26B:
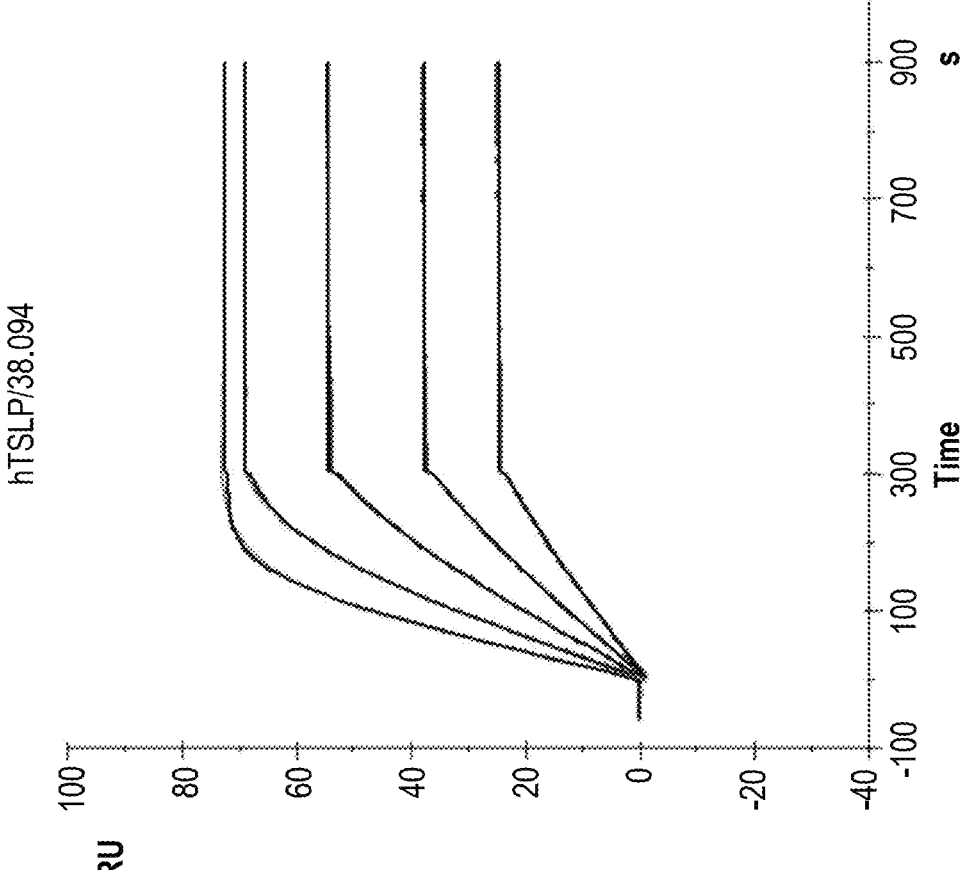
Figure 26C:
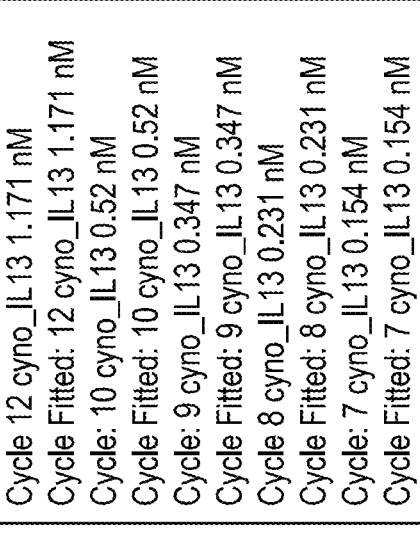
Figure 26C:
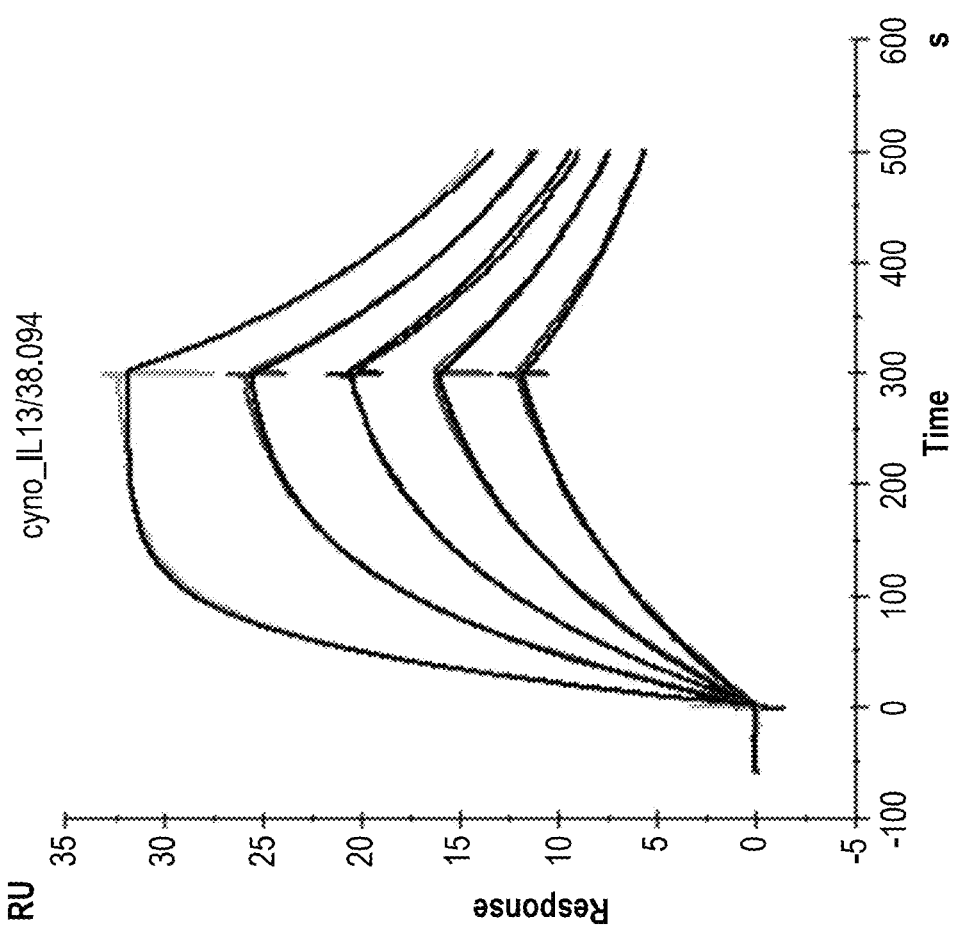
Figure 26D:
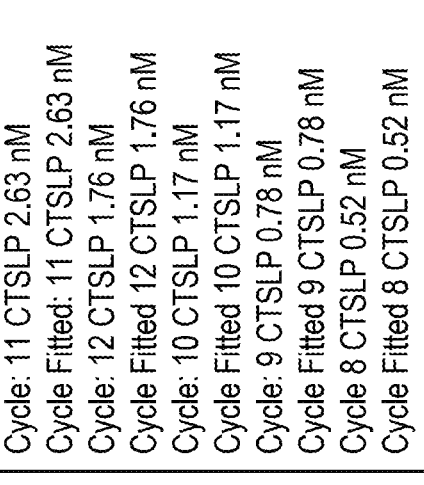
Figure 26D:
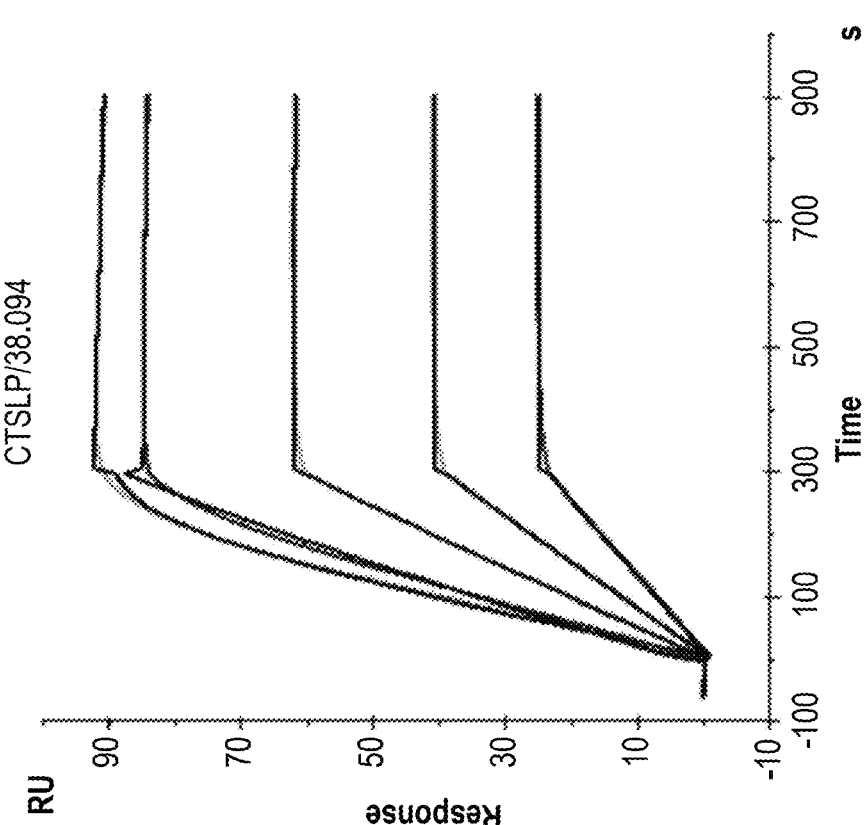

The size exclusion chromatography (SEC) scans and nano-differential scanning fluorimetry (DSF) analysis of the melting point for antibody BDG38.09 are shown in FIGS. 25A and 25B.

The size exclusion chromatography (SEC) scans and nano-differential scanning fluorimetry (DSF) analysis of the melting point for antibody BDG38.094 are shown in FIGS. 25A and 25B. SEC analysis (FIG. 25A) was performed using BioResolve SEC mAb Column, 200A, 2.5 μm, 4.6× 300 mm at 0.4 ml/min in PBS as a mobile phase and analyzed at 280 nm. BDG38.094 shows a predominant monodisperse peak with undetectable aggregates. DSF analysis (FIG. 25B) was performed using nanoDSF at a 1° C./min from 20-95° C. NanoDSF is monitoring the thermal unfolding of BDG38.094 according to the intrinsic fluorescence change at 350 and 330 nm. The top half of the graph shows the fluorescence ratio of 350 nm/330 nm as a function of temperature and the bottom half shows the first derivative as a function of temperature. BDG38.094 was analyzed at 0.5 mg/ml in PBS showed to have a T-onset of 62.4° C. and Tm of 65.3° C. suggesting a relatively stable fold.

The binding affinities of antibody BDG38.094 to human/cyno IL-13 and human/cyno TSLP are shown in FIGS. 26A-26D. Surface Plasmon Resonance (SPR) analysis of BDG38.094 binding to human IL-13 (FIG. 26A), human TSLP (FIG. 26B), cyno IL-13 (FIG. 26C) and cyno TSLP (FIG. 26D) using BiacoreT200. CMS chip was coated with human antibody capture kit to obtain 3000-5000 RU and the antibody, served as the capture, was injected at a flow rate of 10 ul/ml to obtain 250-350 RU. Human/cyno TSLP and human/cyno IL-13 served as analytes in a concentration range of 30-0.153 nM. Contact time was 300 sec and dissociation time was 600 sec (for cyno IL-13 dissociation time was 200 sec)) at a flow rate of 30 ul/min BDG38.094 shows a high affinity to all cytokines with KD values for hIL-13: 1.38E-11 M for hTSLP: <1E-12 M (below limit of detection), for cyno IL-13: 2.70E-10 M and for cyno TSLP: 2.75E-12 M.
Antibody BDG38.138

Figure 27A:
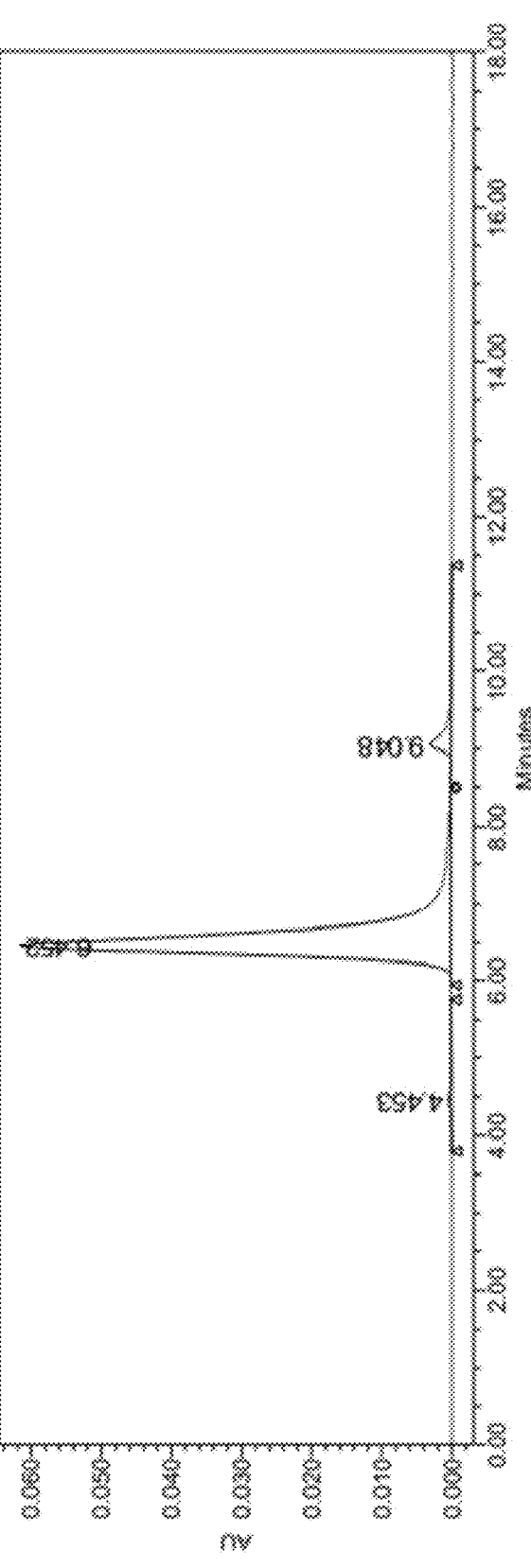
FIGS. 27A and 27B show size exclusion chromatography (SEC) scans (FIG. 27A), and nano-differential scanning fluorimetry (DSF) analysis of the melting point (FIG. 27B) for antibody BDG38.138. Shown representative DSF analysis of the melting point of indicated IgGs (analyzed in duplicates). Light gray dashed line in the upper graph represents the T-onset and bold gray dashed lines represents the Tm1 and Tm2.
Figure 27B:
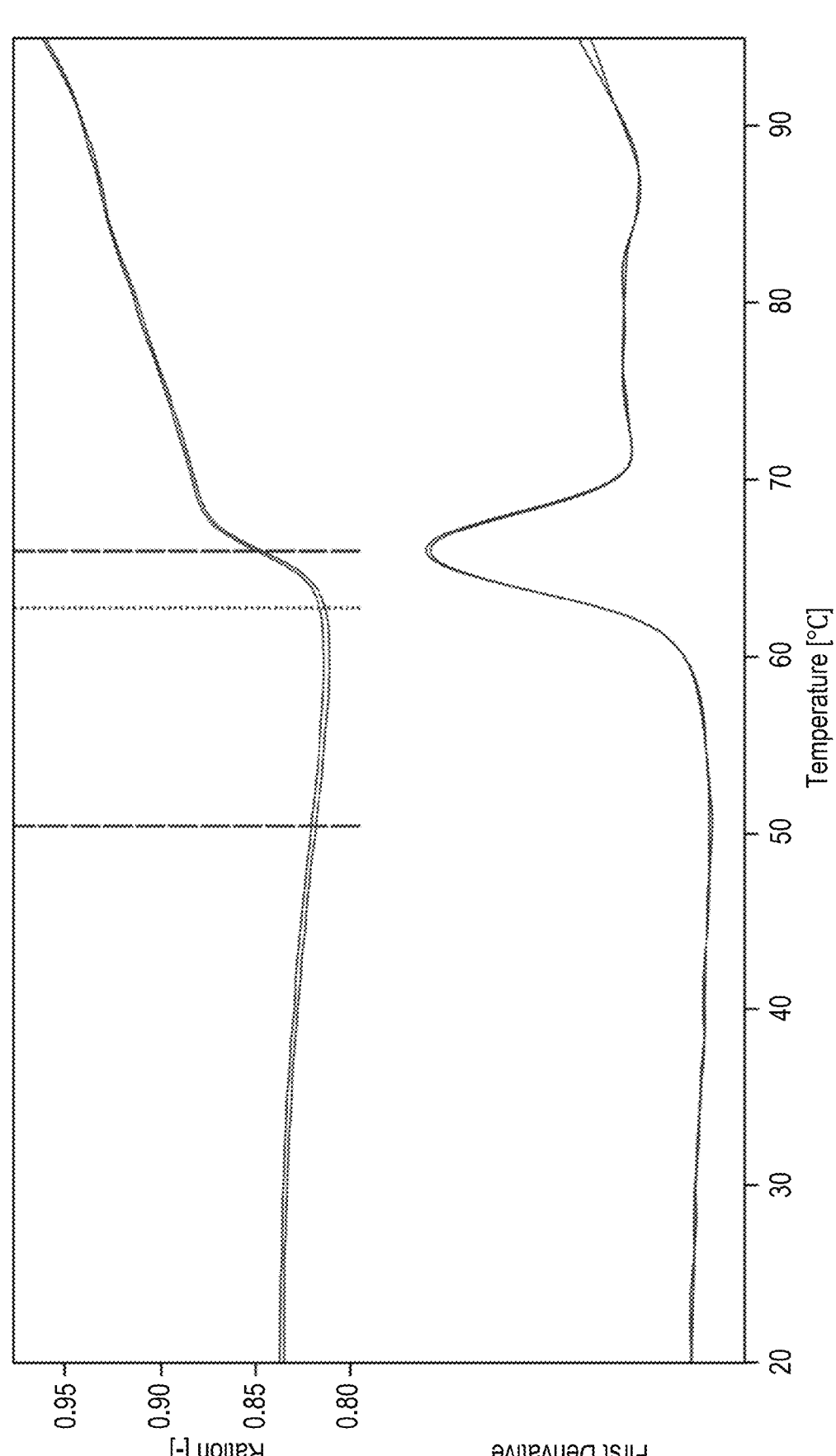
Figure 28A:
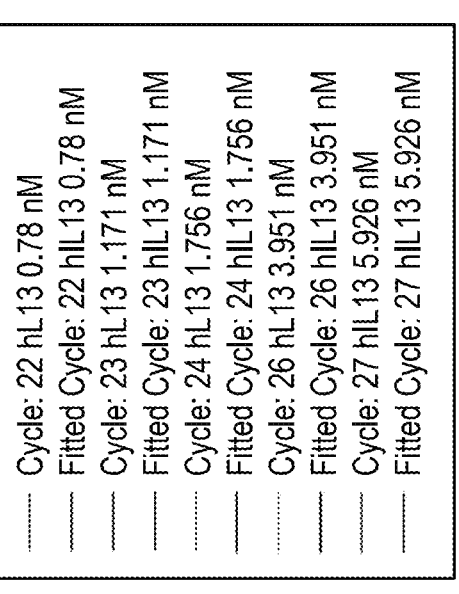
FIGS. 28A-28D show binding affinities of a representative clone.
Figure 28A:
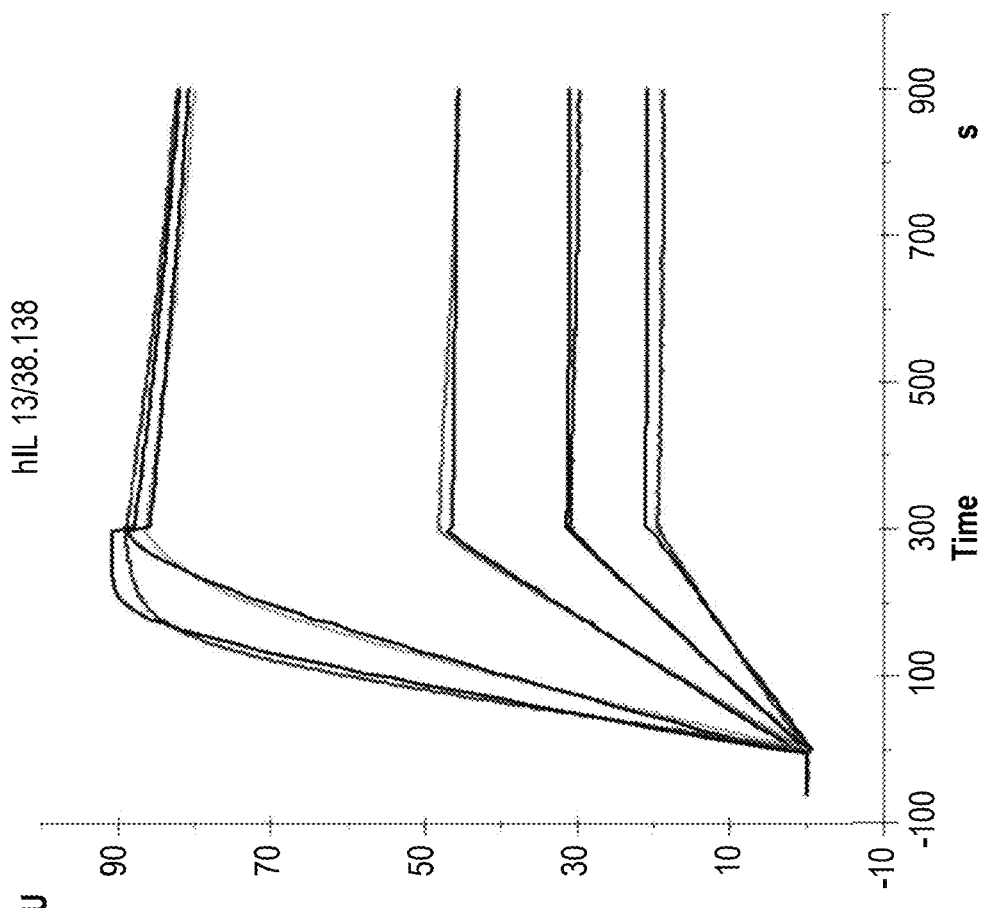
Figure 28B:
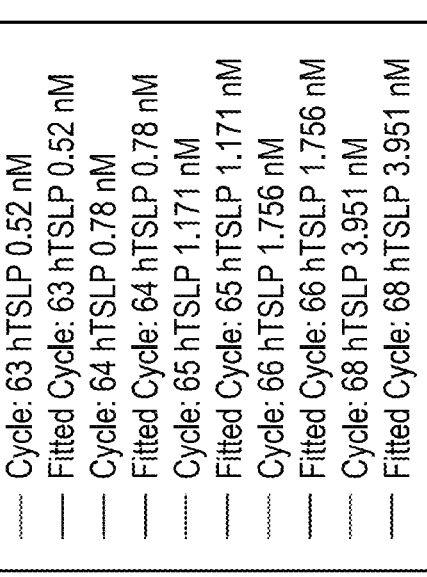
Figure 28B:
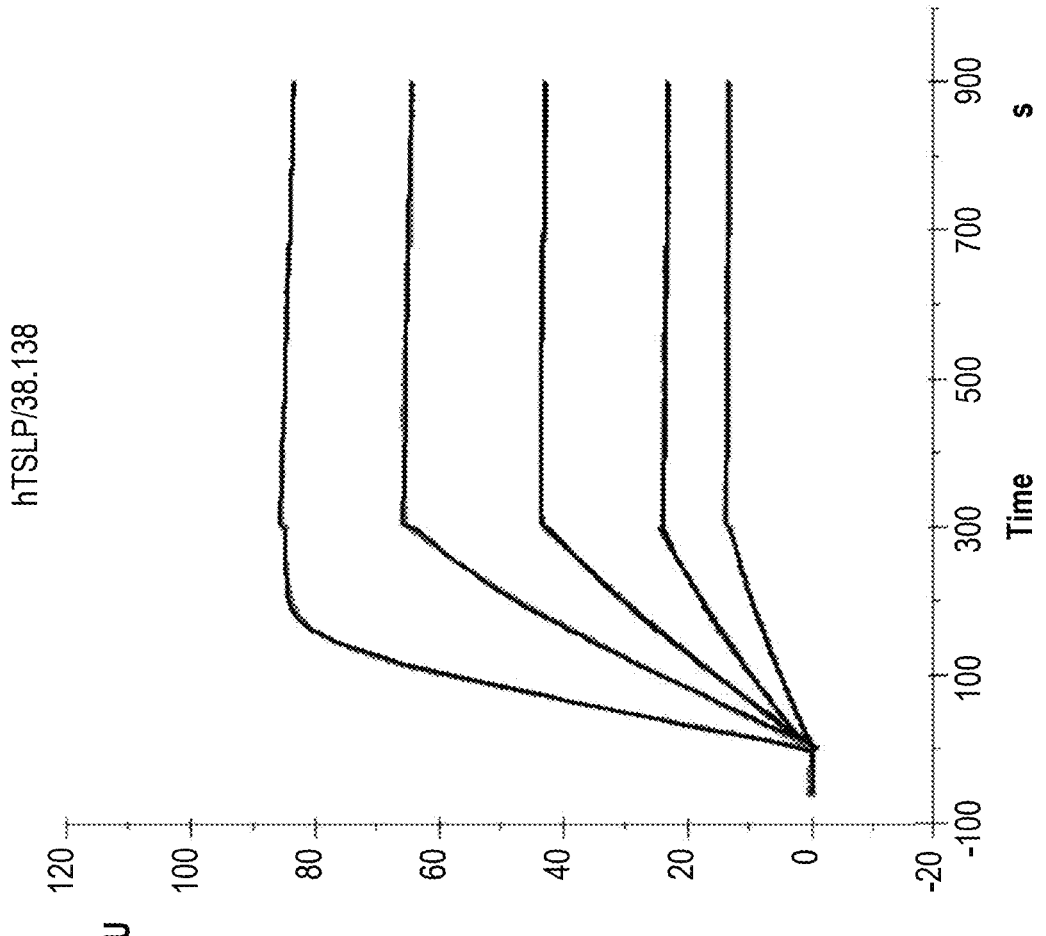
Figure 28C:
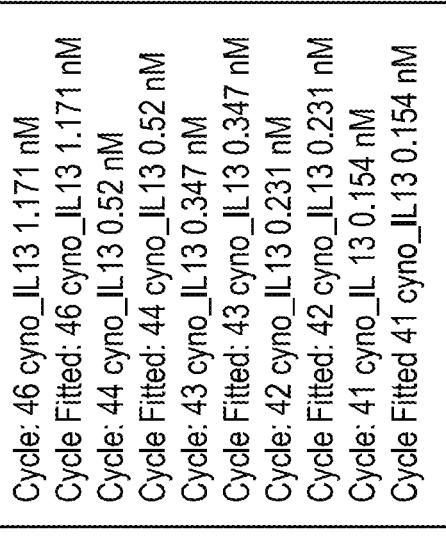
Figure 28C:
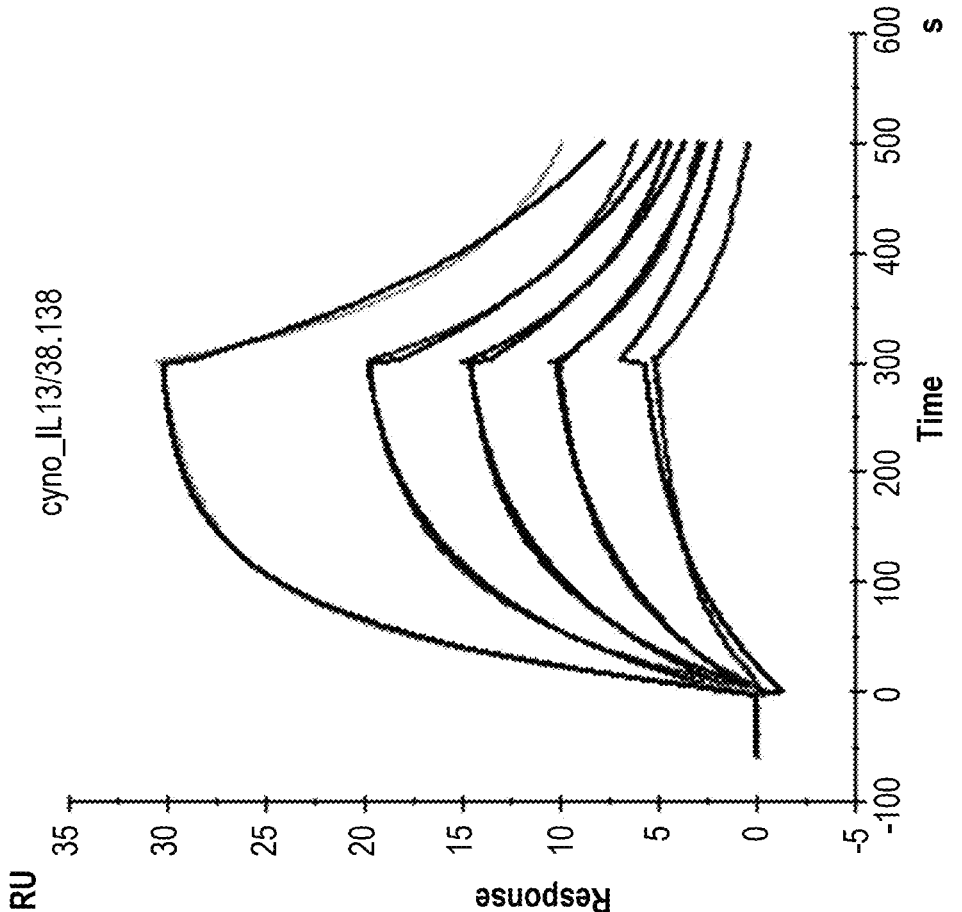
Figure 28D:
Figure 28D:
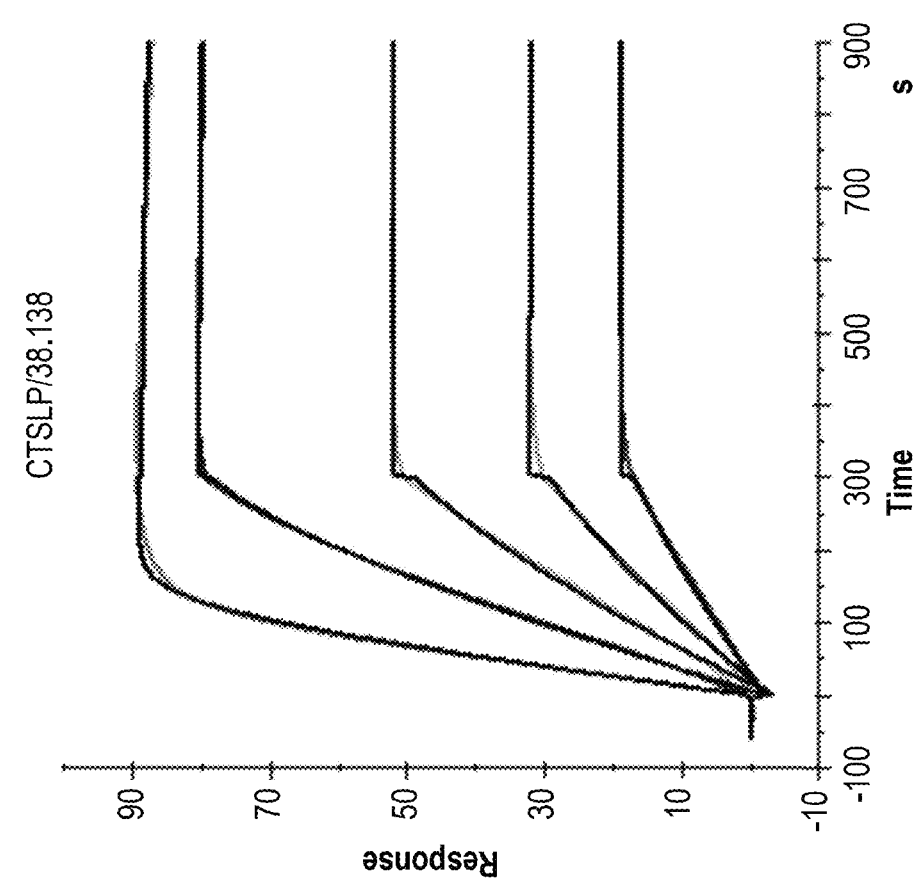
Figure 29A:
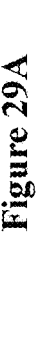
FIGS. 29A-29D show the results of analyzing BDG38.138 and BDG38.145, which each have different Fc formats. The SPR results demonstrate that antibody clones BDG38.138 and BDG38.145 have similar affinities for human IL-13 and human TSLP.
Figure 29B:
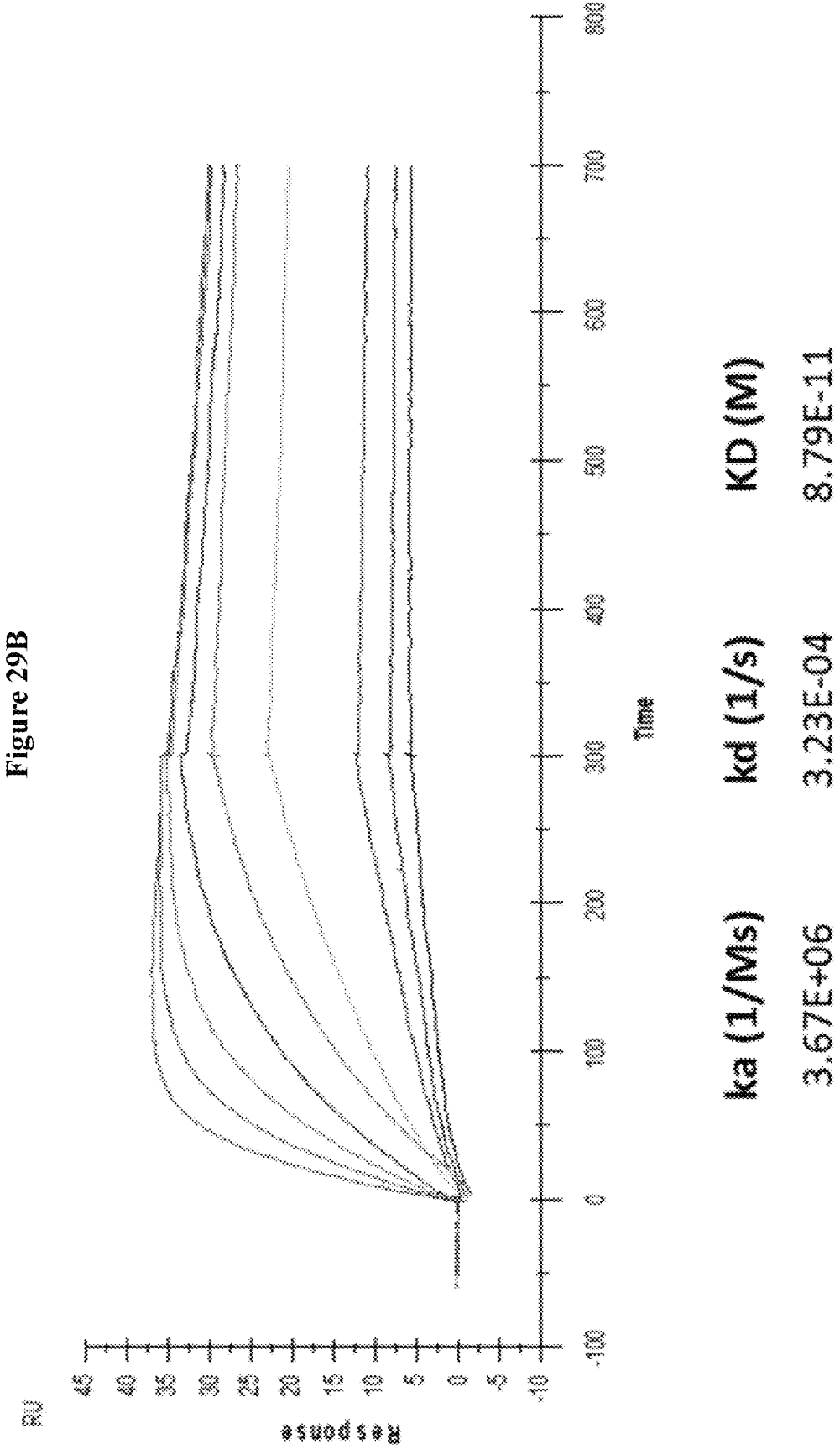
Figure 29C:
Figure 29D:
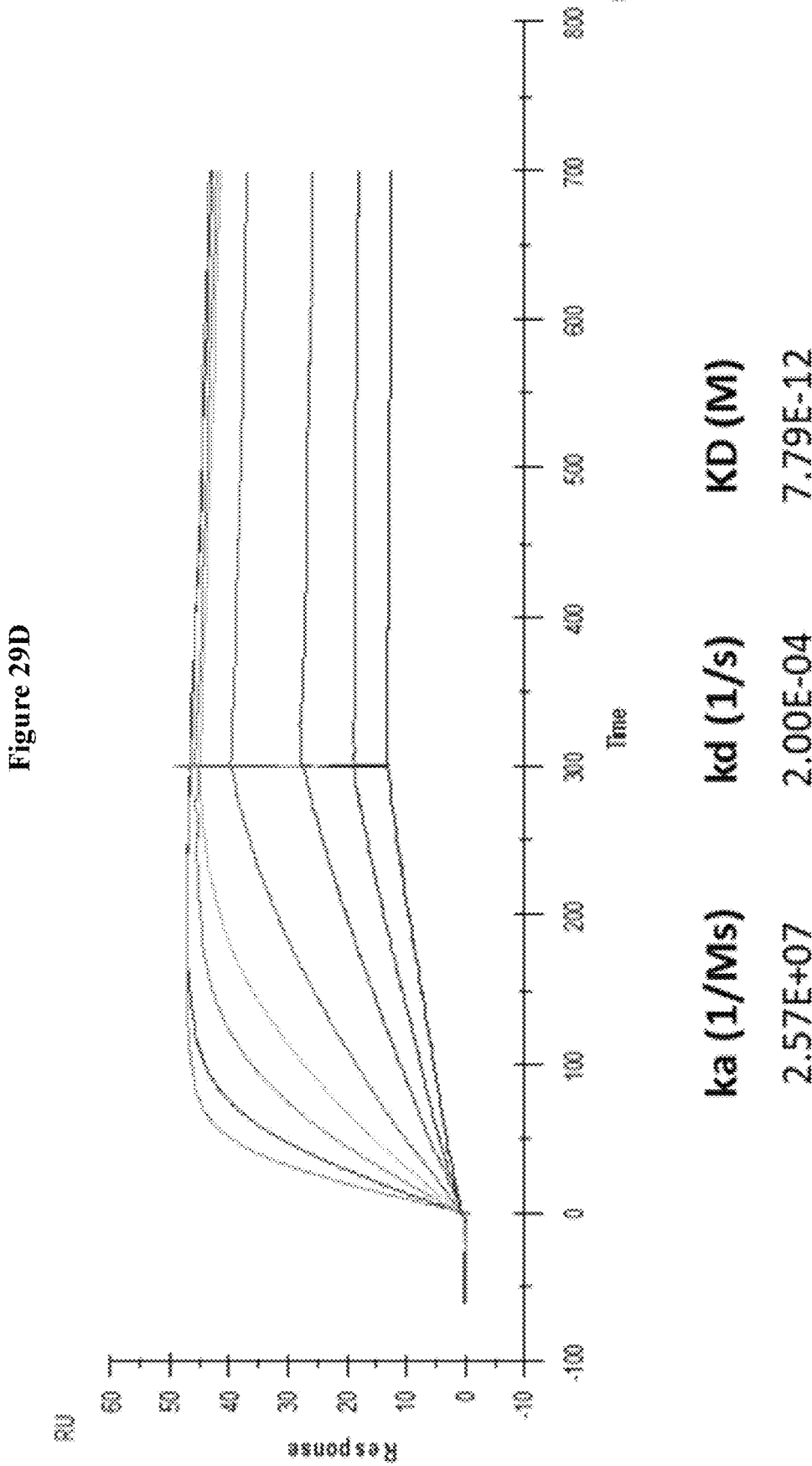

The size exclusion chromatography (SEC) scans and nano-differential scanning fluorimetry (DSF) analysis of the melting point for antibody BDG38.138 are shown in FIGS. 27A and 27B.

SEC was performed using BioResolve SEC mAb Column, 200 Å, 2.5 μm, 4.6×300 mm at 0.4 ml/min in PBS as a mobile phase and analyzed at 280 nm. BDG38.138 shows a predominant monodisperse peak with 0.8% aggregates. DSF analysis was performed using nanoDSF at a 1° C./min from 20-95° C. NanoDSF is monitoring the thermal unfolding of BDG38.138 according to the intrinsic fluorescence change at 350 and 330 nm. The top half of the graph shows the fluorescence ratio of 350 nm/330 nm as a function of temperature and the bottom half shows the first derivative as a function of temperature. BDG38.138 was analyzed at 0.5 mg/ml in PBS showed to have a T-onset of 62.8° C. and Tm of 66° C. suggesting a relatively stable fold.

The binding affinities of antibody BDG38.138 to human/cyno IL-13 and human/cyno TSLP are shown in FIGS. 28A-28D. (Surface Plasmon Resonance (SPR) analysis of BDG38.138 binding to human IL-13 (FIG. 28A), human TSLP (FIG. 28B), cyno IL-13 (FIG. 28C) and cyno TSLP (FIG. 28D) using BiacoreT200. CMS chip was coated with human antibody capture kit to obtain 3000-5000 RU and the antibody, served as the capture, was injected at a flow rate of 10 ul/ml to obtain 250-350 RU. Human/cyno TSLP and h/cyno IL-13 served as analytes in a concentration range of 30-0.153 nM. Contact time was 300 sec and dissociation time was 600 sec (for cyno IL-13 dissociation time was 200 sec) at a flow rate of 30 ul/min BDG38.138 shows a high affinity to all cytokines with KD values for hIL-13: 1.34E-11 M, for hTSLP: 2.85E-12 M, for cynoIL-13: 8.49E-10 M and for cyno TSLP: 1.35E-12 M.

Summary:

The presented data demonstrate that BDG dual antibodies are highly monomeric and stable molecules (Table 11). Those antibodies can bind human IL-13, cynomolgus IL-13, human TSLP and cynomolgus TSLP with picomolar affinities (FIGS. 16A-16F). Unlike different bi-specific antibodies, each BDG dual antibody mentioned in the patent is a standard IgG1 that can bind the above mentioned antigens (IL-13 and TSLP). In the case of antibody clone BDG38.138 it is a standard IgG1 with the Fc mutations as described herein. (LALA, PG) that can bind the above-mentioned antigens.

```
The full length heavy chain (HC) for BDG38.138
is set forth in SEQ ID NO: 408:
QMQLVESGGGVVQPGRSLRLSCAASGFAFRTYGMHWVRQAPGKGLEW

VAVIWDDGSNTHYADSVKGRFTITRDNSKNTLNLQMNSLRAEDTAVY

YCVRAPQWYLTAEAFDLWGQGTMVTVSSASTKGPSVFPLAPSSKSTS

GGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCP

APEAAGGPSVFLFPPKPKDTLMISRTPEVTCVVVDVSHEDPEVKFNW

YVDGVEVHNAKTKPREEQYNSTYRVVSVLTVLHQDWLNGKEYKCKVS

NKALGAPIEKTISKAKGQPREPQVYTLPPSRDELTKNQVSLTCLVKG

FYPSDIAVEWESNGQPENNYKTTPPVLDSDGSFFLYSKLTVDKSRWQ

QGNVFSCSVMHEALHNHYTQKSLSLSPGK.

The full length light chain (LC) for BDG38.138
is set forth in SEQ ID NO: 409:
SYVLTQPPSVSVAPGETASITCGGNMIGGYLVHWYQQKPGQAPVLVI

YDDVDRPSRIPERFSGSNSGNTATLTISRVEAGDEADYYCQVWDHNS

NHMVFGGGTKLTVLGQPKAAPSVTLFPPSSEELQANKATLVCLISDF

YPGAVTVAWKADSSPVKAGVETTTPSKQSNNKYAASSYLSLTPEQWK

SHRSYSCQVTHEGSTVEKTVAPTECS.
```

Since some of the antibody's binding was above the limit of detection IC50 competition ELISA against Tezepelumab was done (Table 13, FIGS. 14A-14C). This data supports the SPR analysis and demonstrates that BDG dual antibodies can compete with Tezepelumab over binding to TSLP.

BDG antibodies demonstrated functional inhibition of IL-13 signaling in HEK reporter cells, by blocking signal transduction of IL-13 through STATE (Table 15, FIG. 22).

Similarly, BDG antibodies inhibited TSLP mediated STAT5 phosphorylation in MUTZ cells, expressing the natural TSLP-receptor heterocomplex comprising TSLP-R and IL-7Rα.

To test the effect of a dual antibody, hPBMC was treated with both hTSLP and hIL-13 for 48 hours in the presence of rising concentration of BDG antibodies or benchmark antibodies (Table 12, FIGS. 24A and 24B). In this setup TSLP treatment led to increase in TARC level and 11-13 treatment led to increase in CD23 levels. While BDG dual antibodies inhibited CD23 expression similarly to the anti-IL-13 benchmark (Tralokinumab), anti-TSLP benchmark had only minor effect. Similarly, while BDG dual antibodies inhibited TARC secretion similarly to Tezepelumab, anti-IL-13 benchmark had only minor effect on the level of TARC. This demonstrates that BDG dual antibodies inhibit as a single IgG1 molecule having both functions of TSLP and IL-13.

Example 6: Biochemical Comparison of Antibodies Having the Same VH/VL Regions with Different Fc Formats (hIgG1 LALA (BDG38.145) Vs LALAPG (BDG38.138))

Objective: To examine the biochemical properties of hIgG1 antibodies with different Fc formats, wherein the antibodies comprise the CDR regions as follows: HCDR1 is SEQ ID NO: 349, HCDR2 is SEQ ID NO: 350, HCDR3 is SEQ ID NO: 351, LCDR1 is SEQ ID NO: 364, LCDR2 is amino acids sequence DDV, LCDR3 is 384, and comprise the VH/VL regions as follows: VH is SEQ ID NO: 337 and VL is SEQ ID NO: 338. Specifically, two hIgG1 antibodies comprising the identical CDR and VH/VL regions with those of clone 38.138 were compared, wherein the Fc regions differed so that the effects of the 2 Fc formats could be compared.

The formats for comparison were 38.138 (hIgG1 LALA-PG) and 38.145 (hIgG1 LALA). BDG38.138 and BSG38.145 share the same VH and VL sequences, and only differ in the Fc mutations. As used throughout, the names "BDG38.138" and "38.138" have the same meanings and indicate the same antibody, similarly, the names "BDG38.145" and "38.145" have the same meanings and indicate the same antibody.

The full length heavy chain (HC) amino acid sequence is provided for BDG38.138 in Example 5. The full length heavy chain (HC) amino acid sequence for BDG38.145 is set forth in SEQ ID NO: 410: QMQLVESGGG VVQPGRSLRLSCAASGFAFRTYGMHWVRQAPGK-GLEWVAVIWDDG SNTHYADSVKGRFTITRDN SKN TLNLQMNSLRAEDTAVYYCVRAPQWYLTAEAFDL WGQGTMVTVSSASTKGPSVFPLAPSSKSTSGGTAAL-GCLVKDYFPEPVTVSWNSGALT SGVHTFPAVLQSSG-LYSLSSVVTVPSSSLGTQTYICNVNHKPSNT KVDK KVEPKSCDKT HTCPPCPAPEAAGGPSVFLFPPKPKDT LMISRTPEVTCVVVDVSHEDPEVKFNWYVDG VEV HNAKTKPREEQYNSTYRVVSVLTVLHQDWLNG KEYKCKVSNKALPAPIEKTISK AKGQPREPQV YTLP PSRDELTKNQVSLTCLVKGFYPSDIAVEWESNGQPEN NYKTTPP VLDSDGSFFLYSKLTVDKSRWQQGNVFS CSVMHEALHNHYTQKSLSLSPGK (SEQ ID NO: 410). The full length light chain (LC) for both BDG38.138 and BDG38.145 is set forth in SEQ ID NO: 109, as presented in Example 5.

Methods

Surface Plasmon Resonance (SPR)—Kinetic measurements of 38.138 and 38.145 for hIL-13 and hTSLP were done using Biacore 5200 [Cytiva, USA] on CMS chip

[Cytiva, br-10005-30]. The chip was crosslinked with a human antibody capture kit [Cytiva, USA br-100839] according to manufacturer's protocol to target 5000-8000 RU.

In order to measure kinetics, a multi-cycle strategy was used. Antibodies were captured on the coated chip to reach ~200 RU. Human/CynoIL-13 [Acro Biosystems, IL3-H52H4/IL3-C5249] or human/cynoTSLP [Acro Biosystems, TSP-H52H4/TSP-052H8] were injected from 60 nM to 0.3 nM in 1.5 dilutions in a contact time of 300 sec, at flow rate of 30 ul/min Dissociation was done by injecting PBS-T for 400 sec at a flow rate of 30 ul/min Between each cycle, all channels underwent regeneration using 3M $MgCl_2$. Binding kinetics were determined by the 1:1 Binding model using the Biacore 5200 evaluation software, version 1.1.

Stability at viral inactivation conditions: A total of 4.4 mg/ml of 38.138 and 38.145 were divided into 2.2 mg/ml that was used as a control and 2.2 mg/ml that was incubated at a viral inactivation condition. All samples were buffer exchanged from PBS, pH 7.4 into either Na-acetate, pH 3.5 (treated) or PBS, pH 7.4 (control) using PD10 desalting column [Cytiva, USA 17085101]. Samples were incubated for 1 hour at room temperature followed by a 2n d buffer exchange into PBS, pH 7.4. antibodies concentration and volume were monitored after each buffer exchange and incubation step using 280 nm. At the end of the viral inactivation process, all samples (treated and control) were analyzed using SDS-PAGE R/NR, SEC, ELISA EC50 and HIC.

Size exclusion chromatography (SEC)—SEC analysis was done by loading 12 µg from each viral inactivation sample on BioResolve SEC mAb 200A 2.5 um 4.6×300 mm column (Waters Corporation MA, USA) that was preequilibrated with PBS, pH 7.4 at a flow rate of 0.4 ml/min, room temperature. Chromatogram analysis was obtained at 280 nm using an ACQUITY Arc HPLC system (Waters Corporation MA, USA).

SDS-PAGE under reduced and non-reducing conditions—For SDS-PAGE analysis, samples were prepared by mixing viral inactivation and control samples with lithium dodecyl sulfate (LDS) [GenScript, USA M00676] with or without 2-mercaptoethanol for reducing and non-reducing conditions, respectively. Samples were boiled at 80° C. for 5 min, and a total of 2.5 pg was loaded on a gradient 4-20% SDS-PAGE [Invitrogen, MA USA; XP04125BOX].

Hydrophobic interaction chromatography (HIC)— HIC analysis was done by spiking 7.5 µg from each viral inactivation sample into buffer A (2M ammonium sulphate, 0.1M sodium phosphate) to achieve a final ammonium sulphate concentration of 1M. A Proteomix HIC Butyl-NP5 5 µm Non-Porous 4.6×35 mm column (Sepax, USA) was used with a linear gradient from 90% A and 10% B buffer (0.1M sodium phosphate, pH 6.5) to 100% B buffer over 20 min at a flow rate of 1 ml/min, at 30° C. Chromatogram analysis was obtained at 280 nm using the ACQUITY Arc HPLC system (Waters Corporation MA, USA).

ELISA EC50—EC50 ELISA was performed to evaluate affinity integrity of the variants post viral inactivation process. A high binding 96 wells plate was coated with 50 ng/well of either hIL-13 or hTSLP and incubated over night at 4° C. Following coating, plates were washed 3 times using PBS-T and blocking solution containing 1.5% BSA in PBS-T was applied over plates for 1 hour incubation at room temperature. After a 2n d washing step, 2-fold dilution of each viral inactivation or control sample from 70 nM to 0.068 nM were added to well in the plates and incubated for 1 hour at room temperature. A $3^{rd}$ step of washing was performed and goat anti human Fc-HRP (Jackson, USA; 109-035-008) was applied over the plates and incubated for 30 min at room temperature. Development of plates was done after a $4^{th}$ washing step using 3,3',5,5'-Tetramethylbenzidine (TMB) (SURMODICS, USA; TMBW-0100-01) and reaction was stopped using stop solution [SURMODICS, USA; LSTP-0100-01]. Signals were recorded at 450 nm and analysis was done using GraphPad Prism software (GraphPad Software, LLC), using "[Agonist] vs. response—Variable slope (four parameters)" analysis Differential Scanning Fluorimetry (DSF) measurements—To compare the thermal stability of 38.138 and 38.145, Differential Scanning Fluorimetry was performed using a NanoDSF Prometheus NT48 instrument assessing the thermal transition from the native to unfolded state. Antibodies at 0.5 mg/ml concentration in PBS pH 7.4 were loaded and DSF was performed at a temperature increment of 1° C./min.

PBMCs activation and treatment—Peripheral blood mononuclear cells (PBMCs) (Cell Generation, Israel; CAT: 10102510) were used to determine hIL-13 and hTLSP inhibition. PBMCs were thawed and cultured in growth medium consisting of RPMI—1640, 10% FBS, 1% Glutamax, 1% Sodium-Pyruvate, 0.1% 2-ME, 1% Pen-Strep and 1% nonessential AA. The cells were seeded in 96 well plate at $5\times10^5$ cells/well and were allowed to rest for 1 hour at 37° C., 5% $CO_2$. hIL-13-His (Acro Biosystems, USA; CAT: IL3-H52H4) at a concentration of 0.7 nM and hTSLP-His (Acro Biosystems, USA; CAT: TSP-H52Hb) at a concentration of 70 pM were added to the cells, followed immediately by addition of antibodies in serial dilutions, to a total of to a total of 200 uL/well. Cells were incubated for 48 hours at 37° C., 5% $CO_2$.

CD23 expression in monocytes—$IC_{50}$ of antibody inhibition of hIL-13 was determined by measuring CD23 expression level in monocytes. At the end of 48 hours incubation of the cells with different concentrations of antibodies, monocytes were detached from the bottom of the wells using cold PBS and scraping. Cells were labeled using PE-CF594-conjugated anti-CD3 (BD Bioscience, USA; CAT: 562280), PE/Cyanine7-conjugated anti-CD14 (BioLegend, USA; CAT: 301814), APC-conjugated anti-CD19 (Bio Legend, USA; CAT: 302212) and FITC-conjugated anti-CD23 (BioLegend, USA; CAT: 338506) antibodies. CD23 percentage of CD14+ population was measured using CytoFLEX flow cytometer (Beckman Coulter, USA).

TARC levels in PBMCs supernatant—TARC levels were determined using TARC DUOSET ELISA kit (R&D systems, USA; CAT: DY364) according to the manufacturer's instructions. Briefly, ELISA high binding protein plates were coated with capture antibody (antibodies being assessed), diluted in PBS. Plates were sealed and incubated overnight at 4° C. The following day plates were washed and blocked using 1% BSA in PBS at room temperature, with shaking for 1 hour. The plates were washed three times in phosphate-buffered saline with Tween 20 (PBST), and supernatant from the PBMCs plates was diluted 1:1 in 1% BSA in PBS, transferred to the wells and incubated at room temperature with shaking for 2 hours. The plates were washed three times in PBST. Detection was performed using the kit's detection antibody (biotinylated) in PBS 1% BSA at room temperature with shaking for 2 hours followed by three washes in PBST and addition of Streptavidin—HRP in PBS 1% BSA for 30 minutes. Following 3 washes in PBST, the plates were developed by adding TMB and TMB-stop solution, and 450 nm. Values were analyzed using standard sample curve.

Results:

Specifications of Fc mutations:

Clone 38.138, human IgG1 with the Fc-modification LALA-PG (substituting alanine for leucine at positions 234 and 235 and substituting proline for glycine at position 329 of the Fc region).

Clone 38.145, human IgG1 with the Fc-modification LALA (substituting alanine for leucine at positions 234 and 235).

Clones 38.138 and 38.145 were compared in a series of biochemical assays: Surface Plasmon Resonance (SPR) analyses for human IL-13 (hIL-13) and human TSLP (hTSLP) in repetitions show similar kinetics for both formats. SPR was performed by capturing the antibody (38.138 or 38.145) onto an anti-hFc precoated CMS chip, and a serial dilution of IL-13/TSLP was injected in a multi-cycle strategy.

FIGS. 29A-29D show the results of SPR (Surface Plasmon Resonance) analysis for the binding of hIgG1-LALAPG (38.138) or hIgG1-LALA (38.145) to human IL-13 and human TSLP. The antibodies comprising either the Fc LALA mutations or the Fc LALAPG mutations demonstrated similar affinities to both hIL-13 and hTSLP.

The stability of hIgG1-LALAPG (38.138) or hIgG1-LALA (38.145) under viral inactivation conditions was tested. Viral inactivation is a necessary process in biotherapeutic molecule production which is designed to enhance the safety of products that may contain or can become contaminated with viruses during production or processing. For immunoglobulin mAb products, low pH is the most frequently used method for viral inactivation; the common process includes incubation of the Ab in a low pH buffer for 1 hour at room temperature.

Stability was assessed by concentration measurement, SDS-PAGE, SEC, HIC, and binding following the viral inactivation process. Clones 38.138 (hIgG1 LALAPG) and 38.145 (hIgG1 LALA) were incubated for 1 hour with sodium acetate (NaAc) pH 3.5 at room temperature. Concentrations were monitored throughout the buffer exchange/inactivation process.

Figure 30A:
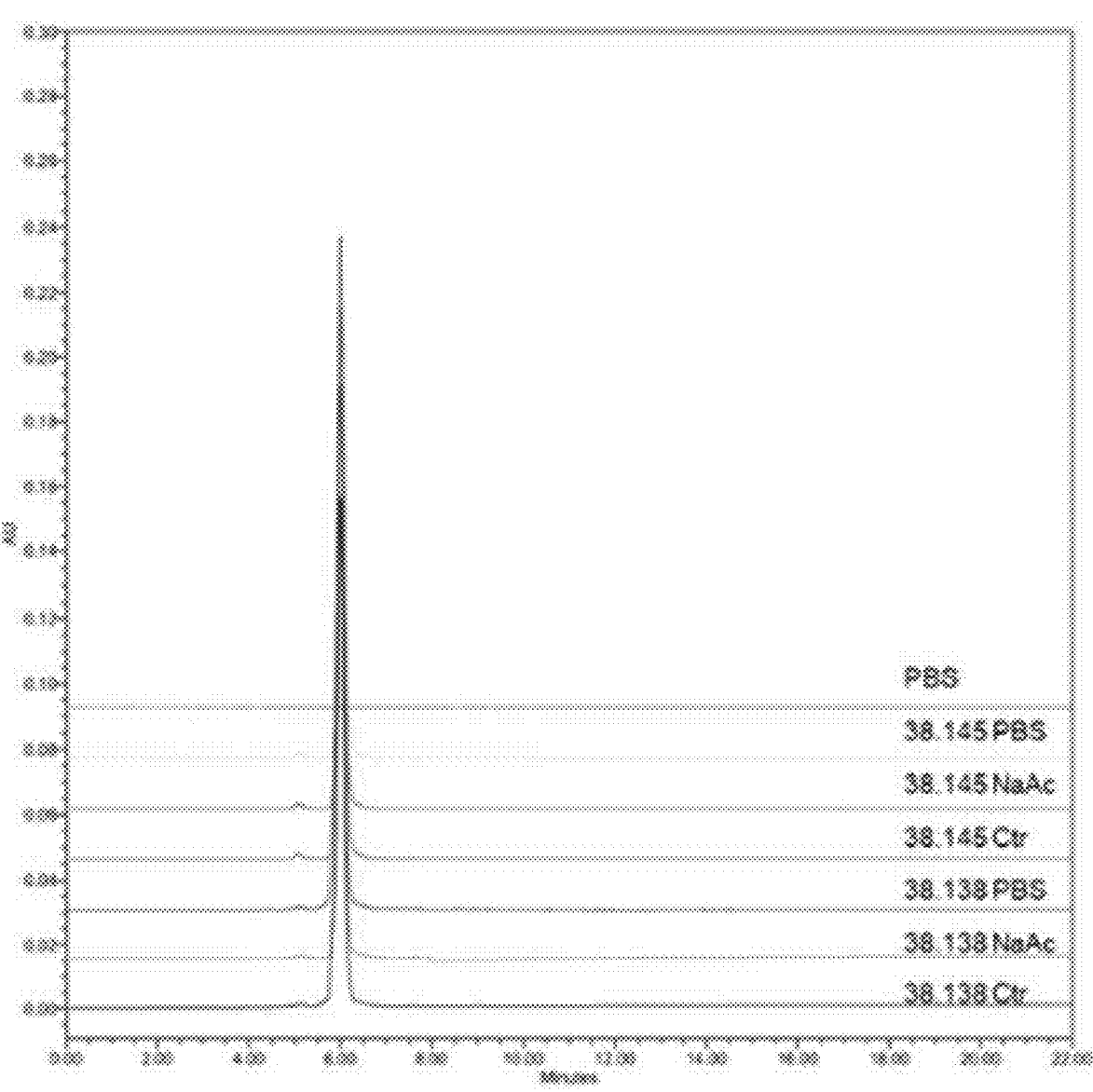
FIGS. 30A-30C demonstrate that clones BDG38.138 and BDG38.145 with different Fc formats, show similar stability under viral inactivation conditions.
Figure 30B:
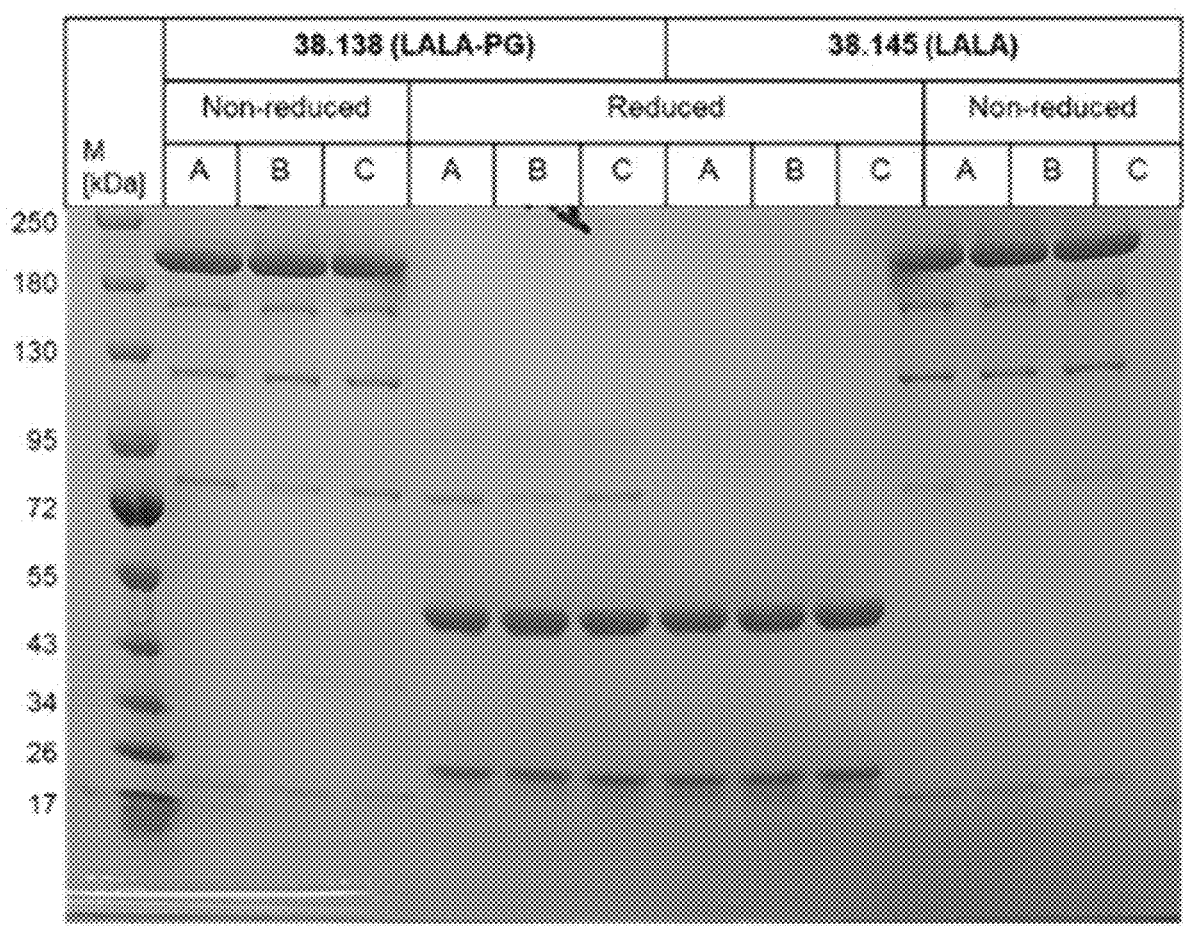
Figure 30C:
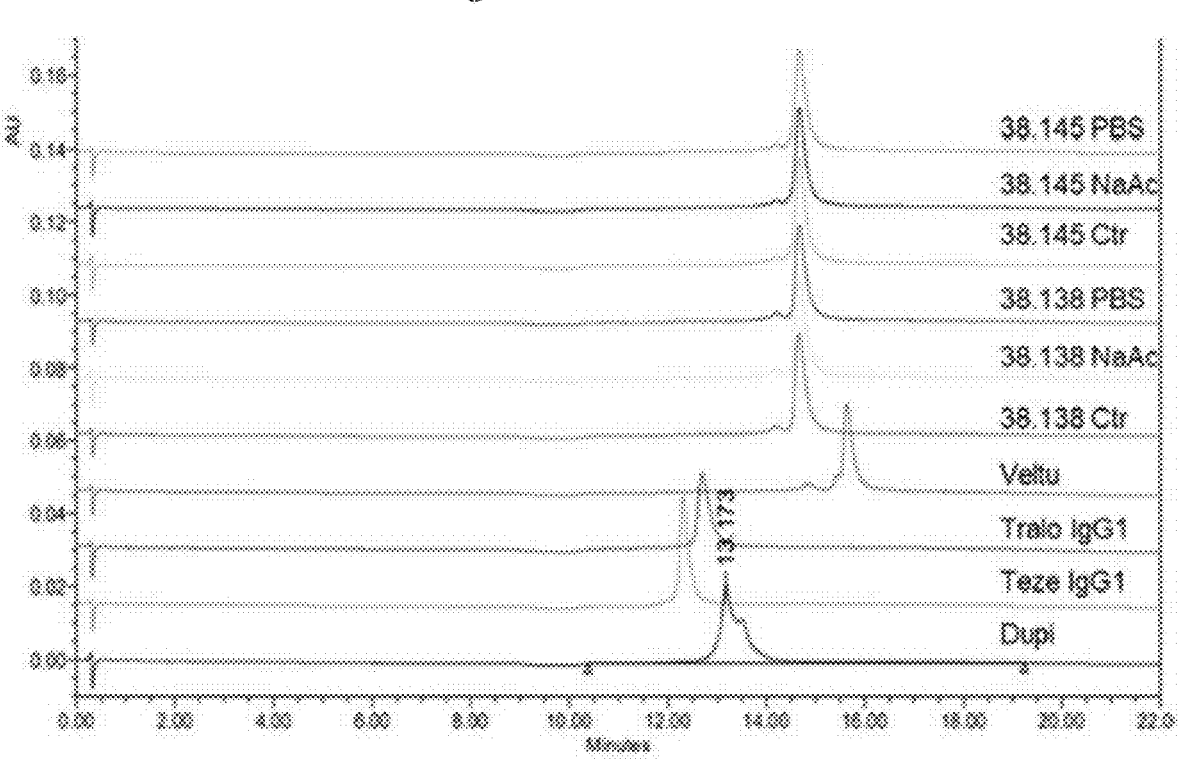

FIGS. 30A-30B show the biochemical properties of 38.138 (hIgG1 LALAPG) and 38.145 (hIgG1 LALA) following incubation at viral inactivation conditions. Samples were buffer exchanged from PBS, pH 7.4 into either Na-acetate, pH 3.5 (treated) or PBS, pH 7.4 (control), then incubated for 1 hour at room temperature followed by a 2nd buffer exchange into PBS, pH 7.4. Antibody concentration and volume were monitored after each buffer exchange and incubation step to evaluate if any material was lost in the process. At the end of the viral inactivation process, all samples (treated and control) were analyzed using SDS-PAGE, size exclusion chromatography (SEC), and Hydrophobic interaction chromatography (HIC). The binding of the treated antibodies to hIL-13 and hTSLP was measured by ELISA. The dual binding anti-IL-13/TSLP antibodies in IgG1 LALAPG and IgG1 LALA format showed similar biochemical stability under viral inactivation conditions.

To determine ELISA EC50 measurements, wells were coated with the respective cytokine, then incubated with clones 38.138 or 38.145 after incubation under viral inactivation conditions (NaAc) or control conditions (non-treated antibodies). Control antibodies went through the same steps of the viral inactivation process but in PBS instead of Sodium Acetate (NaAc) at a concentration range of 0.06 nM to 70 nM. Further, wells were washed and developed using HRP conjugated secondary antibody.

Figure 31A:
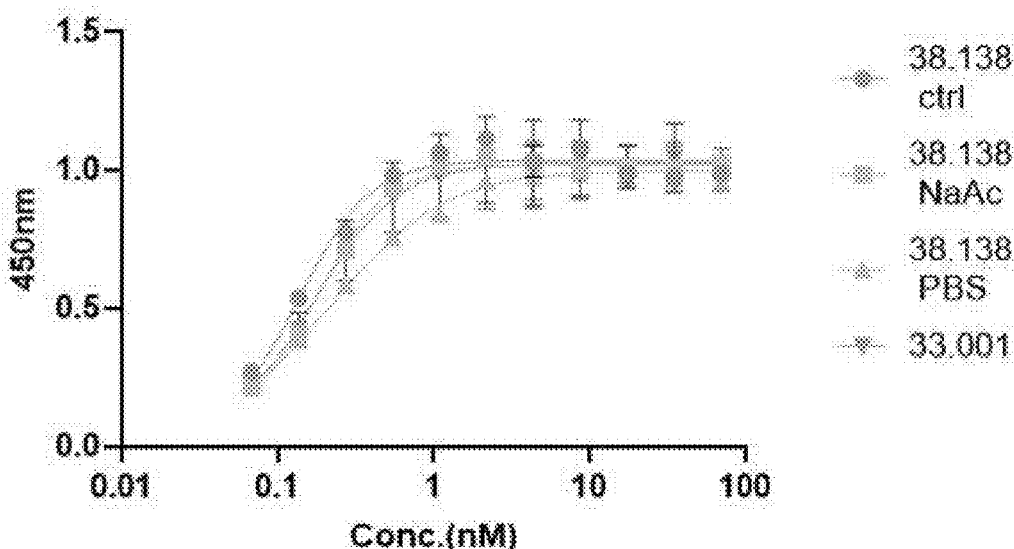
FIGS. 31A-31D show that BDG38.138 and BDG38.145, having identical VH/VL sequences but different Fc formats show similar binding under viral inactivation conditions. Binding of 38.138 (hIgG1 LALAPG) and 38.145 (hIgG1 LALA), treated and non-treated in viral inactivation conditions, to human TSLP and human IL-13 was measured by ELISA EC50.
Figure 31B:
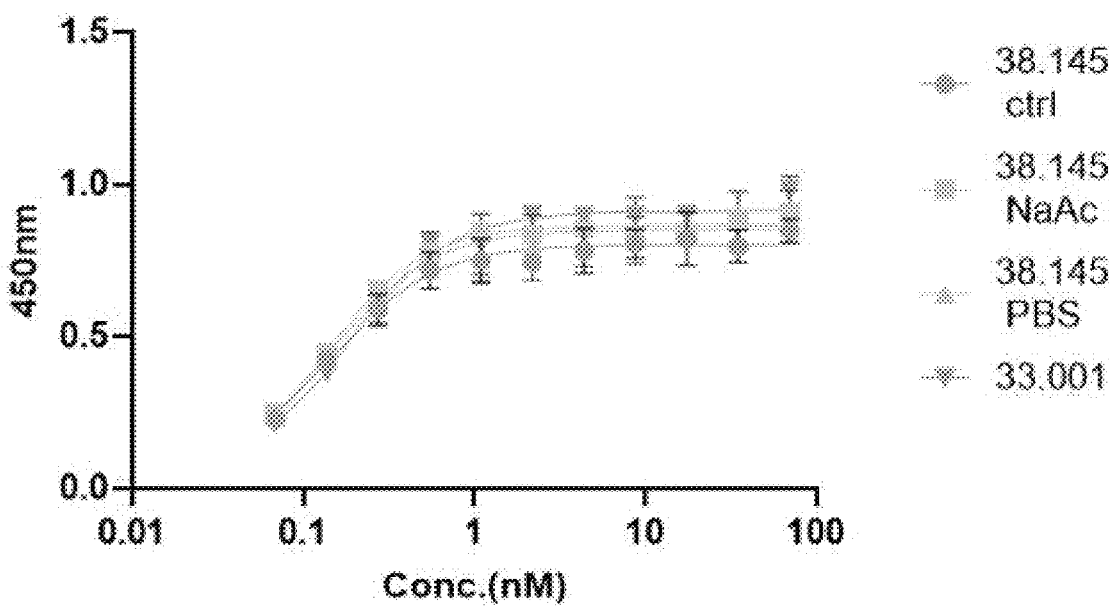
Figure 31C:
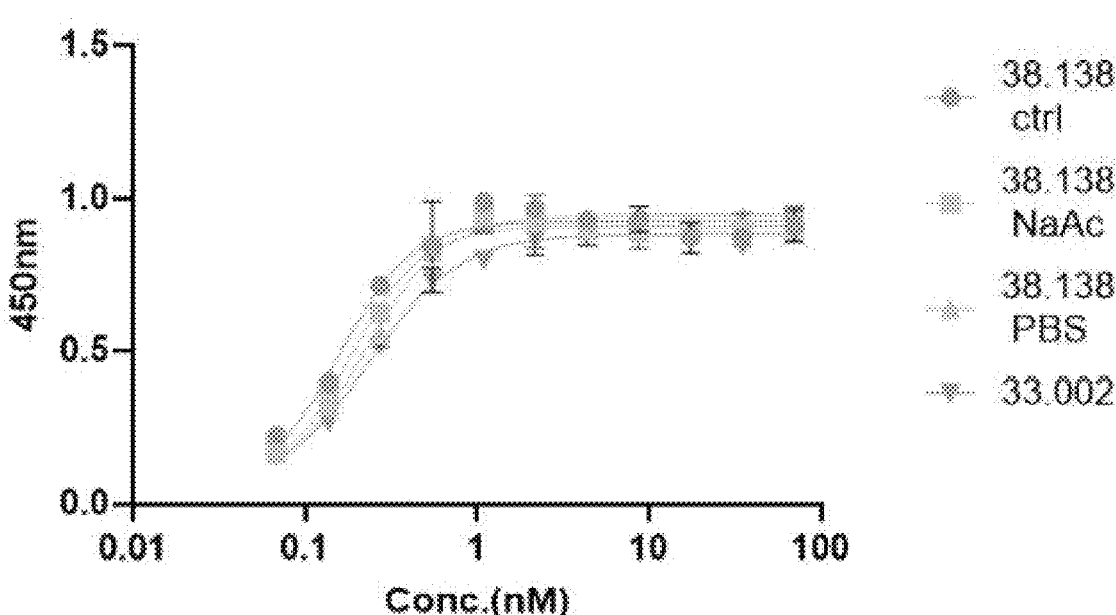
Figure 31D:
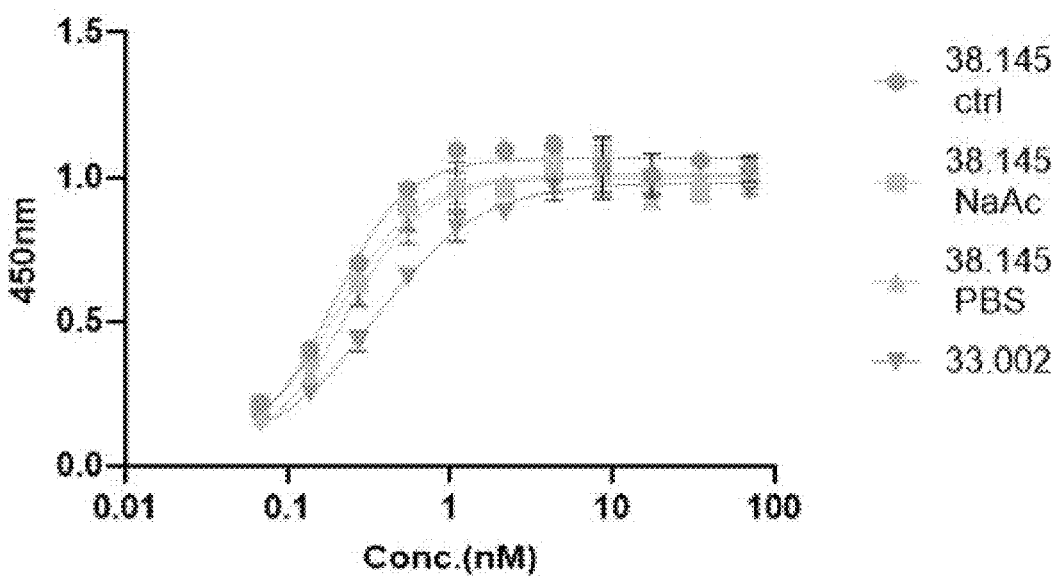

FIGS. 31A-31C present ELISA EC50 binding of 38.138 (hIgG1 LALAPG) and 38.145 (hIgG1 LALA) antibodies that had been treated with NaAc or PBS (control).i.e., viral inactivation conditions, to human TSLP and human IL-13. Anti-TSLP antibody 33.001 (Tezepelumab IgG1) and anti-IL-13 antibody 33.02 (Tralokinumab IgG1) were used as positive controls.

Additionally, Clone 38.138 and Clone 38.145 having the two Fc formats were compared for functional activity in human PBMCs, testing the CD23 expression in monocytes and TARC levels.

Figure 32A:
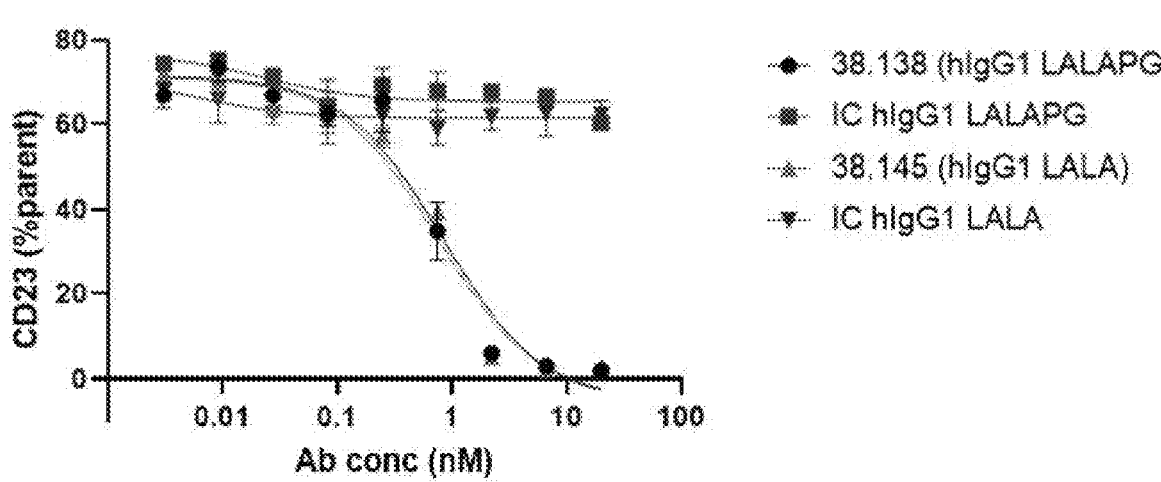
FIGS. 32A and 32B show comparison of 38.138 and 38.145 antibodies having identical VH/VL sequences but with different Fc formats, incubated with hPBMCs. hPBMCs were stimulated with 0.7 nm hIL-13 and 70 pM hTSLP Immediately following stimulation, cells were treated with antibodies: 38.138 (hIgG1 LALAPG) and 38.145 (hIgG1 LALA), and their respective isotype controls (IC) in concentrations ranging from 0.03 nM to 20 nM. Following 48 hours incubations, cells were analyzed for CD23 expression by flow cytometry, and TARC levels in the supernatant were measured by ELISA.
Figure 32B:
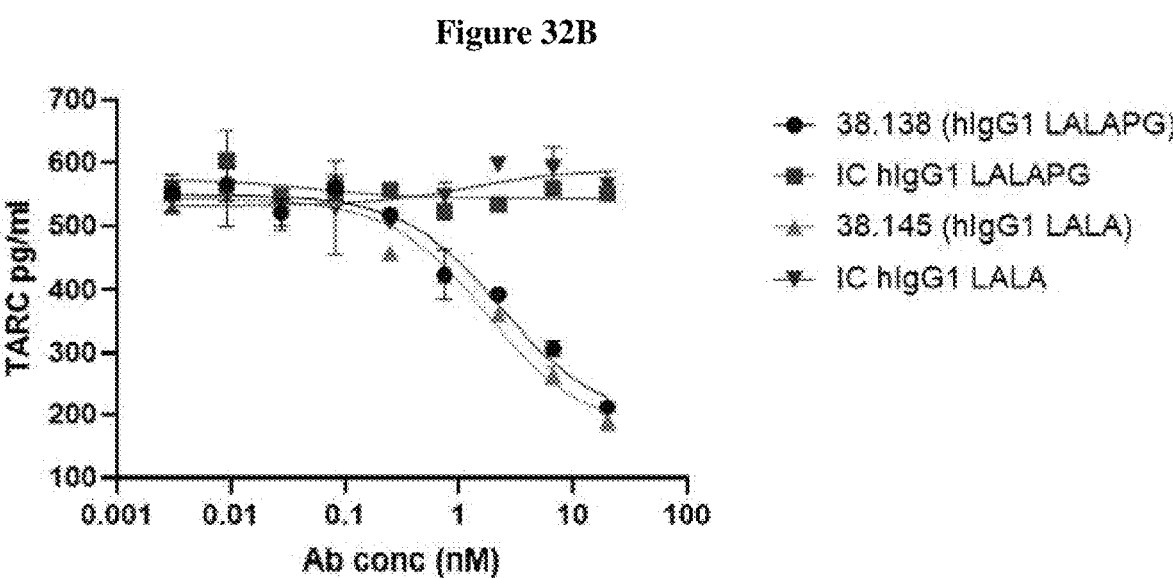
Figure 33A:
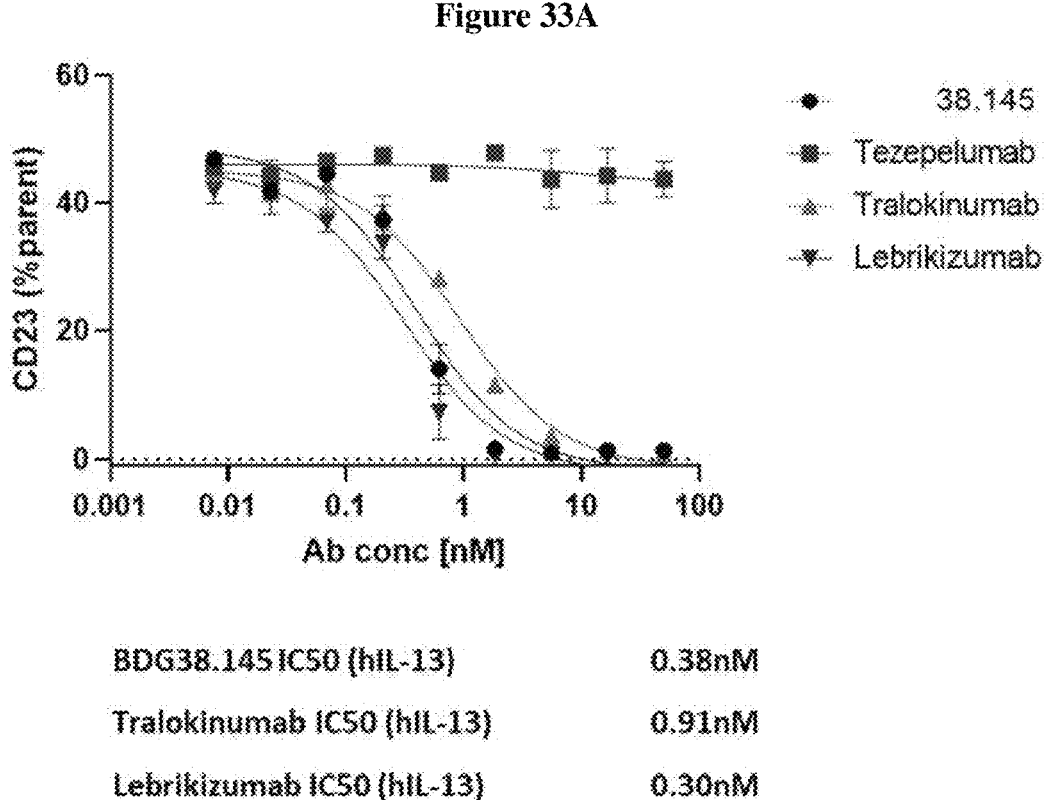
FIGS. 33A-33B show CD23 expression in monocytes is inhibited by antibody clone BDG38.145. hPBMCs were stimulated for 48 h with 0.7 nm IL-13.
Figure 33A:
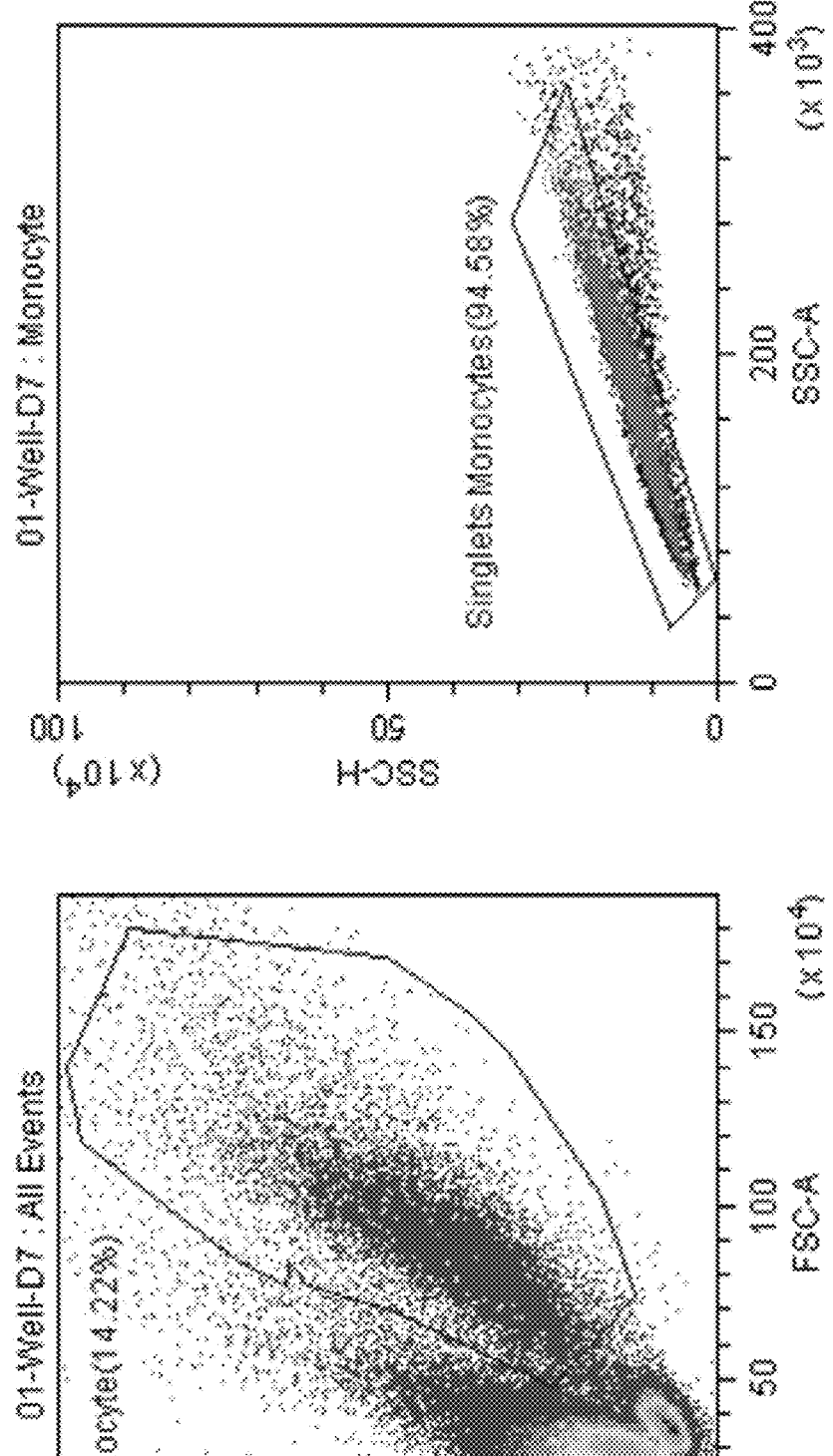
Figure 33B:
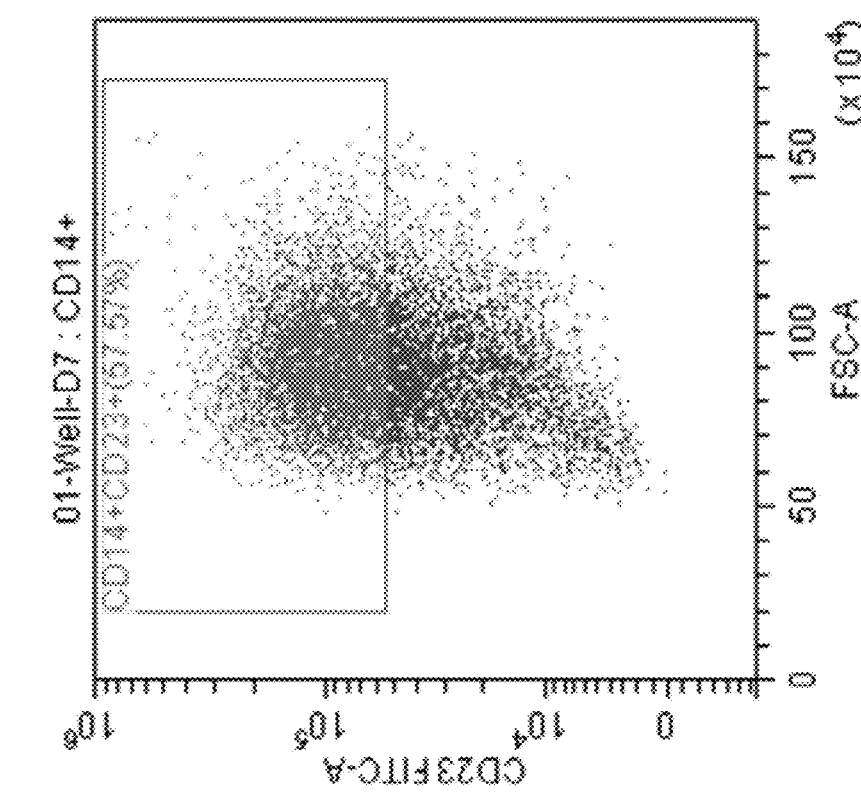
Figure 33B:
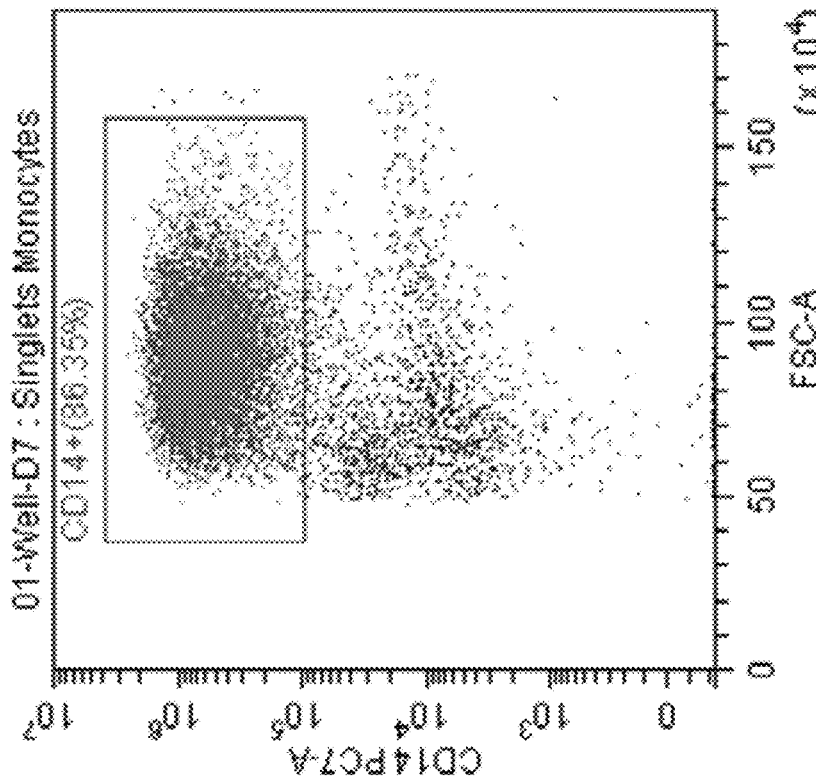

FIG. 32A shows antibodies 38.138 (hIgG1 LALAPG) and 38.145 (hIgG LALA) exhibit similar inhibition of CD23 expression in hPBMCs. IC50 of antibody inhibition of IL-13 was determined by measuring CD23 expression level in monocytes. At the end of 48 hours incubation of the cells with different concentrations of antibodies, the cells were detached from the bottom of the wells and labeled using PE-CF594-conjugated anti-CD3, PE-Cy7-conjugated anti-CD14, APC-conjugated anti-CD19 and FITC-conjugated anti-CD23 antibodies. CD23 percentage of CD14+ population was measured using flow cytometry. FIG. 32B shows antibodies 38.138 (hIgG1 LALAPG) and 38.145 (hIgG LALA) inhibit TARC expression in a similar manner IC50 of antibody inhibition of hTSLP and hIL-13 was determined by TARC inhibition as measured by ELISA.

Summary: The biochemical comparison performed here demonstrates that antibodies 38.138 (hIgG1 LALAPG) and 38.145 (hIgG LALA) exhibit similar functionality.

Example 7: Functional Comparison of Antibodies Having the Same VH/VL Regions with Different Fc Formats (hIgG1 LALA (BDG38.145) Vs LALAPG (BDG38.138)

Objective: To examine the functional properties of antibodies having the same VH/VL regions as clone 38.138 but having two different Fc formats. The two different Fc formats comprised mutations in the Fc region that result in reduced binding to the Fc receptor and the inability of the IgG1 to bind to antibody-dependent cellular cytotoxicity components. The formats for comparison were 38.138 (hIgG1 LALA-PG) and 38.145 (hIgG1 LALA). BDG38.138 and BSG38.145 share the same VH and VL sequences, and only differ in the Fc mutations.

Methods

PBMCs activation and treatment—Peripheral blood mononuclear cells (PBMCs) (Cell Generation, USA; CAT: 10102510) were used to determine hIL-13 and hTLSP inhibition by the antibodies. PBMCs were thawed and cultured in growth medium comprising of RPMI—1640, 10% PBS, 1% Glutamax, 1% Sodium-Pyruvate, 0.1% 2-ME, 1% Pen-Strep and 1% nonessential AA. The cells were seeded in 96 well plate at $5 \times 10^5$ cells/well and were allowed to rest for 1 hour at 37° C., 5% $CO_2$. hIL-13-His (Acro Biosystems, USA; CAT: IL3-H52H4) at a concentration of 0.7 nM, hTSLP-His (Acro Biosystems, USA; CAT: TSP-H52Hb) at a concentration of 70 pM, or a combination of both cytokines at these concentrations were added to the cells, followed immediately by addition of antibodies in serial dilutions, to a total of 200 uL/well. Cells were incubated for 48 hours at 37° C., 5% $CO_2$.

CD23 expression in monocytes—$IC_{50}$ of antibody inhibition of hIL-13 was determined by measuring CD23 expression level in monocytes. At the end of 48 hours incubation of the cells with different concentrations of antibodies, monocytes were detached from the bottom of the wells using cold PBS and scraping. Cells were labeled using anti-CD3 (BD Bioscience, USA; CAT: 562280), anti-CD14 (BioLegend, USA; CAT: 301814), anti-CD19 (BioLegend, USA; CAT: 302212) and anti-CD23 (BioLegend, USA; CAT: 338506) antibodies. CD23 percentage of CD14+ population was measured using CytoFLEX flow cytometer (Beckman Coulter, USA).

TARC levels in PBMCs supernatant—TARC levels were determined using TARC DUOSET ELISA kit (R&D systems, USA; CAT: DY364) according to the manufacturer's instructions. Briefly, ELISA high binding protein plates were coated with capture antibody, diluted in PBS. Plates were sealed and incubated overnight at 4° C. The following day plates were washed and blocked using 1% BSA in PBS at room temperature with shaking for 1 hour. The plates were washed three times in PBST, and supernatant from the PBMCs plates was diluted 1:1 in 1% BSA in PBS, transferred to the wells and incubated at room temperature with shaking for 2 hours. The plates were washed three times in PBST. Detection was performed using the kit's detection antibody (biotinylated) in PBS 1% BSA at room temperature with shaking for 2 hours followed by three washes in PBST and addition of Streptavidin-HRP in PBS 1% BSA for 30 minutes. Following 3 washes in PBST, the plates were developed by adding TMB and TMB-stop solution, and 450 nm. Values were analyzed using standard sample curve.

Results

The effect of inhibition of IL-13 and TSLP by either BDG38.138 or BDG38.145 antibodies was tested on human PBMCs. Total PBMC culture includes different cell types such as lymphocytes (including CD4+ T cells, Innate lymphoid cells (ILCs)), and monocytes. The effect of IL-13 and TSLP was assessed by measuring two readouts: CD23 expression levels on monocytes and TARC levels in PBMCs supernatant. The results for BDG38.138 are presented in Example 6 FIGS. 32A and 32B.

CD23 (FcεRII) is the "low affinity" receptor for IgE. Stimulation of PBMCs with IL-13 induces expression of CD23 in B cells and monocytes (May et al., (2012) Preclinical development of CAT-354, an IL-13 neutralizing antibody, for the treatment of severe uncontrolled asthma. British Journal of Pharmacology (2012) 166 177-193).

hPBMCs were stimulated with 0.7 nM IL-13 and treated with antibody 38.145 (LALA version), anti-IL-13, or anti- TSLP benchmarks (anti-IL13 and anti-TSLP positive controls) in increasing amounts ranging from 00 nM to 50 nM. After 48 hours of incubation the cells were analyzed by flow cytometry for CD23 expression on monocytes (defined as CD14+ cells) (FIG. 33). BDG 38.145 antibody's ability to neutralize IL-13 was better than anti-IL-13 Ab tralokinumab, the IC50 values being 0.38 nM and 0.91 nM, respectively. The IC50 value of lebrikizumab (anti-TSLP) is 0.38 nM, similar to the IC50 value of the 38.145 antibody.

Figure 34A:
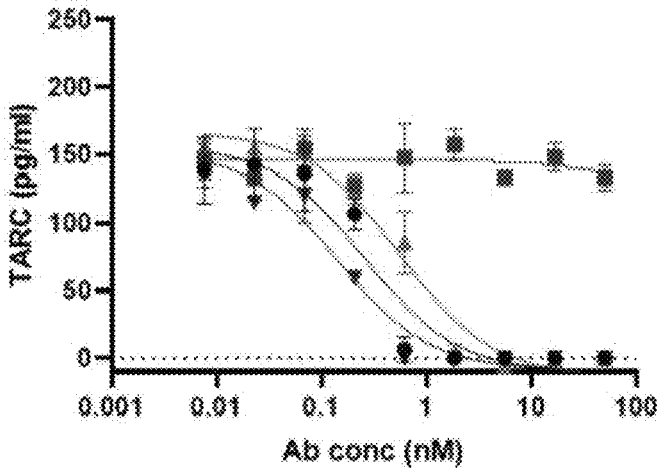
Figure 34B:
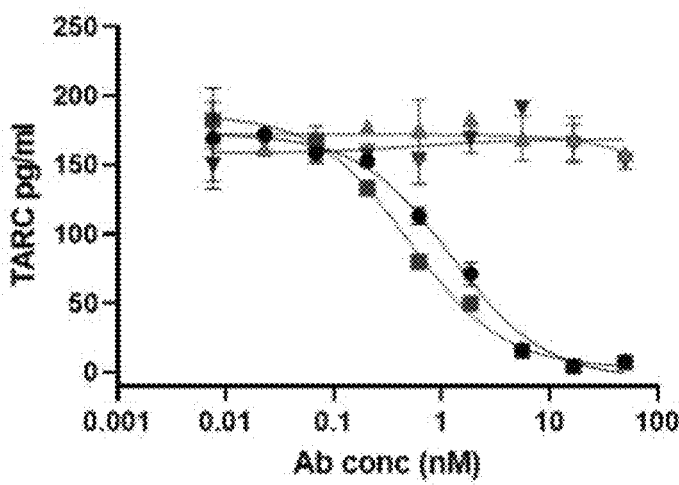

TARC (Thymus and Activation Regulated Chemokine, CCL17) is a chemokine produced in the thymus and by antigen-presenting cells like dendritic cells, macrophages, and monocytes. TARC-mediated recruitment of Th2 cells and CLA+ CD4+ T cells plays a key role in allergic diseases and serves as a clinical biomarker for AD severity as well as efficacy of treatment. Both IL-13 and TSLP directly upregulate TARC production by dendritic cells.

hPBMCs were stimulated with either 0.7 nm IL-13, 70 pM TSLP or with the combination of both cytokines, and treated with BDG38.138 and BDG38.145 antibodies, anti-IL-13, or anti-TSLP positive controls, in increasing amounts ranging from 0 nM to 50 nM. After 48 hours of incubation supernatant was collected to test TARC levels by ELISA (FIGS. 34A-34C).

When cells were stimulated with IL-13 alone (FIG. 34A), treatment with anti-IL-13 antibodies or 38.145 reduced TARC levels to 0, while anti-TSLP antibody, Tezepelumab, had no effect on TARC levels. According to these results, 38.145 inhibits IL-13 signaling in hPBMCs better than tralokinumab and similar to lebrikizumab. When cells were stimulated with TSLP alone (FIG. 34B), treatment with anti-TSLP Ab or 38.145 antibody reduced TARC levels to 0, while anti IL-13 Abs had no effect on TARC levels. This demonstrates that 38.145 inhibits TSLP signaling comparably with Tezepelumab. When cells were stimulated with both cytokines (FIG. 34C), the additive effect of IL-13 and TSLP on TARC levels can be seen in the maximal TARC levels, reaching ~320 pg/ml. Treatment with either anti IL-13 Abs or anti TSLP antibodies shows only partial inhibition of TARC levels, while treatment with BDG38.145 lowered TARC levels to 0. These results demonstrate the dual blockade of IL-13 and TSLP, where BDG38.145 completely downregulated TARC levels in IL-13 and TSLP stimulated hPBMCs, while antibodies targeting each cytokine demonstrate partial inhibition.

What is claimed is:

1. An isolated anti-IL-13, anti-TSLP dual binding antibody comprising a heavy chain variable region (VH) and a light chain variable region (VL), wherein said VH comprises heavy chain complementarity determining regions (HCDRs) HCDR1, HCDR2, and HCDR3, and said VL comprises light chain complementarity determining regions (LCDRs) LCDR1, LCDR2, and LCDR3, wherein (a) the HCDR1 comprises the amino acid sequence set forth in any one of SEQ ID NOs: 349, 355, 149 and 136;

(b) the HCDR2 comprises the amino acid sequence set forth in any one of SEQ ID NOs: 350, 352, 354, 356, and 150 or the sequence set forth as: I HX1 Y D G S N K (SEQ ID NO:142), wherein HX1 is any amino acid;

(c) the HCDR3 comprises the amino acid sequence set forth in any one of SEQ ID NOs: 351, 353, 357, 358, and 151 or the sequence set forth as: A R HX2 HX3 HX4 HX5 HX6 HX7 HX8 HX9 HX10 HX11 F D HX12 (SEQ ID NO:143), wherein HX2, HX3, HX4, HX5, HX6, HX7, HX8, HX9, HX10, HX11, and HX12 are any amino acid;

(d) the LCDR1 comprises the amino acid sequence of one of SEQ ID NOs: 364, 359, 362, 366, and 152 or the sequence set forth as LX1, LX2, G S K LX3 V (SEQ ID NO:144), wherein LX1, LX2, and LX3 are any amino acid;

(e) the LCDR2 comprises the amino acid sequence of DDV or DDS, or the sequence set forth as D D LX4, wherein LX4 is any amino acid; and (f) the LCDR3 comprises the amino acid sequence set forth in any one of SEQ ID NOs: 384, 361, 363, 365, 368, 370-374, 376-383, 385-407, and 154 or the sequence set forth as Q V W D LX5 LX6 S D LX7 V V (SEQ ID NO:146), wherein LX5, LX6, and LX7 are any amino acid.

2. The isolated dual binding antibody of claim 1, wherein the amino acid sequences of the HCDRs and LCDRs of said antibody are selected from any one of the following sets:

(a) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 384;

(b) HCDR1 comprises the amino acid sequence set forth in SEQ ID NO: 349, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 365;

(c) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 361;

(d) HCDR1 comprises the amino acid sequence set forth in SEQ ID NO: 349, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 371;

(e) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 362, LCDR2 comprises the amino acid sequence DDV, and LCDR3 comprises the amino acid sequence set forth in SEQ ID NO: 384;

(f) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO: 353, LCDR1 comprises the amino acid sequence set forth in SEQ ID NO: 362, LCDR2 comprises the amino acid sequence DDV, and LCDR3 comprises the amino acid sequence set forth in SEQ ID NO: 363;

(g) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 368;

(h) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 370;

(i) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO: 353, LCDR1 comprises the amino acid sequence set forth in SEQ ID NO: 362, LCDR2 comprises the amino acid sequence DDS, and LCDR3 comprises the amino acid sequence set forth in SEQ ID NO: 372;

(j) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 373;

(k) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 374;

(l) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 376;

(m) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 362, LCDR2 comprises the amino acid sequence DDV, and LCDR3 comprises the amino acid sequence set forth in SEQ ID NO: 377;

(n) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 378;

(o) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(p) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 380;

(q) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(r) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 381;

(s) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 369, LCDR2 comprises the amino acid sequence DDS, and LCDR3 comprises the amino acid sequence set forth in SEQ ID NO: 370;

(t) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 382;

(u) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 370;

(v) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 383;

(w) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 385;

(x) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 386;

(y) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 387;

(z) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 388;

(aa) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 389;

(bb) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(cc) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 390;

(dd) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 391;

(ee) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 392;

(ff) HCDR1 comprises the amino acid sequence set forth in SEQ ID NO: 355, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 393;

(gg) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 394;

(hh) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 395;

(ii) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 396;

(jj) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 397;

(kk) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 398;

(ll) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 388;

(mm) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 394;

(nn) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 398;

(oo) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 399;

(pp) HCDR1 is set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 400;

(qq) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 398;

(rr) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 378;

(ss) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 401;

(tt) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 369, LCDR2 comprises the amino acid sequence DDS, and LCDR3 comprises the amino acid sequence set forth in SEQ ID NO: 402;

(uu) HCDR1 comprises the amino acid sequence set forth in SEQ ID NO:349, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 369, LCDR2 comprises the amino acid sequence DDS, and LCDR3 comprises the amino acid sequence set forth in SEQ ID NO: 403;

(vv) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 375, LCDR2 comprises the amino acid sequence DDS, and LCDR3 comprises the amino acid sequence set forth in SEQ ID NO: 376;

(ww) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 402;

(xx) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 353, LCDR1 comprises the amino acid sequence set forth in SEQ ID NO: 359, LCDR2 comprises the amino acid sequence DDV, and LCDR3 comprises the amino acid sequence set forth in SEQ ID NO: 404;

(yy) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 405;

(zz) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 406;

(aaa) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 407; and (bbb) HCDR1 comprises the amino acid sequence set forth in SEQ ID NO: 355, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379.

3. The isolated dual binding antibody of claim 1, wherein said VH and said VL comprise the amino acid sequences set forth in SEQ ID NOs: 337 and 338, respectively; SEQ ID NOs: 213 and 214, respectively; SEQ ID NOs: 209 and 210, respectively; SEQ ID NOs: 219 and 220, respectively; SEQ ID NOs: 249 and 250, respectively; SEQ ID NOs: 155 and 156, respectively; SEQ ID NOs: 157 and 158, respectively; SEQ ID NOs: 4 and 3, respectively; SEQ ID NOs: 6 and 5, respectively; SEQ ID NOs: 8 and 7, respectively; SEQ ID NOs: 10 and 9, respectively; SEQ ID NOs: 12 and 11, respectively; SEQ ID NOs: 14 and 13, respectively; SEQ ID NOs: 16 and 15, respectively; SEQ ID NOs: 18 and 17, respectively; SEQ ID NOs: 20 and 19, respectively; SEQ ID NOs: 22 and 21, respectively; SEQ ID NOs: 24 and 23, respectively; SEQ ID NOs: 26 and 25, respectively; SEQ ID NOs: 28 and 27, respectively; SEQ ID NOs: 30 and 29, respectively; SEQ ID NOs: 32 and 31, respectively; SEQ ID NOs: 34 and 33, respectively; SEQ ID NOs: 36 and 35, respectively; SEQ ID NOs: 38 and 37, respectively; SEQ ID NOs: 40 and 39, respectively; SEQ ID NOs: 42 and 41, respectively; SEQ ID NOs: 44 and 43, respectively; SEQ ID NOs: 46 and 45, respectively; SEQ ID NOs: 48 and 47, respectively; SEQ ID NOs: 50 and 49, respectively; SEQ ID NOs: 52 and 51, respectively; or SEQ ID NOs: 54 and 53, respectively.

4. The isolated dual binding antibody of claim 1, wherein said antibody comprises an IgG, an Fv, an scFv, an Fab, an F (ab')$_2$, a minibody, a diabody, or a triabody, wherein said IgG is IgG1, IgG2, IgG3, or IgG4.

5. The isolated dual binding antibody of claim 4, wherein said IgG comprises a heavy chain (HC) comprising a mutation that reduces binding to an Fc receptor, wherein said dual binding antibody comprising this mutation is unable to bind to antibody-dependent cellular cytotoxicity components.

6. The isolated dual binding antibody of claim 5, wherein said mutation is a L234A L235A P329G (LALAPG) mutation or a L234A L235A (LALA) mutation.

7. The isolated dual binding antibody of claim 6, wherein said VH and said VL comprise the amino acid sequences set forth in SEQ ID NOs: 337 and 338, respectively, and said antibody comprises said L234A L235A P329G (LALAPG) mutation or said L234A L235A (LALA) mutation.

8. The isolated dual binding antibody of claim 7, wherein said antibody comprises a heavy chain (HC) and a light chain (LC), and wherein the amino acid sequence of said HC and LC are set forth in SEQ ID NOs: 408 and 409, respectively, or SEQ ID NOs: 410 and 409, respectively.

9. A composition comprising the isolated dual binding antibody of claim 1 and a pharmaceutically acceptable carrier.

10. An isolated polynucleotide construct encoding the isolated dual binding antibody of claim 1.

11. An expression vector comprising the polynucleotide construct of claim 10.

12. A host cell comprising the expression vector of claim 11.

13. An isolated anti-IL-13, anti-TSLP dual binding antibody comprising a heavy chain variable region (VH) and a light chain variable region (VL), wherein said VH comprises heavy chain complementarity determining regions (HCDRs) HCDR1, HCDR2, and HCDR3, said VL comprises light chain complementarity determining regions (LCDRs) LCDR1, LCDR2, and LCDR3, wherein the HCDR1, HCDR2, and HCDR3 comprise the amino acid sequences of SEQ ID NOs: 349, 350, and 351, respectively, and the LCDR1, LCDR2, and LCDR3 comprise the amino acid sequences of SEQ ID NO: 364, DDV and SEQ ID NO: 384, respectively.

14. An isolated anti-IL-13, anti-TSLP dual binding antibody comprising a heavy chain variable region (VH) and a light chain variable region (VL), wherein said VH and said VL comprise the amino acid sequences set forth in SEQ ID NOs: 337 and 338, respectively.

15. An isolated anti-IL-13, anti-TSLP dual binding antibody, comprising a heavy chain (HC) comprising a heavy chain variable region (VH) and a light chain (LC) comprising a light chain variable region (VL), wherein said HC comprises a L234A L235A P329G (LALAPG) mutation or a L234A L235A (LALA) mutation, and wherein the amino acid sequences of said VH and VL are set forth in SEQ ID NOs: 337 and 338, respectively.

16. The isolated dual binding antibody of claim 15, wherein the amino acid sequences of said HC and LC are set forth in SEQ ID NOs: 408 and 409, respectively, or SEQ ID NOs: 410 and 409, respectively.

17. A method of treating a subject suffering from a disease or condition, said method comprises administering to said subject a composition comprising an isolated anti-IL-13, anti-TSLP dual binding antibody comprising a heavy chain variable region (VH) and a light chain variable region (VL), wherein said VH comprises heavy chain complementarity determining regions (HCDRs) HCDR1, HCDR2, and HCDR3, said VL comprises light chain complementarity determining regions (LCDRs) LCDR1, LCDR2, and LCDR3, wherein (a) the HCDR1 comprises the amino acid sequence set forth in any one of SEQ ID NOs: 349, 355, 149 and 136;

(b) the HCDR2 comprises the amino acid sequence set forth in any one of SEQ ID NOs: 350, 352, 354, 356, and 150 or the sequence set forth as: I HX1 Y D G S N K (SEQ ID NO:142), wherein HX1 is any amino acid;

(c) the HCDR3 comprises the amino acid sequence set forth in any one of SEQ ID NOs: 351, 353, 357, 358, and 151 or the sequence set forth as: A R HX2 HX3 HX4 HX5 HX6 HX7 HX8 HX9 HX10 HX11 F D HX12 (SEQ ID NO: 143), wherein HX2, HX3, HX4, HX5, HX6, HX7, HX8, HX9, HX10, HX11, and HX12 are any amino acid;

(d) the LCDR1 comprises the amino acid sequence of one of SEQ ID NOs: 364, 359, 362, 366, 369, 375, and 152 or the sequence set forth as LX1, LX2, G S K LX3 V (SEQ ID NO:144), wherein LX1, LX2, and LX3 are any amino acid;

(e) the LCDR2 comprises the amino acid sequence of DDV or DDS, or the sequence set forth as D D LX4, wherein LX4 is any amino acid; and (f) the LCDR3 comprises the amino acid sequence set forth in any one of SEQ ID NOs: 384, 361, 363, 365, 368, 370-374, 376-383, 385-407, and 154 or the sequence set forth as Q V W D LX5 LX6 S D LX7 V V (SEQ ID NO:146), wherein LX5, LX6, and LX7 are any amino acid.

18. The method of claim 17, wherein the amino acid sequences of the HCDRs and LCDRs of said antibody are selected from any one of the following sets:

(a) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 384;

(b) HCDR1 comprises the amino acid sequence set forth in SEQ ID NO: 349, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 365;

(c) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 361;

(d) HCDR1 comprises the amino acid sequence set forth in SEQ ID NO: 349, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 371;

(e) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 362, LCDR2 comprises the amino acid sequence DDV, and LCDR3 comprises the amino acid sequence set forth in SEQ ID NO: 384;

(f) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO: 353, LCDR1 comprises the amino acid sequence set forth in SEQ ID NO: 362, LCDR2 comprises the amino acid sequence DDV, and LCDR3 comprises the amino acid sequence set forth in SEQ ID NO: 363;

(g) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO:

351, LCDR1 comprises the amino acid sequence set forth in SEQ ID NO: 366, LCDR2 comprises the amino acid sequence DDS, and LCDR3 comprises the amino acid sequence set forth in SEQ ID NO: 368;

(h) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 370;

(i) HCDR1 comprises the amino acid sequence set forth in SEQ ID NO: 349, HCDR2 comprises the amino acid sequence set forth in SEQ ID NO: 352, HCDR3 comprises the amino acid sequence set forth in SEQ ID NO: 353, LCDR1 comprises the amino acid sequence set forth in SEQ ID NO: 362, LCDR2 comprises the amino acid sequence DDS, and LCDR3 comprises the amino acid sequence set forth in SEQ ID NO: 372;

(j) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 373;

(k) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 364, LCDR2 comprises the amino acid sequence DDV, and LCDR3 comprises the amino acid sequence set forth in SEQ ID NO: 374;

(l) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 376;

(m) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 362, LCDR2 comprises the amino acid sequence DDV, and LCDR3 comprises the amino acid sequence set forth in SEQ ID NO: 377;

(n) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 378;

(o) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(p) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 359, LCDR2 comprises the amino acid sequence DDV, and LCDR3 comprises the amino acid sequence set forth in SEQ ID NO: 380;

(q) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(r) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 381;

(s) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 369, LCDR2 comprises the amino acid sequence DDS, and LCDR3 comprises the amino acid sequence set forth in SEQ ID NO: 370;

(t) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 382;

(u) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351,
LCDR1 comprises the amino acid sequence set forth in SEQ ID NO: 369,
LCDR2 comprises the amino acid sequence DDS, and LCDR3 comprises the amino acid sequence set forth in SEQ ID NO: 370;

(v) HCDR1 comprises the amino acid sequence set forth in SEQ ID NO: 355, HCDR2 comprises the amino acid sequence set forth in SEQ ID NO: 356,
HCDR3 comprises the amino acid sequence set forth in SEQ ID NO: 351,
LCDR1 comprises the amino acid sequence set forth in SEQ ID NO: 369,
LCDR2 comprises the amino acid sequence DDS, and LCDR3 comprises the amino acid sequence set forth in SEQ ID NO: 383;

(w) HCDR1 comprises the amino acid sequence set forth in SEQ ID NO: 355, HCDR2 comprises the amino acid sequence set forth in SEQ ID NO: 352,
HCDR3 comprises the amino acid sequence set forth in SEQ ID NO: 351, LCDR1 comprises the amino acid sequence set forth in SEQ ID NO: 366,
LCDR2 comprises the amino acid sequence DDS, and LCDR3 comprises the amino acid sequence set forth in SEQ ID NO: 385;

(x) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 386;

(y) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 387;

(z) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 388;

(aa) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 389;

(bb) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379;

(cc) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 390;

(dd) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 391;

(ee) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO:

351, LCDR1 comprises the amino acid sequence set forth in SEQ ID NO: 375, LCDR2 comprises the amino acid sequence DDS, and LCDR3 comprises the amino acid sequence set forth in SEQ ID NO: 392;

(ff) HCDR1 comprises the amino acid sequence set forth in SEQ ID NO: 355, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 393;

(gg) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 394;

(hh) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 395;

(ii) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 396;

(jj) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 397;

(kk) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 398;

(ll) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 388;

(mm) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 394;

(nn) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 398;

(oo) HCDR1 comprises the amino acid sequence set forth in SEQ ID NO: 355, HCDR2 comprises the amino acid sequence set forth in SEQ ID NO: 352, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 399;

(pp) HCDR1 is set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 400;

(qq) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 398;

(rr) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 378;

(ss) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 401;

(tt) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 369, LCDR2 comprises the amino acid sequence DDS, and LCDR3 comprises the amino acid sequence set forth in SEQ ID NO: 402;

(uu) HCDR1 comprises the amino acid sequence set forth in SEQ ID NO:349, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 369, LCDR2 comprises the amino acid sequence DDS, and LCDR3 comprises the amino acid sequence set forth in SEQ ID NO: 403;

(vv) HCDR1 comprises the amino acid sequence set forth in SEQ ID NO: 355, HCDR2 comprises the amino acid sequence set forth in SEQ ID NO: 356, HCDR3 comprises the amino acid sequence set forth in SEQ ID NO: 358, LCDR1 comprises the amino acid sequence set forth in SEQ ID NO: 375, LCDR2 comprises the amino acid sequence DDS, and LCDR3 comprises the amino acid sequence set forth in SEQ ID NO: 376;

(ww) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 402;

(xx) HCDR1 comprises the amino acid sequence set forth in SEQ ID NO: 349, HCDR2 comprises the amino acid sequence set forth in SEQ ID NO: 350, HCDR3 comprises the amino acid sequence set forth in SEQ ID NO: 353, LCDR1 comprises the amino acid sequence set forth in SEQ ID NO: 359, LCDR2 comprises the amino acid sequence DDV, and LCDR3 comprises the amino acid sequence set forth in SEQ ID NO: 404;

(yy) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 357, LCDR1 comprises the amino acid sequence set forth in SEQ ID NO: 375, LCDR2 comprises the amino acid sequence DDS, and LCDR3 comprises the amino acid sequence set forth in SEQ ID NO: 405;

(zz) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 366, LCDR2 comprises the amino acid sequence DDS, and LCDR3 comprises the amino acid sequence set forth in SEQ ID NO: 406;

(aaa) HCDR1 comprises the amino acid sequence set forth in SEQ ID NO: 355, HCDR2 comprises the amino acid sequence set forth in SEQ ID NO: 350, HCDR3 comprises the amino acid sequence set forth in SEQ ID NO: 351, LCDR1 comprises the amino acid sequence set forth in SEQ ID NO: 375, LCDR2 comprises the amino acid sequence DDS, and LCDR3 comprises the amino acid sequence set forth in SEQ ID NO: 407; and (bbb) HCDR1 comprises the amino acid sequence set forth in SEQ ID NO: 355, HCDR2 comprises the amino acid sequence set forth in SEQ ID NO: 354, HCDR3 comprises the amino acid sequence set forth in SEQ ID NO: 351, LCDR1 comprises the amino acid sequence set forth in SEQ ID NO: 369, LCDR2 comprises the amino acid sequence DDS, and LCDR3 comprises the amino acid sequence set forth in SEQ ID NO: 379.

19. The method of claim 17, wherein said disease or condition is an allergic or respiratory condition, an inflammatory or autoimmune condition, or tumors or cancers.

20. The method of claim 17, wherein said disease or condition is asthma, allergic asthma, nonallergic asthma, severe asthma, mild asthma, chronic obstructive pulmonary disease (COPD), a condition involving airway inflammation, cystic fibrosis, allergic lung disease, airway hyperresponsiveness, goblet cell metaplasia, mucus hypersecretion, airway remodeling, pulmonary fibrosis, atopic dermatitis, urticaria, eczema, allergic enterogastritis, allergic rhinitis, inflammatory bowel diseases, liver cirrhosis or fibrosis, or a combination thereof.

21. A method of treating a subject suffering from a disease or condition, said method comprises administering to said subject a composition comprising an isolated anti-IL-13, anti-TSLP dual binding antibody comprising a heavy chain (HC) comprising a heavy chain variable region (VH) and a light chain (LC) comprising a light chain variable region (VL), wherein said HC comprises a L234A L235A P329G (LALAPG) mutation or a L234A L235A (LALA) mutation, and wherein the amino acid sequences of said VH and VL are set forth in SEQ ID NOs: 337 and 338, respectively.

22. The method of claim 21, wherein amino acid sequences of said HC and LC are set forth in SEQ ID NOs: 408 and 409, respectively, or SEQ ID NOs: 410 and 409, respectively.

\* \* \* \* \*

SEQUENCE LISTING

```
Sequence total quantity: 410
SEQ ID NO: 1            moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 1
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVHEAFD IWGQGTMVTV  120
SS                                                                 122

SEQ ID NO: 2            moltype = AA  length = 108
FEATURE                 Location/Qualifiers
REGION                  1..108
                        note = Description of Artificial Sequence: Synthetic
                         polypeptide
source                  1..108
                        mol_type = protein
```

```
                              organism = synthetic construct
SEQUENCE: 2
SYVLTQPPSV SVAPGQTARI TCGGNNLGSK SVHWYQQKPG QAPVLVVYDD SDRPSWIPER  60
FSGSNSGNTA TLTISRGEAG DEADYYCQVW DSSSDHVVFG GGTKLTVL               108

SEQ ID NO: 3              moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 3
SYVLTQPPSV SVAPGQTARI TCGGNLIGSK LVHWYQQKPG QAPVLVVYDD SDRPSLIPER  60
FSGSNSGNTA TLTISRVEAG DEADYYCQVW DSSSDGVVFG GGTKLTVL               108

SEQ ID NO: 4              moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 4
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELTAEAFD IWGQGTMVTV  120
SS                                                                 122

SEQ ID NO: 5              moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 5
SYVLTQPPSV SVAPGQTARI TCGGNLIGSK LVHWYQQKPG QAPVLVVYDD SDRPSLIPER  60
FSGSNSGNTA TLTISRVEAG DEADYYCQVW DSSSDGVVFG GGTKLTVL               108

SEQ ID NO: 6              moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 6
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVAEAFD LWGQGTMVTV  120
SS                                                                 122

SEQ ID NO: 7              moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 7
SYVLTQPPSV SVAPGQTARI TCGGNLIGSK LVHWYQQKPG QAPVLVVYDD SDRPSLIPER  60
FSGSNSGNTA TLTISRVEAG DEADYYCQVW DTSSDGVVFG GGTKLTVL               108

SEQ ID NO: 8              moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 8
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWQLVAEAFD IWGQGTMVTV  120
SS                                                                 122
```

```
SEQ ID NO: 9              moltype = AA   length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 9
SYVLTQPPSV SVAPGQTARI TCGGNLIGSK LVHWYQQKPG QAPVLVVYDD SDRPSAIPER   60
FSGSNSGNTA TLTISRVEAG DEADYYCQVW DTSSDGVVFG GGTKLTVL              108

SEQ ID NO: 10             moltype = AA   length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 10
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWQLVAEAFD IWGQGTMVTV  120
SS                                                                122

SEQ ID NO: 11             moltype = AA   length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 11
SYVLTQPPSV SVAPGQTARI TCGGNLIGSK LVHWYQQKPG QAPVLVVYDD SDRPSLIPER   60
FSGSNSGNTA TLTISRVEAG DEADYYCQVW DTSSDGVVFG GGTKLTVL              108

SEQ ID NO: 12             moltype = AA   length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 12
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD LWGQGTMVTV  120
SS                                                                122

SEQ ID NO: 13             moltype = AA   length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 13
SYVLTQPPSV SVAPGQTARI TCGGNLLGSK LVHWYQQKPG QAPVLVVYDD SDRPSAIPER   60
FSGSNSGNTA TLTISRVEAG DEADYYCQVW DSSSDHVVFG GGTKLTVL              108

SEQ ID NO: 14             moltype = AA   length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 14
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD IWGQGTMVTV  120
SS                                                                122

SEQ ID NO: 15             moltype = AA   length = 108
FEATURE                  Location/Qualifiers
REGION                   1..108
```

-continued

```
                              note = Description of Artificial Sequence: Synthetic
                               polypeptide
source                        1..108
                              mol_type = protein
                              organism = synthetic construct
SEQUENCE: 15
SYVLTQPPSV SVAPGQTARI TCGGNLIGSK LVHWYQQKPG QAPVLVVYDD SDRPSRIPER   60
FSGSNSGNTA TLTISRVEAG DEADYYCQVW DSSSDHVVFG GGTKLTVL                 108

SEQ ID NO: 16                 moltype = AA   length = 122
FEATURE                       Location/Qualifiers
REGION                        1..122
                              note = Description of Artificial Sequence: Synthetic
                               polypeptide
source                        1..122
                              mol_type = protein
                              organism = synthetic construct
SEQUENCE: 16
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWMLVAEAFD LWGQGTMVTV   120
SS                                                                  122

SEQ ID NO: 17                 moltype = AA   length = 108
FEATURE                       Location/Qualifiers
REGION                        1..108
                              note = Description of Artificial Sequence: Synthetic
                               polypeptide
source                        1..108
                              mol_type = protein
                              organism = synthetic construct
SEQUENCE: 17
SYVLTQPPSV SVAPGQTARI TCGGNLIGSK LVHWYQQKPG QAPVLVVYDD SDRPSRIPER   60
FSGSNSGNTA TLTISRVEAG DEADYYCQVW DSSSDHVVFG GGTKLTVL                 108

SEQ ID NO: 18                 moltype = AA   length = 122
FEATURE                       Location/Qualifiers
REGION                        1..122
                              note = Description of Artificial Sequence: Synthetic
                               polypeptide
source                        1..122
                              mol_type = protein
                              organism = synthetic construct
SEQUENCE: 18
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWEWVAEAFD LWGQGTMVTV   120
SS                                                                  122

SEQ ID NO: 19                 moltype = AA   length = 108
FEATURE                       Location/Qualifiers
REGION                        1..108
                              note = Description of Artificial Sequence: Synthetic
                               polypeptide
source                        1..108
                              mol_type = protein
                              organism = synthetic construct
SEQUENCE: 19
SYVLTQPPSV SVAPGQTARI TCGGNLIGSK LVHWYQQKPG QAPVLVVYDD SDRPSRIPER   60
FSGSNSGNTA TLTISRVEAG DEADYYCQVW DSSSDHVVFG GGTKLTVL                 108

SEQ ID NO: 20                 moltype = AA   length = 122
FEATURE                       Location/Qualifiers
REGION                        1..122
                              note = Description of Artificial Sequence: Synthetic
                               polypeptide
source                        1..122
                              mol_type = protein
                              organism = synthetic construct
SEQUENCE: 20
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD MWGQGTMVTV   120
SS                                                                  122

SEQ ID NO: 21                 moltype = AA   length = 108
FEATURE                       Location/Qualifiers
REGION                        1..108
                              note = Description of Artificial Sequence: Synthetic
                               polypeptide
source                        1..108
                              mol_type = protein
```

-continued

```
                             organism = synthetic construct
SEQUENCE: 21
SYVLTQPPSV SVAPGQTARI TCGGNLIGSK LVHWYQQKPG QAPVLVVYDD SDRPSKIPER  60
FSGSNSGNTA TLTISRVEAG DEADYYCQVW DSSSDHVVFG GGTKLTVL              108

SEQ ID NO: 22               moltype = AA   length = 122
FEATURE                     Location/Qualifiers
REGION                      1..122
                            note = Description of Artificial Sequence: Synthetic
                             polypeptide
source                      1..122
                            mol_type = protein
                            organism = synthetic construct
SEQUENCE: 22
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELVAEAFD LWGQGTMVTV 120
SS                                                                122

SEQ ID NO: 23               moltype = AA   length = 108
FEATURE                     Location/Qualifiers
REGION                      1..108
                            note = Description of Artificial Sequence: Synthetic
                             polypeptide
source                      1..108
                            mol_type = protein
                            organism = synthetic construct
SEQUENCE: 23
SYVLTQPPSV SVAPGQTARI TCGGNLIGSK LVHWYQQKPG QAPVLVVYDD SDRPSDIPER  60
FSGSNSGNTA TLTISRVEAG DEADYYCQVW DTSSDHVVFG GGTKLTVL              108

SEQ ID NO: 24               moltype = AA   length = 122
FEATURE                     Location/Qualifiers
REGION                      1..122
                            note = Description of Artificial Sequence: Synthetic
                             polypeptide
source                      1..122
                            mol_type = protein
                            organism = synthetic construct
SEQUENCE: 24
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWEYVAEAFD LWGQGTMVTV 120
SS                                                                122

SEQ ID NO: 25               moltype = AA   length = 108
FEATURE                     Location/Qualifiers
REGION                      1..108
                            note = Description of Artificial Sequence: Synthetic
                             polypeptide
source                      1..108
                            mol_type = protein
                            organism = synthetic construct
SEQUENCE: 25
SYVLTQPPSV SVAPGQTARI TCGGNIIGSK LVHWYQQKPG QAPVLVVYDD GDRPSGIPER  60
FSGSNSGNTA TLTISRVEAG DEADYYCQVW DTSSDHVVFG GGTKLTVL              108

SEQ ID NO: 26               moltype = AA   length = 122
FEATURE                     Location/Qualifiers
REGION                      1..122
                            note = Description of Artificial Sequence: Synthetic
                             polypeptide
source                      1..122
                            mol_type = protein
                            organism = synthetic construct
SEQUENCE: 26
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELTAEAFD LWGQGTMVTV 120
SS                                                                122

SEQ ID NO: 27               moltype = AA   length = 108
FEATURE                     Location/Qualifiers
REGION                      1..108
                            note = Description of Artificial Sequence: Synthetic
                             polypeptide
source                      1..108
                            mol_type = protein
                            organism = synthetic construct
SEQUENCE: 27
SYVLTQPPSV SVAPGQTARI TCGGNLLGSK LVHWYQQKPG QAPVLVVYDD GDRPSLIPER  60
FSGSNSGNTA TLTISRVEAG DEADYYCQVW DTSSDHVVFG GGTKLTVL              108
```

```
SEQ ID NO: 28          moltype = AA   length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 28
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD LWGQGTMVTV  120
SS                                                                 122

SEQ ID NO: 29          moltype = AA   length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 29
SYVLTQPPSV SVAPGQTARI TCGGNLLGSK LVHWYQQKPG QAPVLVVYDD SDRPSEIPER   60
FSGSNSGNTA TLTISRVEAG DEADYYCQVW DTSSDGVVFG GGTKLTVL              108

SEQ ID NO: 30          moltype = AA   length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 30
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELTAEAFD IWGQGTMVTV  120
SS                                                                 122

SEQ ID NO: 31          moltype = AA   length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 31
SYVLTQPPSV SVAPGQTARI TCGGNLLGSK LVHWYQQKPG QAPVLVVYDD SDRPSWIPER   60
FSGSNSGNTA TLTISRVEAG DEADYYCQVW DTSSDHVVFG GGTKLTVL              108

SEQ ID NO: 32          moltype = AA   length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 32
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELTAEAFD LWGQGTMVTV  120
SS                                                                 122

SEQ ID NO: 33          moltype = AA   length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 33
SYVLTQPPSV SVAPGQTARI TCGGNLIGSK LVHWYQQKPG QAPVLVVYDD SDRPSAIPER   60
FSGSNSGNTA TLTISRVEAG DEADYYCQVW DTSSDHVVFG GGTKLTVL              108

SEQ ID NO: 34          moltype = AA   length = 122
FEATURE                Location/Qualifiers
REGION                 1..122
```

-continued

```
                            note = Description of Artificial Sequence: Synthetic
                             polypeptide
source                      1..122
                            mol_type = protein
                            organism = synthetic construct
SEQUENCE: 34
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELTSEAFD LWGQGTMVTV  120
SS                                                                 122

SEQ ID NO: 35              moltype = AA  length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 35
SYVLTQPPSV SVAPGQTARI TCGGNLIGSK LVHWYQQKPG QAPVLVVYDD SDRPSEIPER  60
FSGSNSGNTA TLTISRVEAG DEADYYCQVW DSSSDGVVFG GGTKLTVL                108

SEQ ID NO: 36              moltype = AA  length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 36
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWELTSEAFD LWGQGTMVTV  120
SS                                                                 122

SEQ ID NO: 37              moltype = AA  length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 37
SYVLTQPPSV SVAPGQTARI TCGGNIIGSK LVHWYQQKPG QAPVLVVYDD SDRPSGIPER  60
FSGSNSGNTA TLTISRVEAG DEADYYCQVW DSGSDHVVFG GGTKLTVL                108

SEQ ID NO: 38              moltype = AA  length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 38
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARAP QWLLVAEAFD LWGQGTMVTV  120
SS                                                                 122

SEQ ID NO: 39              moltype = AA  length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 39
SYVLTQPPSV SVAPGQTARI TCGGNIIGSK LVHWYQQKPG QAPVLVVYDD SDRPSDIPER  60
FSGSNSGNTA TLTISRVEAG DEADYYCQVW DSGSDGVVFG GGTKLTVL                108

SEQ ID NO: 40              moltype = AA  length = 122
FEATURE                    Location/Qualifiers
REGION                     1..122
                           note = Description of Artificial Sequence: Synthetic
                            polypeptide
source                     1..122
                           mol_type = protein
```

-continued

```
                              organism = synthetic construct
SEQUENCE: 40
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD LWGQGTMVTV  120
SS                                                                 122

SEQ ID NO: 41            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 41
SYVLTQPPSV SVAPGQTARI TCGGNLIGSK LVHWYQQKPG QAPVLVVYDD GDRPSWIPER   60
FSGSNSGNTA TLTISRVEAG DEADYYCQVW DSGSDGVVFG GGTKLTVL                108

SEQ ID NO: 42            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 42
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD LWGQGTMVTV  120
SS                                                                 122

SEQ ID NO: 43            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 43
SYVLTQPPSV SVAPGQTARI TCGGNLIGSK LVHWYQQKPG QAPVLVVYDD SDRPSRIPER   60
FSGSNSGNTA TLTISRVEAG DEADYYCQVW DSGSDGVVFG GGTKLTVL                108

SEQ ID NO: 44            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 44
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWVLVSEAFD LWGQGTMVTV  120
SS                                                                 122

SEQ ID NO: 45            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 45
SYVLTQPPSV SVAPGQTARI TCGGNIIGSK LVHWYQQKPG QAPVLVVYDD SDRPSAIPER   60
FSGSNSGNTA TLTISRVEAG DEADYYCQVW DSSSDGVVFG GGTKLTVL                108

SEQ ID NO: 46            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 46
QMQLVESGGG VVQPGRSLRL SCAASGFTFR TYGMHWVRQA PGKGLEWVAV IWYDGSNKHY   60
ADSVKGRFTI TRDNSKNTLN LQMNSLRAED TAVYYCARAP QWELVAEAFD LWGQGTMVTV  120
```

-continued

```
SS                                                            122

SEQ ID NO: 47            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 47
SYVLTQPPSV SVAPGQTARI TCGGNNIGSK LVHWYQQKPG QAPVLVVYDD SDRPSGIPER  60
FSGSNSGNTA TLTISRVEAG DEADYYCQVW DSSSDGVVFG GGTKLTVL               108

SEQ ID NO: 48            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 48
QMQLVESGGG VVQPGRSLRL SCAASGFTFR TYGMHWVRQA PGKGLEWVAV ISYDGSNKHY  60
ADSVKGRFTI TRDNSKNTLN LQMNSLRAED TAVYYCARSP QWEWVHEAFD MWGQGTMVTV  120
SS                                                            122

SEQ ID NO: 49            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 49
SYVLTQPPSV SVAPGQTARI TCGGNILGSK LVHWYQQKPG QAPVLVVYDD SDRPSEIPER  60
FSGSNSGNTA TLTISRVEAG DEADYYCQVW DTSSDGVVFG GGTKLTVL               108

SEQ ID NO: 50            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 50
QMQLVESGGG VVQPGRSLRL SCAASGFTFR TYGMHWVRQA PGKGLEWVAV ISYDGSNKHY  60
ADSVKGRFTI TRDNSKNTLN LQMNSLRAED TAVYYCARSP QWEWVHEAFD LWGQGTMVTV  120
SS                                                            122

SEQ ID NO: 51            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 51
SYVLTQPPSV SVAPGQTARI TCGGNNIGSK LVHWYQQKPG QAPVLVVYDD SDRPSRIPER  60
FSGSNSGNTA TLTISRVEAG DEADYYCQVW DTSSDGVVFG GGTKLTVL               108

SEQ ID NO: 52            moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 52
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARSP QWEWVHEAFD LWGQGTMVTV  120
SS                                                            122

SEQ ID NO: 53            moltype = AA  length = 108
FEATURE                  Location/Qualifiers
```

```
REGION                  1..108
                        note = Description of Artificial Sequence: Synthetic
                         polypeptide
source                  1..108
                        mol_type = protein
                        organism = synthetic construct
SEQUENCE: 53
SYVLTQPPSV SVAPGQTARI TCGGNLIGSK LVHWYQQKPG QAPVLVVYDD GDRPSWIPER  60
FSGSNSGNTA TLTISRVEAG DEADYYCQVW DSSSDGVVFG GGTKLTVL                108

SEQ ID NO: 54           moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 54
QMQLVESGGG VVQPGRSLRL SCAASGFTFR TYGMHWVRQA PGKGLEWVAV IWYDGSNKHY  60
ADSVKGRFTI TRDNSKNTLN LQMNSLRAED TAVYYCARSP QWEWVHEAFD LWGQGTMVTV  120
SS                                                                 122

SEQ ID NO: 55           moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 55
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgcagttt attactgtgc ccgtgcacca  300
cagtgggaat tagtacacga agcattcgat atctggggtc agggtactat ggtgaccgtt  360
agctct                                                             366

SEQ ID NO: 56           moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 56
tcttacgtgc tgactcaacc accatcagtg tctgtagcac caggccagac cgcacgtatt  60
acctgtggcg gtaacaatct gggctctaag tctgttcact ggtatcagca aaaaccaggc  120
caggcaccag tactggttgt gtacgatgat tccgatcgtc caagctggat tccagagcgt  180
ttcagcggct ctaattccgg caacaccgct actctgacta tttcccgtgg ggaagccggc  240
gatgaagccg actactattg ccaggtctgg gactcttctt ccgaccatgt agtctttggc  300
gggggcacca aactgaccgt tttg                                         324

SEQ ID NO: 57           moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 57
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacggcgga agcattcgat atttggggcc agggcactat ggtgaccgtt  360
agctct                                                             366

SEQ ID NO: 58           moltype = DNA   length = 324
FEATURE                 Location/Qualifiers
misc_feature            1..324
                        note = Description of Artificial Sequence: Synthetic
                         polynucleotide
source                  1..324
```

```
                        mol_type = other DNA
                        organism = synthetic construct
SEQUENCE: 58
tcttacgtgc tgactcaacc accatcagtg tctgtagcac caggccagac cgcacgtatt  60
acctgtggcg gtaacctgat cggctctaag ctggttcact ggtatcagca aaaaccaggc  120
caggcaccag tactggttgt gtacgatgat agcgatcgtc caagcctgat tccagagcgt  180
ttcagcggct ctaattccgg caacaccgct actctgacta tttcccgtgt tgaagccggc  240
gatgaagccg actactattg ccaggtctgg gactctagct ccgacggtgt agtctttggc  300
gggggcacca aactgaccgt tttg                                         324

SEQ ID NO: 59             moltype = DNA   length = 366
FEATURE                   Location/Qualifiers
misc_feature             1..366
                         note = Description of Artificial Sequence: Synthetic
                          polynucleotide
source                   1..366
                         mol_type = other DNA
                         organism = synthetic construct
SEQUENCE: 59
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtagcgga agcattcgat ctgtgggggcc agggcactat ggtgaccgtt  360
agctct                                                            366

SEQ ID NO: 60             moltype = DNA   length = 324
FEATURE                   Location/Qualifiers
misc_feature             1..324
                         note = Description of Artificial Sequence: Synthetic
                          polynucleotide
source                   1..324
                         mol_type = other DNA
                         organism = synthetic construct
SEQUENCE: 60
tcttacgtgc tgactcaacc accatcagtg tctgtagcac caggccagac cgcacgtatt  60
acctgtggcg gtaacctgat cggctctaag ctggttcact ggtatcagca aaaaccaggc  120
caggcaccag tactggttgt gtacgatgat agcgatcgtc caagcctgat tccagagcgt  180
ttcagcggct ctaattccgg caacaccgct actctgacta tttcccgtgt tgaagccggc  240
gatgaagccg actactattg ccaggtctgg gactctagct ccgacggtgt agtctttggc  300
gggggcacca aactgaccgt tttg                                         324

SEQ ID NO: 61             moltype = DNA   length = 366
FEATURE                   Location/Qualifiers
misc_feature             1..366
                         note = Description of Artificial Sequence: Synthetic
                          polynucleotide
source                   1..366
                         mol_type = other DNA
                         organism = synthetic construct
SEQUENCE: 61
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggcagt tagtagcgga agcattcgat atttggggcc agggcactat ggtgaccgtt  360
agctct                                                            366

SEQ ID NO: 62             moltype = DNA   length = 324
FEATURE                   Location/Qualifiers
misc_feature             1..324
                         note = Description of Artificial Sequence: Synthetic
                          polynucleotide
source                   1..324
                         mol_type = other DNA
                         organism = synthetic construct
SEQUENCE: 62
tcttacgtgc tgactcaacc accatcagtg tctgtagcac caggccagac cgcacgtatt  60
acctgtggcg gtaacctgat cggctctaag ctggttcact ggtatcagca aaaaccaggc  120
caggcaccag tactggttgt gtacgatgat agcgatcgtc caagccttat tccagagcgt  180
ttcagcggct ctaattccgg caacaccgct actctgacta tttcccgtgt tgaagccggc  240
gatgaagccg actactattg ccaggtctgg gacaccagct ccgacggtgt agtctttggc  300
gggggcacca aactgaccgt tttg                                         324

SEQ ID NO: 63             moltype = DNA   length = 366
FEATURE                   Location/Qualifiers
misc_feature             1..366
```

-continued

```
                              note = Description of Artificial Sequence: Synthetic
                               polynucleotide
source                        1..366
                              mol_type = other DNA
                              organism = synthetic construct
SEQUENCE: 63
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtggcagt tagtagccga agcattcgat atatggggcc agggcactat ggtgaccgtt   360
agctct                                                              366

SEQ ID NO: 64            moltype = DNA   length = 324
FEATURE                  Location/Qualifiers
misc_feature            1..324
                              note = Description of Artificial Sequence: Synthetic
                               polynucleotide
source                        1..324
                              mol_type = other DNA
                              organism = synthetic construct
SEQUENCE: 64
tcttacgtgc tgactcaacc accatcagtg tctgtagcac caggccagac cgcacgtatt    60
acctgtggcg gtaacctgat cggctctaag ctggttcact ggtatcagca aaaaccaggc   120
caggcaccag tactggttgt gtacgatgat agcgatcgct caagcgctat tccagagcgt   180
ttcagcggct ctaattccgg caacaccgct actctgacta tttcccgtgt tgaagccggc   240
gatgaagccg actactattg ccaggtctgg gacactagct ccgacggtgt agtctttggc   300
ggggcacca aactgaccgt tttg                                           324

SEQ ID NO: 65            moltype = DNA   length = 366
FEATURE                  Location/Qualifiers
misc_feature            1..366
                              note = Description of Artificial Sequence: Synthetic
                               polynucleotide
source                        1..366
                              mol_type = other DNA
                              organism = synthetic construct
SEQUENCE: 65
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtggcgga agcattcgat ctttggggcc agggcactat ggtgaccgtt   360
agctct                                                              366

SEQ ID NO: 66            moltype = DNA   length = 324
FEATURE                  Location/Qualifiers
misc_feature            1..324
                              note = Description of Artificial Sequence: Synthetic
                               polynucleotide
source                        1..324
                              mol_type = other DNA
                              organism = synthetic construct
SEQUENCE: 66
tcttacgtgc tgactcaacc accatcagtg tctgtagcac caggccagac cgcacgtatt    60
acctgtggcg gtaacctgat cggctctaag ctggttcact ggtatcagca aaaaccaggc   120
caggcaccag tactggttgt gtacgatgat agcgatcgtc caagccttat tccagagcgt   180
ttcagcggct ctaattccgg caacaccgct actctgacta tttcccgtgt tgaagccggc   240
gatgaagccg actactattg ccaggtctgg gacaccagct ccgacggtgt agtctttggc   300
ggggcacca aactgaccgt tttg                                           324

SEQ ID NO: 67            moltype = DNA   length = 366
FEATURE                  Location/Qualifiers
misc_feature            1..366
                              note = Description of Artificial Sequence: Synthetic
                               polynucleotide
source                        1..366
                              mol_type = other DNA
                              organism = synthetic construct
SEQUENCE: 67
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tggtagccga agcattcgat atctggggcc agggcactat ggtgaccgtt   360
agctct                                                              366
```

```
SEQ ID NO: 68            moltype = DNA  length = 324
FEATURE                  Location/Qualifiers
misc_feature             1..324
                         note = Description of Artificial Sequence: Synthetic
                          polynucleotide
source                   1..324
                         mol_type = other DNA
                         organism = synthetic construct
SEQUENCE: 68
tcttacgtgc tgactcaacc accatcagtg tctgtagcac caggccagac cgcacgtatt   60
acctgtggcg gtaacctgct gggctctaag ctggttcact ggtatcagca aaaaccaggc  120
caggcaccag tactggttgt gtacgatgat agcgatcgtc caagcgcaat tccagagcgt  180
ttcagcggct ctaattccgg caacaccgct actctgacta tttcccgtgt tgaagccggc  240
gatgaagccg actactattg ccaggtctgg gactctagct ccgaccacgt agtctttggc  300
gggggcacca aactgaccgt tttg                                         324

SEQ ID NO: 69            moltype = DNA  length = 366
FEATURE                  Location/Qualifiers
misc_feature             1..366
                         note = Description of Artificial Sequence: Synthetic
                          polynucleotide
source                   1..366
                         mol_type = other DNA
                         organism = synthetic construct
SEQUENCE: 69
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggatgt tagtagcgga agcattcgat ctatggggcc agggcactat ggtgaccgtt  360
agctct                                                            366

SEQ ID NO: 70            moltype = DNA  length = 324
FEATURE                  Location/Qualifiers
misc_feature             1..324
                         note = Description of Artificial Sequence: Synthetic
                          polynucleotide
source                   1..324
                         mol_type = other DNA
                         organism = synthetic construct
SEQUENCE: 70
tcttacgtgc tgactcaacc accatcagtg tctgtagcac caggccagac cgcacgtatt   60
acctgtggcg gtaacctgat cggctctaag ctggttcact ggtatcagca aaaaccaggg  120
caggcaccag tactggttgt gtacgatgat agcgatcgtc caagccggat tccagagcgt  180
ttcagcggct ctaattccgg caacaccgct actctgacta tttcccgtgt tgaagccggc  240
gatgaagccg actactattg ccaggtctgg gactccagct ccgaccatgt agtctttggc  300
gggggcacca aactgaccgt tttg                                         324

SEQ ID NO: 71            moltype = DNA  length = 366
FEATURE                  Location/Qualifiers
misc_feature             1..366
                         note = Description of Artificial Sequence: Synthetic
                          polynucleotide
source                   1..366
                         mol_type = other DNA
                         organism = synthetic construct
SEQUENCE: 71
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat gggtagccga agcattcgat ctgtggggcc agggcactat ggtgaccgtt  360
agctct                                                            366

SEQ ID NO: 72            moltype = DNA  length = 324
FEATURE                  Location/Qualifiers
misc_feature             1..324
                         note = Description of Artificial Sequence: Synthetic
                          polynucleotide
source                   1..324
                         mol_type = other DNA
                         organism = synthetic construct
SEQUENCE: 72
tcttacgtgc tgactcaacc accatcagtg tctgtagcac caggccagac cgcacgtatt   60
acctgtggcg gtaacctgat cggctctaag ctggttcact ggtatcagca aaaaccaggc  120
caggcaccag tactggttgt gtacgatgat agcgatcgtc caagccggat tccagagcgt  180
```

```
ttcagcggct ctaattccgg caacaccgct actctgacta tttcccgtgt tgaagccggc   240
gatgaagccg actactattg ccaggtctgg gactccagct ccgaccacgt agtctttggc   300
gggggcacca aactgaccgt tttg                                          324

SEQ ID NO: 73          moltype = DNA   length = 366
FEATURE                Location/Qualifiers
misc_feature           1..366
                       note = Description of Artificial Sequence: Synthetic
                       polynucleotide
source                 1..366
                       mol_type = other DNA
                       organism = synthetic construct
SEQUENCE: 73
caaatgcagc tggtcgagtc tggcggtggg gtagtgcaac caggccgttc tctgcgtctt   60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtagccga ggcattcgat atgtggggcc agggcactat ggtgaccgtt   360
agctct                                                              366

SEQ ID NO: 74          moltype = DNA   length = 324
FEATURE                Location/Qualifiers
misc_feature           1..324
                       note = Description of Artificial Sequence: Synthetic
                       polynucleotide
source                 1..324
                       mol_type = other DNA
                       organism = synthetic construct
SEQUENCE: 74
tcttacgtgc tgactcaacc accatcagtg tctgtagcac caggccagac cgcacgtatt   60
acctgtggcg gtaacctgat cggctctaag ctggttcact ggtatcagca aaaaccaggc   120
caggcaccag tactggttgt gtacgatgat agcgatcgtc caagccggat tccagagcgt   180
ttcagcggct ctaattccgg caacaccgct actctgacta tttcccgtgt tgaagccggc   240
gatgaagccg actactattg ccaggtctgg gactctagct ccgaccatgt agtctttggc   300
gggggcacca aactgaccgt tttg                                          324

SEQ ID NO: 75          moltype = DNA   length = 366
FEATURE                Location/Qualifiers
misc_feature           1..366
                       note = Description of Artificial Sequence: Synthetic
                       polynucleotide
source                 1..366
                       mol_type = other DNA
                       organism = synthetic construct
SEQUENCE: 75
caaatgcagc tggtcgagtc tggcggtggg gtagtgcaac caggccgttc tctgcgtctt   60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtagccga agcattcgat ctgtggggcc agggcactat ggtgaccgtt   360
agctct                                                              366

SEQ ID NO: 76          moltype = DNA   length = 324
FEATURE                Location/Qualifiers
misc_feature           1..324
                       note = Description of Artificial Sequence: Synthetic
                       polynucleotide
source                 1..324
                       mol_type = other DNA
                       organism = synthetic construct
SEQUENCE: 76
tcttacgtgc tgactcaacc accatcagtg tctgtagcac caggccagac cgcacgtatt   60
acctgtggcg gtaacctgat cggctctaag ctggttcact ggtatcagca aaaaccaggc   120
caggcaccag tactggttgt gtacgatgat agcgatcgtc caagcaaaat tccagagcgt   180
ttcagcggct ctaattccgg caacaccgct actctgacta tttcccgtgt tgaagccggc   240
gatgaagccg actactattg ccaggtctgg gactccagct ccgaccatgt agtctttggc   300
gggggcacca aactgaccgt tttg                                          324

SEQ ID NO: 77          moltype = DNA   length = 366
FEATURE                Location/Qualifiers
misc_feature           1..366
                       note = Description of Artificial Sequence: Synthetic
                       polynucleotide
source                 1..366
                       mol_type = other DNA
                       organism = synthetic construct
SEQUENCE: 77
```

-continued

```
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat acgtagcgga agcattcgat ctgtggggcc agggcactat ggtgaccgtt  360
agctct                                                             366
```

SEQ ID NO: 78           moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 78

```
tcttacgtgc tgactcaacc accatcagtg tctgtagcac caggccagac cgcacgtatt   60
acctgtggcg gtaacctgat cggctctaag ctggttcact ggtatcagca aaaaccaggc  120
caggcaccag tactggttgt gtacgatgat agcgatcgtc caagcgatat tccagagcgt  180
ttcagcggct ctaattccgg caacaccgct actctgacta tttcccgtgt tgaagccggc  240
gatgaagccg actactattg ccaggtctgg gacaccagct ccgaccatgt agtctttggc  300
gggggcacca aactgaccgt tttg                                         324
```

SEQ ID NO: 79           moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 79

```
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat aacggccga agcattcgat cttttggggcc agggcactat ggtgaccgtt  360
agctct                                                             366
```

SEQ ID NO: 80           moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 80

```
tcttacgtgc tgactcaacc accatcagtg tctgtagcac caggccagac cgcacgtatt   60
acctgtggcg gtaacatcat cggctctaag ctggttcact ggtatcagca aaaaccaggc  120
caggcaccag tactggttgt gtacgatgat ggcgatcgtc caagcggtat tccagagcgt  180
ttcagcggct ctaattccgg caacaccgct actctgacta tttcccgtgt tgaagccggc  240
gatgaagccg actactattg ccaggtctgg gacactagct ccgaccacgt agtctttggc  300
gggggcacca aactgaccgt tttg                                         324
```

SEQ ID NO: 81           moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 81

```
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtggcgga agcattcgat cttttggggcc agggcactat ggtgaccgtt  360
agctct                                                             366
```

SEQ ID NO: 82           moltype = DNA   length = 324
FEATURE                 Location/Qualifiers
misc_feature            1..324
                        note = Description of Artificial Sequence: Synthetic
                         polynucleotide -continued

```
source                1..324
                      mol_type = other DNA
                      organism = synthetic construct
SEQUENCE: 82
tcttacgtgc tgactcaacc accatcagtg tctgtagcac caggccagac cgcacgtatt  60
acctgtggcg gtaacctgct gggctctaag ctggttcact ggtatcagca aaaaccaggc  120
caggcaccag tactggttgt gtacgatgat ggcgatcgtc caagcctgat tccagagcgt  180
ttcagcggct ctaattccgg caacaccgct actctgacta tttcccgtgt tgaagccggc  240
gatgaagccg actactattg ccaggtctgg gacactagct ccgaccacgt agtctttggc  300
gggggcacca aactgaccgt tttg                                         324

SEQ ID NO: 83          moltype = DNA   length = 366
FEATURE                Location/Qualifiers
misc_feature          1..366
                      note = Description of Artificial Sequence: Synthetic
                       polynucleotide
source                1..366
                      mol_type = other DNA
                      organism = synthetic construct
SEQUENCE: 83
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacggcgga agcattcgat atttggggcc agggcactat ggtgaccgtt  360
agctct                                                            366

SEQ ID NO: 84          moltype = DNA   length = 324
FEATURE                Location/Qualifiers
misc_feature          1..324
                      note = Description of Artificial Sequence: Synthetic
                       polynucleotide
source                1..324
                      mol_type = other DNA
                      organism = synthetic construct
SEQUENCE: 84
tcttacgtgc tgactcaacc accatcagtg tctgtagcac caggccagac cgcacgtatt  60
acctgtggcg gtaacctgct gggctctaag ctggttcact ggtatcagca aaaaccaggc  120
caggcaccag tactggttgt gtacgatgat agcgatcgtc caagcgaaat tccagagcgt  180
ttcagcggct ctaattccgg caacaccgct actctgacta tttcccgtgt tgaagccggc  240
gatgaagccg actactattg ccaggtctgg gacaccagct ccgacggtgt agtctttggc  300
gggggcacca aactgaccgt tttg                                         324

SEQ ID NO: 85          moltype = DNA   length = 366
FEATURE                Location/Qualifiers
misc_feature          1..366
                      note = Description of Artificial Sequence: Synthetic
                       polynucleotide
source                1..366
                      mol_type = other DNA
                      organism = synthetic construct
SEQUENCE: 85
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacggccga agcattcgat ctttggggcc agggcactat ggtgaccgtt  360
agctct                                                            366

SEQ ID NO: 86          moltype = DNA   length = 324
FEATURE                Location/Qualifiers
misc_feature          1..324
                      note = Description of Artificial Sequence: Synthetic
                       polynucleotide
source                1..324
                      mol_type = other DNA
                      organism = synthetic construct
SEQUENCE: 86
tcttacgtgc tgactcaacc accatcagtg tctgtagcac caggccagac cgcacgtatt  60
acctgtggcg gtaacctgct gggctctaag ctggttcact ggtatcagca aaaaccaggc  120
caggcaccag tactggttgt gtacgatgat agcgatcgtc caagctggat tccagagcgt  180
ttcagcggct ctaattccgg caacaccgct actctgacta tttcccgtgt tgaagccggc  240
gatgaagccg actactattg ccaggtctgg gacactagct ccgaccatgt agtctttggc  300
gggggcacca aactgaccgt tttg                                         324

SEQ ID NO: 87          moltype = DNA   length = 366
FEATURE                Location/Qualifiers
```

```
misc_feature           1..366
                       note = Description of Artificial Sequence: Synthetic
                        polynucleotide
source                 1..366
                       mol_type = other DNA
                       organism = synthetic construct
SEQUENCE: 87
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacgtcgga agcattcgat ctttgggggcc agggcactat ggtgaccgtt  360
agctct                                                             366

SEQ ID NO: 88          moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
SEQUENCE: 88
tcttacgtgc tgactcaacc accatcagtg tctgtagcac caggccagac cgcacgtatt   60
acctgtggcg gtaacctgat cggctctaag ctggttcact ggtatcagca aaaaccaggc  120
caggcaccag tactggttgt gtacgatgat agcgatcgtc caagcgcaat tccagagcgt  180
ttcagcggct ctaattccgg caacaccgct actctgacta tttcccgtgt tgaagccggc  240
gatgaagccg actactattg ccaggtctgg gacaccagct ccgaccacgt agtctttggc  300
gggggcacca aactgaccgt tttg                                          324

SEQ ID NO: 89          moltype = DNA  length = 366
FEATURE                Location/Qualifiers
misc_feature           1..366
                       note = Description of Artificial Sequence: Synthetic
                        polynucleotide
source                 1..366
                       mol_type = other DNA
                       organism = synthetic construct
SEQUENCE: 89
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacctccga agcattcgat ctttgggggcc agggcactat ggtgaccgtt  360
agctct                                                             366

SEQ ID NO: 90          moltype = DNA  length = 324
FEATURE                Location/Qualifiers
misc_feature           1..324
                       note = Description of Artificial Sequence: Synthetic
                        polynucleotide
source                 1..324
                       mol_type = other DNA
                       organism = synthetic construct
SEQUENCE: 90
tcttacgtgc tgactcaacc accatcagtg tctgtagcac caggccagac cgcacgtatt   60
acctgtggcg gtaacctgat cggctctaag ctggttcact ggtatcagca aaaaccaggc  120
caggcaccag tactggttgt gtacgatgat agcgatcgtc caagcgaaat tccagagcgt  180
ttcagcggct ctaattccgg caacaccgct actctgacta tttcccgtgt tgaagccggc  240
gatgaagccg actactattg ccaggtctgg gactccagct ccgacggtgt agtctttggc  300
gggggcacca aactgaccgt tttg                                          324

SEQ ID NO: 91          moltype = DNA  length = 366
FEATURE                Location/Qualifiers
misc_feature           1..366
                       note = Description of Artificial Sequence: Synthetic
                        polynucleotide
source                 1..366
                       mol_type = other DNA
                       organism = synthetic construct
SEQUENCE: 91
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggctgt tagtagcgga agcattcgat ctctgggggcc agggcactat ggtgaccgtt  360
```

-continued

```
agctct                                                           366

SEQ ID NO: 92         moltype = DNA  length = 324
FEATURE               Location/Qualifiers
misc_feature          1..324
                      note = Description of Artificial Sequence: Synthetic
                      polynucleotide
source                1..324
                      mol_type = other DNA
                      organism = synthetic construct
SEQUENCE: 92
tcttacgtgc tgactcaacc accatcagtg tctgtagcac caggccagac cgcacgtatt   60
acctgtggcg gtaacatcat cggctctaag ctggttcact ggtatcagca aaaaccaggc  120
caggcaccag tactggttgt gtacgatgat agcgatcgtc caagcggtat tccagagcgt  180
ttcagcggct ctaattccgg caacaccgct actctgacta tttcccgtgt tgaagccggc  240
gatgaagccg actactattg ccaggtctgg gactctggct ccgaccacgt agtctttggc  300
gggggcacca aactgaccgt tttg                                         324

SEQ ID NO: 93         moltype = DNA  length = 366
FEATURE               Location/Qualifiers
misc_feature          1..366
                      note = Description of Artificial Sequence: Synthetic
                      polynucleotide
source                1..366
                      mol_type = other DNA
                      organism = synthetic construct
SEQUENCE: 93
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtata atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtagcgga agcattcgat ctttggggcc agggcactat ggtgaccgtt  360
agctct                                                            366

SEQ ID NO: 94         moltype = DNA  length = 324
FEATURE               Location/Qualifiers
misc_feature          1..324
                      note = Description of Artificial Sequence: Synthetic
                      polynucleotide
source                1..324
                      mol_type = other DNA
                      organism = synthetic construct
SEQUENCE: 94
tcttacgtgc tgactcaacc accatcagtg tctgtagcac caggccagac cgcacgtatt   60
acctgtggcg gtaacatcat cggctctaag ctggttcact ggtatcagca aaaaccaggc  120
caggcaccag tactggttgt gtacgatgat agcgatcgtc caagcggtat tccagagcgt  180
ttcagcggct ctaattccgg caacaccgct actctgacta tttcccgtgt tgaagccggc  240
gatgaagccg actactattg ccaggtctgg gactccggct ccgacggtgt agtctttggc  300
gggggcacca aactgaccgt tttg                                         324

SEQ ID NO: 95         moltype = DNA  length = 366
FEATURE               Location/Qualifiers
misc_feature          1..366
                      note = Description of Artificial Sequence: Synthetic
                      polynucleotide
source                1..366
                      mol_type = other DNA
                      organism = synthetic construct
SEQUENCE: 95
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtagcgga agcattcgat ctgtggggcc agggcactat ggtgaccgtt  360
agctct                                                            366

SEQ ID NO: 96         moltype = DNA  length = 324
FEATURE               Location/Qualifiers
misc_feature          1..324
                      note = Description of Artificial Sequence: Synthetic
                      polynucleotide
source                1..324
                      mol_type = other DNA
                      organism = synthetic construct
SEQUENCE: 96
tcttacgtgc tgactcaacc accatcagtg tctgtagcac caggccagac cgcacgtatt   60
acctgtggcg gtaacctgat cggctctaag ctggttcact ggtatcagca aaaaccaggc  120
```

-continued

```
caggcaccag tactggttgt gtacgatgat ggcgatcgtc caagctggat tccagagcgt   180
ttcagcggct ctaattccgg caacaccgct actctgacta tttcccgtgt tgaagccggc   240
gatgaagccg actactattg ccaggtctgg gactctggct ccgacggtgt agtctttggc   300
gggggcacca aactgaccgt tttg                                          324

SEQ ID NO: 97               moltype = DNA   length = 366
FEATURE                     Location/Qualifiers
misc_feature               1..366
                           note = Description of Artificial Sequence: Synthetic
                            polynucleotide
source                     1..366
                           mol_type = other DNA
                           organism = synthetic construct
SEQUENCE: 97
caaatgcagc tggtcgagtc tggcggtggg gtagtgcaac caggccgttc tctgcgtctt   60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggtct tagtatccga agcattcgat ctttgggggcc agggcactat ggtgaccgtt   360
agctct                                                             366

SEQ ID NO: 98               moltype = DNA   length = 324
FEATURE                     Location/Qualifiers
misc_feature               1..324
                           note = Description of Artificial Sequence: Synthetic
                            polynucleotide
source                     1..324
                           mol_type = other DNA
                           organism = synthetic construct
SEQUENCE: 98
tcttacgtgc tgactcaacc accatcagtg tctgtagcac caggccagac cgcacgtatt   60
acctgtggcg gtaacctgat cggctctaag ctggttcact ggtatcagca aaaaccaggc   120
caggcaccag tactggttgt gtacgatgat agcgatcgtc caagccgtat tccagagcgt   180
ttcagcggct ctaattccgg caacaccgct actctgacta tttcccgtgt tgaagccggc   240
gatgaagccg actactattg ccaggtctgg gactccggct ccgacggtgt agtctttggc   300
gggggcacca aactgaccgt tttg                                          324

SEQ ID NO: 99               moltype = DNA   length = 366
FEATURE                     Location/Qualifiers
misc_feature               1..366
                           note = Description of Artificial Sequence: Synthetic
                            polynucleotide
source                     1..366
                           mol_type = other DNA
                           organism = synthetic construct
SEQUENCE: 99
caaatgcagc tggtcgagtc tggcggtggg gtagtgcaac caggccgttc tctgcgtctt   60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtagcgga ggcattcgat ctgtgggggcc agggcactat ggtgaccgtt   360
agctct                                                             366

SEQ ID NO: 100              moltype = DNA   length = 324
FEATURE                     Location/Qualifiers
misc_feature               1..324
                           note = Description of Artificial Sequence: Synthetic
                            polynucleotide
source                     1..324
                           mol_type = other DNA
                           organism = synthetic construct
SEQUENCE: 100
tcttacgtgc tgactcaacc accatcagtg tctgtagcac caggccagac cgcacgtatt   60
acctgtggcg gtaacatcat cggctctaag ctggttcact ggtatcagca aaaaccaggc   120
caggcaccag tactggttgt gtacgatgat agcgatcgtc caagcgcaat tccagagcgt   180
ttcagcggct ctaattccgg caacaccgct actctgacta tttcccgtgt tgaagccggc   240
gatgaagccg actactattg ccaggtctgg gactccagct ccgacggtgt agtctttggc   300
gggggcacca aactgaccgt tttg                                          324

SEQ ID NO: 101              moltype = DNA   length = 366
FEATURE                     Location/Qualifiers
misc_feature               1..366
                           note = Description of Artificial Sequence: Synthetic
                            polynucleotide
source                     1..366
                           mol_type = other DNA
                           organism = synthetic construct
```

```
SEQUENCE: 101
caaatgcagc tggtcgagtc tggcggtggg gtagtgcaac caggccgttc tctgcgtctt      60
agctgcgccg catctggttt tacctttcgt acctacggta tgcactgggt gcgtcaggca     120
ccaggcaaag gtctggaatg ggtcgcagta atctcttatg atggtagcaa taaacactat     180
gctgactcag tcaaaggccg tttcaccatc acccgtgata acagcaagaa cactcttaac     240
ttacagatga actctctgcg tgccgaagac accgccgttt actactgtgc ccgtagccca     300
cagtgggaat gggtacacga agcattcgat atgtggggcc agggcactat ggtgaccgtt     360
agctct                                                                366

SEQ ID NO: 102          moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 102
tcttacgtgc tgactcaacc accatcagtg tctgtagcac caggccagac cgcacgtatt      60
acctgtggcg gtaacaacat cggctctaag ctggttcact ggtatcagca aaaaccaggc     120
caggcaccag tactggttgt gtacgatgat agcgatcgtc caagcggtat tccagagcgt     180
ttcagcggct ctaattccgg caacaccgct actctgacta tttcccgtgt tgaagccggc     240
gatgaagccg actactattg ccaggtctgg gactctagct ccgacggtgt agtctttggc     300
gggggcacca aactgaccgt tttg                                            324

SEQ ID NO: 103          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 103
caaatgcagc tggtcgagtc tggcggtggg gtagtgcaac caggccgttc tctgcgtctt      60
agctgcgccg catctggttt tacctttcgt acctacggta tgcactgggt gcgtcaggca     120
ccaggcaaag gtctggaatg ggtcgcagta atctcttatg atggtagcaa taaacactat     180
gctgactcag tcaaaggccg tttcaccatc acccgtgata acagcaagaa cactcttaac     240
ttacagatga actctctgcg tgccgaagac accgccgttt actactgtgc ccgttcgcca     300
cagtgggaat gggtacacga agcattcgat ctctggggcc agggcactat ggtgaccgtt     360
agctct                                                                366

SEQ ID NO: 104          moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 104
tcttacgtgc tgactcaacc accatcagtg tctgtagcac caggccagac cgcacgtatt      60
acctgtggcg gtaacatcct gggctctaag ctggttcact ggtatcagca aaaaccaggc     120
caggcaccag tactggttgt gtacgatgat agcgatcgtc caagcgaaat tccagagcgt     180
ttcagcggct ctaattccgg caacaccgct actctgacta tttcccgtgt tgaagccggc     240
gatgaagccg actactattg ccaggtctgg gacaccagct ccgacggtgt agtctttggc     300
gggggcacca aactgaccgt tttg                                            324

SEQ ID NO: 105          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 105
caaatgcagc tggtcgagtc tggcggtggg gtagtgcaac caggccgttc tctgcgtctt      60
agctgcgccg catctggttt tacctttcgt acctacggta tgcactgggt gcgtcaggca     120
ccaggcaaag gtctggaatg ggtcgcagta atctggtatg atggtagcaa taaacactat     180
gctgactcag tcaaaggccg tttcaccatc acccgtgata acagcaagaa cactcttaac     240
ttacagatga actctctgcg tgccgaagac accgccgttt actactgtgc ccgtagccca     300
cagtgggaat gggtacacga agcattcgat ctatggggcc agggcactat ggtgaccgtt     360
agctct                                                                366

SEQ ID NO: 106          moltype = DNA   length = 324
FEATURE                 Location/Qualifiers
misc_feature            1..324
                        note = Description of Artificial Sequence: Synthetic
```

```
                        polynucleotide
source                  1..324
                        mol_type = other DNA
                        organism = synthetic construct
SEQUENCE: 106
tcttacgtgc tgactcaacc accatcagtg tctgtagcac caggccagac cgcacgtatt    60
acctgtggcg gtaacaacat cggctctaag ctggttcact ggtatcagca aaaaccaggc   120
caggcaccag tactggttgt gtacgatgat agcgatcgtc caagccggat tccagagcgt   180
ttcagcggct ctaattccgg caacaccgct actctgacta tttcccgtgt tgaagccggc   240
gatgaagccg actactattg ccaggtctgg gacactagct ccgacggtgt agtctttggc   300
gggggcacca aactgaccgt tttg                                          324

SEQ ID NO: 107        moltype = DNA   length = 366
FEATURE               Location/Qualifiers
misc_feature          1..366
                      note = Description of Artificial Sequence: Synthetic
                       polynucleotide
source                1..366
                      mol_type = other DNA
                      organism = synthetic construct
SEQUENCE: 107
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgttcgcca   300
cagtgggaat gggtacacga agcattcgat ctctgggggc agggcactat ggtgaccgtt   360
agctct                                                              366

SEQ ID NO: 108        moltype = DNA   length = 324
FEATURE               Location/Qualifiers
misc_feature          1..324
                      note = Description of Artificial Sequence: Synthetic
                       polynucleotide
source                1..324
                      mol_type = other DNA
                      organism = synthetic construct
SEQUENCE: 108
tcttacgtgc tgactcaacc accatcagtg tctgtagcac caggccagac cgcacgtatt    60
acctgtggcg gtaacctgat cggctctaag ctggttcact ggtatcagca aaaaccaggc   120
caggcaccag tactggttgt gtacgatgat ggcgatcgtc caagctggat tccagagcgt   180
ttcagcggct ctaattccgg caacaccgct actctgacta tttcccgtgt tgaagccggc   240
gatgaagccg actactattg ccaggtctgg gactccagct ccgacggtgt agtctttggc   300
gggggcacca aactgaccgt tttg                                          324

SEQ ID NO: 109        moltype = DNA   length = 735
FEATURE               Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 109
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgcagttt attactgtgc ccgtgcacca   300
cagtgggaat tagtacacga agcattcgat atctggggtc agggtactat ggtgaccgtt   360
agctctggcg gtggtggtag cggaggcgga ggatcaggtg gaggcggcag ttcttacgtg   420
ctgactcaac caccatcagt gtctgtagca ccaggccaga ccgcacgtat tacctgtggc   480
ggtaacaatc tgggctctaa gtctgttcac tggtatcagc aaaaaccagg ccaggcacca   540
gtactggttg tgtacgatga ttccgatcgt ccaagctgac gcttcagagc gtttcagcgg   600
tctaattccg gcaacaccgc tactctgact atttcccgtg gggaagccgg cgatgaagcc   660
gactactatt gccaggtctg ggactcttct tccgaccatg tagtctttgg cggggggcacc   720
aaactgaccg ttttg                                                    735

SEQ ID NO: 110        moltype = DNA   length = 735
FEATURE               Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 110
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
```

```
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacggcgga agcattcgat atttgggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcctga ttccagagcg tttcagcggc  600
tctaattccg gcaacaccgc tactctgact atttcccgtg ttgaagccgg cgatgaagcc  660
gactactatt gccaggtctg ggactctagc tccgacggtg tagtctttgg cggggggcacc  720
aaactgaccg ttttg                                                    735
```

SEQ ID NO: 111            moltype = DNA   length = 735
FEATURE                   Location/Qualifiers
misc_feature              1..735
                          note = Description of Artificial Sequence: Synthetic
                           polynucleotide
source                    1..735
                          mol_type = other DNA
                          organism = synthetic construct
SEQUENCE: 111

```
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtagcgga agcattcgat ctgtgggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcctga ttccagagcg tttcagcggc  600
tctaattccg gcaacaccgc tactctgact atttcccgtg ttgaagccgg cgatgaagcc  660
gactactatt gccaggtctg ggactctagc tccgacggtg tagtctttgg cggggggcacc  720
aaactgaccg ttttg                                                    735
```

SEQ ID NO: 112            moltype = DNA   length = 735
FEATURE                   Location/Qualifiers
misc_feature              1..735
                          note = Description of Artificial Sequence: Synthetic
                           polynucleotide
source                    1..735
                          mol_type = other DNA
                          organism = synthetic construct
SEQUENCE: 112

```
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggcagt tagtagcgga agcattcgat atttggggcc anggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcctta ttccagagcg tttcagcggc  600
tctaattccg gcaacaccgc tactctgact atttcccgtg ttgaagccgg cgatgaagcc  660
gactactatt gccaggtctg ggacaccagc tccgacggtg tagtctttgg cggggggcacc  720
aaactgaccg ttttg                                                    735
```

SEQ ID NO: 113            moltype = DNA   length = 735
FEATURE                   Location/Qualifiers
misc_feature              1..735
                          note = Description of Artificial Sequence: Synthetic
                           polynucleotide
source                    1..735
                          mol_type = other DNA
                          organism = synthetic construct
SEQUENCE: 113

```
caaatgcagc tggtcgagtc tggcggtggg gtagtgcaac caggccgttc tctgcgtctt  60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggcagt tagtagccga agcattcgat atatggggcc anggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcgcta ttccagagcg tttcagcggc  600
tctaattccg gcaacaccgc tactctgact atttcccgtg ttgaagccgg cgatgaagcc  660
gactactatt gccaggtctg ggacactagc tccgacggtg tagtctttgg cggggggcacc  720
```

-continued

```
aaactgaccg ttttg                                                    735

SEQ ID NO: 114          moltype = DNA   length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 114
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtggcgga agcattcgat cttggggcc anggcactat ggtgaccgtt  360
agctctggtg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcctta ttccagagcg tttcagcggc  600
tctaattccg gcaacaccgc tactctgact atttcccgtg ttgaagccgg cgatgaagcc  660
gactactatt gccaggtctg ggacaccagc tccgacggtg tagtctttgg cggggcacc   720
aaactgaccg ttttg                                                    735

SEQ ID NO: 115          moltype = DNA   length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 115
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tggtagccga agcattcgat atctggggcc anggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tggggctctaa gctggttcac tggtatcagc aaaaaccagg ccaggcacca  540
gtactggttg tgtacgatga tagcgatcgt ccaagcgcaa ttccagagcg tttcagcggc  600
tctaattccg gcaacaccgc tactctgact atttcccgtg ttgaagccgg cgatgaagcc  660
gactactatt gccaggtctg ggactctagc tccgaccacg tagtctttgg cggggcacc   720
aaactgaccg ttttg                                                    735

SEQ ID NO: 116          moltype = DNA   length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 116
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggatgt tagtagcgga agcattcgat ctatggggcc anggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg gcaggcacca  540
gtactggttg tgtacgatga tagcgatcgt ccaagccgga ttccagagcg tttcagcggc  600
tctaattccg gcaacaccgc tactctgact atttcccgtg ttgaagccgg cgatgaagcc  660
gactactatt gccaggtctg ggactccagc tccgaccatg tagtctttgg cggggcacc   720
aaactgaccg ttttg                                                    735

SEQ ID NO: 117          moltype = DNA   length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
```

-continued

```
SEQUENCE: 117
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat gggtagccga agcattcgat ctgtggggcc agggcactat ggtgaccgtt   360
agctctggcg gtggtggtag cggaggcgga ggatcaggtg gaggcggcag ttcttacgtg   420
ctgactcaac caccatcagt gtctgtagca ccaggccaga ccgcacgtat tacctgtggc   480
ggtaacctga tcggctctaa gctggttcac tggtatcagc aaaaaccagg ccaggcacca   540
gtactggttg tgtacgatga tagcgatcgt ccaagccgga ttccagagcg tttcagcggc   600
tctaattccg gcaacaccgc tactctgact atttcccgtg ttgaagccgg cgatgaagcc   660
gactactatt gccaggtctg ggactccagc tccgaccacg tagtctttgg cgggggcacc   720
aaactgaccg ttttg                                                    735

SEQ ID NO: 118          moltype = DNA  length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 118
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtagccga ggcattcgat atgtggggcc agggcactat ggtgaccgtt   360
agctctggcg gtggtggtag cggaggcgga ggatcaggtg gaggcggcag ttcttacgtg   420
ctgactcaac caccatcagt gtctgtagca ccaggccaga ccgcacgtat tacctgtggc   480
ggtaacctga tcggctctaa gctggttcac tggtatcagc aaaaaccagg ccaggcacca   540
gtactggttg tgtacgatga tagcgatcgt ccaagccgga ttccagagcg tttcagcggc   600
tctaattccg gcaacaccgc tactctgact atttcccgtg ttgaagccgg cgatgaagcc   660
gactactatt gccaggtctg ggactctagc tccgaccatg tagtctttgg cgggggcacc   720
aaactgaccg ttttg                                                    735

SEQ ID NO: 119          moltype = DNA  length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 119
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat tagtagccga agcattcgat ctgtggggcc agggcactat ggtgaccgtt   360
agctctggcg gtggtggtag cggaggcgga ggatcaggtg gaggcggcag ttcttacgtg   420
ctgactcaac caccatcagt gtctgtagca ccaggccaga ccgcacgtat tacctgtggc   480
ggtaacctga tcggctctaa gctggttcac tggtatcagc aaaaaccagg ccaggcacca   540
gtactggttg tgtacgatga tagcgatcgt ccaagcaaaa ttccagagcg tttcagcggc   600
tctaattccg gcaacaccgc tactctgact atttcccgtg ttgaagccgg cgatgaagcc   660
gactactatt gccaggtctg ggactccagc tccgaccatg tagtctttgg cgggggcacc   720
aaactgaccg ttttg                                                    735

SEQ ID NO: 120          moltype = DNA  length = 735
FEATURE                 Location/Qualifiers
misc_feature            1..735
                        note = Description of Artificial Sequence: Synthetic
                        polynucleotide
source                  1..735
                        mol_type = other DNA
                        organism = synthetic construct
SEQUENCE: 120
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagta atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtgggaat acgtagcgga agcattcgat ctgtggggcc agggcactat ggtgaccgtt   360
agctctggcg gtggtggtag cggaggcgga ggatcaggtg gaggcggcag ttcttacgtg   420
ctgactcaac caccatcagt gtctgtagca ccaggccaga ccgcacgtat tacctgtggc   480
ggtaacctga tcggctctaa gctggttcac tggtatcagc aaaaaccagg ccaggcacca   540
```

```
gtactggttg tgtacgatga tagcgatcgt ccaagcgata ttccagagcg tttcagcggc    600
tctaattccg gcaacaccgc tactctgact atttcccgtg ttgaagccgg cgatgaagcc    660
gactactatt gccaggtctg ggacaccagc tccgaccatg tagtctttgg cgggggcacc    720
aaactgaccg ttttg                                                     735
```

SEQ ID NO: 121          moltype = DNA   length = 735
FEATURE                 Location/Qualifiers
misc_feature            1..735
                        note = Description of Artificial Sequence: Synthetic
                         polynucleotide
source                  1..735
                        mol_type = other DNA
                        organism = synthetic construct
SEQUENCE: 121

```
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggaat taacggccga agcattcgat ctttggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacatca tcggctctaa gctggttcac tggtatcagc aaaaaccagg ccaggcacca    540
gtactggttg tgtacgatga tggcgatcgt ccaagcggta ttccagagcg tttcagcggc    600
tctaattccg gcaacaccgc tactctgact atttcccgtg ttgaagccgg cgatgaagcc    660
gactactatt gccaggtctg ggacactagc tccgaccacg tagtctttgg cgggggcacc    720
aaactgaccg ttttg                                                     735
```

SEQ ID NO: 122          moltype = DNA   length = 735
FEATURE                 Location/Qualifiers
misc_feature            1..735
                        note = Description of Artificial Sequence: Synthetic
                         polynucleotide
source                  1..735
                        mol_type = other DNA
                        organism = synthetic construct
SEQUENCE: 122

```
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggaat tagtggcgga agcattcgat ctttggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacctgc tgggctctaa gctggttcac tggtatcagc aaaaaccagg ccaggcacca    540
gtactggttg tgtacgatga tggcgatcgt ccaagcctga ttccagagcg tttcagcggc    600
tctaattccg gcaacaccgc tactctgact atttcccgtg ttgaagccgg cgatgaagcc    660
gactactatt gccaggtctg ggacactagc tccgaccacg tagtctttgg cgggggcacc    720
aaactgaccg ttttg                                                     735
```

SEQ ID NO: 123          moltype = DNA   length = 735
FEATURE                 Location/Qualifiers
misc_feature            1..735
                        note = Description of Artificial Sequence: Synthetic
                         polynucleotide
source                  1..735
                        mol_type = other DNA
                        organism = synthetic construct
SEQUENCE: 123

```
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggaat taacggcgga agcattcgat atttggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacctgc tgggctctaa gctggttcac tggtatcagc aaaaaccagg ccaggcacca    540
gtactggttg tgtacgatga tagcgatcgt ccaagcgaaa ttccagagcg tttcagcggc    600
tctaattccg gcaacaccgc tactctgact atttcccgtg ttgaagccgg cgatgaagcc    660
gactactatt gccaggtctg ggacaccagc tccgacggtg tagtctttgg cgggggcacc    720
aaactgaccg ttttg                                                     735
```

SEQ ID NO: 124          moltype = DNA   length = 735
FEATURE                 Location/Qualifiers
misc_feature            1..735
                        note = Description of Artificial Sequence: Synthetic
                         polynucleotide -continued

```
source                   1..735
                         mol_type = other DNA
                         organism = synthetic construct
SEQUENCE: 124
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacggccga agcattcgat cttgggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctgc tgggctctaa gctggttcac tggtatcagc aaaaaccagg ccaggcacca  540
gtactggttg tgtacgatga tagcgatcgt ccaagctgga ttccagagcg tttcagcggc  600
tctaattccg gcaacaccgc tactctgact atttcccgtg ttgaagccgg cgatgaagcc  660
gactactatt gccaggtctg ggacactagc tccgaccatg tagtctttgg cgggggcacc  720
aaactgaccg ttttg                                                   735
```

```
SEQ ID NO: 125           moltype = DNA   length = 735
FEATURE                  Location/Qualifiers
misc_feature             1..735
                         note = Description of Artificial Sequence: Synthetic
                         polynucleotide
source                   1..735
                         mol_type = other DNA
                         organism = synthetic construct
SEQUENCE: 125
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacgtcgga agcattcgat ctttggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcgcaa ttccagagcg tttcagcggc  600
tctaattccg gcaacaccgc tactctgact atttcccgtg ttgaagccgg cgatgaagcc  660
gactactatt gccaggtctg ggacaccagc tccgaccacg tagtctttgg cgggggcacc  720
aaactgaccg ttttg                                                   735
```

```
SEQ ID NO: 126           moltype = DNA   length = 735
FEATURE                  Location/Qualifiers
misc_feature             1..735
                         note = Description of Artificial Sequence: Synthetic
                         polynucleotide
source                   1..735
                         mol_type = other DNA
                         organism = synthetic construct
SEQUENCE: 126
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat taacctccga agcattcgat cttgggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacctga tcggctctaa gctggttcac tggtatcagc aaaaaccagg ccaggcacca  540
gtactggttg tgtacgatga tagcgatcgt ccaagcgaaa ttccagagcg tttcagcggc  600
tctaattccg gcaacaccgc tactctgact atttcccgtg ttgaagccgg cgatgaagcc  660
gactactatt gccaggtctg ggactccagc tccgacggtg tagtctttgg cgggggcacc  720
aaactgaccg ttttg                                                   735
```

```
SEQ ID NO: 127           moltype = DNA   length = 735
FEATURE                  Location/Qualifiers
misc_feature             1..735
                         note = Description of Artificial Sequence: Synthetic
                         polynucleotide
source                   1..735
                         mol_type = other DNA
                         organism = synthetic construct
SEQUENCE: 127
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtggctgt tagtagcgga agcattcgat ctctggggcc agggcactat ggtgaccgtt  360
```

```
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacatca tcggctctaa gctggttcac tggtatcagc aaaaaccagg ccaggcacca    540
gtactggttg tgtacgatga tagcgatcgt ccaagcggta ttccagagcg tttcagcggc    600
tctaattccg gcaacaccgc tactctgact atttcccgtg ttgaagccgg cgatgaagcc    660
gactactatt gccaggtctg ggactctggc tccgaccacg tagtctttgg cggggggcacc    720
aaactgaccg ttttg                                                     735
```

```
SEQ ID NO: 128         moltype = DNA  length = 735
FEATURE                Location/Qualifiers
misc_feature           1..735
                       note = Description of Artificial Sequence: Synthetic
                        polynucleotide
source                 1..735
                       mol_type = other DNA
                       organism = synthetic construct
SEQUENCE: 128
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggaat tagtagcgga agcattcgat ctttggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacatca tcggctctaa gctggttcac tggtatcagc aaaaaccagg ccaggcacca    540
gtactggttg tgtacgatga tagcgatcgt ccaagcgata ttccagagcg tttcagcggc    600
tctaattccg gcaacaccgc tactctgact atttcccgtg ttgaagccgg cgatgaagcc    660
gactactatt gccaggtctg ggactccggc tccgacggtg tagtctttgg cggggggcacc    720
aaactgaccg ttttg                                                     735
```

```
SEQ ID NO: 129         moltype = DNA  length = 735
FEATURE                Location/Qualifiers
misc_feature           1..735
                       note = Description of Artificial Sequence: Synthetic
                        polynucleotide
source                 1..735
                       mol_type = other DNA
                       organism = synthetic construct
SEQUENCE: 129
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggaat tagtagcgga agcattcgat ctgtggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacctga tcggctctaa gctggttcac tggtatcagc aaaaaccagg ccaggcacca    540
gtactggttg tgtacgatga tggcgatcgt ccaagctgga ttccagagcg tttcagcggc    600
tctaattccg gcaacaccgc tactctgact atttcccgtg ttgaagccgg cgatgaagcc    660
gactactatt gccaggtctg ggactctggc tccgacggtg tagtctttgg cggggggcacc    720
aaactgaccg ttttg                                                     735
```

```
SEQ ID NO: 130         moltype = DNA  length = 735
FEATURE                Location/Qualifiers
misc_feature           1..735
                       note = Description of Artificial Sequence: Synthetic
                        polynucleotide
source                 1..735
                       mol_type = other DNA
                       organism = synthetic construct
SEQUENCE: 130
caaatgcagc tggtcgagtc tggcggtggg gtagtgcaac caggccgttc tctgcgtctt    60
agctgcgccg catctggttt tacctttcgt acctacggta tgcactgggt gcgtcaggca    120
ccaggcaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgtgcacca    300
cagtgggtct tagtatccga agcattcgat ctttggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacctga tcggctctaa gctggttcac tggtatcagc aaaaaccagg ccaggcacca    540
gtactggttg tgtacgatga tagcgatcgt ccaagccgta ttccagagcg tttcagcggc    600
tctaattccg gcaacaccgc tactctgact atttcccgtg ttgaagccgg cgatgaagcc    660
gactactatt gccaggtctg ggactccggc tccgacggtg tagtctttgg cggggggcacc    720
aaactgaccg ttttg                                                     735
```

```
SEQ ID NO: 131         moltype = DNA  length = 735
FEATURE                Location/Qualifiers
```

-continued

```
misc_feature          1..735
                      note = Description of Artificial Sequence: Synthetic
                       polynucleotide
source                1..735
                      mol_type = other DNA
                      organism = synthetic construct
SEQUENCE: 131
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtgcacca  300
cagtgggaat tagtagcgga ggcattcgat ctgtggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacatca tcggctctaa gctggttcac tggtatcagc aaaaaccagg ccaggcacca  540
gtactggttg tgtacgatga tagcgatcgt ccaagcgcaa ttccagagcg tttcagcggc  600
tctaattccg gcaacaccgc tactctgact atttcccgtg ttgaagccgg cgatgaagcc  660
gactactatt gccaggtctg ggactccagc tccgacggtg tagtctttgg cggggcacc   720
aaactgaccg ttttg                                                    735

SEQ ID NO: 132          moltype = DNA  length = 735
FEATURE                 Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 132
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctcttatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgtagccca  300
cagtgggaat gggtacacga agcattcgat atgtggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacaaca tcggctctaa gctggttcac tggtatcagc aaaaaccagg ccaggcacca  540
gtactggttg tgtacgatga tagcgatcgt ccaagcggta ttccagagcg tttcagcggc  600
tctaattccg gcaacaccgc tactctgact atttcccgtg ttgaagccgg cgatgaagcc  660
gactactatt gccaggtctg ggactctagc tccgacggtg tagtctttgg cggggcacc   720
aaactgaccg ttttg                                                    735

SEQ ID NO: 133          moltype = DNA  length = 735
FEATURE                 Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 133
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctcttatg atggtagcaa taaacactat  180
gctgactcag tcaaaggccg tttcaccatc acccgtgata acagcaagaa cactcttaac  240
ttacagatga actctctgcg tgccgaagac accgccgttt actactgtgc ccgttcgcca  300
cagtgggaat gggtacacga agcattcgat ctctggggcc agggcactat ggtgaccgtt  360
agctctggcg gtggtggtag cggaggcgga ggatcaggtg gaggcggcag ttcttacgtg  420
ctgactcaac caccatcagt gtctgtagca ccaggccaga ccgcacgtat tacctgtggc  480
ggtaacatcc tgggctctaa gctggttcac tggtatcagc aaaaaccagg ccaggcacca  540
gtactggttg tgtacgatga tagcgatcgt ccaagcgaaa ttccagagcg tttcagcggc  600
tctaattccg gcaacaccgc tactctgact atttcccgtg ttgaagccgg cgatgaagcc  660
gactactatt gccaggtctg ggacaccagc tccgacggtg tagtctttgg cggggcacc   720
aaactgaccg ttttg                                                    735

SEQ ID NO: 134          moltype = DNA  length = 735
FEATURE                 Location/Qualifiers
misc_feature          1..735
                      note = Description of Artificial Sequence: Synthetic
                       polynucleotide
source                1..735
                      mol_type = other DNA
                      organism = synthetic construct
SEQUENCE: 134
caaatgcagc tggtcgagtc tggcggtggg gtagtgcaac caggccgttc tctgcgtctt   60
agctgcgccg catctggttt tacctttcgt acctacggta tgcactgggt gcgtcaggca  120
ccaggcaaag gtctggaatg ggtcgcagta atctggtatg atggtagcaa taaacactat  180
```

```
gctgactcag tcaaaggccg tttcaccatc acccgtgata acagcaagaa cactcttaac    240
ttacagatga actctctgcg tgccgaagac accgccgttt actactgtgc ccgtagccca    300
cagtgggaat gggtacacga agcattcgat ctatggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacaaca tcggctctaa gctggttcac tggtatcagc aaaaaccagg ccaggcacca    540
gtactggttg tgtacgatga tagcgatcgt ccaagccgga ttccagagcg tttcagcggc    600
tctaattccg gcaacaccgc tactctgact atttcccgtg ttgaagccgg cgatgaagcc    660
gactactatt gccaggtctg ggacactagc tccgacggtg tagtctttgg cgggggcacc    720
aaactgaccg ttttg                                                     735
```

```
SEQ ID NO: 135          moltype = DNA  length = 735
FEATURE                 Location/Qualifiers
misc_feature            1..735
                        note = Description of Artificial Sequence: Synthetic
                         polynucleotide
source                  1..735
                        mol_type = other DNA
                        organism = synthetic construct
SEQUENCE: 135
caaatgcagc tggtcgagtc tggcggtggg gtagtgcaac caggccgttc tctgcgtctt    60
agctgcgccg catctggttt tacctttcgt acctacggtg tgcactgggt gcgtcaggca    120
ccagacaaag gtctggaatg ggtcgcagta atctggtatg atggtagcaa taaacactat    180
gctgactcag tcaaaggccg tttcaccatc acccgtgata acagcaagaa cactcttaac    240
ttacagatga actctctgcg tgccgaagac accgccgttt actactgtgc ccgttcgcca    300
cagtgggaat gggtacacga agcattcgat ctctgggggcc agggcactat ggtgaccgtt    360
agctctggcg gtggtggtag cggaggcgga ggatcaggtg gaggcggcag ttcttacgtg    420
ctgactcaac caccatcagt gtctgtagca ccaggccaga ccgcacgtat tacctgtggc    480
ggtaacctga tcggctctaa gctggttcac tggtatcagc aaaaaccagg ccaggcacca    540
gtactggttg tgtacgatga tggcgatcgt ccaagccgga ttccagagcg tttcagcggc    600
tctaattccg gcaacaccgc tactctgact atttcccgtg ttgaagccgg cgatgaagcc    660
gactactatt gccaggtctg ggactccagc tccgacggtg tagtctttgg cgggggcacc    720
aaactgaccg ttttg                                                     735
```

```
SEQ ID NO: 136          moltype = AA  length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 136
GFTFRTYG                                                                        8
```

```
SEQ ID NO: 137          moltype = AA  length = 8
FEATURE                 Location/Qualifiers
REGION                  1..8
                        note = Description of Artificial Sequence: Synthetic peptide
VARIANT                 2
                        note = MOD_RES - Trp or Ser
source                  1..8
                        mol_type = protein
                        organism = synthetic construct
SEQUENCE: 137
IXYDGSNK                                                                        8
```

```
SEQ ID NO: 138          moltype = AA  length = 15
FEATURE                 Location/Qualifiers
REGION                  1..15
                        note = Description of Artificial Sequence: Synthetic peptide
VARIANT                 3
                        note = MOD_RES - Ala or Ser
VARIANT                 7
                        note = MOD_RES - Glu, Gln, Met, Leu or Val
VARIANT                 8
                        note = MOD_RES - Leu, Trp or Tyr
VARIANT                 9
                        note = MOD_RES - Val or Thr
VARIANT                 10
                        note = MOD_RES - His, Ala or Ser
VARIANT                 15
                        note = MOD_RES - Ile, Leu or Met
source                  1..15
                        mol_type = protein
                        organism = synthetic construct
SEQUENCE: 138
ARXPQWXXXX EAFDX                                                               15
```

```
SEQ ID NO: 139          moltype = AA  length = 7
```

-continued

```
FEATURE              Location/Qualifiers
REGION               1..7
                     note = Description of Artificial Sequence: Synthetic peptide
VARIANT              1
                     note = MOD_RES - Asn, Leu or Ile
VARIANT              2
                     note = MOD_RES - Leu or Ile
VARIANT              6
                     note = MOD_RES - Ser or Leu
source               1..7
                     mol_type = protein
                     organism = synthetic construct
SEQUENCE: 139
XXGSKXV                                                                    7

SEQ ID NO: 140       moltype =   length =
SEQUENCE: 140
000

SEQ ID NO: 141       moltype = AA  length = 11
FEATURE              Location/Qualifiers
REGION               1..11
                     note = Description of Artificial Sequence: Synthetic peptide
VARIANT              5
                     note = MOD_RES - Ser or Thr
VARIANT              6
                     note = MOD_RES - Ser or Gly
VARIANT              9
                     note = MOD_RES - His or Gly
source               1..11
                     mol_type = protein
                     organism = synthetic construct
SEQUENCE: 141
QVWDXXSDXV V                                                               11

SEQ ID NO: 142       moltype = AA  length = 8
FEATURE              Location/Qualifiers
REGION               1..8
                     note = Description of Artificial Sequence: Synthetic peptide
VARIANT              2
                     note = MOD_RES - Any amino acid
source               1..8
                     mol_type = protein
                     organism = synthetic construct
SEQUENCE: 142
IXYDGSNK                                                                   8

SEQ ID NO: 143       moltype = AA  length = 15
FEATURE              Location/Qualifiers
REGION               1..15
                     note = Description of Artificial Sequence: Synthetic peptide
VARIANT              3..12
                     note = MOD_RES - Any amino acid
VARIANT              15
                     note = MOD_RES - Any amino acid
source               1..15
                     mol_type = protein
                     organism = synthetic construct
SEQUENCE: 143
ARXXXXXXXX XXFDX                                                           15

SEQ ID NO: 144       moltype = AA  length = 7
FEATURE              Location/Qualifiers
REGION               1..7
                     note = Description of Artificial Sequence: Synthetic peptide
VARIANT              1..2
                     note = MOD_RES - Any amino acid
VARIANT              6
                     note = MOD_RES - Any amino acid
source               1..7
                     mol_type = protein
                     organism = synthetic construct
SEQUENCE: 144
XXGSKXV                                                                    7

SEQ ID NO: 145       moltype =   length =
SEQUENCE: 145
000
```

```
SEQ ID NO: 146          moltype = AA   length = 11
FEATURE                 Location/Qualifiers
REGION                  1..11
                        note = Description of Artificial Sequence: Synthetic peptide
VARIANT                 5..6
                        note = MOD_RES - Any amino acid
VARIANT                 9
                        note = MOD_RES - Any amino acid
source                  1..11
                        mol_type = protein
                        organism = synthetic construct
SEQUENCE: 146
QVWDXXSDXV V                                                    11

SEQ ID NO: 147          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 147
GGGGSGGGGS GGGGS                                                15

SEQ ID NO: 148          moltype = DNA  length = 45
FEATURE                 Location/Qualifiers
misc_feature            1..45
                        note = Description of Artificial Sequence: Synthetic
                         oligonucleotide
source                  1..45
                        mol_type = other DNA
                        organism = synthetic construct
SEQUENCE: 148
ggcggtggtg gtagcggagg cggaggatca ggtggaggcg gcagt            45

SEQ ID NO: 149          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 149
GFAFRTYG                                                        8

SEQ ID NO: 150          moltype = AA   length = 8
FEATURE                 Location/Qualifiers
REGION                  1..8
                        note = Description of Artificial Sequence: Synthetic peptide
source                  1..8
                        mol_type = protein
                        organism = synthetic construct
SEQUENCE: 150
IWYDGSNT                                                        8

SEQ ID NO: 151          moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 151
ARAPQWYLSA EAFDL                                                15

SEQ ID NO: 152          moltype = AA   length = 6
FEATURE                 Location/Qualifiers
REGION                  1..6
                        note = Description of Artificial Sequence: Synthetic peptide
source                  1..6
                        mol_type = protein
                        organism = synthetic construct
SEQUENCE: 152
LIGSKL                                                          6

SEQ ID NO: 153          moltype =    length =
SEQUENCE: 153
000
```

```
SEQ ID NO: 154          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 154
QVWDHSSDHV V                                                    11

SEQ ID NO: 155          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 155
QMQLVESGGG VVQPGRSLRL SCAASGFAFR TYGMHWVRQA PGKGLEWVAV IWYDGSNTHY  60
ADSVKGRFTI TRDNSKNTLN LQMNSLRAED TAVYYCARAP QWYLSAEAFD LWGQGTMVTV  120
SS                                                             122

SEQ ID NO: 156          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 156
SYVLTQPPSV SVAPGQTARI TCGGNLIGSK LVHWYQQKPG QAPVLVVYDD SDRPSRIPER  60
FSGSNSGNTA TLTISRVEAG DEADYYCQVW DHSSDHVVFG GGTKLTVL            108

SEQ ID NO: 157          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 157
QVQLVQSGAE VKKPGASVKV SCKASGFAFR TYGLSWVRQA PGQGLEWMGW IWYDGSNTNY  60
GQEFQGRVTM TTDTSTSTAY MELRSLRSDD TAVYYCARAP QWYLSAEAFD LWGRGTLVTV  120
SS                                                             122

SEQ ID NO: 158          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 158
SYVLTQPPSV SVAPGKTARI TCGGNLIGSK LVHWYQQKPG QAPVLVIYDD SDRPSRIPER  60
FSGSNSGNTA TLTISRVEAG DEADYYCQVW DHSSDHVVFG GGTKLTVL            108

SEQ ID NO: 159          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 159
QMQLVESGGG VVQPGRSLRL SCAASGFTFR TYGMHWVRQA PGKGLEWVAD IWYDGSNKHY  60
ADSVKGRFTI TRDNSKNTLN LQMNSLRAED TAVYYCARAP QWYLVAEPFD LWGQGTMVTV  120
SS                                                             122

SEQ ID NO: 160          moltype = AA   length = 108
FEATURE                 Location/Qualifiers
REGION                  1..108
                        note = Description of Artificial Sequence: Synthetic
                         polypeptide
source                  1..108
```

-continued

```
                              mol_type = protein
                              organism = synthetic construct
SEQUENCE: 160
SYVLTQPPSV SVAPGQTARI TCGGNLIGSK LVHWYQQKPG QAPVLVVYDD SDRPSLIPER    60
FSGSNSGNTA TLTISRVEAG DEADYYCQVW DSSSDGVVFG GGTKLTVL                108

SEQ ID NO: 161            moltype = DNA   length = 366
FEATURE                   Location/Qualifiers
misc_feature              1..366
                          note = Description of Artificial Sequence: Synthetic
                           polynucleotide
source                    1..366
                          mol_type = other DNA
                          organism = synthetic construct
SEQUENCE: 161
caaatgcagc tggtcgagtc tggcggtggg gtagtgcaac caggccgttc tctgcgtctt    60
agctgcgccg catctggttt tgcgtttcgt acctacggta tgcactgggt gcgtcaggca   120
ccaggcaaag gtctggaatg ggtcgcagta atctggtatg atggtagcaa tacccactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtggtact taagcgcgga agcattcgat ctatggggcc agggcactat ggtgaccgtt   360
agctct                                                             366

SEQ ID NO: 162            moltype = DNA   length = 324
FEATURE                   Location/Qualifiers
misc_feature              1..324
                          note = Description of Artificial Sequence: Synthetic
                           polynucleotide
source                    1..324
                          mol_type = other DNA
                          organism = synthetic construct
SEQUENCE: 162
tcttacgtgc tgactcaacc accatcagtg tctgtagcac caggccagac cgcacgtatt    60
acctgtggcg gtaacctgat cggctctaag ctggttcact ggtatcagca aaaaccaggc   120
caggcaccag tactggttgt gtacgatgat agcgatcgtc caagccgtat tccagagcgt   180
ttcagcggct ctaattccgg caacaccgct actctgacta tttcccgtgt tgaagccggc   240
gatgaagccg actactattg ccaggtctgg gaccacagct ccgaccatgt agtctttggc   300
gggggcacca aactgaccgt tttg                                          324

SEQ ID NO: 163            moltype = DNA   length = 366
FEATURE                   Location/Qualifiers
misc_feature              1..366
                          note = Description of Artificial Sequence: Synthetic
                           polynucleotide
source                    1..366
                          mol_type = other DNA
                          organism = synthetic construct
SEQUENCE: 163
caaatgcagc tggtcgagtc tggcggtggg gtagtgcaac caggccgttc tctgcgtctt    60
agctgcgccg catctggttt tacctttcgt acctacggta tgcactgggt gcgtcaggca   120
ccaggcaaag gtctggaatg ggtcgcagac atctggtatg atggtagcaa taaacactat   180
gctgactcag tcaaaggccg tttcaccatc acccgtgata acagcaagaa cactcttaac   240
ttacagatga actctctgcg tgccgaagac accgccgttt actactgtgc ccgtgcacca   300
cagtggtact tagtagcgga accgttcgat ctatggggcc agggcactat ggtgaccgtt   360
agctct                                                             366

SEQ ID NO: 164            moltype = DNA   length = 324
FEATURE                   Location/Qualifiers
misc_feature              1..324
                          note = Description of Artificial Sequence: Synthetic
                           polynucleotide
source                    1..324
                          mol_type = other DNA
                          organism = synthetic construct
SEQUENCE: 164
tcttacgtgc tgactcaacc accatcagtg tctgtagcac caggccagac cgcacgtatt    60
acctgtggcg gtaacctgat cggctctaag ctggttcact ggtatcagca aaaaccaggc   120
caggcaccag tactggttgt gtacgatgat agcgatcgtc caagcctgat tccagagcgt   180
ttcagcggct ctaattccgg caacaccgct actctgacta tttcccgtgt tgaagccggc   240
gatgaagccg actactattg ccaggtctgg gactctagct ccgacggtgt agtctttggc   300
gggggcacca aactgaccgt tttg                                          324

SEQ ID NO: 165            moltype = AA   length = 8
FEATURE                   Location/Qualifiers
REGION                    1..8
                          note = Description of Artificial Sequence: Synthetic peptide
source                    1..8
                          mol_type = protein
                          organism = synthetic construct
```

```
SEQUENCE: 165
GFTFRTYG                                                                    8

SEQ ID NO: 166        moltype = AA   length = 8
FEATURE               Location/Qualifiers
REGION                1..8
                      note = Description of Artificial Sequence: Synthetic peptide
source                1..8
                      mol_type = protein
                      organism = synthetic construct
SEQUENCE: 166
IWYDGSNK                                                                    8

SEQ ID NO: 167        moltype = AA   length = 15
FEATURE               Location/Qualifiers
REGION                1..15
                      note = Description of Artificial Sequence: Synthetic peptide
source                1..15
                      mol_type = protein
                      organism = synthetic construct
SEQUENCE: 167
ARAPQWYLVA EPFDL                                                            15

SEQ ID NO: 168        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 168
QVWDSSSDGV V                                                                11

SEQ ID NO: 169        moltype = AA   length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 169
QMQLVESGGG VVQPGRSLRL SCAASGFAFR TYGMHWVRQA PGKGLEWVAV IWYDGSNTHY  60
ADSVKGRFTI TRDNSKNTLN LQMNSLRAED TAVYYCVRAP QWYLSAEAFD LWGQGTMVTV  120
SS                                                                          122

SEQ ID NO: 170        moltype = AA   length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 170
SYVLTQPPSV SVAPGQTARI TCGGNLIGAK LVHWYQQKPG QAPVLVVYDD SDRPSRIPER  60
FSGSNSGNTA TLTISRVEAG DEADYYCQVW DHSSDHVVFG GGTKLTVL                 108

SEQ ID NO: 171        moltype = AA   length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 171
QMQLVESGGG VVQPGRSLRL SCAASGFAFR TYGMHWVRQA PGKGLEWVAV IWDDGSNTHY  60
ADSVKGRFTI TRDNSKNTLN LQMNSLRAED TAVYYCARAP QWYLSAEAFD LWGQGTMVTV  120
SS                                                                          122

SEQ ID NO: 172        moltype = AA   length = 108
FEATURE               Location/Qualifiers
REGION                1..108
                      note = Description of Artificial Sequence: Synthetic
                       polypeptide
source                1..108
                      mol_type = protein
                      organism = synthetic construct
```

```
SEQUENCE: 172
SYVLTQPPSV SVAPGQTARI TCGGNLIGSK LVHWYQQKPG QAPVLVVYDD SDRPSRIPER  60
FSGSNSGNTA TLTISRVEAG DEADYYCQVW DHSSDHVVFG GGTKLTVL                108

SEQ ID NO: 173            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 173
QMQLVESGGG VVQPGRSLRL SCAASGFAFR TYGMHWVRQA PGKGLEWVAV IWYDGSNTHY  60
ADSVKGRFTI TRDNSKNTLN LQMNSLRAED TAVYYCVRAP QWYLSAEAFD LWGQGTMVTV  120
SS                                                                 122

SEQ ID NO: 174            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 174
SYVLTQPPSV SVAPGQTARI TCGGNLIGSK LVHWYQQKPG QAPVLVVYDD SDRPSRIPER  60
FSGSNSGNTA TLTISRVEAG DEADYYCQVW DYSSNHVVFG GGTKLTVL                108

SEQ ID NO: 175            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 175
QMQLVESGGG VVQPGRSLRL SCAASGFAFD TYGMHWVRQA PGKGLEWVAV IWYDGSNTVY  60
ADSVKGRFTI TRDNSKNTLN LQMNSLRAED TAVYYCARAP QWYLSAEAFD LWGQGTMVTV  120
SS                                                                 122

SEQ ID NO: 176            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 176
SYVLTQPPSV SVAPGQTARI TCGGNLIGSK LVHWYQQKPG QAPVLVVYDD SDRPSRIPER  60
FSGSNSGNTA TLTISRVEAG DEADYYCQVW DHSSDHYVFG GGTKLTVL                108

SEQ ID NO: 177            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 177
QMQLVESGGG VVQPGRSLRL SCAASGFAFR TYGMHWVRQA PGKGLEWVAV IWYDGSNTHY  60
ADSVKGRFTI TRDNSKNTLN LQMNSLRAED TAVYYCVRAP QWYLSAEAFD LWGQGTMVTV  120
SS                                                                 122

SEQ ID NO: 178            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 178
SYVLTQPPSV SVAPGETATI TCGGNLIGSK LVHWYQQKPG QAPVLVVYDD SDRPSRIPER  60
FSGSNSGNTA TLTISRVEAG DEADYYCQVW DHSSDHVVFG GGTKLTVL                108
```

-continued

```
SEQ ID NO: 179          moltype = AA   length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 179
QMQLVESGGG VVQPGRSLRL SCAASGFAFR TYGMHWVRQA PGKGLEWVAV IWYDGSATHY   60
ADSVKGRFTI TRDNSKNTLN LQMNSLRAED TAVYYCVRAP QWYLSAEAFD LWGQGTMVTV  120
SS                                                                 122

SEQ ID NO: 180          moltype = AA   length = 108
FEATURE                 Location/Qualifiers
REGION                  1..108
                        note = Description of Artificial Sequence: Synthetic
                        polypeptide
source                  1..108
                        mol_type = protein
                        organism = synthetic construct
SEQUENCE: 180
SYVLTQPPSV SVAPGQTATI TCGGNLIGSK LVHWYQQKPG QAPVLVVYDD SDRPSRIPER   60
FSGSNIGNTA TLTISRVEAG DEADYYCQVW DHSSDHVVFG GGTKLTVL                108

SEQ ID NO: 181          moltype = AA   length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 181
QMQLVESGGG VVQPGRSLRL SCAASGFDFR TYGMHWVRQA PGKGLEWVAV IWYDGSITHY   60
ADSVKGRFTI TRDNSKNTLN LQMNSLRAED TAVYYCVRAP QWYLTAEAFD LWGQGTMVTV  120
SS                                                                 122

SEQ ID NO: 182          moltype = AA   length = 108
FEATURE                 Location/Qualifiers
REGION                  1..108
                        note = Description of Artificial Sequence: Synthetic
                        polypeptide
source                  1..108
                        mol_type = protein
                        organism = synthetic construct
SEQUENCE: 182
SYVLTQPPSV SVAPGQTARI TCGGNLIGTK LVHWYQQKPG QAPVLVVYDD SDRPSRIPER   60
FSGSNSGNTA TLTISRVEAG DEADYYCQVW DHNEDEVVFG GGTKLTVL                108

SEQ ID NO: 183          moltype = DNA   length = 366
FEATURE                 Location/Qualifiers
misc_feature            1..366
                        note = Description of Artificial Sequence: Synthetic
                        polynucleotide
source                  1..366
                        mol_type = other DNA
                        organism = synthetic construct
SEQUENCE: 183
cagatgcagt tggtggagtc cggaggtgga gtggtgcaac agggcgttc cttgcgtttg    60
tcttgtgctg cttccggatt cgcctttcgt acatatggca tgcattgggt gcgtcaagca   120
cctggtaagg gcctggagtg ggttgccgtt atttggtacg acggctccaa cacccactac   180
gcagatagct gaaaggacg tttcactatt acccgtgata actccaagaa taccctaac    240
ctgcagatga atagcttgcg tgctgaggac acagcagtat attactgcgt ccgtgcacca   300
caatggtacc tgagcgccga ggcctttgat ctgtgggggc agggcacaat ggtgaccgtt   360
tcctca                                                              366

SEQ ID NO: 184          moltype = DNA   length = 324
FEATURE                 Location/Qualifiers
misc_feature            1..324
                        note = Description of Artificial Sequence: Synthetic
                        polynucleotide
source                  1..324
                        mol_type = other DNA
                        organism = synthetic construct
SEQUENCE: 184
agttacgtgc tgacacaacc tccaagtgtt agtgtcgcac caggacaaac agcacgtatt    60
acatgtggag gaaatcttat cggtgccaag ctggtgcact ggtaccagca gaaacctggt   120
caggccccag tactggttgt gtatgatgac agcgaccgtc aagccgtat cccagaacgt    180
```

```
ttttctggga gcaactcagg taatacagcc actctgacca tttcacgtgt tgaggcagga   240
gatgaggccg attattattg ccaagtatgg gaccacagct ctgaccatgt tgtttttggc   300
ggagggacta agctgaccgt gctt                                          324

SEQ ID NO: 185          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 185
cagatgcaac tggtggagtc aggaggcggc gtggtgcagc caggacgttc tctgcgtctg    60
tcttgcgcag cttccgggtt cgcctttcgt acctatggga tgcattgggt gcgtcaggct   120
ccaggtaagg gactggagtg ggtcgctgtt atttgggacg acggaagtaa cactcattac   180
gccgacagcg tgaagggccg tttcacaatt acccgtgaca attccaagaa taccttgaac   240
ctgcagatga actctcttcg tgctgaagat accgccgtgt actattcgc ccgtgctcca    300
cagtggtatc tgtcagcaga ggccttcgac ctgtggggac agggaacaat ggtgaccgta   360
tcttca                                                              366

SEQ ID NO: 186          moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 186
tcctatgtgc tgacacagcc acctagcgtg agcgtcgccc caggtcagac cgctcgtatc    60
acttgtggcg ggaaccttat cggcagcaag ctggtgcact ggtaccagca gaagcctggc   120
caagcacctg tgctggtcgt ttatgacgac tctgaccgtc catcccgtat cccagaacgt   180
ttctctggct ctaactctgg gaataccgct accctgacaa tctcacgtgt tgaagctggc   240
gacgaggcag attattattg ccaagtctgg gatcactcca gcgatcacgt cgtgttcgga   300
ggcggaacaa aattgactgt cctg                                          324

SEQ ID NO: 187          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 187
caaatgcagc tggtggaatc cggggggtggg gtcgtccagc ctggccgtag tctgcgtctt    60
tcctgtgccg catcaggctt tgctttccgt acctacggga tgcactgggt gcgtcaggcc   120
ccaggaaagg gacttgaatg ggtggctgtc atctggtacg atggttccaa cacacactat   180
gccgattcag tgaaagggcg tttcaccatt actcgtgaca atagtaagaa tactctgaat   240
ctgcaaatga attcactgcg tgctgaggac accgctgttt attactgtgt gcgtgctcct   300
cagtggtacc tgagtgccga agctttcgat ttgtggggac agggcacaat ggtgacagtc   360
agttct                                                              366

SEQ ID NO: 188          moltype = DNA   length = 324
FEATURE                 Location/Qualifiers
misc_feature            1..324
                        note = Description of Artificial Sequence: Synthetic
                         polynucleotide
source                  1..324
                        mol_type = other DNA
                        organism = synthetic construct
SEQUENCE: 188
tcttacgtgt tgacacaacc accaagtgtt agtgtcgcac ctggccaaac cgctcgtatc    60
acctgtggtg ggaatcttat tggctctaag ctggtgcact ggtatcagca gaaaccaggc   120
caggctccag tactggtggt gtacgacgac tctgaccgtc caagccgtat cccagagcgt   180
ttcagtggct ctaactccgg gaacacagca actcttacaa tttcacgtgt ggaggccggt   240
gatgaagccg actactattg ccaggtttgg gactacagta gtaatcacgt ggttttcggt   300
ggtggtacca agctgactgt gttg                                          324

SEQ ID NO: 189          moltype = DNA   length = 366
FEATURE                 Location/Qualifiers
misc_feature            1..366
                        note = Description of Artificial Sequence: Synthetic
                         polynucleotide
source                  1..366
                        mol_type = other DNA
                        organism = synthetic construct
SEQUENCE: 189
```

```
cagatgcagc tggttgaatc tggcggcggt gtggtccagc ctggtcgtag cctgcgtctg    60
tcctgtgctg caagcggatt tgcctttgac acctatggga tgcactgggt acgtcaggcc   120
ccaggaaagg gcctggaatg ggtggcagtt atctggtatg atggttctaa taccgtgtat   180
gccgactccg ttaaaggccg tttcactatc acccgtgata atagtaaaaa cacactgaac   240
ctgcagatga atagcttgcg tgctgaggac accgcagtgt actactgtgc ccgtgctcct   300
cagtggtatc tgtcagcaga ggccttcgat ctgtggggc aagggacaat ggtgaccgtg   360
tcttcc                                                              366
```

```
SEQ ID NO: 190              moltype = DNA   length = 324
FEATURE                     Location/Qualifiers
misc_feature                1..324
                            note = Description of Artificial Sequence: Synthetic
                             polynucleotide
source                      1..324
                            mol_type = other DNA
                            organism = synthetic construct
SEQUENCE: 190
agctatgttc tgactcaacc acctagtgtg agtgtggccc ctggtcagac tgcacgtatt    60
acctgtggcg gaaaccttat cggcagtaag ctggttcatt ggtatcagca gaagccagga   120
caggcaccag tgctggtcgt ttacgacgat agtgaccgtc catcacgtat cccagagcgt   180
tttagcgggt ccaattccgg aaatacagca accttgacca ttagccgtgt ggaagccggc   240
gatgaagctg attattactg ccaggtatgg gaccattcct ccgaccacta cgttttggt   300
ggcggaacta agctgacagt cttg                                          324
```

```
SEQ ID NO: 191              moltype = DNA   length = 366
FEATURE                     Location/Qualifiers
misc_feature                1..366
                            note = Description of Artificial Sequence: Synthetic
                             polynucleotide
source                      1..366
                            mol_type = other DNA
                            organism = synthetic construct
SEQUENCE: 191
cagatgcagc ttgttgagag cggcggaggc gtggtgcaac caggccgttc attgcgtctg    60
tcctgcgccg ccagcggctt tgcttttcgt acatacggca tgcactgggt gcgtcaggcc   120
cctggcaagg ggctggaatg ggtcgccgtg atttggtatg acggtagtaa cacccattat   180
gctgattccg tcaagggacg tttcactatc acccgtgaca atagcaaaaa tacactgaat   240
ctgcaaatga attcattgcg tgccgaagac accgccgtat attactgtgt ccgtgcccca   300
cagtggtacc tgagcgctga ggccttcgat ctgtggggtc agggactat ggtgaccgta   360
tcatcc                                                              366
```

```
SEQ ID NO: 192              moltype = DNA   length = 324
FEATURE                     Location/Qualifiers
misc_feature                1..324
                            note = Description of Artificial Sequence: Synthetic
                             polynucleotide
source                      1..324
                            mol_type = other DNA
                            organism = synthetic construct
SEQUENCE: 192
tcttacgtgc ttactcagcc tcctagcgtc tcagtggccc caggcgagac agcaaccatt    60
acatgcgggg gtaatttgat cggtagcaag ctggtgcatt ggtatcagca gaagcctggc   120
caggccccag tgctggttgt atatgacgat agtgatcgtc caagtcgtat ccctgagcgt   180
tttagcggat ctaactccgg caacacagcc acattgacaa tcagccgtgt ggaggcaggc   240
gatgaggccg actactactg ccaagtttgg gaccactcct ctgaccacgt ggtatttggc   300
ggaggaacaa agcttacagt tttg                                          324
```

```
SEQ ID NO: 193              moltype = DNA   length = 366
FEATURE                     Location/Qualifiers
misc_feature                1..366
                            note = Description of Artificial Sequence: Synthetic
                             polynucleotide
source                      1..366
                            mol_type = other DNA
                            organism = synthetic construct
SEQUENCE: 193
cagatgcagc tggttgagag tggaggtggt gtggtgcaac ctgggcgtag cctgcgtttg    60
agctgcgctg cctctggatt tgccttccgt acctatggca tgcactgggt gcgtcaggct   120
ccaggaaagg ggttggaatg ggtggctgtg atttggtacg acgggagcgc cacacattac   180
gcagacagcg ttaagggccg tttcacaatt acccgtgaca atagcaaaaa tacattgaac   240
ctgcagatga attccctgcg tgcagaggat actgcagtgt actattcgt ccgtgcccca   300
cagtggtatc tgtcagccga agccttcgat ctgtggggc agggtactat ggtcaccgta   360
agttcc                                                              366
```

```
SEQ ID NO: 194              moltype = DNA   length = 324
FEATURE                     Location/Qualifiers
misc_feature                1..324
                            note = Description of Artificial Sequence: Synthetic
                             polynucleotide
```

-continued

```
source                 1..324
                       mol_type = other DNA
                       organism = synthetic construct
SEQUENCE: 194
tcttatgttt tgacccaacc tccatccgtt agcgtggctc caggtcaaac agctaccatc   60
acatgtggcg gtaaccttat tggctcaaag ctggttcatt ggtatcaaca gaaaccaggc  120
caagccccag tgctggtggt gtatgacgac agtgaccgtc cttctcgtat tcctgagcgt  180
ttttccggct ctaatattgg caacactgcc accctgacca tttctcgtgt ggaagcagga  240
gatgaggcag actattattg tcaggtttgg gatcactcca gcgatcatgt ggtattcgga  300
ggtgggacaa aacttactgt tctt                                         324

SEQ ID NO: 195         moltype = DNA   length = 366
FEATURE                Location/Qualifiers
misc_feature           1..366
                       note = Description of Artificial Sequence: Synthetic
                       polynucleotide
source                 1..366
                       mol_type = other DNA
                       organism = synthetic construct
SEQUENCE: 195
cagatgcagc tggtggaaag tggtggggga gtcgtgcaac caggacgttc cttgcgtctg   60
tcatgcgctg cttcaggttt cgactttcgt acctacggca tgcattgggt gcgtcaggct  120
ccaggtaaag gacttgagtg ggtcgcagtg atctggtacg acggatcaat tactcactac  180
gccgatagcg tgaaaggccg tttcaccatc acccgtgaca actccaagaa caccctgaac  240
ttgcagatga acagtctgcg tgcagaagac actgcagtat attattgtgt ccgtgcccca  300
cagtggtact tgaccgccga ggcttttgat ctgtggggac agggcacaat ggtgaccgta  360
tctagc                                                            366

SEQ ID NO: 196         moltype = DNA   length = 324
FEATURE                Location/Qualifiers
misc_feature           1..324
                       note = Description of Artificial Sequence: Synthetic
                       polynucleotide
source                 1..324
                       mol_type = other DNA
                       organism = synthetic construct
SEQUENCE: 196
agctacgtgc ttacccagcc accatcagtc agtgtggctc caggccaaac tgcccgtatc   60
acctgcggcg gcaatttgat tggcaccaag cttgtgcact ggtaccaaca gaagccaggg  120
caggcccctg tgctggttgt ctacgacgat agtgatcgtc cttcccgtat tcctgaacgt  180
ttctctggaa gcaattccgg aaacacagcc cacttacca tttctcgtgt tgaggctggg  240
gatgaagccg actactattg ccaggtttgg gaccacaatg aagacgaagt tgtttttgga  300
ggaggaacta agctgacagt tctg                                         324

SEQ ID NO: 197         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 197
GFAFDTYG                                                             8

SEQ ID NO: 198         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 198
GFDFRTYG                                                             8

SEQ ID NO: 199         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 199
IWYDGSAT                                                             8

SEQ ID NO: 200         moltype = AA   length = 8
FEATURE                Location/Qualifiers
REGION                 1..8
                       note = Description of Artificial Sequence: Synthetic peptide
source                 1..8
```

```
                              mol_type = protein
                              organism = synthetic construct
SEQUENCE: 200
IWYDGSIT                                                                   8

SEQ ID NO: 201           moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 201
VRAPQWYLSA EAFDL                                                           15

SEQ ID NO: 202           moltype = AA  length = 15
FEATURE                  Location/Qualifiers
REGION                   1..15
                         note = Description of Artificial Sequence: Synthetic peptide
source                   1..15
                         mol_type = protein
                         organism = synthetic construct
SEQUENCE: 202
VRAPQWYLTA EAFDL                                                           15

SEQ ID NO: 203           moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 203
LIGAKL                                                                     6

SEQ ID NO: 204           moltype = AA  length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 204
LIGTKL                                                                     6

SEQ ID NO: 205           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 205
QVWDYSSNHV V                                                               11

SEQ ID NO: 206           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 206
QVWDHSSDHY V                                                               11

SEQ ID NO: 207           moltype = AA  length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 207
QVWDHNEDEV V                                                               11

SEQ ID NO: 208           moltype = AA  length = 8
FEATURE                  Location/Qualifiers
REGION                   1..8
                         note = Description of Artificial Sequence: Synthetic peptide
```

-continued

```
source                    1..8
                          mol_type = protein
                          organism = synthetic construct
SEQUENCE: 208
IWDDGSNT                                                              8

SEQ ID NO: 209            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 209
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                  122

SEQ ID NO: 210            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 210
SYVLTQPPSV SVAPGQTATI TCGGNMIGAY LVHWYQQKPG QAPLLVVYDD VDRPNRIPER   60
FSGSNSGNTA TLTISRVEAG DEADYYCQVW DHNTDKMVFG GGTKLTVL                108

SEQ ID NO: 211            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 211
QMQLVESGGG VVQPGRSLRL SCAASGFAFR TYGMHWVRQA PGKGLEWVAV IWYDGSATHY   60
ADSVKGRFTI TRDNSKNTLN LQMNSLRAED TAVYYCVRAP QWYLSAEAFD LWGQGTMVTV  120
SS                                                                  122

SEQ ID NO: 212            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 212
SYVLTQPPSV SVAPGETATI TCGGNLIGAY LVHWYQQKPG QAPVLVIYDD VDRPARIPER   60
FSGSNSGNTA TLTISRVEAG DEADYYCQVW DHDTNTMVFG GGTKLTVL                108

SEQ ID NO: 213            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 213
QMQLVESGGG VVQPGRSLRL SCAASGFAFR TYGMHWVRQA PGKGLEWVAV IWDDGSATHY   60
ADSVKGRFTI TRDNSKNTLN LQMNSLRAED TAVYYCVRAP QWYLTAEAFD LWGQGTMVTV  120
SS                                                                  122

SEQ ID NO: 214            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 214
SYVLTQPPSV SVAPGETASI TCGGNMIGGY LVHWYQQKPG QAPLLVIYDD VDRPARIPER   60
```

```
FSGSNSGNTA TLTISRVEAG DEADYYCQVW DHDTNHMVFG GGTKLTVL                                108

SEQ ID NO: 215          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 215
QMQLVESGGG VVQPGRSLTL SCAASGFAFR TYGMHWVRQA PGKGLEWVGV IWYDGSATHY                   60
ADSVKGRFTI TRDNSKNTLN LQMNSLRAED TAVYYCVRAP QWYLTAEAFD LWGQGTMVTV                   120
SS                                                                                122

SEQ ID NO: 216          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 216
SYVLTQPPSV SVAPGETATI TCGGALIGSR LVHWYQQKPG QAPVLVIYDD SDRPSRIPER                   60
FSGSNIGNTA TLTISDVEAG DEADYYCQVW DHSSNTYVFG GGTKLTVL                                108

SEQ ID NO: 217          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 217
QMQLVESGGG VVQPGRSLRL SCAASGFEFR TYGMHWVRQA PGKGLEWLGV IWYDGSNTHY                   60
ADSVKGRFTI TRDNSKNTLN LQMNSLRVED TAVYYCVRAP QWYLTAEAFD LWGQGTMVTV                   120
SS                                                                                122

SEQ ID NO: 218          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 218
SYILTQPPSV SVAPGETATI TCGGNLIGAR LVHWYQQKPG QAPVLVIYDD SDRPSRIPER                   60
FSGSNIGNTA TLTIERVEAG DEADYYCQVW DYYSDHMVFG GGTKLTVL                                108

SEQ ID NO: 219          moltype = AA   length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 219
QMQLVESGGG VVQPGRSLRL SCAASGFAFR TYGMHWVRQA PGKGLEWAV IWYDGSNTHY                    60
ADSVKGRFTI TRDNSKNTLN LQMNSLRAED TAVYYCVRAP QWYLTAEAFD LWGQGTMVTV                   120
SS                                                                                122

SEQ ID NO: 220          moltype = AA   length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 220
SYVLTQPPSV SVAPGETATI TCGGNMIGGY LVHWYQQKPG QAPLLVIYDD VDRPDRIPER                   60
FSGSNSGNTA TLTISRVEAG DEADYYCQVW DHDSNTMVFG GGTKLTVL                                108

SEQ ID NO: 221          moltype = AA   length = 122
FEATURE                 Location/Qualifiers
```

-continued

```
REGION                    1..122
                          note = Description of Artificial Sequence: Synthetic
                           polypeptide
source                    1..122
                          mol_type = protein
                          organism = synthetic construct
SEQUENCE: 221
QMQLVESGGG VVQPGRSLRL SCAASGFAFR TYGMHWVRQA PGKGLEWVAV IWYDGSATHY   60
ADSVKGRFTI TRDNSKNTLN LQMNSLRAED TAVYYCVRAP QWYLSAEAFD LWGQGTMVTV  120
SS                                                                 122

SEQ ID NO: 222            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 222
SYVLTQPPSV SVAPGETATI TCGGNLIGAY LVHWYQQKPG QAPVLVIYDD SDRPDRIPER   60
FSGSNSGNTA TLTISRVEAG DEADYYCQVW DHNTNHMVFG GGTKLTVL               108

SEQ ID NO: 223            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 223
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 224            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 224
SYVLTQPPSV SVAPGQTARI TCGGNMIGAY LVHWYQQKPG QAPLLVIYDD VDRPDRIPER   60
FSGSNSGNTA TLTISRVEAG DEADYYCQVW DHNTQQMVFG GGTKLTVL               108

SEQ ID NO: 225            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 225
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 226            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 226
SYVLTQPPSV SVAPGETATI TCGGNMIGGY LVHWYQQKPG QAPVLVIYDD VDRPDRIPER   60
FSGSNSGNTA TLTISRVEAG DEADYYCQVW DHDTNQVVFG GGTKLTVL               108

SEQ ID NO: 227            moltype = AA  length = 122
FEATURE                   Location/Qualifiers
REGION                    1..122
                          note = Description of Artificial Sequence: Synthetic
                           polypeptide
source                    1..122
```

-continued

```
                          mol_type = protein
                          organism = synthetic construct
SEQUENCE: 227
QMQLVESGGG VVQPGRSLTL SCAASGFEFR TYGMHWVRQA PGKGLEWVGV IWDDGSNTHY  60
ADSVKGRFTI TRDNSKNTLN LQMNSLRAED TAVYYCARAP QWYLTAEAFD LWGQGTMVTV  120
SS                                                                122

SEQ ID NO: 228           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 228
SYILTQPPSV SVAPGQTATI TCGGNLIGAK LVHWYQQKPG QAPVLVIYDD SDRPSRIPER  60
FSGSNIGNTA TLTISDVEEG DEADYYCQVW DYSSDTMVFG GGTKLTVL              108

SEQ ID NO: 229           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 229
QMQLVESGGG VVQPGRSLRL SCAASGFAFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV  120
SS                                                                122

SEQ ID NO: 230           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 230
SYVLTQPPSV SVAPGETATI TCGGNLIGAY LVHWYQQKPG QAPVLVVYDD VDRPDRIPER  60
FSGSNSGNTA TLTISRVEAG DEADYYCQVW DHSTNTMVFG GGTKLTVL              108

SEQ ID NO: 231           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 231
QMQLVESGGG VVQPGRSLTL SCAASGFEFR TYGMHWVRQA PGKGLEWVGV IWYDGSNTHY  60
ADSVKGRFTI TRDNSKNTLN LQMNSLRVED TAVYYCVRAP QWYLTAEAFD LWGQGTMVTV  120
SS                                                                122

SEQ ID NO: 232           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 232
SYVLTQPPSV SVAPGETATI TCGGNLIGAR LVHWYQQKPG QAPVLVIYDD SDRPSRIPER  60
FSGSNIGNTA TLTIERVEAG DEADYYCQVW DYSSNSYVFG GGTKLTVL              108

SEQ ID NO: 233           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 233
QMQLVESGGG VVQPGRSLRL SCAASGFEFR TYGMHWVRQA PGKGLEWVGV IWYDGSNTHY  60
```

```
ADSVKGRFTI TRDNSKNTLN LQMNSLRAED TAVYYCVRAP QWYLTAEAFD LWGQGTMVTV  120
SS                                                                122

SEQ ID NO: 234        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 234
SYVLTQPPSV SVAPGQTARI TCGGNLIGAR LVHWYQQKPG QAPVLVVYDD SDRPSRIPER  60
FSGSNIGNTA TLTISDVEEG DEADYYCQVW DYSSNTYVFG GGTKLTVL              108

SEQ ID NO: 235        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 235
QMQLVESGGG VVQPGRSLRL SCAASGFAFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV  120
SS                                                                122

SEQ ID NO: 236        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 236
SYVLTQPPSV SVAPGQTATI TCGGNMIGAY LVHWYQQKPG QAPVLVIYDD VDRPDRIPER  60
FSGSNSGNTA TLTISRVEAG DEADYYCQVW DHNSNQMVFG GGTKLTVL              108

SEQ ID NO: 237        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 237
QMQLVESGGG VVQPGRSLTL SCAASGFEFR TYGMHWVRQA PGKGLEWVGV IWYDGSNTHY  60
ADSVKGRFTI TRDNSKNTLN LQMNSLRVED TAVYYCVRAP QWYLTAEAFD LWGQGTMVTV  120
SS                                                                122

SEQ ID NO: 238        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 238
SYVLTQPPSV SVAPGETATI TCGGNLIGAR LVHWYQQKPG QAPVLVIYDD SDRPSRIPER  60
FSGSNIGNTA TLTISDVEAG DEADYYCQVW DYSSNTYVFG GGTKLTVL              108

SEQ ID NO: 239        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 239
QMQLVESGGG VVQPGRSLRL SCAASGFEFR TYGMHWVRQA PGKGLEWVGV IWYDGSATHY  60
ADSVKGRFTI TRDNSKNTLN LQMNSLRVED TAVYYCVRAP QWYLTAEAFD LWGQGTMVTV  120
SS                                                                122

SEQ ID NO: 240        moltype = AA  length = 108
```

-continued

```
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 240
SYILTQPPSV SVAPGETATI TCGGNLIGAR LVHWYQQKPG QAPVLVIYDD SDRPSRIPER  60
FSGSNIGNTA TLTISRVEEG DEADYYCQVW DHSSNHYVFG GGTKLTVL              108

SEQ ID NO: 241         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 241
QMQLVESGGG VVQPGRSLTL SCAASGFEFR TYGMHWVRQA PGKGLEWLGV IWDDGSNTHY  60
ADSVKGRFTI TRDNSKNTLN LQMNSLRVED TAVYYCARAP QWYLTAEAFD LWGQGTMVTV 120
SS                                                              122

SEQ ID NO: 242         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 242
SYILTQPPSV SVAPGETARI TCGGNLIGAR LVHWYQQKPG QAPVLVVYDD SDRPSRIPER  60
FSGSNIGNTA TLTIEDVEEG DEADYYCQVW DYYSDHMVFG GGTKLTVL              108

SEQ ID NO: 243         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 243
QMQLVESGGG VVQPGRSLTL SCAASGFEFR TYGMHWVRQA PGKGLEWLGV IWYDGSNTHY  60
ADSVKGRFTI TRDNSKNTLN LQMNSLRVED TAVYYCVRAP QWYLTAEAFD LWGQGTMVTV 120
SS                                                              122

SEQ ID NO: 244         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 244
SYILTQPPSV SVAPGETATI TCGGNLIGSR LVHWYQQKPG QAPVLVIYDD SDRPSRIPER  60
FSGSNIGNTA TLTISDVEAG DEADYYCQVW DHYSNHYVFG GGTKLTVL              108

SEQ ID NO: 245         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 245
QMQLVESGGG VVQPGRSLTL SCAASGFEFR TYGMHWVRQA PGKGLEWLAV IWDDGSNTHY  60
ADSVKGRFTI TRDNSKNTLN LQMNSLRVED TAVYYCVRAP QWYLTAEAFD LWGQGTMVTV 120
SS                                                              122

SEQ ID NO: 246         moltype = AA  length = 108
FEATURE                Location/Qualifiers
REGION                 1..108
                       note = Description of Artificial Sequence: Synthetic
                        polypeptide
```

```
source                    1..108
                          mol_type = protein
                          organism = synthetic construct
SEQUENCE: 246
SYVLTQPPSV SVAPGETATI TCGGNLIGAR LVHWYQQKPG QAPVLVIYDD SDRPSRIPER   60
FSGSNIGNTA TLTISDVEEG DEADYYCQVW DYYSDHMVFG GGTKLTVL                108

SEQ ID NO: 247            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 247
QMQLVESGGG VVQPGRSLTL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 248            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 248
SYVLTQPPSV SVAPGQTARI TCGGNLIGAR LVHWYQQKPG QAPVLVIYDD SDRPSRIPER   60
FSGSNIGNTA TLTIERVEEG DEADYYCQVW DYSADSYVFG GGTKLTVL                108

SEQ ID NO: 249            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 249
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 250            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 250
SYVLTQPPSV SVAPGETASI TCGGNLIGAY LVHWYQQKPG QAPLLVIYDD VDRPARIPER   60
FSGSNSGNTA TLTISRVEAG DEADYYCQVW DHNSNHMVFG GGTKLTVL                108

SEQ ID NO: 251            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 251
QMQLVESGGG VVQPGRSLTL SCAASGFEFR TYGMHWVRQA PGKGLEWVGV IWYDGSATHY   60
ADSVKGRFTI TRDNSKNTLN LQMNSLRAED TAVYYCVRAP QWYLTAEAFD LWGQGTMVTV  120
SS                                                                 122

SEQ ID NO: 252            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 252
```

-continued

```
SYVLTQPPSV SVAPGQTATI TCGGALIGSR LVHWYQQKPG QAPVLVVYDD SDRPSRIPER    60
FSGSNIGNTA TLTISRVEEG DEADYYCQVW DYYSDSYVFG GGTKLTVL                108

SEQ ID NO: 253            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 253
QMQLVESGGG VVQPGRSLRL SCAASGFEFR TYGMHWVRQA PGKGLEWVAV IWDDGSNTHY    60
ADSVKGRFTI TRDNSKNTLN LQMNSLRVED TAVYYCVRAP QWYLTAEAFD LWGQGTMVTV   120
SS                                                                  122

SEQ ID NO: 254            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 254
SYILTQPPSV SVAPGETARI TCGGNLIGAR LVHWYQQKPG QAPVLVIYDD SDRPSRIPER    60
FSGSNIGNTA TLTISRVEEG DEADYYCQVW DYSSDSMVFG GGTKLTVL                108

SEQ ID NO: 255            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 255
QMQLVESGGG VVQPGRSLRL SCAASGFEFR TYGMHWVRQA PGKGLEWLGV IWYDGSATHY    60
ADSVKGRFTI TRDNSKNTLN LQMNSLRAED TAVYYCVRAP QWYLTAEAFD LWGQGTMVTV   120
SS                                                                  122

SEQ ID NO: 256            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 256
SYILTQPPSV SVAPGETATI TCGGNLIGAR LVHWYQQKPG QAPVLVIYDD SDRPSRIPER    60
FSGSNIGNTA TLTIERVEEG DEADYYCQVW DYYSDHYVFG GGTKLTVL                108

SEQ ID NO: 257            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 257
QMQLVESGGG VVQPGRSLTL SCAASGFEFR TYGMHWVRQA PGKGLEWVAV IWDDGSNTVY    60
ADSVKGRFTI TRDNSKNTLN LQMNSLRVED TAVYYCVRAP QWYLTAEAFD LWGQGTMVTV   120
SS                                                                  122

SEQ ID NO: 258            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 258
SYVLTQPPSV SVAPGQTATI TCGGNLIGAR LVHWYQQKPG QAPVLVIYDD SDRPSRIPER    60
FSGSNIGNTA TLTISRVEAG DEADYYCQVW DYSSDSMVFG GGTKLTVL                108

SEQ ID NO: 259            moltype = AA  length = 122
```

-continued

```
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 259
QMQLVESGGG VVQPGRSLRL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 260        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 260
SYILTQPPSV SVAPGETARI TCGGNLIGAR LVHWYQQKPG QAPVLVIYDD SDRPSRIPER   60
FSGSNIGNTA TLTIEDVEEG DEADYYCQVW DYSSDSYVFG GGTKLTVL                108

SEQ ID NO: 261        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 261
QMQLVESGGG VVQPGRSLRL SCAASGFEFR TYGMHWVRQA PGKGLEWVGV IWYDGSNTHY   60
ADSVKGRFTI TRDNSKNTLN LQMNSLRVED TAVYYCVRAP QWYLTAEAFD LWGQGTMVTV  120
SS                                                                 122

SEQ ID NO: 262        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 262
SYVLTQPPSV SVAPGETARI TCGGNLIGAR LVHWYQQKPG QAPVLVIYDD SDRPSRIPER   60
FSGSNIGNTA TLTIERVEEG DEADYYCQVW DYSNSYVFG GGTKLTVL                108

SEQ ID NO: 263        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 263
QMQLVESGGG VVQPGRSLRL SCAASGFEFR TYGMHWVRQA PGKGLEWVGV IWYDGSATHY   60
ADSVKGRFTI TRDNSKNTLN LQMNSLRVED TAVYYCVRAP QWYLTAEAFD LWGQGTMVTV  120
SS                                                                 122

SEQ ID NO: 264        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 264
SYILTQPPSV SVAPGETATI TCGGNLIGAR LVHWYQQKPG QAPVLVIYDD SDRPSRIPER   60
FSGSNIGNTA TLTISRVEEG DEADYYCQVW DYSSNTYVFG GGTKLTVL                108

SEQ ID NO: 265        moltype = AA  length = 122
FEATURE               Location/Qualifiers
REGION                1..122
                      note = Description of Artificial Sequence: Synthetic
                       polypeptide
```

-continued

```
source                    1..122
                          mol_type = protein
                          organism = synthetic construct
SEQUENCE: 265
QMQLVESGGG VVQPGRSLRL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV   120
SS                                                                  122

SEQ ID NO: 266            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 266
SYVLTQPPSV SVAPGETATI TCGGNLIGAR LVHWYQQKPG QAPVLVVYDD SDRPSRIPER   60
FSGSNIGNTA TLTIEDVEAG DEADYYCQVW DYSSNTYVFG GGTKLTVL                108

SEQ ID NO: 267            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 267
QMQLVESGGG VVQPGRSLRL SCAASGFEFR TYGMHWVRQA PGKGLEWVGV IWYDGSNTHY   60
ADSVKGRFTI TRDNSKNTLN LQMNSLRVED TAVYYCVRAP QWYLTAEAFD LWGQGTMVTV   120
SS                                                                  122

SEQ ID NO: 268            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 268
SYVLTQPPSV SVAPGQTATI TCGGNLIGAR LVHWYQQKPG QAPVLVVYDD SDRPSRIPER   60
FSGSNIGNTA TLTISDVEEG DEADYYCQVW DYYSNSYVFG GGTKLTVL                108

SEQ ID NO: 269            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 269
QMQLVESGGG VVQPGRSLTL SCAASGFEFR TYGMHWVRQA PGKGLEWVGV IWYDGSATHY   60
ADSVKGRFTI TRDNSKNTLN LQMNSLRAED TAVYYCVRAP QWYLTAEAFD LWGQGTMVTV   120
SS                                                                  122

SEQ ID NO: 270            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 270
SYILTQPPSV SVAPGETATI TCGGNLIGAR LVHWYQQKPG QAPVLVIYDD SDRPSRIPER   60
FSGSNIGNTA TLTIEDVEEG DEADYYCQVW DYYSDSYVFG GGTKLTVL                108

SEQ ID NO: 271            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 271
```

-continued

```
QMQLVESGGG VVQPGRSLTL SCAASGFEFR TYGMHWVRQA PGKGLEWVGV IWYDGSNTHY   60
ADSVKGRFTI TRDNSKNTLN LQMNSLRVED TAVYYCVRAP QWYLTAEAFD LWGQGTMVTV  120
SS                                                                122

SEQ ID NO: 272          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 272
SYVLTQPPSV SVAPGETATI TCGGNLIGAR LVHWYQQKPG QAPVLVIYDD SDRPSRIPER   60
FSGSNIGNTA TLTIERVEAG DEADYYCQVW DYYSNSYVFG GGTKLTVL              108

SEQ ID NO: 273          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 273
QMQLVESGGG VVQPGRSLTL SCAASGFEFR TYGMHWVRQA PGKGLEWVAV IWDDGSNTVY   60
ADSVKGRFTI TRDNSKNTLN LQMNSLRVED TAVYYCVRAP QWYLTAEAFD LWGQGTMVTV  120
SS                                                                122

SEQ ID NO: 274          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 274
SYILTQPPSV SVAPGQTATI TCGGNLIGSR LVHWYQQKPG QAPVLVIYDD SDRPSRIPER   60
FSGSNIGNTA TLTIEDVEEG DEADYYCQVW DHYSDHMVFG GGTKLTVL              108

SEQ ID NO: 275          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 275
QMQLVESGGG VVQPGRSLTL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV  120
SS                                                                122

SEQ ID NO: 276          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 276
SYILTQPPSV SVAPGQTATI TCGGNLIGAR LVHWYQQKPG QAPVLVIYDD SDRPSRIPER   60
FSGSNIGNTA TLTIERVEEG DEADYYCQVW DYSSDSYVFG GGTKLTVL              108

SEQ ID NO: 277          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 277
QMQLVESGGG VVQPGRSLRL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV  120
SS                                                                122
```

-continued

```
SEQ ID NO: 278             moltype = AA   length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 278
SYILTQPPSV SVAPGETATI TCGGNLIGAR LVHWYQQKPG QAPVLVIYDD SDRPSRIPER  60
FSGSNIGNTA TLTISDVEEG DEADYYCQVW DYYSNSYVFG GGTKLTVL                108

SEQ ID NO: 279             moltype = AA   length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 279
QMQLVESGGG VVQPGRSLRL SCAASGFEFR TYGMHWVRQA PGKGLEWVGV IWYDGSNTHY  60
ADSVKGRFTI TRDNSKNTLN LQMNSLRAED TAVYYCVRAP QWYLTAEAFD LWGQGTMVTV  120
SS                                                                 122

SEQ ID NO: 280             moltype = AA   length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 280
SYILTQPPSV SVAPGQTATI TCGGNLIGAR LVHWYQQKPG QAPVLVIYDD SDRPSRIPER  60
FSGSNIGNTA TLTIERVEEG DEADYYCQVW DYSSNSYVFG GGTKLTVL                108

SEQ ID NO: 281             moltype = AA   length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 281
QMQLVESGGG VVQPGRSLRL SCAASGFEFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV  120
SS                                                                 122

SEQ ID NO: 282             moltype = AA   length = 108
FEATURE                    Location/Qualifiers
REGION                     1..108
                           note = Description of Artificial Sequence: Synthetic
                            polypeptide
source                     1..108
                           mol_type = protein
                           organism = synthetic construct
SEQUENCE: 282
SYILTQPPSV SVAPGETTRI TCGGNLIGAK LVHWYQQKPG QAPVLVIYDD SDRPSRIPER  60
FSGSNIGNTA TLTIEDVEAG DEADYYCQVW DYSSNHMVFG GGTKLTVL                108

SEQ ID NO: 283             moltype = AA   length = 122
FEATURE                    Location/Qualifiers
REGION                     1..122
                           note = Description of Artificial Sequence: Synthetic
                            polypeptide
source                     1..122
                           mol_type = protein
                           organism = synthetic construct
SEQUENCE: 283
QMQLVESGGG VVQPGRSLTL SCAASGFEFR TYGMHWVRQA PGKGLEWVGV IWDDGSATHY  60
ADSVKGRFTI TRDNSKNTLN LQMNSLRVED TAVYYCVRAP QWYLTAEAFD LWGQGTMVTV  120
SS                                                                 122

SEQ ID NO: 284             moltype = AA   length = 108
FEATURE                    Location/Qualifiers
REGION                     1..108
                           note = Description of Artificial Sequence: Synthetic
```

```
                          polypeptide
source                    1..108
                          mol_type = protein
                          organism = synthetic construct
SEQUENCE: 284
SYVLTQPPSV SVAPGETATI TCGGALIGAR LVHWYQQKPG QAPVLVVYDD SDRPSRIPER  60
FSGSNIGNTA TLTISRVEAG DEADYYCQVW DYYANSYVFG GGTKLTVL               108

SEQ ID NO: 285            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 285
QMQLVESGGG VVQPGRSLRL SCAASGFEFR TYGMHWVRQA PGKGLEWLGV IWYDGSNTHY  60
ADSVKGRFTI TRDNSKNTLN LQMNSLRAED TAVYYCVRAP QWYLTAEAFD LWGQGTMVTV  120
SS                                                                 122

SEQ ID NO: 286            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 286
SYILTQPPSV SVAPGQTATI TCGGNLIGAR LVHWYQQKPG QAPVLVIYDD SDRPSRIPER  60
FSGSNIGNTA TLTIERVEEG DEADYYCQVW DYSSDTYVFG GGTKLTVL               108

SEQ ID NO: 287            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 287
QMQLVESGGG VVQPGRSLTL SCAASGFEFR TYGMHWVRQA PGKGLEWVGV IWYDGSNTHY  60
ADSVKGRFTI TRDNSKNTLN LQMNSLRAED TAVYYCVRAP QWYLTAEAFD LWGQGTMVTV  120
SS                                                                 122

SEQ ID NO: 288            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 288
SYVLTQPPSV SVAPGETATI TCGGNLIGAR LVHWYQQKPG QAPVLVIYDD SDRPSRIPER  60
FSGSNIGNTA TLTIEDVEEG DEADYYCQVW DYSSDSYVFG GGTKLTVL               108

SEQ ID NO: 289            moltype = AA  length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 289
QMQLVESGGG VVQPGRSLTL SCAASGFEFR TYGMHWVRQA PGKGLEWVGV IWYDGSNTHY  60
ADSVKGRFTI TRDNSKNTLN LQMNSLRVED TAVYYCVRAP QWYLTAEAFD LWGQGTMVTV  120
SS                                                                 122

SEQ ID NO: 290            moltype = AA  length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
```

-continued

```
SEQUENCE: 290
SYILTQPPSV SVAPGQTATI TCGGNLIGAR LVHWYQQKPG QAPVLVIYDD SDRPSRIPER  60
FSGSNIGNTA TLTIEDVEEG DEADYYCQVW DYSANSYVFG GGTKLTVL                108

SEQ ID NO: 291           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 291
QMQLVESGGG VVQPGRSLTL SCAASGFEFR TYGMHWVRQA PGKGLEWLGV IWYDGSNTHY  60
ADSVKGRFTI TRDNSKNTLN LQMNSLRAED TAVYYCVRAP QWYLTAEAFD LWGQGTMVTV  120
SS                                                                 122

SEQ ID NO: 292           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 292
SYILTQPPSV SVAPGQTATI TCGGNLIGAR LVHWYQQKPG QAPVLVIYDD SDRPSRIPER  60
FSGSNSGNTA TLTISDVEEG DEADYYCQVW DYSSNTYVFG GGTKLTVL                108

SEQ ID NO: 293           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 293
QMQLVESGGG VVQPGRSLTL SCAASGFEFR TYGMHWVRQA PGKGLEWVAV IWDDGSNTHY  60
ADSVKGRFTI TRDNSKNTLN LQMNSLRVED TAVYYCVRAP QWYLTAEAFD LWGQGTMVTV  120
SS                                                                 122

SEQ ID NO: 294           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 294
SYVLTQPPSV SVAPGQTATI TCGGNLIGAR LVHWYQQKPG QAPVLVIYDD SDRPSRIPER  60
FSGSNIGNTA TLTIERVEAG DEADYYCQVW DYYSDTMVFG GGTKLTVL                108

SEQ ID NO: 295           moltype = AA  length = 122
FEATURE                  Location/Qualifiers
REGION                   1..122
                         note = Description of Artificial Sequence: Synthetic
                          polypeptide
source                   1..122
                         mol_type = protein
                         organism = synthetic construct
SEQUENCE: 295
QMQLVESGGG VVQPGRSLTL SCAASGFEFR TYGMHWVRQA PGKGLEWVGV IWDDGSNTHY  60
ADSVKGRFTI TRDNSKNTLN LQMNSLRAED TAVYYCARAP QWYLTAEAFD LWGQGTMVTV  120
SS                                                                 122

SEQ ID NO: 296           moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 296
SYVLTQPPSV SVAPGETATI TCGGNLIGAK LVHWYQQKPG QAPVLVIYDD SDRPSRIPER  60
FSGSNIGNTA TLTIEDVEAG DEADYYCQVW DYSSDTMVFG GGTKLTVL                108
```

```
SEQ ID NO: 297          moltype = AA  length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 297
QMQLVESGGG VVQPGRSLRL SCAASGFEFR TYGMHWVRQA PGKGLEWVGV IWYDGSATHY   60
ADSVKGRFTI TRDNSKNTLN LQMNSLRVED TAVYYCVRAP QWYLTAEAFD LWGQGTMVTV  120
SS                                                                 122

SEQ ID NO: 298          moltype = AA  length = 108
FEATURE                 Location/Qualifiers
REGION                  1..108
                        note = Description of Artificial Sequence: Synthetic
                        polypeptide
source                  1..108
                        mol_type = protein
                        organism = synthetic construct
SEQUENCE: 298
SYILTQPPSV SVAPGETATI TCGGNLIGAR LVHWYQQKPG QAPVLVIYDD SDRPSRIPER   60
FSGSNIGNTA TLTISDVEEG DEADYYCQVW DYSSDHYVFG GGTKLTVL                108

SEQ ID NO: 299          moltype = AA  length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 299
QMQLVESGGG VVQPGRSLRL SCAASGFEFR TYGMHWVRQA PGKGLEWVGV IWYDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 300          moltype = AA  length = 108
FEATURE                 Location/Qualifiers
REGION                  1..108
                        note = Description of Artificial Sequence: Synthetic
                        polypeptide
source                  1..108
                        mol_type = protein
                        organism = synthetic construct
SEQUENCE: 300
SYILTQPPSV SVAPGETATI TCGGNLIGAR LVHWYQQKPG QAPVLVIYDD SDRPSRIPER   60
FSGSNIGNTA TLTISRVEEG DEADYYCQVW DYSSNTYVFG GGTKLTVL                108

SEQ ID NO: 301          moltype = AA  length = 122
FEATURE                 Location/Qualifiers
REGION                  1..122
                        note = Description of Artificial Sequence: Synthetic
                        polypeptide
source                  1..122
                        mol_type = protein
                        organism = synthetic construct
SEQUENCE: 301
QMQLVESGGG VVQPGRSLRL SCAASGFEFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                 122

SEQ ID NO: 302          moltype = AA  length = 108
FEATURE                 Location/Qualifiers
REGION                  1..108
                        note = Description of Artificial Sequence: Synthetic
                        polypeptide
source                  1..108
                        mol_type = protein
                        organism = synthetic construct
SEQUENCE: 302
SYILTQPPSV SVAPGETATI TCGGNLIGAR LVHWYQQKPG QAPVLVIYDD SDRPSRIPER   60
FSGSNSGNTA TLTISDVEAG DEADYYCQVW DYSSDHMVFG GGTKLTVL                108

SEQ ID NO: 303          moltype = AA  length = 122
FEATURE                 Location/Qualifiers
REGION                  1..122
                        note = Description of Artificial Sequence: Synthetic
```

-continued

```
                          polypeptide
source                    1..122
                          mol_type = protein
                          organism = synthetic construct
SEQUENCE: 303
QMQLVESGGG VVQPGRSLRL SCAASGFEFR TYGMHWVRQA PGKGLEWVGV IWYDGSNTHY  60
ADSVKGRFTI TRDNSKNTLN LQMNSLRAED TAVYYCVRAP QWYLTAEAFD LWGQGTMVTV  120
SS                                                                122

SEQ ID NO: 304            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 304
SYILTQPPSV SVAPGETATI TCGGNLIGAR LVHWYQQKPG QAPVLVIYDD SDRPSRIPER  60
FSGSNIGNTA TLTISRVEAG DEADYYCQVW DYSSNTYVFG GGTKLTVL              108

SEQ ID NO: 305            moltype = AA   length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 305
QMQLVESGGG VVQPGRSLRL SCAASGFEFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV  120
SS                                                                122

SEQ ID NO: 306            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 306
SYILTQPPSV SVAPGETATI TCGGNLIGAR LVHWYQQKPG QAPVLVIYDD SDRPSRIPER  60
FSGSNIGNTA TLTISRVEEG DEADYYCQVW DYSSDSYVFG GGTKLTVL              108

SEQ ID NO: 307            moltype = AA   length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 307
QMQLVESGGG VVQPGRSLRL SCAASGFEFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV  120
SS                                                                122

SEQ ID NO: 308            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 308
SYILTQPPSV SVAPGETATI TCGGNLIGAR LVHWYQQKPG QAPVLVIYDD SDRPSRIPER  60
FSGSNIGNTA TLTISDVEAG DEADYYCQVW DYSSDTYVFG GGTKLTVL              108

SEQ ID NO: 309            moltype = AA   length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
```

```
SEQUENCE: 309
QMQLVESGGG VVQPGRSLRL SCAASGFEFR TYGMHWVRQA PGKGLEWVGV IWDDGSNTHY   60
ADSVKGRFTI TRDNSKNTLN LQMNSLRAED TAVYYCVRAP QWYLTAEAFD LWGQGTMVTV  120
SS                                                                122

SEQ ID NO: 310         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 310
SYILTQPPSV SVAPGETATI TCGGNLIGAR LVHWYQQKPG QAPVLVIYDD SDRPSRIPER   60
FSGSNIGNTA TLTISDVEAG DEADYYCQVW DYSSDTYVFG GGTKLTVL               108

SEQ ID NO: 311         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 311
QMQLVESGGG VVQPGRSLRL SCAASGFEFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SS                                                                122

SEQ ID NO: 312         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 312
SYVLTQPPSV SVAPGETATI TCGGNLIGAR LVHWYQQKPG QAPVLVIYDD SDRPSRIPER   60
FSGSNIGNTA TLTIERVEEG DEADYYCQVW DYSSDHMVFG GGTKLTVL               108

SEQ ID NO: 313         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 313
QMQLVESGGG VVQPGRSLRL SCAASGFEFR TYGMHWVRQA PGKGLEWVGV IWDDGSNTHY   60
ADSVKGRFTI TRDNSKNTLN LQMNSLRAED TAVYYCVRAP QWYLTAEAFD LWGQGTMVTV  120
SS                                                                122

SEQ ID NO: 314         moltype = AA  length = 108
FEATURE                Location/Qualifiers
REGION                 1..108
                       note = Description of Artificial Sequence: Synthetic
                        polypeptide
source                 1..108
                       mol_type = protein
                       organism = synthetic construct
SEQUENCE: 314
SYILTQPPSV SVAPGQTARI TCGGNLIGAK LVHWYQQKPG QAPVLVIYDD SDRPSRIPER   60
FSGSNIGNTA TLTIERVEEG DEADYYCQVW DYSSDHMVFG GGTKLTVL               108

SEQ ID NO: 315         moltype = AA  length = 122
FEATURE                Location/Qualifiers
REGION                 1..122
                       note = Description of Artificial Sequence: Synthetic
                        polypeptide
source                 1..122
                       mol_type = protein
                       organism = synthetic construct
SEQUENCE: 315
QMQLVESGGG VVQPGRSLTL SCAASGFEFR TYGMHWVRQA PGKGLEWVGV IWYDGSATHY   60
ADSVKGRFTI TRDNSKNTLN LQMNSLRAED TAVYYCARAP QWYLTAEAFD LWGQGTMVTV  120
SS                                                                122
```

-continued

```
SEQ ID NO: 316          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 316
SYILTQPPSV SVAPGETATI TCGGNLIGAK LVHWYQQKPG QAPVLVIYDD SDRPSRIPER  60
FSGSNIGNTA TLTISDVEAG DEADYYCQVW DYYSDTYVFG GGTKLTVL             108

SEQ ID NO: 317          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 317
QMQLVESGGG VVQPGRSLTL SCAASGFEFR TYGMHWVRQA PGKGLEWVAV IWDDGSNTHY  60
ADSVKGRFTI TRDNSKNTLN LQMNSLRVED TAVYYCVRAP QWYLTAEAFD LWGQGTMVTV 120
SS                                                              122

SEQ ID NO: 318          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 318
SYILTQPPSV SVAPGETATI TCGGNLIGAK LVHWYQQKPG QAPVLVIYDD SDRPSRIPER  60
FSGSNSGNTA TLTISDVEEG DEADYYCQVW DYYADTMVFG GGTKLTVL             108

SEQ ID NO: 319          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 319
QMQLVESGGG VVQPGRSLTL SCAASGFEFR TYGMHWVRQA PGKGLEWVGV IWDDGSNTHY  60
ADSVKGRFTI TRDNSKNTLN LQMNSLRVED TAVYYCARAP QWYLTAEAFD LWGQGTMVTV 120
SS                                                              122

SEQ ID NO: 320          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 320
SYILTQPPSV SVAPGQTATI TCGGNLIGAK LVHWYQQKPG QAPVLVIYDD SDRPSRIPER  60
FSGSNIGNTA TLTISDVEEG DEADYYCQVW DYSSDHMVFG GGTKLTVL             108

SEQ ID NO: 321          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 321
QMQLVESGGG VVQPGRSLTL SCAASGFAFR TYGMHWVRQA PGKGLEWVAV IWDDGSNTHY  60
ADSVKGRFTI TRDNSKNTLN LQMNSLRVED TAVYYCVRAP QWYLTAEAFD LWGQGTMVTV 120
SS                                                              122

SEQ ID NO: 322          moltype = AA  length = 108
FEATURE                 Location/Qualifiers
REGION                  1..108
```

```
                       note = Description of Artificial Sequence: Synthetic
                        polypeptide
source                 1..108
                       mol_type = protein
                       organism = synthetic construct
SEQUENCE: 322
SYILTQPPSV SVAPGETATI TCGGNLIGAR LVHWYQQKPG QAPVLVIYDD SDRPSRIPER  60
FSGSNIGNTA TLTIERVEAG DEADYYCQVW DYSSNSYVFG GGTKLTVL              108

SEQ ID NO: 323        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 323
QMQLVESGGG VVQPGRSLTL SCAASGFEFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV 120
SS                                                              122

SEQ ID NO: 324        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 324
SYILTQPPSV SVAPGETATI TCGGNLIGAK LVHWYQQKPG QAPVLVIYDD SDRPSRIPER  60
FSGSNIGNTA TLTISDVEEG DEADYYCQVW DYYSNTMVFG GGTKLTVL              108

SEQ ID NO: 325        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 325
QMQLVESGGG VVQPGRSLRL SCAASGFEFR TYGMHWVRQA PGKGLEWVGV IWDDGSNTHY  60
ADSVKGRFTI TRDNSKNTLN LQMNSLRAED TAVYYCVRAP QWYLTAEAFD LWGQGTMVTV 120
SS                                                              122

SEQ ID NO: 326        moltype = AA  length = 108
FEATURE               Location/Qualifiers
REGION                1..108
                      note = Description of Artificial Sequence: Synthetic
                       polypeptide
source                1..108
                      mol_type = protein
                      organism = synthetic construct
SEQUENCE: 326
SYILTQPPSV SVAPGETATI TCGGNLIGAR LVHWYQQKPG QAPVLVIYDD SDRPSRIPER  60
FSGSNIGNTA TLTISRVEAG DEADYYCQVW DYSSDHMVFG GGTKLTVL              108

SEQ ID NO: 327        moltype = AA  length = 122
FEATURE               Location/Qualifiers
REGION                1..122
                      note = Description of Artificial Sequence: Synthetic
                       polypeptide
source                1..122
                      mol_type = protein
                      organism = synthetic construct
SEQUENCE: 327
QMQLVESGGG VVQPGRSLRL SCAASGFEFR TYGMHWVRQA PGKGLEWVAV IWDDGSNTHY  60
ADSVKGRFTI TRDNSKNTLN LQMNSLRAED TAVYYCVRAP QWYLTAEAFD LWGQGTMVTV 120
SS                                                              122

SEQ ID NO: 328        moltype = AA  length = 108
FEATURE               Location/Qualifiers
REGION                1..108
                      note = Description of Artificial Sequence: Synthetic
                       polypeptide
source                1..108
                      mol_type = protein
```

-continued

```
                            organism = synthetic construct
SEQUENCE: 328
SYILTQPPSV SVAPGETATI TCGGNLIGAR LVHWYQQKPG QAPVLVIYDD SDRPSRIPER    60
FSGSNIGNTA TLTISRVEAG DEADYYCQVW DYSSDTYVFG GGTKLTVL                108

SEQ ID NO: 329          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 329
QMQLVESGGG VVQPGQSLRL SCAASGFEFR TYGMHWVRQA PGKGLEWLAV IWYDGSNTHY    60
ADSVKGRFTI TRDNSKNTLN LQMNSLRAED TAVYYCVRAP QWYNSAEAFD LWGQGTMVTV   120
SS                                                                 122

SEQ ID NO: 330          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 330
SYVLTQPPSV SVAPGQTARI TCGGNLIGAR LVHWYQQKPG QAPVLVIYDD SDRPSHIPER    60
FSGSNSGNTA TLTISRVEAG DEADYYCQVW DYSADTMVFG GGTKLTVL                108

SEQ ID NO: 331          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 331
QMQLVESGGG VVQPGQSLRL SCAASGFAFR TYGMHWVRQA PGKGLEWLAV IWYDGSNTHY    60
ADSVKGRFTI TRDNSKNTLN LQMNSLRAED TAVYYCVRAP QWYNSAEAFD LWGQGTMVTV   120
SS                                                                 122

SEQ ID NO: 332          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 332
SYVLTQPPSV SVAPGQTARI TCGGNLIGAR LVHWYQQKPG QAPVLVVYDD SDRPSHIPER    60
FSGSNSGNTA TLTISRVEAG DEADYYCQVW DHSADTMVFG GGTKLTVL                108

SEQ ID NO: 333          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 333
QMQLVESGGG VVQPGRSLRL SCAASGFEFR TYGMHWVRQA PGKGLEWLAV IWYDGSNTHY    60
ADSVKGRFTI TRDNSKNTLN LQMNSLRAED TAVYYCVRAP QWYNSAEAFD LWGQGTMVTV   120
SS                                                                 122

SEQ ID NO: 334          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 334
SYVLTQPPSV SVAPGQTARI TCGGNLIGAK LVHWYQQKPG QAPVLVIYDD SDRPSHIPER    60
FSGSNSGNTA TLTISRVEAG DEADYYCQVW DYSSDTMVFG GGTKLTVL                108
```

```
SEQ ID NO: 335          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 335
QMQLVESGGG VVQPGQSLRL SCAASGFEFR TYGMHWVRQA PGKGLEWVAV IWDDGSNTHY 60
ADSVKGRFTI TRDNSKNTLN LQMNSLRAED TAVYYCVRAP QWYLTAEAFD LWGQGTMVTV 120
SS                                                                122

SEQ ID NO: 336          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 336
SYVLTQPPSV SVAPGETATI TCGGNLIGAR LVHWYQQKPG QAPVLVIYDD SDRPSHIPER 60
FSGSNSGNTA TLTISRVEAG DEADYYCQVW DYSADTMVFG GGTKLTVL             108

SEQ ID NO: 337          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 337
QMQLVESGGG VVQPGRSLRL SCAASGFAFR TYGMHWVRQA PGKGLEWVAV IWDDGSNTHY 60
ADSVKGRFTI TRDNSKNTLN LQMNSLRAED TAVYYCVRAP QWYLTAEAFD LWGQGTMVTV 120
SS                                                                122

SEQ ID NO: 338          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 338
SYVLTQPPSV SVAPGETASI TCGGNMIGGY LVHWYQQKPG QAPVLVIYDD VDRPSRIPER 60
FSGSNSGNTA TLTISRVEAG DEADYYCQVW DHNSNHMVFG GGTKLTVL             108

SEQ ID NO: 339          moltype = AA  length = 122
FEATURE                 Location/Qualifiers
REGION                  1..122
                        note = Description of Artificial Sequence: Synthetic
                         polypeptide
source                  1..122
                        mol_type = protein
                        organism = synthetic construct
SEQUENCE: 339
QMQLVESGGG VVQPGRSLRL SCAASGFAFR TYGMHWVRQA PGKGLEWVAV IWDDGSNTHY 60
ADSVKGRFTI TRDNSKNTLN LQMNSLRAED TAVYYCVRAP QWYLSAEAFD LWGQGTMVTV 120
SS                                                                122

SEQ ID NO: 340          moltype = AA  length = 108
FEATURE                 Location/Qualifiers
REGION                  1..108
                        note = Description of Artificial Sequence: Synthetic
                         polypeptide
source                  1..108
                        mol_type = protein
                        organism = synthetic construct
SEQUENCE: 340
SYVLTQPPSV SVAPGETATI TCGGNMIGAY LVHWYQQKPG QAPLLVIYDD VDRPARIPER 60
FSGSNSGNTA TLTISRVEAG DEADYYCQVW DHNSDHMVFG GGTKLTVL             108

SEQ ID NO: 341          moltype = AA  length = 122
FEATURE                 Location/Qualifiers
REGION                  1..122
```

-continued

```
                          note = Description of Artificial Sequence: Synthetic
                           polypeptide
source                    1..122
                          mol_type = protein
                          organism = synthetic construct
SEQUENCE: 341
QMQLVESGGG VVQPGRSLTL SCAASGFEFR TYGMHWVRQA PGKGLEWVGV IWDDGSNTHY   60
ADSVKGRFTI TRDNSKNTLN LQMNSLRVED TAVYYCARAP QWYLTAEAFD LWGQGTMVTV   120
SS                                                                  122

SEQ ID NO: 342            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 342
SYILTQPPSV SVAPGETATI TCGGNLIGAK LVHWYQQKPG QAPVLVIYDD SDRPSRIPER   60
FSGSNIGNTA TLTIEDVEAG DEADYYCQVW DYSANHMVFG GGTKLTVL                 108

SEQ ID NO: 343            moltype = AA   length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 343
QMQLVESGGG VVQPGRSLRL SCAASGFEFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV   120
SS                                                                  122

SEQ ID NO: 344            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 344
SYILTQPPSV SVAPGETATI TCGGALIGSR LVHWYQQKPG QAPVLVIYDD SDRPSRIPER   60
FSGSNIGNTA TLTISDVEEG DEADYYCQVW DYYSNHMVFG GGTKLTVL                 108

SEQ ID NO: 345            moltype = AA   length = 122
FEATURE                   Location/Qualifiers
REGION                    1..122
                          note = Description of Artificial Sequence: Synthetic
                           polypeptide
source                    1..122
                          mol_type = protein
                          organism = synthetic construct
SEQUENCE: 345
QMQLVESGGG VVQPGRSLTL SCAASGFEFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV   120
SS                                                                  122

SEQ ID NO: 346            moltype = AA   length = 108
FEATURE                   Location/Qualifiers
REGION                    1..108
                          note = Description of Artificial Sequence: Synthetic
                           polypeptide
source                    1..108
                          mol_type = protein
                          organism = synthetic construct
SEQUENCE: 346
SYILTQPPSV SVAPGQTATI TCGGNLIGAK LVHWYQQKPG QAPVLVVYDD SDRPSRIPER   60
FSGSNIGNTA TLTIERVEEG DEADYYCQVW DYYSHTMVFG GGTKLTVL                 108

SEQ ID NO: 347            moltype = AA   length = 122
FEATURE                   Location/Qualifiers
REGION                    1..122
                          note = Description of Artificial Sequence: Synthetic
                           polypeptide
source                    1..122
                          mol_type = protein
```

```
                              organism = synthetic construct
SEQUENCE: 347
QMQLVESGGG VVQPGRSLRL SCAASGFEFR TYGMHWVRQA PGKGLEWVGV IWDDGSATHY   60
ADSVKGRFTI TRDNSKNTLN LQMNSLRVED TAVYYCVRAP QWYLTAEAFD LWGQGTMVTV  120
SS                                                                122

SEQ ID NO: 348      moltype = AA   length = 108
FEATURE             Location/Qualifiers
REGION              1..108
                    note = Description of Artificial Sequence: Synthetic
                     polypeptide
source              1..108
                    mol_type = protein
                    organism = synthetic construct
SEQUENCE: 348
SYILTQPPSV SVAPGQTATI TCGGALIGAR LVHWYQQKPG QAPVLVIYDD SDRPSRIPER   60
FSGSNIGNTA TLTISRVEEG DEADYYCQVW DYSSNTYVFG GGTKLTVL                108

SEQ ID NO: 349      moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 349
GFAFRTYG                                                            8

SEQ ID NO: 350      moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 350
IWDDGSNT                                                            8

SEQ ID NO: 351      moltype = AA   length = 15
FEATURE             Location/Qualifiers
REGION              1..15
                    note = Description of Artificial Sequence: Synthetic peptide
source              1..15
                    mol_type = protein
                    organism = synthetic construct
SEQUENCE: 351
VRAPQWYLTA EAFDL                                                    15

SEQ ID NO: 352      moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 352
IWYDGSAT                                                            8

SEQ ID NO: 353      moltype = AA   length = 15
FEATURE             Location/Qualifiers
REGION              1..15
                    note = Description of Artificial Sequence: Synthetic peptide
source              1..15
                    mol_type = protein
                    organism = synthetic construct
SEQUENCE: 353
VRAPQWYLSA EAFDL                                                    15

SEQ ID NO: 354      moltype = AA   length = 8
FEATURE             Location/Qualifiers
REGION              1..8
                    note = Description of Artificial Sequence: Synthetic peptide
source              1..8
                    mol_type = protein
                    organism = synthetic construct
SEQUENCE: 354
IWDDGSAT                                                            8

SEQ ID NO: 355      moltype = AA   length = 8
```

-continued

```
FEATURE                Location/Qualifiers
REGION                 1..8
                       note = Description of Artificial Sequence: Synthetic peptide
source                 1..8
                       mol_type = protein
                       organism = synthetic construct
SEQUENCE: 355
GFEFRTYG                                                              8

SEQ ID NO: 356         moltype = AA   length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 356
IWYDGSNT                                                              8

SEQ ID NO: 357         moltype = AA   length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 357
ARAPQWYLTA EAFDL                                                      15

SEQ ID NO: 358         moltype = AA   length = 15
FEATURE                Location/Qualifiers
REGION                 1..15
                       note = Description of Artificial Sequence: Synthetic peptide
source                 1..15
                       mol_type = protein
                       organism = synthetic construct
SEQUENCE: 358
VRAPQWYNSA EAFDL                                                      15

SEQ ID NO: 359         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 359
MIGAYL                                                                6

SEQ ID NO: 360         moltype =    length =
SEQUENCE: 360
000

SEQ ID NO: 361         moltype = AA   length = 11
FEATURE                Location/Qualifiers
REGION                 1..11
                       note = Description of Artificial Sequence: Synthetic peptide
source                 1..11
                       mol_type = protein
                       organism = synthetic construct
SEQUENCE: 361
QVWDHNTDKM V                                                          11

SEQ ID NO: 362         moltype = AA   length = 6
FEATURE                Location/Qualifiers
REGION                 1..6
                       note = Description of Artificial Sequence: Synthetic peptide
source                 1..6
                       mol_type = protein
                       organism = synthetic construct
SEQUENCE: 362
LIGAYL                                                                6

SEQ ID NO: 363         moltype = AA   length = 11
FEATURE                Location/Qualifiers
REGION                 1..11
                       note = Description of Artificial Sequence: Synthetic peptide
source                 1..11
                       mol_type = protein
```

-continued

```
                          organism = synthetic construct
SEQUENCE: 363
QVWDHDTNTM V                                                          11

SEQ ID NO: 364           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 364
MIGGYL                                                                6

SEQ ID NO: 365           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 365
QVWDHDTNHM V                                                          11

SEQ ID NO: 366           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 366
LIGSRL                                                                6

SEQ ID NO: 367           moltype =    length =
SEQUENCE: 367
000

SEQ ID NO: 368           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 368
QVWDHSSNTY V                                                          11

SEQ ID NO: 369           moltype = AA   length = 6
FEATURE                  Location/Qualifiers
REGION                   1..6
                         note = Description of Artificial Sequence: Synthetic peptide
source                   1..6
                         mol_type = protein
                         organism = synthetic construct
SEQUENCE: 369
LIGARL                                                                6

SEQ ID NO: 370           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 370
QVWDYYSDHM V                                                          11

SEQ ID NO: 371           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 371
QVWDHDSNTM V                                                          11

SEQ ID NO: 372           moltype = AA   length = 11
```

-continued

| FEATURE | Location/Qualifiers |
|---|---|
| REGION | 1..11 |
| | note = Description of Artificial Sequence: Synthetic peptide |
| source | 1..11 |
| | mol_type = protein |
| | organism = synthetic construct |

SEQUENCE: 372
QVWDHNTNHM V                                                          11

| SEQ ID NO: 373 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 373
QVWDHNTQQM V                                                          11

| SEQ ID NO: 374 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 374
QVWDHDTNQV V                                                          11

| SEQ ID NO: 375 | moltype = AA   length = 6 |
|---|---|
| FEATURE | Location/Qualifiers |
| REGION | 1..6 |
| | note = Description of Artificial Sequence: Synthetic peptide |
| source | 1..6 |
| | mol_type = protein |
| | organism = synthetic construct |

SEQUENCE: 375
LIGAKL                                                               6

| SEQ ID NO: 376 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 376
QVWDYSSDTM V                                                          11

| SEQ ID NO: 377 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 377
QVWDHSTNTM V                                                          11

| SEQ ID NO: 378 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 378
QVWDYSSNSY V                                                          11

| SEQ ID NO: 379 | moltype = AA   length = 11 |
|---|---|
| FEATURE | Location/Qualifiers |
| REGION | 1..11 |
| | note = Description of Artificial Sequence: Synthetic peptide |
| source | 1..11 |
| | mol_type = protein |
| | organism = synthetic construct |

SEQUENCE: 379
QVWDYSSNTY V                                                          11

-continued

```
SEQ ID NO: 380        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 380
QVWDHNSNQM V                                                              11

SEQ ID NO: 381        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 381
QVWDHSSNHY V                                                              11

SEQ ID NO: 382        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 382
QVWDHYSNHY V                                                              11

SEQ ID NO: 383        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 383
QVWDYSADSY V                                                              11

SEQ ID NO: 384        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 384
QVWDHNSNHM V                                                              11

SEQ ID NO: 385        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 385
QVWDYYSDSY V                                                              11

SEQ ID NO: 386        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 386
QVWDYSSDSM V                                                              11

SEQ ID NO: 387        moltype = AA   length = 11
FEATURE               Location/Qualifiers
REGION                1..11
                      note = Description of Artificial Sequence: Synthetic peptide
source                1..11
                      mol_type = protein
                      organism = synthetic construct
SEQUENCE: 387
QVWDYYSDHY V                                                              11
```

-continued

```
SEQ ID NO: 388           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 388
QVWDYSSDSY V                                                       11

SEQ ID NO: 389           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 389
QVWDYYSNSY V                                                       11

SEQ ID NO: 390           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 390
QVWDYYSDSY V                                                       11

SEQ ID NO: 391           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 391
QVWDHYSDHM V                                                       11

SEQ ID NO: 392           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 392
QVWDYSSNHM V                                                       11

SEQ ID NO: 393           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 393
QVWDYYANSY V                                                       11

SEQ ID NO: 394           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 394
QVWDYSSDTY V                                                       11

SEQ ID NO: 395           moltype = AA   length = 11
FEATURE                  Location/Qualifiers
REGION                   1..11
                         note = Description of Artificial Sequence: Synthetic peptide
source                   1..11
                         mol_type = protein
                         organism = synthetic construct
SEQUENCE: 395
```

-continued

```
QVWDYSANSY V                                                              11

SEQ ID NO: 396      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 396
QVWDYYSDTM V                                                              11

SEQ ID NO: 397      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 397
QVWDYSSDHY V                                                              11

SEQ ID NO: 398      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 398
QVWDYSSDHM V                                                              11

SEQ ID NO: 399      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 399
QVWDYYSDTY V                                                              11

SEQ ID NO: 400      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 400
QVWDYYADTM V                                                              11

SEQ ID NO: 401      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 401
QVWDYYSNTM V                                                              11

SEQ ID NO: 402      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
SEQUENCE: 402
QVWDYSADTM V                                                              11

SEQ ID NO: 403      moltype = AA  length = 11
FEATURE             Location/Qualifiers
REGION              1..11
                    note = Description of Artificial Sequence: Synthetic peptide
source              1..11
                    mol_type = protein
                    organism = synthetic construct
```

```
SEQUENCE: 403
QVWDHSADTM V                                                                    11

SEQ ID NO: 404          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 404
QVWDHNSDHM V                                                                    11

SEQ ID NO: 405          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 405
QVWDYSANHM V                                                                    11

SEQ ID NO: 406          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 406
QVWDYYSNHM V                                                                    11

SEQ ID NO: 407          moltype = AA   length = 11
FEATURE                 Location/Qualifiers
REGION                  1..11
                        note = Description of Artificial Sequence: Synthetic peptide
source                  1..11
                        mol_type = protein
                        organism = synthetic construct
SEQUENCE: 407
QVWDYYSHTM V                                                                    11

SEQ ID NO: 408          moltype = AA   length = 452
FEATURE                 Location/Qualifiers
source                  1..452
                        mol_type = protein
                        organism = synthetic construct
SEQUENCE: 408
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALGAPIEKT ISKAKGQPRE PQVYTLPPSR  360
DELTKNQVSL TCLVKGFYPS DIAVEWESNG QPENNYKTTP PVLDSDGSFF LYSKLTVDKS  420
RWQQGNVFSC SVMHEALHNH YTQKSLSLSP GK                                452

SEQ ID NO: 409          moltype = AA   length = 214
FEATURE                 Location/Qualifiers
source                  1..214
                        mol_type = protein
                        organism = synthetic construct
SEQUENCE: 409
SYVLTQPPSV SVAPGETASI TCGGNMIGGY LVHWYQQKPG QAPVLVIYDD VDRPSRIPER   60
FSGSNSGNTA TLTISRVEAG DEADYYCQVW DHNSNHMVFG GGTKLTVLGQ PKAAPSVTLF  120
PPSSEELQAN KATLVCLISD FYPGAVTVAW KADSSPVKAG VETTTPSKQS NNKYAASSYL  180
SLTPEQWKSH RSYSCQVTHE GSTVEKTVAP TECS                              214

SEQ ID NO: 410          moltype = AA   length = 452
FEATURE                 Location/Qualifiers
source                  1..452
                        mol_type = protein
                        organism = synthetic construct
SEQUENCE: 410
QMQLVESGGG VVQPGRSLRL SCAASGFAFR TYGMHWVRQA PGKGLEWVAV IWDDGSNTHY   60
ADSVKGRFTI TRDNSKNTLN LQMNSLRAED TAVYYCVRAP QWYLTAEAFD LWGQGTMVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPEAA  240
```

-continued

```
GGPSVFLFPP KPKDTLMISR TPEVTCVVVD VSHEDPEVKF NWYVDGVEVH NAKTKPREEQ 300
YNSTYRVVSV LTVLHQDWLN GKEYKCKVSN KALPAPIEKT ISKAKGQPRE PQVYTLPPSR 360
DELTKNQVSL TCLVKGFYPS DIAVEWESNG QPENNYKTTP PVLDSDGSFF LYSKLTVDKS 420
RWQQGNVFSC SVMHEALHNH YTQKSLSLSP GK          452
```